(12) United States Patent
Sikorski et al.

(10) Patent No.: US 7,094,801 B2
(45) Date of Patent: *Aug. 22, 2006

(54) CHALCONE DERIVATIVES AND THEIR USE TO TREAT DISEASES

(75) Inventors: James A. Sikorski, Atlanta, GA (US); Charles Q. Meng, Alpharetta, GA (US); M. David Weingarten, Cummings, GA (US); Kimberly J. Worsencroft, Alpharetta, GA (US); Liming Ni, Duluth, GA (US)

(73) Assignee: Atherogenics, Inc., Alpharetta, GA (US)

( * ) Notice: Subject to any disclaimer, the term of this patent is extended or adjusted under 35 U.S.C. 154(b) by 113 days.

This patent is subject to a terminal disclaimer.

(21) Appl. No.: 10/324,987

(22) Filed: Dec. 19, 2002

(65) Prior Publication Data
US 2004/0048858 A1    Mar. 11, 2004

Related U.S. Application Data

(60) Provisional application No. 60/342,034, filed on Dec. 19, 2001, provisional application No. 60/386,482, filed on Jun. 5, 2002.

(51) Int. Cl.
  A61K 31/38   (2006.01)
  A61K 31/40   (2006.01)
  A61K 31/535  (2006.01)
  C07D 333/56  (2006.01)
  C07D 409/00  (2006.01)

(52) U.S. Cl. .................. 514/443; 514/422; 514/231.5; 548/527; 549/58; 544/146

(58) Field of Classification Search ................ 514/438, 514/443, 422, 231.5; 549/58, 78; 548/527; 544/146
See application file for complete search history.

(56) References Cited

U.S. PATENT DOCUMENTS

| | | |
|---|---|---|
| 3,862,176 A | 1/1975 | Fauran et al. |
| 4,085,135 A | 4/1978 | Kyogoku et al. |
| 4,522,811 A | 6/1985 | Epstein et al. |
| 4,698,291 A * | 10/1987 | Koibuchi et al. ........... 430/196 |
| 4,855,438 A | 8/1989 | Kaulen et al. |
| 4,904,697 A | 2/1990 | Sunkara et al. |
| 5,068,364 A * | 11/1991 | Takagaki et al. ............ 549/415 |
| 5,155,250 A | 10/1992 | Parker et al. |
| 5,217,999 A | 6/1993 | Levitzki et al. |
| 5,380,747 A | 1/1995 | Medford et al. |
| 5,608,095 A | 3/1997 | Parker et al. |
| 5,631,365 A | 5/1997 | Rosenblum et al. |
| 5,744,614 A | 4/1998 | Merkle et al. |
| 5,750,351 A | 5/1998 | Medford et al. |
| 5,767,115 A | 6/1998 | Rosenblum et al. |
| 5,773,209 A | 6/1998 | Medford et al. |
| 5,773,231 A | 6/1998 | Medford et al. |
| 5,783,596 A | 7/1998 | Medford et al. |
| 5,786,355 A | 7/1998 | Konno et al. |
| 5,792,787 A | 8/1998 | Medford et al. |
| 5,807,884 A | 9/1998 | Medford et al. |
| 5,808,137 A | 9/1998 | Bombardelli et al. |
| 5,811,449 A | 9/1998 | Medford et al. |
| 5,821,260 A | 10/1998 | Medford et al. |
| 5,846,959 A | 12/1998 | Medford et al. |
| 5,877,203 A | 3/1999 | Medford et al. |
| 5,951,841 A | 9/1999 | Wehlage et al. |
| 6,046,212 A | 4/2000 | Zwaagstra et al. |
| 6,069,148 A | 5/2000 | Schmidt et al. |
| 6,140,343 A | 10/2000 | DeNinno et al. |
| 6,147,089 A | 11/2000 | DeNinno et al. |
| 6,147,090 A | 11/2000 | DeNinno et al. |
| 6,159,988 A | 12/2000 | Naik et al. |
| 6,162,445 A | 12/2000 | Bernardon |
| 6,197,786 B1 | 3/2001 | DeNinno et al. |
| 6,310,075 B1 | 10/2001 | DeNinno et al. |
| 6,313,142 B1 | 11/2001 | Damon et al. |
| 6,423,740 B1 | 7/2002 | Bombardelli et al. |
| 6,462,075 B1 | 10/2002 | Bowen et al. |
| 6,608,101 B1 | 8/2003 | Ni et al. |
| 6,677,350 B1 * | 1/2004 | Lin ............................ 514/298 |
| 2003/0232877 A1 | 12/2003 | Sikorski et al. |
| 2003/0236298 A1 | 12/2003 | Meng et al. |

(Continued)

FOREIGN PATENT DOCUMENTS

EP    307762    3/1989

(Continued)

OTHER PUBLICATIONS

Liu et al., Antimalarial Alkoxylated and Hydroxylated Chalones: Structure-Activity Relationship Analysis, *J. Med. Chem.* 2001, 44, 4443-4452.

(Continued)

*Primary Examiner*—Deborah C. Lambkin
(74) *Attorney, Agent, or Firm*—Sherry M. Knowles, Esq.; King&Spalding, LLP

(57) ABSTRACT

The invention relates to compounds, pharmaceutical compositions and methods of using compounds of the general formula

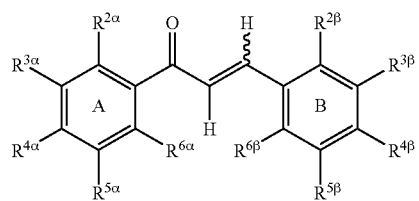

or its pharmaceutically acceptable salt or ester, wherein the substituents are defined in the application.

39 Claims, No Drawings

U.S. PATENT DOCUMENTS

2004/0048858 A1     3/2004    Sikorski et al.

FOREIGN PATENT DOCUMENTS

| | | |
|---|---|---|
| EP | 0 271 307 | 1/1992 |
| EP | 0 476 658 A1 | 3/1992 |
| FR | 2175634 A | 10/1973 |
| GB | 1408754 A | 10/1975 |
| JP | 63010720 | 7/1986 |
| JP | 04217621 | 10/1990 |
| JP | 06092950 | 9/1992 |
| JP | 06116206 | 10/1992 |
| JP | 07330814 | 6/1994 |
| WO | WO 95/15760 | 6/1995 |
| WO | WO 96/08484 A1 | 3/1996 |
| WO | WO 96/20936 | 7/1996 |
| WO | WO 97/12613 | 4/1997 |
| WO | WO 97/33882 A1 | 9/1997 |
| WO | WO 98/04528 A2 | 2/1998 |
| WO | WO 98/23581 | 6/1998 |
| WO | WO 98/23581 A1 | 6/1998 |
| WO | WO 98/35937 A1 | 8/1998 |
| WO | WO 98/40375 A2 | 9/1998 |
| WO | WO 98/51289 | 11/1998 |
| WO | WO 98/51662 | 11/1998 |
| WO | WO 99/00114 | 1/1999 |
| WO | WO 99/00114 A2 | 1/1999 |
| WO | WO 99/14174 A1 | 3/1999 |
| WO | WO 99/14215 A1 | 3/1999 |
| WO | WO 99/15504 A1 | 4/1999 |
| WO | WO 00/18721 A1 | 6/2000 |
| WO | WO 00/18723 A1 | 6/2000 |
| WO | WO 00/18724 A1 | 6/2000 |
| WO | WO 00/38725 A1 | 7/2000 |
| WO | WO 00/47554 | 8/2000 |
| WO | WO 00/17166 A1 | 3/2003 |
| WO | WO 04/056727 A2 | 7/2004 |

OTHER PUBLICATIONS

Herencia et al, Novel Anti-inflammatory Chalcone Derivatives Inhibit the Induction of Nitric Oxide Synthase and Cyclooxygenase-2 in Mouse Peritoneal Macrophages, *FEBS Letters*, 1999, 453, 129-134.

Herencia, et al., in Synthesis and Anti-inflammatory Activity of Chalcone Derivatives, *Bioorganic & Medicinal Chemistry Letters 8* (1998) 1169-1174.

Hsieh et al., Synthesis and Anti-inflammatory Effect of Chalcones and Related Compounds, *Pharmaceutical Research*, 1998, vol. 15, No. 1, 39-46.

Hsieh, et al., Synthesis and Anti-inflammatory Effect of Chalcones, *J. Pharm. Pharmacol.* 2000, 52; 163-171..

Jones R. and N. Bischofberger, *Antiviral Research*, 27 (1995) 1-17.

Yang, Y., et al., *Heterocycles*, 1992, 34(6), 1169-1175.

Zwaagstra, et al., Synthesis and Structure-Activity Relationships of Carboxylated Chalcones: A Novel Series of CysLT$_1$ (LT$_4$) Receptor Antagonists; J. Med. Chem., 1997, 40, 1075-1089.

Abraham, W., et al., "Blockade of Late-phase Airway Reponses and Airway Hyperresponsiveness in Allergic Sheep with a Small-molecule Peptide Inhibitor of VLA-4," *Am. J. Respir. Crit. Care Med.*, 156:696-703 (1997),.

Albertini, J.P., et al., "Increase in Serum Levels of Adhesion Glycoprpteins in NIDDM Effect of Intensive Insulin Treatment," *Diabetologia*, 39:A240 (1996).

Bakhite, E. A., et al., "Synthesis and application of some new oxazole derivatives as antimicrobial agents," *J. Chem. Tech. Biotech.*, 55:157-161 (1992).

Baraczka, K., et al., "A Study Of Increased Levels Of Soluble Vascular Cell Adhesion Molecule-1 ($_s$VCAM-1) In The Cerebrospinal Fluid of Patients With Multiple Sclerosis And systemic Lupus Erythematosus," *Acta. Neurol. Scand.*, 99:95-99 (1999).

Belmont, H.M., et. al., "Up-Regulation of Endothelial Cell Adhesion Molecules Characterizes Disease Activity in Systemic Lupus Erythematosus," *Arthritis & Rheumatism*, 37(3):376-383 (1994).

Boratynska, M., et al., :Soluble cell adhesion molecules in chronic renal graft rejection, *Pol. Arch. Med. Wewn*, 100:410-418 (1998).

Bousquet, J., et. al., "Eosinophilic Inflammation in Asthma" *N. Engl. J. Med.*, 323(15):1033-1039 (1990).

Braunstahl,G.J., et. al., "Nasal allergen provocation induces adhesion molecule expression and tissue eosinophilia in upper and lower airways," *J. Allergy Clin. Immunol.*, 107:469-476 (2001).

Calliste, C.-A., et al., "Chalcones: Structural Requirements for Antioxidant, Estrogenic and Antiproliferative Activities," *Anticancer Research*, 21:3949-3956 (2001).

Cheng, Z.-J., et al., "Broussochalcone A, a potent antioxidant and effective suppressor of inducible nitric oxide synthase in lipoplysaccharide-activated macrophages," *Biochemical Pharmacology*, 61:939-946 (2001).

Corey, E.J., et al., "A synthetic method for formyl-ethynyl conversion (RCHO→RC≡CH or RC≡CR$^1$)," *Tetrahedron Letters*, 1972(36):3769-3772 (1972).

Cosimi, A.B., et al., "In Vivo Effects of Monoclonal Antibody to ICAM-1 (CD54) in Nonhuman Primates with Renal Allografts," *J. Immunol.*, 144(12):4604-4612 (1990).

Dimmock, J.R., et al., "Cytotoxic Activities of Mannich Bases of Chalcones and Related Compounds," *J. Med. Chem.*, 41(7):1014-1026 (1998).

Dimmock, J.R., et al., "Bioactivities of chalcones," *Current Medicinal Chemistry*, 6(12):1125-1149 (1999).

Dinkova-Kostova, A.T., et al., "Potency of Michael reaction acceptors as inducers of enzymes that protect against carcinogenesis depends on their reactivity with sulfhydryl groups," *Proc. Natl. Acad. Sci. U.S.A.*, 98(6):3404-3409 (Mar. 13, 2001).

Elovaara, I., et al., "Adhesion Molecules in Multiple Sclerosis," *Arch. Neurol.*, 57:546-551 (2000).

Endo, A., "The discovery and development of HMG-CoA reductase inhibitors," *J. Lipid Res.*, 33:1569-1582 (1992).

Enghofer, M., et al., "Vascular Cell Adhesion Molecule 1 Mediates Islet Lymphocyte Adhession in Diabetic Insulitis in Mice," *Diabetologia*, 39:A97 (1996).

Frigerio, S.,et al., "Cerebrospinal fluid thrombomodulin and sVCAM-1 in different clinical stages of multiple sclerosis patients," *Neuroimmunol.*, 87:88-93 (1998).

Furuzawa-Carballeda, J., et al., "Interleukin-8, interleukin-10, intercellular Adhesion Molecule-1 and Vascular Cell Adhesion Molecule-1 Expression Levels are Higher in Synovial Tissue for Patients with Rheumatoid Arthritis than in Osteoarthritis," *Scand. J. Immunol.*, 50:215-222 (1999).

Goeke, M.N., et al., "Elevation of Soluble VCAM-1 in the Serum of Patients with Inflammatory Bowel Disease," *Gastroenterology*, 106:A689 (1994).

Goggins, M.G., et al., "Serum VCAM-1 reflects the grade of intestinal inflammation in patients with Crohn's disease," *Gastroenterology*, 108:A825 (1995).

Göke, M., et al., "Elevated serum concentrations of soluble selectin and immunoglobulin type adhe-sion molecules in patients with inflammatory bowel disease," *J. Gasterokenterol.*, 32:480-486 (1997).

Gordon, F.H., et al., "Adhesion Molecule Expression in Inflammatory Bowel Disease (IBD) Patients Treated with Natalizumab (Antegrentm), a Humanized Antibody to A2 Integrin," *Gastroenterology*, 118 (No. 4, Suppl 2), A344 (2000).

Gosset, P., et al., "Expression of E-Selection, ICAM-1 and VCAM-1 on Bronchial Biopsies from Allergic and Non-Allergic Patients," *Int. Arch. Allergy Immunol.*, 106:69-77 (1995).

Groves, R.W., et al., "Vascular cell adhesion molecule-1: Expression in normal and diseased skin and regulation in vivo by interferon gamma," *J. Am. Acad. Dermatol.*, 29:67-72 (1993).

Grünbaum, Z., et al., "Nucleophilic Attacks on Carbon—Carbon Double Bonds. Part X. Nucleophile-catalysed *cis-trans* Isomerisation of *cis*-4-Nitrochalcone and of Diethyl Maleate in 95% Ethanol," *J. Chem. Soc. (B)*, 1966:1133-1137 (1966).

Grundy, S.M., "HMG-CoA Reductase inhibitors for treatment of hypercholesterolemia," *New Engl. J. Med.*, 319:24-33 (Jul. 7, 1988).

Hart, K.K., et al., "Coronary Endothelial Cell VCAM-1 Expression is Enhanced in the Diabetic Mouse Heart," *FASEB J.*, 11(3):A340 (1997).

Ikeda, Y., et al., "Relationship between lupus nephritis activity and the serum level of soluble VCAM-1," *Lupus*, 7:347-354 (1998).

Issekeutz, T.B., et al., "T Lymphocyte Migration to Arthritic Joints and Dermal Inflammation in the Rat: Differing Migration Patterns and the Involvement of VLA-4," *Clinical Immunol. Immunopathol.*, 61:436-447 (1991).

Jones, S.C., et al., "Adhesion molecules in inflammatory bowel disease," *Gut*, 36:724-730 (1995).

Jones, S.M., et al., "VCAM-1 expression on endothelium in lesions from cutaneous lupus erythematosus is increased compared with systemic and localized scleroderma," *British J. Dermatol.*, 135:678-686 (1996).

Kallmann, B.A., et al., "Cytokine-induced modulation of cellular adhesion to human cerebral endothelial cells is mediated by soluble vascular cell adhesion molecule-1," *Brain*, 123:687-697 (2000).

Kaplanski, G., et al., "Increased soluble vascular cell adhesion molecule 1 concentrations in patients with primary or systemic lupus erythematosus-related antiphospholipid syndrome," *Arthritis & Rheumatism*, 43(1):55-64 (2000).

Kitani, A., et al., "Soluble VCAM-1 induces Chemotaxis of Jurkat and Synovial Fluid T Cells Bearing High Affinity Very Late Antigen-4," *U. Immun.*, 161:4931-4938 (1996).

Koga, M., et al., "Relationship Between Circulating Vascular Cell Adhesion Molecule-1 and Microvascular Complications in Type 2 Diabetes Mellitus," *Diabet. Med.*, 15(8):661-667 (1998).

Koizumi, A., et al., "Elevation of serum soluble vascular cell adhesion molecule-1 (sVCAM-1) levels in bronchial asthma," *Clin. Exo. Immunol.*, 101:468-473 (1995).

Kolopp-Sarda, M.N., et al., "Longitudinal Study of Rheumatoid Arthritis Patients Discloses Sustained Elevated Serum Levels of Soluble CD016 (V-CAM)," *Clin. and Exp. Rheumatol.*, 19:165-170 (2001).

Koskinen, P.K., et al., "Adhesion Molecule P-Selectin and Vascular Cell Adhesion Molecule-1 in Enhanced heard Allograft Arteriosclerosis in the Rat," *Circulation*, 95(1):191-196 (1997).

Lai, K.N., et al., "Upregulation of Adhesion Molecule Expression on Endothelial Cells by Anti-DNA Autoantibodies in Systemic Lupus Erythematosus," *Clin Immunol Immunopathol*, 81(3):229-238 (1996).

Lee, Y.-N., et al., "2',5'-Dihydroxychalcone down-regulates endothelial connexin43 gap junctions and affects MAP kinase activation," *Toxicology*, 179:51-60 (2002).

Lee, S.J., et al., "Adhesion molecule expression and regulation on cells of the central nervous system," *J. Neuroimmunol.*, 98:77-88 (1998).

Li, P., et al., "NF-KB Regulations VCAM-1 Expression on Fibroblast-Like Synoviocytes," *J. Immunol.*, 164:5990-5997 (2000).

Lin, C.N., et al., "Novel Antiplatelet Constituents from Formosan Moraceous Plants," *J. Nat. Prod.*, 59(9):834-838 (1996).

Ling, W.H., and Jones, P.J.H., in "Dietary Phytosterols: A Review of Metabolism, Benefits and Side Effects," *Life Sciences*, 57(3):195-206 (1995).

Liu, M., et al., "Antimalarial Alkoxylated and Hydroxylated Chalcones: Structure-Activity Relationship Analysis," *J. Med. Chem.*, 44(25):4443-4452 (2001).

Loftus, E.V., et al., "Colonic Expression of Cell Adhesion Molecules Correlates with Clinical and Histologic Severity in Ulcerative Colitis but not Crohn's Disease," *Gastroenterology*, 108(4):A684 (1995).

Lorini, R., et al., "Elevated Circulating Adhesion Molecules in Children and Adolscents Affected by Insulin-Dependent Diabetes Mellitus," *Hormone Research*, 48(suppl. 2):153 (1997).

Marinova-Mutafcheiva, L., et al., "A Comparative Study into the Mechanisms of Action of Anti-Tumor Necrosis Factor α, Anti-CD4, and combined Anti-tumor Necrosis Factor α/Anti-CD4 Treatment in Early Collagen-Induces Arthritis," *Arthritis Rheum.*, 43(3):638-644 (2000).

Matsuyama, T., et al., "The Role of VCAM-1 Molecule in the Pathogenesis of Rheumatoid Synovitis," *Hum. Cell*, 9:187-191 (1996).

McHale, J.F., et al., "TNF-α and IL-1 Sequentially Induce Endothelial ICAM-1 and VCAM-1 Expression in MRL/lpr Lupus-Prone Mice," *J. Immunol.*, 163:3993-4000 (1996).

Metzger, W.J., et al., "Anti-VLA-4 Antibody and CS-1 Peptide Inhibitor Modifies Airway Inflammation and Bronchial Airway Hyperresponsiveness in the Allergic Rabbit," *J. Allergy Clin. Immunol.*, 93(No. 1, Part 2):183, Abstract No. 125 (1994).

Miranda, C.L., et al., "Prenylated chalcones and flavanones as inducers of quinone reductase in mouse Hepa 1c1c7 cells," *Cancer Letters*, 149:21-29 (2000).

Morales-Ducret, et al., "Vascular Cell Adhesion Molecule-1 Expression in Synovium and on Fibroblast-Like Synoviocytes," *J. Immunol.*, 149:1424-1431 (1992).

Mrowka, C., et al., "Detection of circulating adhesion molecules ICAM-1, VCAM-1 and E-Selectin in Wegener's granulomatosis, systemic lupus erythematosus and chronic renal failure," *Clin. Nephrol.*, 53(5):288-299 (1995).

Nakamura, C., et al., "Synthesis and Biological Activities of Fluorinated Chalcone Derivatives," *Bioorganic & Medicinal Chemistry*, 10:699-706 (2002).

Nielsen, S.F., et al., "Antileishmanial Chalcones: Statistical Design, Synthesis, and Three-Dimen-sional Quantitative Structure-Activity Relationship Analysis," *J. Med. Chem.*, 41:4819-4832 (1998).

Nielsen, S.F., et al., "Modifications of the α, β-Double Bond in Chalcones only Marginally Affect the Antiprotozoal Activities," *Bioorganic & Medicinal Chemistry*, 6:937-945 (1998).

Nickoloff, C., et al., "The Cytokine Network in Psoriasis," *Arch Dermatol.*, 127:871-884 (1991).

O'Brien, K.D., et al., "Vascular Cell Adhesion Molecule-1 is Expressed in Human Coronary Atherosclerotic Plaques," *J. Clin. Invest.*, 92:945-951 (1993).

Oguchi, S., et al., "Monoclonal Antibody Against Vascular Cell Adhesion Molecule-1 Inhibits Neointimal Formation after Periadventitial Carotid Artery Injury in Genetically Hypercholesterolemic Mice," *Arterioscler. Thromb. Vasc. Biol.*, 20:1729-1736 (2000).

Ohkawara, Y., et al., "In Situ Expression of the Cell Adhesion Molecules in Bronchial Tissues from Asthmatics with Air Flow Limitation: In Vivo Evidence of VCAM-1/VLA-4 Interaction in Selective Eosinophil Infiltration," *Am. J. Respir. Cell Mol. Biol.*, 12:4-12 (1995).

Orosz, C.G., et al., "Prevention of Acute Murine Cardiac Allograft Rejection: Anti-CD4 or Anti-Vascular Cell Adhesion Molecule One Monoclonal Antibodies Block Acute Rejection but Permit Persistent Graft-Reactive Alloimmunity and Chronic Tissue Remodeling," *J. Heart and Lung Transplantation*, 16:889-904 (1997).

Orosz, C.G., et al., "Treatment with Anti-Vascular Cell Adhesion Molecule 1 Monoclonal Antibody Induces Long-Term Murine Cardiac Allograft Acceptance," *Transportation*, 56:453-460 (1993).

Otsuki, M., et al., "Circulating Vascular Cell Adhesion Molecule-1 as a Useful Marker for Atherosclerosis in NIDDM Patients," *Diabetologia*, 40:A440 (1997).

Pallis, M., et al., "Distribution of cell adhesion molecules in skeletal muscle from patients with systemic lupus erythematosus," *Ann. Rheum. Dis.*, 52:667-671 (1993).

Papa, N.D., et al., "Anti-endothelial cell IgG fractions from systemic lupus erythematosus patients bind to human endothelial cells and induce a pro-adhesive and a pro-inflammatory phenotype *in vitro,*" *Lupus*, 8:423-429 (1999).

Pelletier, R., et al., "Analysis of Inflammatory Endothelial Changes, including VCAM-1 Expression, in Murine Cardiac Grafts," *Transplatation*, 55(2):315-320 (1993).

Pelletier, R., et al., "Importance of Endothelial VCAM-1 for Inflammatory Leukocytic Infiltration in Vivo," *J. Immunol.*, 149(7):2473-2481 (1992).

Pelletier, R., et al., "Monoclonal Antibody to Anti-VCAM-1 Interferes with Murine Cardiac Allograft Rejection," *Transplatation Proceedings*, 25(1):839-841 (1993).

Pilewski, J.M., et al., "Cell Adhesion Molecules in Asthma: Homing, Activation, and Airway Remodeling," *Am. J. Respir. Cell Mol. Biol.*, 12:1-3 (1995).

Postigo, A.A., et al., "Increased Binding of Synovial T Lymphocytes from Rhematoid Arthritis to Endothelial-Leykocyte Adhesion Molecule-1(ELAM-1) and Vascular Cell Adhesion Molecule-1 (VCAM-1)," *J. Clin. Invest.*, 89:1445-1452 (1992).

Rabb, H.A., et al., "The Role of the Leukocyte Adhesion Molecules VLA-4, LFA-1, and Mac-1 in Allergic Airway Responses in the Rat," *Am. J. Respir. Care. Med.*, 149:1186-1191 (1994).

Rieckmann, P., et al., "Correlation of soluble adhesion molecules in blood and cerebrospinal fluid with magnetic resonance imaging activity in patients with multiple sclerosis," *Mult. Scler.*, 4:178-182 (1998).

Santos, J.L., et al., "Applicability of the case-parent design in the etiological research of Type 1 diabetes in Chile and other genetically mixed populations," *Diabetes Res. Clin. Pract.*, 43:143-146 (1999).

Schopf, R.E., et al., "Soluble intercellular adhesion molecule-1 levels in patients with psoriasis," *Br. J. Dermatol.*, 128:34-37 (1993).

Scudla, V., et al., "Vascular Intercellular Adhesion Molecule-1 (VCAM-1)—a New Indicator of Activity of Systemic Lupus Erythematosus," *Vnitr. Lek.*, 43:307-311 (1997).

Solez K., et al., "Adhesion molecules and rejection of renal allgrafts," *Kidney International*, 51:1476-1480 (1997).

Soriano, A., et al., "VCAM-1, but Not ICAM-1 or MAdCAM-1, Immunoblokade Ameliorates DSS-Induces Colitis in Mice," *Lab. Invest.*, 80(10):1541-1551 (2000).

Sundell, C.L., et al., "Suppression of VCAM-1 and MCP-1 Attenuates Atherosclerosis in LDL Receptor-knockout and ApoE-knockout Mouse Models," *Circulation*, 100(18):1-42 (1999).

Tanio, et al., "Differential Expression of the Cell Adhesion Molecules ICAM-1, VCAM-1, and E-Selectin in Normal and Post-transplantation Myocardium," *Circulation*, 89:1760-1768 (1994).

Ten Hacken, N.H.T., et al., "Vascular cell adhesion molecules in nocturnal asthma: a possible role for VCAM-1 in ongoing airway wall inflammation," *Clin. Exp. Allergy*, 29:1518-1525 (1998).

Uyemura, K., et al., "The Cytokine Network in Lesional and Lesion-Free Psoriatic Skin in Characterized by a T-Helper Type 1 Cell-Mediated Response," *J. Invest. Dermatol.*, 101:701-705 (1993).

Van Dinther-Janssen, A.C.H.M., et al., "The VLA-4/VCAM-1 Pathway in Involved in Lymphocyte Adhesion to Endothelium in Rheumatoid Synovium," *J. Immunol.*, 147(12):4207-4210 (1991).

Wagner, O., et al., "Increased Concentrations of Soluble E-Selection and V-Cam in Gestational Diabetes," *Diabetologia*, 39:A205 (1996).

Wagner, O.F., et al., "Putative Role of Adhesion Molecules in Metabolic Disorders," *Hormone and Metabolic Research*, 29:627-630 (1997).

Wang, J.P., et al., "Investigation of the inhibitory effect of broussochalcone A on respiratory burst in neutrophils," *European Journal of Pharmacology*, 320:201-208 (1997).

Wang, S., et al., "IL-12 Dependent Vascular Cell Adhesion Molecule-1 Expression Contributes to Airway Eosinophilic Inflammation in a Mouse Model of Asthma-Like Reaction," *J. Immunol.*, 166:2741-2749 (2001).

Wetterrau, J.R., et al., "An MTP Inhibitor that Normalizes Atherogenic Lipoprotein Levels in WHHL Rabbits," *Science*, 282:751-754 (Oct. 23, 1998).

Wilkinson, L.S., et al., "Expression of Vascular Cell Adhesion Molecule-1 in Normal and Inflamed Synovium," *Lab. Invest.*, 68(1):82-88 (1993).

Wu, X., et al., "Antimalarial Activity of Ferrocenyl Chalcones," *Bioorganic & Medicinal Chemistry Letters*, 12:2299-2302 (2002).

Wuthrich, R.P., et al., "Vascular cell adhesion molecule-1 (VCAM-1) expression in murine lupus nephritis," *Kidney Int.*, 42:903-914 (1992).

Yamazaki, S., et al., "Isoliquiritigenin suppresses pulmonary metastasis of mouse renal cell carcinoma," *Cancer Letters*, 183:23-30 (2002).

Zembala, M., et al., "Cellular adhesion molecules changes is myocardium during first year post heart transplant," *Ann. of Transplant.*, 2:16-19 (1998).

\* cited by examiner

CHALCONE DERIVATIVES AND THEIR USE TO TREAT DISEASES

This patent application claims priority to U.S. Provisional Patent Application Ser. No. 60/342,034 filed Dec. 19, 2001 and U.S. Provisional Patent Application Ser. No. 60/386,482 filed Jun. 5, 2002.

The present invention is in the field of novel chalcone derivatives, pharmaceutical compositions and methods for treating a variety of diseases and disorders, including inflammation and cardiovascular disease.

BACKGROUND OF THE INVENTION

Adhesion of leukocytes to the endothelium represents a fundamental, early event in a wide variety of inflammatory conditions, autoimmune disorders and bacterial and viral infections. Leukocyte recruitment to endothelium is mediated in part by the inducible expression of adhesion molecules on the surface of endothelial cells that interact with counterreceptors on immune cells. Endothelial cells determine which types of leukocytes are recruited by selectively expressing specific adhesion molecules, such as vascular cell adhesion molecule-1 (VCAM-1), intercellular adhesion molecule-1 (ICAM-1), and E-selectin. VCAM-1 binds to the integrin VLA-4 expressed on lymphocytes, monocytes, macrophages, eosinophils, and basophils but not neutrophils. This interaction facilitates the firm adhesion of these leukocytes to the endothelium. VCAM-1 is an inducible gene that is not expressed, or expressed at very low levels, in normal tissues. VCAM-1 is upregulated in a number of inflammatory diseases, including arthritis (including rheumatoid arthritis), asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

Coronary heart disease (CHD), primarily as a result of atherosclerosis, remains the leading cause of death in industrialized countries. Atherosclerosis is a disease characterized by vascular inflammation, deposition of lipids in the arterial vessel wall and smooth muscle cell proliferation resulting in a narrowing of the vessel passages. In advanced stages of the disease atherosclerotic lesions can become unstable resulting in plaque rupture, thrombosis, myocardial infarction and ischemic heart disease. It is now well accepted that the initiating events in atherosclerosis are local injury to the arterial endothelium that results in the induction of VCAM-1 and recruitment of mononuclear leukocytes that express the integrin counterreceptor, VLA-4, (O'Brien, et al., *J. Clin. Invest.*, 92: 945–951, 1993). Subsequent conversion of leukocytes to foamy macrophages results in the synthesis of a wide variety of inflammatory cytokines, growth factors, and chemoattractants that help propagate formation of the mature atheromatous plaque by further inducing endothelial activation, leukocyte recruitment, smooth muscle cell proliferation, and extracellular matrix deposition. Pharmacological inhibition of VCAM-1 expression has been shown to inhibit atherosclerosis in several animal models (Sundell et al., *Circulation*, 100: 42, 1999). A monoclonal antibody against VCAM-1 has also been shown to inhibit neointimal formation in a mouse model of arterial wall injury (Oguchi, S., et al., *Arterioscler. Thromb. Vasc. Biol.*, 20: 1729–1736, 2000).

Asthma, which is increasing in prevalence and morbidity world-wide, is a chronic inflammatory disease characterized by lung eosinophilia and bronchial hyperreactivity. The interaction between VCAM-1 on lung endothelial cells and VLA-4, which is the integrin counterreceptor expressed on eosinophils, is thought to be important for selective eosinophil recruitment. Eosinophils have been considered an important effector cell in the pathogenesis of asthma and other allergic diseases. Activated eosinophils release proteins such as major basic protein (MBP) that have been demonstrated to induce bronchial hyperreactivity, one of the defining criteria of asthma (Bousquot, et al., *N. Engl. J. Med.*, 323: 1033–1039, 1990). It has been demonstrated that VCAM-1 is markedly upregulated on human bronchial vascular endothelium of subjects with asthma who have air flow limitation, when compared with subjects without asthma (Pilewski, et al., *Am. J. Respir. Cell Mol. Biol.*, 12, 1–3, 1995; Ohkawara, Y., et al., *Am. J. Respir. Cell Mol. Biol.*, 12, 4–12, 1995; Gosset, P., et al., *Int. Arch. Allergy Immunol.* 106: 69–77, 1995; Hacken, N. H., et al., *Clin. Exp. Allergy*, 28 (12): 1518–1525, 1998). An elevation in serum soluble VCAM-1 levels has also been demonstrated in patients undergoing a bronchial asthma attack compared with levels under stable conditions (Montefort, S., Koizumi, A., *Clin. Exp. Immunol.*, 101: 468–73, 1995). Several animal studies further demonstrate a spatial and temporal association between VCAM-1 and asthma. In a mouse model of allergic asthma, VCAM-1 expression was shown to be induced by allergen challenge, and administration of an anti-VCAM-1 antibody was effective in inhibiting eosinophil infiltration that occurred in this model (Metzger, W. J., et al., *J. Allergy Clin. Immunol.*, 93: 183, 1994). Further evidence for the importance of VCAM-1 in allergic asthma comes from work in IL-12 knockout mice. IL-12 knockout mice had fewer eosinophils and VCAM-1 expression than wildtype mice; however, administration of recombinant IL-12 at the time of ova sensitization and challenge restored lung VCAM-1 expression and eosinophilia (Wang, S., et al., *J. Immunol.*, 166:2741–2749, 2001). There are several examples where blocking the integrin receptors for VCAM-1 have had positive effects on animal models of asthma (Rabb et al., *Am. J. Respir. Care Med.* 149: 1186–1191, 1994; Abraham, W, et al., *Am. J. Respir. Crit. Care Med.* 156: 696–703. 1997) further demonstrating the importance of VCAM-1/VLA-4 interactions in allergic inflammation. Eosinophils are also important effector cells in allergic rhinitis. VCAM-1 has been demonstrated to be upregulated 24 hrs after nasal allergen provocation in patients with seasonal allergic rhinitis but not in normal subjects (Braunstahl, G. J., et al., *J. Allergy Clin. Immunol.*, 107: 469–476, 2001).

Rheumatoid arthritis (RA) is a clinical syndrome of unknown cause characterized by symmetric, polyarticular inflammation of synovial-lined joints. The role of adhesion molecules in the pathogenesis of RA has also been well documented, and VCAM-1 expression on synovial fibroblasts is a clinical hallmark of RA (Li, P., et al., *J. Immunol.* 164: 5990–7, 2000). VLA-4/VCAM-1 interactions may be the predominant mechanism for recruitment of leukocytes to the synovium (Dinther-Janssen, et al., *J. Immunol.* 147: 4207–4210, 1991; Issekeutz and Issekeutz, *Clin. Immunol. Immunopathol.* 61:436–447, 1991; Morales-Ducret et al., *J. Immunol.* 149:1424–1431, 1992; Postigo et al., *J. Clin. Invest.* 89:1445–1452, 1992; Matsuyama, T., et al, *Hum.*

*Cell,* 9: 187–192, 1996). In support of this, increased VCAM-1 expression has been found in RA synovial tissue compared with osteoarthritis and control tissue (Wilkinson et al., *Lab. Invest.* 69:82–88, 1993; Furuzawa-Carballeda, J., et al., *Scand. J. Immunol.* 50: 215–222; 1999). Soluble VCAM-1 is higher in RA patients than in control subjects (Kolopp-Sarda, M. N., et al., *Clin. Exp. Rheumatol.* 19: 165–70, 2001). Soluble VCAM-1 has been shown to be chemotactic for T cells (Kitani, A., et al., *J. Immun.* 161: 4931–8, 1998), and in addition to being a possible diagnostic marker for RA, may contribute to its pathogenesis by inducing migration and recruitment of T cells. VCAM-1 expressed on fibroblast-like synoviocytes has also been implicated in enhanced survival of activated synovial fluid B cells (Marinova, Mutafcheia, L., *Arthritis Rheum.* 43: 638–644, 2000) that may further contribute to RA pathogenesis.

Chronic inflammation and accompanying vascular complications and organ damage characterize systemic lupus erythematosis (SLE). Recent studies suggest that VCAM-1 plays a role in SLE. Expression of VCAM-1 is increased on dermal vessel endothelial cells in patients with active systematic lupus erythematosus (Jones, S. M., *British J. Dermatol.* 135: 678–686, 1996) and correlates with increased disease severity (Belmont et al., *Arthritis Rheum.* 37:376–383, 1994). SLE muscle samples with perivascular infiltrate have greater endothelial cell expression of VCAM-1 compared with SLE patients without a perivascular infiltrate or with control samples (Pallis et al., *Ann. Rheum. Dis.* 52:667–671, 1993). Increased expression of VCAM-1 has also been demonstrated in kidneys of lupus-prone MRL/lpr mice compared to nonautoimmune strains and its expression increased with disease severity (McHale, J. F., et al., *J. Immunol.* 163: 3993–4000, 1999). VCAM-1 expression on mesangial cells in vitro can be stimulated by IL-1, TNF-α, and INFγ exposure as well as by anti-endothelial cell IgG fraction and anti-DNA autoantibodies from SLE patients (Wuthrich, *Kidney Int.* 42: 903–914, 1992; Papa, N. D., et al., *Lupus,* 8: 423–429, 1999; Lai, K. N., et al., *Clin Immunol Immunopathol,* 81: 229–238, 1996). Furthermore, soluble VCAM-1 is higher in SLE patients than in normal subjects (Mrowka, C., et al., *Clin. Nephrol.* 43: 288–296, 1995; Baraczka, K., et al., *Acta. Neuro. Scand.* 99: 95–99, 1999; Kaplanski, G., et al., *Arthritis Rheumol.* 43: 55–64, 2000; Ikeda, Y., *Lupus,* 7: 347–354, 1998) and correlates with disease activity (Scudla, V., *Vnitr. Lek.,* 43: 307–311, 1997).

Increased VCAM-1 expression has also been demonstrated in solid organ transplant rejection. Acute transplant rejection occurs when the transplant recipient recognizes the grafted organ as "non-self" and mounts an immune response characterized by massive infiltration of immune cells, edema, and hemorrage that result in the death of the transplanted organ. Acute rejection occurs in a matter of hours or days and has been correlated with increased levels of VCAM-1 in tissues and in plasma (Tanio et al., *Circulation,* 89:1760–1768, 1994; Cosimi et al., *J. Immunol.* 144: 4604–4612, 1990; Pelletier, R., et al., *Transplantation,* 55: 315, 1992). A monoclonal antibody to VCAM-1 has been shown to inhibit cardiac allograft rejection in mice (Pelletier, R., *J. Immunol.,* 149: 2473–2481, 1992; Pelletier, R., et al., *Transplantation Proceedings,* 25: 839–841, 1993; Orosz, C. G., et al., *J. Heart and Lung Transplantation,* 16: 889–904, 1997) and when given for 20 days can cause complete inhibition of rejection and long-term graft acceptance (Orosz C. G., et al., *Transplantasion,* 56: 453–460, 1993). Chronic graft rejection also known as allograft vasculopathy is distinct from acute transplant rejection and is a leading cause of late graft loss after renal and heart transplantation. Histologically it is characterized by concentric neointimal growth within vessels that is largely due to smooth muscle migration and proliferation. It is thought to be the result of endothelial damage brought about by several factors including: ischemia-reperfusion injury, immune complexes, hypertension, hyperlipidemia and viruses. All of these factors have been associated with induction of VCAM-1 in endothelial cells. There is also a strong correlation of soluble and tissue VCAM-1 levels with chronic rejection (Boratynska, M.,. *Pol. Arch. Med. Wewn,* 100: 410–410, 1998; Zembala, M., et al., *Ann. Transplant.* 2: 16–9, 1998; Solez K., et al., *Kidney International.,* 51: 1476–1480, 1997; Koskinen P. K., et al., *Circulation,* 95: 191–6, 1997).

Multiple sclerosis is a common demyelinating disorder of the central nervous system, causing patches of sclerosis (plaques) in the brain and spinal cord. It occurs in young adults and has protean clinical manifestations. It is well documented that VCAM-1 is expressed on brain microvascular endothelial cells in active lesions of multiple sclerosis (Lee S. J., et al., *J. Neuroimmunol.,* 98: 77–88, 1998). Experimental therapy of experimental autoimmune encephalomyelitis, which is an animal model for multiple sclerosis, using antibodies against several adhesion molecules, including VCAM-1, clearly shows that adhesion molecules are critical for the pathogenesis of the disease (Benveniste et al., *J. Neuroimmunol.* 98:77–88, 1999). A time and dose dependent expression of VCAM-1 and release of soluble VCAM-1 were detected in cultures of human cerebral endothelial cells induced by TNFα, but not in peripheral blood mononuclear cells (Kallmann et al., *Brain,* 123:687–697, 2000). Clinical data also show that adhesion molecules in blood and cerebrospinal fluid are up-regulated throughout the clinical spectrum of multiple sclerosis (Baraczka, K., et al., *Acta. Neurol. Scand.* 99: 95–99, 1999; Reickmann, P., et al., *Mult. Scler.,* 4: 178–182, 1998; Frigerio, S., et al., *J. Neuroimmunol.,* 87: 88–93, 1998) supporting the notion that therapies which interfere with cell adhesion molecules such as VCAM-1 may be beneficial in modifying this disease (Elovaara et al., *Arch. Neurol.* 57:546–551, 2000).

Diabetes mellitus is a metabolic disease in which carbohydrate utilization is reduced and that of lipid and protein is enhanced. Evidence has accumulated that increased levels of adhesion molecules may play a functional pathophysiological role in diabetes (Wagner and Jilma, *Hormone and Metabolic Research,* 29: 627–630, 1997; Kado, S., *Diabetes Res. Clin. Pract.,* 46: 143–8, 1999). It is caused by an absolute or relative deficiency of insulin and is characterized by chronic hyperglycemia, glycosuria, water and electrolyte loss, ketoacidosis, and coma. Elevated circulating adhesion molecules including VCAM-1 have been detected in patients with diabetes and in experimental models of diabetes in animals (Lorini et al., *Hormone Research,* 48: 153, 1997; Otsuki et al., *Diabetologia,* 40: A440, 1997; Hart et al., *FASEB J.* 11:A340, 1997; Albertini et al., *Diabetologia,* 39: A240, 1996; Wagner et al., *Diabetologia,* 39: A205, 1996; Enghofer et al., *Diabetologia,* 39: A97, 1996; Koga M., *Diabet. Med.,* 15: 661–667, 1998). In addition, complications of diabetes often include peripheral vasculopathies such as diabetic retinopathy and diabetic nephropathy. It is believed that adhesion of leukocytes to the peripheral vasculature plays a central role in the vasculopathies often associated with diabetes.

Crohn's disease, also known as regional enteritis, is a subacute chronic inflammatory condition of unknown cause, involving the internal ileum and less frequently other parts of the gastrointestinal tract. It is characterized by patchy deep ulcers that may cause fistulas, and narrowing and thickening of the bowel by fibrosis and lymphocytic infiltration. Ulcerative colitis is a chronic disease of unknown cause characterized by ulceration of the colon and rectum, with rectal bleeding, mucosal crypt abscesses, inflammatory pseudopolyps, abdominal pain, and diarrhea. It has been reported that serum VCAM-1 reflects the grade of intestinal inflammation in patients with Crohn's disease or ulcerative colitis (Jones, et al., *Gut*, 36: 724–30, 1995; Goggins et al., *Gastroenterology*, 108: A825, 1995; Goeke and Manns, *Gastroenterology*, 106: A689, 1994; Goeke et al., *J. Gasterokenterol.* 32:480–486, 1997; Loftus et al., *Gastroenterology*, 108: A684, 1995; Tahami et al., *Gastroenterology*, 118: A344, 2000). Antibodies to VCAM-1 have been shown to ameliorate experimentally-induced colitis in mice (Soriano, A., *Lab. Invest.* 80: 1541–1551, 2000).

Psoriasis is a chronic skin disease characterized by erythematous scaling plaques as a result of keratinocyte hyperplasia, influx of immune cells and endothelial activation (Nickoloff, B. J., et al., *J. Invest. Dermatol.*, 127: 871–884, 1991). VCAM-1 is upregulated in psoriatic skin as compared to normal skin (Groves, R. W., *J. Am. Acad. Dermatol.*, 29: 67–72, 1993; Uyemura, K., et al., *J. Invest. Dermatol.* 101: 701–705, 1993) and levels of circulating VCAM-1 correlate with disease activity (Schopf, R. E., *Br. J. Dermatol.*, 128: 34–7, 1993).

U.S. Pat. Nos. 5,750,351; 5,807,884; 5,811,449; 5,846,959; 5,773,231, and 5,773,209 to Medford, et al., as well as the corresponding WO 95/30415 to Emory University indicate that polyunsaturated fatty acids ("PUFAs") and their hydroperoxides ("ox-PUFAs"), which are important components of oxidatively modified low density lipoprotein (LDL), induce the expression of VCAM-1, but not intracellular adhesion molecule-1 (ICAM-1) or E-selectin in human aortic endothelial cells, through a mechanism that is not mediated by cytokines or other noncytokine signals. This is a fundamental discovery of an important and previously unknown biological pathway in VCAM-1 mediated immune responses. As non-limiting examples, linoleic acid, linolenic acid, arachidonic acid, linoleyl hydroperoxide (13-HPODE) and arachidonic hydroperoxide (15-HPETE) induce cell-surface gene expression of VCAM-1 but not ICAM-1 or E-selectin. Saturated fatty acids (such as stearic acid) and monounsaturated fatty acids (such as oleic acid) do not induce the expression of VCAM-1, ICAM-1 or E-selectin.

WO 98/51662, filed by AtheroGenics, Inc. and listing as inventors Russell M. Medford, Patricia K. Somers, Lee K. Hoong, and Charles Q. Meng, claims priority to provisional application U.S. Ser. No. 60/047,020, filed on May 14, 1997. This application discloses the use of a broad group of compounds as cardiovascular protectants that exhibit at least one, and sometimes a composite profile, of reducing cholesterol, lowering LDL, and inhibiting the expression of VCAM-1.

U.S. Pat. No. 5,155,250 to Parker, et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker, et al. discloses that alkylated-4-silyl-phenols inhibit the peroxidation of LDL, lower plasma cholesterol, and inhibit the expression of VCAM-1, and thus are useful in the treatment of atherosclerosis.

WO 98/51289, which claims priority to provisional application U.S. Ser. No. 60/047,020, filed on May 14, 1997 by Emory University listing Patty Somers as sole inventor, discloses the use of a group of compounds as cardiovascular protectants and antiinflammatory agents which exhibit at least one, and sometimes a composite profile, of reducing cholesterol, lowering LDL, and inhibiting the expression of VCAM-1 and thus can be used as antiinflammatory and cardivascular treating agents.

U.S. Pat. Nos. 5,380,747; 5,792,787; 5,783,596; 5,750,351; 5,821,260; 5,807,884; 5,811,449; 5,846,959; 5,877,203; and 5,773,209 to Medford, et al., teach the use of dithiocarbamates of the general formula A-SC(S)-B for the treatment of cardiovascular and other inflammatory diseases. Examples include sodium pyrrolidine-N-carbodithioate, trisodium N,N-di(carboxymethyl)-N-carbodithioate, and sodium N,N-diethyl-N-carbodithioate. The patents teach that the compounds inhibit the expression of VCAM-1.

WO 98/23581 discloses the use of benzamidoaldehydes and their use as cysteine protease inhibitors.

WO 97/12613 of Cornicelli et al. discloses compounds for the inhibition of 15-lipogenase to treat and prevent inflammation or atherosclerosis. Compounds disclosed include benzopyranoindole, benzimidazole, catacholes, benzoxadiazines, benzo[a]phenothiazine, or related compounds thereof.

Japanese Patent No. 06092950 to Masahiko et al. discloses preparation of epoxy compounds wherein electron deficient olefins such as acylstyrene derivatives, styrene derivatives, and cyclohexenone derivatives are efficiently oxidized by a hydrogen peroxide derivative in the presence of a primary or secondary amine in an organic solvent to give said epoxides which are useful intermediates for pharmaceutical and flavoring materials.

U.S. Pat. No. 5,217,999 to Levitzki et al. discloses substituted styrene compound as a method of inhibiting cell proliferation.

Chalcone (1,3-bis-aromatic-prop-2-en-1-ones) compounds are natural products related to flavonoids. WO 99/00114 (PCT/DK98/00283) discloses the use of certain chalcones, 1,3-bis-aromatic-propan-1-ones (dihydrochalcones), and 1,3-bisaromatic-prop-2-yn-1-ones for the preparation of pharmaceutical compositions for the treatment of prophylaxis of a number of serious diseases including i) conditions relating to harmful effects of inflammatory cytokines, ii) conditions involving infection by *Helicobacter* species, iii) conditions involving infections by viruses, iv) neoplastic disorders, and v) conditions caused by microorganisms or parasites.

WO 00/47554 filed by Cor Therapeutics describes a broad class of substituted unsaturated compounds for use as antithrombotic agents.

WO 96/20936 (PCT/KR95/00183) discloses thiazolidin-4-one derivatives of the formula:

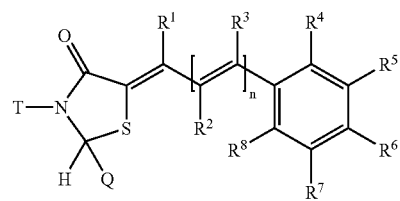

which act as PAF antagonists or 5-lipoxygenase inhibitors. The compounds are used in the prevention and treatment of inflammatory and allergic disorders mediated by platelet-activating factor and/or leukotrienes.

U.S. Pat. No. 4,085,135 discloses 2'-(carboxymethoxy)-chalcones with antigastric and antiduodenal ulcer activities.

U.S. Pat. No. 5,744,614 to Merkle et al. discloses a process for preparing 3,5-diarylpyrazoles and various derivatives thereof by reacting hydrazine hydrate with 1,3-diarylpropenone in the presence of sulfuric acid and an iodine compound.

U.S. Pat. No. 5,951,541 to Wehlage et al. discloses the use of salts of aromatic hydroxy compounds, such as (hydroxyaryl)alkenone salts, as brighteners in aqueous acidic electroplating baths. In addition the invention discloses that such compounds have a lower vapor pressure than the known brighteners, as a single substance and in the electroplating baths, in order to avoid losses of substance. They also have high water solubility properties.

Japanese Patent No. 07330814 to Shigeki et al. discloses benzylacetophenone compounds as photoinitiator compounds.

Japanese Patent No. 04217621 to Tomomi discloses siloxane chalcone derivatives in sunscreens.

U.S. Pat. No. 4,085,135 to Kyogoku et al. discloses a process for preparation of 2'-(carboxymethoxy)-chalcones having antigastric and anti duodenal activities with low toxicity and high absorptive ratio in the body. This patent suggests that the high absorptive ratio in the body is due to the 2'-carboxymethoxy group attached to the chalcone derivative.

U.S. Pat. No. 4,855,438 discloses the process for preparation of optically active 2-hydroxyethylazole derivatives which have fungicidal and plant growth-regulating action by reacting an α-β-unsaturated ketone which could include a chalcone or a chalcone derivative with an enantiomerically pure oxathiolane in the presence of a strongly basic organometallic compound and at temperatures ranging from −80 to 120° C.

European Patent No 307762 assigned to Hofmann-La Roche discloses substituted phenyl chalcones.

E. Bakhite et al. in J. Chem. Tech. Biotech. 1992, 55, 157–161, have disclosed a process for the preparation of some phenyloxazole derivatives of chalcone by condensing 5-(p-acetylphenyl)-2-phenyloxazole with aromatic aldehydes.

Herencia, et al., in Synthesis and Anti-inflammatory Activity of Chalcone Derivatives, *Bioorganic & Medicinal Chemistry Letters* 8 (1998) 1169–1174, discloses certain chalcone derivatives with anti-inflammatory activity.

Hsieh, et al., Synthesis and Antiinflammatory Effect of Chalcones, *J. Pharm. Pharmacol.* 2000, 52; 163–171 describes that certain chalcones have potent antiinflammatory activity.

Zwaagstra, et al., Synthesis and Structure-Activity Relationships of Carboxylated Chalcones: A Novel Series of CysLT$_1$ (LT$_4$) Receptor Antagonists; J. Med. Chem., 1997, 40, 1075–1089 discloses that in a series of 2-, 3-, and 4-(2-quinolinylmethoxy)- and 3- and 4-[2-(2-quinolinyl)ethenyl]-substituted, 2', 3', 4', or 5' carboxylated chalcones, certain compounds are CysLT$_1$ receptor antagonists.

JP 63010720 to Nippon Kayaku Co., LTD discloses that chalcone derivatives of the following formula (wherein R$^1$ and R$^2$ are hydrogen or alkyl, and m and n are 0–3) are 5-lipoxygenase inhibitors and can be used in treating allergies.

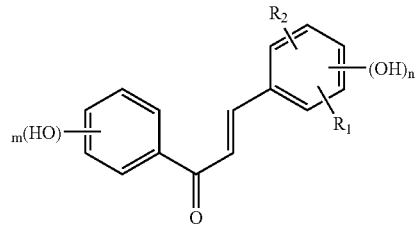

JP 06116206 to Morinaga Milk Industry Co. Ltd, Japan, discloses chalcones of the following structure as 5-lipoxygenase inhibitors, wherein R is acyl and R$^1$–R$^5$ are hydrogen, lower alkyl, lower alkoxy or halo, and specifically that in which R is acyl and R$^1$–R$^5$ are hydrogen.

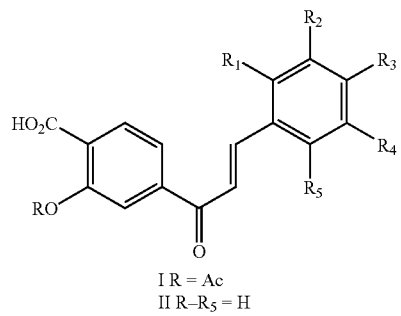

I R = Ac
II R–R$_5$ = H

U.S. Pat. No. 6,046,212 to Kowa Co. Ltd. discloses heterocyclic ring-containing chalcones of the following formula as antiallergic agents, wherein A represents a substituted or unsubstituted phenyl group, a substituted or unsubstituted naphthyl group, or a group:

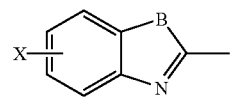

in which X represents a hydrogen or halogen atom or a hydroxyl, lower alkyl or lower alkoxyl group and B represents —CH=CH—, —N(R$_6$)—, R$_6$ is a lower alkyl group or a lower alkoxyalkyl group, —O— or —S—; W represents —CH=CH— or —CH$_2$O—, and R$_{1-5}$ is the same or different and each independently represent a hydrogen or halogen atom, a hydroxyl, a lower alkyl, lower alkoxyl, carboxyl, cyano, alkyloxycarbonyl or tetrazolyl group, a group —CONHR$_7$ in which R$_7$ represents a hydrogen atom or a lower alkyl group, or a group —O(CH$_2$)$_n$ R$_8$ in which R$_8$ represents a carboxyl, alkyloxycarbonyl or tetrazolyl group and n is from 1 to 4, with the proviso that at least one of the groups R$_{1-5}$ represents a carboxyl, cyano, alkyloxycarbonyl or tetrazolyl group, the group —CONHR$_7$ or the group —O(CH$_2$)nR$_8$; or a salt or solvate thereof.

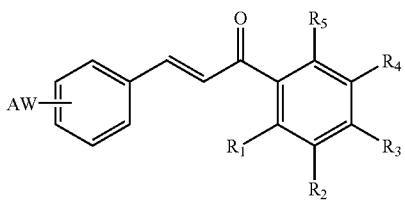

Reported bioactivies of chalcones have been reviewed by Dimmock, et al., in Bioactivities of Chalcones, *Current Medicinal Chemistry* 1999, 6, 1125–1149; Liu et al., Antimalarial Alkoxylated and Hydroxylated Chalones: Structure-Activity Relationship Analysis, *J. Med. Chem.* 2001, 44, 4443–4452; Herencia et al, Novel Anit-inflammatory Chalcone Derivatives Inhibit the Induction of Nitric Oxide Synthase and Cyclooxygenase-2 in Mouse Peritoneal Macrophages, *FEBS Letters,* 1999, 453, 129–134; and Hsieh et al., Synthesis and Anti-inflammatory Effect of Chalcones and Related Compounds, *Pharmaceutical Research,* 1998, Vol.15, No. 1, 39–46.

Given that VCAM-1 is a mediator of chronic inflammatory disorders, it is a goal of the present work to identify new compounds, compositions and methods that can inhibit the expression of VCAM-1. A more general goal is to identify selective compounds and methods for suppressing the expression of redox sensitive genes or activating redox sensitive genes that are suppressed. An even more general goal is to identify selective compounds, pharmaceutical compositions and methods of using the compounds for the treatment of inflammatory diseases.

It is therefore an object of the present invention to provide new compounds for the treatment of disorders mediated by VCAM-1.

It is also an object to provide new pharmaceutical compositions for the treatment of diseases and disorders mediated by the expression of VCAM-1.

It is a further object of the invention to provide compounds, compositions, and methods of treating disorders and diseases mediated by VCAM-1, including cardiovascular and inflammatory diseases.

Another object of the invention is to provide compounds, compositions, and method of treating cardiovascular and inflammatory diseases.

It is another object of the invention to provide compounds, compositions and methods to treat arthritis.

Another object of the invention is to provide compounds, compositions and methods to treat rheumatoid arthritis. The inventions compounds, compositions and methods are also suitable as disease modifying anti-rheumatoid arthritis drugs (DMARDs).

It is yet another object of the invention to provide compounds, compositions and methods to treat asthma.

It is another object of the invention to provide compounds, methods and compositions to inhibit the progression of atherosclerosis.

It is still another object of the invention to provide compounds, compositions, and methods to treat or prevent transplant rejection.

It is a further object of the present invention to provide compounds, methods and compositions for the treatment of lupus.

It is a further object of the present invention to provide compounds, methods and compositions for the treatment of inflammatory bowel disease.

It is a further object of the present invention to provide compounds, methods and compositions for the treatment of autoimmune diabetes.

It is a further object of the present invention to provide compounds, methods and compositions for the treatment of multiple sclerosis.

It is a further object of the present invention to provide compounds, methods and compositions for the treatment of diabetic retinopathy.

It is a further object of the present invention to provide compounds, methods and compositions for the treatment of diabetic nephropathy.

It is a further object of the present invention to provide compounds, methods and compositions for the treatment of diabetic vasculopathy.

It is a further object of the present invention to provide compounds, methods and compositions for the treatment of rhinitis.

It is a further object of the present invention to provide compounds, methods and compositions for the treatment of ischemia-reperfusion injury.

It is a further object of the present invention to provide compounds, methods and compositions for the treatment of post-angioplasty restenosis.

It is a further object of the present invention to provide compounds, methods and compositions for the treatment of chronic obstructive pulmonary disease (COPD).

It is a further object of the present invention to provide compounds, methods and compositions for the treatment of glomerulonephritis.

It is a further object of the present invention to provide compounds, methods and compositions for the treatment of Graves disease.

It is a further object of the present invention to provide compounds, methods and compositions for the treatment of gastrointestinal allergies.

It is a further object of the present invention to provide compounds, methods and compositions for the treatment of conjunctivitis.

It is a further object of the present invention to provide compounds, methods and compositions for the treatment of dermatitis.

It is a further object of the present invention to provide compounds, methods and compositions for the treatment of psoriasis.

SUMMARY OF THE INVENTION

It has been discovered that particular chalcone derivatives inhibit the expression of VCAM-1, and thus can be used to treat a patient with a disorder mediated by VCAM-1. Examples of inflammatory disorders that are mediated by VCAM-1 include, but are not limited to arthritis, asthma, dermatitis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can also be used in the treatment of inflammatory skin diseases that are mediated by VCAM-1, as well as human endothelial disorders that are mediated by VCAM-1, which include, but are not limited to psoriasis, dermatitis, including eczematous dermatitis, Kaposi's sarcoma, multiple sclerosis, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but is not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

Compounds of the present invention are of the formula

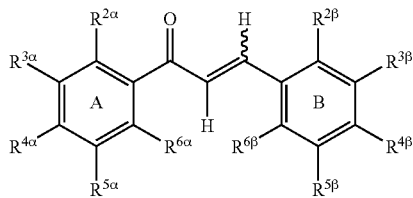

or its pharmaceutically acceptable salt or ester, wherein the substituents are defined herein.

DETAILED DESCRIPTION OF THE INVENTION

It has been discovered that compounds of the invention inhibit the expression of VCAM-1, and thus can be used to treat a patient with a disorder mediated by VCAM-1. These compounds can be administered to a host as monotherapy, or if desired, in combination with another compound of the invention or another biologically active agent, as described in more detail below.

In a 1st embodiment, the invention is represented by Formula I

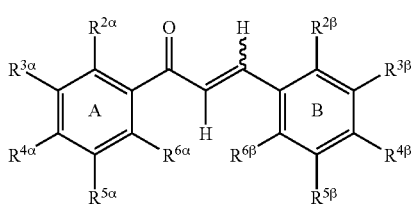

or its pharmaceutically acceptable salt or ester, wherein:
$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group, consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently selected from the group consisting of alkyl, alkenyl and aryl and linked together forming a 4- to 12-membered monocyclic, bicylic, tricyclic or benzofused ring;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked heterocyclic or heteroaryl; and/or wherein when one of $R^{2\beta}$, $R^{3\beta}$, $R^{4\beta}$, $R^{5\beta}$ or $R^{6\beta}$ is a carbon-carbon linked heterocyclic or heteroaryl, only one of $R^{2\alpha}$, $R^{3\alpha}$, $R^{4\alpha}$, $R^{5\alpha}$ or $R^{6\alpha}$ can be —OCH$_3$; and/or wherein when one of $R^{2\alpha}$, $R^{3\alpha}$, $R^{4\alpha}$, $R^{5\alpha}$ or $R^{6\alpha}$ is a carbon-carbon linked heterocyclic or heteroaryl, only one of $R^{2\beta}$, $R^{3\beta}$, $R^{4\beta}$, $R^{5\beta}$ or $R^{6\beta}$ can be —OCH$_3$; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R$^1$)$_2$C(O)OH; and/or at least one of $R^{2\alpha}$, $R^{3\alpha}$, $R^{4\alpha}$, $R^{5\alpha}$, $R^{6\alpha}$ or one of $R^{2\beta}$, $R^{3\beta}$, $R^{4\beta}$, $R^{5\beta}$, $R^{6\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, —SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 2$^{nd}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{2\beta}$, R$^{3\beta}$, R$^{4\beta}$, R$^{5\beta}$ or R$^{6\beta}$, or one of R$^{2\alpha}$, R$^{3\alpha}$, R$^{4\alpha}$, R$^{5\alpha}$ or R$^{6\alpha}$ must be carbon-carbon linked heterocyclic or heteroaryl; and/or wherein when one of R$^{2\beta}$, R$^{3\beta}$, R$^{4\beta}$, R$^{5\beta}$ or R$^{6\beta}$ is a carbon-carbon linked heterocyclic or heteroaryl, only one of R$^{2\alpha}$, R$^{3\alpha}$, R$^{4\alpha}$, R$^{5\alpha}$ or R$^{6\alpha}$ can be —OCH$_3$; and/or wherein when one of R$^{2\alpha}$, R$^{3\alpha}$, R$^{4\alpha}$, R$^{5\alpha}$ or R$^{6\alpha}$ is a carbon-carbon linked heterocyclic or heteroaryl, only one of R$^{2\beta}$, R$^{3\beta}$, R$^{4\beta}$, R$^{5\beta}$ or R$^{6\beta}$ can be —OCH$_3$; and/or R$^{2\alpha}$ and R$^{3\alpha}$ taken together or R$^{3\alpha}$ and R$^{4\alpha}$ taken together or R$^{4\alpha}$ and R$^{5\alpha}$ taken together, or R$^{2\beta}$ and R$^{3\beta}$ taken together or R$^{3\beta}$ and R$^{4\beta}$ taken together or R$^{4\beta}$ and R$^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or R$^{2\alpha}$ and R$^{3\alpha}$ taken together or R$^{3\alpha}$ and R$^{4\alpha}$ taken together or R$^{4\alpha}$ and R$^{5\alpha}$ taken together or R$^{2\beta}$ and R$^{3\beta}$ taken together or R$^{3\beta}$ and R$^{4\beta}$ taken together or R$^{4\beta}$ and R$^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ cannot be —OC(R$^1$)$_2$C(O)OH; and/or at least one of R$^{2\alpha}$, R$^{3\alpha}$, R$^{4\alpha}$, or one of R$^{2\beta}$, R$^{3\beta}$, R$^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 3$^{rd}$ embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N($^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R⁷ and R⁸ are independently selected from the group consisting of alkyl, alkenyl and aryl and linked together forming a 4- to 12-membered monocyclic, bicyclic, tricyclic or benzofused ring;

wherein one of $R^{2\beta}$, $R^{3\beta}$, $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH₃; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR⁷R⁸, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R¹)₂C(O)OH; and/or at least one of $R^{2\alpha}$, $R^{3\alpha}$, $R^{4\alpha}$, $R^{5\alpha}$, or $R^{6\alpha}$ must be selected from the group consisting of cyano, tetrazol-5-yl, carboxy, —C(O)OR², —C(O)NH₂, —C(O)NHR², —C(O)N(R²)₂, —C(O)NR⁷R⁸, —C(O)NHC(O)NHR², —C(O)NHC(O)N(R²)₂, —C(O)NHC(O)NR⁷R⁸, —C(O)NHSO₂NHR², —C(O)NHSO₂N(R²), —C(O)NHSO₂NR⁷R⁸, —C(O)NHC(O)R², —C(O)NHSO₂R², —C(CH₃)₂C(O)OH, —(CH₂)ᵧC(O)OH, wherein y is 1, 2, 3, 4, 5, or 6, thiol, —SC(R¹)₂C(O)OH, —SC(R¹)₂C(O)OR², —SCH₂C(O)OH, —SCF₂C(O)OH, —SO₂NH₂, —SO₂NHR², —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, —OC(R¹)₂C(O)OH, —OC(R¹)₂C(O)OR², —OC(R¹)₂C(O)NH₂, —OC(R¹)₂C(O)NHR², —OC(R¹)₂C(O)N(R²)₂, —OC(R¹)₂C(O)NR⁷R⁸, amino, —NHR², N(R²)₂, NR⁷R⁸, —NHC(R¹)₂C(O)OH, —NHC(R¹)₂C(O)OR², —NHC(O)R², —N(R²)C(O)R², —NHC(O)OR², —NHC(O)SR², —NHSO₂NHR², —NHSO₂R², —NHSO₂NR⁷R⁸, —N(C(O)NHR²)₂, —NR²SO₂R², —NHC(O)NHR², —NHC(O)NR⁷R⁸, and —NHC(O)N(R²)₂;

wherein all R¹, R², R⁷ and R⁸ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂.

In a 4th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)₂-lower alkyl, arylsulfinyl lower alkyl, arylsulfonyl lower alkyl, —C(O)R², R²C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH₂)₂)₁₋₃—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R¹)₂C(O)OH, —OC(R¹)₂C(O)OR², —OC(R¹)₂C(O)NH₂, —OC(R¹)₂C(O)NHR², —OC(R¹)₂C(O)N(R²)₂, —OC(R¹)₂C(O)NR⁷R⁸, amino, alkylamino, acylamino, dialkylamino, cycloalkylamino, arylamino, aralkylamino, heteroarylamino, heteroaralkylamino, heterocyclicamino, heterocyclicalkylamino, —NHR², N(R²)₂, —NR⁷R⁸, —NHC(R¹)₂C(O)OH, —NHC(R¹)₂C(O)OR², —NHC(O)R², —N(R²)C(O)R², —NHC(O)OR², —NHC(O)SR², —NHSO₂NHR², —NHSO₂R², —NHSO₂NR⁷R⁸, —N(C(O)NHR²)₂, —NR²SO₂R², —NHC(O)NHR², —NHC(O)NR⁷R⁸, —NHC(O)N(R²)₂, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R¹)₂C(O)OH, —SC(R¹)₂C(O)OR², —SCH₂C(O)OH, —SCF₂C(O)OH, —SO₂NH₂, —SO₂NHR², —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, sulfonic acid, sulfonate, sulfate, sulfinic acid, sulfenic acid, cyano, tetrazol-5-yl, carboxy, —C(O)OR², —C(O)NH₂, —C(O)NHR², —C(O)N(R²)₂, —C(O)NR⁷R⁸, —C(O)NHC(O)R², —C(O)NHC(O)NHR², —C(O)NHC(O)N(R²)₂, —C(O)NHC(O)NR⁷R⁸, —C(O)NHSO₂R², —C(O)NHSO₂NHR², —C(O)NHSO₂N(R²), —C(O)NHSO₂NR⁷R⁸, —C(CH₃)₂C(O)OH, —(CH₂)ᵧC(O)OH, wherein y is 1, 2, 3, 4, 5, or 6, —PO₂H₂, —PO₃H₂, —P(R²)O₂H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R¹ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R² is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R⁷ and R⁸ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH₃; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N($^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R$^1$)$_2$C(O)OH; and/or at least one of $R^{2\alpha}$, $R^{3\alpha}$, or $R^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, —SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 5th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$-O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N($^2$)$_2$.

In a 6th embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O—lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of cyano, tetrazol-5-yl, carboxy, —C(O)OR$^2$, —C(CH$_3$)$_2$C(O)OH, —(CH$_2$)$_y$C(O)OH, wherein y is 1, 2, 3, 4, 5, or 6;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 7th embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O—lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C (O)R², —NHC(O)OR², —NHC(O)SR², —NHSO₂NHR², —NHSO₂R², —NHSO₂NR⁷R⁸, —N(C(O)NHR²)₂, —NR²SO₂R², —NHC(O)NHR², —NHC(O)NR⁷R⁸, —NHC(O)N(R²)₂, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R¹)₂C(O)OH, —SC(R¹)₂C(O)OR², —SCH₂C(O)OH, —SCF₂C(O)OH, —SO₂NH₂, —SO₂NHR₂, —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, cyano, tetrazol-5-yl, carboxy, —C(O)OR², —C(O)NH₂, —C(O)NHR², —C(O)N(R²)₂, —C(O)NR⁷R⁸, —C(O)NHC(O)R², —C(O)NHC(O)NHR², —C(O)NHC(O)N(R²)₂, —C(O)NHC(O)NR⁷R⁸, —C(O)NHSO₂R², —C(O)NHSO₂NHR², —C(O)NHSO₂N(R²), —C(O)NHSO₂NR⁷R⁸, —C(CH₃)₂C(O)OH, and —(CH₂)ᵧC(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R¹ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, oxo, cyano, carboxy, carboxyalkyl, alkoxycarbonyl, —C(O)NR⁷R⁸, and —C(O)N(R²)₂;

R² is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R⁷ and R⁸ are independently selected from the group consisting of alkyl, alkenyl and aryl and linked together forming a 4- to 12-membered monocyclic, bicyclic, tricyclic or benzofused ring;

wherein one of R⁴ᵝ, R⁵ᵝ or R⁶ᵝ must be a carbon-carbon linked heterocyclic or heteroaryl, and only one of R²ᵅ, R³ᵅ, R⁴ᵅ, R⁵ᵅ or R⁶ᵅ can be —OCH₃;

with the proviso that at least one of R²ᵅ, R³ᵅ, or R⁴ᵅ must be selected from the group consisting of cyano, tetrazol-5-yl, carboxy, —C(O)OR², —C(CH₃)₂C(O)OH, —(CH₂)ᵧC(O)OH, wherein y is 1, 2, 3, 4, 5, or 6;

wherein all R¹, R², R⁷ and R⁸ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂.

In an 8th embodiment, the invention is represented by Formula I or its pharmaceutically acceptable salt or ester, wherein:

R²ᵅ, R³ᵅ, R⁴ᵅ, R⁵ᵅ, R⁶ᵅ, R²ᵝ, R³ᵝ, R⁴ᵝ, R⁵ᵝ and R⁶ᵝ are independently selected from the group consisting of hydrogen, halogen, alkyl, lower alkyl, alkenyl, alkynyl, cycloalkyl, cycloalkylalkyl, haloalkyl, heteroaryl, heteroaryl lower alkyl, heterocyclic, heterocyclic lower alkyl, —C(O)R², R²C(O)alkyl, aminoalkyl, cycloalkylaminoalkyl, arylamino lower alkyl, heteroarylamino lower alkyl, heterocyclicamino lower alkyl, hydroxyl, hydroxyalkyl, polyol alkyl, alkoxy, lower alkoxy, —O(CH₂)₂)₁₋₃—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R¹)₂C(O)N(R²)₂, —OC(R¹)₂C(O)NR⁷R⁸, amino, alkylamino, dialkylamino, cycloalkylamino, arylamino, aralkylamino, heteroarylamino, heteroaralkylamino, heterocyclicamino, heterocyclicalkylamino, —NHR², N(R²)₂, —NR⁷R⁸, —N(R²)C(O)R², —NHSO₂NR⁷R⁸, —N(C(O)NHR²)₂, —NHC(O)NR⁷R⁸, —NHC(O)N(R²)₂, —SO₂NH₂, —SO₂NHR₂, —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, cyano, tetrazol-5-yl, carboxy, —C(O)OR², —C(O)NH₂, —C(O)NHR², —C(O)N(R²)₂, —C(O)NR⁷R⁸, —C(O)NHC(O)R², —C(O)NHC(O)NHR², —C(O)NHC(O)N(R²)₂, —C(O)NHC(O)NR⁷R⁸, —C(O)NHSO₂R², —C(O)NHSO₂NHR², —C(O)NHSO₂N(R²), —C(O)NHSO₂NR⁷R⁸, —C(CH₃)₂C(O)OH, and —(CH₂)ᵧC(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, —C(O)NR⁷R⁸, and —C(O)N(R²)₂;

R¹ is independently selected from the group consisting of hydrogen, lower alkyl, cycloalkyl, aryl, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, oxo, cyano, —C(O)NR⁷R⁸, and —(O)N(R²)₂;

R² is independently selected from the group consisting of alkyl, lower alkyl, cycloalkyl, aryl, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, —C(O)NR⁷R⁸, and —C(O)N(R²)₂;

R⁷ and R⁸ are independently selected from the group consisting of alkyl, alkenyl and aryl and linked together forming a 4- to 12-membered monocyclic, bicyclic, tricyclic or benzofused ring;

wherein one of R⁴ᵝ, R⁵ᵝ or R⁶ᵝ must be a carbon-carbon linked heterocyclic or heteroaryl, and only one of R²ᵅ, R³ᵅ, R⁴ᵅ, R⁵ᵅ or R⁶ᵅ can be —OCH₃;

with the proviso that at least one of R²ᵅ, R³ᵅ, or R⁴ᵅ must be selected from the group consisting of cyano, tetrazol-5-yl, carboxy, —C(O)OR², —C(CH₃)₂C(O)OH, —(CH₂)ᵧC(O)OH, wherein y is 1, 2, 3, 4, 5, or 6;

wherein all R¹, R², R⁷ and R⁸ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, —C(O)NR⁷R⁸, and —C(O)N(R²)₂.

In a 9th embodiment, the invention is represented by Formula I or its pharmaceutically acceptable salt or ester, wherein:

R²ᵅ, R³ᵅ, R⁴ᵅ, R⁵ᵅ, R⁶ᵅ, R²ᵝ, R³ᵝ, R⁴ᵝ, R⁵ᵝ and R⁶ᵝ are independently selected from the group consisting of hydrogen, halogen, alkyl, lower alkyl, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —(O(CH$_2$)$_2$)$_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, N(R$^2$)$_2$, —NR$^7$R$^8$, tetrazol-5-yl, carboxy, —C(O)OR$^2$, —C(O)N(R$^2$)$_2$, —C(O)NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, cycloalkyl, hydroxy, hydroxyalkyl, heterocyclic, amino, aminoalkyl, —NR$^7$R$^8$, —C(O)NR$^7$R$^8$, and —C(O)N(R$^2$)$_2$;

R$^2$ is independently selected from the group consisting of alkyl, lower alkyl, cycloalkyl, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —NR$^7$R$^8$, alkoxy, —C(O)NR$^7$R$^8$, and —C(O)N(R$^2$)$_2$;

R$^7$ and R$^8$ are independently selected from the group consisting of alkyl, alkenyl and aryl and linked together forming a 4- to 8-membered monocyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of tetrazol-5-yl, carboxy, —C(O)OR$^2$, —C(CH$_3$)$_2$C(O)OH, —(CH$_2$)$_y$C(O)OH, wherein y is 1, 2, 3, 4, 5, or 6;

wherein all R$^2$, R$^7$ and R$^8$ substituents can be optionally substituted with one or more selected from the group consisting of halo, lower alkyl, hydroxyalkyl, heterocyclic, amino, aminoalkyl, —NR$^7$R$^8$, —C(O)NR$^7$R$^8$, and —C(O)N(R$^2$)$_2$.

In a 10th embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, lower alkyl, heteroaryl, heteroaryl lower alkyl, heterocyclic, heterocyclic lower alkyl, alkoxy, lower alkoxy, —(O(CH$_2$)$_2$)$_{1-3}$—O-lower alkyl, polyoxyalkylene, heteroaryl lower alkoxy, heterocyclicalkoxy, heterocyclic lower alkoxy, carboxy, —C(O)OR$^2$, —C(O)N(R$^2$)$_2$, and —C(O)NR$^7$R$^8$, all of which can be optionally substituted by one or more selected from the group consisting of halo, alkyl, lower alkyl, cycloalkyl, hydroxy, hydroxyalkyl, heterocyclic, —NR$^7$R$^8$, —C(O)NR$^7$R$^8$, and —C(O)N(R$^2$)$_2$;

R$^2$ is independently selected from the group consisting of alkyl, and lower alkyl, wherein all may be substituted by one or more selected from the group consisting of halo, lower alkyl, —NR$^7$R$^8$, alkoxy, —C(O)NR$^7$R$^8$, and —C(O)N(R$^2$)$_2$;

R$^7$ and R$^8$ are independently alkyl, and linked together forming a 5- to 7-membered monocyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from carboxy or —C(O)OR$^2$;

wherein all R$^2$, R$^7$ and R$^8$ substituents can be optionally substituted with one or more selected from the group consisting of halo, lower alkyl, —NR$^7$R$^8$, —C(O)NR$^7$R$^8$, and —C(O)N(R$^2$)$_2$.

In an 11th embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, heterocyclic lower alkoxy, and carboxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be carboxy.

In a 12th embodiment, the invention is represented by Formula I or its pharmaceutically acceptable salt or ester, wherein:

R$^{2\alpha}$, R$^{3\alpha}$, R$^{4\alpha}$, R$^{5\alpha}$, and R$^{6\alpha}$ are independently selected from the group consisting of hydrogen and carboxy;

R$^{2\beta}$, R$^{3\beta}$, R$^{4\beta}$, R$^{5\beta}$ and R$^{6\beta}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\beta}$, R$^{5\beta}$ or R$^{6\beta}$ must be a carbon-carbon linked heterocyclic or heteroaryl;

with the proviso that at least one of R$^{2\alpha}$, R$^{3\alpha}$, or R$^{4\alpha}$ must be carboxy.

In a 13th embodiment, the invention is represented by Formula I or its pharmaceutically acceptable salt or ester, wherein:

R$^{2\alpha}$, R$^{3\alpha}$, R$^{4\alpha}$, R$^{5\alpha}$, and R$^{6\alpha}$ are independently selected from the group consisting of hydrogen and carboxy;

R$^{2\beta}$, R$^{3\beta}$, R$^{4\beta}$, R$^{5\beta}$ and R$^{6\beta}$ are independently selected from the group consisting of hydrogen, halogen, heteroaryl, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\beta}$, R$^{5\beta}$ or R$^{6\beta}$ must be a carbon-carbon linked heteroaryl;

with the proviso that at least one of R$^{2\alpha}$, R$^{3\alpha}$, or R$^{4\alpha}$ must be carboxy.

In a 14th embodiment, the invention is represented by Formula I or its pharmaceutically acceptable salt or ester, wherein:

R$^{2\alpha}$, R$^{3\alpha}$, R$^{4\alpha}$, R$^{5\alpha}$, and R$^{6\alpha}$ are independently selected from the group consisting of hydrogen and carboxy;

R$^{2\beta}$, R$^{3\beta}$, R$^{4\beta}$, R$^{5\beta}$ and R$^{6\beta}$ are independently selected from the group consisting of hydrogen, fluorine, chlorine, methoxy, ethoxy, propoxy, 3-(1-morpholino) propoxy, 2-(1-morpholino) ethoxy, CH$_3$O(CH$_2$)$_2$O(CH$_2$)$_2$—,

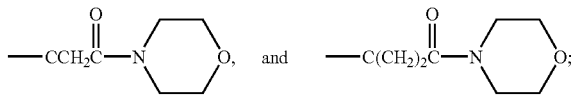

wherein one of $R^{4\beta}$, $R^{5\beta}$ or $R^{6\beta}$ must be selected from the group consisting of thiophen-s-yl, thiophen-3-yl, benzo[b]thiophen-2-yl, benzo[b]thiophen-3-yl, indol-2-yl, indol-3-yl, pyrrol-2-yl, pyrrol-3-yl, 1-methyl-indol-2-yl, 1-methyl-indol-3-yl, N-Boc-indol-2-yl, N-Boc-indol-3-yl, N-Boc-pyrrol-2'yl, and N-Boc-pyrrol-3-yl;

with the proviso that at least one of $R^{2\alpha}$, $R^{3\alpha}$, or $R^{4\alpha}$ must be carboxy.

In a 15th embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen and carboxy;

$R^{2\beta}$, $R^{3\beta}$, $R^{4\beta}$, $R^{5\beta}$ and $R^{6\beta}$ are independently selected from the group consisting of hydrogen, methoxy, 3-(1-morpholino) propoxy, 2-(1-morpholino) ethoxy, and $CH_3O(CH_2)_2O(CH_2)_2$;

wherein one of $R^{4\beta}$, $R^{5\beta}$ or $R^{6\beta}$ must be selected from the group consisting of thiophen-s-yl, benzo[b]thiophen-2-yl, indol-2-yl, 1-methyl-indol-2-yl, N-Boc-indol-2-yl, N-Boc-pyrrol-2'yl, and N-Boc-pyrrol-3-yl;

with the proviso that at least one of $R^{2\alpha}$, $R^{3\alpha}$, or $R^{4\alpha}$ must be carboxy.

In a 16th embodiment, the invention is selected from a compound A compound selected from the group consisting of 4-[3E-(5-Benzo[b]thien-2-yl-2,4-dimethoxyphenyl)-acryloyl]-benzoic acid;
4-[3E-(4-Pyrimidin-5-yl-phenyl)-acryloyl]-benzoic acid;
4-[3E-(4-Thiazol-2-yl-phenyl)-acryloyl]-benzoic acid;
4-[3E-(2,4-Dimethoxy-5-thiophen-2-yl-phenyl)-acryloyl]-benzoic acid;
2-[3E-(5-Benzo[b]thiophen-2-yl-2,4-dimethoxy-phenyl)-acryloyl]-benzoic acid;
4-[3E-(3,4-Dimethoxy-5-thiophen-2-yl-phenyl)-acryloyl]-benzoic acid;
2-[3E-(5-Benzo[b]thiophen-2-yl-2,4-dimethoxy-phenyl)-acryloyl]-benzoic acid, sodium salt;
4-[3E-(4-Thiophen-2-yl-phenyl)-acryloyl]-benzoic acid;
4-[3-{4-(thien-2-yl)-phenyl}-3-oxo-E-propenyl]-benzoic acid, sodium salt;
4-[3-{4-(thien-2-yl)-phenyl}-3-oxo-E-propenyl]-benzoic acid;
4-[3-(2-Methoxy-4-thiophen-2-yl-phenyl)-3-oxo-E-propenyl]-benzoic acid;
4-[3E-(4-Pyrrolidin-1-yl-3-thiophen-2-yl-phenyl)-acryloyl]-benzoic acid;
4-[3E-{4-Fluoro-3-(thiophen-2-yl)-phenyl}-acryloyl]-benzoic acid;
4-(3E-{4-Methoxy-2-[2-(2-methoxyethoxy)ethoxy]-5-thiophen-2-yl-phenyl}-acryloyl)-benzoic Acid;
4-[3E-(2-Fluoro-4-thiophen-2-yl-phenyl)-acryloyl]-benzoic acid;
4-[3E-(2,4-Dimethoxy-5-pyrimidin-5-yl-phenyl)-acryloyl]-benzoic acid;
4-[3E-(2-Cyclopropylmethoxy-4-methoxy-5-thiophen-2-yl-phenyl)-acryloyl]-benzoic acid;
4-{3E-[5-(3,5-Dimethyl-isoxazol-4-yl)-2,4-dimethoxy-phenyl]-acryloyl}-benzoic acid;
4-[3E-(4-Methoxy-2-thiophen-2-yl-phenyl)-acryloyl]-benzoic acid;
2-[3E-(2,4-Dimethoxy-5-thiophen-2-yl-phenyl)-acryloyl]-benzoic acid;
2-{5-[3-(4-Carboxy-phenyl)-3-oxo-E-propenyl]-2,4-dimethoxy-phenyl}-indole-1-carboxylic acid tert-butyl ester;
4-[3E-(2,6-Dimethoxy-4-thiophen-2-yl-phenyl)-acryloyl]-benzoic acid;
4-{3E-[5-(2,4-Dimethoxy-pyrimidin-5-yl)-2,4-dimethoxy-phenyl]-acryloyl}-benzoic acid;
4-[3E-(2,4-Dimethoxy-6-thiophen-2-yl-phenyl)-acryloyl]-benzoic acid;
4-{3E-[2,4-Dimethoxy-5-(5-methyl-thiophen-2-yl)-phenyl]-acryloyl}-benzoic acid;
4-[3E-(4-Methoxy-3-thiophen-2-yl-phenyl)-acryloyl]-benzoic acid;
4-[3E-(3-Thiophen-2-yl-phenyl)-acryloyl]-benzoic acid;
3-[3E-(2,4-Dimethoxy-5-thiophen-2-yl-phenyl)-acryloyl]-benzoic acid;
4-[3E-(3-Benzo[b]thiophen-2-yl-2,4-dimethoxy-phenyl)-acryloyl]-benzoic acid;
4-[3E-(2-Methoxy-5-thiophen-2-yl-phenyl)-acryloyl]-benzoic acid;
4-[3E-(2,4-Dimethoxy-5-pyrazin-2-yl-phenyl)-acryloyl]-benzoic acid;
4-{3E-[4-(1-Carboxy-1-methyl-ethoxy)-2-methoxy-5-thiophen-2-yl-phenyl]-acryloyl}-benzoic acid;
2-[3E-(4-Methoxy-3-thiophen-2-yl-phenyl)-acryloyl]-benzoic acid;
4-(3E-{2-Methoxy-4-[2-(2-methoxy-ethoxy)-ethoxy]-5-thiophen-2-yl-phenyl}-acryloyl)-benzoic acid;
4-{3E-[4-(3-Hydroxy-2-hydroxymethyl-propoxy)-2-methoxy-5-thiophen-2-yl-phenyl]-acryloyl}-benzoic acid;
5-{5-[3-(4-Carboxy-phenyl)-3-oxo-E-propenyl]-2,4-dimethoxy-phenyl}-thiophene-2-carboxylic acid methyl ester;
5-{5-[3-(4-Carboxy-phenyl)-3-oxo-E-propenyl]-2,4-dimethoxy-phenyl}-thiophene-2-carboxylic acid;
4-[3E-(4-Ethoxy-2-methoxy-5-thiophen-2-yl-phenyl)-acryloyl]-benzoic acid;
4-[3E-(4-Hydroxy-2-methoxy-5-thiophen-2-yl-phenyl)-acryloyl]-benzoic acid;
4-[3E-(2,4-Dimethoxy-5-thiazol-2-yl-phenyl)-acryloyl]-benzoic acid;
4-[3E-(5-Benzo[b]thiophen-2-yl-2,4-dimethoxy-phenyl)-acryloyl]-benzoic acid, sodium salt;
2-{5-[3-(4-Carboxy-phenyl)-3-oxo-E-propenyl]-2,4-dimethoxy-phenyl}-pyrrole-1-carboxylic acid tert-butyl ester;
4-[3E-(2-Hydroxy-4-methoxy-5-thiophen-2-yl-phenyl)-acryloyl]-benzoic acid;
4-{3E-[2-(1-Carboxy-1-methyl-ethoxy)-4-methoxy-5-thiophen-2-yl-phenyl]-acryloyl}-benzoic acid;
4-{3E-[4-Methoxy-2-(2-morpholin-4-yl-ethoxy)-5-thiophen-2-yl-phenyl]-acryloyl}-benzoic acid, hydrochloride;
4-{3E-[5-(1H-Indol-2-yl)-2,4-dimethoxy-phenyl]-acryloyl}-benzoic acid;
4-{3E-[2-(3,5-Dimethyl-isoxazol-4-ylmethoxy)-4-methoxy-5-thiophen-2-yl-phenyl]-acryloyl}-benzoic acid;
4-[3E-(2-Pyrrolidin-1-yl-5-thiophen-2-yl-phenyl)-acryloyl]-benzoic acid;
4-{3E-[2-(3-Hydroxy-2-hydroxymethyl-propoxy)-4-methoxy-5-thiophen-2-yl-phenyl]-acryloyl}-benzoic acid;
4-{3E-[2-(3-Morpholin-4-yl-propoxy)-5-thiophen-2-yl-phenyl]-acryloyl}-benzoic acid, hydrochloride;

4-{3E-[4-Methoxy-2-(3-morpholin-4-yl-propoxy)-5-thiophen-2-yl-phenyl]-acryloyl}-benzoic acid, hydrochloride;

4-[3E-(2-Dimethylcarbamoylmethoxy-4-methoxy-5-thiophen-2-yl-phenyl)-acryloyl]-benzoic acid;

4-[3E-(4-Methoxy-2-{2-[2-(2-methoxy-ethoxy)-ethoxy]-ethoxy}-5-thiophen-2-yl-phenyl)-acryloyl]-benzoic acid;

4-{3E-[2,4-Dimethoxy-5-(2-methyl-thiazol-4-yl)-phenyl]-acryloyl}-benzoic acid;

4-{3E-[5-(1H-Benzoimidazol-2-yl)-2,4-dimethoxy-phenyl]-acryloyl}-benzoic acid;

4-[3E-(2-Carbamoylmethoxy-4-methoxy-5-thiophen-2-yl-phenyl)-acryloyl]-benzoic acid;

4-{3E-[4-Methoxy-2-(2-morpholin-4-yl-2-oxo-ethoxy)-5-thiophen-2-yl-phenyl]-acryloyl}-benzoic acid;

4-(3E-{4-Methoxy-2-[2-(1-methyl-pyrrolidin-2-yl)-ethoxy]-5-thiophen-2-yl-phenyl}-acryloyl)-benzoic acid, hydrochloride;

4-{3E-[2,4-Dimethoxy-5-(1H-pyrazol-4-yl)-phenyl]-acryloyl}-benzoic acid;

4-{3E-[2,4-Dimethoxy-5-(2H-tetrazol-5-yl)-phenyl]-acryloyl}-benzoic acid;

4-{3E-[5-(3H-Imidazo[4,5-b]pyridin-2-yl)-2,4-dimethoxy-phenyl]-acryloyl}-benzoic acid;

2-{4-[3E-(2,4-Dimethoxy-5-thiophen-2-yl-phenyl)-acryloyl]-phenyl}-2-methyl-propionic acid;

4-{3E-[5-(2-Cyclopropyl-1H-imidazol-4-yl)-2,4-dimethoxy-phenyl]-acryloyl}-benzoic acid, hydrochloride;

4-{3E-[5-(4-Isobutyl-4H-[1,2,4]triazol-3-yl)-2,4-dimethoxy-phenyl]-acryloyl}-benzoic acid;

4-{3E-[2,4-Dimethoxy-5-(1-methyl-1H-indol-2-yl)-phenyl]-acryloyl}-benzoic acid; and 4-[3E-(5-Benzo[b]thiophen-2-yl-2,4-dimethoxy-phenyl)-acryloyl]-benzoic acid ethyl ester, or its pharmaceutically acceptable salt or ester.

In a 17$^{th}$ embodiment, the invention is a compound selected from the group consisting of 4-[3E-(5-Benzo[b]thien-2-yl-2,4-dimethoxyphenyl)-acryloyl]-benzoic acid;

4-[3E-(2,4-Dimethoxy-5-thiophen-2-yl-phenyl)-acryloyl]-benzoic acid;

4-(3E-{4-Methoxy-2-[2-(2-methoxyethoxy)ethoxy]-5-thiophen-2-yl-phenyl}-acryloyl)-benzoic Acid; and 4-{3E-[4-Methoxy-2-(2-morpholin-4-y-ethoxy)-5-thiophen-2-yl-phenyl]-acryloyl}-benzoic acid, hydrochloride, or its pharmaceutically acceptable salt or ester.

In an 18th embodiment, the invention is

4-[3E-(5-Benzo[b]thien-2-yl-2,4-dimethoxyphenyl)-acryloyl]-benzoic acid or its pharmaceutically acceptable salt or ester.

In a 19$^{th}$ embodiment, the invention is 4-[3E-(2,4-Dimethoxy-5-thiophen-2-yl-phenyl)-acryloyl]-benzoic acid, or its pharmaceutically acceptable salt or ester.

In a 20$^{th}$ embodiment, the invention is 4-(3E-{4-Methoxy-2-[2-(2-methoxyethoxy)ethoxy]-5-thiophen-2-yl-phenyl}-acryloyl)-benzoic Acid; and, or its pharmaceutically acceptable salt or ester.

In a 21st embodiment, the invention is 4-{3E-[4-Methoxy-2-(2-morpholin-4-yl-ethoxy)-5-thiophen-2-yl-phenyl]-acryloyl}-benzoic acid, hydrochloride, or its pharmaceutically acceptable salt or ester.

In a 22$^{nd}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen and carboxy;

$R^{2\beta}$, $R^{3\beta}$, $R^{4\beta}$, $R^{5\beta}$ and $R^{6\beta}$ are independently selected from the group consisting of hydrogen, halogen, heteroaryl, heterocyclic, lower alkoxy, —$(O(CH_2)_2)_{1-3}$—O-lower alkyl, heteroaryl lower alkoxy, and heterocyclic lower alkoxy, all of which can be optionally substituted by one or more selected from the group consisting of hydroxy, hydroxyalkyl, —$NR^7R^8$, —$C(O)NR^7R^8$, and —$(O)N(R^2)_2$;

$R^2$ is lower alkyl;

$R^7$ and $R^8$ are independently alkyl, and linked together forming a 6-membered monocyclic or benzofused ring;

wherein one of $R^{4\beta}$, $R^{5\beta}$ or $R^{6\beta}$ must be a carbon-carbon linked heterocyclic;

with the proviso that at least one of $R^{2\alpha}$, $R^{3\alpha}$, or $R^{4\alpha}$ must be carboxy.

In a 23rd embodiment, the invention is represented by Formula I or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen and carboxy;

$R^{2\beta}$, $R^{3\beta}$, $R^{4\beta}$, $R^{5\beta}$ and $R^{6\beta}$ are independently selected from the group consisting of hydrogen, halogen, heteroaryl, heterocyclic, lower alkoxy, —$(O(CH_2)_2)_{1-3}$—O-lower alkyl, heteroaryl lower alkoxy, and heterocyclic lower alkoxy, all of which can be optionally substituted by one or more selected from the group consisting of hydroxy, hydroxyalkyl, —$NR^7R^8$, —$C(O)NR^7R^8$, and —$C(O)N(R^2)_2$;

$R^2$ is lower alkyl;

$R^7$ and $R^8$ are independently alkyl, and linked together forming a 6-membered monocyclic or benzofused ring;

wherein one of $R^{4\beta}$, $R^{5\beta}$ or $R^{6\beta}$ must be a carbon-carbon linked tetrahydrofuran-2-yl or dihydrofuran-2-yl;

with the proviso that at least one of $R^{2\alpha}$, $R^{3\alpha}$, or $R^{4\alpha}$ must be carboxy.

In a 24th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —$(O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)OH$, —$OC(R^1)_2C(O)OR^2$, —$OC(R^1)_2C(O)NH_2$, —$OC(R^1)_2C(O)NHR^2$, —$OC(R^1)_2C(O)N(R^1)_2$, —$OC(R^1)_2C(O)NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —$NHR^2$, $N(R^2)_2$, —$NR^7R^8$, —$NHC(R^1)_2C(O)OH$, —$NHC(R^1)_2C(O)OR^2$, —$NHC(O)R^2$, —$N(R^2)C(O)R^2$, —$NHC(O)OR^2$, —$NHC(O)SR^2$, —$NHSO_2NHR^2$, —$NHSO_2R^2$, —$NHSO_2NR^7R^8$, —$N(C(O)NHR^2)_2$, —$NR^2SO_2R^2$, —$NHC(O)NHR^2$, —$NHC(O)NR^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NHR$_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, sulfonic acid, sulfonate, sulfate, sulfinic acid, sulfenic acid, cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)$R^2$, —C(O)NHC(O)NH$R^2$, —C(O)NHC(O)N($R^2$)$_2$, —C(O)NHC(O)N$R^7R^8$, —C(O)NHSO$_2R^2$, —C(O)NHSO$_2$NH$R^2$, —C(O)NHSO$_2$N($R^2$), —C(O)NHSO$_2$N$R^7R^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P($R^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^7$ and $R^8$ are independently selected from the group consisting of alkyl, alkenyl and aryl and linked together forming a 4- to 12-membered monocyclic, bicylic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —C(O)NH$_2$, —C(O)NH$R^2$, —C(O)N($R^2$)$_2$, —C(O)N$R^7R^8$, —C(O)NHC(O)NH$R^2$, —C(O)NHC(O)N($R^2$)$_2$, —C(O)NHC(O)N$R^7R^8$, —C(O)NHSO$_2$NH$R^2$, —C(O)NHSO$_2$N($R^2$), —C(O)NHSO$_2$N$R^7R^8$, —C(O)NHC(O)$R^2$, —C(O)NHSO$_2R^2$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$.

In a 25th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroaralkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, alkylamino, acylamino, dialkylamino, cycloalkylamino, arylamino, aralkylamino, heteroarylamino, heteroaralkylamino, heterocyclicamino, heterocyclicalkylamino-NH$R^2$, N($R^2$)$_2$, —N$R^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —NHSO$_2$NH$R^2$, —NHSO$_2R^2$, —NHSO$_2$N$R^7R^8$, —N(C(O)NH$R^2$)$_2$, —N$R^2$SO$_2R^2$, —NHC(O)NH$R^2$, —NHC(O)N$R^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NHR$_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)$R^2$, —C(O)NHC(O)NH$R^2$, —C(O)NHC(O)N($R^2$)$_2$, —C(O)NHC(O)N$R^7R^8$, —C(O)NHSO$_2R^2$, —C(O)NHSO$_2$NH$R^2$, —C(O)NHSO$_2$N($R^2$), —C(O)NHSO$_2$N$R^7R^8$, and —C(CH$_3$)$_2$C(O)OH, —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —$OCH_3$;

with the proviso that at least one of $R^{2\alpha}$, $R^{3\alpha}$, or $R^{4\alpha}$ must be selected from the group consisting of —$C(O)NH_2$, —$C(O)NHR^2$, —$C(O)N(R^2)_2$, —$C(O)NR^7R^8$, —$C(O)NHC(O)NHR^2$, —$C(O)NHC(O)N(R^2)_2$, —$C(O)NHC(O)NR^7R^8$, —$C(O)NHSO_2NHR^2$, —$C(O)NHSO_2N(R^2)$, —$C(O)NHSO_2NR^7R^8$, —$C(O)NHC(O)R^2$, and —$C(O)NHSO_2R^2$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$.

In a 26th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, alkyl, lower alkyl, alkenyl, alkynyl, cycloalkyl, cycloalkylalkyl, haloalkyl, heteroaryl, heteroaryl lower alkyl, heterocyclic, heterocyclic lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, polyol alkyl, alkoxy, lower alkoxy, —$O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, —$OC(R^1)_2C(O)NR^7R^8$, amino, alkylamino, dialkylamino, cycloalkylamino, arylamino, aralkylamino, heteroarylamino, heteroaralkylamino, heterocyclicamino, heterocyclicalkylamino, —$NHR^2$, $N(R^2)_2$, —$NR^7R^8$, —$N(R^2)C(O)R^2$, —$NHSO_2NR^7R^8$, —$N(C(O)NHR^2)_2$, —$NHC(O)NR^7R^8$, —$NHC(O)N(R^2)_2$, —$SO_2NH_2$, —$SO_2NHR_2$, —$SO_2N(R^2)_2$, $SO_2NR^7R^8$, —$SO_2NHC(O)R^2$, —$SO_2NHC(O)NHR^2$, —$SO_2NHC(O)N(R^2)_2$, —$SO_2NHC(O)NR^7R^8$, cyano, tetrazol-5-yl, —$C(O)OR^2$, —$C(O)NH_2$, —$C(O)NHR^2$, —$C(O)N(R^2)_2$, —$C(O)NR^7R^8$, —$C(O)NHC(O)R^2$, —$C(O)NHC(O)NHR^2$, —$C(O)NHC(O)N(R^2)_2$, —$C(O)NHC(O)NR^7R^8$, —$C(O)NHSO_2R^2$, —$C(O)NHSO_2NHR^2$, —$C(O)NHSO_2N(R^2)$, —$C(O)NHSO_2NR^7R^8$, and —$C(CH_3)_2C(O)OH$, —$(CH_2)_yC(O)OH$, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^1$ is independently selected from the group consisting of hydrogen, lower alkyl, cycloalkyl, aryl, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —$OCH_3$;

with the proviso that at least one of $R^{2\alpha}$, $R^{3\alpha}$, or $R^{4\alpha}$ must be selected from the group consisting of —$C(O)NH_2$, —$C(O)NHR^2$, —$C(O)N(R^2)_2$, —$C(O)NR^7R^8$, —$C(O)NHC(O)NHR^2$, —$C(O)NHC(O)N(R^2)_2$, —$C(O)NHC(O)NR^7R^8$, —$C(O)NHSO_2NHR^2$, —$C(O)NHSO_2N(R^2)$, —$C(O)NHSO_2NR^7R^8$, —$C(O)NHC(O)R^2$, and —$C(O)NHSO_2R^2$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$.

In a 27th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, alkyl, lower alkyl, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —$O(CH_2)_2)_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, $N(R^2)_2$, —$NR^7R^8$, —$N(R^2)C(O)R^2$, —$C(O)NH_2$, —$C(O)NHR^2$, —$C(O)N(R^2)_2$, —$C(O)NR^7R^8$, and —$C(CH_3)_2C(O)OH$, —$(CH_2)_yC(O)OH$, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^1$ is independently selected from the group consisting of hydrogen, lower alkyl, cycloalkyl, arylalkyl, heteroarylalkyl, and heterocyclicalkyl, wherein all may be optionally substituted by one or more selected from the group consisting of halo, lower alkyl, hydroxyalkyl, heterocyclic, amino, aminoalkyl, —$NR^7R^8$, alkoxy, —$C(O)NR^7R^8$, and —$C(O)N(R^2)_2$;

$R^2$ is independently selected from the group consisting of alkyl, lower alkyl, alkenyl, alkynyl, cycloalkyl, heteroaryl, heterocyclic, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —$NR^7R^8$, alkoxy, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 8-membered monocyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —C(O)NH$_2$, —C(O)NHR$^2$, —C(O)N(R$^2$)$_2$, —C(O)NR$^7$R$^8$, —C(O)NHC(O)R$^2$, and —C(O)NHSO$_2$R$^2$;

wherein all R$^1$, R$^2$, R$^7$ and R$^8$ substituents can be optionally substituted with one or more selected from the group consisting of halo, lower alkyl, hydroxyalkyl, heterocyclic, amino, aminoalkyl, —NR$^7$R$^8$, —C(O)NR$^7$R$^8$, and —C(O)N(R$^2$)$_2$.

In a 28$^{th}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, lower alkyl, heteroaryl, heteroaryl lower alkyl, heterocyclic, heterocyclic lower alkyl, alkoxy, lower alkoxy, —O(CH$_2$)$_2$)$_{1-3}$—O-lower alkyl, polyoxyalkylene, heteroaryl lower alkoxy, heterocyclicalkoxy, heterocyclic lower alkoxy, —N(R$^2$)C(O)R$^2$, —C(O)NH$_2$, and —C(O)NHR$^2$, all of which can be optionally substituted by one or more selected from the group consisting of halo, alkyl, lower alkyl, akenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, and lower alkyl which may be optionally substituted by one or more selected from the group consisting of halo, lower alkyl, —NR$^7$R$^8$, alkoxy, —C(O)NR$^7$R$^8$, and —C(O)N(R$^2$)$_2$;

R$^2$ is independently selected from the group consisting of alkyl, lower alkyl, alkenyl, alkynyl, heteroaryl, and heterocyclic, wherein all may be substituted by one or more selected from the group consisting of halo, lower alkyl, —NR$^7$R$^8$, alkoxy, carboxy, carboxyalkyl, alkoxycarbonyl, —C(O)NR$^7$R$^8$, and —C(O)N(R$^2$)$_2$;

R$^7$ and R$^8$ are independently alkyl, and linked together forming a 5- to 7-membered monocyclic ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —C(O)NH$_2$, —C(O)NHR$^2$, —C(O)NHC(O)R$^2$, and —C(O)NHSO$_2$R$^2$;

wherein all R$^2$, R$^7$ and R$^8$ substituents can be optionally substituted with one or more selected from the group consisting of halo, lower alkyl, heterocyclic, amino, aminoalkyl, and —NR$^7$R$^8$.

In a 29th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, heteroaryl, heterocyclic, lower alkoxy, —O(CH$_2$)$_2$)$_{1-3}$—O-lower alkyl, heteroaryl lower alkoxy, heterocyclic lower alkoxy, —N(R$^2$)C(O)R$^2$, —C(O)NH$_2$, and —C(O)NHR$^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is hydrogen;

R$^2$ is lower alkyl;

R$^7$ and R$^8$ are independently alkyl, and linked together forming a 6-membered monocyclic ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —C(O)NH$_2$, —C(O)NHR$^2$, —C(O)NHC(O)R$^2$, and —C(O)NHSO$_2$R$^2$;

wherein all R$^2$, R$^7$ and R$^8$ substituents can be optionally substituted with one or more selected from the group consisting of heterocyclic, amino, aminoalkyl, and —NR$^7$R$^8$.

In a 30th embodiment, the invention is represented by the following compounds:

4-[3E-(5-Benzo[b]thiophen-2-yl-2,4-dimethoxy-phenyl)-acryloyl]-N-(2-morpholin-4-yl-ethyl)-benzamide;

4-[3E-(5-Benzo[b]thiophen-2-yl-2,4-dimethoxy-phenyl)-acryloyl]-N-(2,2,2-trifluoro-ethyl)-benzamide;

4-{3E-[4-Methoxy-2-(2-morpholin-4-yl-ethoxy)-5-thiophen-2-yl-phenyl]-acryloyl}-benzamide;

4-[3E-(5-Benzo[b]thiophen-2-yl-2,4-dimethoxy-phenyl)-acryloyl]-benzamide;

4-{3E-[4-Methoxy-2-(3-morpholin-4-yl-propoxy)-5-thiophen-2-yl-phenyl]-acryloyl}-benzamide;

N-Acetyl-4-[3E-(5-benzo[b]thiophen-2-yl-2,4-dimethoxy-phenyl)-acryloyl]-benzamide; and 4-[3E-(5-Benzo[b]thiophen -2-yl-2,4-dimethoxy-phenyl)-acryloyl]-N-isobutyryl-benzamide.

In a 31$^{st}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroaryalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 32nd embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NH$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, cyano, tetrazol-5-yl, carboxy, —C(O)OR$^2$, —C(O)NH$_2$, —(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of $R^{2\alpha}$, $R^{3\alpha}$, or $R^{4\alpha}$ must be selected from the group consisting of thiol, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NHR$^2$, —SO$_2$N($R^2$)$_2$, SO$_2$NR$^7$R$^8$, —SO$_2$NHC(O)$R^2$, —SR$_2$, —SO$_2$NHC(O)NHR$^2$, —SO$_2$NHC(O)N($R^2$)$_2$, —SO$_2$NHC(O)NR$^7$R$^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N($R^2$)$_2$.

In a 33$^{rd}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, alkyl, lower alkyl, alkenyl, alkynyl carbocycle, cycloalkyl, cycloalkylalkyl, haloalkyl, heteroaryl, heteroaryl lower alkyl, heterocyclic, heterocyclic lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, polyol alkyl, alkoxy, lower alkoxy, —O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)N($R^2$)$_2$, —OC($R^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N($R^2$)$_2$, —NR$^7$R$^8$, —N($R^2$)C(O)$R^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N($R^2$)$_2$, —SC($R^1$)$_2$C(O)OH, —SC($R^1$)$_2$C(O)O$R^2$, —SCH$_2$C(O)OH—SO$_2$NH$_2$, —SO$_2$NHR$^2$, —SO$_2$N($R^2$)$_2$, SO$_2$NR$^7$R$^8$, —SO$_2$NHC(O)$R^2$, —SR$_2$, —SO$_2$NHC(O)NHR$^2$, —SO$_2$NHC(O)N($R^2$)$_2$, —SO$_2$NHC(O)NR$^7$R$^8$, cyano, tetrazol-5-yl, —C(O)O$R^2$, —C(O)NH$_2$, —C(O)NHR$^2$, —C(O)N($R^2$)$_2$, —C(O)NR$^7$R$^8$, —C(O)NHC(O)$R^2$, —C(O)NHC(O)NHR$^2$, —C(O)NHC(O)N($R^2$)$_2$, —C(O)NHC(O)NR$^7$R$^8$, —C(O)NHSO$_2$R$^2$, —C(O)NHSO$_2$NHR$^2$, —C(O)NHSO$_2$N($R^2$), —C(O)NHSO$_2$NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N($R^2$)$_2$;

$R^1$ is independently selected from the group consisting of hydrogen, lower alkyl, cycloalkyl, arylarylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N($R^2$)$_2$;

$R^2$ is independently selected from the group consisting of alkyl, lower alkyl, cycloalkyl, aryl, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —SC($R^1$)$_2$C(O)OH, —SC($R^1$)$_2$C(O)O$R^2$, —SCH$_2$C(O)OH, —SO$_2$NH$_2$, —SO$_2$NHR$_2$, —SO$_2$N($R^2$)$_2$, SO$_2$NR$^7$R$^8$, —SO$_2$NHC(O)$R^2$, —SO$_2$NHC(O)NHR$^2$, —SO$_2$NHC(O)N($R^2$)$_2$, —SO$_2$NHC(O)NR$^7$R$^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N($R^2$)$_2$.

In a 34th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, alkyl, lower alkyl, alkenyl, alkynyl, carbocycle, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —O(CH$_2$)$_2$)$_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, N($R^2$)$_2$, —NR$^7$R$^8$, —N($R^2$)C(O)$R^2$, —SCH$_2$C(O)OH—SO$_2$NH$_2$, —SO$_2$NHR$_2$, —SO$_2$N($R^2$)$_2$, SO$_2$NR$^7$R$^8$, —SO$_2$NHC(O)$R^2$, —SR$_2$, —SO$_2$NHC(O)NHR$^2$, —SO$_2$NHC(O)N($R^2$)$_2$, —SO$_2$NHC(O)NR$^7$R$^8$, —C(O)N($R^2$)$_2$, —C(O)NR$^7$R$^8$, and —C(O)NHSO$_2$R$^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N($R^2$)$_2$;

$R^1$ is independently selected from the group consisting of hydrogen, lower alkyl, cycloalkyl, arylalkyl, heteroarylalkyl, and heterocyclicalkyl, wherein all may be optionally substituted by one or more selected from the group consisting of halo, lower alkyl, hydroxyalkyl, heterocyclic, amino, aminoalkyl, —NR$^7$R$^8$, alkoxy, —C(O)NR$^7$R$^8$, and —C(O)N($R^2$)$_2$;

$R^2$ is independently selected from the group consisting of alkyl, lower alkyl, cycloalkyl, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —NR$^7$R$^8$, alkoxy, —C(O)NR$^7$R$^8$, and —C(O)N($R^2$)$_2$;

$R^7$ and $R^8$ are independently selected from the group consisting of alkyl, alkenyl and aryl and linked together forming a 4- to 8-membered monocyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of —SC($R^1$)$_2$C(O)O$R^2$, —SCH$_2$C(O)OH, —SO$_2$NH$_2$, —SO$_2$NHR$_2$, —SO$_2$N($R^2$)$_2$, SO$_2$NR$^7$R$^8$, —SO$_2$NHC(O)$R^2$, —SO$_2$NHC(O)NHR$^2$, —SO$_2$NHC(O)N($R^2$)$_2$, —SO$_2$NHC(O)NR$^7$R$^8$;

wherein all $R^1$, $R^2$, $R^7$ and $R^8$ substituents can be optionally substituted with one or more selected from the group consisting of halo, alkyl, lower alkyl, hydroxyalkyl, heterocyclic, amino, aminoalkyl, —$NR^7R^8$, —$C(O)NR^7R^8$, and —$C(O)N(R^2)_2$.

In a 35th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, lower alkyl, alkenyl, alkynyl, carbocycle, heteroaryl, heteroaryl lower alkyl, heterocyclic, heterocyclic lower alkyl, hydroxyl, alkoxy, lower alkoxy, —$(O(CH_2)_2)_{1-3}$—O-lower alkyl, polyoxyalkylene, heteroaryl lower alkoxy, heterocyclicalkoxy, heterocyclic lower alkoxy, —$N(R^2)C(O)R^2$, —$SCH_2C(O)OH$—$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, and —$C(O)NHSO_2R^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^1$ is independently selected from the group consisting of hydrogen and lower alkyl, which may be optionally substituted by one or more selected from the group consisting of halo, lower alkyl, —$NR^7R^8$, alkoxy, —$C(O)NR^7R^8$, and —$C(O)N(R^2)_2$;

$R^2$ is independently selected from the group consisting of alkyl and lower alkyl, which may be substituted by one or more selected from the group consisting of halo, lower alkyl, —$NR^7R^8$, alkoxy, —$C(O)NR^7R^8$, and —$C(O)N(R^2)_2$;

$R^7$ and $R^8$ are independently alkyl, and linked together forming a 5- to 7-membered monocyclic ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —$OCH_3$;

with the proviso that at least one of $R^{2\alpha}$, $R^{3\alpha}$, or $R^{4\alpha}$ must be selected from the group consisting of —$SC(R^1)_2C(O)OR^2$, —$SCH_2C(O)OH$, —$SO_2NH_2$, —$SO_2NHR_2$, —$SO_2N(R^2)_2$, $SO_2NR^7R^8$, and —$SO_2NHC(O)R^2$;

wherein all $R^1$, $R^2$, $R^7$ and $R^8$ substituents can be optionally substituted with one or more selected from the group consisting of halo, —$NR^7R^8$, —$C(O)NR^7R^8$, and —$C(O)N(R^2)_2$.

In a 36th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, alkenyl, alkynyl, carbocycle, heteroaryl, heterocyclic, hydroxyl, lower alkoxy, —$(O(CH_2)_2)_{1-3}$—O-lower alkyl, heteroaryl lower alkoxy, heterocyclic lower alkoxy, —$N(R^2)C(O)R^2$, —$SO_2NH_2$, —$SO_2NHR_2$, $SO_2NHC(O)R^2$, —$SR_2$, —$SO_2NHC(O)NHR^2$, —$SO_2NHC(O)N(R^2)_2$, —$SO_2NHC(O)NR^7R^8$, and —$C(O)NHSO_2R^2$, all of which can be optionally substituted by one or more selected from the group consisting of alkenyl, acyl, hydroxy, hydroxyalkyl, amino, aminoalkyl, —$NR^7R^8$, alkoxy, oxo, cyano, —$C(O)NR^7R^8$, and —$C(O)N(R^2)_2$;

$R^1$ is hydrogen;

$R^2$ is lower;

$R^7$ and $R^8$ are independently alkyl, and linked together forming a 6-membered monocyclic ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —$OCH_3$;

with the proviso that at least one of $R^{2\alpha}$, $R^{3\alpha}$, or $R^{4\alpha}$ must be selected from the group consisting of —$SC(R^1)_2C(O)OR^2$, —$SO_2NH_2$, —$SO_2NR^7R^8$, and —$SO_2NHC(O)R^2$.

In a 37th embodiment, the invention is represented by the following compound:

4-[3E-(4-Thiophen-2-yl-phenyl)-acryloyl]-benzenesulfonamide;

4-[3E-(5-Benzo[b]thiophen-2-yl-2,4-dimethoxy-phenyl)-acryloyl]-benzenesulfonamide;

4-{3E-[4-Methoxy-2-(2-morpholin-4-yl-ethoxy)-5-thiophen-2-yl-phenyl]-acryloyl}-benzenesulfonamide;

2-{5-Methoxy-2-[3-oxo-3-(4-sulfamoyl-phenyl)-E-propenyl]-4-thiophen-2-yl-phenoxy}-2-methyl-propionic acid;

2-{2,4-Dimethoxy-5-[3-oxo-3-(4-sulfamoyl-phenyl)-E-propenyl]-phenyl}-indole-1-carboxylic acid tert-butyl ester;

4-{3E-[5-(1H-Indol-2-yl)-2,4-dimethoxy-phenyl]-acryloyl}-benzenesulfonamide;

4-{3E-[4-Methoxy-2-(3-morpholin-4-yl-propoxy)-5-thiophen-2-yl-phenyl]-acryloyl}-benzenesulfonamide;

4-{3E[2-(3-Hydroxy-2-hydroxymethyl-propoxy)-4-methoxy-5-thiophen-2-yl-phenyl]-acryloyl}-benzenesulfonamide;

4-[3E-(5-Benzo[b]thiophen-2-yl-2,4-dimethoxy-phenyl)-acryloyl]-N-isobutyryl-benzenesulfonamide;

4-{3E-[4-Methoxy-2-(2-morpholin-4-yl-ethoxy)-5-thiophen-2-yl-phenyl]-acryloyl}benzenesulfonamide, hydrochloride;

4-{3E-[4-Methoxy-2-(1H-tetrazol-5-ylmethoxy)-5-thiophen-2-yl-phenyl]-acryloyl}-benzenesulfonamide;

4-[3E-(2,4-Dimethoxy-5-pyridin-3-yl-phenyl)-acryloyl]-benzenesulfonamide;

4-{3E-[4-(3-Hydroxy-2-hydroxymethyl-propoxy)-2-methoxy-5-thiophen-2-yl-phenyl]-acryloyl}-benzenesulfonamide;

4-{3E-[5-(4-Isobutyl-4H-[1,2,4]triazol-3-yl)-2,4-dimethoxy-phenyl]-acryloyl}-benzenesulfonamide;

4-{3E-[5-(2-Cyclopropyl-1H-imidazol-4-yl)-2,4-dimethoxy-phenyl]-acryloyl}-benzenesulfonamide;

4-{3E-[5-(3H-Imidazo[4,5-b]pyridin-2-yl)-2,4-dimethoxy-phenyl]-acryloyl}-benzenesulfonamide;

4-{3E-[2-(1H-Benzoimidazol-2-ylmethoxy)-4-methoxy-5-thiophen-2-yl-phenyl]-acryloyl}-benzenesulfonamide;

4-{3E-[4-Methoxy-2-(pyridin-2-ylmethoxy)-5-thiophen-2-yl-phenyl]-acryloyl}-benzenesulfonamide;

4-{3E-[2-(Benzotriazol-1-ylmethoxy)-4-methoxy-5-thiophen-2-yl-phenyl]-acryloyl}-benzenesulfonamide; and 4-{3E-[2,4-Dimethoxy-5-(1-methyl-1H-indol-2-yl)-phenyl]-acryloyl}-benzenesulfonamide.

In a 38th embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-$S(O)_2$-lower alkyl, arylsulfinyl lower alkyl, arylsulfonyl lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 39$^{th}$ embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, heterocyclic lower alkoxy, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is lower alkyl optionally substituted by alkoxycarbonyl.

R$^7$ and R$^8$ are independently alkyl, and linked together forming a 6-membered monocyclic ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of amino, —N(C(O)NHR$^2$)$_2$, NR$^2$SO$_2$R$^2$ and —NR$^2$SO$_2$R$^2$;

wherein all R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 40th embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from the group consisting of —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 41st embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, heterocyclic lower alkoxy, —OC(R$^1$)$_2$C(O)OH, —OC(R$^1$)$_2$C(O)N(R$^2$)$_2$, —OC(R$^1$)$_2$C(O)NR$^7$R$^8$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is hydrogen or lower alkyl optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is lower alkyl optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently alkyl, and linked together forming a 6-membered monocyclic ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$;

with the proviso that at least one of R$^{2\alpha}$, R$^{3\alpha}$, or R$^{4\alpha}$ must be selected from —OC(R$^1$)$_2$C(O)OH;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 42$^{nd}$ embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —C(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^1$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$; and/or R$^{2\alpha}$ and R$^{3\alpha}$ taken together or R$^{3\alpha}$ and R$^{4\alpha}$ taken together or R$^{4\alpha}$ and R$^{5\alpha}$ taken together, or R$^{2\beta}$ and R$^{3\beta}$ taken together or R$^{3\beta}$ and R$^{4\beta}$ taken together or R$^{4\beta}$ and R$^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or At least one of R$^{2\alpha}$, R$^{3\alpha}$, or R$^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 43$^{rd}$ embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from group consisting of hydrogen, halogen, heteroaryl, heterocyclic, lower alkoxy, —(O(CH$_2$)$_2$)$_{1-3}$—O-lower alkyl, heteroaryl lower alkoxy, heterocyclic lower alkoxy, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently alkyl or lower alkyl;

R$^7$ and R$^8$ are independently selected from the group consisting of alkyl, linked together forming a 6-membered monocyclic ring;

wherein one of R$^{4\beta}$, R$^{5\beta}$ or R$^{6\beta}$ must be a carbon-carbon linked heterocyclic or heteroaryl, and only one of R$^{2\alpha}$, R$^{3\alpha}$, R$^{4\alpha}$, R$^{5\alpha}$ or R$^{6\alpha}$ can be —OCH$_3$; and/or R$^{3\alpha}$ and R$^{4\alpha}$ taken together or R$^{4\alpha}$ and R$^{5\alpha}$ taken together, or R$^{3\beta}$ and R$^{4\beta}$ taken together or R$^{4\beta}$ and R$^{5\beta}$ taken together form a heterocyclic ring optionally substituted by one or more alkoxycarbonylalkyl, carboxyalkyl, or hydroxyalkyl groups.

In a 44$^{th}$ embodiment, the invention is represented by Formula I or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR², N(R²)₂, —NR⁷R⁸, —NHC(R¹)₂C(O)OH, —NHC(R¹)₂C(O)OR², —NHC(O)R², —N(R²)C(O)R², —NHC(O)OR², —NHC(O)SR², —NHSO₂NHR², —NHSO₂R², —NHSO₂NR⁷R⁸, —N(C(O)NHR²)₂, —NR²SO₂R², —NHC(O)NHR², —NHC(O)NR⁷R⁸, —NHC(O)N(R²)₂, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R¹)₂C(O)OH, —SC(R¹)₂C(O)OR², —SCH₂C(O)OH, —SCF₂C(O)OH, —SO₂NH₂, —SO₂NHR₂, —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, sulfonic acid, sulfonate, sulfate, sulfinic acid, sulfenic acid, cyano, tetrazol-5-yl, carboxy, —C(O)OR², —C(O)NH₂, —C(O)NHR², —C(O)N(R²)₂, —C(O)NR⁷R⁸, —C(O)NHC(O)R², —C(O)NHC(O)NHR², —C(O)NHC(O)N(R²)₂, —C(O)NHC(O)NR⁷R⁸, —C(O)NHSO₂R², —C(O)NHSO₂NHR², —C(O)NHSO₂N(R²), —C(O)NHSO₂NR⁷R⁸, —C(CH₃)₂C(O)OH, —(CH₂)ᵧC(O)OH, wherein y is 1, 2, 3, 4, 5, or 6, —PO₂H₂, —PO₃H₂, —P(R²)O₂H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R¹ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R² is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R⁷ and R⁸ are independently selected from the group consisting of alkyl, alkenyl and aryl and linked together forming a 4- to 12-membered monocyclic, bicylic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH₃; and/or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R¹)₂C(O)OH; and/or at least one of $R^{2\alpha}$, $R^{3\alpha}$, or $R^{4\alpha}$ must be selected from the group consisting of cyano, tetrazol-5-yl, carboxy, —C(O)OR², —C(O)NH₂, —C(O)NHR², —C(O)N(R²)₂, —C(O)NR⁷R⁸, —C(O)NHC(O)NHR², —C(O)NHC(O)N(R²)₂, —C(O)NHC(O)NR⁷R⁸, —C(O)NHSO₂NHR², —C(O)NHSO₂N(R²), —C(O)NHSO₂NR⁷R⁸, —C(O)NHSO₂R², —C(CH₃)₂C(O)OH, —(CH₂)ᵧC(O)OH, wherein y is 1, 2, 3, 4, 5, or 6, thiol, —SC(R¹)₂C(O)OH, —SC(R¹)₂C(O)OR², —SCH₂C(O)OH, —SCF₂C(O)OH, —SO₂NH₂, —SO₂NHR₂, —SO₂N(R²)₂, SO₂NR⁷R⁸, —SO₂NHC(O)R², —SR₂, —SO₂NHC(O)NHR², —SO₂NHC(O)N(R²)₂, —SO₂NHC(O)NR⁷R⁸, —OC(R¹)₂C(O)OH, —OC(R¹)₂C(O)OR², —OC(R¹)₂C(O)NH₂, —OC(R¹)₂C(O)NHR², —OC(R¹)₂C(O)N(R²)₂, —OC(R¹)₂C(O)NR⁷R⁸, amino, —NHR², N(R²)₂, NR⁷R⁸, —NHC(R¹)₂C(O)OH, —NHC(R¹)₂C(O)OR², —NHC(O)R², —N(R²)C(O)R², —NHC(O)OR², —NHC(O)SR², —NHSO₂NHR², —NHSO₂R², —NHSO₂NR⁷R⁸, —N(C(O)NHR²)₂, —NR²SO₂R², —NHC(O)NHR², —NHC(O)NR⁷R⁸, and —NHC(O)N(R²)₂, wherein all R¹, R², R⁷ and R⁸ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂.

In a 45$^{th}$ embodiment, the invention is represented by Formula I or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, heteroaryl, heterocyclic, lower alkoxy, —(O(CH₂)₂)₁₋₃—O-lower alkyl, heteroaryl lower alkoxy, heterocyclic lower alkoxy, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, carboxy, carboxyalkyl, alkoxycarbonyl, —C(O)NR⁷R⁸, and —C(O)N(R²)₂;

R² is independently alkyl or lower alkyl;

R⁷ and R⁸ are independently selected from the group consisting of alkyl, linked together forming a 6-membered monocyclic ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH₃; and/or $R^{3\alpha}$ and $R^{4\alpha}$ taken together or $R^{4\alpha}$ and $R^{5\alpha}$ taken together or $R^{3\beta}$ and $R^{4\beta}$ taken together or $R^{4\beta}$ and $R^{5\beta}$ taken together form a 5-membered ring containing one nitrogen, which may optionally be substituted with one or more selected from the group consisting of alkyl, lower alkyl, cycloalkyl, hydroxyalkyl, aminoalkyl, carboxyalkyl, alkoxycarbonyl; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R¹)₂COOH.

In a 46th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)₂-lower alkyl, arylsulfinyl lower alkyl, arylsulfonyl lower alkyl, —C(O)R², R²C (O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O— lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{2\alpha}$, R$^{3\alpha}$, R$^{4\alpha}$, R$^{5\alpha}$ or R$^{6\alpha}$, or one of R$^{2\beta}$, R$^{3\beta}$, R$^{4\beta}$, R$^{5\beta}$ or R$^{6\beta}$ must be a carbon-carbon linked heterocyclic or heteroaryl; and/or wherein when one of R$^{2\alpha}$, R$^{3\alpha}$, R$^{4\alpha}$, R$^{5\alpha}$ or R$^{6\alpha}$ is a carbon-carbon linked heterocyclic or heteroaryl, only one of R$^{2\beta}$, R$^{3\beta}$, R$^{4\beta}$, R$^{5\beta}$ or R$^{6\beta}$ can be —OCH$_3$; and/or wherein when one of R$^{2\beta}$, R$^{3\beta}$, R$^{4\beta}$, R$^{5\beta}$ or R$^{6\beta}$ is a carbon-carbon linked heterocyclic or heteroaryl, only one of R$^{2\alpha}$, R$^{3\alpha}$, R$^{4\alpha}$, R$^{5\alpha}$ or R$^{6\alpha}$ can be —OCH$_3$; and/or R$^{2\beta}$ and R$^{3\beta}$ taken together or R$^{3\beta}$ and R$^{4\beta}$ taken together or R$^{4\beta}$ and R$^{5\beta}$ taken together, or R$^{2\alpha}$ and R$^{3\alpha}$ taken together or R$^{3\alpha}$ and R$^{4\alpha}$ taken together or R$^{4\alpha}$ and R$^{5\alpha}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or R$^{2\beta}$ and R$^{3\beta}$ taken together or R$^{3\beta}$ and R$^{4\beta}$ taken together or R$^{4\beta}$ and R$^{5\beta}$ taken together or R$^{2\alpha}$ and R$^{3\alpha}$ taken together or R$^{3\alpha}$ and R$^{4\alpha}$ taken together or R$^{4\alpha}$ and R$^{5\alpha}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ cannot be —OC(R$^1$)$_2$C(O)OH; and/or at least one of R$^{2\beta}$, R$^{3\beta}$, R$^{4\beta}$, or one of R$^{2\alpha}$, R$^{3\alpha}$, R$^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 47th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C (O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{2\alpha}$, R$^{3\alpha}$, R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that R$^{2\beta}$ and R$^{3\beta}$ taken together or R$^{3\beta}$ and R$^{4\beta}$ taken together or R$^{4\beta}$ and R$^{5\beta}$ taken together, or R$^{2\alpha}$ and R$^{3\alpha}$ taken together or R$^{3\alpha}$ and R$^{4\alpha}$ taken together or R$^{4\alpha}$ and R$^{5\alpha}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; or R$^{2\beta}$ and R$^{3\beta}$ taken together or R$^{3\beta}$ and R$^{4\beta}$ taken together or R$^{4\beta}$ and R$^{5\beta}$ taken together or R$^{2\alpha}$ and R$^{3\alpha}$ taken together or R$^{3\alpha}$ and R$^{4\alpha}$ taken together or R$^{4\alpha}$ and R$^{5\alpha}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ cannot be —OC(R$^1$)$_2$C(O)OH; and with the proviso that at least one of R$^{2\beta}$, R$^{3\beta}$, R$^{4\beta}$, R$^{5\beta}$, or R$^{6\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 48th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, alkylamino, acylamino, dialkylamino, cycloalkylamino, arylamino, aralkylamino, heteroarylamino, heteroaralkylamino, heterocyclicamino, heterocyclicalkylamino, —NH$R^2$, N($R^2$)$_2$, —N$R^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —NHSO$_2$NH$R^2$, —NHSO$_2$$R^2$, —NHSO$_2$N$R^7R^8$, —N(C(O)NH$R^2$)$_2$, —N$R^2$SO$_2$$R^2$, —NHC(O)NH$R^2$, —NHC(O)N$R^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NH$R_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, sulfonic acid, sulfonate, sulfate, sulfinic acid, sulfenic acid, cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)$R^2$, —C(O)NHC(O)NH$R^2$, —C(O)NHC(O)N($R^2$)$_2$, —C(O)NHC(O)N$R^7R^8$, —C(O)NHSO$_2$$R^2$, —C(O)NHSO$_2$NH$R^2$, —C(O)NHSO$_2$N($R^2$), —C(O)NHSO$_2$N$R^7R^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P($R^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^2$ is independently selected from the group consisting of alkyl, lower alkyl, alkenyl, alkynyl, carbocycle, cycloalkyl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$, or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$;

with the proviso that $R^{2\beta}$ and $R^{3\beta}$ taken together or $R^{3\beta}$ and $R^{4\beta}$ taken together or $R^{4\beta}$ and $R^{5\beta}$ taken together, or $R^{2\alpha}$ and $R^{3\alpha}$ taken together or $R^{3\alpha}$ and $R^{4\alpha}$ taken together or $R^{4\alpha}$ and $R^{5\alpha}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —N$R^7R^8$, and halo; or $R^{2\beta}$ and $R^{3\beta}$ taken together or $R^{3\beta}$ and $R^{4\beta}$ taken together or $R^{4\beta}$ and $R^{5\beta}$ taken together or $R^{2\alpha}$ and $R^{3\alpha}$ taken together or $R^{3\alpha}$ and $R^{4\alpha}$ taken together or $R^{4\alpha}$ and $R^{5\alpha}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$; provided that $R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ cannot be —OC($R^1$)$_2$C(O)OH; and with the proviso that at least one of $R^{2\beta}$, $R^{3\beta}$, or $R^{4\beta}$ must be selected from the group consisting of cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)NH$R^2$, —C(O)NHC(O)N($R^2$)$_2$, —C(O)NHC(O)N$R^7R^8$, —C(O)NHSO$_2$NH$R^2$, —C(O)NHSO$_2$N($R^2$), —C(O)NHSO$_2$N$R^7R^8$, —C(O)NHC(O)$R^2$, —C(O)NHSO$_2$$R^2$, —C(CH$_3$)$_2$C(O)OH, —(CH$_2$)$_y$C(O)OH, wherein y is 1, 2, 3, 4, 5, or 6, thiol, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NH$R_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, —NH$R^2$, N($R^2$)$_2$, N$R^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —NHSO$_2$NH$R^2$, —NHSO$_2$$R^2$, —NHSO$_2$N$R^7R^8$, —N(C(O)NH$R^2$)$_2$, —N$R^2$SO$_2$$R^2$, —NHC(O)NH$R^2$, —NHC(O)N$R^7R^8$, and —NHC(O)N($R^2$)$_2$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$.

In a 49th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —(O)N(R$^2$)$_2$.

In a 50th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$;

with the proviso that at least one of $R^{2\beta}$, $R^{3\beta}$, or $R^{4\beta}$ must be selected from the group consisting of cyano, tetrazol-5-yl, carboxy, —C(O)O$R^2$, —C(CH$_3$)$_2$C(O)OH, —(CH$_2$)$_y$C(O)OH, wherein y is 1, 2, 3, 4, 5, or 6;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$.

In a 51st embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)NH$_2$, —OC($R^1$)$_2$C(O)NHR$^2$, —OC($R^1$)$_2$C(O)N($R^2$)$_2$, —OC($R^1$)$_2$C(O)$NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N($R^2$)$_2$, —$NR^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)S$R^2$, —NHSO$_2$NHR$^2$, —NHSO$_2R^2$, —NHSO$_2$N$R^7R^8$, —N(C(O)NHR$^2$)$_2$, —NR$^2$SO$_2R^2$, —NHC(O)NHR$^2$, —NHC(O)N$R^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NHR$^2$, —SO$_2$N($R^2$)$_2$, SO$_2$N$R^7R^8$, —SO$_2$NHC(O)$R^2$, —S$R_2$, —SO$_2$NHC(O)NHR$^2$, —SO$_2$NHC(O)N($R^2$)$_2$, —SO$_2$NHC(O)N$R^7R^8$, cyano, tetrazol-5-yl, carboxy, —C(O)O$R^2$, —C(O)NH$_2$, —C(O)NHR$^2$, —C(O)N($R^2$)$_2$, —C(O)N$R^7R^8$, —C(O)NHC(O)$R^2$, —C(O)NHC(O)NHR$^2$, —C(O)NHC(O)N($R^2$)$_2$, —C(O)NHC(O)N$R^7R^8$, —C(O)NHSO$_2R^2$, —C(O)NHSO$_2$NHR$^2$, —C(O)NHSO$_2$N($R^2$), —C(O)NHSO$_2$N$R^7R^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, oxo, cyano, carboxy, carboxyalkyl, alkoxycarbonyl, —C(O)$NR^7R^8$, and —C(O)N($R^2$)$_2$;

$R^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$;

with the proviso that at least one of $R^{2\beta}$, $R^{3\beta}$, or $R^{4\beta}$ must be selected from the group consisting of cyano, tetrazol-5-yl, carboxy, —C(O)O$R^2$, —C(CH$_3$)$_2$C(O)OH, —(CH$_2$)$_y$C(O)OH, wherein y is 1, 2, 3, 4, 5, or 6;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$.

In an 52$^{nd}$ embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, alkyl, lower alkyl, alkenyl, alkynyl, cycloalkyl, cycloalkylalkyl, haloalkyl, heteroaryl, heteroaryl lower alkyl, heterocyclic, heterocyclic lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, polyol-alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)N (R$^2$)$_2$, —OC(R$^1$)$_2$C(O)NR$^7$R$^8$, amino, alkylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —N(R$^2$)C(O)R$^2$, —NHSO$_2$NR$^7$R$^8$, —N(C(O)NHR$^2$)$_2$, —NHC(O)NR$^7$R$^8$, —NHC(O)N(R$^2$)$_2$, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$;

R$^1$ is independently selected from the group consisting of hydrogen, lower alkyl, cycloalkyl, aryl, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, oxo, cyano, —C(O)NR$^7$R$^8$, and —C(O)N(R$^2$)$_2$;

R$^2$ is independently selected from the group consisting of alkyl, lower alkyl, cycloalkyl, aryl, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of cyano, tetrazol-5-yl, carboxy, —C(O)OR$^2$, —C(CH$_3$)$_2$C(O)OH, (CH$_2$)$_y$C(O)OH, wherein y is 1, 2, 3, 4, 5, or 6;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$.

In a 53$^{rd}$ embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, alkyl, lower alkyl, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —(O(CH$_2$)$_2$)$_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, N(R$^2$)$_2$, —NR$^7$R$^8$, tetrazol-5-yl, carboxy, —C(O) OR$^2$, —C(O)N(R$^2$)$_2$, —C(O)NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, cycloalkyl, hydroxy, hydroxyalkyl, heterocyclic, amino, aminoalkyl, —NR$^7$R$^8$, —C(O)NR$^7$R$^8$, and —C(O)N(R$^2$)$_2$;

R$^2$ is independently selected from the group consisting of alkyl, lower alkyl, cycloalkyl, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —NR$^7$R$^8$, alkoxy, —C(O)NR$^7$R$^8$, and —C(O)N(R$^2$)$_2$;

R$^7$ and R$^8$ are independently selected from the group consisting of alkyl, alkenyl and aryl and linked together forming a 4- to 8-membered monocyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of tetrazol-5-yl, carboxy, —C(O)OR$^2$, —C(CH$_3$)$_2$C(O)OH, —(CH$_2$)$_y$C(O)OH, wherein y is 1, 2, 3, 4, 5, or 6;

wherein all R$^1$, R$^2$, R$^7$ and R$^8$ substituents can be optionally substituted with one or more selected from the group consisting of halo, lower alkyl, hydroxyalkyl, heterocyclic, amino, aminoalkyl, —NR$^7$R$^8$, —C(O)NR$^7$R$^8$, and —C(O) N(R$^2$)$_2$.

In a 54th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, lower alkyl, heteroaryl, heteroaryl lower alkyl, heterocyclic, heterocyclic lower alkyl, alkoxy, lower alkoxy, —(O(CH$_2$)$_2$)$_{1-3}$—O-lower alkyl, polyoxyalkylene, heteroaryl lower alkoxy, heterocyclicalkoxy, heterocyclic lower alkoxy, carboxy, —C(O)OR$^2$, —C(O)N(R$^2$)$_2$, and —C(O) NR$^7$R$^8$, all of which can be optionally substituted by one or more selected from the group consisting of halo, alkyl, lower alkyl, cycloalkyl, hydroxy, hydroxyalkyl, heterocyclic, —NR$^7$R$^8$, —C(O)NR$^7$R$^8$, and —C(O)N(R$^2$)$_2$;

R$^2$ is independently selected from the group consisting of alkyl, and lower alkyl, wherein all may be substituted by one or more selected from the group consisting of halo, lower alkyl, —NR$^7$R$^8$, alkoxy, —C(O)NR$^7$R$^8$, and —C(O)N(R$^2$)$_2$;

R$^7$ and R$^8$ are independently alkyl, and linked together forming a 5- to 7-membered monocyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from carboxy or —C(O)OR$^2$;

wherein all R$^1$, R$^2$, R$^7$ and R$^8$ substituents can be optionally substituted with one or more selected from the group consisting of halo, lower alkyl, —NR$^7$R$^8$, —C(O)NR$^7$R$^8$, and —C(O)N(R$^2$)$_2$.

In a 55th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, —(O (CH$_2$)$_2$)$_{1-3}$—O-lower alkyl, heteroaryl lower alkoxy, heterocyclic lower alkoxy, and carboxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be carboxy.

In a 56th embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\alpha}$, R$^{5\alpha}$ or R$^{6\alpha}$ must be a carbon-carbon linked heterocyclic or heteroaryl;

with the proviso that at least one of R$^{2\beta}$, R$^{3\beta}$, or R$^{4\beta}$ must be carboxy.

In a 57th embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\alpha}$, R$^{5\alpha}$ or R$^{6\alpha}$ must be a carbon-carbon linked heteroaryl;

with the proviso that at least one of R$^{2\beta}$, R$^{3\beta}$, or R$^{4\beta}$ must be carboxy.

In a 58th embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, fluorine, chlorine, methoxy, ethoxy, propoxy, 3-(1-morpholino) propoxy, 2-(1-morpholino) ethoxy, CH$_3$O(CH$_2$)$_2$O(CH$_2$)$_2$—,

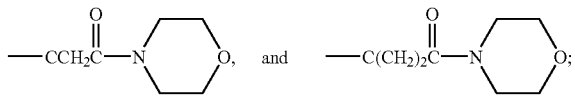

wherein one of R$^{4\alpha}$, R$^{5\alpha}$ or R$^{6\alpha}$ must be selected from the group consisting of thiophen-s-yl, thiophen-3-yl, benzo[b]thiophen-2-yl, benzo[b]thiophen-3-yl, indol-2-yl, indol-3-yl, pyrrol-2-yl, pyrrol-3-yl, 1-methyl-indol-2-yl, 1-methyl-indol-3-yl, N-Boc-indol-2-yl, N-Boc-indol-3-yl, N-Boc-pyrrol-2'yl, and N-Boc-pyrrol-3-yl;

with the proviso that at least one of R$^{2\beta}$, R$^{3\beta}$, or R$^{4\beta}$ must be carboxy.

In a 59th embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, methoxy, 3-(1-morpholino) propoxy, 2-(1-morpholino) ethoxy, and CH$_3$O(CH$_2$)$_2$O(CH$_2$)$_2$;

wherein one of R$^{4\alpha}$, R$^{5\alpha}$ or R$^{6\alpha}$ must be selected from the group consisting of thiophen-s-yl, benzo[b]thiophen-2-yl, indol-2-yl, 1-methyl-indol-2-yl, N-Boc-indol-2-yl, N-Boc-pyrrol-2'yl, and N-Boc-pyrrol-3-yl;

with the proviso that at least one of R$^{2\beta}$, R$^{3\beta}$, or R$^{4\beta}$ must be carboxy.

In a 60th embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\alpha}$, R$^{5\alpha}$ or R$^{6\alpha}$ must be a carbon-carbon linked heterocyclic;

with the proviso that at least one of R$^{2\beta}$, R$^{3\beta}$, or R$^{4\beta}$ must be carboxy.

In a 23rd embodiment, the invention is represented by Formula I or its pharmaceutically acceptable salt or ester, wherein:

R$^{2\beta}$, R$^{3\beta}$, R$^{4\beta}$, R$^{5\beta}$, and R$^{6\beta}$ are independently selected from the group consisting of hydrogen and carboxy;

R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;

R$^2$ is lower alkyl;

R$^7$ and R$^8$ are independently alkyl, and linked together forming a 6-membered monocyclic or benzofused ring;

wherein one of R$^{4\alpha}$, R$^{5\alpha}$ or R$^{6\alpha}$ must be a carbon-carbon linked tetrahydrofuran-2-yl or dihydrofuran-2-yl;

with the proviso that at least one of R$^{2\beta}$, R$^{3\beta}$, or R$^{4\beta}$ must be carboxy.

Embodiment 6c. Amide Branch

In a 61st embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of —C(O)NH$_2$, —C(O)NHR$^2$, —C(O)N(R$^2$)$_2$, —C(O)N$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 62nd embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino-NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)

NHSO$_2$NR$^7$R$^8$, and —C(CH$_3$)$_2$C(O)OH, —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, and —C(O)NHSO$_2$R$^2$;

wherein all R$^1$, R$^2$, R$^7$ and R$^8$ substituents can be optionally substituted with one or more selected from the group consisting of halo, alkyl, (lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 63$^{rd}$ embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, alkyl, lower alkyl, alkenyl, alkynyl, cycloalkyl, cycloalkylalkyl, haloalkyl, heteroaryl, heteroaryl lower alkyl, heterocyclic, heterocyclic lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)N(R$^2$)$_2$, —OC(R$^1$)$_2$C(O)NR$^7$R$^8$, amino, alkylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —N(R$^2$)C(O)R$^2$, —NHSO$_2$NR$^7$R$^8$, —N(C(O)NHR$^2$)$_2$, —NHC(O)NR$^7$R$^8$, —NHC(O)N(R$^2$)$_2$, —SO$_2$NH$_2$, —SO$_2$NHR$_2$, —SO$_2$N(R$^2$)$_2$, SO$_2$NR$^7$R$^8$, —SO$_2$NHC(O)R$^2$, —SO$_2$NHC(O)NHR$^2$, —SO$_2$NHC(O)N(R$^2$)$_2$, —SO$_2$NHC(O)NR$^7$R$^8$, cyano, tetrazol-5-yl, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, and —C(CH$_3$)$_2$C(O)OH, —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, cycloalkyl, aryl, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$;

R$^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, and —C(O)NHSO$_2$R$^2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$.

In a 64th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, alkyl, lower alkyl, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —(O(CH$_2$)$_2$)$_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, N(R$^2$)$_2$, —NR$^7$R$^8$, —N(R$^2$)C(O)R$^2$, —C(O)NH$_2$, —C(O)NHR$^2$, —C(O)N(R$^2$)$_2$, —C(O)NR$^7$R$^8$, and —C(CH$_3$)$_2$C(O)OH, —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^1$ is independently selected from the group consisting of hydrogen, lower alkyl, cycloalkyl, arylalkyl, heteroarylalkyl, and heterocyclicalkyl, wherein all may be optionally substituted by one or more selected from the group consisting of halo, lower alkyl, hydroxyalkyl, heterocyclic, amino, aminoalkyl, —$NR^7R^8$, alkoxy, —C(O)$NR^{78}$, and —C(O)N($R^2$)$_2$;

$R^2$ is independently selected from the group consisting of alkyl, lower alkyl, alkenyl, alkynyl, cycloalkyl, heteroaryl, heterocyclic, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —$NR^7R^8$, alkoxy, carboxy, carboxyalkyl, alkoxycarbonyl, —C(O)$NR^7R^8$, and —C(O)N($R^2$)$_2$;

$R^7$ and $R^8$ are independently selected from the group consisting of alkyl, alkenyl and aryl and linked together forming a 4- to 8-membered monocyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —C(O)$NH_2$, —C(O)$NHR^2$, —C(O)N($R^2$)$_2$, —C(O)$NR^7R^8$, —C(O)NHC(O)$R^2$, and —C(O)$NHSO_2R^2$;

wherein all $R^1$, $R^2$, $R^7$ and $R^8$ substituents can be optionally substituted with one or more selected from the group consisting of halo, lower alkyl, hydroxyalkyl, heterocyclic, amino, aminoalkyl, —$NR^7R^8$, —C(O)$NR^7R^8$, and —C(O)N($R^2$)$_2$.

In a 65$^{th}$ embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, lower alkyl, heteroaryl, heteroaryl lower alkyl, heterocyclic, heterocyclic lower alkyl, alkoxy, lower alkoxy, —(O($CH_2$)$_2$)$_{1-3}$—O-lower alkyl, polyoxyalkylene, heteroaryl lower alkoxy, heterocyclicalkoxy, heterocyclic lower alkoxy, —N($R^2$)C(O)$R^2$, —C(O)$NH_2$, and —C(O)$NHR^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^1$ is independently selected from the group consisting of hydrogen, and lower alkyl which may be optionally substituted by one or more selected from the group consisting of halo, lower alkyl, —$NR^7R^8$, alkoxy, —C(O)$NR^7R^8$, and —C(O)N($R^2$)$_2$;

$R^2$ is independently selected from the group consisting of alkyl, lower alkyl, alkenyl, alkynyl, heteroaryl, and heterocyclic, wherein all may be substituted by one or more selected from the group consisting of halo, lower alkyl, —$NR^7R^8$, alkoxy, carboxy, carboxyalkyl, alkoxycarbonyl, —C(O)$NR^7R^8$, and —C(O)N($R^2$)$_2$;

$R^7$ and $R^8$ are independently alkyl, and linked together forming a 5- to 7-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —C(O)$NH_2$, —C(O)$NHR^2$, —C(O)NHC(O)$R^2$, and —C(O)$NHSO_2R^2$;

wherein all $R^2$, $R^7$ and $R^8$ substituents can be optionally substituted with one or more selected from the group consisting of halo, lower alkyl, heterocyclic, amino, aminoalkyl, and —$NR^7R^8$.

In a 66th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, heteroaryl, heterocyclic, lower alkoxy, —(O($CH_2$)$_2$)$_{1-3}$—O-lower alkyl, heteroaryl lower alkoxy, heterocyclic lower alkoxy, —N($R^2$)C(O)$R^2$, —C(O)$NH_2$, and —C(O)$NHR^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —C(O)$NR^7R^8$, and —C(O)N($R^2$)$_2$;

$R^1$ is hydrogen;

$R^2$ is lower alkyl;

$R^7$ and $R^8$ are independently alkyl, and linked together forming a 6-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$; with the proviso that at least one of $R^{2\beta}$, $R^{3\beta}$, or $R^{4\beta}$ must be selected from the group consisting of —C(O)$NH_2$, —C(O)$NHR^2$, —C(O)NHC(O)$R^2$, and —C(O)$NHSO_2R^2$;

wherein all $R^2$, $R^7$ and $R^8$ substituents can be optionally substituted with one or more selected from the group consisting of heterocyclic, amino, aminoalkyl, and —$NR^7R^8$.

In a 67th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O($CH_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)$NH_2$, —OC($R^1$)$_2$C(O)$NHR^2$, —OC($R^1$)$_2$C(O)N($R^2$)$_2$, —OC($R^1$)$_2$C(O)$NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —$NHR^2$, N($R^2$)$_2$, —$NR^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —$NHSO_2NHR^2$, —$NHSO_2R^2$, —$NHSO_2NR^7R^8$, —N(C(O)$NHR^2$)$_2$, —$NR^2SO_2R^2$, —NHC(O)$NHR^2$, —NHC(O)$NR^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 68th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N($^2$)$_2$, —SO$_2$NHC(O)NR$^7$R$^8$, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of thiol, —$SC(R^1)_2C(O)OH$, —$SC(R^1)_2C(O)OR^2$, —$SCH_2C(O)OH$, —$SCF_2C(O)OH$, —$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$.

In a 69th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, alkyl, lower alkyl, alkenyl, alkynyl, carbocycle, cycloalkyl, cycloalkylalkyl, haloalkyl, heteroaryl, heteroaryl lower alkyl, heterocyclic, heterocyclic lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, polyol alkyl, alkoxy, lower alkoxy, —$(O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)N(R^2)_2$, —$OC(R^1)_2C(O)NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —$NHR^2$, $N(R^2)_2$, —$NR^7R^8$, —$N(R^2)C(O)R^2$, —$NHSO_2NR^7R^8$, —$N(C(O)NHR^2)_2$, —$NR^2SO_2R^2$, —$NHC(O)NHR^2$, —$NHC(O)NR^7R^8$, —$NHC(O)N(R^2)_2$, —$SC(R^1)_2C(O)OH$, —$SC(R^1)_2C(O)OR^2$, —$SCH_2C(O)OH$—$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, cyano, tetrazol-5-yl, —$C(O)OR^2$, —$C(O)NH_2$, —$C(O)NHR^2$, —$C(O)N(R^2)_2$, —$C(O)NR^7R^8$, —$C(O)NHC(O)R^2$, —$C(O)NHC(O)NHR^2$, —$C(O)NHC(O)N(R^2)_2$, —$C(O)NHC(O)NR^7R^8$, —$C(O)NHSO_2R^2$, —$C(O)NHSO_2NHR^2$, —$C(O)NHSO_2N(R^2)$, —$C(O)NHSO_2NR^7R^8$, —$C(CH_3)_2C(O)OH$, and —$(CH_2)_yC(O)OH$, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^1$ is independently selected from the group consisting of hydrogen, lower alkyl, cycloalkyl, arylarylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^2$ is independently selected from the group consisting of alkyl, lower alkyl, cycloalkyl, aryl, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —$SC(R^1)_2C(O)OH$, —$SC(R^1)_2C(O)OR^2$, —$SCH_2C(O)OH$, —$SO_2NH_2$, —$SO_2NHR_2$, —$SO_2N(R^2)_2$, $SO_2NR^7R^8$, —$SO_2NHC(O)R^2$, —$SO_2NHC(O)NHR^2$, —$SO_2NHC(O)N(R^2)_2$, —$SO_2NHC(O)NR^7R^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$.

In a 70th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, alkyl, lower alkyl, alkenyl, alkynyl, carbocycle, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —$(O(CH_2)_2)_{1-3}$—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, $N(R^2)_2$, —$NR^7R^8$, —$N(R^2)C(O)R^2$, —$SCH_2C(O)OH$ —$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, —$C(O)N(R^2)_2$, —$C(O)NR^7R^8$, and —$C(O)NHSO_2R^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^1$ is independently selected from the group consisting of hydrogen, lower alkyl, cycloalkyl, arylalkyl, heteroarylalkyl, and heterocyclicalkyl, wherein all may be optionally substituted by one or more selected from the group consisting of halo, lower alkyl, hydroxyalkyl, heterocyclic, amino, aminoalkyl, —$NR^7R^8$, alkoxy, —$C(O)NR^7R^8$, and —$C(O)N(R^2)_2$;

$R^2$ is independently selected from the group consisting of alkyl, lower alkyl, cycloalkyl, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —$NR^7R^8$, alkoxy, —$C(O)NR^7R^8$, and —$C(O)N(R^2)_2$;

$R^7$ and $R^8$ are independently selected from the group consisting of alkyl, alkenyl and aryl and linked together forming a 4- to 8-membered monocyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —$SC(R^1)_2C(O)OR^2$, —$SCH_2C(O)OH$, —$SO_2NH_2$, —$SO_2NHR_2$, —$SO_2N(R^2)_2$, $SO_2NR^7R^8$, —$SO_2NHC(O)R^2$, —$SO_2NHC(O)NHR^2$, —$SO_2NHC(O)N(R^2)_2$, —$SO_2NHC(O)NR^7R^8$;

wherein all $R^1$, $R^2$, $R^7$ and $R^8$ substituents can be optionally substituted with one or more selected from the group consisting of halo, alkyl, lower alkyl, hydroxyalkyl, heterocyclic, amino, aminoalkyl, —$NR^7R^8$, —$C(O)NR^7R^8$, and —$C(O)N(R^2)_2$.

In a 71st embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, lower alkyl, alkenyl, alkynyl, carbocycle, heteroaryl, heteroaryl lower alkyl, heterocyclic, heterocyclic lower alkyl, hydroxyl, alkoxy, lower alkoxy, —$(O(CH_2)_2)_{1-3}$—O-lower alkyl, polyoxyalkylene, heteroaryl lower alkoxy, heterocyclicalkoxy, heterocyclic lower alkoxy, —$N(R^2)C(O)R^2$, —$SCH_2C(O)OH$—$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, and —$C(O)NHSO_2R^2$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, —$C(O)NR^7R^8$, and —$C(O)N(R^2)_2$;

$R^1$ is independently selected from the group consisting of hydrogen and lower alkyl, which may be optionally substituted by one or more selected from the group consisting of halo, lower alkyl, —$NR^7R^8$, alkoxy, —$C(O)NR^7R^8$, and —$C(O)N(R^2)_2$;

$R^2$ is independently selected from the group consisting of alkyl and lower alkyl, which may be substituted by one or more selected from the group consisting of halo, lower alkyl, —$NR^7R^8$, alkoxy, —$C(O)NR^7R^8$, and —$C(O)N(R^2)_2$;

$R^7$ and $R^8$ are independently alkyl, and linked together forming a 5- to 7-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —$SC(R^1)_2C(O)OR^2$, —$SCH_2C(O)OH$, —$SO_2NH_2$, —$SO_2NHR_2$, —$SO_2N(R^2)_2$, $SO_2NR^7R^8$, and —$SO_2NHC(O)R^2$;

wherein all $R^1$, $R^2$, $R^7$ and $R^8$ substituents can be optionally substituted with one or more selected from the group consisting of halo, —$NR^7R^8$, —$C(O)NR^7R^8$, and —$C(O)N(R^2)_2$.

In a 72nd embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, alkenyl, alkynyl, carbocycle, heteroaryl, heterocyclic, hydroxyl, lower alkoxy, —$(O(CH_2)_2)_{1-3}$—O-lower alkyl, heteroaryl lower alkoxy, heterocyclic lower alkoxy, —$N(R^2)C(O)R^2$, —$SO_2NH_2$, —$SO_2NHR_2$, $SO_2NHC(O)R^2$, —$SR_2$, —$SO_2NHC(O)NHR^2$, —$SO_2NHC(O)N(R^2)_2$, —$SO_2NHC(O)NR^7R^8$, and —$C(O)NHSO_2R^2$, all of which can be optionally substituted by one or more selected from the group consisting of alkenyl, acyl, hydroxy, hydroxyalkyl, amino, aminoalkyl, —$NR^7R^8$, alkoxy, oxo, cyano, —$C(O)NR^7R^8$, and —$C(O)N(R^2)_2$;

$R^1$ is hydrogen;

$R^2$ is lower;

$R^7$ and $R^8$ are independently alkyl, and linked together forming a 6-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —$OCH_3$;

with the proviso that at least one of $R^{2\beta}$, $R^{3\beta}$, or $R^{4\beta}$ must be selected from the group consisting of —$SC(R^1)_2C(O)OR^2$, —$SO_2NH_2$, —$SO_2NR^7R^8$, and —$SO_2NHC(O)R^2$.

In a 73rd embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-$S(O)_2$-lower alkyl, arylsulfinyl lower alkyl, arylsulfonyl lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —$(O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)OH$, —$OC(R^1)_2C(O)OR^2$, —$OC(R^1)_2C(O)NH_2$, —$OC(R^1)_2C(O)NHR^2$, —$OC(R^1)_2C(O)N(R^2)_2$, —$OC(R^1)_2C(O)NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —$NHR^2$, $N(R^2)_2$, —$NR^7R^8$, —$NHC(R^1)_2C(O)OH$, —$NHC(R^1)_2C(O)OR^2$, —$NHC(O)R^2$, —$N(R^2)C(O)R^2$, —$NHC(O)OR^2$, —$NHC(O)SR^2$, —$NHSO_2NHR^2$, —$NHSO_2R^2$, —$NHSO_2NR^7R^8$, —$N(C(O)NHR^2)_2$, —$NR^2SO_2R^2$, —$NHC(O)NHR^2$, —$NHC(O)NR^7R^8$, —$NHC(O)N(R^2)_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —$SC(R^1)_2C(O)OH$, —$SC(R^1)_2C(O)OR^2$, —$SCH_2C(O)OH$, —$SCF_2C(O)OH$, —$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, sulfonic acid, sulfonate, sulfate, sulfinic acid, sulfenic acid, cyano, tetrazol-5-yl, carboxy, —$C(O)OR^2$, —$C(O)NH_2$, —$C(O)NHR^2$, —$C(O)N(R^2)_2$, —$C(O)NR^7R^8$, —$C(O)NHC(O)R^2$, —$C(O)NHC(O)NHR^2$, —$C(O)NHC(O)N(R^2)_2$, —$C(O)NHC(O)NR^7R^8$, —$C(O)NHSO_2R^2$, —$C(O)NHSO_2NHR^2$, —$C(O)NHSO_2N(R^2)$, —$C(O)NHSO_2NR^7R^8$, —$C(CH_3)_2C(O)OH$, —$(CH_2)_yC(O)OH$, wherein y is 1, 2, 3, 4, 5, or 6, —$PO_2H_2$, —$PO_3H_2$, —$P(R^2)O_2H$, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 74$^{th}$ embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, —O(CH$_2$)$_2$)$_{1-3}$—O-lower alkyl, heteroaryl lower alkoxy, heterocyclic lower alkoxy, , all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is lower alkyl optionally substituted by alkoxycarbonyl.

R$^7$ and R$^8$ are independently alkyl, and linked together forming a 6-membered monocyclic ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\beta}$, R$^{3\beta}$, or R$^{4\beta}$ must be selected from the group consisting of amino, —N(C(O)NHR$^2$)$_2$, NR$^2$SO$_2$R$^2$ and —NR$^2$SO$_2$R$^2$;

wherein all R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 75th embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently selected from the group consisting of alkyl, alkenyl and aryl and linked together forming a 4- to 12-membered monocyclic, bicylic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$;

with the proviso that at least one of $R^{2\beta}$, $R^{3\beta}$, or $R^{4\beta}$ must be selected from the group consisting of —OC(R$^1$)$_2$C(O) OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 76th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, heteroaryl, heterocyclic, lower alkoxy, —(O(CH$_2$)$_2$)$_{1-3}$—O-lower alkyl, heteroaryl lower alkoxy, heterocyclic lower alkoxy, —OC(R$^1$)$_2$C(O)OH, —OC(R$^1$)$_2$C(O)N(R$^2$)$_2$, —OC(R$^1$)$_2$C(O)NR$^7$R$^8$, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is hydrogen or lower alkyl optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^2$ is lower alkyl optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently alkyl, and linked together forming a 6-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$;

with the proviso that at least one of $R^{2\beta}$, $R^{3\beta}$, or $R^{4\beta}$ must be selected from —OC(R$^1$)$_2$C(O)OH;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 77th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$; and/or $R^{2\beta}$ and $R^{3\beta}$ taken together or $R^{3\beta}$ and $R^{4\beta}$ taken together or $R^{4\beta}$ and $R^{5\beta}$ taken together, or $R^{2\alpha}$ and $R^{3\alpha}$ taken together $R^{3\alpha}$ and $R^{4\alpha}$ taken together, or $R^{4\alpha}$ and $R^{5\alpha}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; and/or at least one of $R^{2\beta}$, $R^{3\beta}$, or $R^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 78th embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, heteroaryl, heterocyclic, lower alkoxy, (O(CH$_2$)$_2$)$_{1-3}$—O-lower alkyl, heteroaryl lower alkoxy, heterocyclic lower alkoxy, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently alkyl or lower alkyl;

R$^7$ and R$^8$ are independently selected from the group consisting of alkyl, linked together forming a 6-membered monocyclic ring;

wherein one of $R^{4\alpha}$, $R^{5\alpha}$ or $R^{6\alpha}$ must be a carbon-carbon linked heterocyclic or heteroaryl, and only one of $R^{2\beta}$, $R^{3\beta}$, $R^{4\beta}$, $R^{5\beta}$ or $R^{6\beta}$ can be —OCH$_3$; and/or $R^{3\beta}$ and $R^{4\beta}$ taken together or $R^{4\beta}$ and $R^{5\beta}$ taken together, or $R^{3\alpha}$ and $R^{4\alpha}$ taken together or $R^{4\alpha}$ and $R^{5\alpha}$ taken together form a heterocyclic ring optionally substituted by one or more alkoxycarbonylalkyl, carboxyalkyl, or hydroxyalkyl groups.

In a 79$^{th}$ embodiment, the invention is represented by Formula I or its pharmaceutically acceptable salt or ester, wherein:

$R^{2\beta}$, $R^{3\beta}$, $R^{4\beta}$, $R^{5\beta}$, $R^{6\beta}$, $R^{2\alpha}$, $R^{3\alpha}$, $R^{4\alpha}$, $R^{5\alpha}$ and $R^{6\alpha}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$; and/or R$^{2\beta}$ and R$^{3\beta}$ taken together or R$^{3\beta}$ and R$^{4\beta}$ taken together or R$^{4\beta}$ and R$^{5\beta}$ taken together or R$^{2\alpha}$ and R$^{3\alpha}$ taken together or R$^{3\alpha}$ and R$^{4\alpha}$ taken together or R$^{4\alpha}$ and R$^{5\alpha}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ cannot be —OC(R$^1$)$_2$C(O)OH; and/or at least one of R$^{2\beta}$, R$^{3\beta}$, or R$^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$, wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

In a 80$^{th}$ embodiment, the invention is represented by Formula I or its pharmaceutically acceptable salt or ester, wherein:

R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ are independently selected from the group consisting of hydrogen, halogen, heteroaryl, heterocyclic, lower alkoxy, (O(CH$_2$)$_2$)$_{1-3}$—O-lower alkyl, heteroaryl lower alkoxy, heterocyclic lower alkoxy, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —(O)N(R$^2$)$_2$;

R$^2$ is independently alkyl or lower alkyl;

R$^7$ and R$^8$ are independently selected from the group consisting of alkyl, linked together forming a 6-membered monocyclic ring;

wherein one of R$^{4\alpha}$, R$^{5\alpha}$ or R$^{6\alpha}$ must be a carbon-carbon linked heterocyclic or heteroaryl, and only one of R$^{2\beta}$, R$^{3\beta}$, R$^{4\beta}$, R$^{5\beta}$ or R$^{6\beta}$ can be —OCH$_3$; and/or R$^{3\beta}$ and R$^{4\beta}$ taken together or R$^{4\beta}$ and R$^{5\beta}$ taken together or R$^{3\alpha}$ and R$^{4\alpha}$ taken together or R$^{4\alpha}$ and R$^{5\alpha}$ taken together form a 5-membered ring containing one nitrogen, which may optionally be substituted with one or more selected from the group consisting of alkyl, lower alkyl, cycloalkyl, hydroxyalkyl, aminoalkyl, carboxyalkyl, alkoxycarbonyl; provided that R$^{2\beta}$, R$^{3\beta}$, R$^{4\beta}$, R$^{5\beta}$, R$^{6\beta}$, R$^{2\alpha}$, R$^{3\alpha}$, R$^{4\alpha}$, R$^{5\alpha}$ and R$^{6\alpha}$ cannot be —OC(R$^1$)$_2$COOH.

As an 81$^{st}$ embodiment, the invention is a pharmaceutical composition comprising any of the above 80 embodiments or any of the specific Examples below together with one or more pharmaceutically acceptable carriers.

An 82$^{nd}$ embodiment includes embodiments 1–80 above or any of the Examples as a means to treat or prophylactically treat an inflammatory disorder including arthritis, rheumatoid arthritis, asthma, diabetic retinopathy, diabetic nephropathy, diabetic vasculopathy, multiple sclerosis, allergic rhinitis, chronic obstructive pulmonary disease, systemic lupus erthematosus, atherosclerosis, and restinosis.

A further embodiment includes the intermediates used to make the final compounds of the invention. Said intermediates are useful as starting materials for making the compounds of the invention as well as having pharmaceutical activity alone.

Another embodiment of the invention includes the process for making both the intermediates as well as the final compounds.

Definitions

A wavy line used as a bond "〰", denotes a bond which can be either the E- or Z-geometric isomer.

When not used as a bond, the wavy line indicates the point of attachment of the particular substituent.

The terms "alkyl" or "alk", alone or in combination, unless otherwise specified, refers to a saturated straight or branched primary, secondary, or tertiary hydrocarbon from 1 to 10 carbon atoms, including, but not limited to methyl, ethyl, propyl, isopropyl, butyl, isobutyl, t-butyl, and sec-butyl. The term "lower alkyl" alone or in combination refers to an alkyl having from 1 to 4 carbon atoms. The alkyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are CF$_3$ and CH$_2$CF$_3$.

The term "alkenyl", alone or in combination, means a non-cyclic alkyl of 2 to 10 carbon atoms having one or more unsaturated carbon-carbon bonds. The alkenyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

The term "alkynyl", alone or in combination, means a non-cyclic alkyl of 2 to 10 carbon atoms having one or more triple carbon-carbon bonds, including but not limited to ethynyl and propynyl. The alkynyl group may be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene et al., *Protective Groups in Organic Synthesis*, John Wiley & Sons, Second Edition, 1991, hereby incorporated by reference. Specifically included are $CF_3$ and $CH_2CF_3$.

The terms "carboxy", "COOH" and "C(O)OH" are used interchangeably.

The terms "alkoxycarbonyl" and "carboalkoxy" are used interchangeably. Used alone or in combination, the terms mean refer to the radical —C(O)OR, wherein R is alkyl as defined herein.

The term "thio", alone or in combination, means the radical —S—.

The term "thiol", alone or in combination, means the radical —SH.

The term "hydroxy", alone or in combination means the radical —OH.

The term "sulfonyl", alone or in combination means the radical —S(O)$_2$—.

The term "oxo" refers to an oxygen attached by a double bond (═O).

The term "carbocycle", alone or in combination, means any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

The term "cycloalkyl", alone or in combination, means a saturated or partially unsaturated cyclic alkyl, having from 1 to 10 carbon atoms, including but not limited to mono- or bi-cyclic ring systems such as cyclopropyl, cyclobutyl, cyclopentyl, cyclohexenyl, and cyclohexyl.

The term "aryl", alone or in combination, means a carbocyclic aromatic system containing one, two or three rings wherein such rings may be attached together in a pendent manner or may be fused. The aryl group can be optionally substituted with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art, for example, as taught in Greene, et al., "Protective Groups in Organic Synthesis", John Wiley and Sons, Second Edition, 1999. In addition, adjacent groups on an aryl ring may combine to form a 5- to 7-membered saturated or partially unsaturated carbocyclic, aryl, heteroaryl or heterocyclic ring, which in turn may be substituted as above.

The term "heterocyclic", alone or in combination, refers to a nonaromatic cyclic group that may be partially (containing at least one double bond) or fully saturated and wherein the ring contains at least one heteroatom selected from oxygen, sulfur, nitrogen, or phosphorus. The terms "heteroaryl" or "heteroaromatic", alone or in combination, refer to an aromatic ring containing at least one heteroatom selected from sulfur, oxygen, nitrogen or phosphorus. The heteroaryl or heterocyclic ring may optionally be substituted by one or more substituent listed as optional substituents for aryl. In addition, adjacent groups on the heteroaryl or heterocyclic ring may combine to form a 5- to 7-membered carbocyclic, aryl, heteroaryl or heterocyclic ring, which in turn may be substituted as above. Nonlimiting examples of heterocylics and heteroaromatics are pyrrolidinyl, tetrahydrofuryl, tetrahydrofuranyl, pyranyl, purinyl, tetrahydropyranyl, piperazinyl, piperidinyl, morpholino, thiomorpholino, tetrahydropyranyl, imidazolyl, pyrolinyl, pyrazolinyl, indolinyl, dioxolanyl, or 1,4-dioxanyl. aziridinyl, furyl, furanyl, pyridyl, pyridinyl, pyridazinyl, pyrimidinyl, benzoxazolyl, 1,2,4-oxadiazolyl, 1,3,4-oxadiazolyl, 1,3,4-thiadiazole, indazolyl, triazinayl, 1,3,5-triazinyl, thienyl, isothiazolyl, imidazolyl, tetrazolyl, pyrazinyl, benzofuranyl, quinolyl, isoquinolyl, benzothienyl, isobenzofuryl, pyrazolyl, indolyl, isoindolyl, benzimidazolyl, purinyl, carbazolyl, oxazolyl, thiazolyl, benzothiazolyl, isothiazolyl, 1,2,4-thiadiazolyl, isooxazolyl, 1,2,4-oxadiazolyl, 1,3,4-oxadiazolyl, pyrrolyl, quinazolinyl, quinoxalinyl, benzoxazolyl, quinolinyl, isoquinolinyl, cinnolinyl, phthalazinyl, xanthinyl, hypoxanthinyl, pyrazole, imidazole, 1,2,3-triazole, 1,2,4-triazole, 1,2,3-oxadiazole, thiazine, pyridazine, triazolopyridinyl or pteridinyl wherein said heteroaryl or heterocyclic group can be optionally substituted with one or more substituent selected from the same substituents as set out above for aryl groups. Functional oxygen and nitrogen groups on the heteroaryl group can be protected as necessary or desired. Suitable protecting groups can include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl.

The term "thienyl", alone or in combination, refers to a five member cyclic group wherein the ring contains one sulfur atom and two double bonds.

The term "benzothienyl", alone or in combination, refers to a five member cyclic group wherein the ring contains one sulfur atom and two double bonds fused to a phenyl ring.

The term "aryloxy", alone or in combination, refers to an aryl group bound to the molecule through an oxygen atom.

The term "heteroaryloxy", alone or in combination, refers to a heteroaryl group bound to the molecule through an oxygen atom.

The term "aralkoxy", alone or in combination, refers to an aryl group attached to an alkyl group which is attached to the molecule through an oxygen atom.

The term "heterocyclearalkoxy" refers to a heterocyclic group attached to an aryl group attached to an alkyl-O-group. The heterocyclic, aryl and alkyl groups can be optionally substituted as described above.

The terms "halo" and "halogen", alone or in combination, refer to chloro, bromo, iodo and fluoro.

The terms "alkoxy" or "alkylthio", alone or in combination, refers to an alkyl group as defined above bonded through an oxygen linkage (—O—) or a sulfur linkage (—S—), respectively. The terms "lower alkoxy" or "lower alkylthio", alone or in combination, refers to a lower alkyl group as defined above bonded through an oxygen linkage (—O—) or a sulfur linkage (—S—), respectively.

The term "acyl", alone or in combination, refers to a group of the formula C(O)R', wherein R' is an alkyl, aryl, alkaryl or aralkyl group, or substituted alkyl, aryl, aralkyl or alkaryl, wherein these groups are as defined above.

The term "acetyl", alone or in combination, refers to the radical —C(O)CH$_3$.

The term "amino", alone or in combination, denotes the radical —NH$_2$ or —NH—.

The term "nitro", alone or in combination, denotes the radical —NO$_2$.

The term "substituted", means that one or more hydrogen on the designated atom or substituent is replaced with a selection from the indicated group, provided that the designated atom's normal valency is not exceeded, and the that the substitution results in a stable compound. When a subsitutent is "oxo" (keto) (i.e., =O), then 2 hydrogens on the atom are replaced.

The term "alditol", as referred to herein, and unless otherwise specified, refers to a carbohydrate in which the aldehyde or ketone group has been reduced to an alcohol moiety. The alditols of the present invention can also be optionally substituted or deoxygenated at one or more positions. Exemplary substituents include hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, amino acid, amino acid esters and amides, phosphonyl, phosphinyl, phosphoryl, thioester, thioether, oxime, hydrazine, carbamate, phosphonic acid, and phosphonate,. Particular exemplary substituents include amine and halo, particularly fluorine. The substituent or alditol can be either unprotected, or protected as necessary, as known to those skilled in the art, for example, as taught in Greene, et al., *Protective Groups in Organic Synthesis*, John Wiley and Sons, Second Edition, 1999, hereby incorporated by reference. The alditol may have 3, 4, 5, 6 or 7 carbons. Examples of useful alditols are those derived from reduction of monosaccharides, including specifically those derived from the reduction of pyranose and furanose sugars.

The term "carbohydrate", as referred to herein, and unless otherwise specified, refers to a compound of carbon, hydrogen and oxygen that contains an aldehyde or ketone group in combination with at least two hydroxyl groups. The carbohydrates of the present invention can also be optionally substituted or deoxygenated at one or more positions. Carbohydrates thus include substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars.

As used herein, the term "patient" refers to warm-blooded animals or mammals, and in particular humans, who are in need of the therapy described herein. The term "host", as used herein, refers to a unicellular or multicellular organism, including cell lines and animals, and preferably a human.

Synthesis of the Active Compounds

The compounds of the present invention can be readily prepared by those skilled in the art of organic synthesis using commonly known methods, many of which are described by J, March, in *Advanced Organic Chemistry*, 4$^{th}$ Edition (Wiley Interscience, New York, 1992) and D. N. Dnar in *The Chemistry of Chalcones and Related Compounds* (Wiley-Interscience, New York, 1981), incorporated herein by reference.

Compounds of the present invention are prepared either by reacting a heteroaryl- or heterocyclic-substituted aryl or heteroaryl ketone with a suitably substituted aryl aldehyde or by reacting a suitably substituted aryl ketone with a heteroaryl- or heterocyclic-substituted aryl or heteroaryl aldehyde. This reaction, which is a condensation reaction, is suitably carried out under base- or acid-catalyzed conditions. The reaction may be suitably carried out in water or protic organic solvents such as lower alcohols (e.g. methanol, ethanol, tert-butanol), lower carboxylic acid (e.g. formic acid, glacial acetic acid, propionic acid), or in aprotic organic solvents such as ethers (e.g. tetrahydrofuran, dioxane, diethyl ether), liquid amides (e.g. dimethylformamide, hexamethylphosphordiamide), dimethylsulfoxide, or hydrocarbons (e.g. toluene, benzene), or mixtures of such solvents. When carrying out the reaction under basic conditions, the base may be selected from sodium, lithium, potassium, barium, calcium, magnesium, aluminum, ammonium, or quarternary ammonium hydroxides, lower alkoxides (e.g. methoxides, ethoxides, tert-butoxides), carbonates, borates, oxides, hydrides, or amides of lower secondary amines (e.g. diisopropyl amides, methylphenyl amides). Primary aromatic amines such as aniline, free secondary amines such as dimethyl amine, diethyl amine, piperidine, or pyrrolidine, tertiary amines such as pyridine, as well as basic ion exchange resins may also be used. Alternatively, a phase-transfer catalyst such as cetyl trimethyl ammonium chloride can also be used to facilitate the reaction, particularly when water is the solvent.

Alternatively, the aldol condensation reaction can also be carried out in an aprotic solvent such as tetrahydrofuran (THF) with an organic base. The preferred solvent is THF and the preferred base is lithium diisopropylamide (LDA). In this manner an aldol reaction may take place first and the subsequent dehydration reaction may take place during an aqueous workup.

Acid catalysts may be selected from hydrogen chloride, hydrogen bromide, hydrogen iodide, sulfuric acid, sulfonic acids (such as paratoluenesulfonic or methansulfonic acid), lower carboxylic acid (such as formic, acetic, or propionic acid), lower halogenated carboxylic acid (such as trifluoroacetic acid), Lewis acids (such as BF$_3$, POCl$_3$, PCl$_5$, FeCl$_3$), or acid ion exchange resins.

The reaction may be carried out at temperatures in the range of −80° C. to +150° C., preferably in the range of 0°

C. to +100° C., and more preferably at room temperature. The time of reaction may be from 30 minutes to approximately 24 hours.

Compounds of the invention may be isolated as either mixtures of cis (Z) and trans (E) geometric isomers or either pure trans (E) isomers. If desired, either the mixtures or the pure trans isomers may be isomerized to the corresponding predominantly cis (Z) iomers using methods well known in the literature.

In the above reactions, it may be preferred or necessary to protect various sensitive or reactive groups present in the starting materials so as to prevent said groups from interfering with the reactions. Such protection may be carried out in a well-known manner as taught by Theodora W. Green and Peter G. M. Wuts, in *Protective Groups in Organic Chemistry Third Edition* (Wiley, 1999) or using methods from references cited therein or of the like. The protecting group may be removed after the reaction in a manner known per se.

The following schemes will prove useful to those skilled in the art in manufacturing the compounds of the invention:

Legend for all Schemes:
1. R, R', R'', R''', and R'''' can be any substitution including H;
2. R, R', R'', R''', and R'''' can be suitably functionalized;
3. R, R', R'', R''', and R'''' can represent multiple substitutions;
4. Two adjacent R, R', R'', R''', or R'''' can form a ring;
5. Dashed double bond can be at any location of a ring;
6. Y, Y', Y'', and Y''' independently represent N(H), O, or S,
7. X and X' independently represent Cl, Br, or I;
8. Each R, R', R'', R''', R'''', Y, Y', Y'', Y''', X or X' is independent in each scheme;
9. HetAr represents suitably substituted heterocyclic aryl;
10. Cy represents cyclohexyl.

Scheme 1

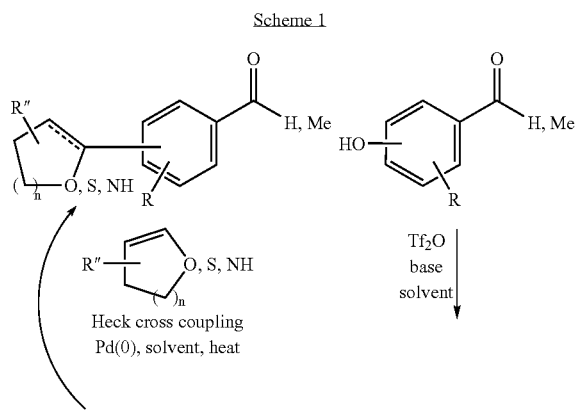

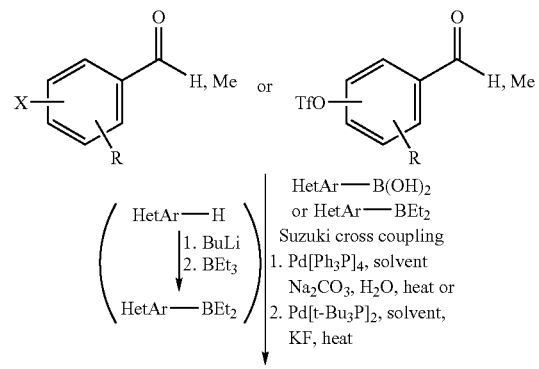

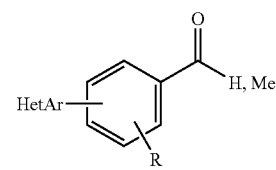

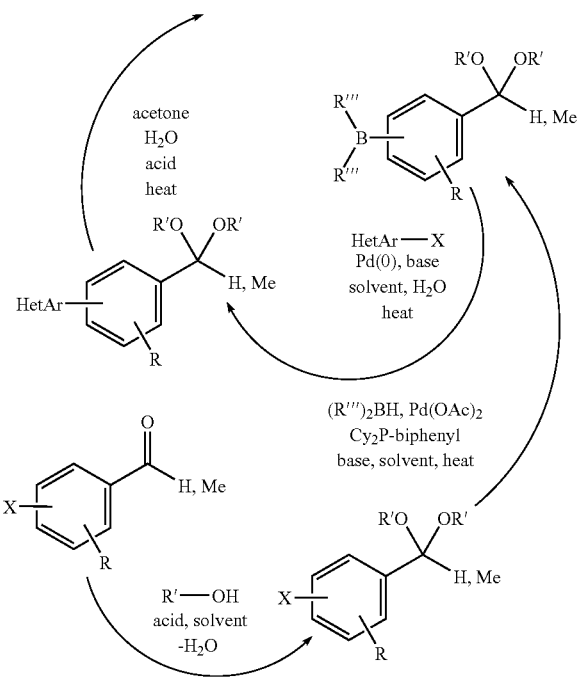

Scheme 2
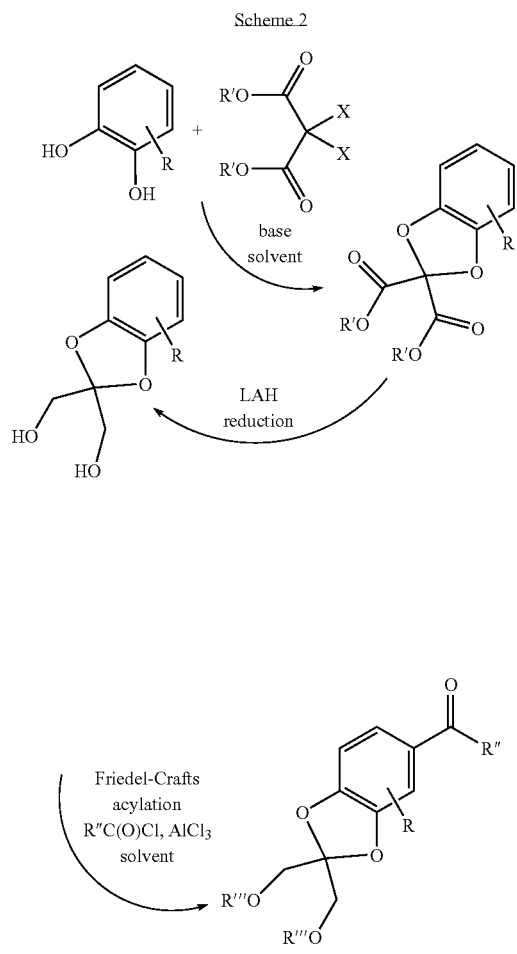
Scheme 3
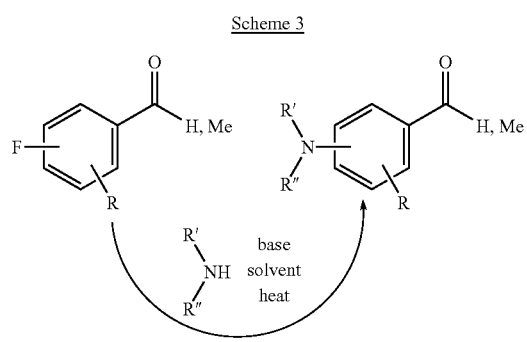
Scheme 4
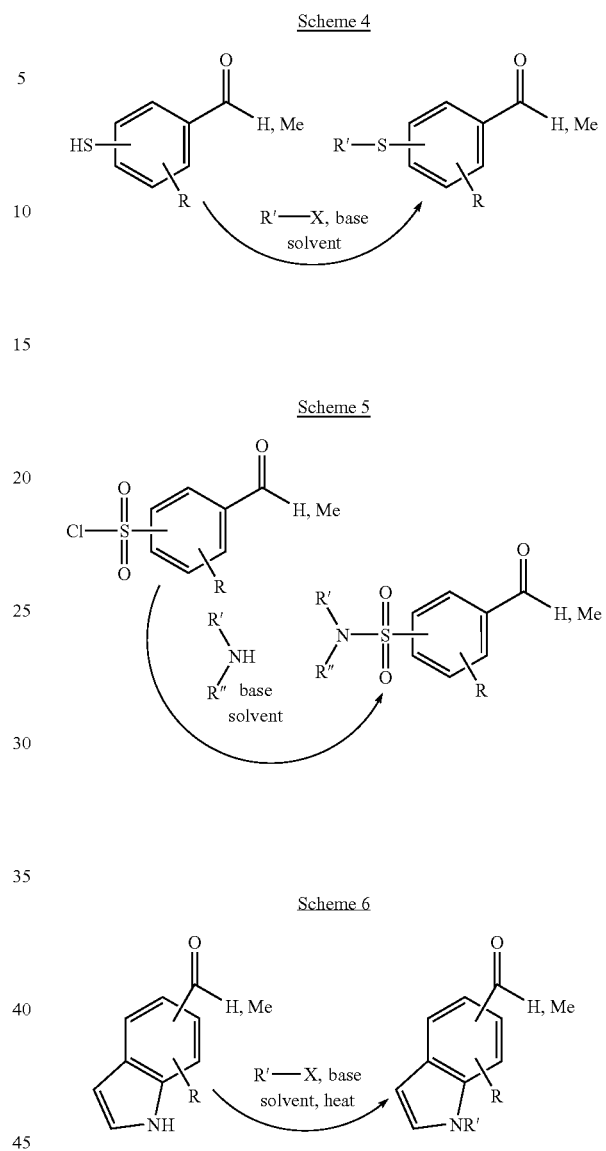
Scheme 5
Scheme 6
Scheme 7
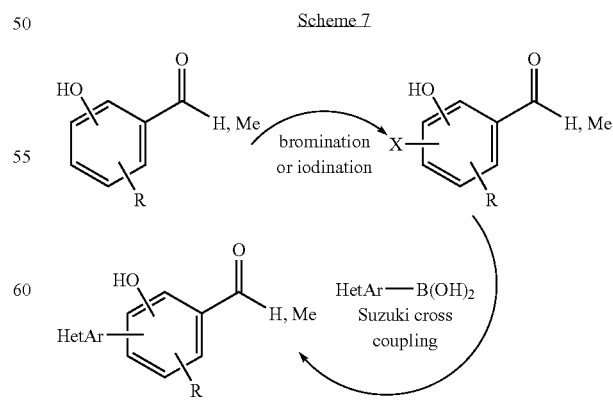

-continued
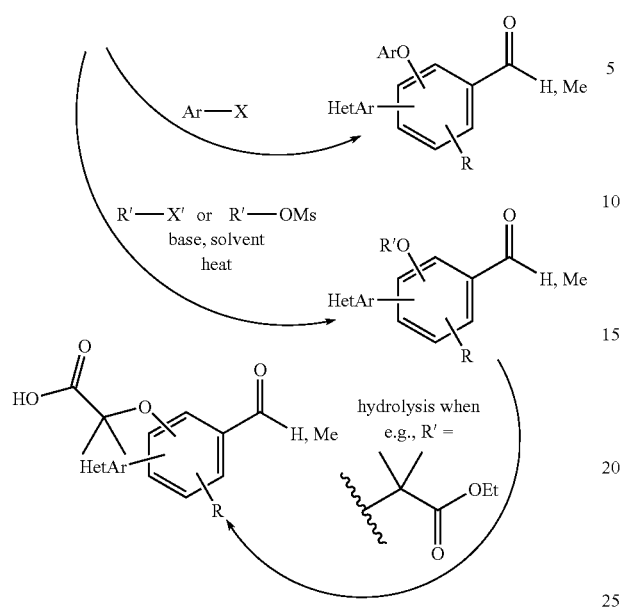
Scheme 8
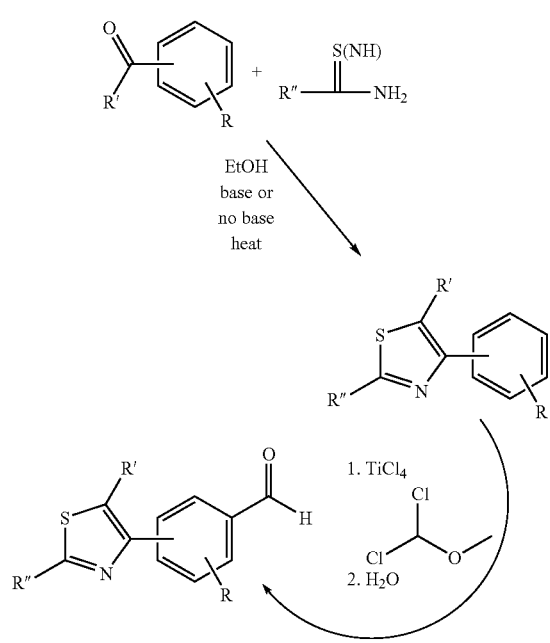
Scheme 9
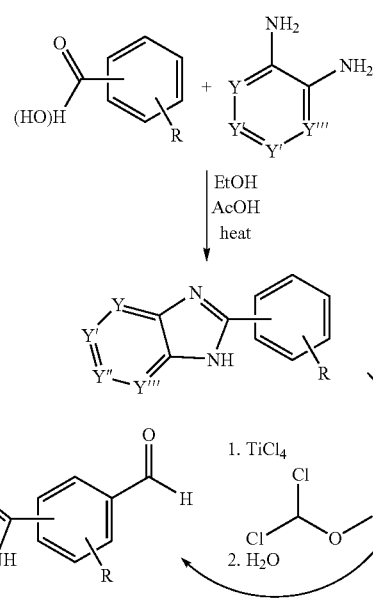
Scheme 10
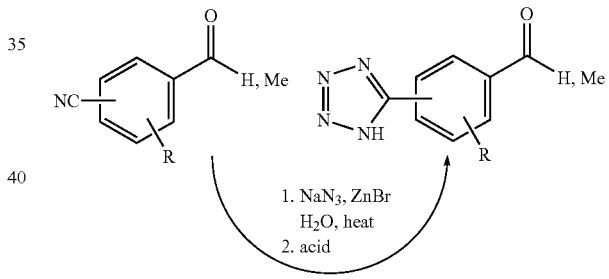
Scheme 11
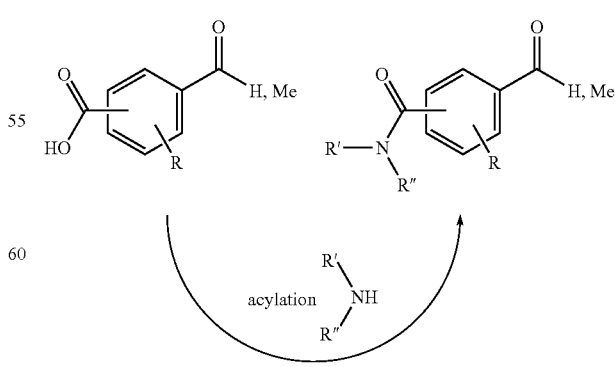

Scheme 12
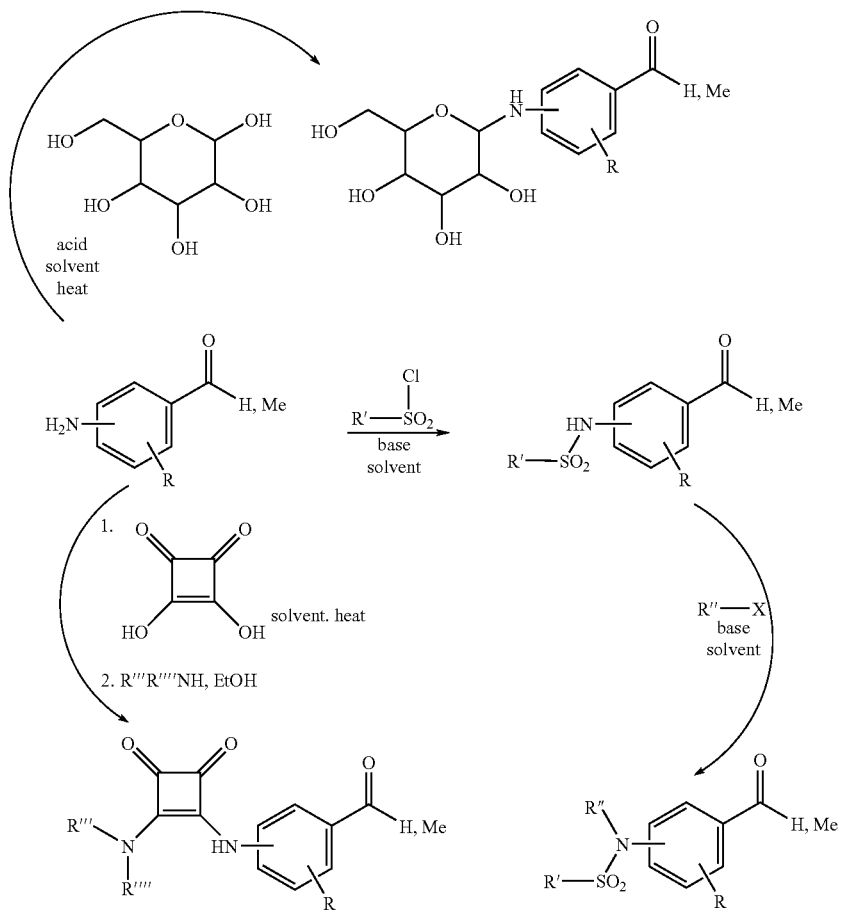
Scheme 13
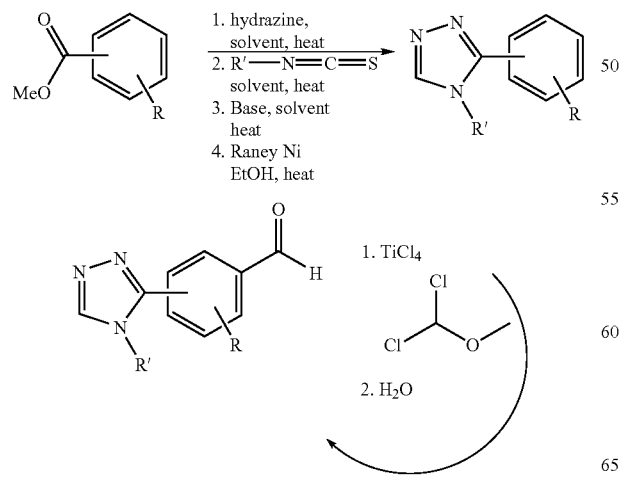
Scheme 14
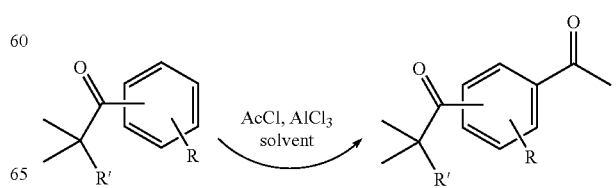

Scheme 15
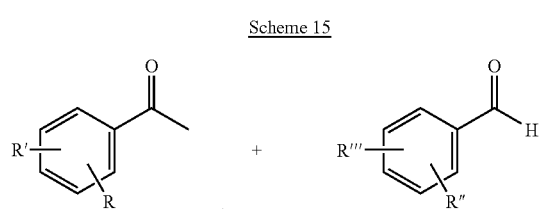
1. NaOH, DMF, H₂O or
2. LiOMe, MeOH, DMF or
3. Surfactant, base, H₂O
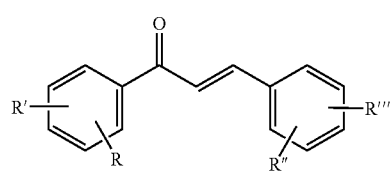
Scheme 16
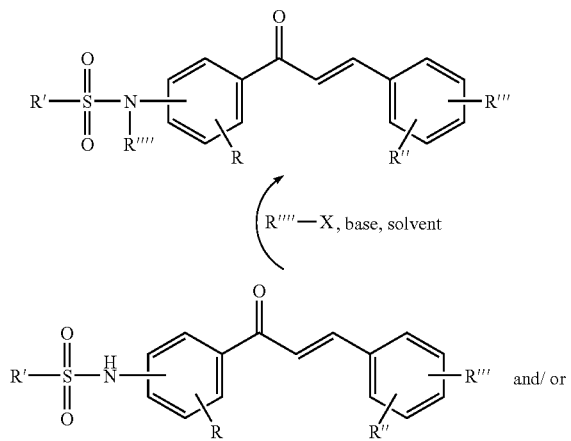
Scheme 17
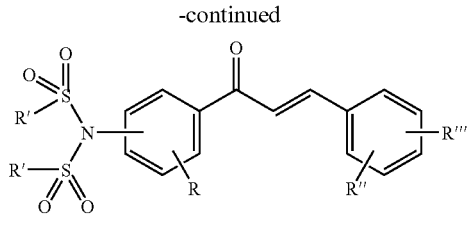
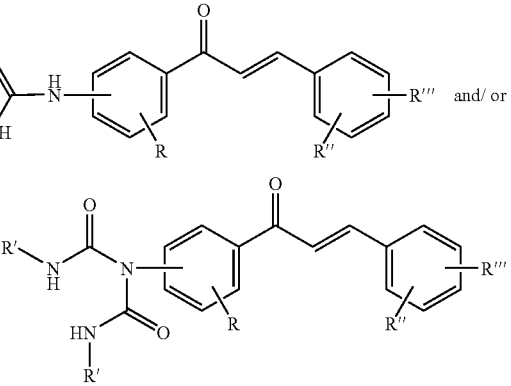
and/ or
Scheme 18
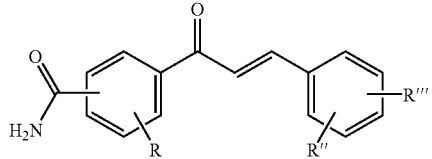
and/ or

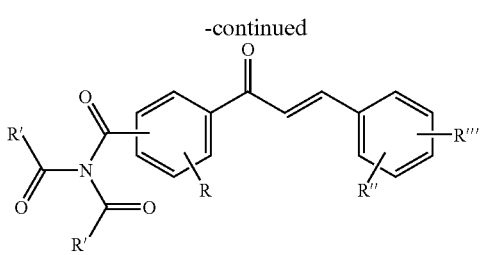

Scheme 19

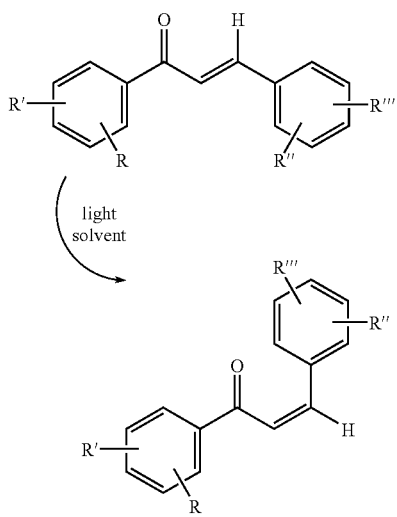

EXAMPLES

The following examples are understood to be illustrative only and are not intended to limit the scope of the present invention in any way. All intermediates and final products have been completely characterized by conventional proton NMR, mass spectral analyses and standard analytical methods known to those skilled in the art.

Example 1

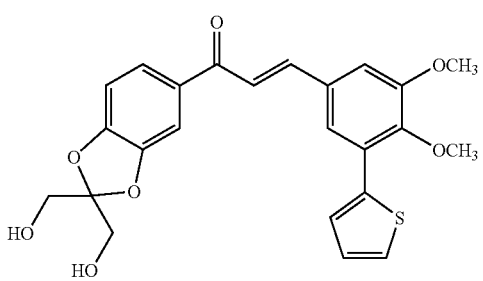

1-(2,2-Bis-hydroxymethyl-benzo[1,3]dioxol-5-yl)-3E-(3,4-dimethoxy-5-thiophen-2-yl-phenyl)-propenone Ex-1A: Catechol (2.2 g, 20 mmol) was dissolved in acetone. Diethyl dibromomalonate (7.0 g, 22 mmol) and potassium carbonate (2.76 g) were added, and the mixture was stirred at room temperature overnight. The solvent was removed under reduced pressure, and water was added to the residue. The residue was extracted with dichloromethane, and the organic phase was washed with brine, dried over magnesium sulfate and evaporated. Chromatography (hexanes/ethyl acetate, 4:1) gave 3.9 g of benzo[1,3]dioxole-2,2-dicarboxylic acid diethyl ester. $^1$H-NMR (CDCl$_3$) δ 6.90–6.97 (m, 4H), 4.37 (q, J=7 Hz, 4H), 1.32 (t, J=7 Hz, 6H).

Ex-1B: [Bis(ethoxycarbonyl)methyldenedioxy]benzene obtained from Ex-1A (3.9 g, 14.7 mmol) was dissolved in THF (100 mL) and cooled with ice-water. Lithium aluminum hydride (1 M solution in THF, 44 mL) was added dropwise, and the mixture was stirred overnight. The reaction was carefully quenched with saturated sodium sulfate until there was no further bubbling. The mixture was stirred overnight, then filtered, and the filtrate was dried over magnesium sulfate. Chromatography (dichloromethane/methanol, 10:1) gave 0.5 g of the desired (2-hydroxymethyl-benzo[1,3]dioxol-2-yl)-methanol. $^1$H-NMR (CDCl$_3$) δ 6.82 (s, 4H), 3.94 (d, J=7 Hz, 4H), 1.98 (t, J=7 Hz, 2H).

Ex-1C: Aluminum chloride (1.3 g) was added to nitromethane followed by the addition of acetyl chloride (1.86 g). Then (2-hydroxymethyl-benzo[1,3]dioxol-2-yl)-methanol obtained from Ex-1B (0.5 g) in nitromethane was added dropwise. The mixture was stirred overnight. Water was added to the reaction mixture, and it was extracted with dichloromethane. The organic phase was washed with brine, dried over magnesium sulfate and evaporated. Chromatography gave 0.28 g of 5-acetyl-benzo[1,3]dioxole-2,2-dicarboxylic acid diethyl ester. $^1$H-NMR (CDCl$_3$) δ 7.56 (d, J=7 Hz, 1H), 7.43 (s, 1H), 6.85 (d, J=7 Hz, 1H), 4.42 (s, 4H), 2.53 (s, 3H), 2.05 (s, 6H).

Ex-1D: A solution of 5-bromo-3,4-dimethoxybenzaldehyde (10.23 g, 41.7 mmol) in 359 mL of ethylene glycol dimethyl ether was purged with nitrogen gas for 30 min. The solution was treated with tetrakis(triphenylphosphine)palladium(0) (5.0 g, 4.3 mmol), thiophene-2-boronic acid (8.01 g, 62.6 mmol), and a solution of 2 N sodium carbonate 72 mL, 3.45 mmol). The reaction was refluxed for 16 h. The reaction mixture was concentrated, diluted with an aqueous solution of saturated sodium bicarbonate (75 mL), and extracted with dichloromethane (2×100 mL). The organic layer was dried over sodium sulfate and concentrated to a brown solid. The crude material was purified by silica gel chromatography (1:1 ethyl acetate/hexanes) to give 9.42 g (90%) of the desired 3,4-dimethoxy-5-(thien-2-yl)benzaldehyde product. $^1$H-NMR (300 MHz, CDCl$_3$) δ 9.94 (s, 1H), 7.79 (d, 1H), 7.57 (dd, 1H), 7.41 (d, 1H), 7.36 (d, 1H), 7.13 (dd, 1H), 3.97 (s, 3H), 3.93 (s, 3H).

5-Acetyl-benzo[1,3]dioxole-2,2-dicarboxylic acid diethyl ester obtained from Ex-1C (0.28 g, 1.11 mmol) and 3,4-dimethoxy-5-(thien-2-yl)benzaldehyde obtained from Ex-1D (0.275 g, 1.11 mmol) were dissolved in ethanol, and 50% sodium hydroxide solution (0.4 mL) was added. The mixture was stirred at room temperature overnight. Most of the solvent was removed under reduced pressure, and water was added to the remainder. The resulting product was extracted with dichloromethane. The organic phase was dried over magnesium sulfate and evaporated. Chromatography gave 0.19 g (38%) of the title compound as a yellow solid, m.p. 74–80° C. $^1$H-NMR (300 MHz, CDCl$_3$) δ 7.74 (d, 1H), 7.63 (dd, 1H), 7.49–7.55 (m, 3H), 7.38 (d, 1H), 7.37 (d, 1H), 7.12 (dd, 1H), 7.07 (d, 1H), 6.88 (d, 1H), 3.99 (s, 4H), 3.99 (s, 4H), 3.98 (s, 3H), 3.88 (s, 3H). Anal. Calculated for C$_{24}$H$_{22}$O$_7$S: C, 63.42; H, 4.88; S, 7.06; found: C, 63.46; H, 5.11; S, 6.55.

Example 2

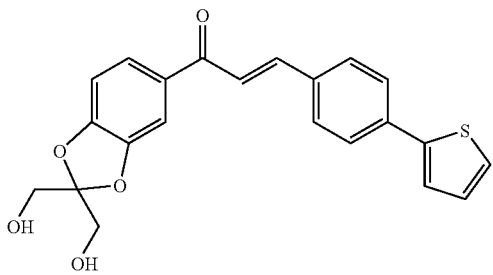

1-(2,2-Bis-hydroxymethyl-benzo[1,3]dioxol-5-yl)-
3E-(4-thiophen-2-yl-phenyl)-propenone Ex-2A: 4-(Thien-2-yl)benzaldehyde was obtained in a similar manner as described in Ex-1D from 4-bromobenzaldehyde. $^1$H-NMR (CDCl$_3$) δ 10.00 (s, 1H), 7.88 (d, J=9 Hz, 2H), 7.77 (d, J=9 Hz, 2H), 7.46 (d, J=4 Hz, 1H), 7.39–7.41 (m, 1H), 7.12–7.15 (m, 1H).

The title compound was obtained when 5-acetyl-benzo[1,3]dioxole-2,2-dicarboxylic acid diethyl ester from Ex-1C was condensed with 4-(Thien-2-yl)benzaldehyde from Ex-2A in a similar manner as described in Ex-1. Yellow solid, mp 166–168° C., 23.6% yield. $^1$H-NMR (CDCl$_3$) δ 7.77 (d, J=15 Hz, 1H), 7.60–7.65 (m, 5H), 7.51 (d, J=2 Hz, 1H), 7.45 (d, J=15 Hz, 1H), 7.37–7.38 (m, 1H), 7.32 (d, J=5 Hz, 1H), 7.09 (dd, J=4, 5 Hz, 1H), 6.88 (d, J=8 Hz, 1H), 3.96 (d, J=7 Hz, 4H). MS m/z=394 ([M]$^+$, 50%), 363 (100%). HRMS (EI) Calcd. for C$_{22}$H$_{18}$O$_5$S: 394.0875. Found: 394.0869.

Example 3

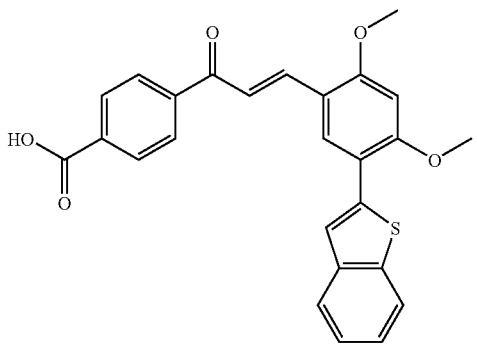

4-[3E-(5-Benzo[b]thien-2-yl-2,4-dimethoxyphenyl)-acryloyl]-benzoic acid

Ex-3A: A sample of 5-bromo-2,4-dimethoxybenzaldehyde (4.9 g, 20.0 mmol) was dissolved in ethylene glycol dimethyl ether (50 mL). Tetrakis(triphenylphosphine)palladium(0) (2.32 g, 2 mmol) was added, and the mixture was stirred at room temperature under nitrogen for 5 min. Benzo[b]thiophene-2-boronic acid (4.27 g, 24 mmol) and sodium carbonate solution (2 M, 20 mL) were added. The mixture was stirred at reflux under nitrogen for 24 hours. Upon cooling to room temperature, the mixture was poured into water and extracted with ethyl acetate. The organic phase was dried over sodium sulfate and evaporated. Silica gel chromatography (hexane/ethyl acetate 2:1 then 1:1) gave 4.75 g (83%) of the desired 5-(benzo[b]thien-2-yl)-2,4-dimethoxybenzaldehyde. $^1$H NMR (CDCl$_3$) δ 10.36 (s, 1H), 8.20 (s, 1H), 7.83–7.78 (m, 2H), 7.68 (s, 1H), 7.36–7.27 (m, 2H), 6.54 (s, 1H), 4.06 (s, 3H), 4.00 (s, 3H).

An alternative procedure: 5-bromo-2,4-dimethoxybenzaldehyde (20 g), benzo[b]thiophene-2-boronic acid (16 g) and THF (200 mL) were sequentially charged into a clean reaction vessel fitted with a reflux condenser, mechanical stirrer and nitrogen inlet adapter. Nitrogen was bubbled into the resulting solution for 20 min followed by the sequential addition of KF (10 g), and Pd($^t$Bu$_3$P)$_2$ (0.417 g). The solution was immediately heated to 60° C. and aged for 1.5 h. (Note: The HPLC assay at this point routinely indicated complete consumption of 5-bromo-2,4-dimethoxybenzaldehyde, <0.5 area % of benzo[b]thiophene-2-boronic acid along with 0.5 area % of an unknown (0.55 RRT). These impurities are removed during crystallization.) Upon completion, as determined by HPLC, the reaction was diluted with H$_2$O (200 mL) and transferred to a separatory funnel containing EtOAc (200 mL) and H$_2$O (200 mL). The layers were cut and the aqueous layer was extracted with EtOAc (100 mL). The combined organic cuts were filtered through a pre-washed pad of solka floc (5 g). The pad of solka floc and spent catalyst were washed with fresh EtOAc (200 mL) and this wash combined with the batch. The resultant filtrate was batch concentrated and solvent switched to 33 wt % 5-(benzo[b]thien-2-yl)-2,4-dimethoxybenzaldehyde in THF in preparation for crystallization. (Note: The internal temperature during batch concentration should be kept above 45° C. to prevent premature crystallization.) The resulting THF solution of 5-(benzo[b]thien-2-yl)-2,4-dimethoxybenzaldehyde was then charged with heptane (20 mL) and slowly cooled to ambient temperature. Crystallization was then completed with the slow addition of heptane (175 mL) and cooling to 4° C. After aging for 1 h, the batch was filtered and then dried on the filter funnel under a stream of N$_2$. The semi-wet cake was then transferred to clean trays and dried to a constant weight in the vacuum oven (40° C., 20 inHg) affording 23.74 g (97% yield) of desired 5-(benzo[b]thien-2-yl)-2,4-dimethoxybenzaldehyde as a light orange crystalline solid, m.p. 134–136° C. HPLC assay of this solid indicated >99.9 LCAP. $^1$H-NMR identical as above.

To a solution of 4-acetylbenzoic acid (1.50 g, 9.1 mmol) and 5-(benzo[b]thien-2-yl)-2,4-dimethoxybenzaldehyde from Ex-3A (3.27 g, 11.0 mmol) in N,N-dimethylformamide (76 mL) was added a solution of sodium hydroxide (5 M, 7.3 mL, 36.5 mmol). The reaction mixture was allowed to stir at room temperature for 2 h and was then diluted with water to a volume of 150 mL. The solution was washed with dichloromethane and acidified with concentrated sulfuric acid to pH=3. The resulting solution was then extracted with dichloromethane. The dichloromethane extract was washed with brine, dried over sodium sulfate and concentrated. The resulting oily product solidified in ethanol. The solid was further stirred in ethanol for one day and collected by filtration. The solid was washed with ethanol, then dried in vacuo to afford the title compound as a yellow solid (2.2 g, 54%). $^1$H NMR (300 MHz, DMSO-d$_6$) δ 8.36 (s, 1H), 8.21 (d, 2H), 8.07 (m, 3H), 7.93 (m, 3H), 7.82 (d, 1H), 7.32 (m, 2H), 6.86 (s, 1H), 4.08 (s, 3H), 4.00 (s, 3H). Anal. Calculated for C$_{26}$H$_{20}$O$_5$S·1/6H$_2$O: C, 69.78; H, 4.58; S, 7.17; found: C, 69.95; H, 4.69; S, 7.15. HPLC purity: 97.9% (area percentage).

An alternative procedure: 5-(Benzo[b]thien-2-yl)-2,4-dimethoxybenzaldehyde from Ex-3A (42.3 g), 4-acetylbenzoic acid (22.1 g), MeOH (250 mL) and DMF (600 mL) were sequentially charged into a clean reaction vessel fitted with a mechanical stirrer and nitrogen inlet adapter. After complete dissolution, LiOMe (10.5 g) was added in one portion and the resulting solution was aged at 40° C. for 2 h. Upon completion, as determined by HPLC, the reaction mixture was transferred to a separatory funnel containing cold H$_2$O (800 mL, precooled to 10 deg C.). An additional 400 mL cold H$_2$O was used to rinse the reaction vessel and this rinse was also added to the seperatory funnel. The combined aqueous was washed with iPrOAc (500 mL) and then acidified to a pH of 3 with 6 N HCl (ca. 60 mL). The resulting heterogeneous solution was aged for 30 min and then the precipitate was filtered, washed with 70% EtOH (100 mL) and dried on the filter funnel under a stream of N$_2$ affording desired acid 5 as a crude yellow solid. The crude dry product and THF (260 mL) were charged into a clean reaction vessel fitted with a mechanical stirrer and nitrogen inlet adapter. Heptane (30 mL) was slowly added to the resulting solution over 30 min and then aged resulting in crystallization. Additional heptane (270 mL) was added over 1 h, aged for an additional 1 h and then filtered. The reaction vessel was then rinsed with 70% EtOH (100 mL) and this rinse was added to the filter cake. The wet cake was then transferred to a clean reaction vessel containing 70% EtOH (750 mL) and the resulting heterogeneous mixture was stirred overnight. The product was then filtered, rinsed with fresh 70% EtOH (100 mL) and then dried on the filter funnel under a stream of N$_2$. The semi-wet cake was then transferred to clean trays and dried to a constant weight in the vacuum oven (40° C., 20 inHg) affording 52.05 g (87% yield) of desired 4-[3-(5-benzo[b]thiophen-2-yl-2,4-dimethoxy-phenyl)-E-acryloyl]-benzoic acid 5 as a yellow crystalline solid, m.p. 231–232° C. (dec.). HPLC assay of this solid indicated >99.9 LCAP. $^1$H-NMR identical as above.

Example 4

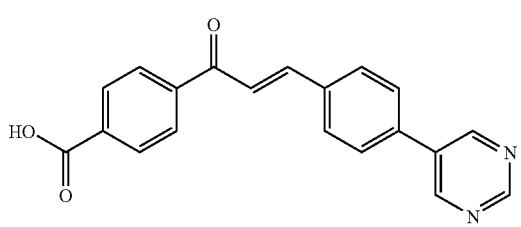

4-[3E-(4-Pyrimidin-5-yl-phenyl)-acryloyl]-benzoic acid

Ex-4A: 4-Pyrimidin-5-yl-benzaldehyde was obtained pyrimidine-5-boronic acid and 4-bromobenzaldehyde in a similar manner as described in Ex-3A, 88.6% yield. $^1$H-NMR (CDCl$_3$) δ 10.11 (s, 1H), 9.28 (s, 1H), 9.01 (s, 2H), 8.05 (d, J=8 Hz, 2H), 7.77 (d, J=8 Hz, 2H).

The title compound was obtained in a similar manner as described in Ex-3 from 4-pyrimidin-5-yl-benzaldehyde (Ex-4A) and 4-acetylbenzoic acid. Yellow solid, mp>260° C., 45% yield. $^1$H-NMR (DMSO-d$_6$) δ 9.21 (s, 2H), 9.19 (s, 1H), 8.24 (d, J=9 Hz, 2H), 8.01–8.09 (m, 5H), 7.9 (d, J=6 Hz, 2H), 7.81 (d, J=15 Hz, H), MS m/z=330 ([M]$^+$, 100%). HRMS (EI) Calcd. for C$_{20}$H$_{14}$N$_2$O$_3$: 330.1004. Found: 330.1000.

Example 5

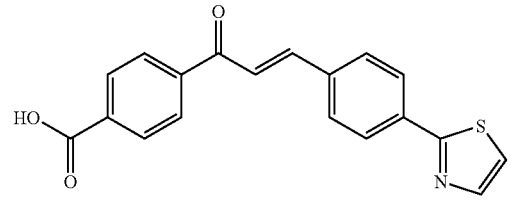

4-[3E-(4-Thiazol-2-yl-phenyl)acryloyl]-benzoic acid

Ex-5A: 4-Thiazol-2-yl-benzaldehyde was prepared from 4-bromobenzaldehyde and thiazole-2-boronic acid in a similar manner as described in Ex-3A, 82% yield. $^1$H-NMR (CDCl$_3$) δ 10.07 (s, 1H), 8.15 (d, J=8 Hz, 2H), 7.95–7.98 (m, 3H), 7.45 (d, J=3 Hz, 1H). HMRS (EI) calcd. for C$_{10}$H$_7$NOS: 189.0248; found: 189.0242.

The title compound was obtained in a similar manner as described in Ex-3 from 4-thiazol-2-yl-benzaldehyde (Ex-5A) and 4-acetylbenzoic acid. Yellow solid, mp 232–235° C., 20% yield. $^1$H-NMR (CDCl$_3$) δ 8.24 (d, J=9 Hz, 2H), 8.11 (d, J=9 Hz, 2H), 8.05 (d, J=9 Hz 2H), 7.93 (d, J=3 Hz, 1H), 7.86 (d, J=15 Hz, 1H), 7.74 (d, J=9 Hz, 2H), 7.57 (d, J=15 Hz, 1H), 7.41 (d, J=3 Hz, 1H), MS m/z=335 ([M]$^+$, 100%). HRMS (EI) Calcd. for C$_{19}$H$_{13}$NO$_3$S: 335.0616. Found: 335.0618.

Example 6

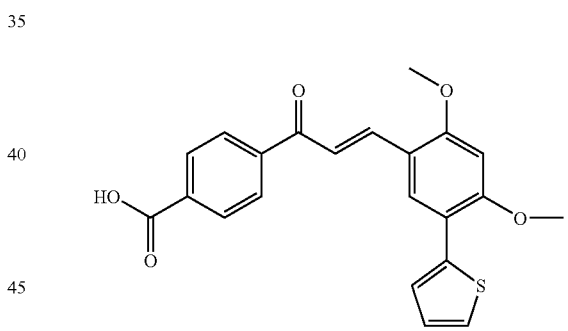

4-[3E-(2,4-Dimethoxy-5-thiophen-2-yl-phenyl)-acryloyl]-benzoic acid

Ex-6A: 5-bromo-2,4-dimethoxybenzaldehyde (20.3 g), thiophene-2-boronic acid (11.6 g) and THF (200 mL) were sequentially charged into a clean reaction vessel fitted with a reflux condenser, mechanical stirrer and nitrogen inlet adapter. Nitrogen was bubbled into the resulting solution for 20 min followed by the sequential addition of KF (10.1 g), and Pd($^t$Bu$_3$P)$_2$ (0.424 g). The solution was immediately heated to 60° C. and aged for 1.5 h. The reaction was diluted with H$_2$O (200 mL) and transferred to a separatory funnel containing EtOAc (200 mL) and H$_2$O (200 mL). The layers were cut and the aqueous layer was extracted with EtOAc (100 mL). The combined organic cuts were filtered through a pre-washed pad of solka floc (5 g). The pad of solka floc and spent catalyst were washed with fresh EtOAc (200 mL) and this wash combined with the batch. The resultant filtrate was concentrated to dryness. The crude product was dissolved in THF (38 mL) and crystallized upon heptane (152 mL) addition. The product was filtered and then dried to a constant weight in the vacuum oven (38° C., 20 inHg) affording 19.32 g (94% yield) of desired 2,4-dimethoxy-5-thiophen-2-yl-benzaldehyde as a light off-white solid, m.p. 125–126° C. $^1$H-NMR (300 MHz, CDCl$_3$): 10.34 (s, 1H), 8.12 (s, 1H), 7.44 (dd, 1H, J=3.5 and 1.5 Hz), 7.31 (dd, 1H, J=5.2 and 1.5 Hz), 7.07 (dd, 1H, J=5.2 and 3.5 Hz), 6.51 (s, 1H), 4.02 (s, 3H), 3.99 (s, 3H).

2,4-Dimethoxy-5-thiophen-2-yl-benzaldehyde from Ex-6A (7.81 g), 4-acetylbenzoic acid (4.9 g), MeOH (60 mL) and DMF (150 mL) were sequentially charged into a clean reaction vessel fitted with a stir bar and nitrogen inlet adapter. After complete dissolution LiOMe (4.60 g) was added and the resulting solution was aged for 5 h. The reaction was diluted with H$_2$O (200 mL) and transferred to a separatory funnel containing iPrOAc (100 mL). The layers were cut and the aqueous layer was acidified to a pH of 1 with 3 N HCl. The resulting precipitate was filtered and then dried on the filter funnel under a stream of N$_2$. The crude product was then dissolved in THF (60 mL) and crystallized with the addition of heptane (60 mL). The product was filtered and then dried to a constant weight in the vacuum oven affording 8.9 g (75% yield) of the title compound as a yellow solid, m.p. 213–216° C. $^1$H-NMR (300 MHz, CDCl$_3$): 8.20 (d, 2H, J=8.5 Hz), 8.09 (d, 1H, J=16.1 Hz), 8.06 (d, 2H, J=8.5 Hz), 7.85 (s, 1H), 7.52 (d, 1H, J=16.1 Hz), 7.40 (m, 1H), 7.30 (dd, 1H, J=5.2 and 1.7 Hz), 7.08 (dd, 1H, J=5.2 and 3.6 Hz), 6.53 (s, 1H), 3.98 (s, 3H), 3.97 (s, 3H); EIMS m/z=394 (M$^+$). Anal. calc. for C$_{22}$H$_{18}$O$_5$S: C, 66.99; H, 4.60; S, 8.13; found: C, 66.71; H, 4.59; S, 8.10.

Example 7

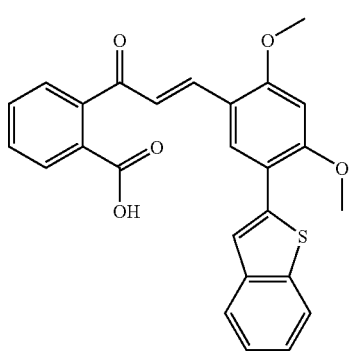

2-[3E-(5-Benzo[b]thiophen-2-yl-2,4-dimethoxy-phenyl)-acryloyl]-benzoic acid

The title compound was obtained starting from 5-(benzo[b]thien-2-yl)-2,4-dimethoxybenzaldehyde from Ex-3A and 2-acetylbenzoinc acid in a similar manner as described in Ex-3. Yellow solid, mp 220–223° C. (dec.). $^1$H-NMR (DMSO-d$_6$) δ 8.01 (s, 1H), 7.88 (d, J=7.3 Hz, 1H), 7.80–7.75 (m, 2H), 7.45–7.24 (m, 7H), 7.11 (d, J=1H), 6.79 (s, 1H), 4.00 (s, 3H), 3.88 (s, 3H). MS m/z=445 (M$^+$, 100%).

Example 8

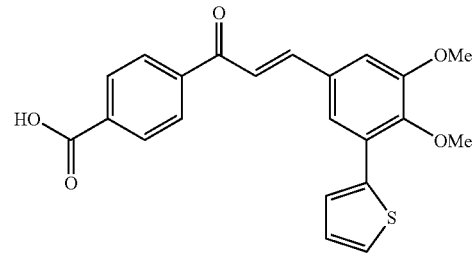

4-[3E-(3,4-Dimethoxy-5-thiophen-2-yl-phenyl)-acryloyl]-benzoic acid

The title compound was obtained in a similar manner as described in Ex-3 from 3,4-dimethoxy-5-(thien-2-yl)benzaldehyde (Ex-1D) and 4-acetylbenzoic acid. Yellow solid, mp 231° C. $^1$H-NMR (DMSO-d$_6$) δ 8.23 (d, 2H), 8.08 (d, 2H), 7.96 (d, 1H), 7.90 (m, 1H), 7.77 (m, 2H), 7.59 (d, 1H), 7.54 (m, 1H), 7.13 (dd, J=4, 4 Hz, 1H). MS m/z=395 ([M+H]$^+$, 100%).

Example 9

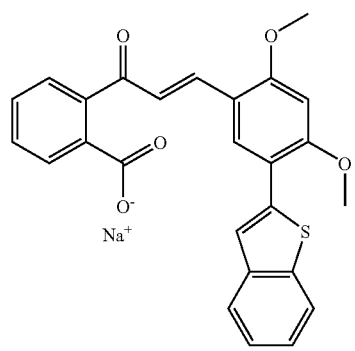

2-[3E-(5-Benzo[b]thiophen-2-yl-2,4-dimethoxy-phenyl)-acryloyl]-benzoic acid, sodium salt To a solution of 2-acetyl-benzoic acid (0.75 g, 4.6 mmol) and 5-benzo[b]thiophen-2-yl-2,4-dimethoxy-benzaldehyde (Ex-3A, 1.64 g, 5.5 mmol) in N,N-dimethylformamide (38 mL) was added sodium hydroxide (5M, 3.7 mL, 18.5 mmol). The reaction mixture was allowed to stir for 2 hours at ambient temperature and was diluted with water (50 mL) and sodium carbonate (2M, 20 mL). The aqueous solution was extracted with dichloromethane. A yellow precipitate formed in dichloromethane and was collected by filtration, washed with dichloromethane, dried in vacuo to give the title compound as a yellow solid (1.53 g, 67%), mp 214–217° C. (dec). $^1$H-NMR (DMSO-d$_6$) δ 7.93–7.87 (m, 3H), 7.77 (d, J=8.0 Hz, 2H), 7.33–7.26 (m, 4H), 7.09–7.06 (m, 2H), 7.01 (d, J=17.0 Hz, 1H), 6.78 (s, 1H), 3.99 (s, 3H), 3.88 (s, 3H). MS m/z=467 ([M+Na]$^+$, 75%), 445 ([M+H]$^+$, 100%). Anal. (C$_{26}$H$_{19}$O$_5$SNa.1.3H$_2$O) Calc. C, 63.55; H, 4.35; S, 6.52; found C, 63.74; H, 4.44; S, 6.55.

Example 10

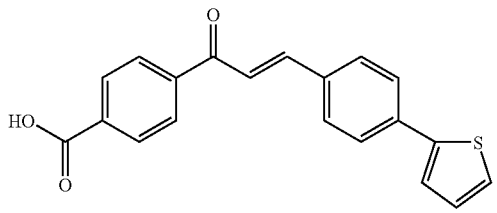

4-[3E-(4-Thiophen-2-yl-phenyl)-acryloyl]-benzoic acid

The title compound was obtained by condensing 4-(thien-2-yl)benzaldehyde from Ex-2A and 4-acetylbezoic acid in a similar manner as described in Ex-3. Yellow solid, 56% yield, mp>260° C. $^1$H-NMR (DMSO-$d_6$) δ 8.01–8.08 (m, 4H), 7.72 (d, J=8 Hz, 2H), 7.68 (s, 2H), 7.61 (d, J=8 Hz, 2H), 7.41 (d, J=4 Hz, 1H), 7.35 (d, J=4 Hz, 1H), 7.04 (dd, J=4, 8 Hz, 1H). MS m/z=334 ([M+Na]$^+$, 100%). Anal. ($C_{22}H_{14}O_3S$) Calc. C, 71.84; H, 4.22; S, 9.59; found C, 71.44; H, 4.32; S, 9.43.

Example 11

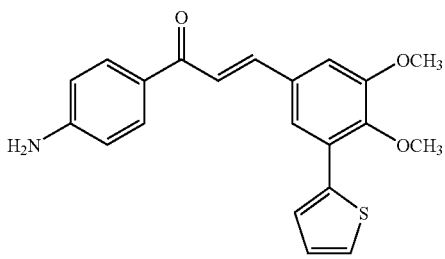

1-(4-Amino-phenyl)-3E-(3,4-dimethoxy-5-thiophen-2-yl-phenyl)-propenone

A suspension of 3,4-dimethoxy-5-(thien-2-yl)benzaldehyde (1.8 g, 7.4 mmol) from Ex-1D in an aqueous solution of 5 N potassium hydroxide (37 mL) was treated with cetyltrimethyl ammonium chloride (39 mL, 29.6 mmol) and 4-aminoacetophenone (1.0 g, 7.4 mmol). The reaction was stirred for 16 h at room temperature. The reaction mixture was titrated with 6 M $H_2SO_4$ to a pH of 7. The mixture was extracted with dichloromethane (2×75 mL). The organic layer was washed with aqueous $NaHCO_3$ (2×25 mL), brine, dried over sodium sulfate, and concentrated to a yellow foam. The crude material was purified by silica gel chromatography (1:1 ethyl acetate and hexanes) to give 720.0 mg (27%) of the title compound as a yellow solid, mp. 67–71° C. $^1$H-NMR (300 MHz, CDCl$_3$) δ 7.94 (d, 2H), 7.75 (d, 1H), 7.54 (s, 1H), 7.53 (s, 1H), 7.46 (d, 1H), 7.39 (d, 1H), 7.13 (d, 1H), 7.11 (m, 1H), 6.72 (d, 2H), 4.16 (s, 2H), 3.97 (s, 3H), 3.87 (s, 3H). Anal. calculated for $C_{21}H_{19}NO_3S·1/5H_2O$: C, 68.60; H, 5.28; S, 8.72; found C, 68.51; H, 5.40, S, 8.69. MS (Pos. Ion ES): calcd for $C_{21}H_{20}NO_3S$, m/z=366 [M+H]$^+$, found: m/z=366 [M+H]$^+$.

Example 12

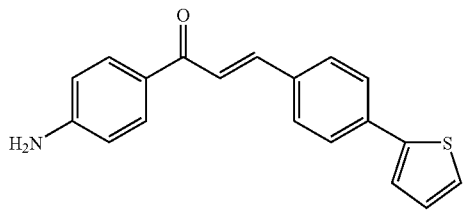

1-(4-Amino-phenyl)-3E-(4-thiophen-2-yl-phenyl)-propenone

The title compound was prepared from 4-(thien-2-yl)benzaldehyde (Ex-2A) and 4-aminoacetophenone in a similar manner as described in Ex-11. Yellow solid, 45% yield, mp 185–187° C. $^1$H-NMR (CDCl$_3$) δ 7.95 (d, 2H), 7.79 (d, 1H), 7.65 (m, 4H), 7.55 (d, 1H), 7.39 (d, 1H), 7.33 (dd,J=5, 5 Hz, 1H), 7.11 (dd, J=5, 5 Hz, 1H), 6.71 (d, 2H), 4.16 (s, 2H). MS m/z=305 ([M]$^+$, 100%). Anal. calculated for $C_{19}H_{15}NOS$: C, 74.72; H, 4.95; S, 10.50; found C, 74.60; H, 5.05; S, 10.42.

Example 13

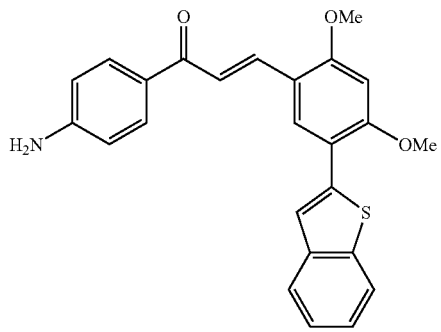

1-(4-Amino-phenyl)-3E-(5-benzo[b]thiophen-2-yl-2,4-dimethoxy-phenyl)-propenone

The title compound was prepared from 5-(benzo[b]thien-2-yl)-2,4-dimethoxybenzaldehyde (Ex-3A) and 4-aminoacetophenone in a similar manner as described in Ex-11. Yellow solid, 24% yield, mp 98–104° C. $^1$H-NMR (CDCl$_3$) δ 8.10 (d, 1H), 7.95 (m, 3H), 7.82 (m, 2H), 7.67 (s, 1H), 7.60 (d, 1H), 7.32 (dd, J=8.8 Hz, 2H), 6.71 (d, 2H), 6.57 (s, 1H), 4.11 (br s, 2H), 4.02 (s, 3H), 3.99 (s, 3H). MS m/z=415 ([M]$^+$, 39%), 384 (100%). Anal. calculated for $C_{25}H_{21}NO_3S·1/3H_2O$: C, 71.24; H, 5.18; S, 7.61; found C, 71.63; H, 5.18; S, 7.55.

Example 14

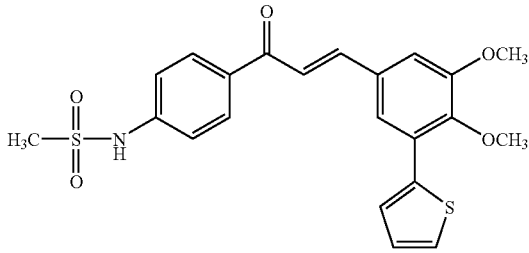

N-{4-[3E-(3,4-Dimethoxy-5-thiophen-2-yl-phenyl)-acryloyl]-phenyl}-methanesulfonamide Ex-14A: A solution of 1-(4-amino-phenyl)-3E-(3,4-dimethoxy-5-thiophen-2-yl-phenyl)-propenone (Ex-11, 472.2 mg, 1.3 mmol) and triethylamine (398.63 µL, 2.86 mmol) was stirred in 20 mL of anhydrous dichloromethane. The mixture was treated with mesyl chloride (100 µL, 1.3 mmol). The reaction mixture was stirred for 16 hours and heated gently for another 4 hours. The crude material was purified by silica gel chromatography (1:3 ethyl acetate/hexane) to give 337.0 mg (quantitative) of 1-[4-bis-(methanesulfonyl)aminophenyl]-3E-[(3,4-dimethoxy-5-(thien-2-yl)phenyl]-propenone. $^1$H-NMR (300 MHz, CDCl$_3$) δ 8.06 (d, 2H), 7.76 (d, 1H), 7.53 (m, 2H), 7.49 (d, 2H), 7.38 (m, 1H), 7.36 (d, 1H), 7.10 (m, 1H), 7.08 (m, 1H), 3.94 (s, 3H), 3.86 (s, 3H), 3.42 (s, 6H).

A solution of 1-[4-bis-(methanesulfonyl)aminophenyl]-3E-[(3,4-dimethoxy-5-(thien-2-yl)phenyl]-propenone (378.86 mg, 0.73 mmol) from Ex-14A in tetrahydrofuran (6.6 mL) was treated with aqueous 1N NaOH (1.4 mL, 1.4 mmol). The reaction was stirred at room temperature for 1 h. The reaction was titrated with 1 N HCl to a pH of 6. The crude material was purified by silica gel chromatography (5% MeOH/CH$_2$Cl$_2$ with 1% acetic acid) to give 269.2 mg (83%) of the title compound as a solid, 83% yield, mp. 71–75° C. $^1$H-NMR (300 MHz, CDCl$_3$) δ 8.04 (d, 2H), 7.76 (d, 1H), 7.52 (m, 2H), 7.40 (d, 1H), 7.37 (m, 1H), 7.29 (d, 2H), 7.10 (m, 1H), 7.08 (m, 1H), 3.95 (s, 3H), 3.86 (s, 3H), 3.12 (s, 1H), 3.09 (s, 3H). MS (Pos. Ion ES): calcd for C$_{22}$H$_{22}$NO$_5$S$_2$: m/z=444 [M+H]$^+$, found: m/z=444 [M+H]$^+$. HRMS m/z: calc. 444.0939, found 444.0953.

Example 15

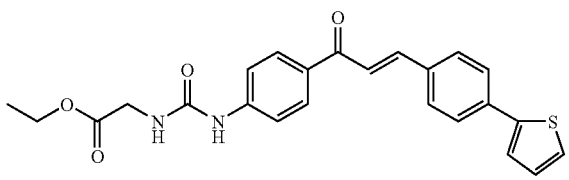

(3-{4-[3E-(4-Thiophen-2-yl-phenyl)-acryloyl]-phenyl}-ureido)-acetic acid ethyl ester A solution of 1-(4-amino-phenyl)-3-(4-thiophen-2-yl-phenyl)-propenone (Ex-12, 250 mg, 0.80 mmol) and isocyanato-acetic acid ethyl ester (105.7 mg, 0.80 mmol) in toluene (15 mL) was refluxed for 16 hours. The reaction mixture was cooled to room temperature and the crude product precipitated out of solution. The material was suctioned filtered and dried on hi-vac to give 280.2 mg (79%) of the title compound as a yellow solid, mp 209–212° C. $^1$H-NMR (DMSO-d6) δ 9.29 (br s, 1H), 8.08 (d, 2H), 7.90 (m, 3H), 7.71 (d, 3H), 7.60 (m, 4H), 7.14 (t, 1H), 6.61 (t, 1H), 4.09 (q, 2H), 3.86 (dd, J=2,6 Hz, 2H), 1.17 (t, 3H). MS m/z=435 ([M+H]$^+$, 100%). HRMS m/z: calc. 435.1378, found 435.1375.

Example 16

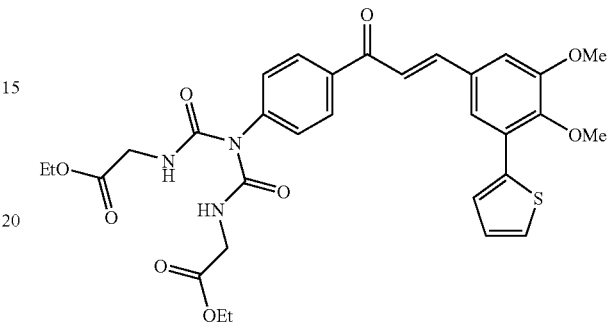

(3-[Ethoxycarbonylmethylaminocarbonyl]-3-{4-[3E-(3,4-dimethoxy-5-thiophen-2-yl-phenyl)-acryloyl]-phenyl}-ureido)-acetic acid ethyl ester A solution of 1-(4-aminophenyl)-3E-[(3,4-dimethoxy-5-(thien-2-yl)phenyl]-propenone (Ex-11, 500 mg, 1.37 mmol) and ethyl isocyanatoacetate (177 mg, 1.37 mmol) in anhydrous methylene chloride (20 mL) was stirred at room temperature for 5 hours. Due to no reaction, the reaction mixture was concentrated, diluted with toluene (20 mL), treated with ethyl isocyanatoacetate (177 mg, 1.37 mmol), and refluxed for 14 hours. The reaction was concentrated, diluted with methylene chloride (50 mL), and washed with water (3×50 mL). The organic portion was collected, dried over sodium sulfate, and concentrated over silica gel. The crude material was purified by silica gel chromatography (50–75% ethyl acetate/hexanes) to give 178.0 mg (21%) of the title compound as a yellow solid, mp 83–86° C. $^1$H-NMR (CDCl$_3$) δ 8.09 (d, 2H), 7.76 (d, 1H), 7.55 (m, 2H), 7.65 (d, 2H), 7.40 (m, 2H), 7.30 (m, 2H), 7.11 (m, 2H), 4.17 (q, 4H), 4.01 (d, 4H), 3.97 (s, 3H), 3.88 (s, 3H). MS m/z=646 ([M+Na]$^+$, 100%). Anal. calculated for C$_{31}$H$_{33}$N$_3$O$_9$S: C, 59.70; H, 5.33; S, 5.14; found C, 60.18; H, 5.38; S, 5.17.

Example 17

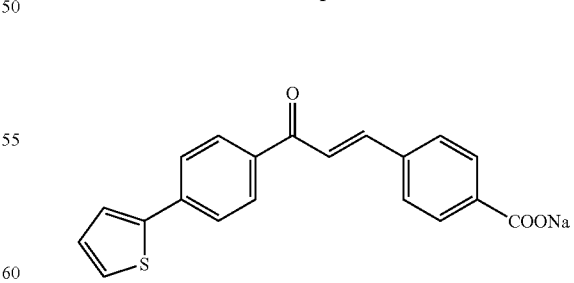

4-[3-{4-(thien-2-yl)-phenyl}-3-oxo-E-propenyl]-benzoic acid, sodium salt

Ex-17A: 4'-Bromoacetophenone (3.98 g, 20 mmol) was dissolved in ethylene glycol dimethyl ether and then the solution was degassed with nitrogen for 15 minutes. Tetrakis (triphenylphosphine)palladium(0) (2.31 g, 2 mmol) was added, and the solution was further degassed for 10 minutes. Thiophene-2-boronic acid (3.07 g, 24 mmol) was added followed by the addition of sodium carbonate solution (2 M, 45 mL). The mixture was stirred at reflux under nitrogen overnight. Most of the solvent was removed, and water was added to the remainder. The solid was filtered out and recrystallized from ethanol and water to give 3.85 g of the desired 4'-(thien-2-yl)acetophenone as a solid, 95% yield. $^1$H-NMR (CDCl$_3$) δ 7.97 (d, J=9 Hz, 2H), 7.70 (d, J=9 Hz, 2H), 7.44 (d, J=4 Hz, 1H), 7.38 (d, J=5 Hz, 1H), 7.11–7.14 (m, 1H), 2.62 (s, 3H). HMRS (EI) calcd. for C$_{12}$H$_{10}$OS: 202.0452; found: 202.0454.

4'-(Thien-2-yl)acetophenone obtained from Ex-17A (0.81 g, 4 mmol) and 4-carboxybenzaldehyde (0.6 g, 4 mmol) were dissolved in dimethylformamide (20 mL). Sodium hydroxide solution (5 M, 3.2 mL) was added over 30 minutes at room temperature, and the mixture was stirred for another 30 minutes at room temperature. The precipitate was filtered off and recrystallized from hot water to give the title compound as a yellow solid, 29% yield, m.p.>260° C. $^1$H-NMR (300 MHz, DMSO-d$_6$) δ 8.17 (d, 2H), 7.89 (d, 1H), 7.87 (d, 2H), 7.81 (d, 2H), 7.76 (d, 2H), 7.72 (d, 1H), 7.69 (d, 1H), 7.64 (d, 1H), 7.17 (dd, 1H). Anal. calculated for C$_{20}$H$_{13}$O$_3$NaS.1/2H$_2$O: C, 65.74; H, 3.86; S, 8.78; found: C, 65.66; H, 4.04; S, 9.04.

Example 18

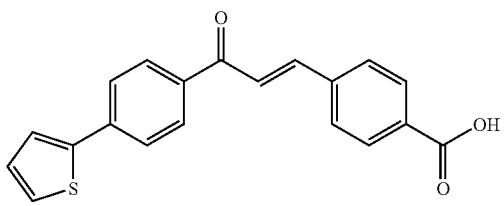

4-[3-{4-(thien-2-yl)-phenyl}-3-oxo-E-propenyl]-benzoic acid

The title compound was prepared by acidifying its sodium salt from Ex-17. Yellow solid, mp 260–265° C., 67% yield. $^1$H-NMR (DMSO-d$_6$) δ 8.18 (d, J=8 Hz, 2H), 8.00 (d, J=15 Hz, 1H), 7.91–7.94 (m, 4H), 7.82 (d, J=8 Hz, 2H), 7.77–7.79 (m, 1H), 7.71 (d, J=3 Hz, 1H), 7.66 (d, J=5 Hz, 1H), 7.16–7.19 (m, 1H), MS m/z=334 ([M]$^+$, 100%). HRMS (EI) Calcd. for C$_{20}$H$_{14}$O$_3$S: 334.0664. Found: 334.0669.

Example 19

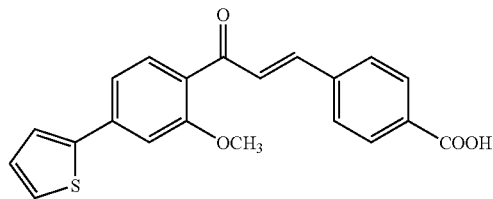

4-[3-(2-Methoxy-4-thiophen-2-yl-phenyl)-3-oxo-E-propenyl]-benzoic acid

Ex-19A: 1-(2-Methoxy-4-thiophen-2-yl-phenyl)-ethanone was prepared from 4-iodo-2-methoxyacetophenone in a similar manner as described in Ex-17A. $^1$H-NMR (CDCl$_3$) δ 7.53 (d, J=7 Hz, 1H), 7.37 (dd, J=2, 5 Hz, 1H), 7.06 (dd, J=4, 6 Hz, 1H), 6.98–7.00 (m, 1H), 6.88–6.95 (m, 2H), 3.84 (s, 3H), 2.10 (s, 3H).

The title compound was prepared by condensing 1-(2-methoxy-4-thiophen-2-yl-phenyl)-ethanone (Ex-19A) and 4-carboxybenzaldehyde in a similar manner as described in Ex-17 except an acidic workup. Yellow solid, mp 193–195° C. $^1$H-NMR (CDCl$_3$) □ 7.70 (d, J=8 Hz, 2H), 7.38 (d, J=8 Hz, 1H), 7.07–7.16 (m, 4H), 6.75–6.80 (m, 4H), 6.42 (d, J=16 Hz, 1H), 3.67 (s, 3H), MS m/z=364 ([M]$^+$, 100%). Anal. Calculated for C$_{21}$H$_{16}$O$_4$S: C, 69.21; H, 4.43; S, 8.80; found: C, 69.02; H, 4.56; S, 8.75.

Example 20

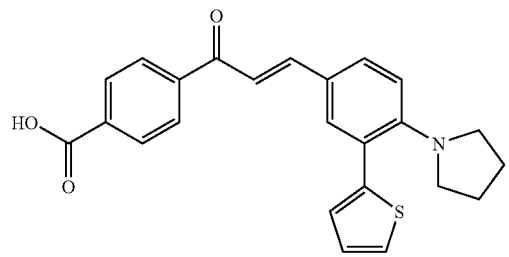

4-[3E-(4-Pyrrolidin-1-yl-3-thiophen-2-yl-phenyl)-acryloyl]-benzoic acid

Ex-20A: A solution of 3-bromo-4-flouro-benzaldehyde (5.0 g, 24.6 mmol) and thiophene-2-boronic acid (4.7 g, 37.0 mmol) in ethylene glycol dimethyl ether (100 mL) was stirred at room temperature under nitrogen for 15 min. Then tetrakis(triphenylphosphine)-palladium(0) (2.8 g, 2.42 mmol) and a sodium carbonate solution (2 M, 33 mL) were added, and the resulting mixture was refluxed under nitrogen overnight. Upon cooling to room temperature the reaction was poured into water (100 mL) and extracted with ethyl acetate (2×100 mL). The organic phase was dried over magnesium sulfate, and the solvent was removed under reduced pressure. Silica gel chromatography (hexane/ethyl acetate, 1:1) gave 4.8 g (95%) of the desired 4-fluoro-3-(thiophen-2-yl)-benzaldehyde product as a yellow oil. $^1$H-NMR (300 MHz, CDCl$_3$) δ 10.0 (s, 1H), 8.18 (dd, 1H, J=7.3 and 2.4 Hz), 7.80 (m, 1H), 7.56 (dd, 1H, J=3.7 and 1.7 Hz), 7.44 (d, 1H, J=5.1 Hz), 7.36 (m, 1H), 7.16 (dd, 1H, J=5.1 and 3.7 Hz).

Ex-20B: A solution of 4-fluoro-3-(thiophen-2-yl)-benzaldehyde (1.11 g, 5.38 mmol) from Ex-20A and pyrrolidine (13.0 g, 183.0 mmol) in dimethylformamide (30 mL) was treated with solid K$_2$CO$_3$ (1.7 g, 12.3 mmol), and the resulting mixture was stirred at reflux for 1 week. Upon cooling to room temperature, the reaction was poured into water (100 mL) and extracted with ethyl acetate (2×100 mL). The organic phase was dried over magnesium sulfate, and the solvent was removed under reduced pressure. Silica gel chromatography (hexane/ethyl acetate, 2:1) gave 400 mg (29%) of the desired 4-pyrrolidin-1-yl-3-(thiophen-2-yl)-benzaldehyde product as a yellow oil. $^1$H-NMR (300 MHz, CDCl$_3$) δ 9.75 (s, 1H), 7.71–7.74 (m, 2H), 7.30 (dd, 1H, J=5.1 and 1.6 Hz), 7.02 (dd, 1H, J=5.1 and 3.7 Hz), 6.96 (m, 1H), 6.81 (d, 1H, J=10.1 Hz), 3.15 (m, 4H), 1.84 (m, 4H).

4-Pyrrolidin-1-yl-3-(thiophen-2-yl)-benzaldehyde (400 mg, 1.55 mmol) from Ex-20B and 4-acetylbenzoic acid (255 mg, 1.55 mmol) were dissolved in dimethylformamide (30 mL). Sodium hydroxide solution (5 N, 1.25 mL) was added in one portion, and the mixture was stirred at room temperature overnight. The reaction was diluted with water (100 mL) and washed with ethyl acetate (100 mL). The aqueous phase was acidified with conc. HCl and extracted with ethyl acetate (2×100 mL). The organic phase was dried over magnesium sulfate and concentrated under reduced pressure. Silica gel chromatography (100% ethyl acetate) followed by recrystallization from ethanol provided 80 mg (13%) of the title compound as a solid, m.p. 212–214° C. with decomposition. $^1$H-NMR (300 MHz, CDCl$_3$) δ 8.21 (d, 2H, J=8.4 Hz), 7.06 (d, 2H, J=8.4 Hz), 7.80 (d, 1H, J=15.3 Hz), 7.58 (d, 1H, J=1.9 Hz), 7.52 (dd, 1H, J=8.5 and 1.9 Hz), 7.33 (m, 1H), 7.32 (d, 1H, 15.3 Hz), 7.01–7.06 (m, 2H), 6.82 (d, 1H, 7.9 Hz), 3.12 (m, 4H), 1.84 (m, 4H). MS m/z=403 ([M]$^+$, 100%). HRMS (EI) Calcd. for $C_{24}H_{21}NO_3S$: 403.1242. Found: 403.1251.

Example 21

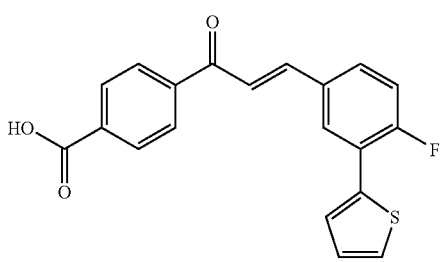

4-[3E-{4-Fluoro-3-(thiophen-2-yl)-phenyl}-acryloyl]-benzoic acid

4-Fluoro-3-thiophen-2-yl-benzaldehyde (1.0 g, 4.85 mmol, from Ex-20A) and 4-acetylbenzoic acid (0.80 g, 4.87 mmol) were dissolved in dimethylformamide (55 mL). Sodium hydroxide solution (5 N, 3.88 mL) was added in one portion, and the mixture was stirred at room temperature for 3 h. The reaction was diluted with water (100 mL) and washed with ethyl acetate (100 mL). The aqueous phase was acidified with conc. HCl and extracted with ethyl acetate (2×100 mL). The organic phase was dried over magnesium sulfate and concentrated under reduced pressure. Recrystallization from ethanol provided 0.90 g (53%) of the title compound as a solid, m.p. 242–244° C. $^1$H-NMR (300 MHz, d$_6$-DMSO) δ 13.31 (bs, 1H), 8.32 (dd, 1H, J=8.2 and 2.0 Hz), 8.24 (d, 2H, J=8.2 Hz), 8.07 (d, 2H, J=7.9 Hz), 7.98 (d, 1H, J=16.1 Hz), 7.92 (m, 1H), 7.80 (d, 1H, J=16.1 Hz), 7.69–7.73 (m, 2H), 7.41 (dd, 1H, 10.8 and 9.2 Hz), 7.20 (m, 1H). MS m/z=352 ([M]$^+$, 50%), 343 (100%). HRMS (EI) Calcd. for $C_{20}H_{13}FO_3S$: 352.0569. Found: 352.0571.

Example 22

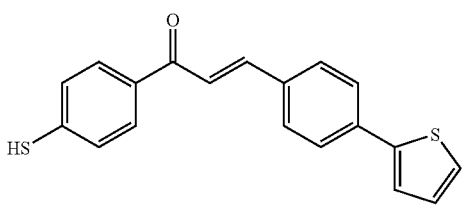

1-(4-Mercapto-phenyl)-3E-(4-thiophen-2-yl-phenyl)-propenone

To a solution of 4-mercaptoacetophenone (prepared according to European Patent Application 0271307) (0.57 g, 3.74 mmol) and 4-(thien-2-yl)-benzaldehyde (0.70 g, 3.74 mmol, Ex. 2A) in N,N-dimethylformamide (20 mL) was added a solution of sodium hydroxide (5 M, 3 mL). The solution was allowed to stir at room temperature for 3 h. The reaction mixture was then acidified with hydrochloric acid (0.5 M) to pH 3. The precipitate was collected by filtration, washed with water, and stirred in ethanol overnight. The resulting yellow solid was collected by filtration, washed with ethanol, and dried in vacuo to afford 0.68 g (56%) of the title compound as a solid, m.p.>110° C. (dec). MS (direct probe) m/z=322 (M$^+$). $^1$H-NMR (CDCl$_3$) δ 7.98–8.01 (d, 1H), 7.90–7.93 (d, 1H), 7.79–7.84 (d, 2H), 7.61–7.66 (m, 3H), 7.33–7.53 (m, 4H), 7.10–7.25 (m, 2H).

Example 23

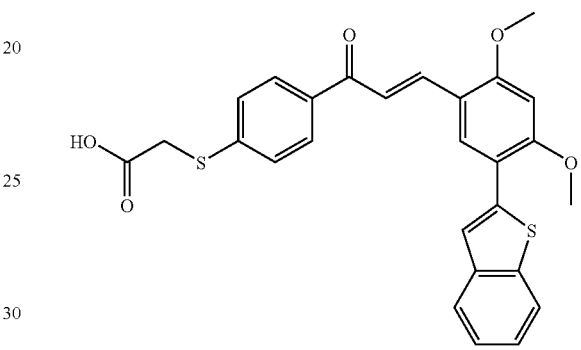

{4-[3E-(5-Benzo[b]thiophen-2-yl-2,4-dimethoxyphenyl)-acryloyl]-phenylthio}-acetic acid Ex-23A: To a solution of methyl bromoacetate (1.01 mL, 10.7 mmol) in potassium hydroxide (5M, 20 mL) was added benzenethiol (1.0 mL, 9.7 mmol). The reaction mixture was allowed to stir overnight at ambient temperature. The cloudy solution was then acidified to pH 3. The resulting solid was filtered, washed with water and dried in vacuo to obtain phenylthioacetic acid (0.55 g). The aqueous filtrate was extracted with dichloromethane. The solution of dichloromethane was washed with brine, dried over sodium sulfate and concentrated to obtain additional phenylthioacetic acid (1.49 g). $^1$H NMR (CDCl$_3$) δ 743–7.40 (m, 2H), 7.34–7.23 (m, 3H), 3.67 (s, 2H).

Ex-23B: To a mixture of alumina chloride (5.5 g, 41.0 mmol) in carbon disulfide (100 mL) was added acetyl chloride (1.17 mL, 16.5 mmol) followed by addition of phenylthioacetic acid (Ex-23A, 1.38 g, 8.2 mmol) and nitromethane (15 mL). The reaction mixture was allowed to stir overnight at ambient temperature and then was poured into ice containing sulfuric acid (6M). The insoluble solid was filtered, washed with, water. After dried in vacuo, the solid was washed with toluene (2×60 mL), filtered and dried under reduced pressure to obtain (4-acetylphenylthio)acetic acid (1.28 g, 74%), m.p. 151–153° C. (Lit. 156–158° C.). $^1$H NMR (DMSO-d$_6$) δ 12.80 (bs, 1H), 7.84 (d, J=9 Hz, 2H), 7.36 (d, J=9 Hz, 2H), 3.92 (s, 2H), 2.49 (s, 3H).

The title compound was prepared by condensing (4-acetylphenylthio)acetic acid (Ex-23B) and 5-(benzo[b]thien-2-yl)-2,4-dimethoxybenzaldehyde (Ex-3A) in a similar manner as described in Ex-22. Yellow solid, mp 136–138° C. (dec.). $^1$H-NMR (DMSO-d$_6$) δ 8.35 (s, 1H), 8.08 (d, J=7.4 Hz, 2H), 8.03 (d, J=16.3 Hz, 1H), 7.93–7.87 (m, 3H), 7.82 (d, J=7.0 Hz, 1H), 7.42 (d, J=7.9 Hz, 2H), 7.37–7.27 (m, 2H), 6.85 (s, 1H), 4.02 (s, 3H), 3.99 (s, 3H), 3.93 (s, 2H). MS m/z=491 ([M+H]$^+$, 100%).

Example 24

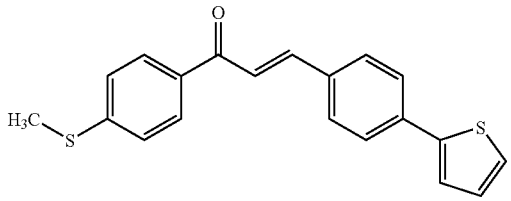

1-(4-Methylthiophenyl)-3E-(4-thiophen-2-yl-phenyl)-propenone

To a mixture of 1-(4-mercapto-phenyl)-3E-(4-thien-2-yl-phenyl)-proenone (Ex-22, 0.33 g, 1.02 mmol) and potassium carbonate (0.54 g, 3.9 mmol) in N,N-dimethylformamide (15 mL) was added iodomethane (0.32 mL, 5.1 mmol). The reaction mixture was allowed to stir at ambient temperature for 2 hours. The insoluble material was filtered. The solution was diluted with ethyl acetate. The solution of ethyl acetate was washed with hydrochloric acid (0.5 M), sodium carbonate (2M) and brine, dried over sodium sulfate, and concentrated. The crude product was purified by flash chromatography. Elution with ethyl acetate (33%, v/v, in hexane) gave the title compound (20 mg, 6%) as a yellow solid, mp 138–140° C. $^1$H-NMR (CCDl$_3$) δ 7.98 (d, J=7.8 Hz, 2H), 7.89–7.86 (m, 1H), 7.83 (d, J=15.3 Hz, 1H), 7.76 (s, 3H), 7.53 (d, J=15.1 Hz, 1H), 7.41 (d, J=3.7 Hz, 1H), 7.35–7.31 (m, 3H), 7.13–7.10 (s, 1H), 2.54 (m, 3H). MS m/z=336 (M$^+$, 100%).

Example 25

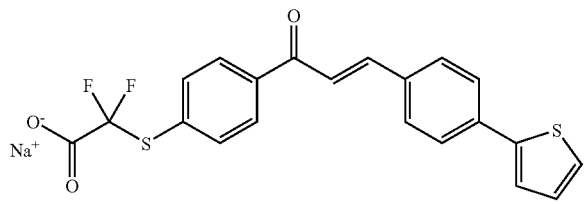

Difluoro-{4-[3E-(4-thiophen-2-yl-phenyl)-acryloyl]-phenylthio}-acetic acid, sodium salt Ex-25A: To a solution of 4-mercaptoacetophenone (prepared according to published procedure, European Patent Application 0271307) (1.16 g, 7.6 mmol) and ethyl bromodifluoroacetate (1.2 mL, 9.15 mmol) in N,N-dimethylformamide (20 mL) was added potassium carbonate (3.2 g, 22.9 mmol). The reaction mixture was allowed to stir overnight at ambient temperature and then was diluted with ethyl acetate. The combined solution of ethyl acetate was subsequently washed with water, hydrochloric acid (0.5M), brine, dried over sodium sulfate and concentrated. The residue was purified by flash chromatography. Elution with ethyl acetate (33%, v/v, in hexane) gave (4-acetyl-phenylthio)-difluoro-acetic acid ethyl ester (1.38 g, 66%). $^1$H NMR (CDCl$_3$) δ 7.97 (d, J=8 Hz, 2H), 7.90 (d, J=8 Hz, 2H), 4.29 (q, J=7 Hz, 2H), 2.62 (s, 3H), 1.29 (t, J=7 Hz, 3H).

The title compound was prepared by condensing (4-acetyl-phenylthio)-difluoro-acetic acid ethyl ester (Ex-25A) and 4-(thien-2-yl)benzaldehyde (Ex-2A) in a similar manner as described in Ex-22. Yellow solid, 3% yield, mp 118–220° C. $^1$H-NMR (CCDl$_3$) δ 8.11 (d, J=7.9 Hz, 2H), 7.95–7.90 (m, 3H), 7.75–7.70 (m, 3H), 7.66 (m, 3H), 7.59 (d, J=5.0 Hz, 1H), 7.16–7.13 (m, 1H). MS m/z=415 ([M–Na]$^+$, 50%), 321 (100%).

Example 26

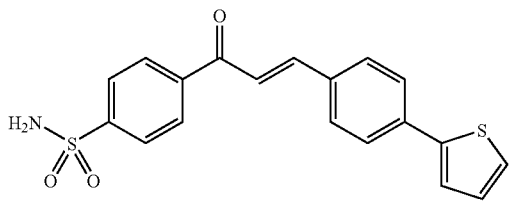

4-[3E-(4-Thiophen-2-yl-phenyl)-acryloyl]-benzenesulfonamide

Ex-26A: To a solution of 4-acetyl-benzenesulfonyl chloride (Hoffman, R. V. Org. Syn. VII, 508; 4.18 g, 19.1 mmol) in acetone (30 mL) was added ammonia (28% in water, 8.2 mL, 57.3 mmol) dropwise at 0° C. The reaction mixture was allowed to stir at 0° C. for 30 min. The precipitate was filtered and the residue was washed with water and dried in vacuo to afford 4-acetyl-benzenesulfonamide as a white solid (3.54 g, 93%). $^1$H NMR (DMSO-d$_6$) δ 8.10 (d, J=9 Hz, 2H), 8.03 (d, J=9 Hz, 2H), 4.86 (bs, 2H), 2.65 (s, 3H).

To a solution of 4-acetyl-benzsulfonamide (Ex-26A, 0.44 g, 2.2 mmol) and 4-thiophen-2-yl-benzaldehyde (Ex-2A, 0.50 g, 2.7 mmol) in DMF (18 mL) was added a solution of NaOH (5 M, 1.77 mL, 8.8 mmol) dropwise. The reaction mixture was allowed to stir at ambient temperature. The reaction was quenched after 2 hours with water. The precipitate was filtered, washed with water, dried in vacuo and purified by stirring in aqueous ethanol overnight. The title compound was collected as a yellow solid (0.45 g, 55%), mp>245° C. $^1$H-NMR (DMSO-d$_6$) δ 8.22 (d, J=8.6 Hz, 2H), 7.96–7.89 (m, 6H), 7.77–7.72 (m, 5H), 7.64 (d, J=4.0 Hz, 1H), 7.60 (d, J=4.6, 1H), 7.15 (m, 1H), 6.65 (bs, 1H). MS m/z=369 ([M+H]$^+$, 100%).

Example 27

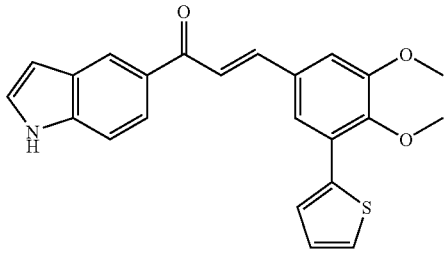

3E-(3,4-Dimethoxy-5-thiophen-2-yl-phenyl)-1-(1H-indol-5-yl)-propenone

To a solution of 1-(1H-indol-5-yl)-ethanone (Yang, Y., et al., *Heterocycles*, 1992, 34(6), 1169–1175) (0.26 g, 1.63 mmol) and 3,4-dimethoxy-5-(thien-2-yl)-benzaldehyde (0.45 g, 1.80 mmol, Ex-1D) in ethanol (30 mL) was added a solution of sodium hydroxide (50%, 0.65 mL, 16 mmol). The reaction mixture was allowed to stir overnight at room temperature. The solution was concentrated. The residue was treated with sulfuric acid (1 M), and the cloudy solution was extracted with dichloromethane. The combined dichloromethane extracts were washed with saturated sodium bicarbonate, brine, dried over sodium sulfate, and concentrated. The residue was purified by column chromatography (silica gel, EtOAc/hexane: 1/3 then 1/1) to give 0.17 g (26%) of the title compound as a yellow solid, m.p. 184.5–186° C. MS (direct probe): m/z=389 (M+). $^1$H-NMR (300 MHz, CDCl$_3$) δ 8.43 (s, 1H), 7.99 (d, 1H), 7.12–7.83 (m, 10H), 6.73 (s, 1H), 3.99 (s, 3H), 3.88 (s, 3H).

Example 28

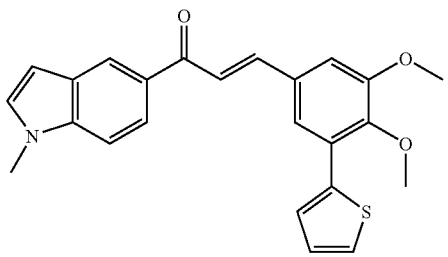

3E-(3,4-Dimethoxy-5-thiophen-2-yl-phenyl)-1-(1-methyl-1H-indol-5-yl)-propenone

Ex-28A: To a solution of 1-(1H-indol-5-yl)-ethanone (Yang, Y. et al, Heterocycles, 1992, 34(6), 1169–1175; 0.45 g, 2.8 mmol) were added iodomethane (3 mL) and cesium carbonate (2.3 g, 7.1 mmol). The reaction mixture was allowed to stir at 55° C. for 1.5 day during which additional iodomethane (11 mL) was added. The reaction was quenched with water. The aqueous solution was extracted with ether. The solution of ether was washed with saturated solution sodium bicarbonate, brine, dried over sodium sulfate and concentrated. The crude product was purified by flash chromatography. Elution with ethyl acetate (33%, v/v, in hexane) gave 1-(1-methyl-1H-indol-5-yl)-ethanone (0.25 g, 51%). $^1$H NMR (CDCl$_3$) δ 8.30 (s, 1H), 7.91 (dd, J=1.2, 8.1 Hz, 1H), 7.34 (d, J=8.6 Hz, 1H), 7.12 (d, J=3.2 Hz, 1H), 6.61 (d, J=3.0, 1H), 3.82 (s, 3H), 2.66 (s, 3H).

The title compound was prepared by condensing 1-(1-methyl-1H-indol-5-yl)-ethanone (Ex-28A) and 3,4-dimethoxy-5-(thien-2-yl)benzaldehyde (Ex-1D) in a similar manner as described in Ex-27. Yellow solid, 43% yield, mp 70–71° C. $^1$H-NMR (CDCl$_3$) δ 8.41 (s, 1H), 8.00 (dd, J=1 Hz, 7 Hz, 1H), 7.80 (d, J=15 Hz, 1H), 7.63 (d, J=15.0 Hz, 1H), 7.58–7.55 (m, 2H), 7.43–7.40 (m, 2H), 7.15–7.12 (m, 3H), 6.66 (d, J=3 Hz, 1H), 3.99 (s, 3H), 3.88 (s, 3H), 3.86 (s, 3H). Anal. (C$_{24}$H$_{21}$NOS.0.25H$_2$O) Calc. C, 70.65; H, 5.31; N, 3.43; S, 7.86; found C, 70.64; H, 5.35; N, 3.43; S, 7.90.

Example 29

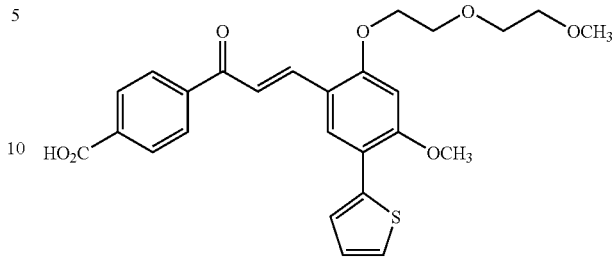

4-(3E-{4-Methoxy-2-[2-(2-methoxyethoxy)ethoxy]-5-thiophen-2-yl-phenyl}-acryloyl)-benzoic Acid Ex-29A: 2-Hydroxy-4-methoxybenzaldehyde (6.0 g, 39 mmol) was dissolved in dichloromethane (50 mL) and cooled to 0° C. using an ice-water bath. Bromine (6.8 g, 43 mmol) in dichloromethane (2 mL) was added dropwise to the cooled solution and stirred for 2 h at 0° C. The mixture was warmed to room temperature and stirred for an additional 1 h and the resulting yellow precipitate was collected. Recrystallization (ethyl acetate/hexanes) yielded 7.1 g (80%) of 5-bromo-2-hydroxy-4-methoxybenzaldehyde as white needles, m.p. 63–64° C. $^1$H-NMR (300 MHz, CDCl$_3$) δ 11.43 (s, 1H), 9.69 (s, 1H), 7.68 (s, 1H), 6.48 (s, 1H), 3.95 (s, 3H). Anal. Calcd. for C$_8$H$_7$BrO$_3$: C, 41.59; H, 3.05. Found: C, 41.86; H, 3.05.

Ex-29B: 5-Bromo-2-hydroxy-4-methoxybenzaldehyde obtained from Ex-29A (1.5 g, 6.5 mmol) and thiophene-2-boronic acid (0.91 g, 7.1 mmol) were dissolved in tetrahydrofuran (15 mL). Nitrogen was bubbled into the solution for 10 min followed by the sequential addition of potassium fluoride (0.80 g, 14 mmol, spray-dried) and bis(tri-t-butylphosphine)palladium(0) (0.033 g, 0.065 mmol). The solution was immediately heated to 60° C. and aged for 1.5 h. Upon completions, as determined by HPLC, the reaction was diluted with water (25 mL) and extracted with ethyl acetate (3×30 mL). The combined organic extracts were dried over sodium sulfate and concentrated to a brown solid. Silica gel chromatography (ethyl acetate/hexanes, 1:3) gave 1.46 g (97%) of 2-hydroxy-4-methoxy-5-thiophen-2-yl-benzaldehyde as a yellow solid, m.p. 118–119° C. $^1$H-NMR (300 MHz, CDCl$_3$) δ 11.48 (s, 1H), 9.79 (s, 1H), 7.72 (s, 1H), 7.37 (dd, 1H), 7.31 (dd, 1H), 7.08 (dd, 1H), 6.54 (s, 1H), 3.98 (s, 3H). Anal. Calcd. for C$_8$H$_7$O$_3$S: C, 61.52; H, 4.30; S, 13.69. Found: C, 61.12; H, 4.34; S, 13.56.

Ex-29C: To a solution of 2-hydroxy-4-methoxy-5-thiophen-2-yl-benzaldehyde from Ex-29B (0.10 g, 0.43 mmol) in N,N-dimethylformamide (3 mL) was added potassium carbonate (0.18 g, 1.3 mmol) and the resulting yellow slurry was heated to 80° C. Once at 80° C., 1-bromo-2-(2-methoxyethoxy)ethane (0.24 g, 1.3 mmol) was added dropwise in three equal portions with stirring at 1 h intervals. After the last addition, the reaction was stirred for an additional 1 h at 80° C. and cooled to room temperature. The mixture was diluted with water (15 mL) and extracted with ethyl acetate (3×15 mL). The combined organic layers was sequentially washed with a saturated ammonium chloride solution (1×15 mL), water (1×15 mL), and brine (1×15 mL), dried over sodium sulfate, and concentrated to a brown oil. Silica gel chromatography (ethyl acetate/hexanes, 4:1) afforded 0.13 g (87%) of 4-methoxy-2-[2-(2-methoxyethoxy)ethoxy]-5-thiophen-2-yl-benzaldehyde as a pale yellow oil. $^1$H-NMR (300 MHz, CDCl$_3$) δ 10.38 (s, 1H), 8.12 (s, 1H), 7.44 (dd, 1H), 7.30 (dd, 1H), 7.07 (dd, 1H), 6.57 (s, 1H), 4.33 (t, 2H), 4.00 (s, 3H), 3.94 (t, 2H), 3.74 m, 2H), 3.59 (m, 2H), 3.40 (s, 3H). HRMS (EI) Calcd. for C$_{17}$H$_{20}$O$_5$S: 336.1031. Found: 336.1027.

4-Methoxy-2-[2-(2-methoxyethoxy)ethoxy]-5-thiophen-2-yl-benzaldehyde obtained from Ex-29C (0.13 g, 0.37 mmol) and 4-acetylbenzoic acid (0.061 g, 0.37 mmol) were dissolved in a tetrahydrofuran-methanol solution (2 mL, 7:3). After complete dissolution, lithium methoxide (0.057 g, 1.5 mmol) was added and the resulting bright orange slurry was stirred in the dark at room temperature for 4 h. Upon completion, as determined by HPLC, the mixture was diluted with water (10 mL), acidified with a 1 N hydrochloric acid solution, and extracted with ethyl acetate (3×15 mL). The combined organic extracts were dried over sodium sulfate and evaporated to dryness. The crude oil was taken up in ethyl alcohol (3 mL) and warmed to 60° C. to obtain complete dissolution and allowed to cool to room temperature. The resulting precipitate was collected and dried in vacuo to yield 0.14 g (85%) of the title compound as a yellow solid, m.p. 145–146° C. $^1$H-NMR (300 MHz, DMSO-d$_6$) δ 8.22 (m, 3H), 8.09 (d, 2H), 8.01 (d, 2H), 7.66 (dd, 1H), 7.52 (d, 1H), 7.13 (dd, 1H), 6.88 (s, 1H), 4.36 (t, 2H), 4.00 (s, 3H), 3.88 (t, 2H), 3.65 (m, 2H), 3.46 (m, 2H), 3.22 (s, 3H). Anal. Calcd. for C$_{26}$H$_{26}$NO$_7$S: C, 64.71; H, 5.43; S, 6.64. Found: C, 64.64; H, 5.44; S, 6.61.

Example 30

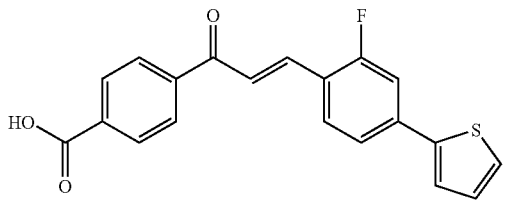

4-[3E-(2-Fluoro-4-thiophen-2-yl-phenyl)-acryloyl]-benzoic acid

Ex-30A: 2-Fluoro-4-thiophen-2-yl-benzaldehyde was prepared in a similar manner as described in Ex-3A from thiophene-2-boronic acid and 4-bromo-2-fluorobenzaldehide (93% yield). $^1$H-NMR (300 MHz, d$_6$-DMSO): 10.13 (s, 1H), 7.81 (d, 1H, J=8.0 Hz), 7.76 (m, 1H), 7.67 (m, 2H), 7.59 (dd, 1H J=8.0 and 2.1 Hz), 7.17 (dd, 1H J=5.2 and 3.7 Hz).

The title compound was prepared by condensing 2-fluoro-4-thiophen-2-yl-benzaldehyde (Ex-30A) and 4-acetylbezoic acid in a similar manner as described in Ex-3. Yellow solid, 71% yield, m.p.>260° C. $^1$H-NMR (300 MHz, d$_6$-DMSO): 8.19 (d, 2H, J=8.4 Hz), 8.12 (d, 1H, J=8 Hz), 8.06 (d, 2H, J=8 Hz), 7.95 (d, 1H, J=16 Hz), 7.80 (d, 1H, J=16 Hz), 7.71 (d, 1H, J=3.5 Hz), 7.62 (m, 2H), 7.56 (d, 1H, J=8 Hz), 7.15 (m, 1H). MS m/z=352 ([M]$^+$, 100%). HRMS (EI) Calcd. for C$_{20}$H$_{13}$NO$_3$S: 352.0569. Found: 352.0560.

Example 31

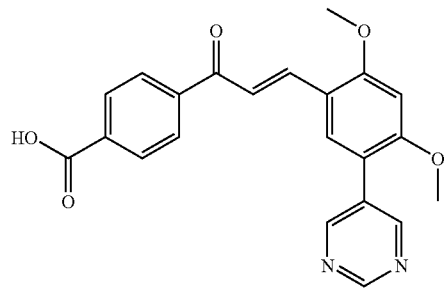

4-[3E-(2,4-Dimethoxy-5-pyrimidin-5-yl-phenyl)-acryloyl]-benzoic acid

Ex-31A: 2,4-Dimethoxy-5-pyrimidin-5-yl-benzaldehyde was prepared from 5-bromo-2,4-dimethoxybenzaldehyde and pyrimidine-5-boronic acid in a similar manner as described in Ex-3A, 98% yield. $^1$H-NMR (CDCl$_3$) δ 10.37 (s, 1H), 9.15 (s, 1H), 8.87 (s, 2H) 7.86 (s, 1H), 6.57 (s, 1H), 4.03 (s, 3H), 3.96 (s, 3H).

The title compound was prepared by condensing 2,4-dimethoxy-5-pyrimidin-5-yl-benzaldehyde (Ex-31A) and 4-acetylbezoic acid in a similar manner as described in Ex-3. Yellow solid, mp>260° C., 26% yield. $^1$H-NMR (DMSO-d$_6$) δ 9.11 (s, 1H), 8.96 (s, 2H), 8.13–8.16 (m, 3H), 8.01–8.09 (m, 3H), 7.90 (d, J=15 Hz, 1H), 6.85 (s, 1H), 3.99 (s, 3H), MS m/z=391 ([M+H]$^+$, 100%). HRMS (ES+) Calcd. for C$_{22}$H$_{18}$N$_2$O$_5$: 391.1294. Found: 391.1295.

Example 32

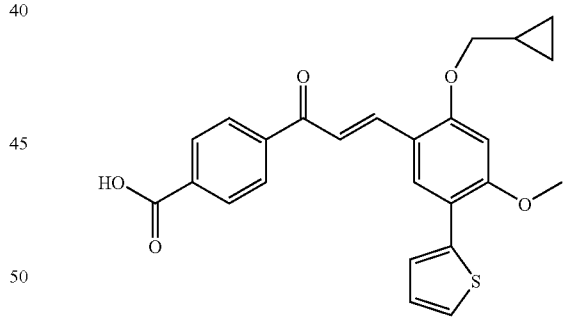

4-[3E-(2-Cyclopropylmethoxy-4-methoxy-5-thiophen-2-yl-phenyl)-acryloyl]-benzoic acid Ex-32A: 2-Cyclopropylmethoxy-4-methoxy-5-thiophen-2-yl-benzaldehyde was prepared in a similar manner as described in Ex-29C from 2-hydroxy-4-methoxy-5-thiophen-2-yl-benzaldehyde (Ex. 29B) and chloromethylcyclopropane, 18% yield. $^1$H-NMR (CDCl$_3$) δ 10.41 (s, 1H), 8.24 (s, 1H), 7.43 (d, 1H), 7.29 (d, 1H), 7.06 (t, 1H), 6.45 (s, 1H), 3.95 (m, 5H), 1.31 (m, 1H), 0.68 (m, 2H), 0.40 (q, 2H).

The title compound was prepared by condensing 2-cyclopropylmethoxy-4-methoxy-5-thiophen-2-yl-benzaldehyde (Ex-32B) and 4-acetylbenzoic acid in a similar manner as described in Ex-3. Yellow solid, mp 187–191° C. $^1$H-NMR (DMSO-d6) δ 8.22 (d, 2H), 8.19 (s, 1H), 7.01 (m, 4H), 7.62 (d, 1H), 7.47 (d, 1H), 7.09 (t, 1H), 6.76 (s, 1H), 4.06 (d, 2H), 3.94 (s, 3H), 1.34 (m, 1H), 0.62 (q, 2H), 0.38 (q, 2H). MS m/z=434 ([M]$^+$, 82%), 363 (100%). 10%. Anal. for $C_{25}H_{22}O_5S$. HRMS m/z: calc. 435.1266, found 435.1266.

Example 33

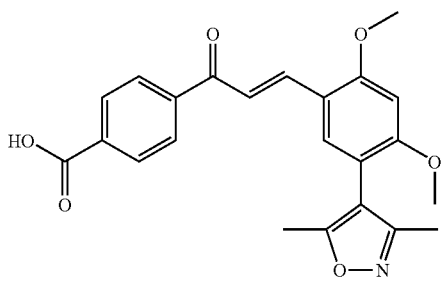

4-{3E-[5-(3,5-Dimethyl-isoxazol-4-yl)-2,4-dimethoxy-phenyl]-acryloyl}-benzoic acid Ex-33A: 5-(3,5-Dimethyl-isoxazol-4-yl)-2,4-dimethoxy-benzaldehyde was prepared from 5-bromo-2,4-dimethoxy-benzaldehyde and 3,5-dimethyl-isoxazole-4-boronic acid in a similar manner as described in Ex-3A, 75% yield. $^1$H-NMR (CDCl$_3$) δ 10.34 (s, 1H), 7.63 (s, 1H), 6.52 (s, 1H), 4.00 (s, 3H), 3.90 (s, 3H), 2.12 (s, 6H).

The title compound was prepared by condensing 5-(3,5-dimethyl-isoxazol-4-yl)-2,4-dimethoxy-benzaldehyde (Ex-33A) and 4-acetylbenzoic acid in a similar manner as described in Ex-3. Yellow solid, mp>260° C., 7% yield. $^1$H-NMR (DMSO-d$_6$) δ 8.15 (d, J=8 Hz, 2H), 8.04 (d, J=16 Hz, 1H), 8.02 (d, J=8 Hz, 2H), 7.89 (s, 1H), 7.81 (d, J=16 Hz, 1H), 6.79 (s, 1H), 4.00 (s, 3H), 3.97 (s, 3H), 2.23 (s, 3H) 2.05 (s, 3H) MS m/z=407 ([M]$^+$, 60%), 376 (100%). HMRS (EI) calcd. for $C_{23}H_{21}NO_6$: 407.1369; found: 407.1375.

Example 34

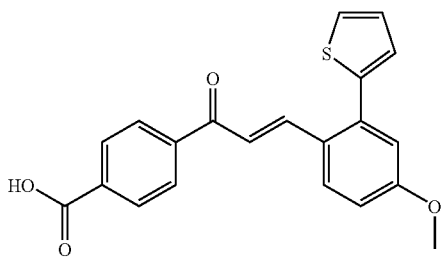

4-[3E-(4-Methoxy-2-thiophen-2-yl-phenyl)-acryloyl]-benzoic acid

Ex-34A: A solution of 2-hydroxy-4-methoxy-benzaldehyde (5.0 g, 32.86 mmol) in dichloromethane (65 mL) was cooled to 0° C. and then pyridine (13.3 mL, 164.4 mmol) was added in 1 portion. Triflic anhydride (14.8 mL, 87.97 mmol) was then added over 2 h while maintaining an internal temperature below 5° C. The resulting solution was allowed to warm to room temperature overnight and then was slowly poured into ice water (100 mL). After diluting further with 1 N HCl (100 mL) the solution was extracted with dichloromethane (2×100 mL). The organic phase was washed with sat NaHCO$_3$ (100 mL) and dried over magnesium sulfate. The solvent was then removed under reduced pressure. Silica gel chromatography (hexane/ethyl acetate, 1:1) gave 1.65 g (18%) of the desired trifluoro-methane-sulfonic acid 2-formyl-5-methoxy-phenyl ester. $^1$H-NMR (300 MHz, CDCl$_3$): 10.12 (s, 1H), 7.94 (dd, 1H, J=8.7 Hz), 7.03 (dd, 1H, J=8.7 and 2.4 Hz), 6.87 (d, 1H, J=2.4 Hz), 3.92 (s, 3H).

Ex-34B: A solution of trifluoro-methanesulfonic acid 2-formyl-5-methoxy-phenyl ester (Ex-34A, 1.6 g, 5.63 mmol) in 1,4-dioxane (15 mL) was stirred at room temperature under nitrogen for 5 min. Thiophene-2-boronic acid (1.08 g, 8.44 mmol), tetrakis(triphenylphosphine)palladium (0) (0.65 g, 0.56 mmol) and a potassium phosphate (2.2 g, 10.36 mmol) were then added and the resulting mixture was heated to 95° C. under nitrogen overnight. Upon cooling to room temperature the reaction was diluted with EtOAc (25 mL) and water (25 mL) and the layers were cut. The organic phase was concentrated under reduced pressure. Silica gel chromatography (hexane/ethyl acetate, 4:1) gave 1.1 g (90%) of the desired 4-methoxy-2-thiophen-2-yl-benzaldehyde product. $^1$H-NMR (300 MHz, CDCl$_3$): 10.06 (s, 1H), 8.03 (m, 1H), 7.45 (m, 1H), 7.14 (m, 1H), 7.09 (m, 1H), 7.00 (m, 2H), 3.91 (s, 3H).

The title compound was prepared by condensing 4-methoxy-2-thiophen-2-yl-benzaldehyde (Ex-34A) and 4-acetyl-benzoic acid in a similar manner as described in Ex-3. Yellow solid, 61% yield, m.p. 209–211° C. $^1$H-NMR (300 MHz, d$_6$-DMSO): 8.14 (m, 3H), 8.04 (d, 2H, J=9.2 Hz), 7.89 (d, 1H, J=15.5 Hz), 7.76 (d, 1H, J=15.5 Hz), 7.70 (d, 1H, J=5.0 Hz), 7.18 (dd, 1H, J=5.6 and 3.6 Hz), 7.11 (d, 1H, J=2.1 Hz), 7.05 (dd, 1H, J=8.8 and 1.8 Hz), 6.98 (d, 1H, J=1.8 Hz), 3.83 (s, 3H). MS m/z=364 ([M]$^+$, 100%). HRMS (EI) Calcd. for $C_{21}H_{16}O_4S$: 364.0769. Found: 364.0761.

Example 35

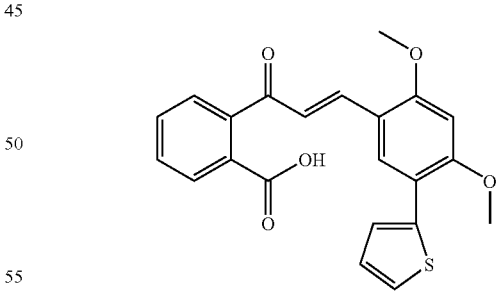

2-[3E-(2,4-Dimethoxy-5-thiophen-2-yl-phenyl)-acryloyl]-benzoic acid

The title compound was prepared by condensing 2,4-dimethoxy-5-(thiophen-2-yl)-benzaldehyde (Ex-6A) and 2-acetylbenzoic acid in a similar manner as described in Ex-3. Yellow solid, 47% yield, mp 196–198° C. $^1$H-NMR (DMSO-d6) δ 8.00 (s, 1H), 7.84 (d, 1H), 7.61 (m, 3H), 7.45 (m, 3H), 7.21 (d, 1H), 7.08 (t, 1H), 6.75 (s, 1H), 3.95 (s, 3H), 3.86 (s, 3H). MS m/z=394 ([M]+, 100%). Anal. calculated for C22H18O5S: C, 66.99; H, 4.60; S, 8.13. found C, 67.08; H, 4.17; S, 7.97.

Example 36

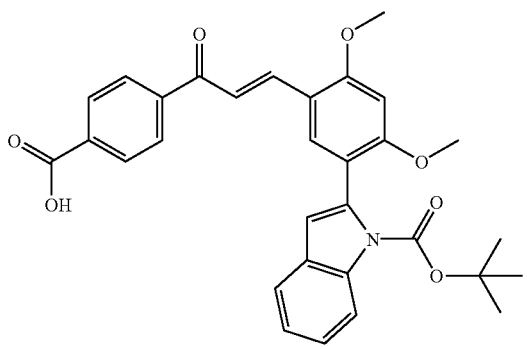

2-{5-[3-(4-Carboxy-phenyl)-3-oxo-E-propenyl]-2,4-dimethoxy-phenyl}-indole-1-carboxylic acid tert-butyl ester Ex-36A: 2-(5-Formyl-2,4-dimethoxy-phenyl)-indole-1-carboxylic acid tert-butyl ester was prepared from 5-bromo-2,4-dimethoxybenzaldehyde and N-Boc-indole-2-boronic acid in a similar manner as described in Ex-3A. Yellow oil, 79% yield. $^1$H-NMR (CDCl3) δ 10.36 (s, 1H), 8.15 (d, J=8 Hz, 1H), 7.88 (s, 1H), 7.45 (d, J=8 Hz, 3H), 7.27–7.35 (m, 1H), 7.19–7.27 (m, 1H), 6.52 (s, 1H), 6.47 (s, 1H), 4.00 (s, 3H), 3.86 (s, 3H), 1.42 (s, 9H).

The title compound was prepared by condensing 2-(5-formyl-2,4-dimethoxy-phenyl)-indole-1-carboxylic acid tert-butyl ester (Ex-36A) and 4-acetylbenzoic acid in a similar manner as described in Ex-3. Yellow solid, 8% yield, mp 182–183° C. $^1$H-NMR (CDCl$_3$) δ 8.21 (d, J=8 Hz, 2H), 8.19 (d, J=13 Hz, 1H), 8.16 (d, J=7 Hz, 1H), 8.07 (d, J=8 Hz, 2H), 7.69 (s, 1H), 7.54 (d, J=7 Hz, 1H), 7.52 (d, J=13 Hz, 1H), 7.29–7.35 (m, 1H), 7.23 (d, J=7 Hz, 1H), 6.55 (s, 1H), 6.50 (s, 1H), 4.00 (s, 3H), 3.85 (s, 3H), 3.81 (s, 3H). MS m/z=528 ([M+H]$^+$, 100%). Anal. calc. for C$_{31}$H$_{29}$NO$_7$H$_2$O: C, 68.25; H, 5.73; N, 2.56; found: C, 68.63; H, 5.62; N, 2.45.

Example 37

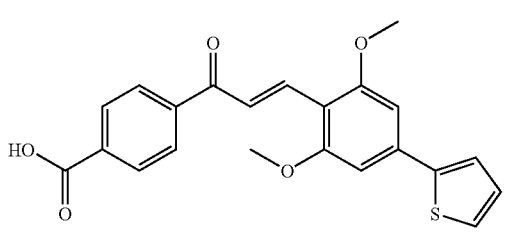

4-[3E-(2,6-Dimethoxy-4-thiophen-2-yl-phenyl)-acryloyl]-benzoic acid

Ex-37A: 2,6-Dimethoxy-4-thiophen-2-yl-benzaldehyde was prepared in a similar manner as described in Ex-34A and Ex-34B. 75% yield, m.p. 168–170° C. $^1$H-NMR (300 MHz, CDCl$_3$): 10.48 (s, 1H), 7.43 (dd, 1H, J=3.6 and 1.3 Hz), 7.41 (d, 1H, J=5.3 Hz), 7.13 (dd, 1H, J=5.3 and 3.6 Hz), 6.79 (s, 2H), 3.96 (s, 6H).

The title compound was prepared by condensing 2,6-dimethoxy-4-thiophen-2-yl-benzaldehyde (Ex-37A) and 4-acetylbenzoic acid in a similar manner as described in Ex-3. Yellow solid, 79% yield, m.p. 256–258° C. $^1$H-NMR (300 MHz, d$_6$-DMSO): 8.11 (d, 1H, J=15.9 Hz), 8.10 (m, 4H), 8.05 (d, 1H, J=15.9 Hz), 7.73 (d, 1H, J=3.6 Hz), 7.61 (d, 1H, J=5.3 Hz), 7.16 (dd, 1H, J=5.3 and 3.6 Hz), 6.95 (s, 2H), 3.98 (s, 6H). MS m/z=394 ([M]$^+$, 100%). HRMS (EI) Calcd. for C$_{22}$H$_{18}$O$_5$S: 394.0875. Found: 394.0877.

Example 38

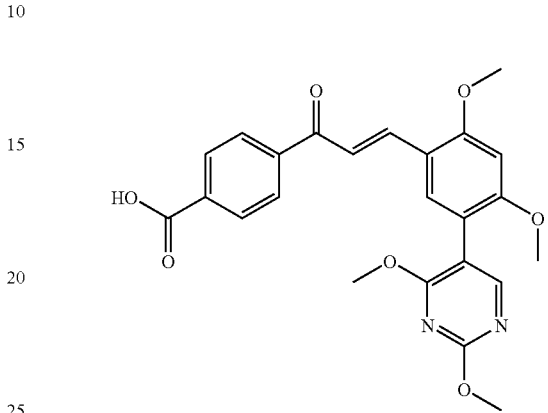

4-{3E-[5-(2,4-Dimethoxy-pyrimidin-5-yl)-2,4-dimethoxy-phenyl]-acryloyl}-benzoic acid Ex-38A: 5-(2,4-Dimethoxy-pyrimidin-5-yl)-2,4-dimethoxy-benzaldehyde was prepared from 5-bromo-2,4-dimethoxybenzaldehyde and 2,4-Dimethoxy-pyrimidin-5-boronic acid in a similar manner as described in Ex-3A, 75% yield. $^1$H-NMR (CDCl$_3$) δ 10.34 (s, 1H), 8.13 (s, 1H), 7.74 (s, 1H), 6.51 (s, 1H), 4.03 (s, 3H), 3.99 (s, 3H), 3.95 (s, 3H), 3.88 (s, 3H).

The title compound was prepared by condensing 5-(2,4-dimethoxy-pyrimidin-5-yl)-2,4-dimethoxy-benzaldehyde (Ex-38A) and 4-acetylbenzoic acid in a similar manner as described in Ex-3. Yellow solid, mp 203–205° C., 22% yield. $^1$H-NMR (DMSO-d$_6$) δ 8.11–9.15 (m, 3H), 7.99–8.06 (m, 3H), 7.88 (s, 1H), 7.76 (d, J=17 Hz, 1H), 6.76 (s, 1H), 3.96 (s, 3H), 3.90 (s, 3H), 3.83 (s, 3H) 3.81 (s, 3H). MS m/z=451 ([M+H]$^+$). HRMS (ES+) Calcd. for C$_{24}$H$_{22}$N$_2$O$_7$: 451.1505. Found: 451.1524.

Example 39

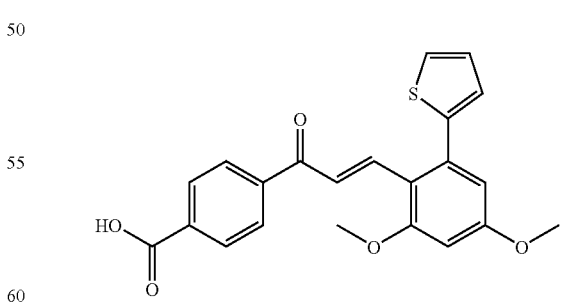

4-[3E-(2,4-Dimethoxy-6-thiophen-2-yl-phenyl)-acryloyl]-benzoic acid

Ex-39A: 2,4-Dimethoxy-6-thiophen-2-yl-benzaldehyde was prepared in a similar manner as described in Ex-34A, 40% yield. $^1$H-NMR (CDCl$_3$) δ 10.02 (s, 1H), 7.40 (d, 1H), 7.07 (m, 2H), 6.58 (d, 1H), 6.50 (d, 1H), 3.93 (s, 3H), 3.89 (s, 3H).

The title compound was prepared by condensing 2,4-dimethoxy-6-thiophen-2-yl-benzaldehyde (Ex-39A) and 4-acetylbenzoic acid in a similar manner as described in Ex-3. Yellow solid, 61% yield, mp 231° C. (dec.). $^1$H-NMR (DMSO-d6) δ 8.02 (d, 2H), 7.93 (d, 2H), 7.73 (m, 3H), 7.15 (t, 1H), 7.07 (d, 1H), 6.72 (d, 1H), 6.62 (d, 1H). MS m/z=394 ([M]$^+$, 6%), 245 (100%). HRMS m/z: calc. 395.0953, found 395.0949.

Example 40

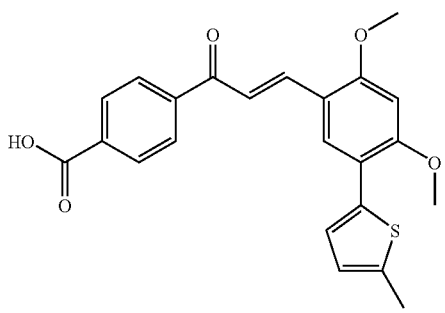

4-{3E-[2,4-Dimethoxy-5-(5-methyl-thiophen-2-yl)-phenyl]-acryloyl}-benzoic acid

Ex-40A: 2,4-Dimethoxy-5-(5-methyl-thiophen-2-yl)-benzaldehyde was prepared from 5-bromo-2,4-dimethoxy-benzaldehyde and 5-methyl-thiophene-2-boronic acid in a similar manner as described in Ex-3A, 100% yield. $^1$H-NMR (CDCl$_3$) δ 10.33 (s, 1H), 8.05 (s, 1H), 7.22 (d, J=4 Hz, 1H), 6.72 (d, J=4 Hz, 1H), 6.49 (s, 1H), 4.00 (s, 3H), 3.97 (s, 3H), 2.50 (s, 3H). HMRS (EI) calcd. for C$_{14}$H$_{14}$O$_3$S: 262.0664; found: 262.0665.

The title compound N was prepared by condensing 2,4-dimethoxy-5-(5-methyl-thiophen-2-yl)-benzaldehyde (Ex-40A) and 4-acetylbenzoic acid in a similar manner as described in Ex-3. Yellow solid, mp 213–215° C., 27% yield. $^1$H-NMR (DMSO-d$_6$) δ 8.18 (d, J=7 Hz, 2H), 8.17 (s, 1H), 8.00–8.06 (m, 3H), 7.85 (d, J=15 Hz, 1H), 7.42 (d, J=4 Hz, 1H), 6.78 (m, 2H), 3.96 (s, 3H), 3.95 (s, 3H), 2.42 (s, 3H). MS m/z=408 ([M]$^+$, 100%). HMRS (EI) calcd. for C$_{23}$H$_{20}$O$_5$S: 408.1031; found: 408.1023.

Example 41

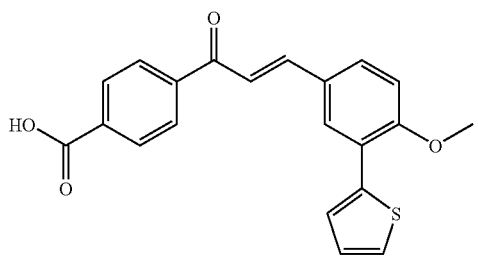

4-[3E-(4-Methoxy-3-thiophen-2-yl-phenyl)-acryloyl]-benzoic acid

Ex-41A: 4-Methoxy-3-(thiophen-2-yl)-benzaldehyde was prepared from 3-bromo-4-methoxybenzaldehyde and thiophene-2-boronic acid in a similar manner as described in Ex-3A. Orange oil, 96% yield. $^1$H-NMR (CDCl$_3$) δ 9.94 (s, 1H), 8.16 (d, J=1.8 Hz, 1H), 7.80 (dd, J=2.4, 8.4 Hz, 1H), 7.57 (dd, J=1.8, 3.6 Hz, 1H), 7.38 (d, J=5.1 Hz, 1H), 7.12 (dd, J=3.6, 5.1 Hz, 1H), 7.09 (d, J=8.4 Hz, 1H), 4.02 (s, 3H). HRMS m/z: calc. 218.0402, found 218.0406.

The title compound was prepared by condensing 4-methoxy-3-(thiophen-2-yl)-benzaldehyde (Ex-41A) and 4-acetylbenzoic acid in a similar manner as described in Ex-3. Yellow solid, mp 219–220° C., 71% yield. $^1$H-NMR (DMSO-D$_6$) δ 13.36 (br s, 1H), 8.25–8.31 (m, 3H), 8.11 (d, J=8 Hz, 2H), 7.85–7.98 (m, 3H), 7.78–7.80 (m, 1H), 7.61 (d, J=5 Hz, 1H), 7.25 (d, J=9 Hz, 1H), 7.17 (dd, J=4, 6 Hz, 1H), 3.99 (s, 3H). HRMS m/z=calc. 365.0848, found 365.0833.

Example 42

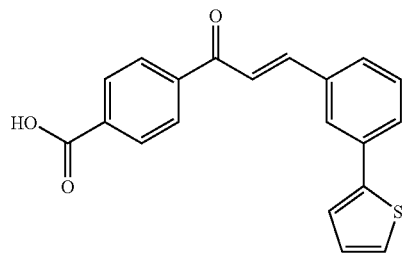

4-[3E-(3-Thiophen-2-yl-phenyl)-acryloyl]-benzoic acid

Ex-42A: 3-(Thiophen-2-yl)-benzaldehyde was prepared from 3-bromobenzaldehyde and thiophene-2-boronic acid in a similar manner as described in Ex-3A. Orange oil, 93% yield. $^1$H-NMR (CDCl$_3$) δ 10.06 (s, 1H), 8.10 (s, 1H), 7.86 (d, J=8.4 Hz, 1H), 7.78 (d, J=7.2 Hz, 1H), 7.55 (dd, J=7.2, 8.4 Hz, 1H), 7.40 (dd, J=1.5, 3.6 Hz, 1H), 7.34 (dd, J=1.5, 5.3 Hz, 1H), 7.11 (dd, J=3.6, 5.3 Hz, 1H). HRMS m/z: calc. 188.0296. found 188.0293.

The title compound was prepared by condensing 3-(thiophen-2-yl)-benzaldehyde (Ex-42A) and 4-acetylbenzoic acid in a similar manner as described in Ex-3. Yellow solid, mp 238° C. (dec), 71% yield. $^1$H-NMR (DMSO-D$_6$) δ 13.40 (bs, 1H), 8.29 (d, J=8 Hz, 2H), 8.22 (s, 1H), 8.13 (d, J=8 Hz, 2H), 8.04 (s, 1H), 7.87 (s, 1H), 7.83 (d, J=8 Hz, 1H), 7.73 (d, J=9 Hz, 1H), 7.69 (d, J=4 Hz, 1H), 7.63 (d, J=5 Hz, 1H), 7.52 (t, J=8 Hz, 1H), 7,20 (dd, J=4, 5 Hz, 1H). HRMS m/z=calc. 335.0742, found 335.0749.

Example 43

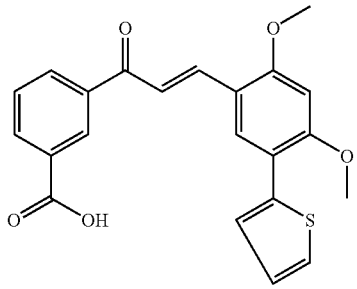

3-[3E-(2,4-Dimethoxy-5-thiophen-2-yl-phenyl)-acryloyl]-benzoic acid

The title compound was prepared by condensing 2,4-dimethoxy-5-(thiophen-2-yl)-benzaldehyde (Ex-6A) and 3-acetylbenzoic acid in a similar manner as described in Ex-3. Yellow solid, 65% yield, mp 179–182° C. $^1$H-NMR (DMSO-d6) δ 8.54 (s, 1H), 8.39 (d, 1H), 8.25 (s, 1H), 8.15 (d, 1H), 8.04 (d, 1H), 7.90 (d, 1H), 7.67 (m, 2H), 7.48 (d, 1H), 7.09 (t, 1H), 6.81 (s, 1H), 3.98 (s, 3H), 3.97 (s, 3H). MS m/z=394 ([M]$^+$, 72%), 363 (100%). Anal. calculated for C22H18O5S: C, 66.99; H, 4.60; S, 8.13; found C, 66.80; H, 4.60; S, 8.07.

Example 44

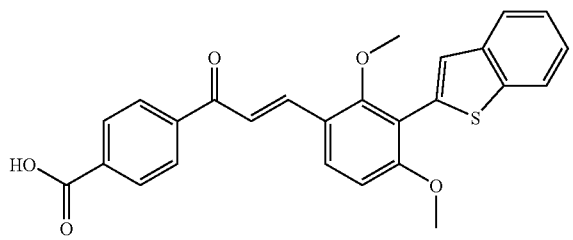

4-[3E-(3-Benzo[b]thiophen-2-yl-2,4-dimethoxy-phenyl)-acryloyl]-benzoic acid

Ex-44A: 3-Benzo[b]thiophen-2-yl-2-hydroxy-4-methoxy-benzaldehyde was prepared through Suzuki coupling as described in Ex-3A using 3-bromo-2-hydroxy-4-methoxy-benzaldehyde (obtained as a minor product from Ex-29A). $^1$H-NMR (CDCl$_3$) δ 12.08 (s, 1H), 9.80 (s, 1H), 7.80–7.87 (m, 2H), 7.70 (s, 1H), 7.56 (d, J=9 Hz, 1H), 7.31–7.35 (m, 2H), 6.71 (d, J=9 Hz, 1H), 3.97 (s, 3H). HRMS m/z: calc. 284.0507, found 284.0502.

Ex-44B: 3-Benzo[b]thiophen-2-yl-2-hydroxy-4-methoxy-benzaldehyde (Ex-44A, 57.4 mg, 0.202 mmol) was dissolved in acetone (5 mL) and potassium carbonate (31 mg, 0.22 mmol) was added. Methyl iodide (25 uL, 0.40 mmol) was added and the solution was heated to reflux for 3.5 h. After cooling, the crude reaction mix was concentrated on the rotavap. The resulting residue was taken up in 10 mL of a 1:9 mix of saturated, aqueous NH$_4$Cl to water and extracted with EtOAc (2×15 mL). The organic phase was dried over sodium sulfate, filtered, and concentrated to provide 58.5 mg of 3-benzo[b]thiophen-2-yl-2,4-dimethoxy-benzaldehyde as an orange, oily residue which was used without further purification, 97% yield. $^1$H-NMR (CDCl$_3$) δ 10.31 (s, 1H), 7.92 (d, J=9 Hz, 1H), 7.81–7.88 (m, 2H), 7.56 (d, 1H), 7.33–7.39 (m, 2H), 6.88 (d, J=9 Hz, 1H), 3.91 (s, 3H), 3.64 (s, 3H).

The title compound was prepared by condensing 3-benzo[b]thiophen-2-yl-2,4-dimethoxy-benzaldehyde (Ex-44B) and 4-acetylbenzoic acid in a similar manner as described in Ex-3. Yellow solid, mp 237° C. (dec.), 64% yield. $^1$H-NMR (DMSO-d$_6$) δ 13.37 (bs, 1H), 8.20–8.25 (m, 3H), 8.11 (d, J=8 Hz, 2H), 8.02 (d, J=8 Hz, 1H), 7.96 (d, J=9 Hz, 2H), 7.88–7.91 (m, 1H), 7.65 (s, 1H), 7.35–7.43 (m, 2H), 7.14 (d, J=9 Hz, 1H), 3.90 (s, 3H), 3.53 (s, 3H). HRMS m/z=calc. 445.1110, found 445.1112.

Example 45

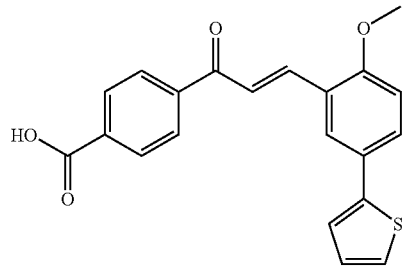

4-[3E-(2-Methoxy-5-thiophen-2-yl-phenyl)-acryloyl]-benzoic acid

Ex-45A: 2-Methoxy-5-(thiophen-2-yl)-benzaldehyde was prepared from 5-bromo-2-methoxybenzaldehyde and thiophene-2-boronic acid in a similar manner as described in Ex-3A. $^1$H NMR (CDCl$_3$) δ 10.49 (s, 1H), 8.07 (d, J=3 Hz, 1H), 7.79 (dd, J=3, 9.0 Hz, 1H), 7.28–7.26 (m, 2H), 7.09–7.06 (m, 1H), 7.02 (d, J=9 Hz, 1H), 3.97 (s, 3H).

The title compound was prepared by condensing 2-methoxy-5-(thiophen-2-yl)-benzaldehyde (Ex-45A) and 4-acetylbenzoic acid in a similar manner as described in Ex-3. Yellow solid, mp 195–196° C. $^1$H-NMR (DMSO-d$_6$) δ 8.23–8.20 (m, 3H), 8.08–7.96 (m, 4H), 7.67 (dd, J=2.1, 6.8 Hz, 1H), 7.55 (d, J=3.8 Hz, 1H), 7.49 (d, J=5.1 Hz, 1H), 7.16–7.11 (m, 2H), 3.90 (s, 3H). MS m/z=364 (M$^+$, 100%).

Example 46

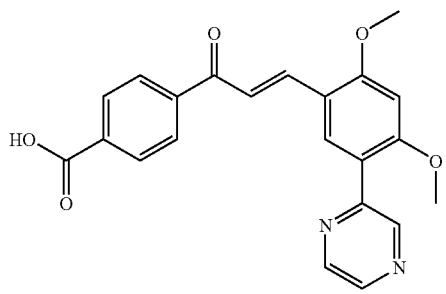

4-[3E-(2,4-Dimethoxy-5-pyrazin-2-yl-phenyl)-acryloyl]-benzoic acid

Ex-46A: 5-Bromo-2,4-dimethoxybenzaldehyde (4.92 g, 20.1 mmol) was dissolved in benzene (41 mL). Ethylene glycol (3 mL, 54 mmol) and p-toluenesulfonic acid (25 mg, 0.13 mmol) were added and the solution was refluxed with a Dean-Stark trap attached. After 6 h, the reaction was cooled and washed with water (1×20 mL), saturated, aqueous $NaHCO_3$ (1×20 mL), and water (1×20 mL). The organic phase was dried over sodium sulfate, filtered, concentrated, and dried to provide 5.32 g of 2-(5-bromo-2,4-dimethoxy-phenyl)-[1,3]dioxolane as a faint yellow oil which solidified upon standing (92% yield). $^1$H-NMR ($CDCl_3$) δ 7.67 (s, 1H), 6.47 (s, 1H), 6.06 (s, 1H), 4.11–4.13 (m, 2H), 3.98–4.03 (m, 2H), 3.91 (s, 3H), 3.87 (s, 3H). HRMS (ES+) Calcd. for $C_{11}H_{13}BrO_4$: 289.0075. Found: 289.0077.

Ex-46B: 2-(5-Bromo-2,4-dimethoxy-phenyl)-[1,3]dioxolane (Ex-46A, 4.78 g, 10.5 mmol) was dissolved in dioxane (75 mL) and the solution was purged with nitrogen for 15 min. $Pd(OAc)_2$ (188 mg, 0.84 mmol), $Et_3N$ (6.91 mL, 49.6 mmol), and 2-(dicyclohexylphosphino)biphenyl (1.16 g, 3.31 mmol) were added. 4,4,5,5-Tetramethyl-[1,3,2]dioxaborolane (3.6 mL, 24.8 mmol) was added slowly, accompanied by gas evolution and the darkening of the reaction solution. The solution was heated at reflux for 2.5 h and then cooled. Saturated, aqueous $NH_4Cl$ (60 mL) and water (20 mL) were added and the solution extracted with EtOAc (1×100 mL). The organic phase was dried over sodium sulfate, filtered, and concentrated to a dark oil. The oil was purified via silica gel chromatography (1:1 EtOAc/hexanes after a column pre-wash of 5% $Et_3N$ in 1:1 EtOAc/hexanes) to provide 3.27 g of 2-(5-[1,3]dioxolan-2-yl-2,4-dimethoxy-phenyl)-4,4,5,5-tetramethyl-[1,3,2]dioxaborolane as a yellow solid (with some starting borolane present), 59% yield. $^1$H-NMR ($CDCl_3$) δ 7.85 (s, 1H), 6.39 (s, 1H), 6.07 (s, 1H), 4.13–4.18 (m, 2H), 3.98–4.02 (m, 2H), 3.89 (s, 3H), 3.84 (s, 3H), 1.33 (s, 9H).

Ex-46C: 2-(5-[1,3]Dioxolan-2-yl-2,4-dimethoxy-phenyl)-4,4,5,5-tetramethyl-[1,3,2]dioxaborolane (Ex-46B, 2.22 g, 6.60 mmol, containing borolane impurity) was dissolved in DME (60 mL) and 2-iodopyrazine (0.59 mL, 6.0 mmol) was added. 2M aqueous $Na_2CO_3$ (17.8 mL, 35.6 mmol) was added and the mixture was purged with nitrogen for 20 min. Tetrakis(triphenylphosphine)palladium(0) (0.69 g, 0.60 mmol) was added and the mixture was heated at reflux for 2.5 h. After cooling, water (50 mL) was added and the mixture was extracted with $CH_2Cl_2$ (2×30 mL). The organic phase was washed with brine (1×20 mL), dried over sodium sulfate, filtered, and concentrated. Purification of the resulting yellow-orange solids via silica chromatography (50–80% EtOAc/hexanes) provided 1.02 g of 2-(5-[1,3]dioxolan-2-yl-2,4-dimethoxy-phenyl)-pyrazine as a yellow solid (59% yield). $^1$H-NMR ($CDCl_3$) δ 9.10 (d, J=2 Hz, 1H), 8.61 (m, 1H), 8.39 (d, J=3 Hz, 1H), 8.07 (s, 1H), 6.57 (s, 1H), 6.14 (s, 1H), 4.13–4.18 (m, 2H), 4.01–4.05 (m, 2H), 3.95 (s, 3H), 3.93 (s, 3H).

Ex-46D: 2-(5-[1,3]Dioxolan-2-yl-2,4-dimethoxy-phenyl)-pyrazine (1.02 g, 3.54 mmol) was dissolved in acetone and p-toluenesulfonic acid (100 mg, 0.53 mmol) and water (5 mL) were added. The solution was stirred for 3 h at room temperature, then concentrated on the rotavap. The resulting mixture was diluted with water (50 mL) and extracted with EtOAc (3×100 mL). The organic phase was washed with 25% saturated aqueous $NaHCO_3$, dried over sodium sulfate, filtered, and concentrated. Drying gave 0.30 g of 2,4-dimethoxy-5-pyrazin-2-yl-benzaldehyde as a yellow solid (18% yield). $^1$H-NMR ($CDCl_3$) δ 10.35 (s, 1H), 9.06 (d, J=2 Hz, 1H), 8.63–8.65 (m, 1H), 8.45 (d, J=2 Hz, 1H), 8.39 (s, 1H), 6.56 (s, 1H), 4.03 (s, 3H), 4.01 (s, 3H). HRMS m/z: calc. 244.0848, found 244.0853.

The title compound was prepared by condensing 2,4-dimethoxy-5-pyrazin-2-yl-benzaldehyde (Ex-46D) and 4-acetylbenzoic acid in a similar manner as described in Ex-3. Yellow solid, mp 238° C. (dec.), 4% yield. $^1$H-NMR (DMSO-$D_6$) δ 9.04 (d, J=2 Hz, 1H), 8.75–8.76 (m, 1H), 8.56 (d, J=2 Hz, 1H), 8.32 (s, 1H), 8.19 (d, J=9 Hz, 2H), 8.05–8.11 (m, 3H), 7.83 (d, J=16 Hz, 1H), 6.90 (s, 1H), 4.05 (s, 3H), 4.00 (s, 3H). HRMS m/z=calc. 391.1294. found 391.1313.

Example 47

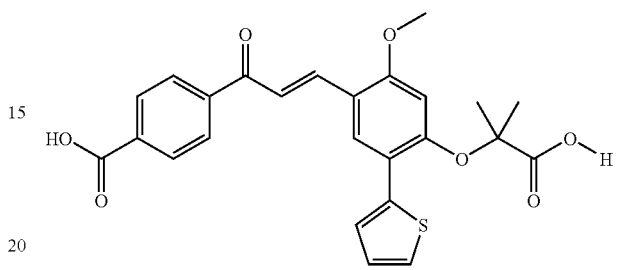

4-{3E-[4-(1-Carboxy-1-methyl-ethoxy)-2-methoxy-5-thiophen-2-yl-phenyl]-acryloyl}-benzoic acid Ex-47A: 5-Bromo-4-hydroxy-2-methoxy-benzaldehyde was prepared in an analogous fashion as described in Ex-29A using 4-hydroxy-2-methoxybenzaldehyde. The crude solid was slurried in water to remove residual HBr and dried in vacuo to give the bromide as an off-white solid (98%), mp 199–201° C. $^1$H-NMR (300 MHz, DMSO-$d_6$) δ 11.58 (s, 1H), 10.07 (s, 1H), 7.75 (s, 1H), 6.69 (s, 1H), 3.87 (s, 3H). MS (EI) m/z=230 ([M]$^+$, 100%). Anal. Calcd. for $C_8H_7BrO_3$·¼$H_2O$: C, 40.79; H, 3.21; Found: C, 40.66; H, 3.01.

Ex-47B: 4-Hydroxy-2-methoxy-5-thiophen-2-yl-benzaldehyde was prepared in an analogous fashion as described in Ex-29B. Silica gel chromatography (ethyl acetate/hexanes, 2:1) gave the expected product as a solid (85%), mp 200° C. (dec.). $^1$H-NMR (300 MHz, $CDCl_3$) δ 10.31 (s, 1H), 7.89 (s, 1H), 7.42 (dd, 1H, J=4.8, 1.2 Hz), 7.14–7.19 (m, 2H), 6.59 (s, 1H), 6.14 (brs, 1H), 3.94 (s, 3H). MS (EI) m/z: 234 ([M]$^+$, 100%). Anal. Calcd. for $C_{12}H_{10}O_3S$·$H_2O$: C, 57.13; H, 4.79; S, 12.71. Found: C, 57.16; H, 4.47; S, 12.48.

Ex-47C: 2-(4-Formyl-5-methoxy-2-thiophen-2-yl-phenoxy)-2-methyl-propionic acid ethyl ester was prepared in an analogous fashion as described in Ex-29C using ethyl 2-bromoisobutyrate. Silica gel chromatography (ethyl acetate/hexanes, 1:1) gave the expected product as a solid (82%), mp 111–113° C. $^1$H-NMR (300 MHz, $CDCl_3$) δ 10.32 (s, 1H), 8.14 (s, 1H), 7.45 (dd, 1H, J=3.7, 1.3 Hz), 7.30 (dd, 1H, J=5.2, 1.3 Hz), 7.07 (dd, 1H, J=5.2, 3.7 Hz), 6.35 (s, 1H), 4.25 (q, 2H, J=7.2 Hz), 3.85 (s, 3H), 1.76 (s, 6H), 1.23 (t, 3H, J=7.2 Hz). MS (EI) m/z=348 ([M]$^+$, 100%). Anal. Calcd. for $C_{18}H_{20}O_5S$: C, 62.05; H, 5.79; S, 9.20. Found: C, 61.81; H, 5.81; S, 9.12.

Ex-47D: To a solution of 2-(4-formyl-5-methoxy-2-thiophen-2-yl-phenoxy)-2-methyl-propionic acid ethyl ester (0.29 g, 0.83 mmol) in a mixture of tetrahydrofuran, water and methanol (9 mL, 4:1:1) was added lithium hydroxide (0.10 g, 2.49 mmol) and the resulting yellow slurry was stirred at rt for 5 h. The mixture was diluted with water (5 mL) and extracted with ethyl acetate (1×5 mL). The aqueous layer was acidified with a 1 N HCl solution and extracted with ethyl acetate (3×15 mL). The combined organic layers was dried over sodium sulfate and concentrated to afford 0.13 g (87%) of 2-(4-formyl-5-methoxy-2-thiophen-2-yl-phenoxy)-2-methyl-propionic acid as a pale green solid, mp 183–184° C. $^1$H-NMR (300 MHz, CDCl$_3$) δ 10.32 (s, 1H), 8.12 (s, 1H), 7.40 (d, 1H, J=3.6 Hz), 7.32 (d, 1H, J=4.8 Hz), 7.08 (dd, 1H, J=4.8, 3.6 Hz), 6.47 (s, 1H), 3.86 (s, 3H), 1.78 (s, 6H). MS (EI) m/z=320 ([M]$^+$, 100%). Anal. Calcd. for C$_{16}$H$_{16}$O$_5$S: C, 59.99; H, 5.03; S, 10.01. Found: C, 60.04; H, 5.26; S, 9.70.

2-(4-Formyl-5-methoxy-2-thiophen-2-yl-phenoxy)-2-methyl-propionic acid (Ex-47, 0.23 g, 0.72 mmol) and 4-acetylbenzoic acid (0.12 g, 0.72 mmol) were dissolved in a dimethylformamide-methanol solution (5 mL, 7:3). After complete dissolution, lithium methoxide (0.11 g, 2.9 mmol) was added and the resulting orange slurry was stirred in the dark at room temperature for 4 h. Upon completion, as determined by HPLC, the mixture was diluted with water (15 mL), acidified with a 1 N hydrochloric acid solution, and extracted with ethyl acetate (4×25 mL). The combined organic extracts were dried over sodium sulfate and evaporated to dryness. The crude oil was taken up in a tetrahydrofuran-heptane solution (5 mL, 10:1) and warmed to 60° C. to obtain complete dissolution and allowed to cool to room temperature. The resulting precipitate was collected on filter paper and dried in vacuo to yield 0.30 g (90%) of the title compound as a dark yellow solid, mp 135–137° C. $^1$H-NMR (300 MHz, DMSO-d$_6$) δ 8.32 (s, 1H), 8.23 (d, 2H, J=8.4 Hz), 8.10 (d, 2H, J=8.4 Hz), 7.99 (d, 2H, J=15.6 Hz), 7.71 (d, 1H, J=3.0 Hz), 7.54 (d, 1H, J=5.1 Hz), 7.14 (dd, 1H, J=5.1, 3.0 Hz), 6.49 (s, 1H), 3.85 (s, 3H), 1.69 (s, 6H). MS (ESI) m/z=467 ([M+H]$^+$, 100%). Anal. Calcd. for C$_{25}$H$_{28}$O$_8$S.EtOH: C, 63.27; H, 5.51; S, 6.26. Found: C, 63.40; H, 5.19; S, 6.38.

Example 48

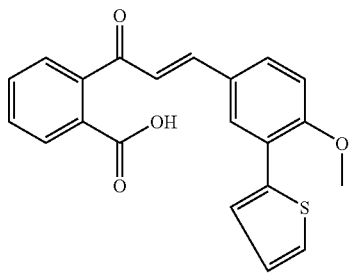

2-[3E-(4-Methoxy-3-thiophen-2-yl-phenyl)-acryloyl]-benzoic acid

The title compound was prepared by condensing 4-methoxy-3-(thiophen-2-yl)-benzaldehyde (Ex-41A) and 2-acetylbenzoic acid in a similar manner as described in Ex-3. Beige solid with green tint, mp 79–81° C., 44% yield. $^1$H-NMR (DMSO-D$_6$) δ 8.07 (d, J=2 Hz, 1H), 7.91 (d, J=8 Hz, 1H), 7.73 (dd, J=2, 4 Hz, 1H), 7.67–7.70 (m, 2H), 7.63 (dd, J=2, 7 Hz, 1H), 7.57 (dd, J=2,5 Hz, 1H), 7.50 (d, J=8 Hz, 1H), 7.22 (d, J=2 Hz, 2H), 7.19 (d, J=8 Hz, 1H), 7.12 (dd, J=4, 5 Hz, 1H), 3.96 (s, 3H). HRMS m/z=calc. 365.0848, found 365.0853.

Example 49

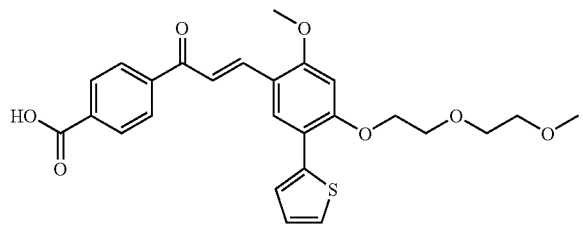

4-(3E-{2-Methoxy-4-[2-(2-methoxy-ethoxy)-ethoxy]-5-thiophen-2-yl-phenyl}-acryloyl)-benzoic acid Ex-49A: To a solution of 4-hydroxy-2-methoxy-5-thiophen-2-yl-benzaldehyde (Ex-47B, 0.50 g, 2.14 mmol) and tri(ethylene glycol) monomethyl ether (0.38 g, 3.2 mmol) in tetrahydrofuran (20 mL) was added triphenylphosphine (0.84 g, 3.2 mmol) and the resulting mixture was cooled to 0° C. Diethyl azodicarboxylate (0.55 g, 3.2 mmol) was then added drop wise, stirred at 0° C. for 30 min, and allowed to warm to rt. The solution was stirred for an additional 24 and concentrated under reduced pressure to a brown oil. Silica gel chromatography (ethyl acetate/hexanes, 8:1) afforded 0.31 g (45%) of the expected 2-methoxy-4-[2-(2-methoxy-ethoxy)-ethoxy]-5-thiophen-2-yl-benzaldehyde as a viscous clear oil. $^1$H-NMR (300 MHz, CDCl$_3$) δ 10.34 (s, 1H), 8.13 (s, 1H), 7.48 (d, 1H, J=3.6 Hz), 7.30 (t, 1H, J=5.1 Hz), 7.06 (dd, 1H, J=5.1, 3.6 Hz), 6.56 (s, 1H), 4.34 (t, 2H, J=5.1 Hz), 3.94 (t, 2H, J=5.1 Hz), 3.96 (s, 3H), 3.72–3.75 (m, 2H), 3.56–3.59 (m, 2H), 3.39 (s, 3H). MS (ESI) m/z=337 ([M+H]$^{30}$, 100%). HRMS (EI) Calcd. for C$_{17}$H$_{20}$O$_5$S: 336.1031. Found: 336.1028.

The title compound was prepared by condensing 2-methoxy-4-[2-(2-methoxy-ethoxy)-ethoxy]-5-thiophen-2-yl-benzaldehyde (Ex-49A) and 4-acetylbenzoic acid in a similar manner as described in Ex-3. Yellow solid, mp 174–175° C., 61% yield. $^1$H-NMR (300 MHz, DMSO-d$_6$) δ 8.28 (s, 1H), 8.23 (d, 2H, J=8.1 Hz), 8.05–8.11 (m, 3H), 7.91 (d, 1H, J=15.3 Hz), 7.72 (d, 1H, J=2.7 Hz), 7.52 (d, 1H, J=4.2 Hz), 7.11–7.15 (m, 1H), 6.86 (s, 1H), 4.39 (t, 2H, J=3.9 Hz), 3.99 (s, 3H), 3.89 (t, 2H, J=3.9 Hz), 3.64 (t, 2H, J=3.9 Hz), 3.48 (t, 2H, J=3.9 Hz), 3.25 (s, 3H). MS (ESI) m/z=483 ([M+H]+, 100%). Anal. Calcd. for C$_{26}$H$_{26}$O$_7$S: C, 64.71; H, 5.43; S, 6.64. Found: C, 64.43; H, 5.34; S, 6.54.

Example 50

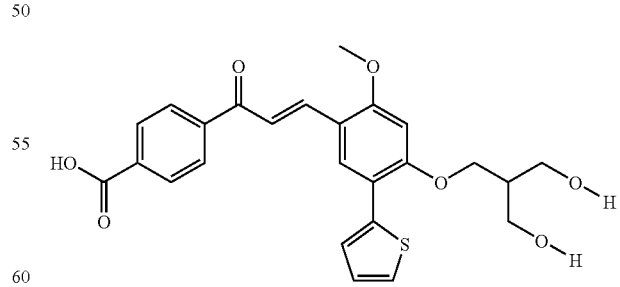

4-{3E-[4-(3-Hydroxy-2-hydroxymethyl-propoxy)-2-methoxy-5-thiophen-2-yl-phenyl]-acryloyl}-benzoic acid Ex-50A: To a solution of 3-(tert-butyl-dimethyl-silanyloxy)-2-(tert-butyl-dimethyl-silanyloxymethyl)-propan-1-ol (25.0 g, 74.3 mmol) and triethylamine (22.6 g, 223 mmol) in dichloromethane (150 mL) at 0° C. was added mesyl chloride (12.8 g, 111 mmol) and the resulting slurry was stirred at 0° C. for 15 min and allowed to warm to rt. The solution was stirred for an additional 3 h at rt and diluted with water (130 mL) and ethyl acetate (350 mL). The layers were separated and the aqueous was extracted with ethyl acetate (1×150 mL). The combined organic extracts were washed with a saturated sodium bicarbonate (1×200 mL), a 50% sodium chloride solution (2×200 mL), dried over sodium sulfate and concentrated to afford 29.5 g (97%) of the expected methanesulfonic acid 3-(tert-butyl-dimethyl-silanyloxy)-2-(tert-butyl-dimethyl-silanyloxymethyl)-propyl ester as a yellow oil, 97% yield. $^1$H-NMR (300 MHz, CDCl$_3$) δ 4.29 (d, 2H, J=5.7 Hz), 3.61–3.68 (m, 4H), 2.99 (s, 3H), 2.04–2.11 (m, 1H), 0.88 (s, 18H), 0.049 (s, 12H). HRMS (ESI) Calcd. for C$_{17}$H$_{40}$O$_5$SSi$_2$: 413.2213. Found 413.2226.

Ex-50B: 4-[3-(tert-Butyldimethyl-silanyloxy)-2-(tert-butyl-dimethyl-silanyloxymethyl)-propoxy]-2-methoxy-5-thiophen-2-yl-benzaldehyde was prepared in an analogous fashion as described in EX-29C using methanesulfonic acid 3-(tert-butyl-dimethyl-silanyloxy)-2-(tert-butyl-dimethyl-silanyloxymethyl)-propyl ester (Ex-50A). Silica gel chromatography (ethyl acetate/hexanes, 1:6) gave the expected product as a pale green solid, 90% yield. $^1$H-NMR (300 MHz, CDCl$_3$) δ 10.34 (s, 1H), 8.13 (s, 1H), 7.41 (dd, 1H, J=3.6, 1.2 Hz), 7.28 (dd, J=5.1, 1.2 Hz), 7.05 (dd, 1H, J=5.1, 3.6 Hz), 6.54 (s, 1H), 4.22 (d, 2H, J=5.7 Hz), 3.96 (s, 3H), 3.80 (d, 4H, J=5.7 Hz), 2.33 (pentet, 1H, J=5.7 Hz), 0.88 (s, 18H), 0.012 (s, 12H). MS (ESI) m/z=551 ([M+H]$^+$, 100%). HRMS (EI) Calcd. for C$_{28}$H$_{46}$O$_5$SSi$_2$: 550.2604. Found: 550.2593.

Ex-50C: To a solution of 4-[3-(tert-butyl-dimethyl-silanyloxy)-2-(tert-butyl-dimethyl-silanyloxymethyl)-propoxy]-2-methoxy-5-thiophen-2-yl-benzaldehyde (Ex-50B, 0.78 g, 1.41 mmol) in tetrahydrofuran (5 mL) was added tetrabutylammonium fluoride (1 M in tetrahydrofuran, 3.0 mL, 2.9 mmol) and the mixture was stirred at rt for 30 min. The reaction was diluted with ethyl acetate (50 mL) and washed with a 50% ammonium chloride solution (1×30 mL), water (2×30 mL), brine (1×30 mL), dried over sodium sulfate and concentrated to a crude yellow solid. Silica gel chromatography afforded 0.37 g (99%) of the expected 4-(3-hydroxy-2-hydroxymethyl-propoxy)-2-methoxy-5-thiophen-2-yl-benzaldehyde as a pale yellow solid, 90% yield, mp 144–145° C. $^1$H-NMR (300 MHz, CDCl$_3$) δ 10.33 (s, 1H), 8.10 (s, 1H), 7.38 (dd, 1H, J=3.6, 1.5 Hz), 7.30 (dd, 1H, J=5.1, 1.5 Hz), 7.07 (dd, 1H, J=5.1, 3.6 Hz), 6.59 (s, 1H), 4.35 (d, 2H, J=6.0 Hz), 4.02 (t, 4H, J=4.8 Hz), 3.96 (s, 3H), 2.33 (pentet, 1H, J=6.0 Hz), 1.89 (t, 2H, J=4.8 Hz). MS (ESI) m/z=323 ([M+H]$^+$, 100%). Anal. Calcd. for C$_{16}$H$_{18}$O$_5$S: C, 59.61; H, 5.63; S, 9.95. Found: C, 59.34; H, 5.75; S, 9.82.

The title compound was prepared by condensing 4-(3-hydroxy-2-hydroxymethyl-propoxy)-2-methoxy-5-thiophen-2-yl-benzaldehyde (Ex-50C) and 4-acetylbenzoic acid in a similar manner as described in Ex-3. Yellow solid, mp 199–201° C., 60% yield. $^1$H-NMR (300 MHz, DMSO-d$_6$) δ 8.31 (s, 1H), 8.23 (d, 2H, J=8.7 Hz), 8.06–8.11 (m, 3H), 7.93 (d, 1H, J=15.0 Hz), 7.71 (d, 1H, J=3.3 Hz), 7.54 (d, 1H, J=5.1 Hz), 7.13–7.16 (m, 1H), 6.87 (s, 1H), 4.62 (brs, 2H), 4.27 (d, 2H, J=5.1 Hz), 4.00 (s, 3H), 3.62 (brs, 4H), 2.11–2.15 (m, 1H). MS (ESI) m/z=469 ([M+H]$^+$, 100%). Anal. Calcd. for C$_{25}$H$_{24}$O$_7$S.¼H$_2$O: C, 63.48; H, 5.22; S, 6.78. Found: C, 63.45; H, 5.29; S, 6.61.

Example 51

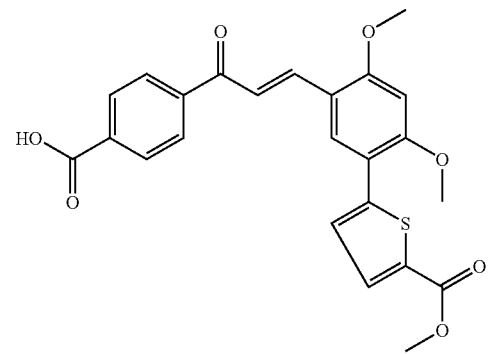

5-{5-[3-(4-Carboxy-phenyl)-3-oxo-E-propenyl]-2,4-dimethoxy-phenyl}-thiophene-2-carboxylic acid methyl ester Ex-51A: 5-(5-Formyl-2,4-dimethoxy-phenyl)-thiophene-2-carboxylic acid methyl ester was prepared-starting from 5-bromo-thiophene-2-carboxylic acid methyl ester in a similar manner as described in Ex-46A through -46D. Yellow solid, 18% yield. $^1$H-NMR (CDCl$_3$) δ 10.32 (s, 1H), 8.16 (s, 1H), 7.74 (d, J=4.4 Hz, 1H), 7.42 (d, J=4.4 Hz, 1H), 6.51 (s, 1H), 4.05 (s, 3H), 3.98 (s, 3H), 3.90 (s, 3H). HRMS (ES+) Calcd. for C$_{15}$H$_{14}$O$_5$S: 307.0640. Found: 307.0630.

4-Acetylbenzoic acid (24 mg, 0.15 mmol) and 5-(5-formyl-2,4-dimethoxy-phenyl)-thiophene-2-carboxylic acid methyl ester (Ex-51A, 46 mg, 0.15 mmol) were dissolved in DMF (4 mL). Lithium methoxide, 1M in methanol (0.29 mL) was added and the solution stirred at room temperature overnight. The reaction solution was poured into cold 1N HCl (3 mL) and extracted with EtOAc (3×20 mL); the organic phase was washed with brine (1×10 mL), dried over sodium sulfate, filtered, and concentrated. The resulting orange residue was purified via silica gel chromatography (0–10% MeOH/CH$_2$Cl$_2$) to provide 89 mg of yellow solid which still contained DMF. The solid was slurried in EtOH for several hours, filtered, and dried to provide 31 mg of final product as a yellow solid (47% yield). $^1$H-NMR (DMSO-d$_6$) δ 8.47 (s, 1H), 8.23 (d, J=9 Hz, 2H), 8.01–8.11 (m, 4H), 7.89 (d, J=4 Hz, 1H), 7.82 (d, J=4 Hz, 1H), 6.90 (s, 1H), 4.09 (s, 3H), 4.03 (s, 3H), 3.84 (s, 3H). HRMS (ES+) Calcd. for C$_{24}$H$_{20}$O$_7$S: 453.1008. Found: 453.1020.

Example 52

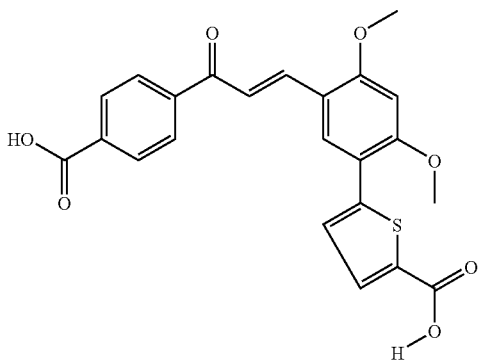

5-{5-[3-(4-Carboxy-phenyl)-3-oxo-E-propenyl]-2,4-dimethoxy-phenyl}-thiophene-2-carboxylic acid The title compound was prepared through routine hydrolysis of 5-{5-[3-(4-Carboxy-phenyl)-3-oxo-propenyl]-2,4-dimethoxy-phenyl}-thiophene-2-carboxylic acid methyl ester (Ex-51). Orange solid, mp>260° C., 43% yield. $^1$H-NMR (DMSO-d$_6$) δ 8.43 (s, 1H), 8.26 (d, J=8 Hz, 2H), 8.01–8.12 (m, 4H), 7.82 (d, J=4 Hz, 1H), 7.71 (d, J=4 Hz, 1H), 6.89 (s, 1H), 4.08 (s, 3H), 4.03 (s, 3H).

Example 53

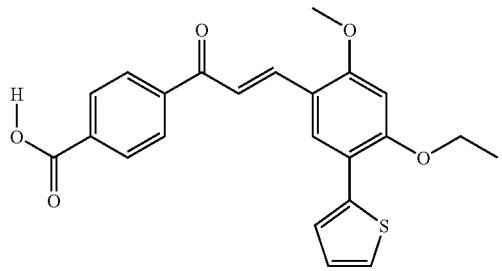

4-[3E-(4-Ethoxy-2-methoxy-5-thiophen-2-yl-phenyl)-acryloyl]-benzoic acid

Ex-53A: Reaction of 4-hydroxy-2-methoxy-5-thiophen-2-yl-benzaldehyde (Ex-47B) and (2-ethoxymethyl-5-hydroxymethyl-[1,3]dioxolan-4-yl)methanol was preformed under the Mitsunobu condition using triphenylphosphine and diethyl azodicarboxylate in THF. However, the expected product, 4-(2-ethoxymethyl-5-hydroxymethyl-[1,3]dioxolan-4-ylmethoxy)-2-methoxy-5-thiophen-2-yl-benzaldehyde, was not obtained. Instead, 4-ethoxy-2-methoxy-5-thiophen-2-yl-benzaldehyde was formed via cleavage of the cyclic ethyl orthoformate group under the reaction conditions. Silica gel chromatography (ethyl acetate/hexanes, 1:2) gave 0.16 g (90%) of 4-ethoxy-2-methoxy-5-thiophen-2-yl-benzaldehyde, mp 101–103° C. $^1$H-NMR (300 MHz, CDCl$_3$) δ 10.33 (s, 1H), 8.15 (s, 1H), 7.48 (d, 1H, J=3.6 Hz), 7.29 (d, 1H, J=5.2 Hz), 7.07 (dd, 1H, J=5.2, 3.6 Hz), 6.50 (s, 1H), 4.25 (q, 2H, J=7.2 Hz), 3.97 (s, 3H), 1.59 (t, 3H, J=7.2 Hz). MS (EI) m/z=262 ([M]$^+$, 100%). HMRS (EI) Calcd. for C$_{14}$H$_{14}$O$_3$S: 262.0664. Found: 262.0667.

The title compound was prepared by condensing 4-ethoxy-2-methoxy-5-thiophen-2-yl-benzaldehyde (Ex-53A) and 4-acetylbenzoic acid in a similar manner as described in Ex-3. Yellow solid, mp 210–212° C., 76% yield. $^1$H-NMR (300 MHz, DMSO-d$_6$) δ 8.31 (s, 1H), 8.23 (d, 2H, J=9.0 Hz), 8.06–8.11 (m, 3H), 7.92 (d, 1H, J=16.2 Hz), 7.71 (d, 1H, J=3.9 Hz), 7.52 (d, 1H, J=5.1 Hz), 7.13 (dd, 1H, J=5.1, 3.9 Hz), 6.82 (s, 1H), 4.33 (q, 2H, J=6.1 Hz), 3.99 (s, 3H), 1.48 (t, 3H, J=6.1 Hz). MS (ESI) m/z=409 ([M+H]$^+$, 100%). Anal. Calcd. for C$_{23}$H$_{20}$O$_5$S.½H$_2$O: C, 66.17; H, 5.07; S, 7.68. Found: C, 65.88; H, 5.24; S, 7.36.

Example 54

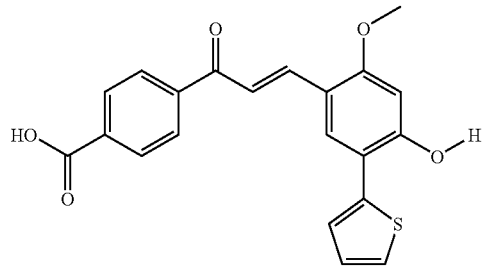

4-[3E-(4-Hydroxy-2-methoxy-5-thiophen-2-yl-phenyl)-acryloyl]-benzoic acid

4-Hydroxy-2-methoxy-5-thiophen-2-yl-benzaldehyde (Ex-47B, 0.30 g, 0.86 mmol) and 4-acetylbenzoic acid (0.13 g, 0.86 mmol) were dissolved in a dimethylformamide-methanol solution (6 mL, 7:3). After complete dissolution, lithium methoxide (0.12 g, 3.3 mmol) was added and the resulting red slurry was stirred in the dark at room temperature for 18 h. The mixture was diluted with water (15 mL), acidified with a 1 N hydrochloric acid solution, and extracted with ethyl acetate (4×25 mL). The combined organic extracts were dried over sodium sulfate and evaporated to dryness. The crude oil was subjected to silica gel chromatography (CH$_2$Cl$_2$:MeOH, 20:1) to yield an orange solid containing residual amounts of starting acid. The solid was taken up in ethyl alcohol (5 mL) to remove acid impurity and the resulting precipitate was collected on filter paper and dried in vacuo to yield 0.010 g (5%) of the title compound as an orange solid, mp 243° C. (dec). $^1$H-NMR (300 MHz, DMSO-d$_6$) δ 8.18–8.23 (m, 3H), 8.06–8.09 (m, 2H), 8.02 (s, 1H), 7.85 (d, 1H, J=15.6 Hz), 7.68 (d, 1H, J=3.6 Hz), 7.47 (d, 1H, J=5.1 Hz), 7.11 (dd, 1H, J=5.1, 3.6 Hz), 6.67 (s, 1H), 4.13 (s, 1H), 3.89 (s, 3H). MS (ESI) m/z=381 ([M+H]$^{30}$, 100%). HRMS (ESI) Calcd. for C$_{21}$H$_{16}$O$_5$S: 381.0796. Found: 381.0800.

Example 55

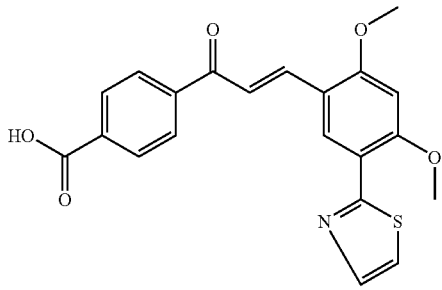

4-[3E-(2,4-Dimethoxy-5-thiazol-2-yl-phenyl)-acryloyl]-benzoic acid

Ex-55A: 2,4-Dimethoxy-5-thiazol-2-yl-benzaldehyde was prepared from 2-bromothiazole in a similar manner as described in Ex-46A through -46D. Off-white solid, 83% yield. $^1$H-NMR (CDCl$_3$) δ 10.34 (s, 1H), 8.86 (s, 1H), 7.89 (d, J=3.6 Hz, 1H), 7.36 (d, J=3.6 Hz, 1H), 6.56 (s, 1H), 4.12 (s, 3H), 4.02 (s, 3H). HRMS m/z: calc. 249.0460, found 249.0461.

The title compound was prepared by condensing 2,4-dimethoxy-5-thiazol-2-yl-benzaldehyde (Ex-55A) and 4-acetylbenzoic acid in a similar manner as described in Ex-3. Yellow solid, mp>260° C., 65% yield. $^1$H-NMR (DMSO-d$_6$) δ 13.33 (bs, 1H), 8.74 (s, 1H), 8.22 (d, J=8 Hz, 2H), 8.04–8.12 (m, 3H), 7.95 (d, J=2 Hz, 1H), 7.82 (d, J=16 Hz, 1H), 7.76 (d, J=3 Hz, 1), 6.94 (s, 1H), 4.14 (s, 3H), 4.05 (s, 1H). HRMS m/z=calc. 396.0906, found 396.0903.

Example 56

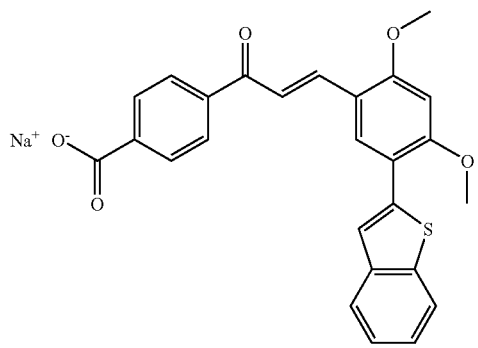

4-[3E-(5-Benzo[b]thiophen-2-yl-2,4-dimethoxy-phenyl)-acryloyl]-benzoic acid, sodium salt To a solution of 4-[3E-(5-benzo[b]thiophen-2-yl-2,4-dimethoxy-phenyl)-acryloyl]-benzoic acid (5.77 g, 13.0 mmol) in tetrahydrofuran (50 mL) was added sodium methoxide (0.70 g, 12.3 mmol). The reaction mixture was allowed to stir for 2 hours at ambient temperature. The precipitate was then filtered, washed with tetrahydrofuran and dried in vacuo to give the title compound (5.13 g, 85%) as a yellow solid, mp>235° C. $^1$H-NMR (DMSO-d$_6$) δ 8.35 (s, 1H), 8.08 (d, J=8.4 Hz, 2H), 8.00–7.89 (m, 4H), 7.82 (d, J=7.6 Hz, 1H), 7.35–7.29 (m, 4H), 6.85 (s, 1H), 4.02 (s, 3H), 3.99 (s, 3H). MS m/z=443 (M$^+$, 100%).

Example 57

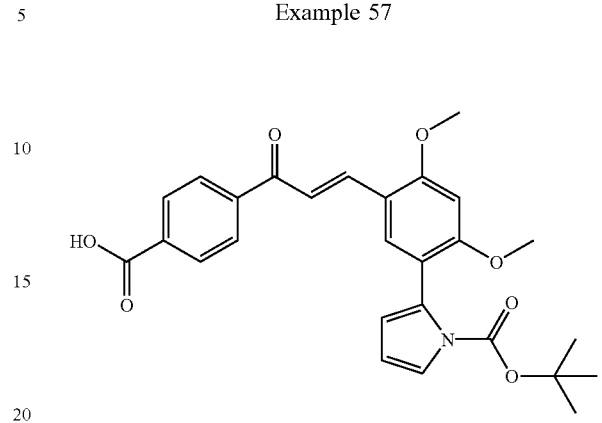

2-{5-[3-(4-Carboxy-phenyl)-3-oxo-E-propenyl]-2,4-dimethoxy-phenyl}-pyrrole-1-carboxylic acid tert-butyl ester Ex-57A: 2-(5-Formyl-2,4-dimethoxy-phenyl)-pyrrole-1-carboxylic acid tert-butyl ester was prepared from pyrrole-1-carboxylic acid tert-butyl ester-2-boronic acid in a similar manner as described in Ex-3A, 81% yield. $^1$H-NMR (CDCl$_3$) δ 10.32 (s, 1H), 7.76 (s, 1H), 7.31–7.33 (m, 1H), 6.43 (s, 1H), 6.22–6.24 (m, 1H), 6.14–6.16 (m, 1H), 3.98 (s, 3H), 3.85 (s, 3H), 1.40 (s, 9H), HRMS (EI) Calcd. for C$_{18}$H$_{21}$NO$_5$: 331.1420. Found: 331.1421.

The title compound was prepared by condensing 2-(5-formyl-2,4-dimethoxy-phenyl)-pyrrole-1-carboxylic acid tert-butyl ester (Ex-57A) and 4-acetylbenzoic acid in a similar manner as described in Ex-3. Yellow solid, mp 205–207° C., 6% yield. $^1$H-NMR (DMSO-d$_6$) δ 8.19 (d, J=5 Hz, 2H), 8.00–8.10 (m, 3H), 7.87 (s, 1H), 7.80 (d, J=16 Hz, 1H), 7.27–7.28 (m, 1H), 6.71 (s, 1H), 6.22–6.23 (m, 1H), 6.14–6.16 (m, 1H), 3.96 (s, 3H), 3.79 (s, 3H), 1.29 (s, 9H). MS m/z=476 ([M−H]$^+$). HMRS (EI) calcd. for C$_{27}$H$_{27}$NO$_7$: 477.1788; found: 477.1793.

Example 58

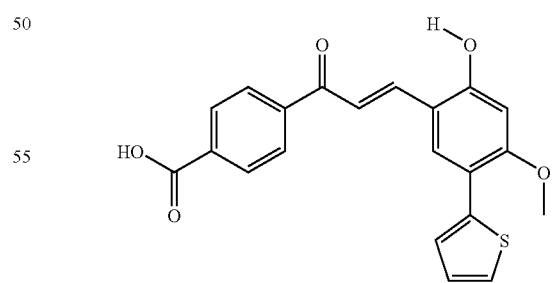

4-[3E-(2-Hydroxy-4-methoxy-5-thiophen-2-yl-phenyl)-acryloyl]-benzoic acid

2-Hydroxy-4-methoxy-5-thiophen-2-yl-benzaldehyde (Ex-29B, 0.10 g, 0.43 mmol) and 4-acetylbenzoic acid (0.070 g, 0.43 mmol) were dissolved in a dimethylformamide-methanol solution (2.8 mL, 7:3). After complete dissolution, lithium methoxide (0.065 g, 1.7 mmol) was added and the resulting red slurry was stirred in the dark at room temperature for 18 h. The mixture was diluted with water (10 mL), acidified with a 1 N hydrochloric acid solution, and extracted with ethyl acetate (3×20 mL). The combined organic extracts were dried over sodium sulfate and evaporated to dryness. The crude oil was taken up in ethyl alcohol (5 mL) and warmed to 60° C. to obtain complete dissolution and allowed to cool to room temperature. Note: the compound appears to decompose with heating. The resulting precipitate was collected on filter paper and dried in vacuo to yield 0.025 g (15%) of the title compound as a dark yellow solid, mp 125° C. (dec). $^1$H-NMR (300 MHz, DMSO-$d_6$) δ 10.73 (s, 1H), 8.18–8.22 (m, 3H), 8.09 (d, 2H, J=8.1 Hz), 8.05 (s, 1H), 7.87 (d, 1H, J=14.7 Hz), 7.60 (d, 1H, J=3.0 Hz), 7.49 (d, 1H, J=4.2 Hz), 7.11 (dd, 1H, J=4.2, 3.0 Hz), 6.67 (s, 1H), 3.90 (s, 3H). MS (ESI) m/z=381 ([M+H]$^+$, 100%). Anal. Calcd. for $C_{21}H_{16}O_5S$·EtOH: C, 64.77; H, 5.20; S, 7.52. Found: C, 64.68; H, 5.00; S, 7.77.

Example 59

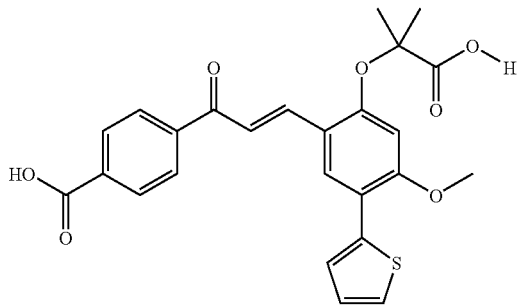

4-{3E-[2-(1-Carboxy-1-methyl-ethoxy)-4-methoxy-5-thiophen-2-yl-phenyl]-acryloyl}-benzoic acid Ex-59A: 2-(2-Formyl-5-methoxy-4-thiophen-2-yl-phenoxy)-2-methyl-propionic acid ethyl ester was prepared in an analogous fashion as described in Ex-29C using ethyl 2-bromoisobutyrate. Silica gel chromatography (ethyl acetate/hexanes, 1:2) gave the expected product as a dark yellow solid (97%), mp 87–88° C. $^1$H-NMR (300 MHz, CDCl$_3$) δ 10.37 (s, 1H), 8.14 (s, 1H), 7.45 (dd, 1H, J=3.6, 1.2 Hz), 7.30 (d, 1H, J=5.4 Hz), 7.07 (dd, 1H, J=5.1, 3.6 Hz), 6.42 (s, 1H), 4.25 (q, 2H, J=6.9 Hz), 3.90 (s, 3H), 1.72 (s, 6H), 1.26 (t, 3H, J=6.9 Hz). MS (ESI) m/z=349 ([M+H]$^+$, 100%). Anal. Calcd. for $C_{18}H_{20}O_5S$: C, 62.05; H, 5.79; S, 9.20. Found: C, 62.15; H, 5.82; S, 9.06.

Ex-59B: 2-(2-Formyl-5-methoxy-4-thiophen-2-yl-phenoxy)-2-methyl-propionic acid was prepared in an analogous fashion as described in Ex-47D. The crude solid was dried in vacuo to afford the product as a pale yellow solid (98%), mp 187–188° C. $^1$H-NMR (300 MHz, CDCl$_3$) δ 9.33 (s, 1H), 7.99 (s, 1H), 7.47 (dd, 1H, J=3.6, 1.5 Hz), 7.37 (d, 1H, J=4.8 Hz), 7.11 (dd, 1H, J=4.8, 3.6 Hz), 6.67 (s, 1H), 4.00 (s, 3H), 1.75 (s, 6H). MS (ESI) m/z=321 ([M+H]$^+$, 100%). Anal. Calcd. for $C_{16}H_{16}O_5S$: C, 59.99; H, 5.03; S, 10.01. Found: C, 59.80; H, 5.12; S, 9.87.

2-(2-Formyl-5-methoxy-4-thiophen-2-yl-phenoxy)-2-methyl-propionic acid (Ex-59B, 0.12 g, 0.39 mmol) and 4-acetylbenzoic acid (0.064 g, 0.39 mmol) were dissolved in a dimethylformamide-methanol solution (2.7 mL, 7:3). After complete dissolution, lithium methoxide (0.060 g, 1.6 mmol) was added and the resulting bright orange slurry was stirred in the dark at room temperature for 2 h. Upon completion, as determined by HPLC, the mixture was diluted with water (15 mL), acidified with a 1 N hydrochloric acid solution, and extracted with ethyl acetate (3×15 mL). The combined organic extracts were dried over sodium sulfate and evaporated to dryness. The crude oil was taken up in ethyl alcohol (5 mL) and warmed to 60° C. to obtain complete dissolution and allowed to cool to room temperature. The resulting precipitate was collected on filter paper and dried in vacuo to yield 0.15 g (85%) of the title compound as a dark yellow solid, mp 223–225° C. $^1$H-NMR (300 MHz, DMSO-$d_6$) δ 8.31 (s, 1H), 8.23 (d, 2H, J=8.1 Hz), 8.10 (d, 2H, J=8.1 Hz), 8.06 (s, 1H), 7.95 (d, 1H, J=16.2 Hz), 7.69 (d, 1H, J=3.0 Hz), 7.55 (d, 1H, J=5.1 Hz), 7.14 (dd, 1H, J=5.1, 3.0 Hz), 6.58 (s, 1H), 3.88 (s, 3H), 1.66 (s, 6H). MS (ESI) m/z=467 ([M+H]$^+$, 100%). Anal. Calcd. for $C_{25}H_{22}O_7S$·⅓$H_2O$: C, 63.55; H, 4.84; S, 6.79. Found: C, 63.39; H, 5.02; S, 6.53.

Example 60

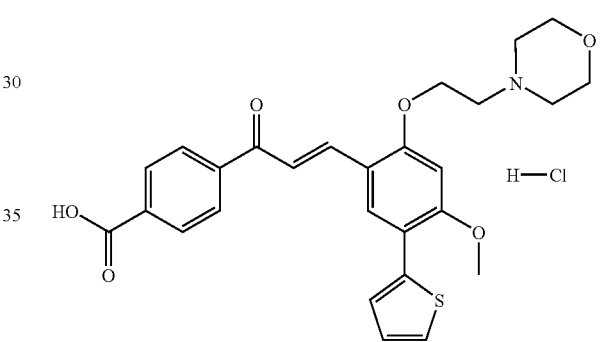

4-{3E-[4-Methoxy-2-(2-morpholin-4-yl-ethoxy)-5-thiophen-2-yl-phenyl]-acryloyl}-benzoic acid, hydrochloride Ex-60A: 4-Methoxy-2-(2-morpholin-4-yl-ethoxy)-5-thiophen-2-yl-benzaldehyde was prepared in an analogous fashion as described in Ex-29C using 4-(2-chloroethyl)morpholine. Silica gel chromatography (80 to 100% ethyl acetate/hexanes then 5% methanol/methylene chloride) gave of the expected product as a off-white solid (81%). $^1$H-NMR (300 MHz, CDCl$_3$) δ 10.36 (s, 1H), 8.12 (s, 1H), 7.44 (dd, 1H, J=3.6, 1.5 Hz), 7.30 (dd, 1H, J=5.1, 1.5 Hz), 7.07 (dd, 1H, J=5.1, 3.6 Hz), 6.53 (s, 1H), 4.27 (t, 2H, J=6.3 Hz), 4.00 (s, 3H), 3.72–3.76 (m, 4H), 2.89 (t, 2H, J=6.3 Hz), 2.60–2.63 (m, 4H). MS (ESI) m/z=348 ([M+H]$^+$, 100%). HRMS (EI) Calcd. for $C_{18}H_{21}NO_4S$: 347.1191. Found: 347.1188.

4-Methoxy-2-(2-morpholin-4-yl-ethoxy)-5-thiophen-2-yl-benzaldehyde (Ex-60A, 0.15 g, 0.43 mmol) and 4-acetylbenzoic acid (0.071 g, 0.43 mmol) were dissolved in a dimethylformamide-methanol solution (3.0 mL, 7:3). After complete dissolution, lithium methoxide (0.065 g, 1.7 mmol) was added and the resulting bright orange slurry was stirred in the dark at room temperature for 2 h. Upon completion, as determined by HPLC, the mixture was diluted with water (10 mL), acidified with a 1 N hydrochloric acid solution, and extracted with an ethyl acetate:tetrahydrofuran mixture (1:1, 6×20 mL). The combined organic extracts were dried over sodium sulfate and evaporated to dryness. The crude solid was slurried in ethyl alcohol (5 mL) to remove residual impurities and the resulting solid was collected on filter paper and dried in vacuo to yield 0.21 g (98%) of the title compound as a dark yellow solid, mp: 255° C. (dec). $^1$H-NMR (300 MHz, DMSO-$d_6$) δ 8.34 (s, 1H), 8.26 (d, 2H, J=8.7 Hz), 8.11 (d, 2H, J=8.7 Hz), 8.08 (s, 1H), 7.95 (d, 1H, J=15.9 Hz), 7.71 (d, 1H, J=3.3 Hz), 7.55 (d, 1H, J=4.5 Hz), 7.15 (dd, 1H, J=4.5, 3.3 Hz), 6.94 (s, 1H), 4.68 (brs, 2H), 4.04 (s, 3H), 3.98 (brs, 2H), 3.81–3.88 (brm, 2H), 3.70 (brs, 2H), 3.54–3.58 (brm, 2H), 3.29 (brs, 2H). MS (ESI) m/z=494 ([M+H]$^+$, 100%). Anal. Calcd. for $C_{27}H_{28}ClNO_6S$: C, 61.18; H, 5.32; Cl, 6.69; N, 2.64; S, 6.05. Found: C, 61.18; H, 5.41; Cl, 6.16; N, 2.73; S, 5.87.

Example 61

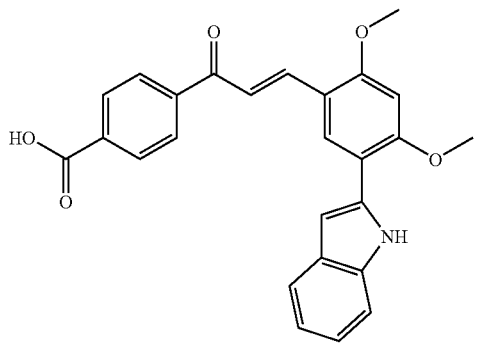

4-{3E-[5-(1H-Indol-2-yl)-2,4-dimethoxy-phenyl]-acryloyl}-benzoic acid

Ex-61A: 2-(5-Formyl-2,4-dimethoxy-phenyl)-indole-1-carboxylic acid tert-butyl ester (Ex-36A, 2.0 g, 5.2 mmol) was dissolved in 100 ml of THF, and Bu$_4$NF (6.86 g, 26 mmol) was added. The reaction mixture was stirred at room temperature overnight. No reaction occured at this condition. Then, Bu$_4$NF (6.86 g, 26 mmol) was added to the mixture, and the mixture was stirred at reflux for 4 days. The reaction was about 50% completion (HPLC). The reaction mixture was poured into CH$_2$Cl$_2$, and washed with water and brine. The organic phase was dried over MgSO$_4$, and concentrated. The residue was purified by column chromatography (EtOAc: Hex, 2:1) to give 0.45 g (30%) of 5-(1H-indol-2-yl)-2,4-dimethoxy-benzaldehyde. $^1$H-NMR (CDCl$_3$) δ 10.37 (s, 1H), 9.25 (br, 1H), 8.28 (s, 1H), 7.63 (d, J=8 Hz, 1H), 7.39 (d, J=8 Hz, 1H), 7.08–7.20 (m, 2H), 6.92 (d, J=2 Hz, 1H), 6.56 (s, 1H) 4.11 (s, 3H), 4.00 (s, 3H). HMRS (EI) calcd. for $C_{17}H_{15}NO_3$: 281.1052; found: 281.1049.

The title compound was prepared by condensing 5-(1H-indol-2-yl)-2,4-dimethoxy-benzaldehyde (Ex-61A) and 4-acetylbenzoic acid in a similar manner as described in Ex-3. Red solid, mp 210–212° C., 66% yield. $^1$H-NMR (Aceton-$d_6$) δ 10.53 (br, s, 1H), 8.32 (s, 1H), 8.14–8.21 (m, 5H), 7.89 (d, J=15 Hz, 1H), 7.52 (d, J=8 Hz, 1H), 7.38 (d, J=7 Hz, 1H), 6.97–7.07 (m, 3H), 6.87 (s, 1H), 4.07 (s, 3H), 4.02 (s, 3H), MS m/z=427 ([M]$^+$). HMRS (EI) calcd. for $C_{26}H_{21}NO_5$: 427.1420; found: 427.1435.

Example 62

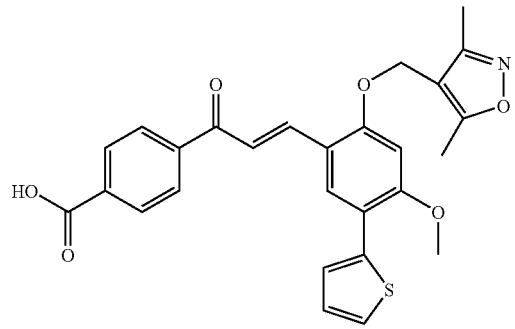

4-{3E-[2-(3,5-Dimethyl-isoxazol-4-ylmethoxy)-4-methoxy-5-thiolphen-2-yl-phenyl]-acryloyl}-benzoic acid Ex-62A: 2-(3,5-Dimethyl-isoxazol-4-ylmethoxy)-4-methoxy-5-thiophen-2-yl-benzaldehyde was prepared in a similar manner as described in Ex-29C using 4-chloromethyl-3,5-dimethyl-isoxazole. $^1$H-NMR (CDCl$_3$) δ 10.26 (s, 1H), 8.14 (s, 1H), 7.45 (d, J=6 Hz, 1H), 7.32 (d, J=5 Hz, 1H), 7.07–710 (m, 1H), 6.58 (s, 1H), 4.96 (s, 2H), 4.04 (s, 3H), 2.46 (s, 3H), 2.32 (s, 3H).

The title compound was prepared by condensing 2-(3,5-dimethyl-isoxazol-4-ylmethoxy)-4-methoxy-5-thiophen-2-yl-benzaldehyde (Ex-62A) and 4-acetylbenzoic acid in a similar manner as described in Ex-3. Yellow solid, mp 213–215° C. $^1$H-NMR (CDCl$_3$) δ 8.20 (d, J=9 Hz, 2H), 7.88–8.03 (m, 4H), 7.58 (d, J=16 Hz, 1H), 7.44 (d, J=4 Hz, 1H), 7.34 (d, J=5 Hz, 1H), 7.12 (dd, J=4, 5 Hz, 1H), 6.63 (s, 1H), 4.97 (s, 2H), 4.01 (s, 3H), 2.46 (s, 3H), 2.34 (s, 3H). MS m/z=490 ([M+H]$^+$). HRMS (ES+) Calcd. for $C_{27}H_{22}NO_6S$: 490.1324. Found: 490.1321.

Example 63

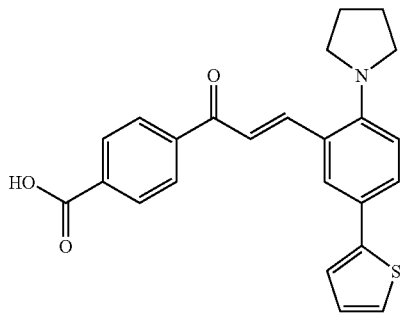

4-[3E-(2-Pyrrolidin-1-yl-5-thiophen-2-yl-phenyl)-acryloyl]-benzoic acid

Ex-63A: A solution of 2-fluoro-5-thiophen-2-yl-benzaldehyde (1.42 g, 6.89 mmol) in pyrrolidine was refluxed (10 mL). After 4.5 days the reaction mixture was cooled and diluted with ethyl acetate. The solution of ethyl acetate was washed with hydrochloric acid (0.5M) sodium carbonate (2M) and saturated solution of sodium bicarbonate, dried over sodium sulfate, and concentrated. The crude product was purified by flash chromatography. Elution with ethyl acetate (20%, v/v, in hexane) afforded 2-pyrrolidin-1-yl-5-thiophen-2-yl-benzaldehyde (0.5 g, 32%). $^1$H NMR (CDCl$_3$)

δ 10.14 (s, 1H), 7.94 (d, J=2 Hz, 1H), 7.62 (dd, J=2.7, 9 Hz, 1H), 7.22–7.20 (m, 2H), 7.07–7.04 (m, 1H), 6.86 (d, J=9 Hz, 1H), 3.41 (m, 4H), 2.01 (m, 4H).

The title compound was prepared by condensing 2-pyrrolidin-1-yl-5-thiophen-2-yl-benzaldehyde (Ex-63A) and 4-acetylbenzoic acid in a similar manner as described in Ex-3. Red solid, mp 208–209° C. $^1$H-NMR (DMSO-d$_6$) δ 12.50 (bs, 1H), 8.22 (d, J=8.5 Hz, 2H), 8.09–7.99 (m, 4H), 7.73 (d, J=15.5 Hz, 1H), 7.52–7.41 (m, 3H), 7.10–7.07 (m, 1H), 6.93 (d, J=9.0 Hz, 1H), 3.28 (m, 4H), 1.87 (m, 4H).

Example 64

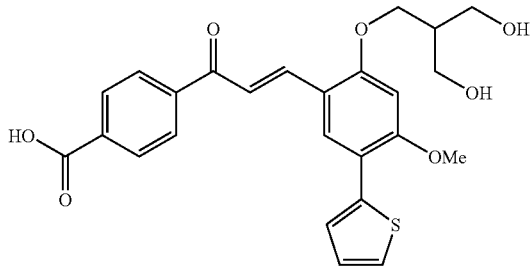

4-{3E-[2-(3-Hydroxy-2-hydroxymethyl-propoxy)-4-methoxy-5-thiophen-2-yl-phenyl]-acryloyl}-benzoic acid Ex-64A: To a solution of 2-hydroxy-4-methoxy-5-thiophen-2-yl-benzaldehyde (10.0 g, 42.7 mmol) in N,N-dimethylformamide (100 mL) was added potassium carbonate (11.8 g, 85.4 mmol) and the resulting yellow slurry was heated to 80° C. Once at 80° C., methanesulfonic acid 3-(tert-butyl-dimethyl-silanyloxy)-2-(tert-butyl-dimethyl-silanyloxymethyl)-propyl ester (Ex-50A, 19.5 g, 46.9 mmol) was added dropwise and the reaction was stirred for an additional 24 h at 80° C. and cooled to room temperature. The mixture was diluted with water (500 mL) and extracted with ethyl acetate (3×150 mL). The combined organic layers was sequentially washed with a saturated sodium bicarbonate solution (1×150 mL), water (1×150 mL), and brine (1×150 mL), dried over sodium sulfate, and concentrated to a brown oil. Silica gel chromatography (100% ethyl acetate to 10% ethyl acetate/hexanes) gave 19.0 g (81%) of 2-[3-(tert-butyl-dimethyl-silanyloxy)-2-(tert-butyl-dimethyl-silanyloxymethyl)-propoxy]-4-methoxy-5-thiophen-2-yl-benzaldehyde as an off-white solid, mp 91–92° C. $^1$H-NMR (300 MHz, CDCl$_3$) δ 10.37 (s, 1H), 8.12 (s, 1H), 7.44 (dd, 1H, J=3.6, 1.2 Hz), 7.29 (d, 1H, J=5.1 Hz), 7.07 (dd, 1H, J=5.1, 3.6 Hz), 6.54 (s, 1H), 4.19 (d, 2H, J=6.0 Hz), 3.99 (s, 3H), 3.72–3.82 (m, 4H), 2.28 (pentet, 1H, J=6.0 Hz), 0.88 (s, 18H), 0.048 (s, 12H). MS (EI) m/z=550 ([M]$^+$, 100%). Anal. Calcd. for C$_{28}$H$_{46}$O$_5$SSi$_2$: C, 61.05; H, 8.42; S, 5.82. Found: C, 61.20; H, 8.74; S, 5.69.

Ex-64B: 2-(3-Hydroxy-2-hydroxymethyl-propoxy)-4-methoxy-5-thiophen-2-yl-benzaldehyde was prepared in an analogous fashion as described in Ex-50C. Silica gel chromatography (ethyl acetate/hexanes, 1:9) gave the expected product as an off-white solid. $^1$H-NMR (300 MHz, CDCl$_3$) δ 10.17 (s, 1H), 8.03 (s, 1H), 7.43 (dd, 1H, J=3.6, 1.2 Hz), 7.31 (d, 1H, J=5.1 Hz), 7.08 (dd, 1H, J=5.1, 3.6 Hz), 6.58 (s, 1H), 4.32 (d, 2H, J=6.0 Hz), 4.01 (s, 3H), 3.95–3.99 (m, 4H), 2.51 (t, 2H, J=5.1 Hz), 2.33 (pentet, 1H, J=5.4 Hz). MS (EI) m/z=322 ([M]$^+$, 100%). HRMS (EI) Calcd. for C$_{16}$H$_{18}$O$_5$S: 322.0875. Found: 322.0873.

The title compound was prepared by condensing 2-(3-hydroxy-2-hydroxymethyl-propoxy)-4-methoxy-5-thiophen-2-yl-benzaldehyde (Ex-64B) and 4-acetylbenzoic acid in a similar manner as described in Ex-3. Light orange solid, mp 219–220° C., 61% yield. $^1$H-NMR (300 MHz, DMSO-d$_6$) δ 8.36 (s, 1H), 8.20 (d, 2H, J=7.5 Hz), 8.05–8.11 (m, 3H), 7.93 (d, 1H, J=16.2 Hz), 7.67 (d, 1H, J=3.0 Hz), 7.52 (d, 1H, J=5.1 Hz), 7.13 (dd, 1H, J=5.1, 3.0 Hz), 6.88 (s, 1H), 4.66 (brs, 2H), 4.23 (d, 2H, J=6.3 Hz), 4.01 (s, 3H), 3.55–3.66 (m, 4H), 2.09–2.14 (m, 1H). MS (ESI) m/z=469 ([M+H]$^+$, 100%). Anal. Calcd. for C$_{25}$H$_{24}$O$_7$S.H$_2$O: C, 61.72; H, 5.39; S, 6.59. Found: C, 61.93; H, 5.30; S, 7.06.

Example 65

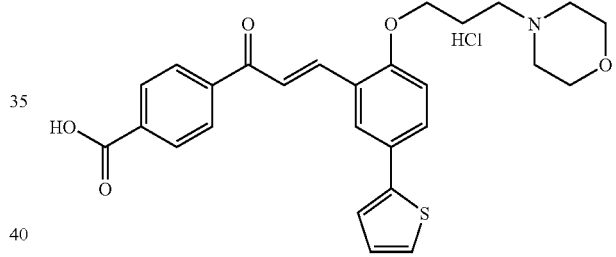

4-{3E-[2-(3-Morpholin-4yl-propoxy)-5-thiophen-2-yl-phenyl]-acryloyl}-benzoic acid, hydrochloride Ex-65A: 2-(3-Morpholin-4-yl-propoxy)-5-thiophen-2-yl-benzaldehyde was prepared in a similar manner as described in Ex-60A, 80% yield. $^1$H-NMR (DMSO-D6) δ 10.36 (s, 1H), 7.90 (dd, J=3, 5 Hz, 1H), 7.82 (d, 1H), 7.48 (d, 1H), 7.44 (d, 1H), 7.25 (d, 1H), 7.09 (t, 1H), 4.18 (t, 2H), 3.53 (m, 4H), 3.28 (br s, 2H), 2.43 (m, 4H), 1.89 (q, 2H).

The title compound was prepared by condensing 2-(3-morpholin-4-yl-propoxy)-5-thiophen-2-yl-benzaldehyde (Ex-65A) and 4-acetylbenzoic acid in a similar manner as described in Ex-3. Yellow solid, 67% yield, mp 234–236° C. $^1$H-NMR (DMSO-d6) δ 13.32 (br s, 1H), 11.10 (br s, 1H), 8.21 (m, 3H), 8.02 (m, 3H), 7.67 (dd, J=2,2 Hz, 1H), 7.56 (d, 1H), 7.50 (d, 1H), 7.14 (m, 2H), 4.21 (t, 2H), 3.86 (m, 4H), 3.23 (m, 6H), 2.29 (q, 2H). MS m/z=478 ([M+H]$^+$, 100%). Anal. calculated for C$_{27}$H$_{28}$ClNO$_5$S.3/2H$_2$O: C, 59.94; H, 5.78; S, 5.93; found C, 60.20; H, 5.65; S, 5.94

Example 66

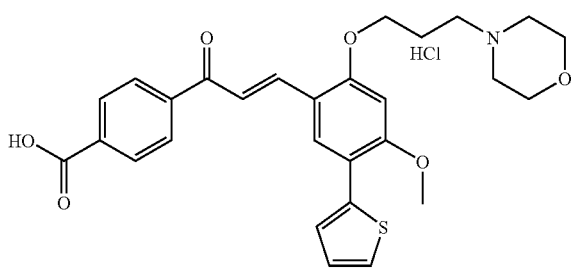

4-{3E-[4-Methoxy-2-(3-morpholin-4-yl-propoxy)-5-thiophen-2-yl-phenyl]-acryloyl}-benzoic acid, hydrochloride Ex-66A: 4-Methoxy-2-(3-morpholin-4-yl-propoxy)-5-thiophen-2-yl-benzaldehyde was prepared in a similar manner as described in Ex-60A, 78% yield. $^1$H-NMR (DMSO-D6) δ 10.21 (s, 1H), 7.88 (s, 1H), 7.46 (m, 2H), 7.06 (t, 1H), 6.82 (s, 1H), 4.24 (t, 2H), 4.00 (s, 3H), 3.53 (m, 4H), 3.28 (m, 2H), 2.34 (m, 4H), 1.93 (q, 2H).

The title compound was prepared by condensing 4-methoxy-2-(3-morpholin-4-yl-propoxy)-5-thiophen-2-yl-benzaldehyde (Ex-66A) and 4-acetylbenzoic acid in a similar manner as described in Ex-3. Yellow solid, 72% yield, mp 188–191° C. (dec). $^1$H-NMR (DMSO-d6) δ 12.63 (br s, 1H), 11.08 (br s, 1H), 8.33 (s, 1H), 8.22 (d, 2H), 8.05 (m, 3H), 7.89 (d, 1H), 7.65 (d, 1H), 7.49 (d, 1H), 7.10 (t, 1H), 6.84 (s, 1H), 4.30 (t, 2H), 3.98 (s, 3H), 3.84 (m, 4H), 3.21 (m, 6H), 2.28 (q, 2H). MS m/z=508 ([M+H]$^+$, 100%). Anal. calculated for $C_{28}H_{32}ClNO_7S \cdot H_2O$: C, 59.83; H, 5.74; S, 5.70; found C, 59.69; H, 5.80; S: 5.55.

Example 67

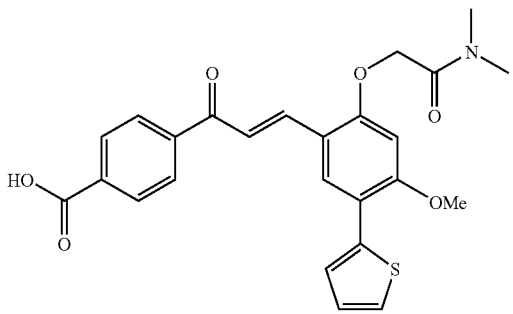

4-[3E-(2-Dimethylcarbamoylmethoxy-4-methoxy-5-thiophen-2-yl-phenyl)-acryloyl]-benzoic acid Ex-67A: 2-(2-Formyl-5-methoxy-4-thiophen-2-yl-phenoxy)-N,N-dimethyl-acetamide was prepared in an analogous fashion as described in Ex-29C using 2-chloro-N,N-dimethylacetamide. Methylene chloride was used in place of ethyl acetate for the work up procedure. The crude solid was slurried in ethyl acetate (25 mL) to remove residual impurities. The resulting solid was collected on filter paper and dried in vacuo to give the expected product as a pale yellow solid (85%), mp 197–198° C. $^1$H-NMR (300 MHz, CDCl$_3$) δ 10.38 (s, 1H), 8.13 (s, 1H), 7.44 (d, 1H, J=3.6 Hz), 7.30 (dd, 1H, J=5.1, 1.8 Hz), 7.07 (dd, 1H, J=5.1, 3.6 Hz), 6.73 (s, 1H), 4.89 (s, 2H), 3.99 (s, 3H), 3.15 (s, 3H), 2.99 (s, 3H). MS (EI) m/z=319 ([M]$^+$, 100%). Anal. Calcd. for $C_{16}H_{17}NO_4S \cdot \frac{1}{3}H_2O$: C, 59.50; H, 5.43; N, 4.34; S, 9.93. Found: C, 59.65; H, 5.42; N, 4.40; S, 9.69.

The title compound was prepared by condensing 2-(2-formyl-5-methoxy-4-thiophen-2-yl-phenoxy)-N,N-dimethyl-acetamide (Ex-67A) and 4-acetylbenzoic acid in a similar manner as described in Ex-3. Yellow solid, mp 228–229° C., 75% yield. $^1$H-NMR (300 MHz, DMSO-d$_6$) δ 8.31 (d, 2H, J=9.3 Hz), 8.22 (d, 2H, J=13.3 Hz), 8.08 (d, 2H, J=9.3 Hz), 7.95 (s, 1H), 7.65 (d, 1H, J=2.7 Hz), 7.52 (d, 1H, J=5.1 Hz), 7.13 (dd, 1H, J=5.1, 2.7 Hz), 6.85 (s, 1H), 5.11 (s, 2H), 3.99 (s, 3H), 3.06 (s, 3H), 2.93 (s, 3H). MS (EI) m/z=465 ([M]$^+$, 100%). HRMS (EI) Calcd. for $C_{25}H_{23}NO_6S$: 465.1246. Found: 465.1246.

Example 68

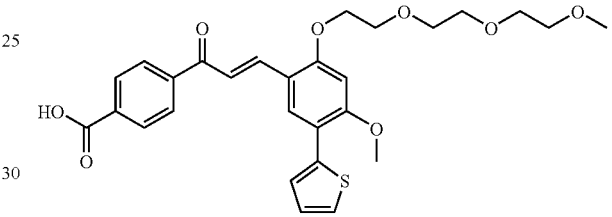

4-[3E-(4-Methoxy-2-{2-[2-(2-methoxy-ethoxy)-ethoxy]-ethoxy}-5-thiophen-2-yl-phenyl)-acryloyl]-benzoic acid Ex-68A: Methanesulfonic acid 2-[2-(2-methoxy-ethoxy)-ethoxy]-ethyl ester was prepared in an analogous fashion as described in Ex-50A using di(ethylene glycol) methyl ether. The crude orange oil was dried in vacuo to give the expected product (oil) and was used without any further purification (99%). $^1$H-NMR (300 MHz, CDCl$_3$) δ 4.37–4.40 (m, 2H), 3.76–3.78 (m, 2H), 3.61–3.70 (m, 6H), 3.53–3.57 (d, 2H), 3.38 (s, 3H), 3.08 (s, 3H). MS (ESI) m/z=243 ([M+H]$^+$, 100%). HRMS (ESI) Calcd. for $C_8H_{18}O_6S$: 243.0902. Found: 243.0914.

Ex-68B: 4-Methoxy-2-{2-[2-(2-methoxy-ethoxy)-ethoxy]-ethoxy}-5-thiophen-2-yl-benzaldehyde was prepared in an analogous fashion as as described in Ex-29C using methanesulfonic acid 2-[2-(2-methoxy-ethoxy)-ethoxy]-ethyl ester (Ex-68A). Silica gel chromatography (ethyl acetate/hexanes, 8:1) gave the expected product as a pale yellow oil (70%). $^1$H-NMR (300 MHz, CDCl$_3$) δ 10.38 (s, 1H), 8.12 (s, 1H), 7.44 (d, 1H, J=3.6 Hz), 7.30 (d, 1H, J=5.4 Hz), 7.07 (dd, 1H, J=5.4, 3.6 Hz), 6.57 (s, 1H), 4.31 (t, 2H, J=4.8 Hz), 3.99 (s, 3H), 3.94 (t, 2H, J=4.8 Hz), 3.74–3.78 (m, 2H), 3.62–3.69 (m, 4H), 3.53–3.56 (m, 2H), 3.37 (s, 3H). MS (EI) m/z=380 ([M]$^+$, 100%). HRMS (ESI) Calcd. for $C_8H_{18}O_6S$: 243.0902. Found: 243.0914.

The title compound was prepared by condensing 4-methoxy-2-{2-[2-(2-methoxy-ethoxy)-ethoxy]-ethoxy}-5-thiophen-2-yl-benzaldehyde (Ex-68B) and 4-acetylbenzoic acid in a similar manner as described in Ex-3. Yellow solid, mp 137–138° C., 82% yield. $^1$H-NMR (300 MHz, DMSO-d$_6$) δ 8.20–8.23 (m, 3H), 8.09 (d, 2H, J=8.3 Hz), 8.01 (m, 2H), 7.66 (d, 1H, J=3.6 Hz), 7.52 (d, 1H, J=5.1 Hz), 7.13 (dd, 1H, J=5.1, 3.6 Hz), 6.88 (s, 1H), 4.37 (t, 2H, J=3.6 Hz), 4.01 (s, 3H), 3.89 (t, 2H, J=3.6 Hz), 3.64–3.67 (m, 2H), 3.53–3.56 (m, 2H), 3.47–3.50 (m, 2H), 3.36–3.95 (m, 2H), 3.19 (s, 3H). MS (ESI) m/z=527 ([M+H]$^+$, 100%). Anal. Calcd. for $C_{28}H_{30}O_8S$: C, 63.86; H, 5.74; S, 6.09. Found: C, 64.08; H, 5.77; S, 6.09.

Example 69

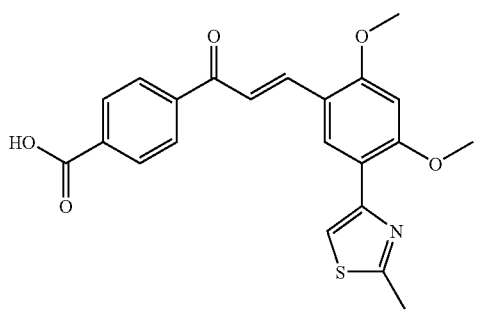

4-{3E-[2,4-Dimethoxy-5-(2-methyl-thiazol-4-yl)-phenyl]-acryloyl}-benzoic acid

Ex-69A: A solution of 2-bromo-1-(3,4-dimethoxy-phenyl)-ethanone (0.62 g, 2.39 mmol) and thioacetamide (0.18 g, 2.39 mmol) in ethanol (30 mL) was refluxed for 2 hours and the solvent was removed under reduced pressure. The product, 4-(3,4-dimethoxy-phenyl)-2-methyl-thiazole (0.56 g, 100%) was obtained as a white solid and used without further purification. To a suspension of 4-(3,4-dimethoxy-phenyl)-2-methyl-thiazole obtained above (0.70 g, 2.97 mmol) in dichloromethane (60 mL) at 0° C. was added dichloromethyl methyl ether (0.40 mL, 4.46 mmol) followed by addition of titanium tetrachloride (1.0 M solution in dichloromethane, 8.9 mL, 8.9 mmol) dropwise. The reaction mixture was allowed to stir overnight at ambient temperature and then poured into ice. The aqueous solution was extracted with dichloromethane. The solution of dichloromethane was washed with hydrochloric acid (0.5M), saturated solution of sodium bicarbonate and brine, dried over sodium sulfate and concentrated. The product, 2,4-dimethoxy-5-(2-methyl-thiazol-4-yl)-benzaldehyde, was obtained as a white solid. $^1$H NMR (CDCl$_3$) δ 10.33 (s, 1H), 8.67 (s, 1H), 7.56 (s, 1H), 6.52 (s, 1H), 4.03 (s, 3H), 3.99 (s, 3H), 2.75 (s, 3H).

The title compound was prepared by condensing 2,4-dimethoxy-5-(2-methyl-thiazol-4-yl)-benzaldehyde (Ex-69A) and 4-acetylbenzoic acid in a similar manner as described in Ex-3. Yellow solid, mp 201–202° C. (dec.). $^1$H-NMR (DMSO-d$_6$) δ 8.47 (s, 1H), 8.14–7.97 (m, 5H), 7.76 (s, 1H), 7.65 (d, J=15.8 Hz, 1H), 6.81 (s, 1H), 4.00 (s, 3H), 3.98 (s, 3H), 2.69 (s, 3H). MS m/z=409 (M$^+$, 70%), 378 ([M–OCH$_3$]$^+$, 100%).

Example 70

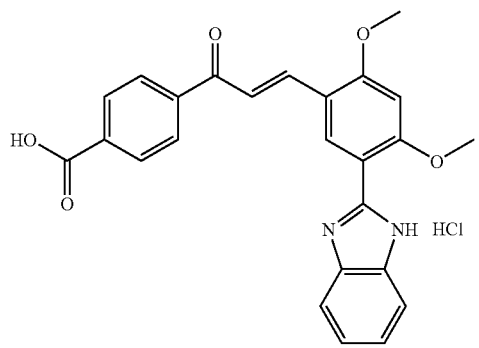

4-{3E-[5-(1H-Benzoimidazol-2-yl)-2,4-dimethoxy-phenyl]-acryloyl}-benzoic acid

Ex-70A: A solution of benzene-1,2-diamine (2.60 g, 24.1 mmol) and 2,4-dimethoxy-benzaldehyde (4.0 g, 24.1 mmol) in ethanol (60 mL) containing catalytic amount of acetic acid was refluxed overnight. Solvent was then evaporated under reduced pressure. The residue oil was triturated in ethyl acetate to obtain 2-(2,4-dimethoxy-phenyl)-1H-benzoimidazole (0.76 g, 12%). The crude product was used without further purification. To a solution of 2-(2,4-dimethoxy-phenyl)-1H-benzoimidazole obtained above (0.76 g, 2.99 mmol) in dichloromethane (20 mL) was added dichloromethyl methyl ether (0.41 mL, 4.48 mmol) followed by addition of titanium tetrachloride (1.0M in dichloromethane, 9.0 mL, 9.0 mmol) at 0° C. The reaction mixture was allowed to stir overnight at ambient temperature and then poured into ice. A solution of sodium hydroxide (5M) was added dropwise until the pH of the solution was about 12. The basic solution was extracted with dichloromethane. The combined solution of dichloromethane was subsequently washed with brine, dried over sodium carbonate and concentrated. The product, 5-(1H-benzoimidazol-2-yl)-2,4-dimethoxy-benzaldehyde (0.40 g, 47%), was obtain and used without further purification. $^1$H NMR (CDCl$_3$) δ 10.32 (s, 1H), 10.27 (bs, 1H), 9.03 (s, 1H), 7.83 (d, J=9 Hz, 1H), 7.48–7.45 (m, 1H), 7.31–7.22 (m, 1H), 6.58 (s, 1H), 4.18 (s, 3H), 4.01 (s, 3H). MS m/z=282 (M$^+$, 100%).

The title compound was prepared by condensing 5-(1H-benzoimidazol-2-yl)-2,4-dimethoxy-benzaldehyde (Ex-70A) and 4-acetylbenzoic acid in a similar manner as described in Ex-3. Yellow solid, mp>240° C. (dec.). $^1$H-NMR (DMSO-d$_6$) δ 8.72 (s, 1H), 12.10 (s, 1H), 8.18 (d, J=8.4 Hz, 2H), 8.08–8.02 (m, 3H), 7.80 (d, J=15.4 Hz, 1H), 7.59 (s, 2H), 7.17–7.13 (m, 2H), 6.89 (s, 1H), 4.10 (s, 3H), 4.03 (s, 3H). MS m/z=429 ([M+H]$^+$, 100%).

Example 71

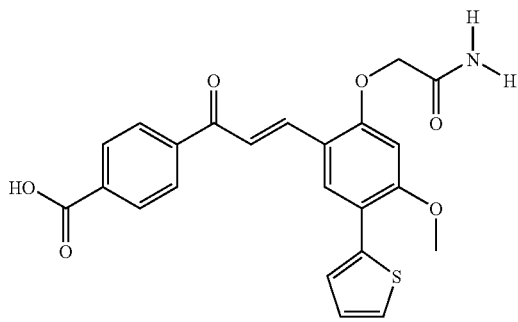

4-[3E-(2-Carbamoylmethoxy-4-methoxy-5-thiophen-2-yl-phenyl)-acryloyl]-benzoic acid Ex-71A: 2-(2-Formyl-5-methoxy-4-thiophen-2-yl-phenoxy)-acetamide was prepared in an analogous fashion as described in Ex-29C using 2-bromoacetamide. Silica gel chromatography (ethyl acetate/hexanes, 8:1) gave the expected product as a pale yellow solid (75%), mp: 178–179° C. $^1$H-NMR (300 MHz, CDCl$_3$) δ 10.05 (s, 1H), 7.99 (s, 1H), 7.67 (brs, 1H), 7.44 (d, 1H, J=3.6 Hz), 7.34 (d, 1H, J=5.4 Hz), 7.10 (dd, 1H, J=5.4, 3.6 Hz), 6.48 (s, 1H), 5.67 (brs, 1H), 4.64 (s, 2H), 4.02 (s, 3H). MS (EI) m/z=291 ([M]$^+$, 100%). Anal. Calcd. for C$_{14}$H$_{13}$NO$_4$S: C, 57.72; H, 4.50; N, 4.81; S, 11.01. Found: C, 57.63; H, 4.50; N, 4.87; S, 11.03.

The title compound was prepared by condensing 2-(2-formyl-5-methoxy-4-thiophen-2-yl-phenoxy)-acetamide (Ex-71A) and 4-acetylbenzoic acid in a similar manner as described in Ex-3. Yellow solid, 70% yield, mp 235° C. (dec.). $^1$H-NMR (300 MHz, DMSO-d$_6$) δ 8.26–8.30 (m, 3H), 8.08–8.11 (m, 4H), 7.67 (d, 1H, J=2.7 Hz), 7.65 (brs, 1H), 7.53 (d, 1H, J=4.0 Hz), 7.49 (brs, 1H), 7.13 (m, 1H), 6.77 (s, 1H), 4.75 (s, 2H), 3.97 (s, 3H). MS (EI) m/z=437 ([M]$^+$, 100%). HRMS (EI) Calcd. for C$_{23}$H$_{19}$NO$_6$S: 437.0933. Found: 437.0924.

Example 72

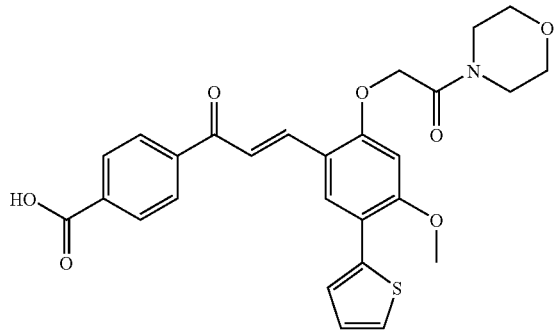

4-{3E-[4-Methoxy-2-(2-morpholin-4-yl-2-oxo-ethoxy)-5-thiophen-2-yl-phenyl]-acryloyl}-benzoic acid Ex-72A: 4-Methoxy-2-(2-morpholin-4-yl-2-oxo-ethoxy)-5-thiophen-2-yl-benzaldehyde was prepared in an analogous fashion as described in Ex-29C using 4-(2-chloroacetyl)morpholine. Silica gel chromatography (80% ethyl acetate/hexanes to 100% ethyl acetate) gave the expected product as a pale yellow solid, mp 200–201° C. $^1$H-NMR (300 MHz, CDCl$_3$) δ 10.33 (s, 1H), 8.12 (s, 1H), 7.44 (d, 1H, J=3.6 Hz), 7.31 (d, 1H, J=5.1 Hz), 7.08 (dd, 1H, J=5.1, 3.6 Hz), 6.74 (s, 1H), 4.89 (s, 2H), 4.00 (s, 3H), 3.67 (brs, 8H). MS (ESI) m/z=362 ([M+H]$^+$, 100%). Anal. Calcd. for C$_{18}$H$_{19}$NO$_5$S: C, 59.82; H, 5.30; N, 3.88; S, 8.87. Found: C, 59.88; H, 5.36; N, 3.90; S, 8.75.

The title compound was prepared by condensing 4-methoxy-2-(2-morpholin-4-yl-2-oxo-ethoxy)-5-thiophen-2-yl-benzaldehyde (Ex-72A) and 4-acetylbenzoic acid in a similar manner as described in Ex-3. Orange solid, mp 231–233° C., 70% yield. $^1$H-NMR (300 MHz, DMSO-d$_6$) δ 8.28–8.35 (m, 3H), 8.21 (s, 1H), 8.07–8.11 (m, 3H), 7.66 (d, 1H, J=3.3 Hz), 7.52 (d, 1H, J=5.1 Hz), 7.13 (dd, 1H, J=5.1, 3.3 Hz), 6.87 (s, 1H), 5.13 (s, 2H), 4.00 (s, 3H), 3.65 (brm, 4H), 3.54–3.55 (m, 4H). MS (EI) m/z=507 ([M]$^+$, 100%). Anal. Calcd. for C$_{27}$H$_{25}$NO$_7$S.½EtOH: C, 63.55; H, 5.61; N, 2.60; S, 5.95. Found: C, 63.13; H, 5.55; N, 2.53; S, 5.84.

Example 73

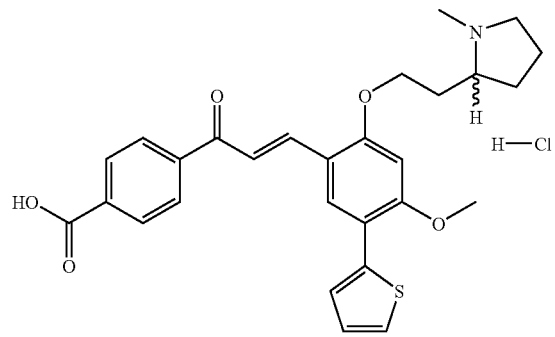

4-(3E-{4-Methoxy-2-[2-(1-methyl-pyrrolidin-2-yl)-ethoxy]-5-thiophen-2-yl-phenyl}-acryloyl)-benzoic acid, hydrochloride Ex-73A: Methanesulfonic acid 2-(1-methyl-pyrrolidin-2-yl)-ethyl ester was prepared in an analogous fashion as described in Ex-50A using (S)-(−)-1-methyl-2-pyrrolidinemethanol. The crude orange oil was dried in vacuo to give the expected product and was used without any further purification (40%). $^1$H-NMR (300 MHz, CDCl$_3$) δ 4.99–5.04 (m, 1H), 4.41–4.51 (m, 1H), 4.19–4.29 (m, 1H), 3.88–3.94 (m, 1H), 3.49 (s, 3H), 3.17–3.29 (m, 1H), 2.95–3.05 (m, 1H), 2.74 (s, 3H), 2.41–2.58 (m, 3H), 1.98–2.08 (m, 2H). MS (EI) m/z=207 ([M]$^+$, 100%). HRMS (EI) Calcd. for C$_{18}$H$_{19}$NO$_5$S: 207.0929. Found: 207.0922.

Ex-73B: 4-Methoxy-2-[2-(1-methyl-pyrrolidin-2-yl)-ethoxy]-5-thiophen-2-yl-benzaldehyde was prepared in an analogous fashion as described in Ex-29C using Methanesulfonic acid 2-(1-methyl-pyrrolidin-2-yl)-ethyl ester (Ex-73A). Silica gel chromatography (10% methanol/methylene chloride to 15% methanol/methylene chloride) gave 0.50 g (70%) of the expected product as a pale yellow oil. $^1$H-NMR (300 MHz, CDCl$_3$, major isomer) δ 10.35 (s, 1H), 8.09 (s, 1H), 7.42–7.44 (m, 1H), 7.30 (d, 1H, J=5.1 Hz), 7.06–7.09

(m, 1H), 6.49 (s, 1H), 4.80 (m, 1H), 4.20–4.26 (m, 1H), 3.98 (s, 3H), 2.64–2.84 (m, 2H), 2.47 (s, 3H), 1.80–2.33 (m, 7H). MS (EI) m/z=345 ([M]+, 100%). HRMS (EI) Calcd. for $C_{18}H_{19}NO_5S$: 345.1399. Found: 345.1401.

The title compound was prepared by condensing 4-methoxy-2-[2-(1-methyl-pyrrolidin-2-yl)-ethoxy]-5-thiophen-2-yl-benzaldehyde (Ex-73B) and 4-acetylbenzoic acid in a similar manner as described in Ex-3. Dark Yellow solid, 52%, mp 206–208° C. $^1$H-NMR (300 MHz, DMSO-$d_6$, major isomer) δ 8.30 (s, 1H), 8.25 (d, 2H, J=7.8 Hz), 8.07–8.12 (m, 3H), 7.94 (d, 1H, J=15.6 Hz), 7.68 (d, 1H, J=3.3 Hz), 7.52 (d, 1H, J=5.1 Hz), 7.14 (dd, 1H, J=5.1, 3.3 Hz), 6.86 (s, 1H), 5.05 (m, 1H), 4.34 (m, 1H), 4.00 (s, 3H), 3.40–3.46 (m, 2H), 2.81 (s, 3H), 2.40–2.44 (m, 1H), 2.16–2.27 (m, 2H), 1.81–2.00 (m, 4H). MS (ESI) m/z=492 ([M+H]+, 100%). Anal. Calcd. for $C_{28}H_{30}ClNO_5S\cdot\frac{1}{2}H_2O$: C, 60.59; H, 5.99; N, 2.52; S, 5.78. Found: C, 60.70; H, 5.85; N, 2.64; S, 6.15.

Example 74

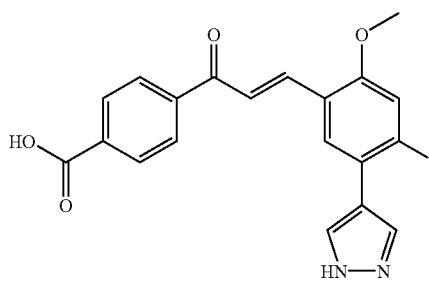

4-{3E-[2,4-Dimethoxy-5-(1H-pyrazol-4-yl)-phenyl]-acryloyl}-benzoic acid

Ex-74A: A solution of 4-(4,4,5,5-tetramethyl-[1,3,2]dioxaborolan-2-yl)-1H-pyrazole (0.33 g, 1.70 mmol) and di-tert-butyl dicarbonate (0.51 g, 2.34 mmol) in dichloromethane (10 mL) was allowed to stir overnight at ambient temperature. The solution was then washed with saturated solution of sodium bicarbonate and brine, dried over sodium sulfate, and concentrated. The crude product of 4-(4,4,5,5-tetramethyl-[1,3,2]dioxaborolan-2-yl)-pyrazole-1-carboxylic acid tert-butyl ester (0.61 g) was used in next step without further purification.

Ex-74B: To a mixture of 2,4-dimethoxy-5-bromo-benzaldehye (0.28 g, 1.13 mmol), 4-(4,4,5,5-tetramethyl-[1,3,2]dioxaborolan-2-yl)-pyrazole-1-carboxylic acid tert-butyl ester (Ex-76A, 0.61 g, 1.70 mmol), bis(tri-tert-butylphosphine)palladium (43 mg, 0.085 mmol) and potassium fluoride (0.24 g, 4.08 mmol) was added degassed tetrahydrofuran (15 mL). The reaction mixture was heated at 60° C. for one day. Additional potassium fluoride (0.24 g, 4.08 mmol) and water (20 μL) were added. The reaction mixture continued to stir at 60° C. for another 8 hours. The reaction was then quenched by water. The aqueous solution was extracted with ethyl acetate. The solution of ethyl acetate was washed with saturated solution of sodium bicarbonate, brine, dried over sodium sulfate and concentrated. The crude product was purified by flash chromatography. Elution with ethyl acetate (50%, v/v, in hexane) afforded 4-(5-formyl-2,4-dimethoxy-phenyl)-pyrazole-1-carboxylic acid tert-butyl ester (0.15 g, 40%) as white solid. $^1$H NMR (CDCl$_3$) δ 10.35 (s, 1H), 8.43 (s, 1H), 8.09 (s, 1H), 8.02 (s, 1H), 6.52 (s, 1H), 4.02 (s, 3H), 3.99 (s, 3H), 1.68 (s, 9H). MS m/z=333 ([M+H]+, 100%).

The title compound was prepared by condensing 2,4-dimethoxy-5-(1H-pyrazol-4-yl)-benzaldehyde (Ex-74B) and 4-acetylbenzoic acid in a similar manner as described in Ex-3 including an acid work-up. Yellow solid, mp>250° C. $^1$H-NMR (DMSO-$d_6$) δ 12.42 (bs, 1H), 8.20–8.03 (m, 8H), 7.85 (d, J=16.1 Hz), 6.74 (s, 1H), 3.95 (s, 3H), 3.94 (s, 3H). MS m/z=379 ([M+H]+, 100%).

Example 75

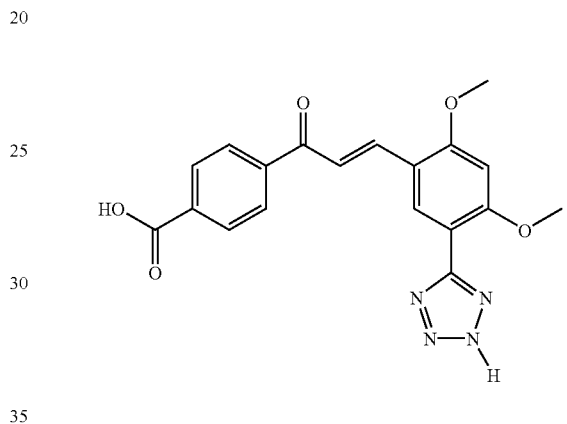

4-{3E-[2,4-Dimethoxy-5-(2H-tetrazol-5-yl)-phenyl]-acryloyl}-benzoic acid

Ex-75A: A solution of 2-(5-bromo-2,4-dimethoxy-phenyl)-[1,3]dioxolane (Ex-46A, 1.16 g, 4.9 mmol), sodium azide (641.3 mg, 9.86), and zinc bromide (552.2 mg, 2.46 mmol) in water (14 mL) and isopropanol (17 mL) were mixed and refluxed for 18 hours. The reaction mixture was quenched with 3N HCl (60 mL) and extracted with ethyl acetate (2×75 mL). The organic was concentrated to a white solid. The solid was stirred in 0.25N NaOH (100 mL) for one hour. The suspension was filtered and the filtrate was collected and acidified with 1N HCl to a pH of 2. The aqueous solution was extracted with ethyl acetate:THF (40%). The organics were collected and concentrated to a crude brown solid of 2,4-dimethoxy-5-(2H-tetrazol-5-yl)-benzaldehyde (77.8 mg, 7%). $^1$H-NMR (DMSO-d6) δ 10.09 (s, 1H), 7.97 (s, 1H), 6.89 (s, 1H), 4.04 (s, 3H), 4.02 (s, 3H). MS m/z=234 ([M]+, 94%), 191 (100%).

The title compound was prepared by condensing 2,4-dimethoxy-5-(2H-tetrazol-5-yl)-benzaldehyde (Ex-75A) and 4-acetylbenzoic acid in a similar manner as described in Ex-3. Yellow solid, 19% yield, mp 218° C. (dec). $^1$H-NMR (DMSO-d6) δ 8.58 (s, 1H), 8.20 (d, 2H), 8.03 (m, 3H), 7.85 (d, 1H), 6.90 (s, 1H), 4.04 (s, 3H), 4.02 (s, 3H). MS m/z=422 ([M+CH$_3$CN+H]+, 100%). HRMS m/z: calc. 381.1199, found 381.1184.

Example 76

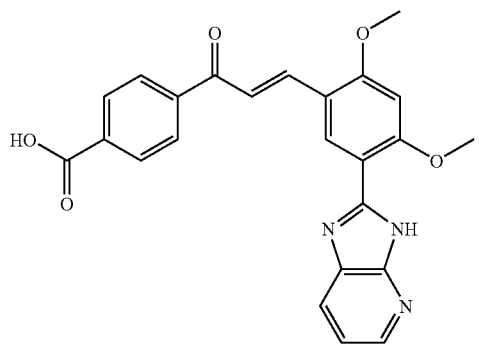

4-{3E-[5-(3H-Imidazo[4,5-b]pyridin-2-yl)-2,4-dimethoxy-phenyl]-acryloyl}-benzoic acid Ex-76A: To a suspension of 2,4-dimethoxybenzoic acid (0.36 g, 2 mmol) and 8 ml of POCl$_3$ in a 50 ml of a round-bottom flask, 2,3-diaminopyridine (0.22 g, 2 mmol) was added. The mixture was heated to reflux for 4 hours and then cooled to room temperature. The reaction mixture was then concentrated to remove most of the POCl$_3$. The residue was carefully treated with 1N HCl at 0° C. using a water-ice bath, then neutralized with NaOH (50%). The off-white solid was filtered to give 2-(2,4-dimethoxy-phenyl)-3H-imidazo[4,5-b]pyridine (0.44 g, 88%). $^1$H-NMR (DMSO-d$_6$) δ 8.28–8.36 (m, 2H), 7.97 (d, J=8 Hz, 1H), 7.21–7.25 (m, 1H), 6.80 (s, 1H), 6.78 (d, J=9 Hz, 1H), 4.05 (s, 3H), 3.91 (s, 3H). HRMS (ES+) Calcd. for C$_{24}$H$_{19}$N$_3$O$_5$: 430.1403. Found: 430.1414.

Ex-76B: To a suspension of 2-(2,4-dimethoxy-phenyl)-3H-imidazo[4,5-b]pyridine (0.44 g, 1.7 mmol) in 20 ml of CH$_2$Cl$_2$, 1,1-dichlorodimethyl ether (0.55 g, 4.8 mmol) was added. The mixture was cooled to 0° C. with a water-ice bath, and 7 ml (7 mmol) of TiCl$_4$ (1.0 m in CH$_2$Cl$_2$) was added dropwise. The mixture was stirred at 0° C. for 2 hrs, then room temperature for overnight. The reaction mixture was poured into ice-water and the precipitate was filtered to give 0.31 g (63%) of 5-(3H-imidazo[4,5-b]pyridin-2-yl)-2,4-dimethoxy-benzaldehyde as a white solid. $^1$H-NMR (DMSO-d$_6$) δ 10.22 (s, 1H), 8.67 (s, 1H), 8.56 (d, J=5 Hz, 1H), 8.44 (d, J=8 Hz, 1H), 7.57–7.61 (m, 1H), 6.97 (s, 1H), 4.19 (s, 3H), 4.06 (s, 3H). HMRS (EI) calc. for C$_{15}$H$_{13}$N$_3$O$_3$: 283.0957; found: 283.0952.

The title compound was prepared by condensing 5-(3H-imidazo[4,5-b]pyridin-2-yl)-2,4-dimethoxy-benzaldehyde (Ex-76B) and 4-acetylbenzoic acid in a similar manner as described in Ex-3. Yellow solid, mp 222–224° C., 60% yield. $^1$H-NMR (DMSO-d$_6$) δ 8.75 (s, 1H), 8.38–8.40 (m, 1H), 8.18 (d, J=9 Hz, 2H), 7.99–8.08 (m, 4H), 7.83 (d, J=15 Hz, 1H), 7.28–7.33 (m, 1H), 6.91 (s, 1H), 4.11 (s, 3H), 4.04 (s, 3H). MS m/z=430 ([M+H]$^+$).

Example 77

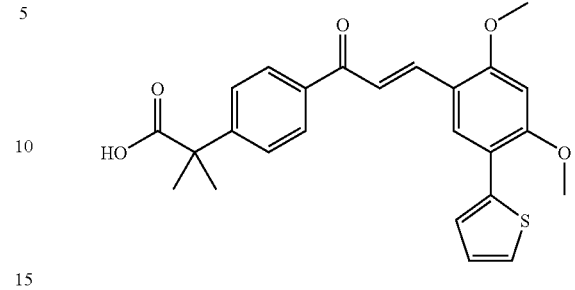

2-{4-[3E-(2,4-Dimethoxy-5-thiophen-2-yl-phenyl)-acryloyl]-phenyl}-2-methyl-propionic acid Ex-77A: To a mixture of aluminum chloride (2.8 g, 20.8 mmol) in carbon disulfide (50 mL) was added acetyl chloride (0.74 mL, 10.4 mmol) followed by addition of 2-methyl-2-phenyl-propionic acid ethyl ester (1.0 g, 5.2 mmol). The reaction mixture was refluxed for 2 hours and then poured into ice containing sulfuric acid (6M). The mixture was partitioned. The aqueous layer was extracted with ethyl acetate. The solution of ethyl acetate was washed with hydrochloric acid (0.5M), saturated solution of sodium bicarbonate and brine, dried over sodium sulfate and concentrated. The crude product was purified by flash chromatography. Elution with ethyl acetate (33%, v/v, in hexane) gave 2-(4-acetyl-phenyl)-2-methyl-propionic acid ethyl ester (0.57 g, 47%). $^1$H NMR (CDCl$_3$) δ 7.92 (d, J=7.6 Hz, 2H), 7.42 (d, J=7.6 Hz, 2H), 4.13 (q, J=7.2 Hz, 2H), 2.59 (s, 3H), 1.61 (s, 3H), 1.59 (s, 3H), 1.18 (t, J=7.2 Hz, 3H).

The title compound was prepared by condensing 2-(4-acetyl-phenyl)-2-methyl-propionic acid (Ex-77A) and 2,4-dimethoxy-5-thiophen-2-yl-benzaldehyde (Ex-6A) in a similar manner as described in Ex-3. White foam. $^1$H-NMR (CCl$_3$) δ 8.11–7.86 (m, 5H), 7.62–7.46 (m, 3H), 7.42 (d, J=3.2 Hz, 1H), 7.31 (d, J=5.3 Hz, 1H), 7.10–7.08 (m, 1H), 6.54 (s, 1H), 3.99 (s, 3H), 3.97 (s, 3H), 1.67 (s, 3H), 1.65 (s, 3H). MS m/z=436 (M$^+$, 55%), 405 ([M–OCH$_3$]$^+$, 100%).

Example 78

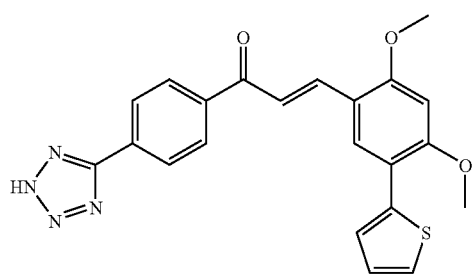

3E-(2,4-Dimethoxy-5-thiophen-2-yl-phenyl)-1-[4-(2H-tetrazol-5-yl)-phenyl]-propenone Ex-78A: A suspension of 4-acetylbenzonitrile (2.9 g, 20.0 mmol), sodium azide (1.43 g, 22.0 mmol) and zinc bromide (4.5 g, 20.0 mmol) in water (50 mL) was refluxed for one day. Additional water (40 mL), HCl (3M, 30 mL) and EtOAc (200 mL) were added subsequently. The mixture was stirred until no solid in the aqueous layer. The mixture was then portioned. The aqueous solution was further extracted with EtOAc (3×60 mL). The combined EtOAc was concentrated. The residue was treated with NaOH (0.25 M, 200 mL). After stirred for 50 min, insoluble material was filtered, washed with NaOH (1M). The filtrate was then acidified with HCl (conc.) to pH 3. The resulting white precipitate was filtered, washed with water and dried in vacuo to obtain 1-[4-(2H-tetrazol-5-yl)-phenyl]-ethanone as white solid. $^1$H NMR (DMSO-d$_6$) δ 8.17–8.10 (m, 4H), 2.61 (s, 3H). MS m/z=188 (M$^+$).

The title compound was prepared by condensing 1-[4-(2H-tetrazol-5-yl)-phenyl]-ethanone (Ex-78A) and 2,4-dimethoxy-5-thiophen-2-yl-benzaldehyde (Ex-6A) in a similar manner as described in Ex-3. Yellow solid, mp 235° C. (dec.). $^1$H-NMR (DMSO-d$_6$) δ 8.33 (d, J=8.4 Hz, 2H), 8.26 (s, 1H), 8.20 (d, J=8.9 Hz, 2H), 8.08 (d, J=16.0 Hz, 1H), 7.93 (d, J=15.0 Hz, 1H), 7.66–7.64 (m, 1H), 7.50–7.48 (m, 1H), 7.12–7.09 (m, 1H), 6.81 (s, 1H), 3.983 (s, 3H), 3.976 (s, 3H). MS m/z=418 (M$^+$, 100%).

Example 79

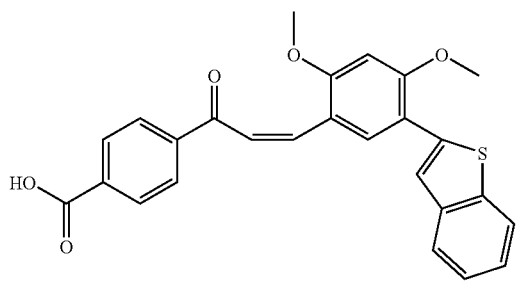

4-[3Z-(5-Benzo[b]thien-2-yl-2,4-dimethoxyphenyl)-acryloyl]-benzoic acid

A solution of 4-[3E-(5-benzo[b]thien-2-yl-2,4-dimethoxyphenyl)-acryloyl]-benzoic acid (Ex-3, 101.4 mg, 0.23 mmol) in ethyl acetate (889 ml) was stirred in a well lighted-area at room temperature for 36 hours. The solution was concentrated to a yellow solid. The crude material was purified on reversed-phase preparative plates (20×20 cm, RP-18 F$_{254}$, 1 mm) eluted with MEOH/ACN/H$_2$O (45:45:10) to give 22.2 mg of the title compound, which was 86% the cis isomer by NMR analysis. $^1$H-NMR (DMSO-D$_6$, major isomer) δ 7.98 (s, 4H), 7.86 (m, 2H), 7.76 (d, J=9 Hz 1H), 7.56 (s, 1H), 7.28 (m, 2H), 7.17 (d, J=12 Hz, 1H), 6.78 (d, J=12 Hz, 2H), 6.71 (s, 1H), 3.94 (s, 3H), 3.77 (s, 3H).

Example 80

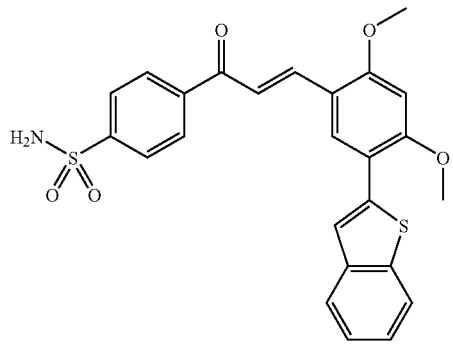

4-[3E-(5-Benzo[b]thiophen-2-yl-2,4-dimethoxyphenyl)-acryloyl]-benzenesulfonamide To a solution of 4-acetyl-benzsulfonamide (Ex-26A, 0.20 g, 1.0 mmol) and 5-benzo[b]thiophene-2-yl-2,4-dimethoxyphenylbenzaldehyde (Ex-3A, 0.31 g, 1.05 mmol) in DMF (5 mL) and methanol (2 mL) was added lithium methoxide (0.15 g, 4.0 mmol). The reaction mixture was allowed to stir at ambient temperature. The reaction was quenched with water (30 mL) after 2 hours. The aqueous solution was acidified to pH 4 with HCl (3 M) and extracted with ethyl acetate. The combined solution of ethyl acetate was subsequently washed with brine, dried (Na$_2$SO$_4$) and concentrated. The solid residue was stirred in ethanol (10 mL) for 1.5 hours, filtered, washed with aqueous ethanol (50%) and dried in vacuo. The title compound was obtained as a yellow solid (0.3 g, 63%), mp 204–205° C. (dec.). $^1$H-NMR (DMSO-d$_6$) δ 8.35 (s, 1H), 8.27 (d, J=7.7 Hz, 2H), 8.06 (d, J=16.0 Hz, 1H), 7.97–7.92 (m, 4H), 7.88 (d, J=6.6 Hz, 1H), 7.81 (d, J=7.4 Hz, 1H), 7.53 (s, 2H), 7.37–7.27 (m, 2H), 6.85 (s, 1H), 4.09 (s, 3H), 4.03 (s, 3H).

Example 81

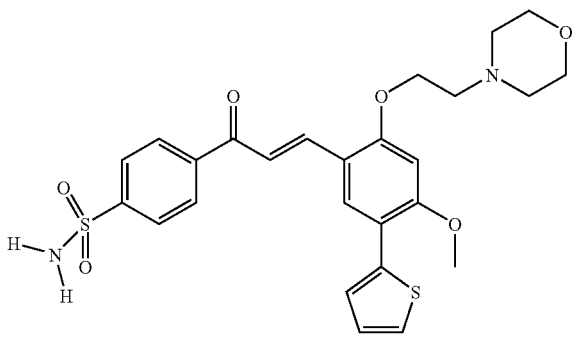

4-{3E-[4-Methoxy-2-(2-morpholin-4-yl-ethoxy)-5-thiophen-2-yl-phenyl]-acryloyl}-benzenesulfonamide 4-Acetyl-benzenesulfonamide (Ex-26A) (0.10 g, 0.29 mmol) and 4-acetylbenzenesulfonamide (0.057 g, 0.29 mmol) were dissolved in a dimethylformamide-methanol solution (2.0 mL, 7:3). After complete dissolution, lithium methoxide (0.044 g, 1.2 mmol) was added and the resulting orange slurry was stirred in the dark at room temperature for 4 h. Upon completion, as determined by HPLC, the mixture was diluted with water (15 mL) and extracted with ethyl acetate (3×25 mL). The combined organic extracts were dried over sodium sulfate and evaporated to dryness. The crude oil was taken up in ethanol (2 mL) and warmed to 60° C. to obtain complete dissolution and allowed to cool to room temperature. The resulting precipitate was collected on filter paper and dried in vacuo to yield 0.13 g (82%) of the title compound as a yellow solid, mp 186–188° C. $^{1}$H-NMR (300 MHz, DMSO-$d_6$) δ 8.23–8.28 (m, 3H), 7.93–8.09 (m, 4H), 7.66 (d, 1H, J=3.0 Hz), 7.56 (brs, 1H), 7.52 (d, 1H, J=5.1 Hz), 7.13 (dd, 1H, J=5.1, 3.0 Hz), 6.89 (s, 1H), 4.34 (t, 2H, J=6 Hz), 4.01 (s, 3H), 3.54–3.58 (m, 4H), 2.38 (t, 2H), J=6 Hz), 2.51–2.53 (m, 4H). MS (ESI) m/z=529 ([M+H]$^{+}$, 100%). Anal. Calcd. for $C_{26}H_{28}N_{2}O_{6}S_{2}$: C, 59.07; H, 5.34; N, 5.30; S, 12.13. Found: C, 58.90; H, 5.3; N, 5.37; S, 12.01.

Example 82

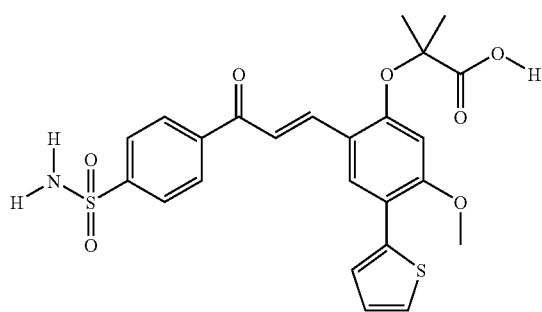

2-{5-Methoxy-2-[3-oxo-3-(4-aminosulfonyl-phenyl)-E-propenyl]-4-thiophen-2-yl-phenoxy}-2-methyl-propionic acid The title compound was prepared by condensing 4-acetyl-benzenesulfonamide (Ex-26A) and 2-(2-formyl-5-methoxy-4-thiophen-2-yl-phenoxy)-2-methyl-propionic acid (Ex-59B) in a similar manner as described in Ex-22. Yellow solid, mp 164–165° C., 85% yield. $^{1}$H-NMR (300 MHz, DMSO-$d_6$) δ 8.21–8.28 (m, 3H), 7.96–8.12 (m, 4H), 7.67 (d, 1H, J=3.0 Hz), 7.56 (brs, 3.0H), 7.14 (dd, 1H, J=5.7, 3.0 Hz), 6.57 (s, 1H), 3.88 (s, 3H), 1.66 (s, 6H). MS (ESI) m/z=502 ([M+H]$^{+}$, 100%). Anal. Calcd. for $C_{24}H_{23}NO_{7}S_{2}$: C, 57.47; H, 4.62; N, 2.79; S, 12.79. Found: C, 57.70; H, 4.74; N, 2.85; S, 12.51.

Example 83

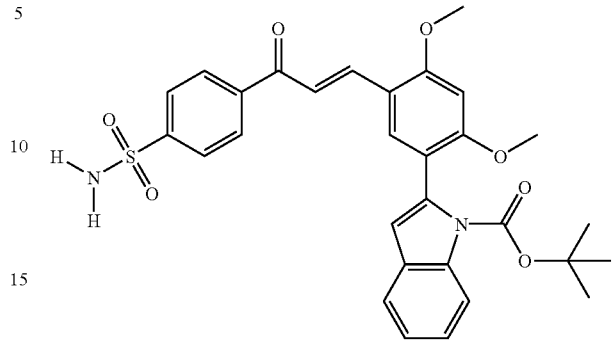

2-{2,4-Dimethoxy-5-[3-oxo-3-(4-aminosulfonyl-phenyl)-E-propenyl]-phenyl}-indole-1-carboxylic acid tert-butyl ester The title compound was prepared by condensing 4-acetyl-benzenesulfonamide (Ex-26A) and 2-(5-formyl-2,4-dimethoxy-phenyl)-indole-1-carboxylic acid tert-butyl ester (Ex-36A) in a similar manner as described in Ex-22. Yellow solid, 40% yield, mp 120–122° C. $^{1}$H-NMR (CDCl$_3$) δ 8.01–8.19 (m, 6H), 7.68 (s, 1H), 7.56 (d, J=8 Hz, 1H), 7.46 (d, J=16 Hz, 1H), 7.21–7.35 (m, 2H), 6.53 (d, J=14 Hz, 2H), 5.01 (s, 2H), 4.00 (s, 3H), 3.85 (s, 3H), 1.42 (s, 9H), MS m/z=563 ([M+H]$^{+}$). HRMS (ES+) Calcd. for $C_{30}H_{30}N_{2}O_{7}S$: 563.1852. Found: 563.1862.

Example 84

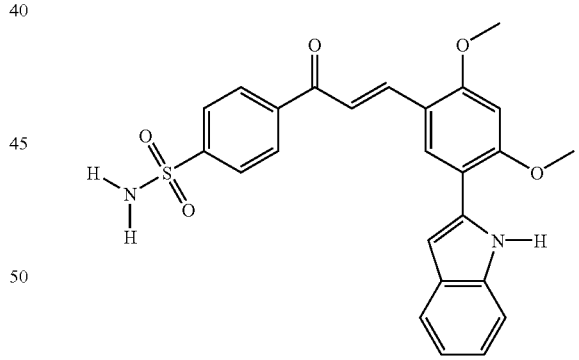

4-{3E-[5-(1H-Indol-2-yl)-2,4-dimethoxy-phenyl]-acryloyl}-benzenesulfonamide

The title compound was prepared by condensing 4-acetyl-benzenesulfonamide (Ex-26A) and 5-(1H-indol-2-yl)-2,4-dimethoxy-benzaldehyde (Ex-61A) in a similar manner as described in Ex-22. Red solid, 70% yield, mp 185–187° C. $^{1}$H-NMR (DMSO-$d_6$) δ 11.15 (br, s, 1H), 8.33 (s, 1H), 8.24 (d, J=8 Hz, 2H), 8.07 (d, J=15 Hz, 1H), 7.98 (d, J=8 Hz, 2H), 7.80 (d, J=15 Hz, 1H), 7.41–7.55 (m, 4H), 7.03–7.08 (m, 1H), 6.93–6.99 (m, 2H), 6.83 (s, 1H), 4.04 (s, 3H), 3.99 (s, 3H). MS m/z=463 ([M+H]⁺). HRMS (ES+) Calcd. for $C_{25}H_{22}N_2O_5S$: 463.1327. Found: 463.1316.

Example 85

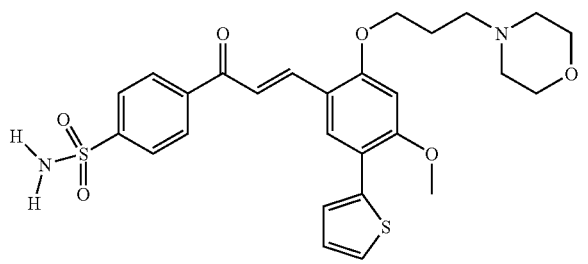

4-{3E-[4-Methoxy-2-(3-morpholin-4-yl-propoxy)-5-thiophen-2-yl-phenyl]-acryloyl}-benzenesulfonamide The title compound was prepared by condensing 4-acetyl-benzenesulfonamide (Ex-26A) and 4-methoxy-2-(3-morpholin-4-yl-propoxy)-5-thiophen-2-yl-benzaldehyde (Ex-66A) in a similar manner as described in Ex-22. Yellow solid, 48% yield, mp 193–196° C. ¹H-NMR (DMSO-d6) δ 8.24 (m, 3H), 8.06 (s, 1H), 7.96 (d, 2H), 7.89 (d, 1H), 7.63 (d, 1H), 7.51 (m, 1H), 7.10 (dd, J=3, 4 Hz, 1H), 6.81 (s, 1H), 4.23 (t, 2H), 3.98 (s, 3H), 3.55 (t, 4H), 2.47 (m, 2H), 2.35 (t, 4H), 1.98 (q, 2H). MS m/z=542 ([M]⁺, 38%), 100 (100%). Anal. calculated for $C_{27}H_{30}N_2O_6S_2 \cdot 3/5H_2O$: C, 58.59; H, 5.68; S, 11.59; found C, 58.59, H: 5.55, S, 11.40.

Example 86

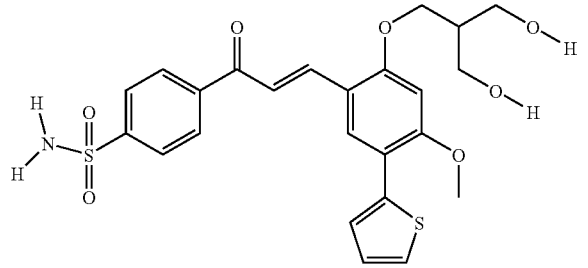

4-{3E-[2-(3-Hydroxy-2-hydroxymethyl-propoxy)-4-methoxy-5-thiophen-2-yl-phenyl]-acryloyl}-benzenesulfonamide 2-(3-Hydroxy-2-hydroxymethyl-propoxy)-4-methoxy-5-thiophen-2-yl-benzaldehyde (Ex-64B) (8.0 g, 24.8 mmol) and 4-acetylbenzenesulfonamide (4.9 g, 24.8 mmol) were dissolved in a dimethylformamide-methanol solution (170 mL, 7:3). After complete dissolution, lithium methoxide (3.8 g, 99.2 mmol) was added and the resulting red-orange slurry was stirred in the dark at room temperature for 3 h. Upon completion, as determined by HPLC, the mixture was diluted with water (500 mL) and extracted with ethyl acetate (6×200 mL). The combined organic extracts were dried over sodium sulfate and evaporated to dryness. The crude oil was taken up in ethanol (150 mL) and warmed to 60° C. to obtain complete dissolution and allowed to cool to room temperature. The resulting precipitate was collected on filter paper and dried in vacuo to yield 7.0 g (60%) of the title compound as a light orange solid, mp 123–124° C. ¹H-NMR (300 MHz, DMSO-d₆) δ 8.25–8.29 (m, 3H), 7.90–8.11 (m, 4H), 7.66 (d, 1H, J=3.0 Hz), 7.56 (brs, 1H), 7.52 (d, 1H, J=5.1 Hz), 7.13 (dd, 1H, J=5.1, 3.0 Hz), 6.88 (s, 1H), 4.67 (t, 2H, J=10.8 Hz), 4.24 (d, 2H, J=6.0 Hz), 4.00 (s, 3H), 3.54–3.65 (m, 4H), 2.09–2.13 (m, 1H). MS (ESI) m/z=504 ([M+H]⁺, 100%). Anal. Calcd. $C_{24}H_{25}NO_7S_2 \cdot H_2O$: C, 57.24; H, 5.00; N, 2.78; S, 12.73. Found: C, 56.72; H, 5.27; N, 2.71; S, 12.11.

Example 87

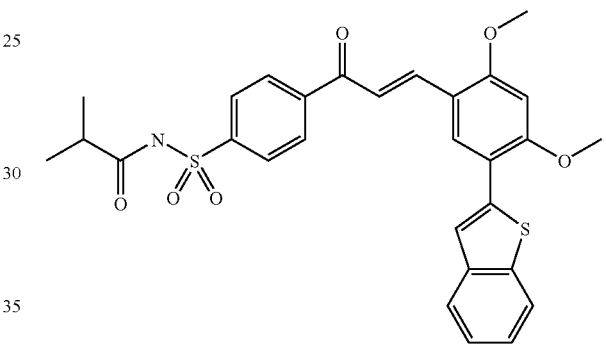

4-[3E-(5-Benzo[b]thiophen-2-yl-2,4-dimethoxy-phenyl)-acryloyl]-N-isobutyryl-benzenesulfonamide A solution of 4-[3E-(5-benzo[b]thiophen-2-yl-2,4-dimethoxy-phenyl)-acryloyl]-benzenesulfonamide (Ex-80, 0.15 g, 0.31 mmol) in tetrahydrofuran (3 mL) was cooled to −78° C. and a solution of lithium bis(trimethylsilyl)amide (1.0 M in tetrahydrofuran, 0.63 mL, 0.63 mmol) was added dropwise. The solution was allowed to stir at this temperature for 1 hour and warm up to 0° C. Isobutyric acid anhydride (0.31 mL, 1.88 mmol) was added at this temperature. The solution was allowed to stir at 0° C. for 10 min and ambient temperature for 2 hours. The reaction then was quenched with water. The aqueous solution was extracted with ethyl acetate. The combined solution of ethyl acetate was washed with brine, dried over sodium sulfate and concentrated. The residual material was stirred in ethanol for 3 hours, filtered and dried in vacuo to give the title compound as a yellow solid (0.15 g, 87%), mp>240° C. (dec.). ¹H-NMR (CDCl₃) δ 8.21 (d, J=8.6 Hz, 2H), 8.13 (d, J=8.7 Hz, 2H), 8.09 (s, 1H), 8.02 (bs, 1H), 7.94 (s, 1H), 7.85–7.78 (m, 2H), 7.68 (s, 1H), 7.55 (d, J=16.9 Hz, 1H), 7.38–7.30 (m, 2H), 6.58 (s, 1H), 4.04 (s, 3H), 4.01 (s, 3H), 2.47–2.38 (m, 1H), 1.14 (d, J=7.1 Hz, 6H). MS m/z=549 (M⁺, 100%).

Example 88

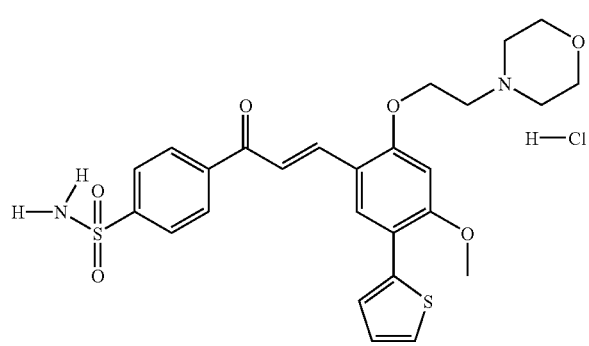

4-{3E-[4-Methoxy-2-(2-morpholin-4-yl-ethoxy)-5-thiophen-2-yl-phenyl]-acryloyl}-benzenesulfonamide, hydrochloride Th 4-{3-[4-Methoxy-2-(2-morpholin-4-yl-ethoxy)-5-thiophen-2-yl-phenyl]-acryloyl}-benzenesulfonamide (Ex-81, 0.065 g, 0.12 mmol) was dissolved in tetrahydrofuran (5 mL) and 3 N HCl (1 mL) was added drop wise to the solution. The resulting yellow slurry was stirred in the dark at room temperature for 30 min. The precipitate was collected and dried in vacuo to yield 0.054 g (78%) of the title compound as a yellow solid, mp 235° C. (dec). $^1$H-NMR (300 MHz, DMSO-$d_6$): δ 8.31–8.34 (m, 3H), 8.13 (d, 1H, J=15.0 Hz), 7.92–8.01 (m, 3H), 7.70 (d, 1H, J=4.0 Hz), 7.54 (m, 3H), 7.15–7.17 (m, 1H), 6.92 (s, 1H), 4.64 (brs, 2H), 4.03 (s, 5H), 3.72–3.79 (m, 4H), 3.56–3.60 (m, 4H). MS (ESI) m/z=529 ([M+H]$^+$, 100%). Anal. Calcd. for $C_{26}H_{29}ClN_2O_6S_2$: C, 55.26; H, 5.17; Cl, 6.27; N, 4.96; S, 11.35. Found: C, 55.31; H, 5.17; Cl, 6.32; N, 4.98; S, 11.20.

Example 89

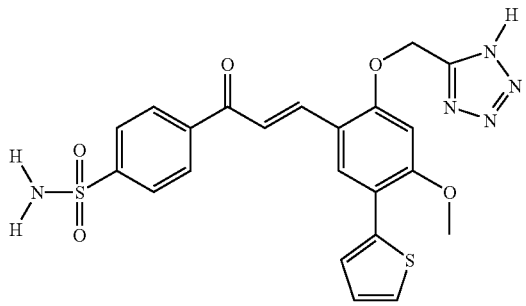

4-{3E-[4-Methoxy-2-(1H-tetrazol-5-ylmethoxy)-5-thiophen-2-yl-phenyl]-acryloyl}-benzenesulfonamide Ex-89A: (2-Acetyl-5-methoxy-4-thiophen-2-yl-phenoxy)-acetonitrile was prepared in an analogous fashion as described in Ex-29C using iodoacetonitrile. The crude solid was slurried in ethyl acetate (50 mL) to remove residual impurities. The resulting solid was collected on filter paper and dried in vacuo to give the expected product as an orange solid (70%), mp 175–176° C. $^1$H-NMR (300 MHz, CDCl$_3$) δ 10.29 (s, 1H), 8.17 (s, 1H), 7.48 (d, 1H, J=3.6 Hz), 7.35 (d, 1H, J=5.1 Hz), 7.10 (dd, 1H, J=5.1, 3.6 Hz), 6.64 (s, 1H), 4.96 (s, 2H), 4.06 (s, 3H). MS (EI) m/z=273 ([M]$^+$, 99%), 233 (100%). Anal. Calcd. for $C_{14}H_{11}NO_3S$: C, 61.52; H, 4.06; N, 5.12; S, 11.73. Found: C, 61.65; H, 4.20; N, 5.16; S, 11.59.

Ex-89B: (2-Acetyl-5-methoxy-4-thiophen-2-yl-phenoxy)-acetonitrile (Ex-89A, 0.30 g, 1.1 mmol) was slurried in a mixture of water:isopropanol (3 mL, 2:1) to obtain a well-dispersed solution. Sodium azide (0.079 g, 1.2 mmol) followed by zinc bromide (0.25 g, 1.1 mmol) were added and the reaction was heated to reflux and vigorously stirred for 24 h. Additional solvent (1 mL, 1:1 water:isopropanol) was added after 10 h at reflux due to evaporation. The reaction was diluted with an ethyl acetate:tetrahydrofuran mixture (25 mL, 2:1) and a 3 N HCl solution (10 mL) and vigorously stirred until a homogenous solution was obtained (1 h). The layers were separated and the aqueous was extracted with ethyl acetate (3×50 mL). The combined organic extracts were dried over sodium sulfate and concentrated to a dark green solid. Silica gel chromatography (15% methanol/methylene chloride containing 1% acetic acid) gave 0.22 g (65%) of 4-methoxy-2-(1H-tetrazol-5-ylmethoxy)-5-thiophen-2-yl-benzaldehyde as a pale green solid. $^1$H-NMR (300 MHz, DMSO-$d_6$) δ 10.33 (s, 1H), 7.97 (s, 1H), 7.52–7.56 (m, 2H), 7.10–7.12 (m, 2H), 5.81 (s, 2H), 4.05 (s, 3H). MS (ESI) m/z=317 ([M+H]$^+$, 100%), HRMS (ESI) Calcd. for $C_{27}H_{25}NO_7S$: 317.0708. Found: 317.0712.

The title compound was prepared by condensing 4-acetyl-benzenesulfonamide (Ex-26A) and 4-methoxy-2-(1H-tetrazol-5-ylmethoxy)-5-thiophen-2-yl-benzaldehyde (Ex-89A) in a similar manner as described in Ex-22. Yellow solid, mp 163–164° C. (dec), 60% yield. $^1$H-NMR (300 MHz, DMSO-$d_6$) δ 8.31–8.34 (m, 3H), 7.92–8.15 (m, 4H), 7.70 (d, 1H, J=4.0 Hz), 7.54 (m, 3H), 7.15–7.17 (m, 1H), 6.92 (s, 1H), 4.64 (brs, 2H), 4.03 (s, 5H). MS (ESI) m/z=498 ([M+H]$^+$, 100%). Anal. Calcd. for $C_{22}H_{19}N_5O_5S_2 \cdot 1\frac{1}{2}H_2O$: C, 50.37; H, 4.23; N, 13.35; S, 12.23. Found: C, 50.48; H, 4.24; N, 12.95; S, 12.35.

Example 90

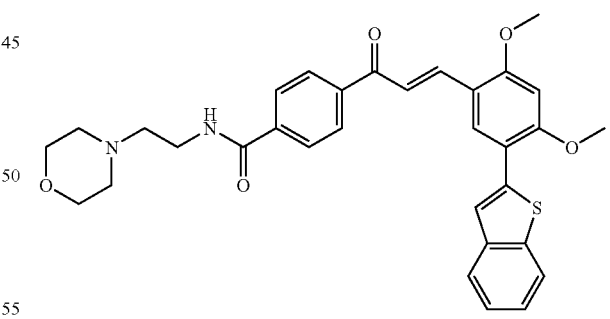

4-[3E-(5-Benzo[b]thiophen-2-yl-2,4-dimethoxy-phenyl)-acryloyl]-N-(2-morpholin-4-yl-ethyl)-benzamide To a solution of 4-[3E-(5-Benzo[b]thien-2-yl-2,4-dimethoxyphenyl)-acryloyl]-benzoic acid (Ex-3, 0.44 mg, 1 mmol) and 2-morpholin-4-yl-ethylamine (0.18 mL) in dichloromethane (20 mL) was added 1-(3-dimethylaminopropyl)-3-ethylcarbodiimide hydrochloride (0.38 g, 2 mmol) and the mixture was stirred at room temperature for four hours. It was poured into brine (100 mL) and extracted with dichloromethane (2×50 mL). The organic phase was dried and evaporated. Chromatography (dichloromethane/methanol 50:1) gave the title compound as a yellow solid (0.43 g, 77%). $^1$H-NMR (300 MHz, CDCl$_3$) δ 8.12 (d, J=16 Hz, 1H), 8.09 (d, J=8 Hz, 2H), 7.95 (s, 1H), 7.90 (d, J=8 Hz, 2H), 7.77–7.85 (m, 2H), 7.68 (s, 1H), 7.56 (d, J=16 Hz, 1H), 7.29–7.40 (m, 2H), 6.80–6.85 (br s, 1H), 6.58 (s, 1H), 4.04 (s, 3H), 4.01 (s, 3H), 3.75 (t, J=5 Hz, 4H), 3.59 (quad, J=5 Hz, 2H), 2.64 (t, J=5 Hz, 2H), 2.53 (t, J=5 Hz, 4H). Anal. calc. for C$_{32}$H$_{32}$N$_2$O$_5$S.H$_2$O: C, 67.94; H, 5.88; N, 4.95; found: C, 68.12; H, 5.92; N, 4.96.

Example 91

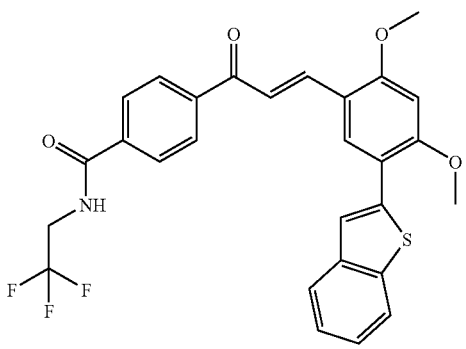

4-[3E-(5-Benzo[b]thiophen-2-yl-2,4-dimethoxy-phenyl)-acryloyl]-N-(2,2,2-trifluoro-ethyl)-benzamide The title compound was prepared in a similar manner as described in Ex-90. Yellow solid, 53% yield, mp 215–217° C. $^1$H-NMR (Aceton-d$_6$) δ 8.46 (br, s, H), 8.12–8.24 (m, 4H), 8.06 (d, J=8 Hz, 2H), 7.78–7.91 (m, 4H), 7.28–7.36 (m, 2H), 6.92 (s, 1H), 4.08 (s, 3H), 4.06 (s, 3H), 2.79 (s, 2H). MS m/z=526 ([M+H]$^+$). HRMS (ES+) Calcd. for C$_{28}$H$_{22}$F$_3$NO$_4$S: 526.1300. Found: 526.1324.

Example 92

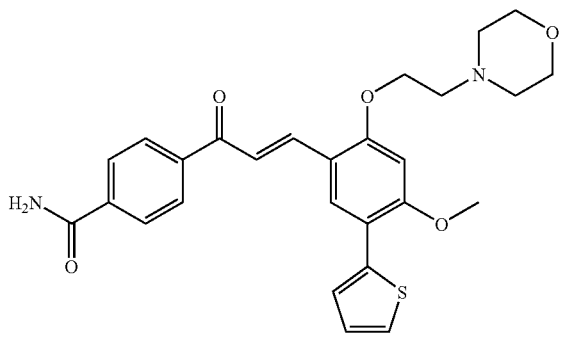

4-{3E-[4-Methoxy-2-(2-morpholin-4-yl-ethoxy)-5-thiophen-2-yl-phenyl]-acryloyl}-benzamide Ex-92A: To a solution of 4-acetyl-benzoic acid (0.5 g, 3.05 mmol) in tetrahydrofuran (10 mL) was added carbonyldiimidazole (0.74 g, 4.75 mmol). The solution was allowed to stir at ambient temperature for one hour and cooled to 0° C. followed by addition of ammonia (28% in water, 3 mL, 21 mmol). The solution was continued to stir at 0° C. for another one hour. The solvent was removed under reduced pressure. The residue was treated with water, filtered, washed with water, dried in vacuo to give 4-acetyl-benzamide (0.25 g, 50%) as a white solid. $^1$H NMR (DMSO-d$_6$) δ 8.11 (bs, 1H), 8.00 (d, J=9 Hz, 2H), 7.95 (d, J=9 Hz, 2H), 7.53 (bs, 1H), 2.59 (s, 3H).

To a solution of 4-acetyl-benzamide (Ex-92A, 0.25 g, 1.53 mmol) and 2-(2-morpholin-4-yl-ethoxy)-4-methoxy-5-thiophen-2-yl-benzaldehyde (Ex-60A, 0.53 g, 1.53 mmol) in DMF (7 mL) and methanol (3 mL) was added lithium methoxide. The solution was allowed to stir at ambient temperature. The reaction was quenched with water after 2 hours. The aqueous solution was extracted with ethyl acetate. The combined extract was washed with NaHCO$_3$, NH$_4$Cl, brine, dried (Na$_2$SO$_4$) and concentrated. The residue was stirred in ethanol overnight to afford the title compound as a yellow solid (0.43 g, 57%), mp 183–184° C. $^1$H-NMR (CDCl$_3$) δ 8.09–8.04 (m, 3H), 7.93 (d, J=8.3 Hz, 2H), 7.87 (s, 1H), 7.57 (d, J=15.7 Hz, 1H), 7.42 (d, J=3.9 Hz, 1H), 7.32 (d, 4.4 Hz, 1H), 7.11–7.08 (m, 1H), 6.55 (s, 1H), 6.25 (bs, 1H), 5.75 (bs, 1H), 4.25 (t, J=5.9 Hz, 2H), 3.98 (s, 3H), 3.71 (t, J=4.2 Hz, 4H), 2.92 (t, J=5.7 Hz, 2H), 2.59 (t, J=4.6 Hz, 4H). MS m/z=493 ([M+H]$^+$, 100%).

Example 93

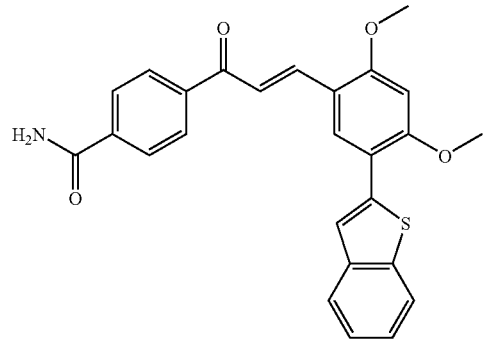

4-[3E-(5-Benzo[b]thiophen-2-yl-2,4-dimethoxy-phenyl)-acryloyl]-benzamide

To a solution of 4-acetyl-benzamide (0.3 g, 1.84 mmol) and 5-(benzo[b]thein-2yl)-2,4-dimethoxybenzaldehyde (0.55 g, 1.84 mmol) in a mixture of N,N-dimethylformamide (7 mL) and methanol (3 mL) was added lithium methoxide (0.14 g, 3.68 mmol). The reaction mixture was allowed to stir at ambient temperature for 9 hours. The resulting precipitate was collected by filtration, washed with methanol, dried in vacuo to obtain the title compound as a yellow solid (5.56 g, 68%). Alternatively, to mixture of 4-[3E-(5-benzo[b]thiophen-2-yl-2,4-dimethoxy-phenyl)-acryloyl]-benzoic acid (Ex-3, 3.0 g, 6.75 mmol), 1-(3-dimethylaminopropyl) 3-ethylcarbodiimide hydrochloride (1.81 g, 9.45 mmol), 1-hydroxybenzotriazole hydrate (1.09 g, 8.10 mmol) and ammonium chloride (1.81 g, 33.7 mmol) in N,N-dimethyl-formamide (60 mL) was added triethylamine (2.4 mL, 16.9 mmol). The reaction mixture was allowed to stir overnight at ambient temperature. Any insoluble material was removed by filtration. The filtrate was diluted with ethyl acetate to 180 mL. The solution of ethyl acetate was washed with a saturated solution of sodium bicarbonate, brine, dried over sodium sulfate and concentrated to give the title compound as a yellow solid (2.82 g, 94%), mp 240–241° C. $^1$H-NMR (DMSO-d$_6$) δ 8.37 (s, 1H), 8.19 (d, J=7.8 Hz, 2H), 8.12 (d, J=15.3 Hz, 1H), 8.04–7.91 (m, 6H), 7.83 (d, J=7.5 Hz, 1H), 7.55 (s, 1H), 7.36–7.30 (m, 2H), 6.87 (s, 1H), 4.04 (s, 3H), 4.01 (s, 3H). MS m/z=444 ([M+H]$^+$, 100%).

Example 94

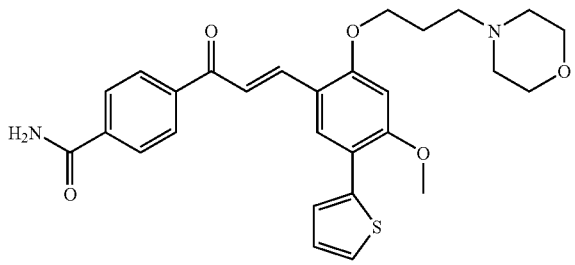

4-{3E-[4-Methoxy-2-(3-morpholin4-yl-propoxy)-5-thiophen-2-yl-phenyl]-acryloyl}-benzamide The title compound was prepared by condensing 4-Acetyl-benzamide (Ex-92A) and 4-methoxy-2-(3-morpholin-4-yl-propoxy)-5-thiophen-2-yl-benzaldehyde (Ex-66A) in a similar manner as described in Ex-92. Orange solid, mp 81–83° C. $^1$H-NMR (CDCl$_3$) δ 8.08 (m, 3H), 7.94 (d, 2H), 7.86 (s, 1H), 7.56 (d, 1H), 7.41 (d, 1H), 7.32 (d, 1H), 7.10 (m, 1H), 6.55 (s, 1H), 4.19 (t, 2H), 3.99 (s, 3H), 3.72 (t, 4H), 2.59 (t, 2H), 2.12 (t, 4H), 1.98 (quintet, 2H). MS m/z=506 ([M]$^+$, 34%), 100 (100%). 28%. Anal. calculated for C$_{28}$H$_{30}$N$_2$O$_5$S.2/5H$_2$O: C, 65.45; H, 6.04; S, 6.24; found C, 65.30; H, 6.16; S, 6.17.

Example 95

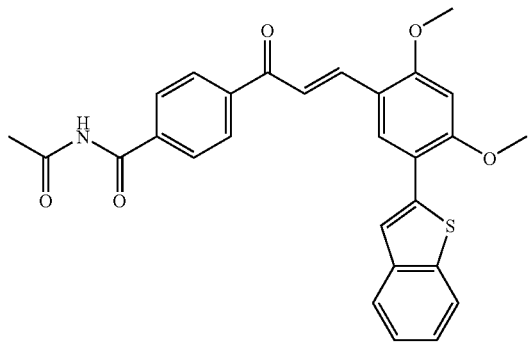

N-Acetyl-4-[3E-(5-benzo[b]thiophen-2-yl-2,4-dimethoxy-phenyl)-acryloyl]-benzamide A suspension of 4-[3E-(5-benzo[b]thiophen-2-yl-2,4-dimethoxy-phenyl)-acryloyl]-benzamide (Ex-93, 0.5 g, 1.13 mmol) in THF (15 mL) was cooled to −78° C. followed by addition of lithium bis(trimethylsilyl)amide (1.0 M in THF, 2.3 mL, 2.3 mmol). The mixture was stirred at this temperature for 1 hour and warmed up to 0° C. Acetic anhydride (0.48 mL, 6.8 mmol) was then added dropwise. After the addition was complete the reaction mixture was warmed up to ambient temperature and stirred for 2 hours. The reaction was quenched with water. The aqueous solution was extracted with ethyl acetate. The combined extract was washed with NH$_4$Cl, brine, dried and concentrated. The residue was purified by flash chromatography. Elution with 50% EtOAc/hexane gave the title compound as yellow solid (0.16 g, 29%), mp 228–229° C. $^1$H-NMR (CCDl$_3$) δ 8.52 (s, 1H), 8.15–8.10 (m, 3H), 7.96 (d, J=7.6 Hz, 2H), 7.85–7.77 (m, 2H), 7.67 (s, 1H), 7.55 (d, J=16.7 Hz, 1H), 7.34–7.29 (m, 3H), 6.58 (s, 1H), 4.05 (s, 3H), 4.01 (s, 3H), 2.65 (s, 3H). MS m/z=485 (M$^+$, 100%).

Example 96

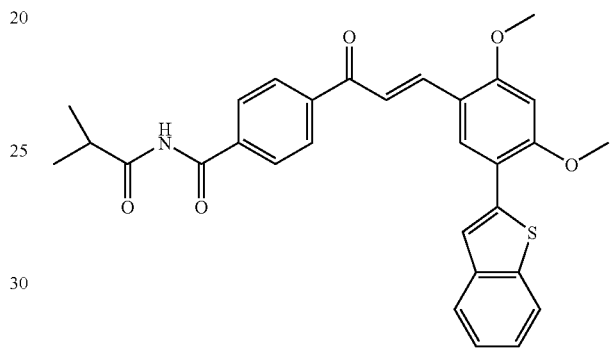

4-[3E-(5-Benzo[b]thiophen-2-yl-2,4-dimethoxy-phenyl)-acryloyl]-N-isobutyryl-benzamide The title compound was prepared in a similar manner as described in Ex-95 from -[3E-(5-benzo[b]thiophen-2-yl-2,4-dimethoxy-phenyl)-acryloyl]-benzamide (Ex-93) and isobutyric anhydride. Yellow solid, mp 208–209° C. $^1$H-NMR (CCDl$_3$) δ 8.14 (s, 1H), 8.15–8.10 (m, 3H), 7.96 (d, J=7.2 Hz, 2H), 7.85–7.77 (m, 2H), 7.67 (s, 1H), 7.56 (d, J=16.2 Hz, 1H), 7.38–7.29 (m, 3H), 6.59 (s, 1H), 4.05 (s, 3H), 4.01 (s, 3H), 3.68–3.59 (m, 1H), 1.28 (d, J=6.2 Hz, 6H). MS m/z=513 (M$^+$, 93%), 425 (100%).

Example 97

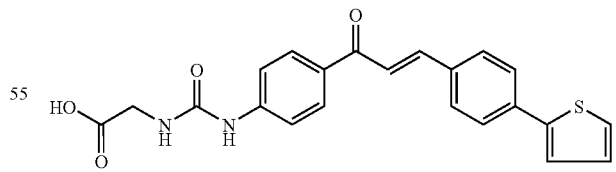

4(3E-{4-[3-(4-Thiophen-2-yl-phenyl)-acryloyl]-phenyl}-ureido)-acetic acid

A solution of (3-{4-[3-(4-thiophen-2-yl-phenyl)-acryloyl]-phenyl}-ureido)-acetic acid ethyl ester (Ex-15, 151.3 mg, 0.35 mmol) in THF:MeOH:H$_2$O (2:1:1, 6 mL) was treated with lithium monohydrate (73.2 mg, 1.74 mmol) and stirred for 4 hours. The reaction mixture was titrated with 5N HCl to a pH2. The mixture was extracted with ethyl acetate (30 mL). The organic phase was collected, dried over Na$_2$SO$_4$, and concentrated to a pure yellow solid (131.7 mg, 93%), mp 222–225° C. $^1$H-NMR (DMSO-d6) δ 9.27 (br s, 1H), 8.14 (d, 2H), 7.87 (m, 3H), 7.71 (d, 3H), 7.56 (m, 4H), 7.14 (t, 1H), 6.54 (t, 1H), 3.78 (d, 2H). MS m/z=407 ([M+H]$^+$, 88%), 306 (100%). Anal. calculated for C$_{22}$H$_{18}$N$_2$O$_4$S.1/2H$_2$O: C, 63.60; H, 4.61; S, 7.72; found C, 63.23; H, 4.70; S: 7.66.

Example 98

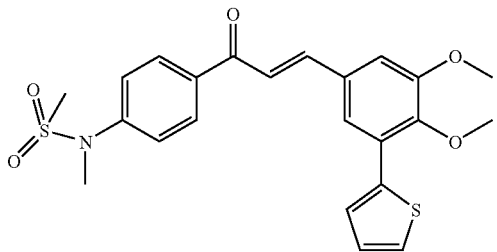

N-{4-[3E-(3,4-Dimethoxy-5-thiophen-2-yl-phenyl)-acryloyl]-phenyl}-N-methyl-methanesulfonamide A solution of N-{4-[3E-(3,4-dimethoxy-5-thiophen-2-yl-phenyl)-acryloyl]-phenyl}-methanesulfonamide (Ex-14, 90 mg, 0.20 mmol) in anhydrous DMF was treated with potassium carbonate (56.1 mg, 0.41). Methyl iodide (126.32 uL, 2.03 mmol) was added to the reaction mixture which was then refluxed for 1.5 hours under inert conditions. The reaction was diluted with water (25 mL) and extracted with diethyl ether (2×50 mL). The organic portion was dried over sodium sulfate, filtered, and concentrated to a yellow oil. The crude material was purified by silica gel chromatography (30–50% ethyl acetate/hexanes) to give 42 mg (45%) of the title compound as a yellow solid. $^1$H-NMR (CDCl$_3$) δ 8.06 (d, 2H), 7.59 (d, 1H), 7.54 (m, 4H), 7.42 (m, 2H), 7.12 (m, 2H), 3.97 (s, 3H), 3.88 (s, 3H), 3.40 (s, 3H), 2.89 (s, 3H). MS m/z=457 ([M]$^+$, 100%).

Example 99

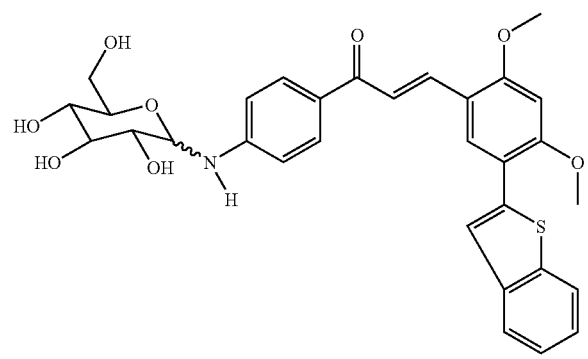

3E-(5-Benzo[b]thiophen-2-yl-2,4-dimethoxy-phenyl)-1-[4-(D-glucopyranosylamino)-phenyl]-propenone Ex-99A: D-Glucose (1.8 g, 10 mmol) and 4-aminoacetophenone (1.35 g, 10 mmol) were mixed in ethanol (50 ml), acetic acid (5 drops) was added, and the mixture was stirred at reflux for 2 hours. Water (2 ml) was added and the mixture became a homogeneous solution and was then stirred at reflux for 4 hours. Upon cooling to room temperature the precipitate was filtered out, rinsed with ethanol, and dried to give 4-(D-glucopyranosylamino)acetophenone as a white solid (1.21 g, 41%), mp 209–210° C. (dec). $^1$H-NMR (DMSO-D$_6$) δ 7.71 (d, J=8 Hz, 2H), 7.06 (d, J=8 Hz, 1H), 6.69 (d, J=8 Hz, 2H), 4.98 (d, J=4 Hz, 1H), 4.89 (d, J=7 Hz), 4.38–4.45 (m, 2H), 3.55–3.64 (m, 1H), 3.30–3.46 (m, 1H), 3.00–3.30 (m, 4H), 2.38 (s, 3H). MS m/z=297 ([M]$^+$, 15%), 148 (100%).

4-(D-Glucopyranosylamino)acetophenone (Ex-99A, 326 mg, 0.6 mmol) and (benzo[b]thien-2-yl)-2,4-dimethoxybenzaldehyde (Ex-3A, 150 mg, 0.5 mmol) were mixed in DMF (10 ml) and methanol (5 ml). Lithium methoxide (120 mg) was added, and the mixture was stirred at room temperature for 18 hours. Lithium methoxide (120 mg) was added again and the mixture was stirred overnight. Saturated sodium chloride solution (50 ml) was added and the mixture was extracted with dichloromethane. Chromatography (dichloromethane/methanol 10:1) gave an oily yellow residue as the title compound (20 mg, 6%). $^1$H-NMR (DMSO-D$_6$) δ 8.29 (s, 1H), 7.78–8.02 (m, 7H), 7.25–7.38 (m, 2H), 7.15 (d, 1H), 6.84 (s, 1H), 6.77 (d, 2H), 4.99 (d, 1H), 4.86–4.95 (m, 2H), 4.41–4.49 (m, 2H), 4.02 (s, 3H), 3.98 (s, 3H), 3.00–3.45 (m, 6H). MS m/z=578 ([M+H]$^+$, 100%).

Example 100

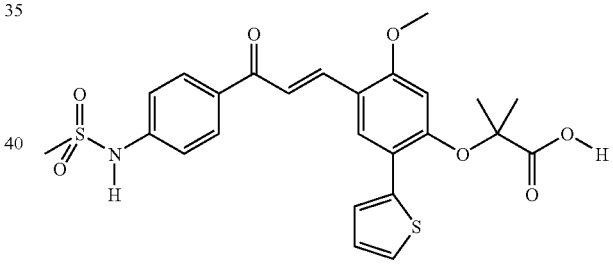

2-{4-[3-(4-Methanesulfonylamino-phenyl)-3-oxo-E-propenyl]-5-methoxy-2-thiophen-2-yl-phenoxy}-2-methyl-propionic acid Ex-100A: A solution of 4-aminoacetophenone (5.0 g, 37.0 mmol) and pyridine (3.0 mL) in anhydrous dichloromethane (300 mL) was treated with mesyl chloride (2.86 mL, 37.0 mmol). The reaction was stirred for 84 hours at room temperature under nitrogen, and then quenched with saturated NH$_4$Cl solution (100 mL). The organic phase was collected, washed with water (100 mL) and brine, dried over sodium sulfate, and concentrated over silica. The material was purified by silica gel chromatography (50% ethyl acetate/hexanes) to give 4.72 g (60%) of N-(4-acetyl-phenyl)-methanesulfonamide as a yellowish oil. $^1$H-NMR (DMSO-d6) δ 10.28 (s, 1H), 7.90 (d, 1H), 7.24 (d, 1H), 3.06 (s, 3H), 2.48 (s, 3H).

A solution of N-(4-acetyl-phenyl)-methanesulfonamide (Ex-100A, 279.6 mg, 1.31 mmol) and 2-(4-formyl-5-methoxy-2-thiophen-2-yl-phenoxy)-2-methyl-propionic acid (Ex-47D, 400 mg, 1.20 mmol) in DMF (5.25 mL) and MeOH (2.25 mL) was treated with lithium methoxide (182.2 mg, 4.8 mmol) and stirred for 5 hours at room temp. under nitrogen atmosphere. The reaction mixture was diluted with water (25 mL) which was then extracted with isopropyl acetate (2×50 mL). The aqueous portion was collected and acidified to a pH of 3 with 3N HCl. The aqueous solution was then extracted with isopropyl acetate (2×50 mL). The organic was collected, dried over sodium sulfate, and concentrated to a green solid. Attempted to recrystallize crude material from ethanol/hexanes; however, this mixture was concentrated and stirred with ethyl acetate (3 mL) to give 95.6 mg (14%) of the title compound as a yellow solid, mp 181–183° C. $^1$H-NMR (DMSO-d6) δ 10.31 (br s, 1H), 8.24 (s, 1H), 8.12 (d, 2H), 7.95 (d, 1H), 7.87 (d, 1H), 7.67 (d, 1H), 7.50 (d, 1H), 7.30 (d, 2H), 7.09 (t, 1H), 6.45 (s, 1H), 3.81 (s, 3H), 3.08 (s, 3H), 1.65 (s, 6H). MS m/z=516 ([M+H]$^+$, 100%). HRMS m/z: calc. 516.1150, found 516.1165.

Example 101

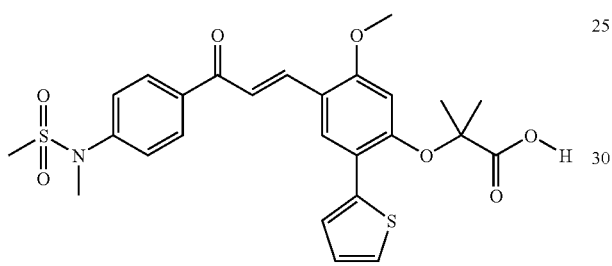

2-(4-{3-[4-(Methanesulfonyl-methyl-amino)-phenyl]-3-oxo-E-propenyl}-5-methoxy-2-thiophen-2-yl-phenoxy)-2-methyl-propionic acid Ex-101A: A solution of N-(4-acetyl-phenyl)-methanesulfonamide (Ex-100A, 2.0 g, 9.4 mmol) in anhydrous DMF (300 mL) was treated with potassium carbonate (2.59 g, 18.8 mmol), followed by the addition of methyl iodide (5.85 mL, 94 mmol). The reaction mixture refluxed for two hours and was then treated with more methyl iodide (5.85 mL, 94 mmol). The reaction refluxed for another two hours, and reaction completeness was confirmed by HPLC analysis. The reaction was quenched with water (100 mL) and extracted with ethyl acetate (2×100 mL). The organic phase was collected, dried over sodium sulfate, and concentrated to a clear oil with residual DMF. Water (25 mL) was added to precipitate a white solid. The white solid was then filtered and dried by vacuum oven at 20° C. (−20 mm Hg) to give 1.37 g (64%) of N-(4-acetyl-phenyl)-N-methyl-methanesulfonamide. $^1$H-NMR (CDCl$_3$) δ 7.88 (d, 2H), 7.48 (d, 2H), 3.38 (s, 3H), 2.86 (s, 3H), 2.60 (s, 3H). HRMS m/z: calc. 530.1307, found 530.1313.

A solution of N-(4-acetyl-phenyl)-N-methyl-methanesulfonamide (Ex-101A, 298 mg, 1.31 mmol) and 2-(4-formyl-5-methoxy-2-thiophen-2-yl-phenoxy)-2-methyl-propionic acid (Ex-47D, 400 mg, 1.20 mmol) in DMF (5.25 mL) and MeOH (2.25 mL) was treated with lithium methoxide (182 mg, 4.8 mmol) and stirred for 6 hours at room temperature under nitrogen atmosphere. The reaction mixture was diluted with water (25 mL) which was then extracted with isopropyl acetate (2×50 mL). The aqueous portion was collected and acidified to a pH of 3 with 3N HCl. The aqueous solution was then extracted with isopropyl acetate (2×50 mL).

The organic was collected, dried over sodium sulfate, and concentrated to a yellow foam. The crude material was purified by silica gel chromatography (50% ethyl acetate/hexanes; 10% MeOH/CH$_2$CL$_2$) to give 293 mg (42%) of the title compound as a yellow solid, mp 197–200° C. $^1$H-NMR (DMSO-d6) δ 8.20 (s, 1H), 8.12 (d, 2H), 8.00 (d, 1H), 7.83 (d, 1H), 7.66 (dd, J=2, 2 Hz, 1H), 7.53 (d, 2H), 7.44 (d, 1H), 7.06 (dd, J=2, 4 Hz, 1H), 6.78 (s, 1H), 3.82 (s, 3H), 3.28 (s, 3H), 2.98 (s, 3H), 1.56 (s, 3H). MS m/z=530 ([M+H]$^+$, 100%).

Example 102

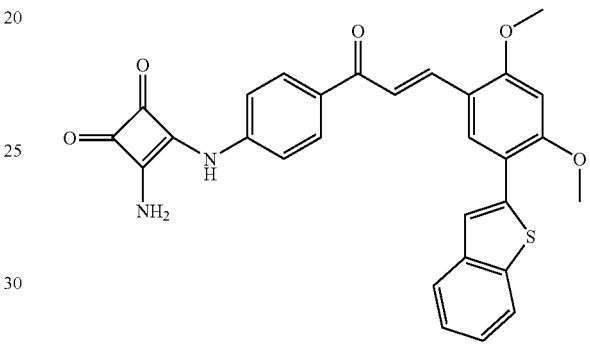

3-Amino-4-{4-[3E-(5-benzo[b]thiophen-2-yl-2,4-dimethoxy-phenyl)-acryloyl]-phenylamino}-cyclobut-3-ene-1,2-dione Ex-102A: To a solution of 2.7 g (20 mmol) of 4'-aminoacetophenone in 90 mL of ethanol, 4.5 g (20 mmol) of 3,4-dibutoxy-3-cyclobutene-1,2-dione (Aldrich) was added. The mixture was then heated to reflux overnight. A light yellow precipitate formed. To the reaction mixture, 20 mL (40 mmol) of ammonia (2.0 M in ethanol) was added, and the resultant mixture was stirred at room temperature for 2 hr. The light yellow solid was filtered and washed with ethanol to give 2.4 g (52%) of 3-(4-acetyl-phenylamino)-4-amino-cyclobut-3-ene-1,2-dione. $^1$H-NMR (DMSO-d$_6$) δ 9.99 (br, 1H), 7.90 (d, J=8 Hz, 2H), 7.50 (d, J=8 Hz, 2H), 4.31 (br, 2H), 2.48 (s, 3H). HMRS (EI) calcd. for C$_{12}$H$_{10}$N$_2$O$_3$: 230.0691; found: 230.0691.

3-(4-Acetyl-phenylamino)-4-amino-cyclobut-3-ene-1,2-dione (Ex-102A, 0.46 g, 2 mmol), and 5-(benzo[b]thien-2-yl)-2,4-dimethoxybenzaldehyde (Ex-3A, 0.596 g, 2 mmol) were dissolved in DMF (10 mL) under nitrogen, and 4.0 ml (4 mmol) of LiOMe (1.0 M in MeOH) was added. The mixture was stirred under nitrogen at room temperature overnight. The reaction mixture was poured into ice-water, acidified to pH1 with 3N HCl, extracted with dichloromethane. The combined organic phase was then washed with brine and water, dried over MgSO$_4$, column chromatography (5% MeOH in CH$_2$Cl$_2$) to give 57 mg (5.4%) title compound as a yellow solid, mp>260° C. $^1$H-NMR (DMSO-d$_6$) δ 10.08 (s, 1H), 8.36 (s, 1H), 8.18 (d, J=8 Hz, 2H), 8.03 (d, J=15 Hz, 1H), 7.82–7.95 (m, 4H), 7.57 (d, J=8 Hz, 2H), 7.27–7.37 (m, 2H), 6.85 (s, 1H), 4.02 (s, 3H), 3.99 (s, 3H), 3.26 (s, 2H). MS m/z=511[M+H]+, (20%), 416 (100%). HRMS (ES+) Calcd. for $C_{29}H_{22}N_2O_5S$: 511.1327. Found: 511.1326.

Example 103

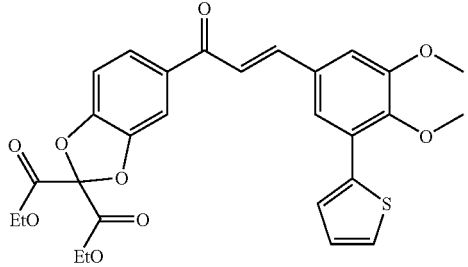

5-[3E-(3,4-Dimethoxy-5-thiophen-2-yl-phenyl)-acryloyl]-benzo[1,3]dioxole-2,2-dicarboxylic acid, diethyl ester Ex-103A: To a solution of KOH (1.25 M, 200 mL) were added 3,4-dihydroxy-acetophenone (2.0 g, 13.1 mmol) and cetyltrimethylamonium chloride (25% in water, 17 mL, 13.1 mmol). The suspension was stirred at ambient temperature for 10 min followed by the addition of a suspension of 3,4-dimethoxy-5-thiophen-2yl-benzaldehyde (Ex-6A, 3.9 g, 15.8 mmol) in ethanol (10 mL). The reaction mixture was allowed to stir at ambient temperature overnight and was acidified with concentrated HCl to pH 3, saturated with NaCl, extracted with $CH_2Cl_2$. The combined solution of $CH_2Cl_2$ was washed with brine, dried ($Na_2SO_4$) and concentrated under reduced pressure. The crude product was purified by flash chromatography. Elution with 50% EtOAc/hexane gave 1-(3,4-dihydroxy-phenyl)-3E-(3,4-dimethoxy-5-thiophen-2-yl-phenyl)-propenone as a yellow oil. $^1H$ NMR (DMSO-$d_6$) δ 7.88 (s, 1H), 7.83–7.81 (m, 2H), 7.76 (d, J=2.4 Hz, 1H), 7.68–7.74 (m, 2H), 7.61–7.57 (m, 1H), 7.51 (s, 1H), 7.50 (d, J=5.2 Hz, 1H), 7.13 (t, J=4.5 Hz, 1H), 6.85 (d, J=8.7 Hz, 1H), 3.92 (s, 3H), 3.77 (s, 3H). MS m/z=382 (M+, 100%).

1-(3,4-Dihydroxy-phenyl)-3E-(3,4-dimethoxy-5-thiophen-2-yl-phenyl)-propenone (106 mg), diethyl dibromomalonate (380 mg) and potassium carbonate (500 mg) was mixed in acetone (15 ml) and the mixture was stirred at room temperature over a weekend. It was poured into ethyl acetate (100 ml) and washed with water (100 ml). The organic layer was dried and evaporated. Chromatography (hexanes/ethyl acetate 4:1) gave an oily residue. Crystallization from hexanes and dichloromethane gave the title compound as a slightly yellow solid (70 mg), mp 125–126° C. $^1H$-NMR (DMSO-d6) δ 7.76 (d, J=15 Hz, 1H), 7.73 (dd, J=2, 7 Hz, 1H), 7.64 (d, J=2 Hz, 1H), 7.54 (d, J=1 Hz, 1H), 7.53 (d, J=2 Hz, 1H), 7.39 (d, J=5 Hz, 1H), 7.38 (d, J=15 Hz, 1H), 7.11 (dd, J=2, 5 Hz, 1H), 7.08 (d, J=1 Hz, 1H), 7.05 (d, J=7 Hz, 1H), 3.97 (s, 3H), 3.87 (s, 3H), 4.41 (quad, J=7 Hz, 4H), 1.30 (t, J=7 Hz, 6H).

Example 104

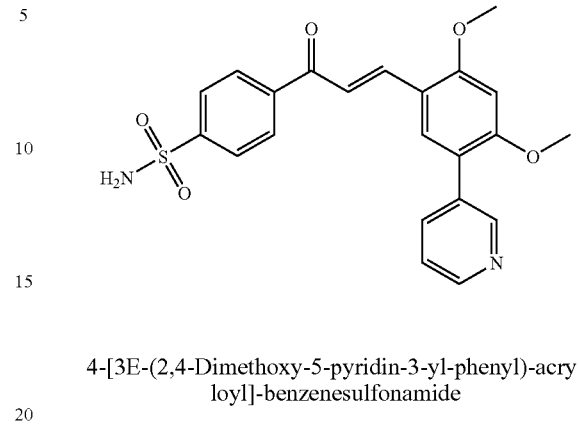

4-[3E-(2,4-Dimethoxy-5-pyridin-3-yl-phenyl)-acryloyl]-benzenesulfonamide

Ex-104A: 2,4-Dimethoxy-5-pyridin-3-yl-benzaldehyde was prepared in a similar manner as described in Ex-3A from pyridine-3-boronic acid and 5-bromo-2,4-dimethoxy-benzaldehyde, 68% yield. $^1H$-NMR (CDCl$_3$) δ 10.33 (s, 1H), 8.71 (d, J=1 Hz, 1H), 8.51–8.53 (m, 1H), 7.81 (s, 1H), 7.74–7.78 (m, 1H), 7.27–7.31 (m, 1H), 6.52 (s, 1H), 3.99 (s, 3H), 3.91 (s, 3H). HMRS (EI) calcd. for $C_{14}H_{13}NO_3$: 243.0895; found: 243.0888.

The title compound was prepared by condensing 2,4-dimethoxy-5-pyridin-3-yl-benzaldehyde (Ex-104A) and 4-acetyl-benzenesulfonamide (Ex-26A) in a similar manner as described in Ex-22. Yellow solid, 51% yield, mp 253–255° C. $^1H$-NMR (DMSO-d6) δ 8.69 (d, J=1 Hz, 1H), 8.50 (d, J=4 Hz, 1H), 8.25 (d, J=9 Hz, 2H), 8.08 (d, J=15 Hz, 1H), 8.02 (s, 1H), 7.84–7.94 (m, 4H), 7.51 (s, 2H), 7.40–7.44 (m, 1H), 6.82 (s, 1H), 3.98 (s, 3H), 3.88 (s, 3H). MS m/z=424([M]+, 45%), 393 (100%). HMRS (EI) calcd. for $C_{22}H_{20}N_2O_5S$: 424.1093; found 424.1100.

Example 105

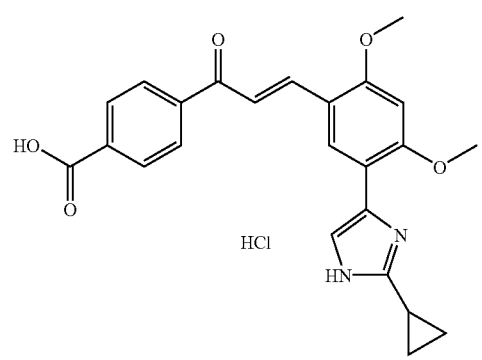

4-{3E-[5-(2-Cyclopropyl-1H-imidazol-4-yl)-2,4-dimethoxy-phenyl]-acryloyl}-benzoic acid, hydrochloride Ex-105A: A solution of 2-bromo-1-(3,4-dimethoxy-phenyl)-ethanone (0.3 g, 1.16 mmol), cyclopropanecarboxamidine (0.14 g, 1.16 mmol) and sodium hydroxide (0.18 g, 4.5 mmol) in ethanol was refluxed overnight. The solvent was removed under reduced pressure, the residue taken up to water. The aqueous solution was then extracted with dichloromethane which was subsequently washed with brine, dried over sodium bicarbonate and concentrated. The crude product was purified by flash chromatography. Elution with ethyl acetate (50%, v/v, in hexane) then methanol (10%, v/v in dichloromethane) afforded 2-cyclopropyl-4-(2,4-dimethoxy-phenyl)-1H-imidazole as white solid (0.1 5 g, 53%): $^1$HNMR (CDCl$_3$) δ 9.50 (bs, 1H), 7.63 (s, 1H), 7.20 (s, 1H), 6.57–6.53 (m, 2H), 3.93 (s, 3H), 3.03 (s, 3H), 1.97–1.93 (m, 1H), 1.00–0.94 (m, 4H). MS m/z=245 ([M+H]$^+$, 100%).

Ex-105B: To a solution of 2-cyclopropyl-4-(2,4-dimethoxy-phenyl)-1H-imidazole (0.51 g, 2.09 mmol) was added dichloromethyl methyl ether (0.28 mL, 3.13 mmol) followed by addition of titanium tetrachloride (1.0M in dichloromethane, 8.4 mL, 8.4 mmol) dropwise at 0° C. The solution was allowed to warm up to ambient temperature and stir for 4.5 hours. The reaction mixture was then poured into ice. The aqueous layer was adjusted to pH 12 and extracted with dichloromethane. The combined solution of dichloromethane was washed with saturated solution of sodium bicarbonate, brine, dried over sodium sulfate and concentrated to afford 5-(2-cyclopropyl-1H-imidazol-4-yl)-2,4-dimethoxy-benzaldehyde which was used without further purification. $^1$H NMR (DMSO-d$_6$) δ 13.95 (bs, 1H), 10.22 (s, 1H), 8.09 (s, 1H), 7.70 (s, 1H), 6.88 (s, 1H), 4.04 (s, 3H), 4.00 (s, 3H), 2.25 (m, 1H), 1.20 (m, 4H). MS m/z=245 ([M+H]$^+$, 100%).

The title compound was prepared by condensing 5-(2-cyclopropyl-1H-imidazol-4-yl)-2,4-dimethoxy-benzaldehyde (Ex-105B) and 4-acetylbenzoic acid in a similar manner as described in Ex-3. Yellow solid, m.p.>240° C. $^1$H NMR (DMSO-d$_6$) δ 13.31 (bs, 1H), 8.29 (d, J=8.9 Hz, 2H), 8.06–8.01 (m, 3H), 7.91 (s, 1H), 7.67 (s, 1H), 6.83 (s, 1H), 4.02 (s, 3H), 3.98 (s, 3H), 1.29–1.22 (m, 4H). MS m/z=419 ([M+H]$^+$, 100%).

Example 106

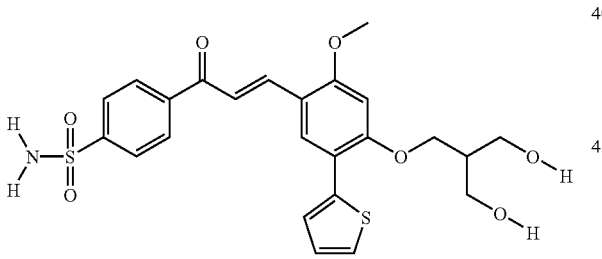

4-{3E-[4-(3-Hydroxy-2-hydroxymethyl-propoxy)-2-methoxy-5-thiophen-2-yl-phenyl]-acryloyl}-benzenesulfonamide The title compound was prepared by condensing 4-(3-hydroxy-2-hydroxymethyl-propoxy)-2-methoxy-5-thiophen-2-yl-benzaldehyde (Ex-50C) and 4-acetyl-benzenesulfonamide (Ex-26A) in a similar manner as described in Ex-22. Yellow solid, 72% yield, mp 191–192° C. $^1$H-NMR (300 MHz, DMSO-d$_6$) δ 8.29–8.32 (m, 3H), 8.09 (d, 1H, J=16.0 Hz), 7.99 (d, 2H, J=8.1 Hz), 7.92 (d, 1H, J=16.0 Hz), 7.70 (d, 1H, J=3.3 Hz), 7.53–7.56 (m, 3H), 7.14 (dd, 1H, J=5.4, 3.3 Hz), 6.87 (s, 1H), 4.61 (t, 2H, J=5.1 Hz), 4.28 (d, 2H, J=5.1 Hz), 4.00 (s, 3H), 3.60–3.67 (m, 4H), 2.11–2.15 (m, 1H). MS (ESI) m/z=504 ([M+H]$^+$, 100%). Anal. Calcd. for C$_{24}$H$_{25}$NO$_7$S$_2$·½H$_2$O: C, 56.23; H, 5.11; N, 2.73; S, 12.51. Found: C, 56.32; H, 5.06; N, 2.83; S, 12.55.

Example 107

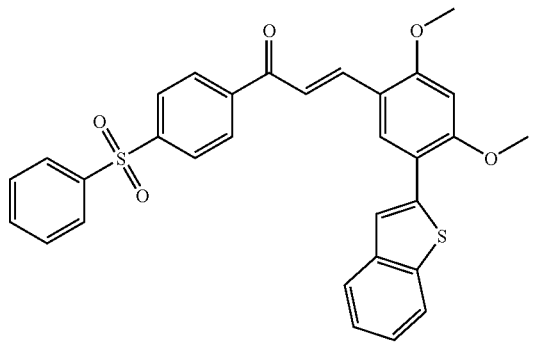

1-(4-Benzenesulfonyl-phenyl)-3E-(5-benzo[b]thiophen-2-yl-2,4-dimethoxy-phenyl)-propenone The title compound was prepared by condensing 1-(4-benzenesulfonyl-phenyl)-ethanone with 5-(benzo[b]thien-2-yl)-2,4-dimethoxybenzaldehyde (Ex-3A) in a similar manner as described in Ex-3, 5% yield. The product was purified using column chromatography. Yellow solid, mp 127–128° C. $^1$H-NMR (CDCl$_3$) δ 8.05–8.11 (m, 5H), 7.97 (d, J=7 Hz, 2H), 7.91 (s, 1H), 7.76–7.84 (m, 2H), 7.66 (s, 1H), 7.46–7.60 (m, 4H), 7.26–7.37 (m, 2H), 6.56 (s, 1H), 4.03 (s, 3H), 3.99 (s, 3H). MS m/z=540 ([M]$^+$, 100%). HRMS (EI) Calcd. for C$_{13}$H$_{24}$O$_5$S$_2$: 540.1605. Found: 540.1074.

Example 108

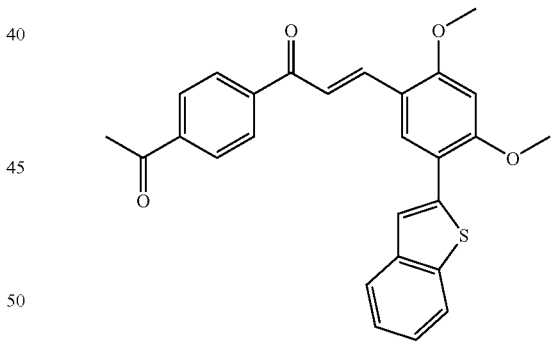

1-(4-Acetyl-phenyl)-3E-(5-benzo[b]thiophen-2-yl-2,4-dimethoxy-phenyl)-propenone

The title compound was prepared by condensing 1-(4-acetyl-phenyl)-ethanone with 5-(benzo[b]thien-2-yl)-2,4-dimethoxybenzaldehyde (Ex-3A) in a similar manner as described in Ex-3. The product was purified using column chromatography. Yellow solid, 2% yield, mp 165–167° C. $^1$H-NMR (CDCl$_3$) δ 8.06–8.12 (m, 5H), 7.92 (s, 1H), 7.75–7.82 (m, 2H), 7.65 (s, 1H), 7.55 (d, J=15 Hz, 1H), 7.28–7.33 (m, 2H), 6.56 (s, 1H), 4.01 (s, 3H), 3.98 (s, 3H). MS m/z=442 ([M]$^+$, 100%). HMRS (EI) calcd. for C$_{27}$H$_{22}$O$_4$S: 442.1239; found: 442.1229.

Example 109

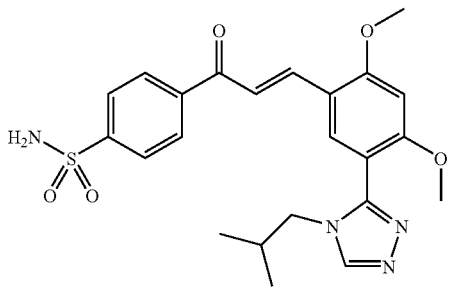

4-{3E-[5-(4-Isobutyl-4H-[1,2,4]triazol-3-yl)-2,4-dimethoxy-phenyl]-acryloyl}-benzenesulfonamide Ex-109A: A solution of 2,4-dimethoxy-benzoic acid methyl ester (4.24 g, 21.6 mmol) and hydrazine (3.4 mL, 108.1 mmol) in methanol (50 mL) was refluxed overnight. Solvent was removed under reduced pressure. The residue was re-dissolved in ethyl acetate. The solution of ethyl acetate was washed with saturated solution of sodium bicarbonate and brine, dried over sodium carbonate and concentrated to afford 2,4-dimethoxy-benzoic acid hydrazide (3.31 g, 78%) as a white solid: $^1$H NMR (CDCl$_3$) δ 8.77 (bs, 1H), 8.15 (d, J=8.8 Hz, 1H), 6.58 (dd, J=8.8, 2.2 Hz, 1H), 6.46 (d, J=2.2 Hz, 1H), 4.10 (bs, 2H), 3.91 (s, 3H), 3.83 (s, 3H).

Ex-109B: A solution of 2,4-dimethoxy-benzoic acid hydrazide (Ex-109A, 1.0 g, 5.1 mmol) and isobutyl-isothiocyanate (0.70 g, 6.1 mmol) in ethanol (30 mL) was refluxed for 8 hours. The precipitate was filtered, washed with ethanol, dried in vacuo to afford 1-(2,4-dimethoxy-benzoyl) amino-3-isobutyl-thiourea (1.43 g). Additional product (0.1 g, 96% overall) was obtained by concentrating the mother liquid. $^1$H NMR (CDCl$_3$) δ 10.71 (bs, 1H), 9.23 (bs, 1H), 8.03 (d, J=8.6 Hz, 1H), 6.98 (bs, 1H), 6.59 (dd, J=8.6, 2.6 Hz, 1H), 6.51 (d, J=2.6 Hz, 1H), 4.02 (s, 3H), 3.86 (s, 3H), 3.41 (dd, J=6.4, 6.6 Hz, 2H), 1.96–1.87 (m, 1H), 0.91 (d, J=6.5 Hz, 6H).

Ex-109C: A solution of 1-(2,4-dimethoxy-benzoyl) amino-3-isobutyl-thiourea (Ex-109B, 0.5 g, 1.61 mmol) and sodium hydroxide (0.999M, 4.8 mL, 4.8 mmol) in ethanol (30 mL) was refluxed for one day. The solvent was removed under reduced pressure and the residue redissolved in ethyl acetate. The solution of ethyl acetate was washed with water and brine, dried over sodium sulfate, and concentrated to give 5-(2,4-dimethoxy-phenyl)-4-isobutyl-4H-[1,2,4]triazole-3-thiol (0.1 g). Additional product (0.36 g, 98% overall) was obtained by extracting the water wash with dichloromethane and a mixture of isopropyl alcohol (33%, v/v, in dichloromethane). $^1$H NMR (CDCl$_3$) δ 10.82 (bs, 1H), 7.24 (d, J=8.1 Hz, 1H), 6.56 (dd, J=8.1, 2.4 Hz, 1H), 6.51 (d, J=2.4 Hz, 1H), 3.85 (s, 3H), 3.77 (s, 3H), 3.72 (d, J=6.7 Hz, 2H), 2.17–2.08 (m, 1H), 0.70 (d, J=6.7 Hz, 6H).

Ex-109D: To a solution of 5-(2,4-dimethoxy-phenyl)-4-isobutyl-4H-[1,2,4]triazole-3-thiol (Ex-109C, 0.1 g, 0.34 mmol) in ethanol (10 mL) was added wet Raney Ni (0.27 g, 4.6 mmol). The suspension of ethanol was refluxed overnight and then passed through a bed of Hyflo Super Gel and diatomaceous earth. The filtrate was concentrated to afford 3-(2,4-dimethoxy-phenyl)-4-isobutyl-4H-[1,2,4]triazole (0.09 g, 100%) as a white solid: $^1$H NMR (CDCl$_3$) δ 8.15 (s, 1H), 7.34 (d, J=7.8 Hz, 1H), 6.57 (dd, J=7.8, 2.3 Hz, 1H), 6.51 (d, J=2.3 Hz, 1H), 3.85 (s, 3H), 3.75 (s, 3H), 3.62 (d, J=7.5 Hz, 2H), 1.89–1.80 (m, 1H), 0.76 (d, J=6.6 Hz, 6H).

Ex-109E: To a solution of 3-(2,4-dimethoxy-phenyl)-4-isobutyl-4H-[1,2,4]triazole (Ex-109D, 0.78 g, 2.98 mmol) was added dichloromethyl methyl ether (0.4 mL, 4.48 mmol) followed by addition of titanium tetrachloride (1.0M in dichloromethane, 9.0 mL, 9.0 mmol) over 10 min at 0° C. The reaction mixture was allowed to stir at 0° C. for 30 min and ambient temperature overnight. The reaction mixture was poured into ice. The aqueous solution was extracted with dichloromethane and isopropyl alcohol (33%, v/v, in dichloromethane). The combined dichloromethane and isopropyl alcohol were washed with brine, dried over sodium sulfate and concentrated. The aqueous solution was treated with sodium hydroxide to pH 12 and extracted again with isopropyl alcohol (33%, v/v, in dichloromethane) to give additional product. The crude product was purified by flash chromatography. Elution with methanol (10%, v/v, in dichloromethane) afford 5-(4-isobutyl-4H-[1,2,4]triazol-3-yl)-2,4-dimethoxy-benzaldehyde (0.24 g, 28%): $^1$H NMR (CDCl$_3$) δ 10.30 (s, 1H), 8.17 (s, 1H), 7.90 (s, 1H), 6.51 (s, 1H), 4.00 (s, 3H), 3.87 (s, 3H), 3.58 (d, J=7.2 Hz, 2H), 1.91–1.80 (m, 1H), 0.77 (d, J=6.5 Hz, 6H).

To a solution of 4-acetyl-benzenesulfonamide (Ex-26A, 0.12 g, 0.62 mmol) and 5-(4-isobutyl-4H-[1,2,4]triazol-3-yl)-2,4-dimethoxy-benzaldehyde (Ex-109E, 0.18 g, 0.62 mmol) in N,N-dimethylformamide (9 mL) was added lithium methoxide (1.0M in methanol, 2.4 mL, 2.4 mmol). The solution was allowed to stir overnight. The reaction was quenched with water. The aqueous solution was washed ethyl acetate, acidified to pH 5, extracted with dichloromethane, isopropyl alcohol (33%, v/v, in dichloromethane). The combined dichloromethane and isopropyl alcohol was washed with brine, dried over sodium sulfate and concentrated. The crude product was then stirred in ethanol (50%, v/v, in acetone) to give the title compound as a light yellow solid: m.p.>240° C. $^1$H NMR (DMSO-d$_6$) δ 8.60 (s, 1H), 8.26 (d, J=8.1 Hz, 2H), 8.06 (d, J=15.3 Hz, 1H), 8.07 (s, 1H), 7.91 (d, J=8.1 Hz, 2H), 7.84 (d, J=15.3 Hz, 1H), 7.50 (s, 1H), 6.84 (s, 1H), 4.01 (s, 3H), 3.87 (s, 3H), 3.61 (d, J=7.3 Hz, 2H), 1.81–1.74 (m, 1H), 0.67 (d, J=16.7 Hz, 6H). MS m/z=471 ([M+H]$^+$, 100%).

Example 110

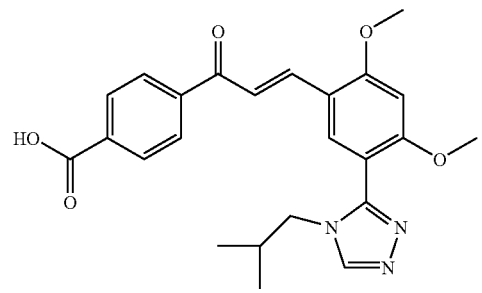

4-{3E-[5-(4-Isobutyl-4H-[1,2,4]triazol-3-yl)-2,4-dimethoxy-phenyl]-acryloyl}-benzoic acid To a solution of 4-acetyl-benzoic acid (0.12 g, 0.75 mmol) and 5-(4-isobutyl-4H-[1,2,4]triazol-3-yl)-2,4-dimethoxy-benzaldehyde (Ex-109E, 0.24 g, 0.83 mmol) in N,N-dimethylformamide (6 mL) was added lithium methoxide (1.0M in methanol, 3.0 mL, 3.0 mmol). The solution was allowed to stir overnight and additional lithium methoxide (0.11 g, 2.8 mmol). The reaction was quenched with water after 20 hours. The aqueous solution was washed ethyl acetate, acidified to pH 4. The precipitate was filtered, washed with ethanol and dried in vacuo to afford the title compound as a light yellow solid: m.p.>240° C. (dec.). $^1$H NMR (DMSO-d$_6$) δ 8.59 (s, 1H), 8.18 (d, J=7.9 Hz, 2H), 8.07 (s, 1H), 8.04–8.01 (m, 3H), 7.85 (d, J=15.7 Hz, 1H), 6.84 (s, 1H), 4.06 (s, 3H), 3.92 (s, 3H), 3.66 (d, J=7.2 Hz, 2H), 1.87–1.74 (m, 1H), 0.72 (d, J=6.7 Hz, 6H). MS m/z=436 ([M+H]+, 100%).

Example 111

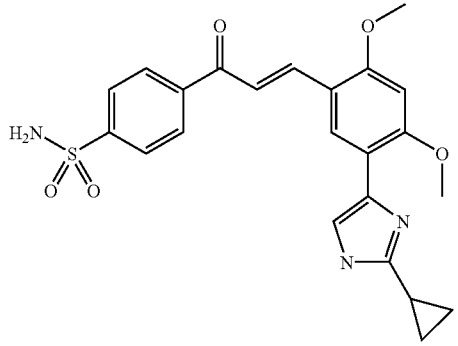

4-{3E-[5-(2-Cyclopropyl-1H-imidazol-4-yl)-2,4-dimethoxy-phenyl]-acryloyl}-benzenesulfonamide To a solution of 4-acetyl-benzenesulfonamide (Ex-26A, 0.12 g, 0.59 mmol) and 5-(2-cyclopropyl-1H-imidazol-4-yl)-2,4-dimethoxy-benzaldehyde (Ex-105B, 0.16 g, 0.59 mmol) in N,N-dimethylformamide (16 mL) was added lithium methoxide (1.0M in methanol, 2.4 mL, 2.4 mmol). The reaction mixture was allowed to stir for 18 hours at ambient temperature. The reaction was quenched with water. The aqueous solution was extracted with dichloromethane. The combined dichloromethane was concentrated. The crude product was purified by flash chromatography. Elution with methanol (10%, v/v, in dichloromethane) gave the title compound as red solid: m.p. 156–160° C. $^1$H NMR (DMSO-d$_6$) δ 11.65 (bs, 1H), 8.32 (s, 1H), 8.19 (d, J=9.0 Hz, 2H), 8.00 (d, J=15.7 Hz, 1H), 7.95 (d, J=9.0 Hz, 2H), 7.62–7.52 (m, 2H), 7.24 (bs, 1H), 6.73 (s, 1H), 3.96 (s, 3H), 3.94 (s, 3H), 1.98–1.94 (m, 1H), 0.88–0.85 (m 4H). MS m/z=454 ([M+H]+, 100%).

Example 112

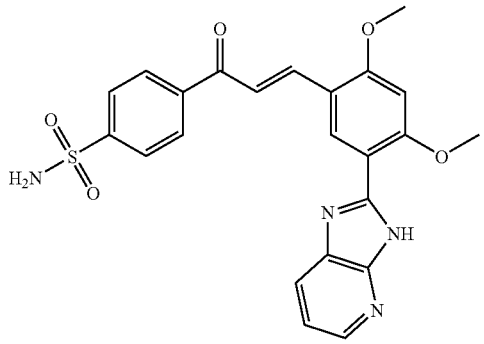

4-{3E-[5-(3H-Imidazo[4,5-b]pyridin-2-yl)-2,4-dimethoxy-phenyl]-acryloyl}-benzenesulfonamide The title compound was prepared by condensing 5-(3H-imidazo[4,5-b]pyridin-2-yl)-2,4-dimethoxy-benzaldehyde (Ex-76A) with 4-acetyl-benzenesulfonamide (Ex-26A) in a similar manner as described in Ex-22. Yellow solid, 26% yield, mp>260° C. $^1$H-NMR (DMSO-d6) δ 8.73 (s, 1H), 8.31 (dd, J=1, 4 Hz, 1H), 8.26 (d, J=8 Hz, 2H), 8.05 (d, J=16 Hz, 1H), 7.89–7.97 (m, 3H), 7.82 (d, J=16 Hz, 1H), 7.17–7.21 (m, 1H), 6.89 (s, 1H), 4.09 (s, 3H), 4.03 (s, 3H). MS m/z=465([M+H]+, 65%), 256 (100%). HRMS (ES+) Calcd. for C$_{23}$H$_{20}$N$_4$O$_5$S: 465.1232. Found: 465.1240.

Example 113

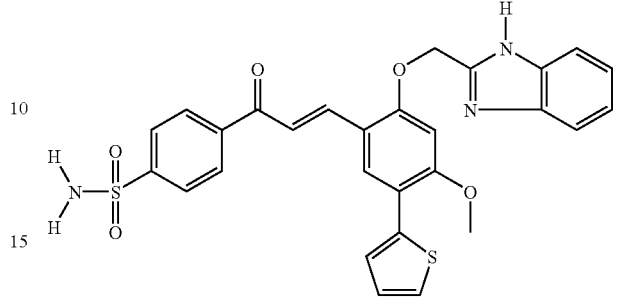

4-{3E-[2-(1H-Benzoimidazol-2-ylmethoxy)-4-methoxy-5-thiophen-2-yl-phenyl]-acryloyl}-benzenesulfonamide Ex-113A: 2-(1H-Benzoimidazol-2-ylmethoxy)-4-methoxy-5-thiophen-2-yl-benzaldehyde was prepared in a similar manner as described in Ex-29C. Off-white solid, 67% yield, mp 230° C. (dec). $^1$H-NMR (300 MHz, DMSO-d$_6$) □ 10.44 (s, 1H), 8.00 (s, 1H), 7.79–7.84 (m, 2H), 7.49–7.57 (m, 4H), 7.16 (s, 1H), 7.12 (dd, 1H, J=5.4, 3.6 Hz), 5.91 (s, 2H), 4.07 (s, 3H). MS (ESI) m/z=365 ([M+H]+, 100%). Anal. Calcd. for C$_{20}$H$_{17}$ClN$_2$O$_3$S.⅓H$_2$O: C, 59.04; H, 4.38; N, 6.88; S, 7.88. Found: C, 59.07; H, 4.25; N, 6.85; S, 7.77.

The title compound was prepared by condensing 2-(1H-benzoimidazol-2-ylmethoxy)-4-methoxy-5-thiophen-2-yl-benzaldehyde (Ex-113A) and 4-acetyl-benzenesulfonamide (Ex-26A) in a similar manner as described in Ex-22. Light orange solid, 56% yield, mp 235–237° C. (dec). $^1$H-NMR (300 MHz, DMSO-d$_6$) δ 8.27 (s, 1H), 8.19 (d, 2H, J=8.4 Hz), 8.11 (d, 1H, J=15.4 Hz), 7.98 (d, 1H, J=15.4 Hz), 7.89 (d, 2H, J=8.4 Hz), 7.66–7.70 (m, 3H), 7.53–7.55 (m, 3H), 7.22–7.27 (m, 2H), 7.12–7.15 (m, 2H), 5.59 (s, 2H), 4.01 (s, 3H). MS (ESI) m/z=546 ([M+H]+, 100%). Anal. Calcd. for C$_{28}$H$_{23}$N$_3$O$_5$S$_2$: C, 61.64; H, 4.25; N, 7.70; S, 11.75. Found: C, 61.49; H, 4.47; N, 7.74; S, 11.58.

Example 114

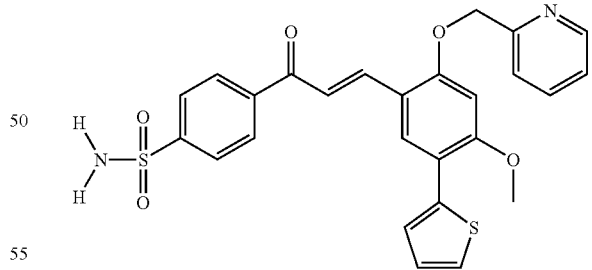

4-{3E-[4-Methoxy-2-(pyridin-2-ylmethoxy)-5-thiophen-2-yl-phenyl]-acryloyl}-benzenesulfonamide Ex-114A: 4-Methoxy-2-(pyridin-2-ylmethoxy)-5-thiophen-2-yl-benzaldehyde was prepared in a similar manner as described in Ex-29C. Yellow solid, 93% yield, mp 93–94° C. $^1$H-NMR (300 MHz, CDCl$_3$) δ 10.49 (s, 1H), 8.62 (d, 1H, J=5.1 Hz), 8.13 (s, 1H), 7.77 (dt, 1H, J=7.5, 1.5 Hz), 7.58 (d, 1H, J=7.5 Hz), 7.44 (dd, 1H, J=3.6, 1.5 Hz), 7.28–7.31 (m, 2H), 7.07 (dd, 1H, J=5.4, 3.6 Hz), 6.64 (s, 1H), 5.39 (s, 2H), 3.94 (s, 3H). MS (ESI) m/z=326 ([M+H]$^+$, 100%). Anal. Calcd. for $C_{18}H_{15}NO_3S$: C, 66.44; H, 4.65; N, 4.30; S, 9.85. Found: C, 66.43; H, 4.72; N, 4.37; S, 9.81.

The title compound was prepared by condensing 4-methoxy-2-(pyridin-2-ylmethoxy)-5-thiophen-2-yl-benzaldehyde (Ex-114A) and 4-acetyl-benzenesulfonamide (Ex-26A) in a similar manner as described in Ex-22. Yellow solid, 90% yield, mp 188–189° C. $^1$H-NMR (300 MHz, DMSO-d$_6$) δ 8.66 (d, 1H, J=3.6 Hz), 8.28 (s, 1H), 8.21 (d, 2H, J=7.8 Hz), 8.11 (d, 1H, J=15.4 Hz), 7.89–7.99 (m, 4H), 7.57–7.68 (m, 4H), 7.53 (dd, 1H, J=5.4, 1.5 Hz), 7.41–7.45 (m, 1H), 7.13 (dd, 1H, J=5.4, 3.6 Hz), 7.02 (s, 1H), 5.45 (s, 2H), 3.99 (s, 3H). MS (ESI) m/z=507 ([M+H]$^+$, 100%). Anal. Calcd. for $C_{26}H_{22}N_2O_5S_2 \cdot \frac{1}{2}H_2O$: C, 60.57; H, 4.50; N, 5.43; S, 12.44. Found: C, 60.92; H, 4.54; N, 5.48; S, 12.32.

Example 115

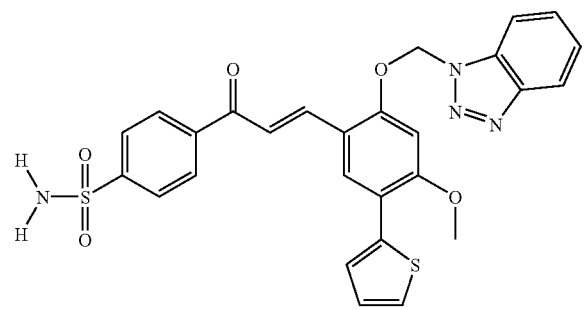

4-{3E-[2-(Benzotriazol-1-ylmethoxy)-4-methoxy-5-thiophen-2-yl-phenyl]-acryloyl}-benzenesulfonamide Ex-115A: 2-(Benzotriazol-1-ylmethoxy)-4-methoxy-5-thiophen-2-yl-benzaldehyde was prepared in a similar manner as described in Ex-29C. Off-white solid, 92% yield, mp 137–138° C. $^1$H-NMR (300 MHz, CDCl$_3$) δ 10.30 (s, 1H), 8.10 (d, 1H, J=8.1 Hz), 8.06 (s, 1H), 7.75 (d, 1H, J=8.1 Hz), 7.57–7.62 (m, 1H), 7.40–7.48 (m, 2H), 7.30 (d, 1H, J=5.1 Hz), 7.08 (s, 1H), 7.05 (dd, 1H, J=5.1, 3.6 Hz), 6.74 (s, 2H), 4.01 (s, 3H). MS (ESI) m/z=366 ([M+H]$^+$, 100%). Anal. Calcd. for $C_{19}H_{15}N_3O_3S$: C, 62.45; H, 4.14; N, 11.50; S, 8.78. Found: C, 62.69; H, 4.30; N, 11.52; S, 8.62.

The title compound was prepared by condensing 2-(benzotriazol-1-ylmethoxy)-4-methoxy-5-thiophen-2-yl-benzaldehyde (Ex-115A) and 4-acetyl-benzenesulfonamide (Ex-26A) in a similar manner as described in Ex-22. Light yellow solid, 56% yield, mp 255° C. (dec). $^1$H-NMR (300 MHz, DMSO-d$_6$) δ 8.21 (s, 1H), 8.09 (d, 3H, J=9.4 Hz), 8.01 (d, 1H, J=7.8 Hz), 7.93 (d, 2H, J=7.8 Hz), 7.75 (d, 2H, J=9.4 Hz), 7.56–7.69 (m, 4H), 7.42–7.47 (m, 4H), 7.38 (s, 1H), 7.13 (dd, 1H, J=5.4, 3.6 Hz), 7.05 (s, 2H), 4.05 (s, 3H). MS (ESI) m/z=547 ([M+H]$^+$, 100%). Anal. Calcd. $C_{27}H_{22}N_4O_5S_2$: C, 59.33; H, 4.06; N, 10.25; S, 11.73. Found: C, 59.45; H, 4.27; N, 9.92; S, 11.27.

Example 116

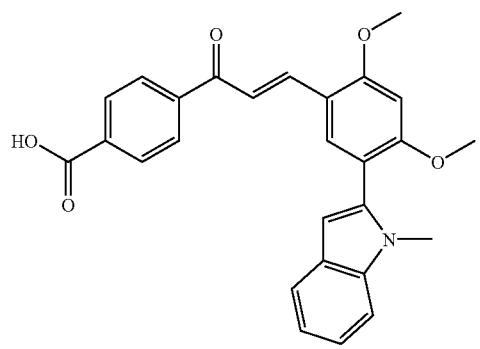

4-{3E-[2,4-Dimethoxy-5-(1-methyl-1H-indol-2-yl)-phenyl]-acryloyl}-benzoic acid

Ex-116A: To a solution of N-methyl indole (1.3 g, 10 mmol) in 50 ml THF, t-BuLi (1.7 m in THF, 7.1 ml, 12 mmol) was slowly added at 0° C. under nitrogen. The mixture was stirred at room temperature for 1 hr, BEt$_3$ (1.0 M in THF, 12 ml, 12 mmol) was added, and the mixture stirred for another 1 hr at room temperature. Then, PdCl$_2$(PPh$_3$)$_2$ (0.35 g, 0.5 mmol) and 5-bromo-2,4-dimethoxybenzaldehyde (3.7 g, 15 mmol) were added, and the mixture was heated to about 60° C. for 30 minutes. The reaction mixture was poured into 50 ml 10% NaOH and treated with 30% H$_2$O$_2$ and then stirred for 10 minutes. The mixture was extracted with EtOAc and combined organic phase was washed with H$_2$O and brine, dried over MgSO4, and absorbed to small amount of silica gel. Column chromatography (EtOAc:Hexane, 1:2) gave 0.72 g (25%) 2,4-dimethoxy-5-(1-methyl-1H-indol-2-yl)-benzaldehyde. $^1$H-NMR (CDCl$_3$) δ 10.33 (s, 1H), 7.84 (s, 1H), 7.60 (d, J=8 Hz, 1H), 7.31 (d, J=8 Hz, 1H), 7.18–7.24 (m, 1H), 7.07–7.12 (m, 1H), 6.53 (s, 1H), 6.46 (s, 1H), 4.00 (s, 3H), 3.89 (s, 3H), 3.53 (s, 3H). HRMS (EI) Calcd. for $C_{18}H_{17}NO_3$: 295.1208. Found: 295.1202.

The title compound was prepared by condensing 4-acetyl-benzoic acid and 2,4-dimethoxy-5-(1-methyl-1H-indol-2-yl)-benzaldehyde (Ex-116A) in a similar manner as described in Ex-3. Yellow solid, 87% yield, mp 157–160° C. $^1$H-NMR (DMSO-d6) δ 8.17 (d, J=8 Hz, 2H), 8.08 (d, J=15 Hz, 1H), 7.99–9.02 (m 3H), 7.83 (d, J=15 Hz, 1H), 7.52 (d, J=8 Hz, 1H), 7.42 (d, J=8 Hz, 1H), 7.10–7.15 (m, 1H), 6.99–7.04 (m, 1H), 6.85 (s, 1H), 6.42 (s, 1H), 4.01 (s, 3H), 3.88 (s, 3H), 3.50 (s, 3H). MS m/z=442 ([M+H]$^+$, 100%). HRMS (ES+) Calcd. for $C_{27}H_{23}NO_5$: 442.1654. Found: 442.1633.

Example 117

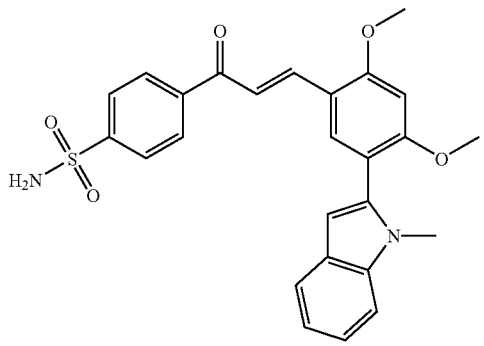

4-{3E-[2,4-Dimethoxy-5-(1-methyl-1H-indol-2-yl)-phenyl]-acryloyl}-benzenesulfonamide The title compound was prepared by condensing 4-acetyl-benzenesulfonamide (Ex-26A) and 2,4-dimethoxy-5-(1-methyl-1H-indol-2-yl)-benzaldehyde (Ex-116A) in a similar manner as described in Ex-3. Yellow solid, 90% yield, mp 148–150° C. $^1$H-NMR (CDCl$_3$) δ 8.17 (d, J=16 Hz, 1H), 8.09 (d, J=9 Hz, 2H), 8.01 (d, J=9 Hz, 2H), 7.68 (s, 1H), 7.64 (d, J=8 Hz, 1H), 7.47 (d, J=16 Hz, 1H), 7.35 (d, J=8 Hz, 1H), 7.22–7.26 (m, 1H), 7.11–7.16 (m, 1H), 6.58 (s, 1H), 6.50 (s, 1H), 4.92 (br, 2H), 4.02 (s, 3H), 3.90 (s, 3H), 3.58 (s, 3H). MS m/z=477 ([M+H]$^+$, 100%). HRMS (ES+) Calcd. for C$_{26}$H$_{24}$NO$_5$S: 477.1484. Found: 477.1487.

Example 118

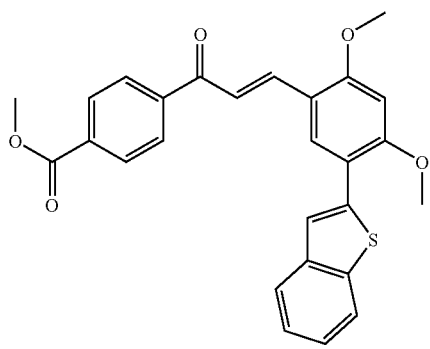

4-[3E-(5-Benzo[b]thiophen-2-yl-2,4-dimethoxy-phenyl)-acryloyl]-benzoic acid methyl ester The title compound was prepared by esterification of 4-[3E-(5-Benzo[b]thiophen-2-yl-2,4-dimethoxy-phenyl)-acryloyl]-benzoic acid (Ex-3) with methanol in the presence of EDCI and DMAP. Yellow solid, 34% yield, m.p. 149–151° C. $^1$H-NMR (300 MHz, CDCl$_3$): 8.17 (d, 2H, J=6.7 Hz), 8.10 (d, 1H, J=15.8 Hz), 8.05 (d, 2H, J=6.7 Hz), 7.95 (s, 1H), 7.82 (m, 2H), 7.67 (s, 1H), 7.57 (d, 1H, J=15.8 Hz), 7.33 (m, 2H), 6.58 (s, 1H), 4.04 (s, 3H), 4.00 (s, 3H), 3.97 (s, 3H). MS m/z=458 ([M]$^+$, 100%). HRMS (EI) Calcd. for C$_{27}$H$_{22}$O$_5$S: 458.118 Found: 458.1196.

Example 119

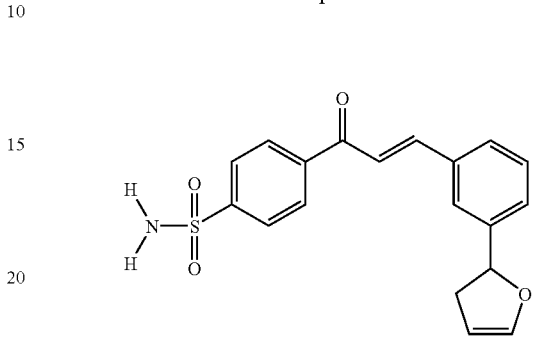

4-{3-[3E-(2,3-Dihydro-furan-2-yl)-phenyl]-acryloyl}-benzenesulfonamide

Ex-119A: 5-Bromobenzaldehyde (0.5 g, 2.7 mmol) and 2,3-dihydrofuran (0.56 g, 8.1 mmol) were dissolved in dioxane (5.0 mL). Nitrogen was bubbled into the solution for 15 min followed by the sequential addition of cesium carbonate (0.96 g, 2.9 mmol) and bis(tri-t-butylphosphine)palladium(0) (0.014 g, 0.027 mmol). The solution was immediately heated to 45° C. and aged for 24 h. Upon completion, as determined by HPLC, the reaction was diluted with water (20 mL) and extracted with ethyl acetate (3×20 mL). The combined organic extracts were dried over sodium sulfate and concentrated to a brown oil. Silica gel chromatography (ethyl acetate/hexanes, 1:9) gave 0.18 g (40%) of 3-(2,3-dihydro-furan-2-yl)-benzaldehyde as a clear, colorless oil. $^1$H-NMR (300 MHz, CDCl$_3$) δ 10.03 (s, 1H), 7.88 (s, 1H), 7.82 (d, 1H, J=7.2 Hz), 7.62–7.64 (m, 1H), 7.53 (t, 1H, J=7.2 Hz), 6.48 (q, 1H, J=Hz), 5.60 (dd, 1H, J=8.1, 10.8 Hz), 4.98 (q, 1H, J=3.3 Hz), 3.15 (ddt, 1H, J=15.0, 8.1, 2.5 Hz), 2.59 (ddt, 1H, J=15.0, 8.1, 2.5 Hz). MS (EI) m/z=174 ([M]$^+$, 100%). HRMS (EI) Calcd. for C$_{11}$H$_{10}$O$_2$: 174.0681. Found: 174.0677.

The title compound was prepared by condensing 4-acetyl-benzenesulfonamide (Ex-26A) and 3-(2,3-dihydro-furan-2-yl)-benzaldehyde (Ex-119A) in a similar manner as described in Ex-3. Tan solid, 40% yield, mp 152–153° C. $^1$H-NMR (300 MHz, DMSO-d$_6$) δ 8.31 (d, 2H, J=7.5 Hz), 7.99 (d, 2H, J=7.5 Hz), 7.95 (d, 1H, J=15.8 Hz), 7.85 (brs, 3H), 7.78 (d, 1H, J=15.8 Hz), 7.57 (brs, 1H), 7.44–7.52 (m, 2H), 6.62 (q, 1H, J=2.4 Hz), 5.58 (dd, 1H, J=8.7, 10.8 Hz), 5.59 (q, 1H, J=2.4 Hz), 3.10 (ddt, 1H, J=15.0, 8.1, 2.5 Hz), 2.54 (ddt, 1H, J=15.0, 8.1, 2.5 Hz). MS (ESI) m/z=356 ([M+H]$^+$, 100%). Anal. Calcd. for C$_{19}$H$_{17}$NO$_4$S.⅓H$_2$O: C, 63.56; H, 4.89; N, 3.90; S, 8.93. Found: C, 63.64; H, 4.88; N, 4.00; S, 8.71.

Example 120

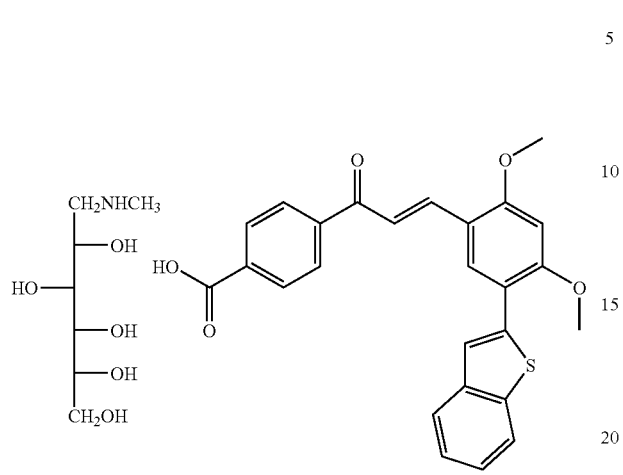

4-[3E-(5-Benzo[b]thien-2-yl-2,4-dimethoxyphenyl)-acryloyl]-benzoic acid, N-methyl-D-glucamine salt 4-[3E-(5-Benzo[b]thien-2-yl-2,4-dimethoxyphenyl)-acryloyl]-benzoic acid of Ex. 3 was then made into a meglumine salt by suspending the 4-[3E-(5-benzo[b]thien-2-yl-2,4-dimethoxy-phenyl)-acryloyl]-benzoic acid (4.45 g, 10 mmol) and N-methyl-D-glucamine (1.95 g, 10 mmol) in THF (100 mL). The mixture was stirred at room temperature for 5 minutes. Then, ethanol (100 mL) was added. This mixture was stirred at room temperature for 30 minutes. THF (20 mL) and ethanol (20 mL) were added and the mixture was heated slightly until it became a solution. This solution was stirred for 30 minutes and evaporated to a yellow foam. Crystallization from methanol gave the desired 4-[3E-(5-benzo[b]thien-2-yl-2,4-dimethoxy-phenyl)-acryloyl]-benzoic acid N-methyl-D-glucamine salt as a yellow solid (4 g, 63%), mp 75–80° C. (changing forms). $^1$H NMR (300 MHz, DMSO-$d_6$) δ 8.39 (s, 1H), 8.14 (d, 2H), 8.02–8.10 (m, 3H), 7.94–7.98 (m, 3H), 7.86 (d, 1H), 7.36 (m, 2H), 6.89 (s, 1H), 4.06 (s, 3H), 4.04 (s, 3H), 3.94 (m, 1H), 3.71 (d, 1H), 3.61 (m, 1H), 3.39–3.55 (m, 3H), 3.04 (m, 1H), 2.95 (m, 1H), 2.54 (s, 3H). Anal. Calculated for $C_{33}H_{37}NO_{10}S \cdot 1.3H_2O$: C, 59.77; H, 6.02; N, 2.11; S, 4.84; found: C, 59.84; H, 5.75; N, 2.05; S, 4.70; Parent EIMS m/z=443 (M$^+$).

Using the above procedure for producing the meglumine salt or procedures well known in the art, any of the compounds of the invention can be likewise made into a hydroxyl amine salt and in particular the meglumine salt.

Example 121

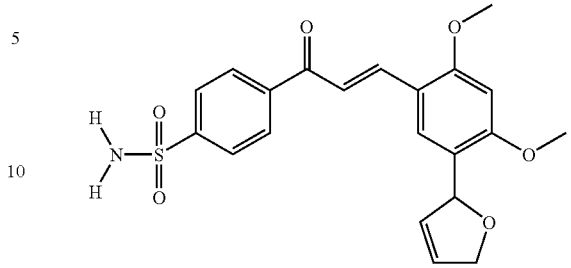

4-{3E-[5-(2,5-Dihydro-furan-2-yl)-2,4-dimethoxy-phenyl]-acryloyl}-benzenesulfonamide Ex-121A: 5-Bromo-2,4-dimethoxybenzaldehyde (1.0 g, 4.0 mmol) and 2,3-dihydrofuran (0.85 g, 12.2 mmol) were dissolved in dioxane (10.0 mL). Nitrogen was bubbled into the solution for 15 min followed by the sequential addition of cesium carbonate (1.4 g, 4.5 mmol) and bis(tri-t-butylphosphine)palladium (0) (0.021 g, 0.041 mmol). The solution was immediately heated to 45° C. and aged for 72 h. Additional equivalents of cesium carbonate (0.70 g, 2.1 mmol), 2,3-dihydrofuran (0.85 g, 12.2 mmol), and Pd catalyst (0.0021 g, 0.0041 mmol) were added after 24 h and 48 h to drive the reaction to completion. Upon completion, as determined by HPLC, the reaction was diluted with water (30 mL) and extracted with ethyl acetate (3×30 mL). The combined organic extracts were dried over sodium sulfate and concentrated to an orange oil. Silica gel chromatography (ethyl acetate/hexanes, 1:2) afforded 0.32 g (50%) of 5-(2,5-dihydro-furan-2-yl)-2,4-dimethoxy-benzaldehyde as a pale yellow solid, mp 84–85° C. $^1$H-NMR (300 MHz, CDCl$_3$) δ 10.29 (s, 1H), 7.79 (s, 1H), 6.42 (s, 1H), 5.99–6.06 (m, 2H), 5.89–5.92 (m, 1H), 4.80–4.87 (m, 1H), 4.71–4.77 (m, 1H), 3.95 (s, 3H), 3.92 (s, 3H). MS (EI) m/z=234 ([M]$^+$, 100%). Anal. Calcd. $C_{13}H_{14}O_4$: C, 66.66; H, 6.02. Found: C, 66.49; H, 6.08.

5-(2,5-Dihydro-furan-2-yl)-2,4-dimethoxy-benzaldehyde (Ex-121A, 0.10 g, 0.43 mmol) and 4-acetylbenzenesulfonamide (Ex-26A, 0.085 g, 0.43 mmol) were dissolved in a dimethylformamide-methanol solution (2.9 mL, 7:3). After complete dissolution, lithium methoxide (0.065 g, 1.7 mmol) was added and the resulting orange slurry was stirred in the dark at room temperature for 4 h. Upon completion, as determined by HPLC, the mixture was diluted with water (15 mL) and extracted with ethyl acetate (3×20 mL). The combined organic extracts were dried over sodium sulfate and evaporated to dryness. The crude oil was taken up in ethanol (2 mL) and warmed to 60° C. to obtain complete dissolution and allowed to cool to room temperature. The resulting precipitate was collected on filter paper and dried in vacuo to yield 0.13 g (70%) of the title compound as a yellow solid, mp 194–195° C. $^1$H-NMR (300 MHz, DMSO-$d_6$) δ 8.23 (d, 2H, J=8.2 Hz), 8.03 (d, 1H, J=15.3 Hz), 7.97 (d, 2H, J=8.2 Hz), 7.69 (s, 1H), 7.65 (d, 1H, J=15.3 Hz), 7.55 (brs, 2H), 6.73 (s, 1H), 6.06–6.09 (m, 1H), 5.90–5.98 (m, 2H), 4.86–4.92 (m, 1H), 4.63–4.68 (m, 1H), 3.96 (s, 3H), 3.92 (s, 3H). MS (ESI) m/z=416 ([M+H]$^+$, 100%). Anal. Calcd. $C_{21}H_{21}NO_6S$: C, 60.71; H, 5.09; N, 3.37; S, 7.72. Found: C, 60.95; H, 5.24; N, 3.46; S, 7.72.

Example 122

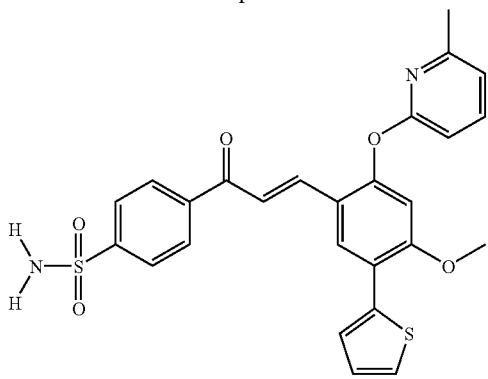

4-{3E-[4-Methoxy-2-(6-methyl-pyridin-2-yloxy)-5-thiophen-2-yl-phenyl]-acryloyl}-benzenesulfonamide Ex-122A: To a solution of 2-hydroxy-4-methoxy-5-thiophen-2-yl-benzaldehyde (0.68 g, 2.9 mmol) and 2-bromo-6-methylpyridine (0.25 g, 1.4 mmol) in toluene (1.0 mL) was added ethyl acetate (0.0063 g, 0.072 mmol, 1-naphthoic acid (0.50 g, 2.9 mmol), 5 Å molecular sieves (0.36 g), cesium carbonate (0.94 g, 2.9 mmol), and copper(I) triflate-benzene complex (0.020 g, 0.036 mmol). The phenoxide crashed out of solution upon addition of cesium carbonate and additional toluene (1 mL) was added to facilitate stirring. The heterogeneous solution was immediately heated to 110° C. and aged for 24 h. Upon completion, as determined by HPLC, the reaction was diluted with a 5% sodium hydroxide solution (10 mL) and ethyl acetate (10 mL) and stirred for 30 min. The layers were separated and the aqueous layer was extracted with ethyl acetate (5×20 mL). The combined organic extracts were washed with a 50% brine solution (1×25 mL), brine (1×25 mL), dried over sodium sulfate and concentrated to an dark brown semi-solid. Silica gel chromatography (ethyl acetate/hexanes, 1:4) afforded 0.30 g (65%) of 4-methoxy-2-(6-methyl-pyridin-2-yloxy)-5-thiophen-2-yl-benzaldehyde as a light orange solid, mp 140–141° C. $^1$H-NMR (300 MHz, CDCl$_3$) δ 10.21 (s, 1H), 8.23 (s, 1H), 7.64 (dd, 1H, J=7.8, 7.2 Hz), 7.52 (d, 1H, J=3.3 Hz), 7.35 (d, 1H, J=5.1 Hz), 7.10 (dd, 1H, J=5.1, 3.3 Hz), 6.94 (d, 1H, J=7.2 Hz), 6.78 (d, 1H, J=7.8 Hz), 6.75 (s, 1H), 3.92 (s, 3H), 2.44 (s, 3H). HRMS (EI) Calcd. for C$_{18}$H$_{15}$NO$_3$S: 325.0773. Found: 325.0775. Anal. Calcd. C$_{18}$H$_{15}$NO$_3$S: C, 66.44; H, 4.65; N, 4.30; S, 9.85. Found: C, 60.00; H, 4.58; N, 4.05; S, 9.84.

4-Methoxy-2-(6-methyl-pyridin-2-yloxy)-5-thiophen-2-yl-benzaldehyde (Ex-122A, 0.20 g, 0.62 mmol) and 4-acetylbenzenesulfonamide (Ex-26A, 0.12 g, 0.62 mmol) were dissolved in a dimethylformamide-methanol solution (4.2 mL, 7:3). After complete dissolution, lithium methoxide (0.093 g, 2.5 mmol) was added and the resulting orange slurry was stirred in the dark at room temperature for 3 h. Upon completion, as determined by HPLC, the mixture was diluted with water (10 mL) and extracted with ethyl acetate (3×20 mL). The combined organic extracts were dried over sodium sulfate and evaporated to dryness. The crude oil was taken up in ethanol (2 mL) and warmed to 60° C. to obtain complete dissolution and allowed to cool to room temperature. The resulting precipitate was collected on filter paper and dried in vacuo to yield 0.25 g (82%) of the title compound as a yellow solid, mp 164–165° C. $^1$H-NMR (300 MHz, DMSO-d$_6$) δ 8.47 (s, 1H), 8.24 (d, 2H, J=8.1 Hz), 7.98 (d, 1H, J=15.3 Hz), 7.96 (d, 2H, J=8.1 Hz), 7.78–7.85 (m, 2H), 7.77 (d, 1H, J=15.3 Hz), 7.62 (d, 1H, J=5.1 Hz), 7.57 (s, 2H), 7.19 (dd, 1H, J=5.1, 3.6 Hz), 7.04 (d, 1H, J=7.5 Hz), 6.99 (s, 1H), 6.91 (d, 1H, J=8.4 Hz), 3.90 (s, 3H), 2.33 (s, 3H). Anal. Calcd. C$_{26}$H$_{22}$N$_2$O$_5$S$_2$: C, 61.64; H, 4.38; N, 5.53; S, 12.66. Found: C, 61.88; H, 4.47; N, 5.59; S, 12.62.

Example 123

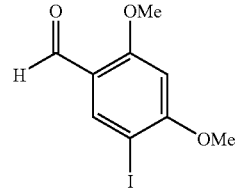

5-Iodo-2,4-dimethoxy-benzaldehyde

To a solution of 2,4-dimethoxy-benzaldehyde (20.0 g, 120.4 mmol) in methanol (550 mL) was added a solution of iodine monochloride (23.25 g, 144.9 mmol) in methanol (60 mL) dropwise over 20 min. The solution was allowed to stir at ambient temperature for 3 hours and then poured into a solution of hydrochloric acid (0.5 M, 600 mL). The resulting precipitate was collected by filtration, washed with water, and dried in vacuo. The crude product was further recrystallized from a mixture of tetrahydrofuran and heptane (1:1, v/v) to give the title compound as a white solid (30.62 g, 87.5%), m.p. 170–172° C. $^1$H NMR (CDCl$_3$) δ 10.19 (s, 1H), 8.22 (s, 1H), 6.39 (s, 1H), 3.97 (s, 3H), 3.95 (s, 3H).

Example 124

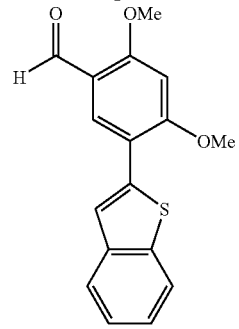

5-Benzo[b]thiophen-2-yl-2,4-dimethoxy-benzaldehyde

Ex-123A: Potassium fluoride (0.42 g, 7.2 mmol), 5-iodo-2,4-dimethoxy-benzaldehyde (Ex-123, 1.0 g, 3.42 mmol), 2-benzo[b]thiophene boronic acid (0.67 g, 3.77 mmol), degased tetrahydrofuran (10 mL), tris(dibenzylideneacetone)dipalladium (19 mg, 0.02 mmol), and tri-tert-butylphosphine (100 mg, 0.05 mmol) were sequentially charged into a flask equipped with a condenser and nitrogen inlet adapter. The reaction mixture was heated at 60° C. for one hour under nitrogen. HPLC analysis indicated of 100% conversion of 5-iodo-2,4-dimethoxy-benzaldehyde (Ex-123) to the title compound prepared through another route (Ex-3A).

Using one or more of the preceding methods, additional substituted 1-[2,2-bis(hydroxymethyl)-benzo[1,3]dioxol-5-yl]-3-[(heteroaryl or heterocyclic)phenyl]-2-propen-1-ones, 4-[3-{(heteroaryl or heterocyclic)phenyl}acryloyl]-benzoic acids, 1-[(amino)phenyl]-3-[(heteroaryl or heterocyclic)phenyl]-2-propen-1-ones, 4-[3-{(heteroaryl or heterocyclic)-phenyl}-3-oxo-propenyl]-benzoic acids, 1-(1H-indol-5-yl)-3-{(heteroaryl or heterocyclic)-phenyl}-propen-2-ones, 1-[(heteroaryl or heterocyclic)phenyl]-3-phenyl-2-propen-1-ones, and substituted 3-[(heteroaryl or heterocyclic)phenyl]-1-phenyl-2-propen-1-ones can be prepared by one skilled in the art using similar methods, as shown in Example Tables 1 through 33.

EXAMPLE TABLE 1

Substituted 4-[3-{2-Isopropoxy-4-methoxy-(5-heteroaryl or 5-heterocyclic)phenyl}-acryloyl]-benzoic Acids.

A

B

| Ex. No. | R$^{5\beta}$ | Ex. No. | R$^{5\beta}$ | Ex. No. | R$^{5\beta}$ |
|---|---|---|---|---|---|
| 200A 200B | furan-2-yl | 201A 201B | thiophen-2-yl | 202A 202B | 1H-pyrrol-2-yl |
| 203A 203B | furan-3-yl | 204A 204B | thiophen-3-yl | 205A 205B | 1H-pyrrol-3-yl |
| 206A 206B | benzofuran-3-yl | 207A 207B | benzothiophen-3-yl | 208A 208B | thiazol-5-yl |
| 209A 209B | pyrimidin-5-yl | 210A 210B | 1H-indol-2-yl | 211A 211B | thiazol-4-yl |
| 212A 212B | oxazol-2-yl | 213A 213B | 1H-indol-3-yl | 214A 214B | thiazol-2-yl |
| 215A 215B | oxazol-5-yl | 216A 216B | 1H-indol-4-yl | 217A 217B | 1H-imidazol-2-yl |

EXAMPLE TABLE 1-continued
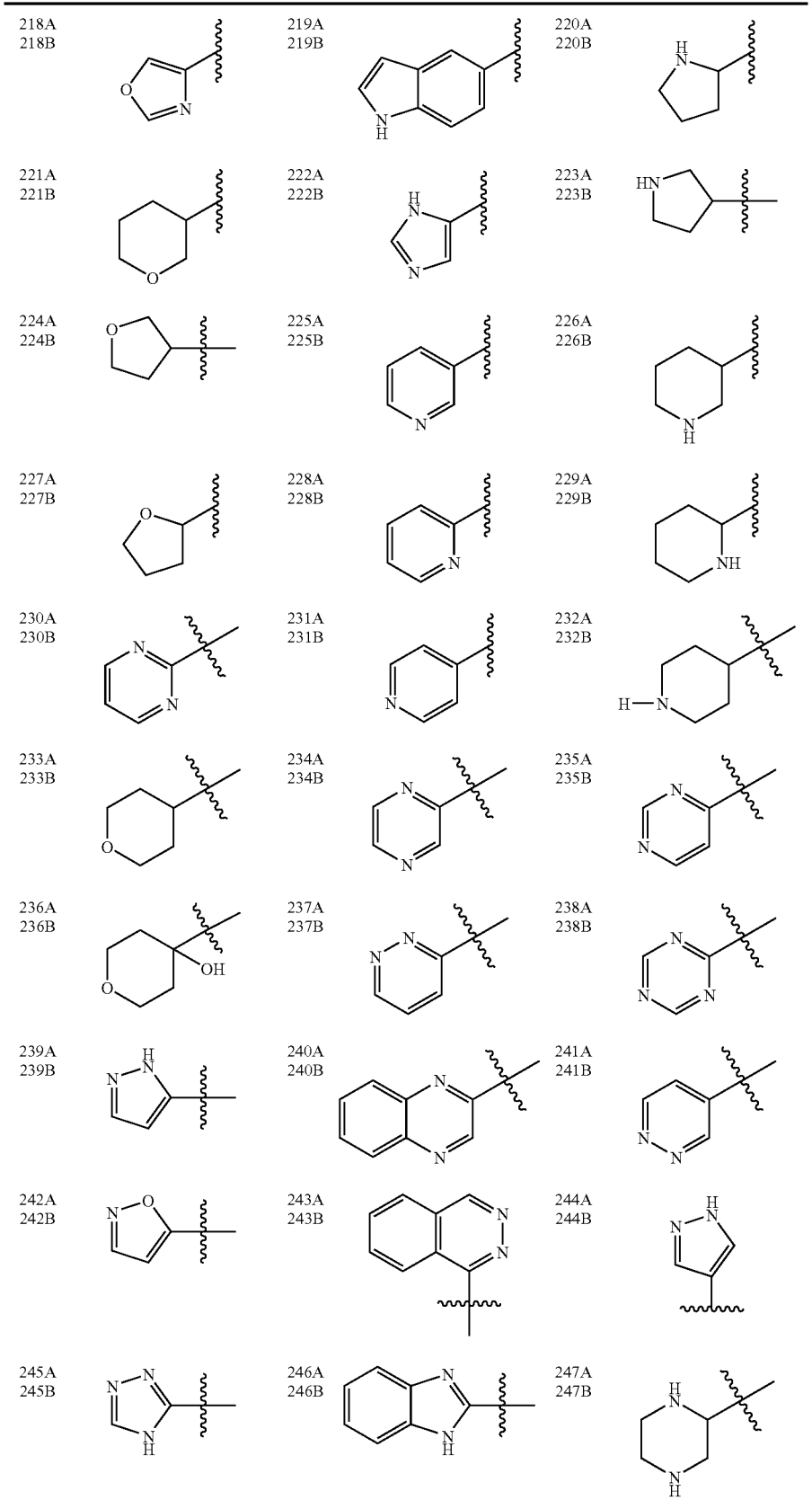

EXAMPLE TABLE 1-continued
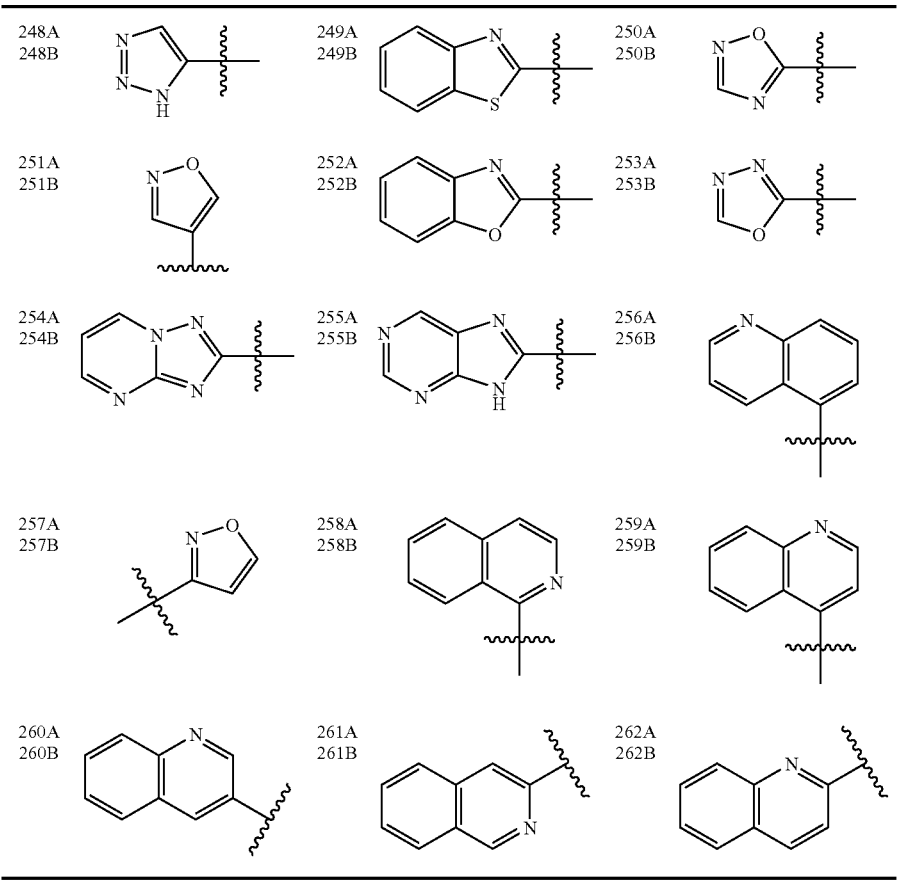
EXAMPLE TABLE 12
Substituted 4-[3-{2-Cyclopropylmethoxy-4-methoxy-(5-heteroaryl or 5-heterocyclic)phenyl}-acryloyl]-benzoic Acids.
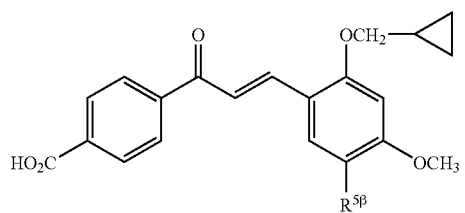
A
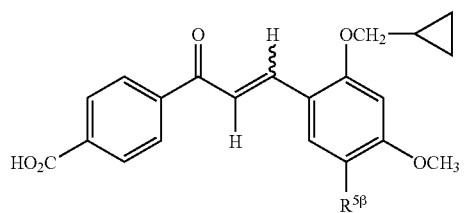
B EXAMPLE TABLE 12-continued
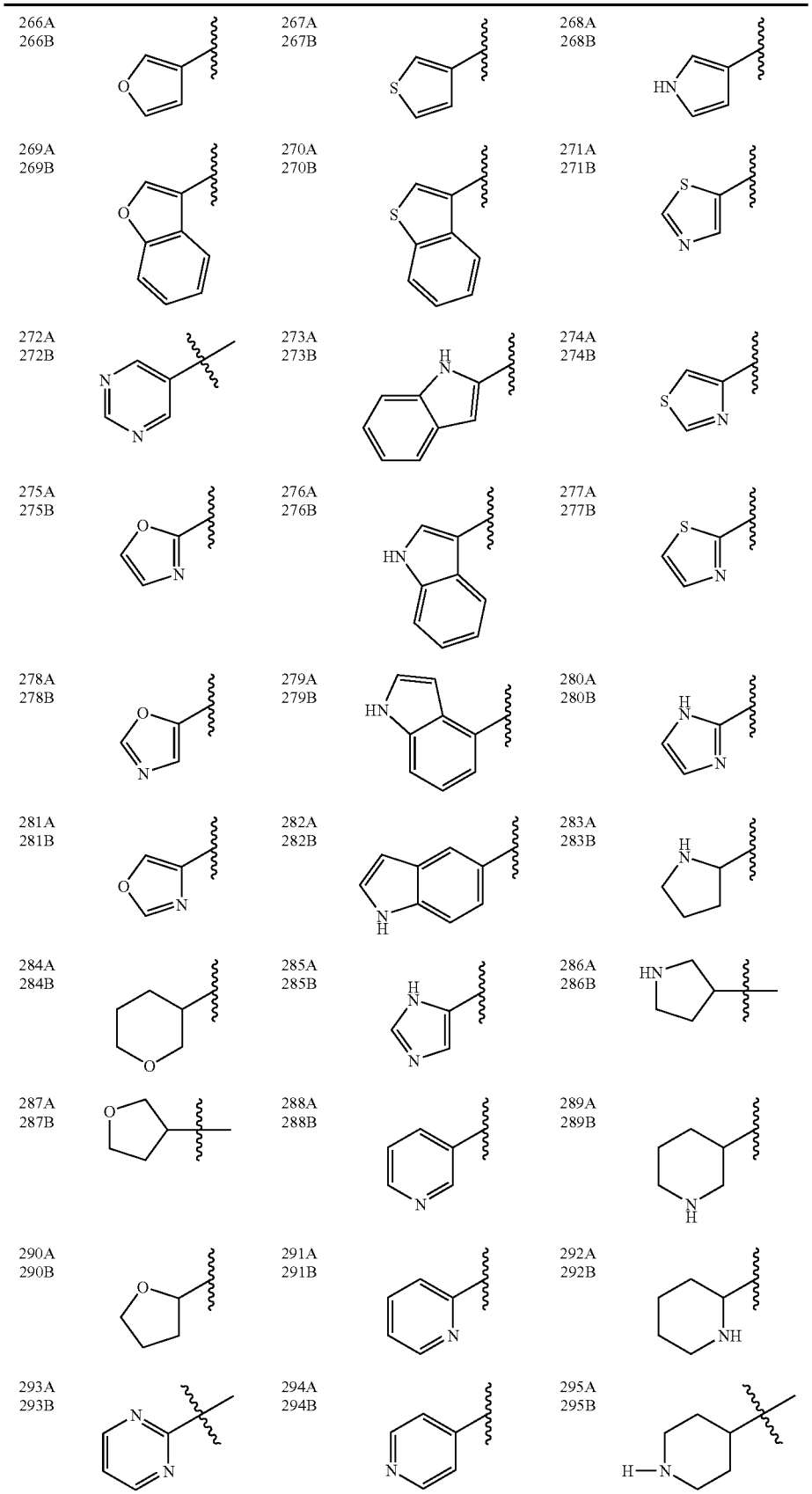

EXAMPLE TABLE 12-continued
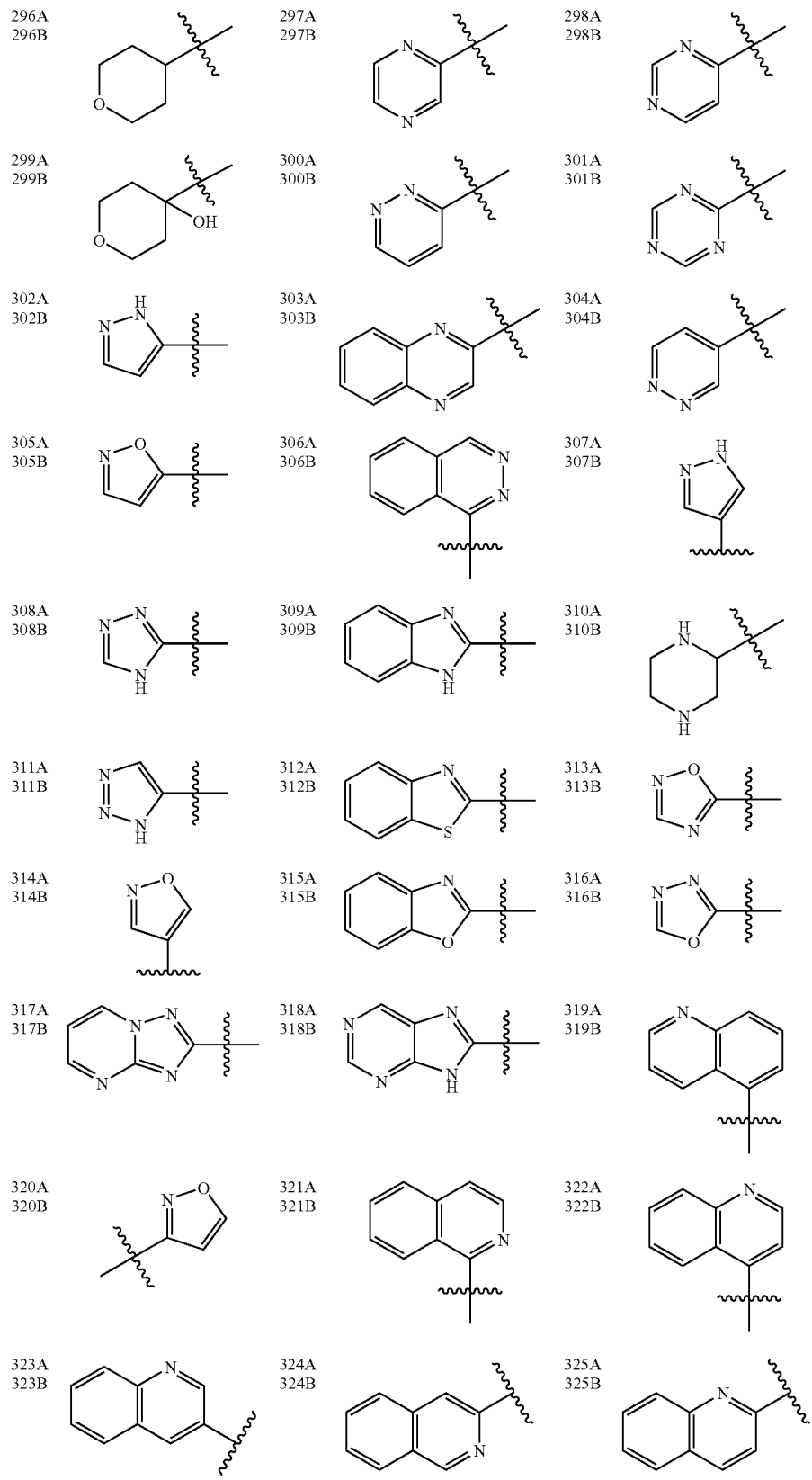

EXAMPLE TABLE 12-continued
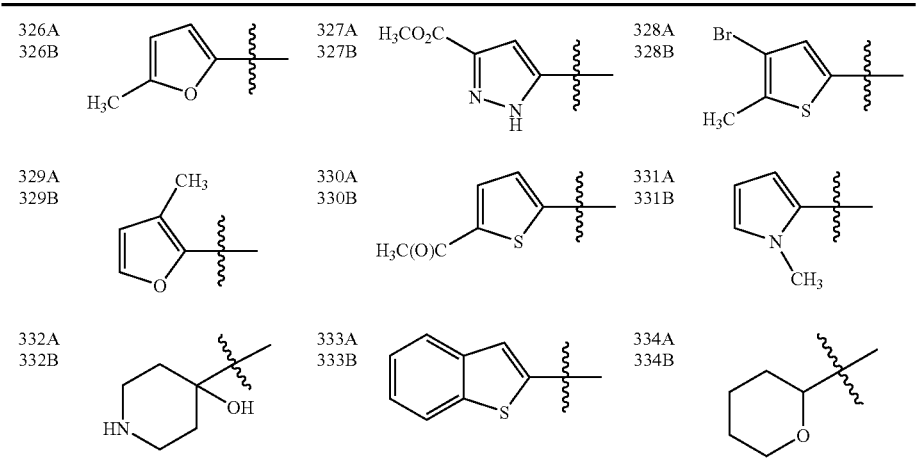
EXAMPLE TABLE 3
Substituted 4-[3-{2,4-dimethoxy-(6-Heteroaryl or 6-heterocyclic)phenyl}-acryloyl]-benzoic Acids.
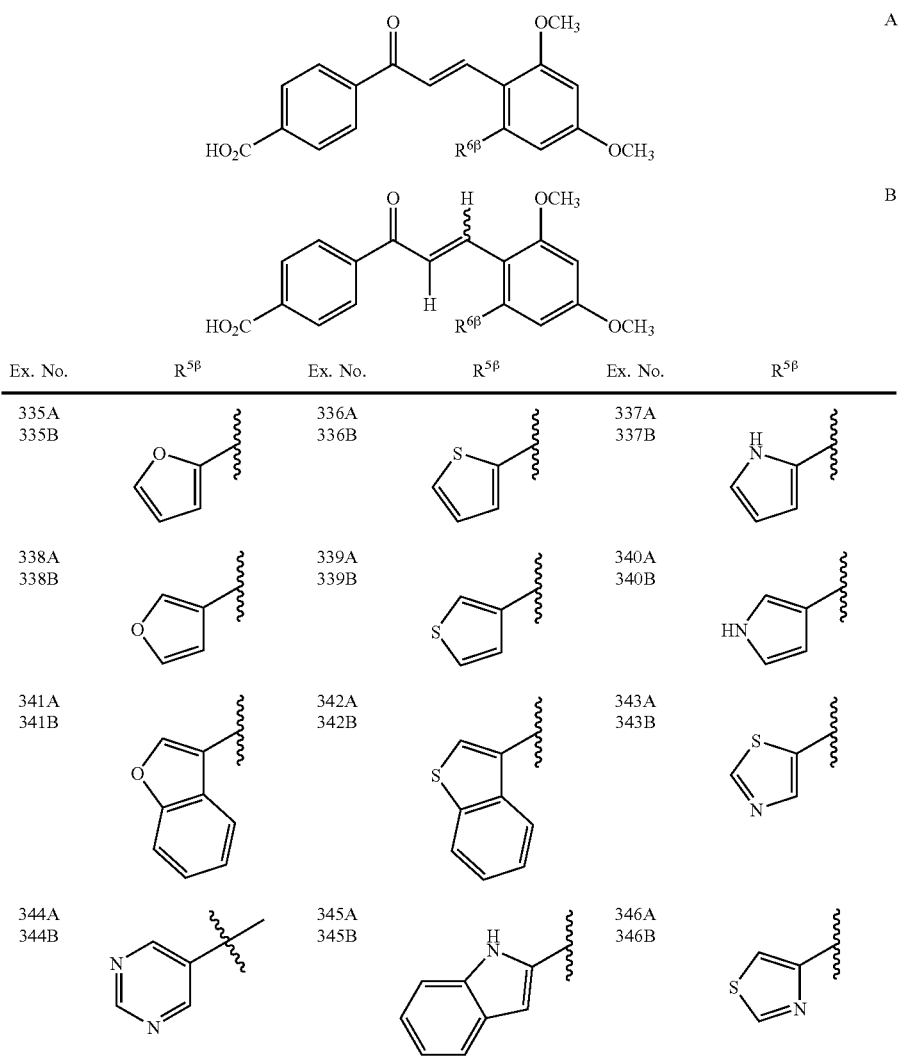

EXAMPLE TABLE 3-continued
Substituted 4-[3-{2,4-dimethoxy-(6-Heteroaryl or 6-heterocyclic)phenyl}-acryloyl]-benzoic Acids.
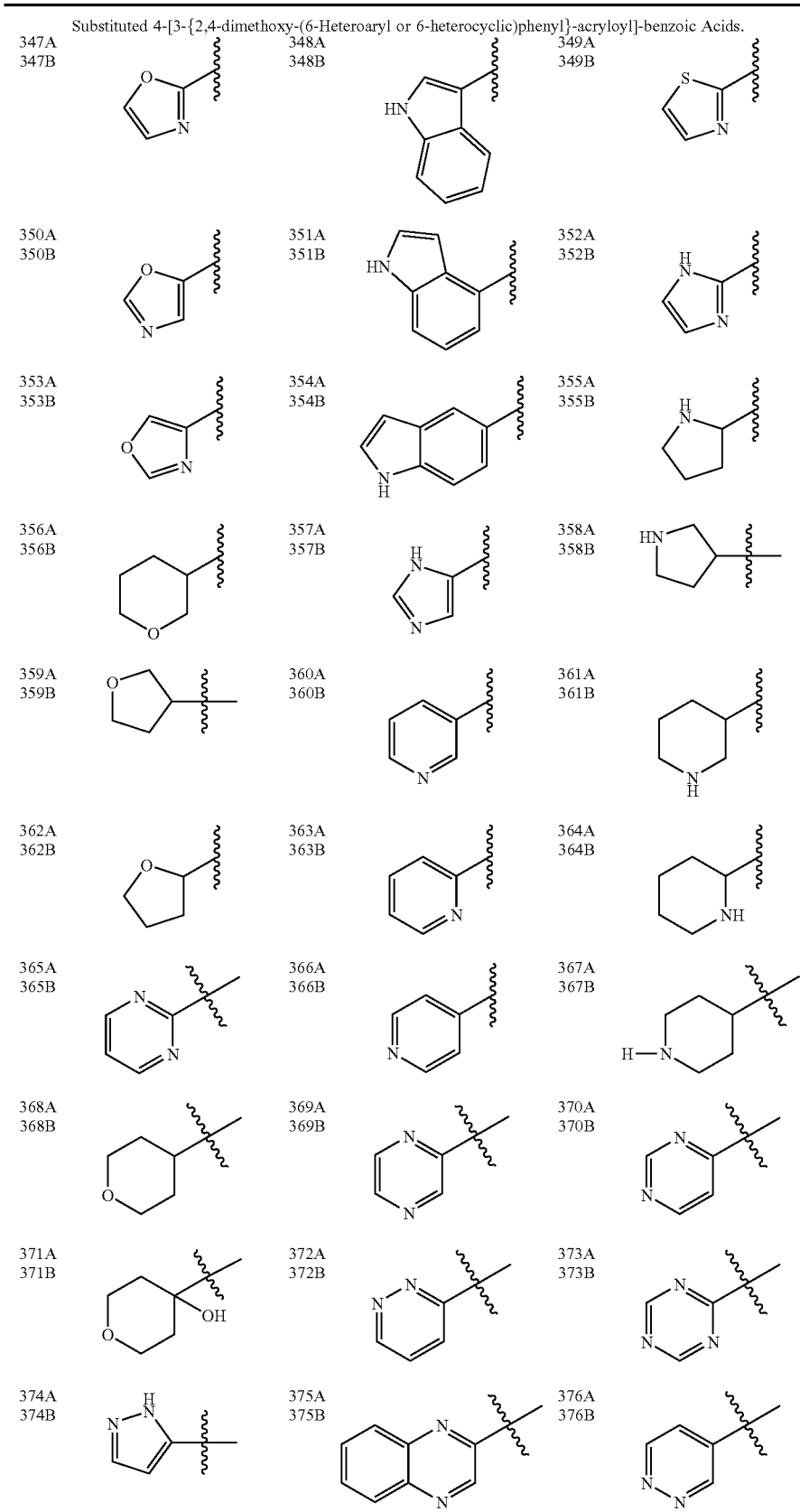

EXAMPLE TABLE 3-continued
Substituted 4-[3-{2,4-dimethoxy-(6-Heteroaryl or 6-heterocyclic)phenyl}-acryloyl]-benzoic Acids.
| | | | | | |
|---|---|---|---|---|---|
| 377A 377B | 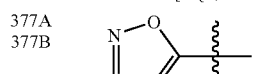 | 378A 378B | 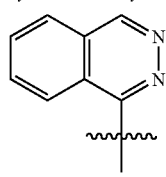 | 379A 379B | 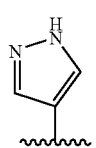 |
| 380A 380B | 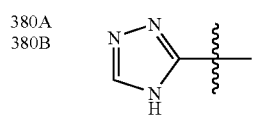 | 381A 381B | 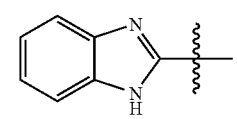 | 382A 382B | 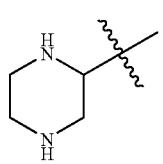 |
| 383A 383B | 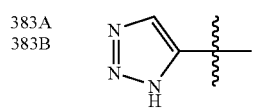 | 384A 384B | 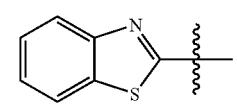 | 385A 385B | 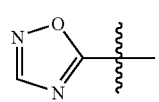 |
| 386A 386B | 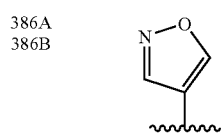 | 387A 387B | 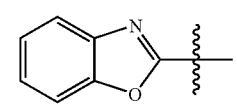 | 388A 388B | 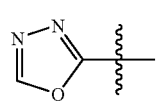 |
| 389A 389B | 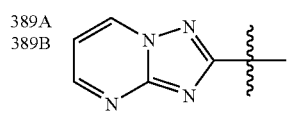 | 390A 390B | 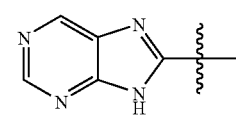 | 391A 391B | 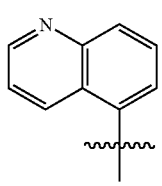 |
| 392A 392B | 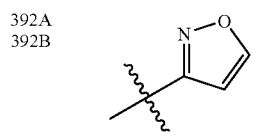 | 393A 393B | 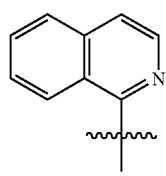 | 394A 394B | 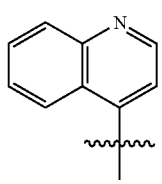 |
| 395A 395B | 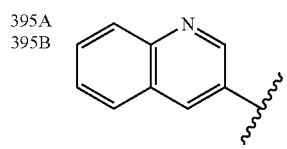 | 396A 396B | 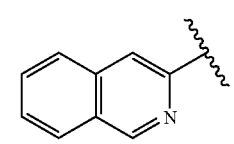 | 397A 397B | 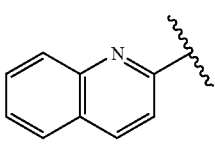 |

EXAMPLE TABLE 4

Substituted 1-(2,2-Bis-hydroxymethyl-benzo[1,3]dioxol-5-yl)-3-[2,4-dimethoxy-(5-heteroaryl or 5-heterocylic)phenyl]-2-propen-1-ones.

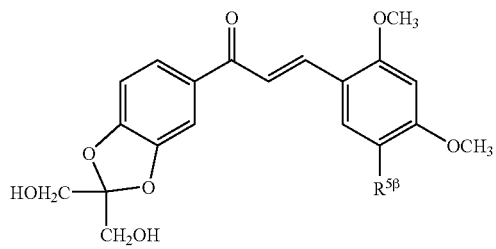 A

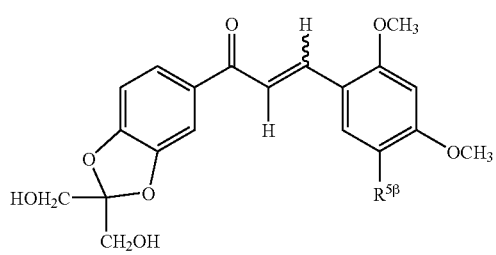 B

| Ex. No. | $R^{5\beta}$ | Ex. No. | $R^{5\beta}$ | Ex. No. | $R^{5\beta}$ |
|---|---|---|---|---|---|
| 398A 398B | furan-2-yl | 399A 399B | thiophen-2-yl | 400A 400B | 1H-pyrrol-2-yl |
| 401A 401B | furan-3-yl | 402A 402B | thiophen-3-yl | 403A 403B | 1H-pyrrol-3-yl |
| 404A 404B | benzofuran-3-yl | 405A 405B | benzothiophen-3-yl | 406A 406B | thiazol-5-yl |
| 407A 407B | pyrimidin-5-yl | 408A 408B | 1H-indol-2-yl | 409A 409B | thiazol-4-yl |
| 410A 410B | oxazol-2-yl | 411A 411B | 1H-indol-3-yl | 412A 412B | thiazol-2-yl |
| 413A 413B | oxazol-5-yl | 414A 414B | 1H-indol-4-yl | 415A 415B | 1H-imidazol-2-yl |

EXAMPLE TABLE 4-continued
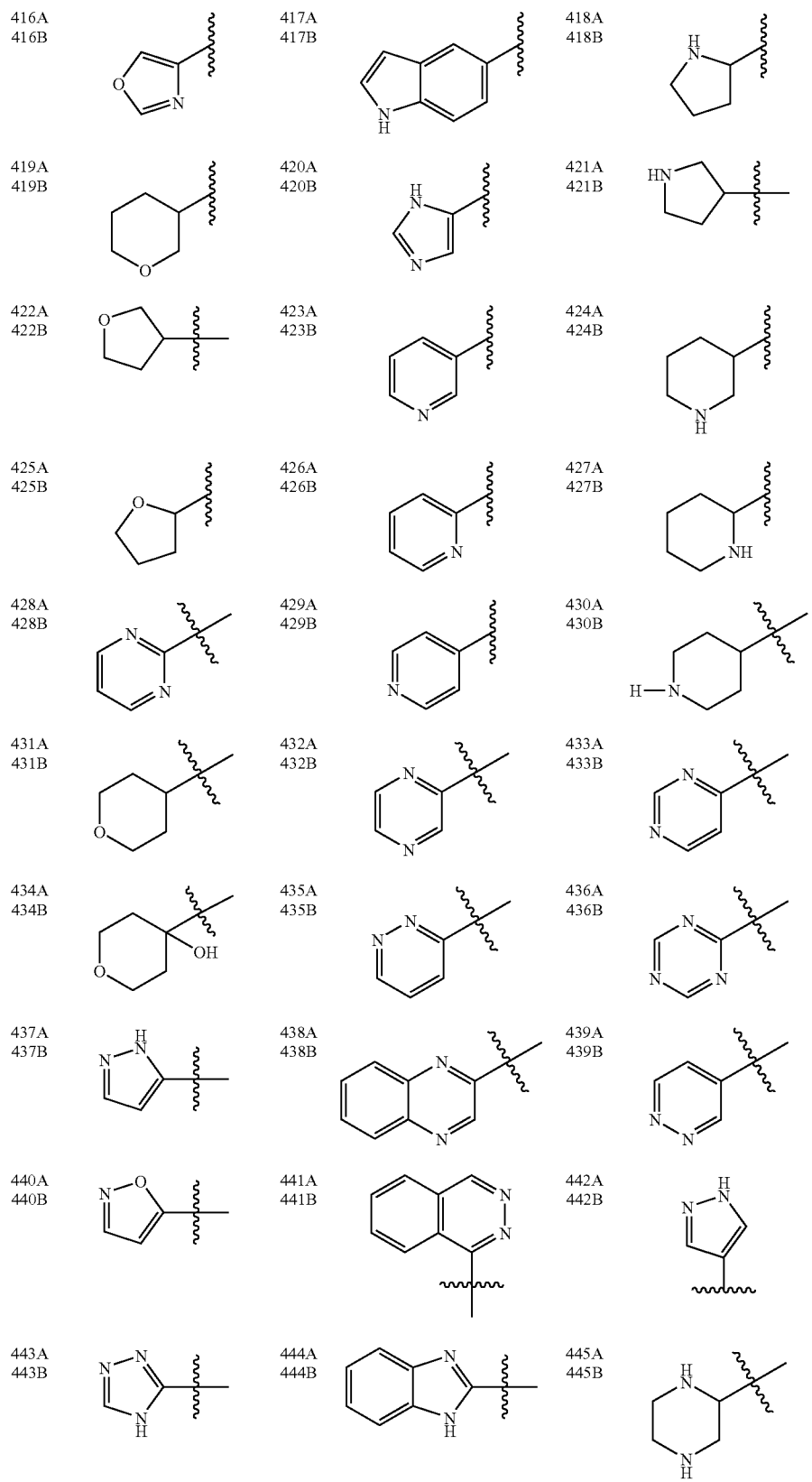

EXAMPLE TABLE 4-continued
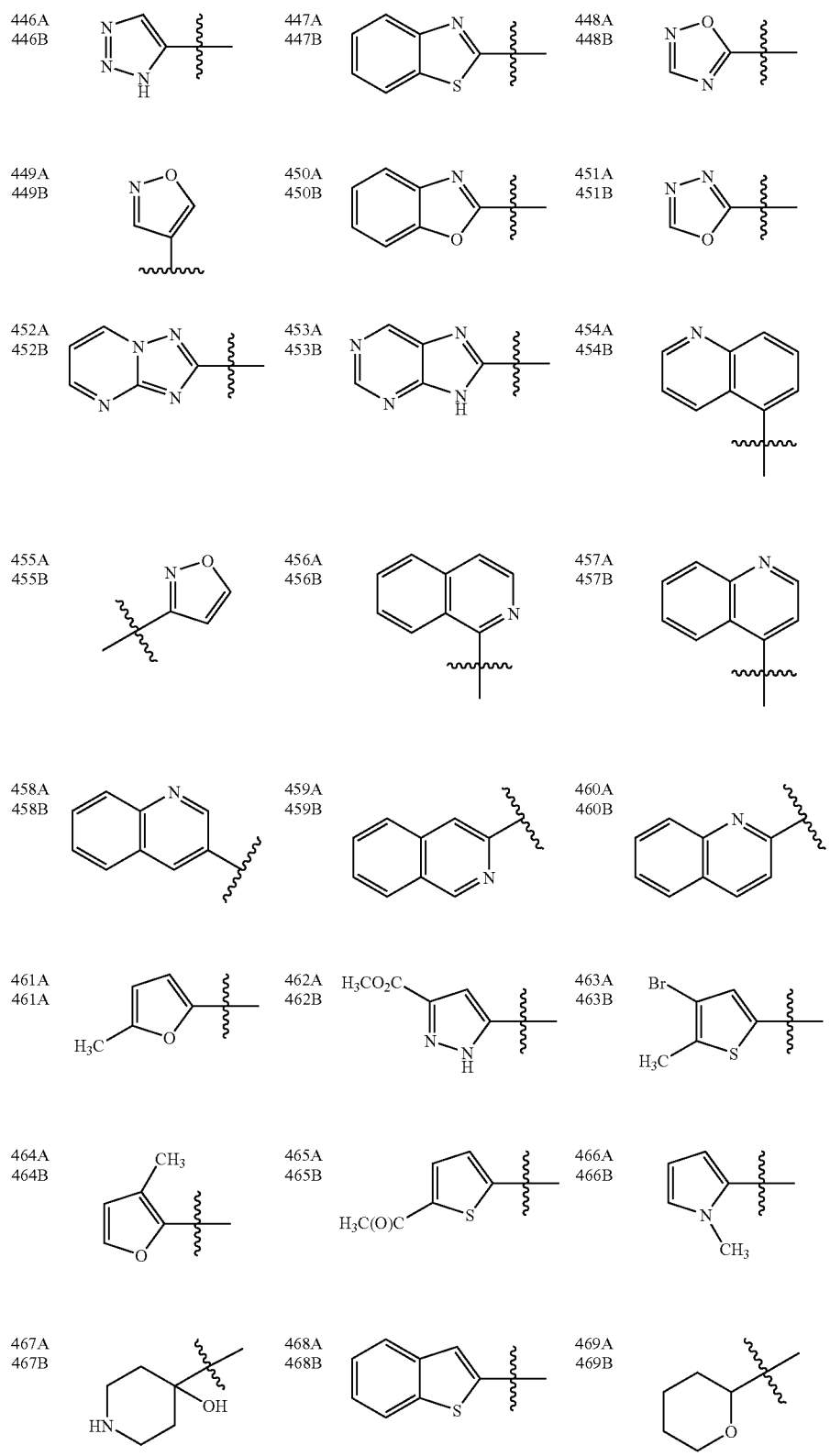

EXAMPLE TABLE 5

Substituted 1-(3-Aminophenyl)-3-[2,4-dimethoxy-(5-heteroaryl or 5-heterocylic)phenyl]-2-propen-1-ones.

A

B

| Ex. No. | $R^{5\beta}$ | Ex. No. | $R^{5\beta}$ | Ex. No. | $R^{5\beta}$ |
|---|---|---|---|---|---|
| 470A<br>470B | 2-furyl | 471A<br>471B | 2-thienyl | 472A<br>472B | 2-pyrrolyl |
| 473A<br>473B | 3-furyl | 474A<br>474B | 3-thienyl | 475A<br>475B | 3-pyrrolyl |
| 476A<br>476B | 3-benzofuryl | 477A<br>477B | 3-benzothienyl | 478A<br>478B | 5-thiazolyl |
| 479A<br>479B | 5-pyrimidinyl | 480A<br>480B | 2-indolyl | 481A<br>481B | 4-thiazolyl |
| 482A<br>482B | 2-oxazolyl | 483A<br>483B | 3-indolyl | 484A<br>484B | 2-thiazolyl |
| 485A<br>485B | 5-oxazolyl | 486A<br>486B | 4-indolyl | 487A<br>487B | 2-imidazolyl |

EXAMPLE TABLE 5-continued
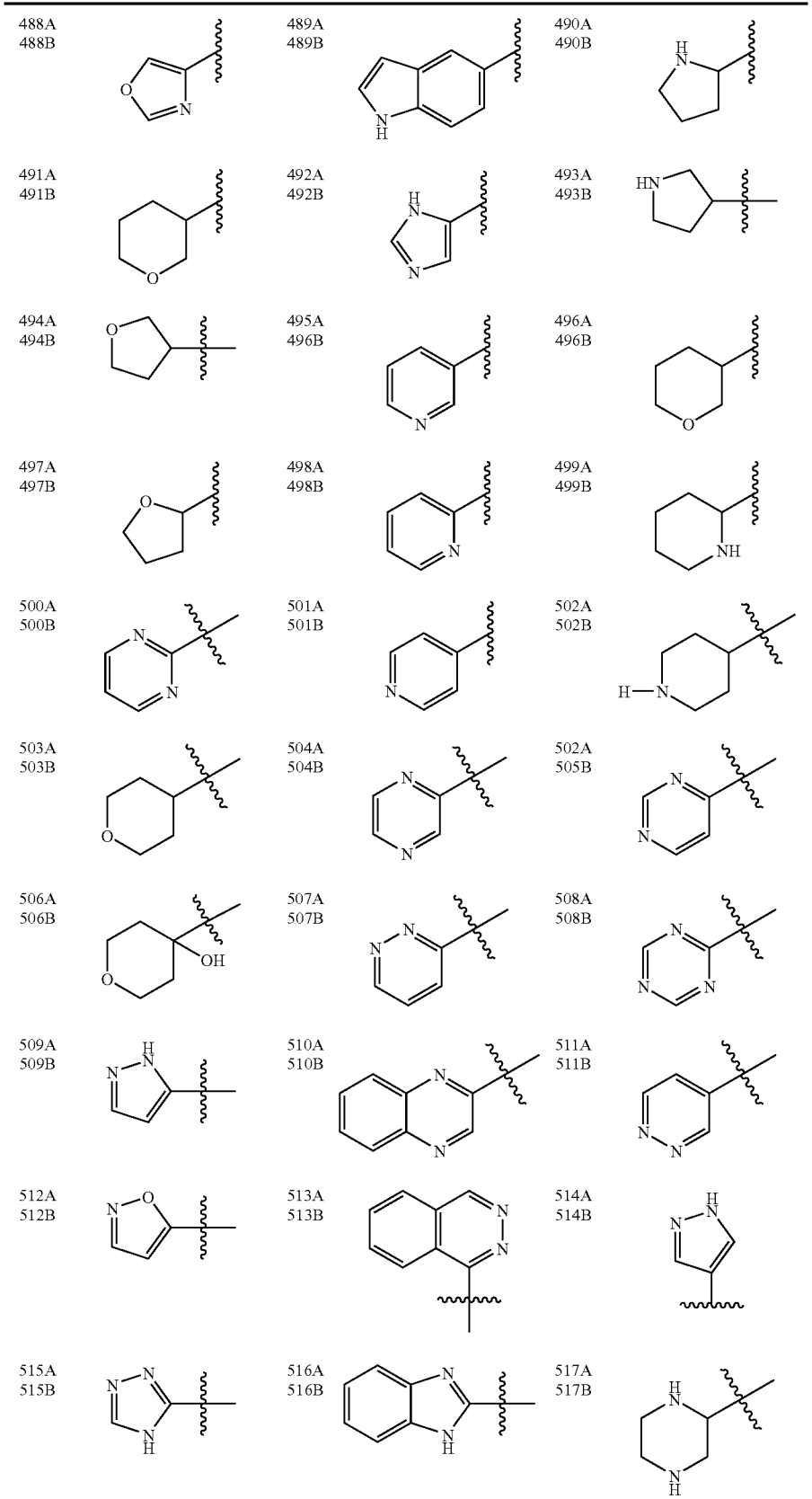

EXAMPLE TABLE 5-continued
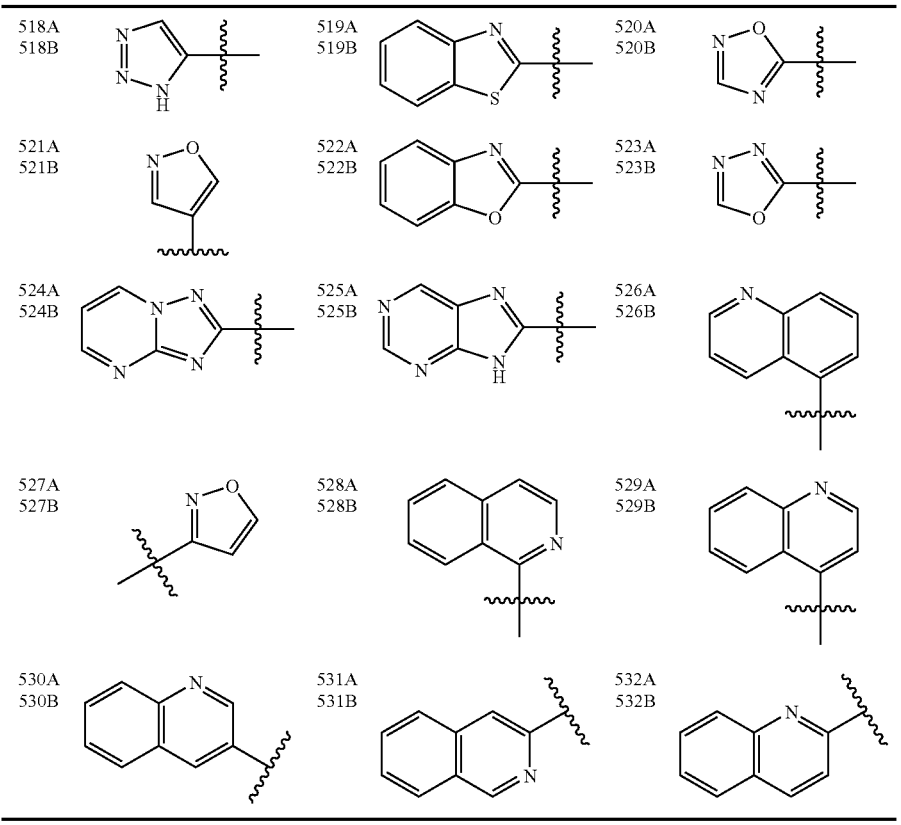
EXAMPLE TABLE 6
Substituted 1-(4-Aminophenyl)-3-[2,4-dimethoxy-(5-heteroaryl or 5-heterocylic)phenyl]-2-propen-1-ones.
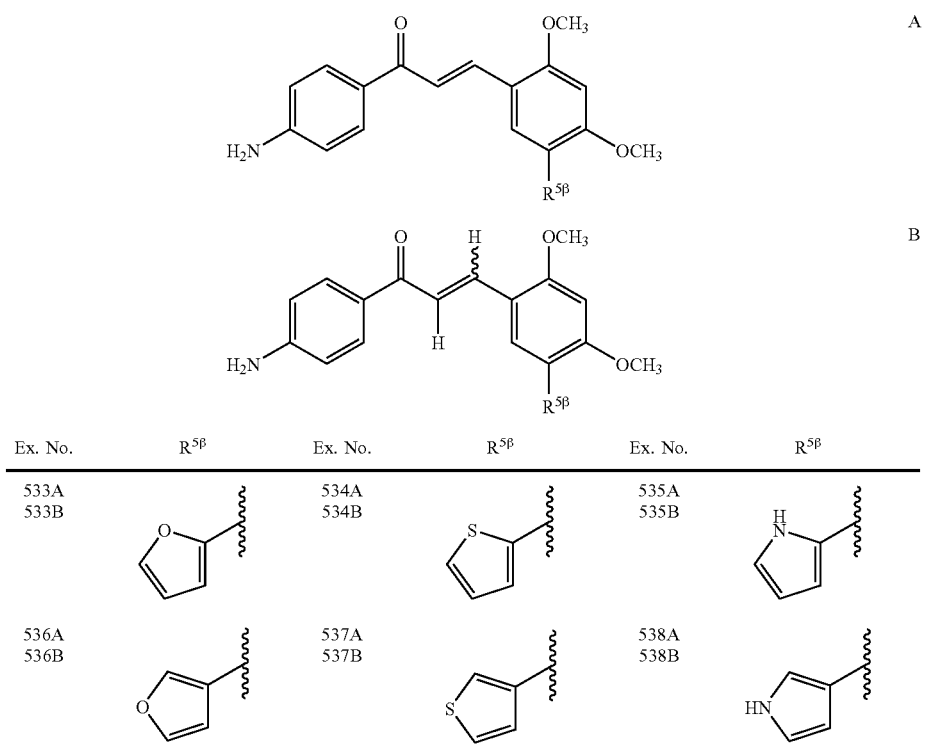

EXAMPLE TABLE 6-continued
| | | | | | |
|---|---|---|---|---|---|
| 539A 539B | 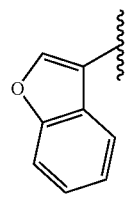 | 540A 540B | 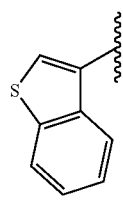 | 541A 541B | 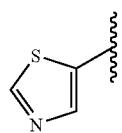 |
| 542A 542B | 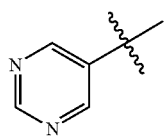 | 543A 543B | 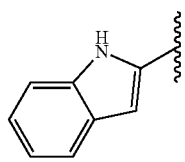 | 544A 544B | 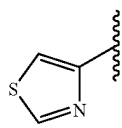 |
| 545A 545B | 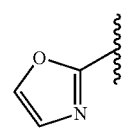 | 546A 546B | 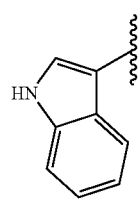 | 547A 547B | 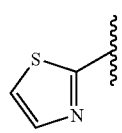 |
| 548A 548B | 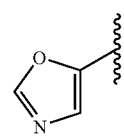 | 549A 549B | 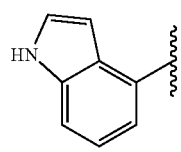 | 550A 550B | 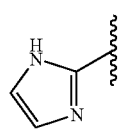 |
| 551A 551B | 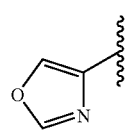 | 552A 552B | 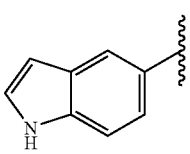 | 553A 553B | 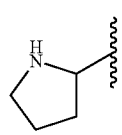 |
| 554A 554B | 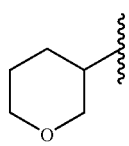 | 555A 555B | 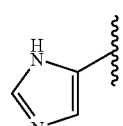 | 556A 556B | 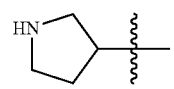 |
| 557A 557B | 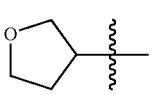 | 558A 558B | 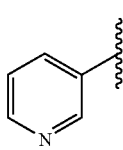 | 559A 559B | 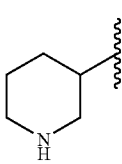 |
| 560A 560B | 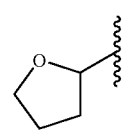 | 561A 561B | 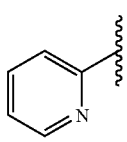 | 562A 562B | 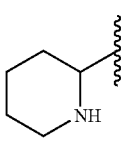 |
| 563A 563B | 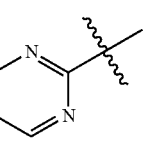 | 564A 564B | 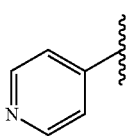 | 565A 565B | 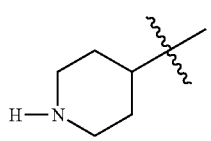 |

EXAMPLE TABLE 6-continued
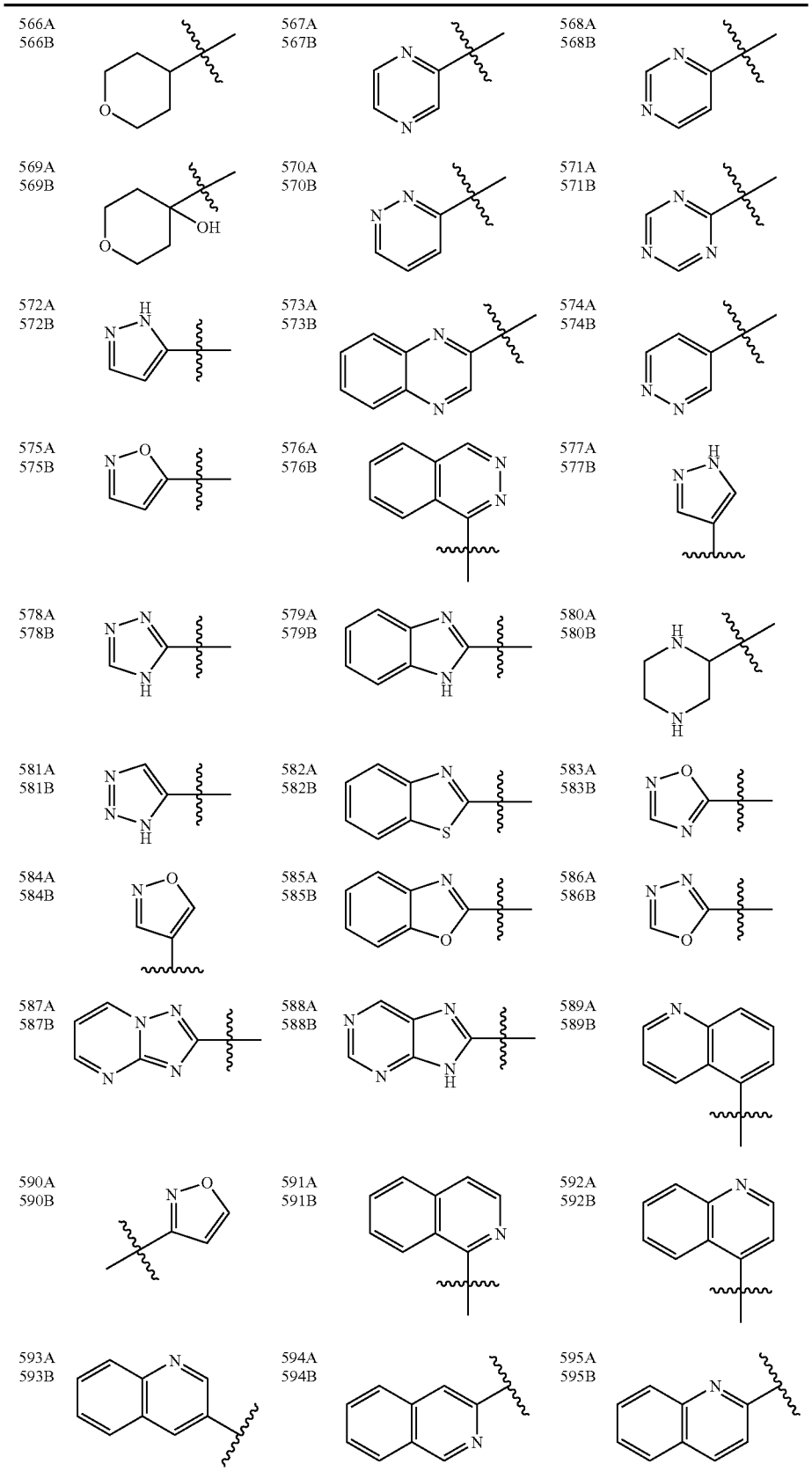

EXAMPLE TABLE 6-continued
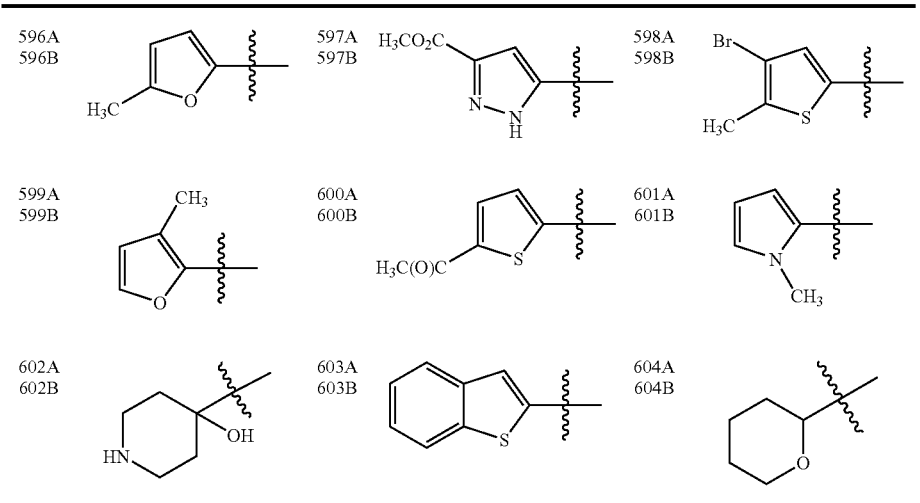
EXAMPLE TABLE 7
Substituted 1-{4-(Pyrrolidin-1-yl)phenyl}-3-[2,4-dimethoxy-(5-heteroaryl or 5-heterocylic)phenyl]-2-propen-1-ones.
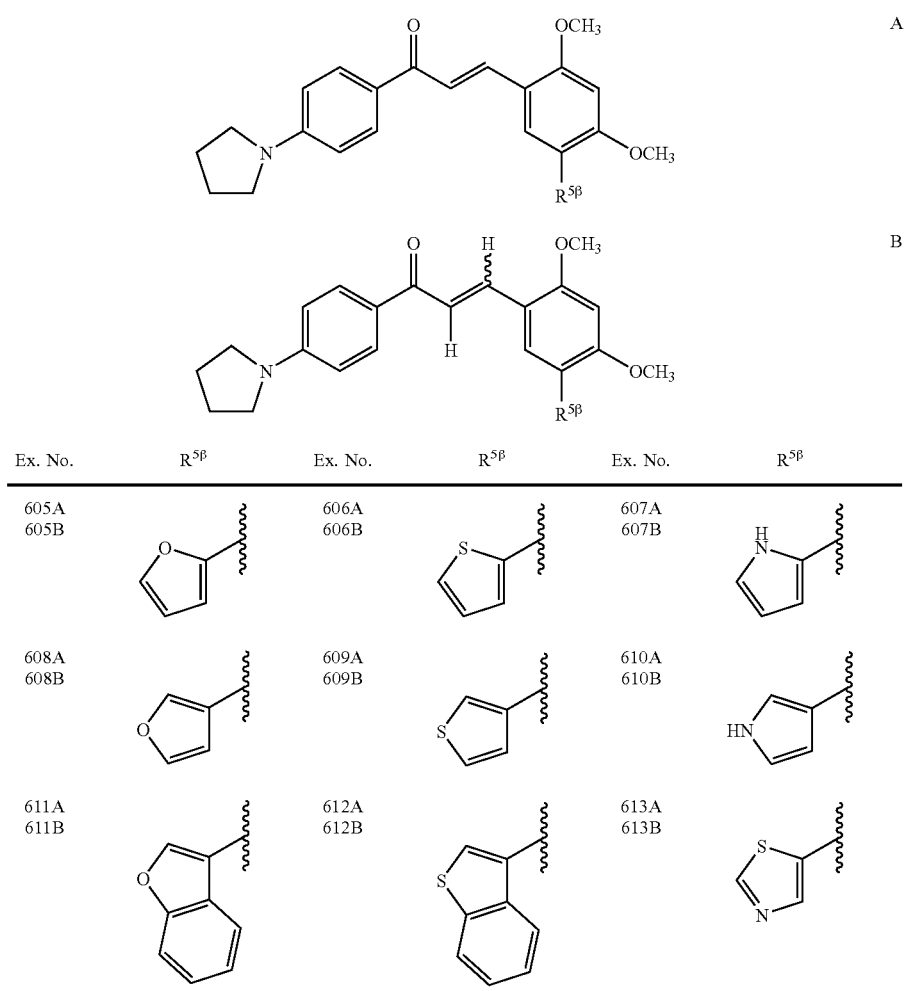

EXAMPLE TABLE 7-continued
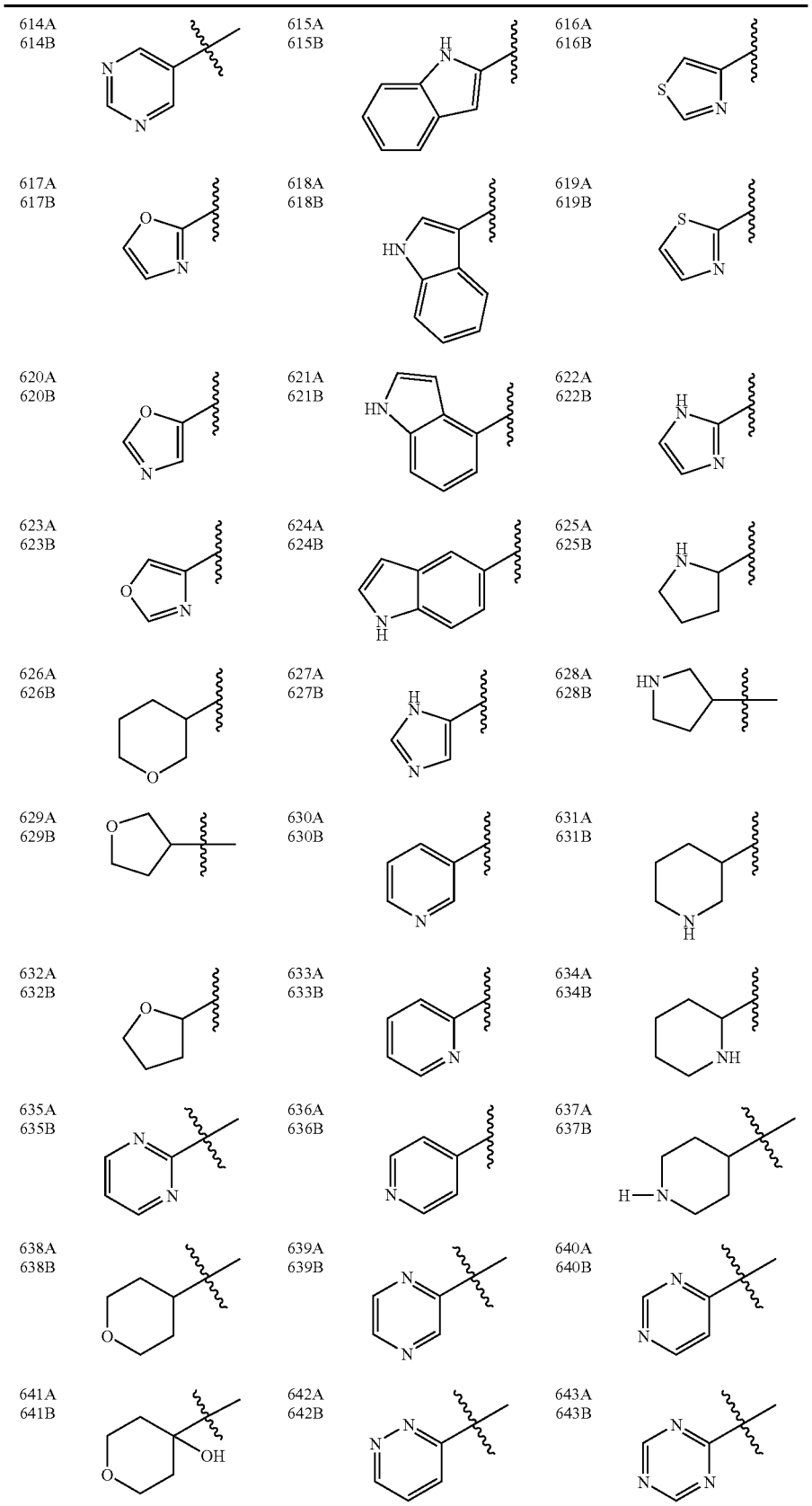

EXAMPLE TABLE 7-continued
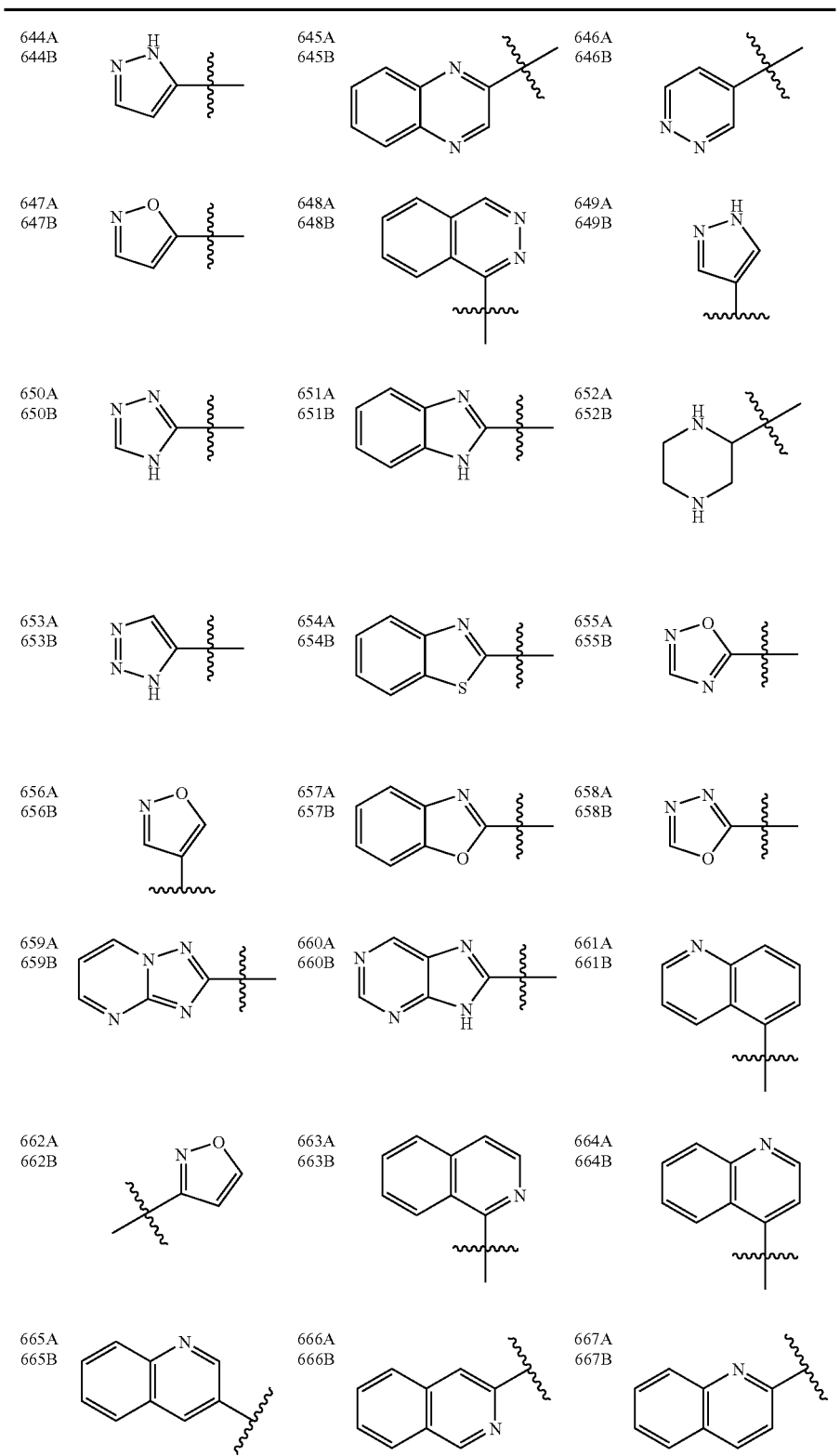

EXAMPLE TABLE 8

Substituted 1-{4-(Methanesulfonylamino)phenyl}-3-[2,4-dimethoxy-(5-heteroaryl or 5-heterocylic)phenyl]-2-propen-1-ones.

A

B

| Ex. No. | $R^{5\beta}$ | Ex. No. | $R^{5\beta}$ | Ex. No. | $R^{5\beta}$ |
|---|---|---|---|---|---|
| 668A 668B | 2-furyl | 669A 669B | 2-thienyl | 670A 670B | 1H-pyrrol-2-yl |
| 671A 671B | 3-furyl | 672A 672B | 3-thienyl | 673A 673B | 1H-pyrrol-3-yl |
| 674A 674B | benzofuran-3-yl | 675A 675B | benzothiophen-3-yl | 676A 676B | thiazol-5-yl |
| 677A 677B | pyrimidin-5-yl (α-methyl) | 678A 678B | 1H-indol-2-yl | 679A 679B | thiazol-4-yl |
| 680A 680B | oxazol-2-yl | 681A 681B | 1H-indol-3-yl | 682A 682B | thiazol-2-yl |
| 683A 683B | oxazol-5-yl | 684A 684B | 1H-indol-4-yl | 685A 685B | 1H-imidazol-2-yl |

EXAMPLE TABLE 8-continued
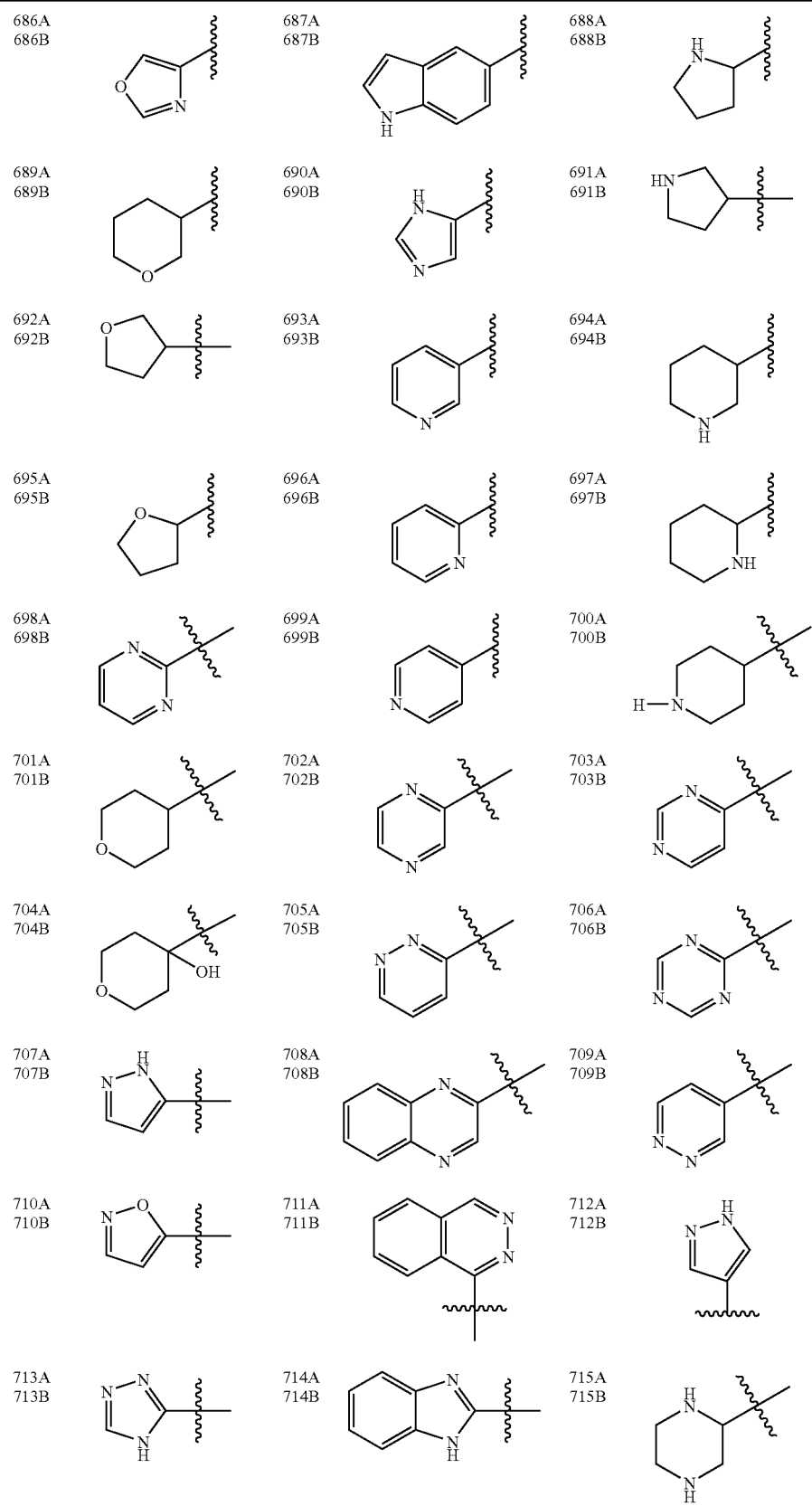

EXAMPLE TABLE 8-continued
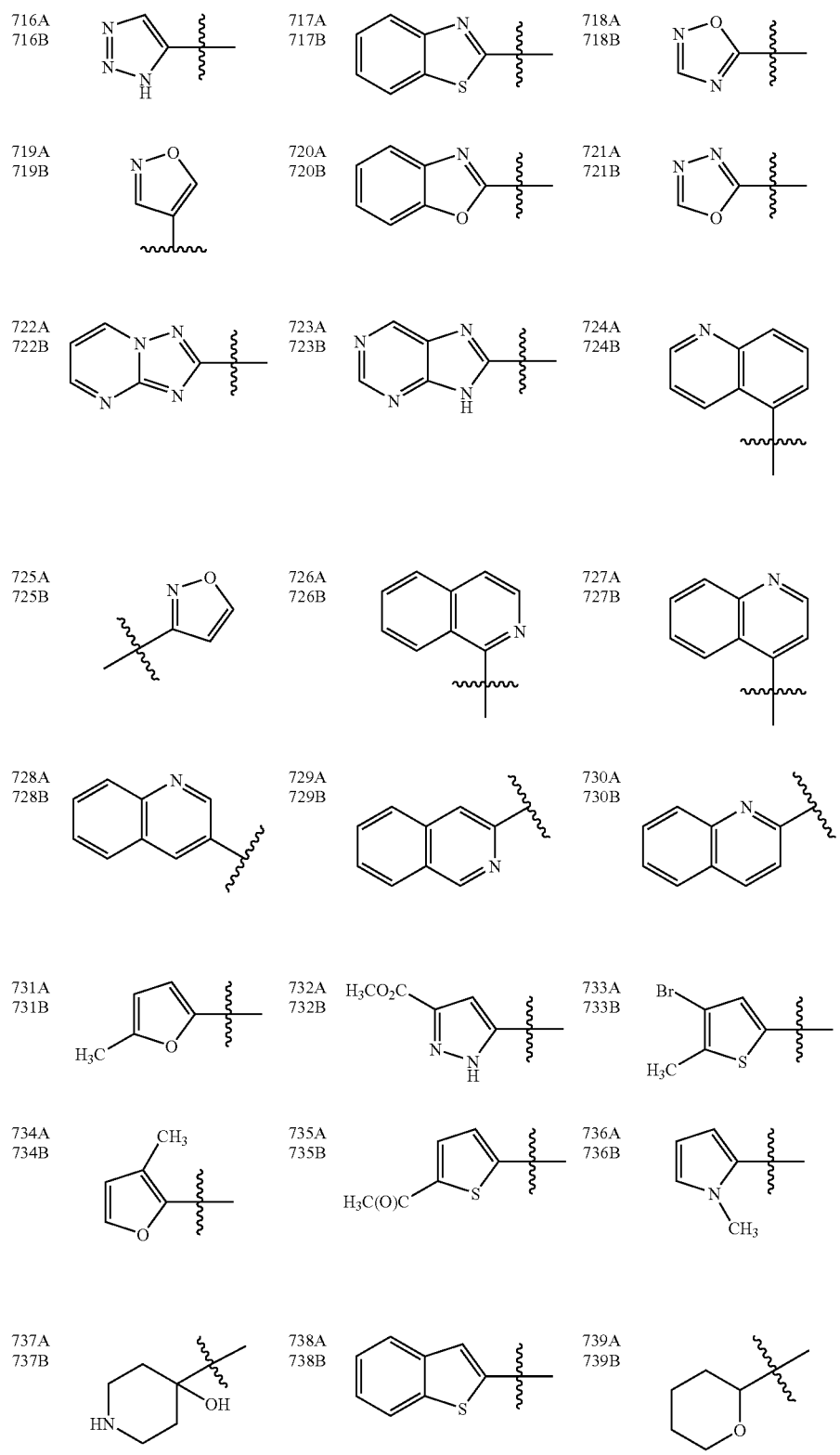

EXAMPLE TABLE 9

Substituted 1-{4-(Methanesulfonylamino)phenyl}-3-[3,4-dimethoxy-(5-heteroaryl or 5-heterocylic)phenyl]-2-propen-1-ones.

A

B

| Ex. No. | R⁵ᵝ | Ex. No. | R⁵ᵝ | Ex. No. | R⁵ᵝ |
|---|---|---|---|---|---|
| 740A 740B | 2-furyl | 741A 741B | 2-thienyl | 742A 742B | 2-pyrrolyl |
| 743A 743B | 3-furyl | 744A 744B | 3-thienyl | 745A 745B | 3-pyrrolyl |
| 746A 746B | 3-benzofuryl | 747A 747B | 3-benzothienyl | 748A 748B | 5-thiazolyl |
| 749A 749B | 5-pyrimidinyl | 750A 750B | 2-indolyl | 751A 751B | 4-thiazolyl |
| 752A 752B | 2-oxazolyl | 753A 753B | 3-indolyl | 754A 754B | 2-thiazolyl |
| 755A 755B | 5-oxazolyl | 756A 756B | 4-indolyl | 757A 757B | 2-imidazolyl |

EXAMPLE TABLE 9-continued
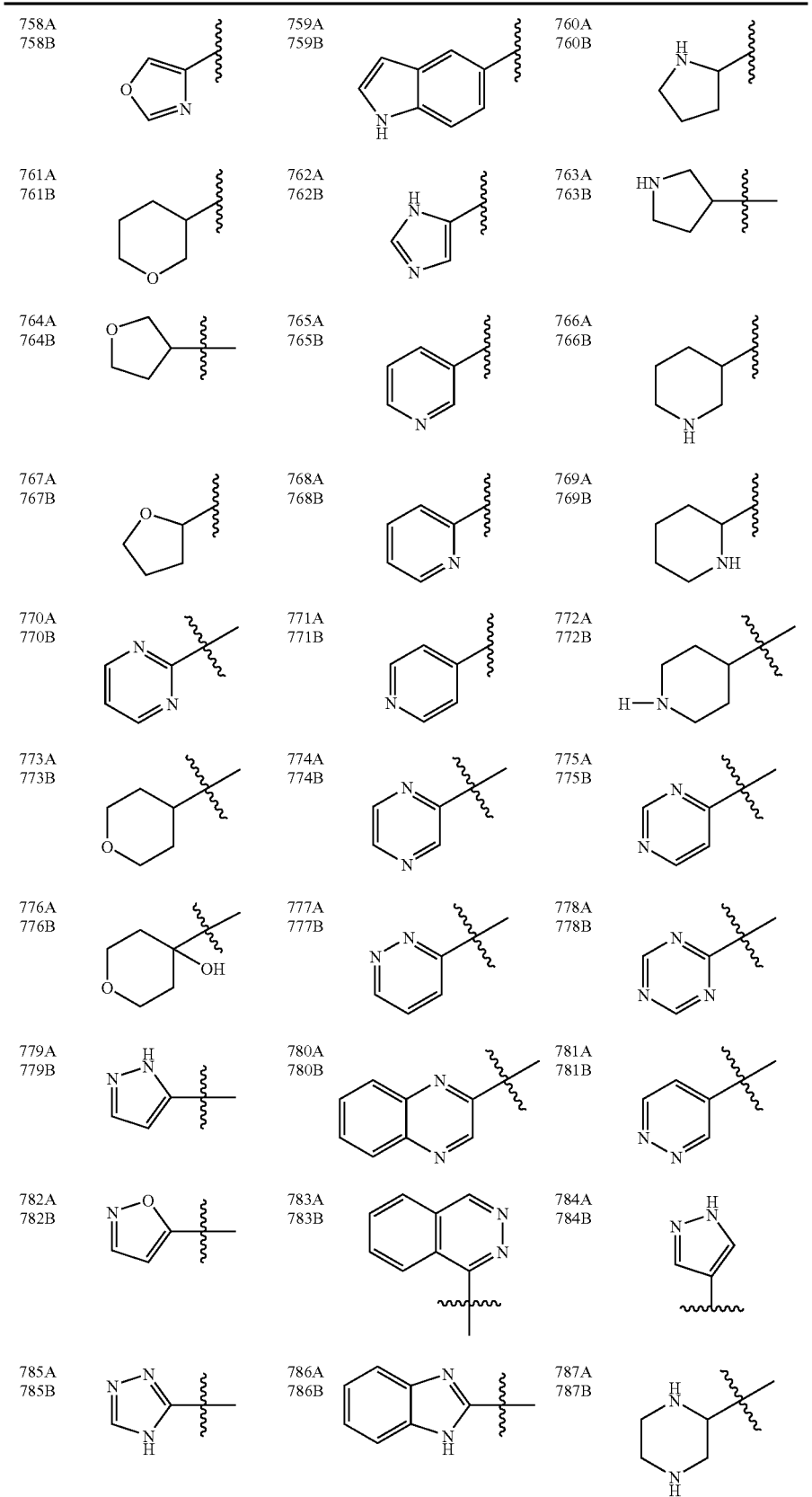

EXAMPLE TABLE 9-continued
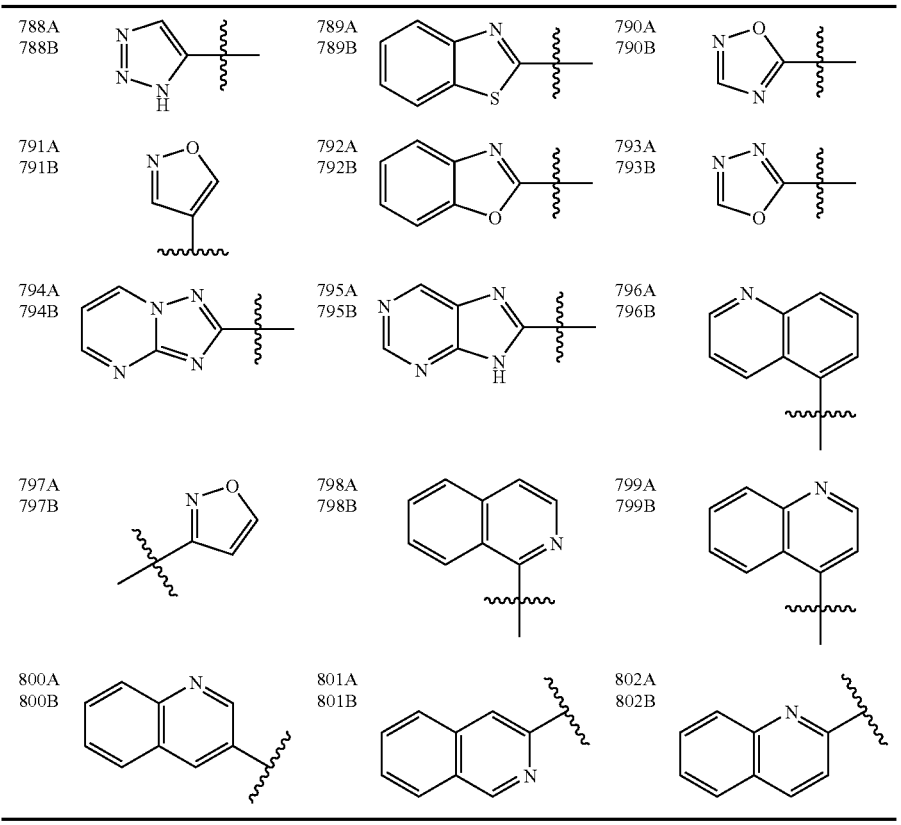
EXAMPLE TABLE 10
Substituted 1-{4-(Amino)phenyl}-3-[3,4-dimethoxy-(5-heteroaryl or 5-heterocylic)phenyl]-2-propen-1-ones.
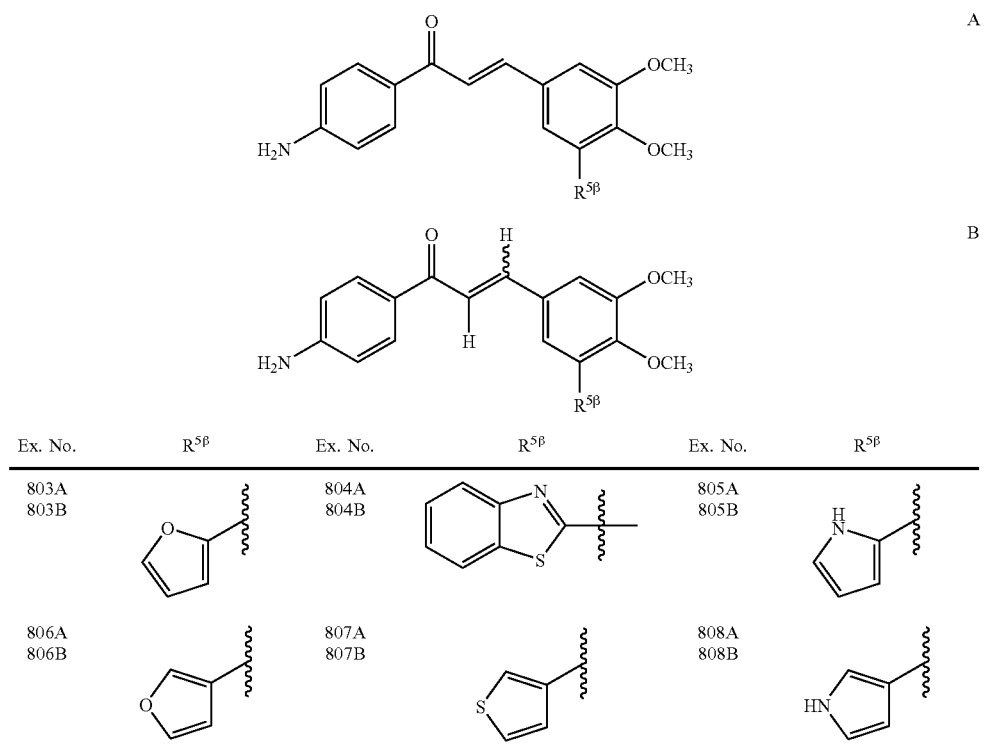

EXAMPLE TABLE 10-continued
| | | | | | |
|---|---|---|---|---|---|
| 809A 809B | 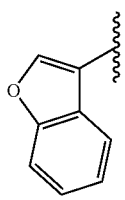 | 810A 810B | 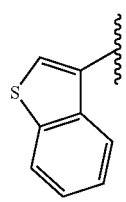 | 811A 811B | 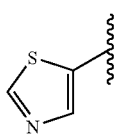 |
| 812A 812B | 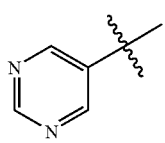 | 813A 813B | 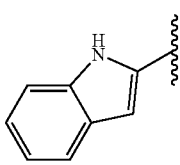 | 814A 814B | 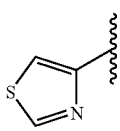 |
| 815A 815B | 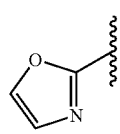 | 816A 816B | 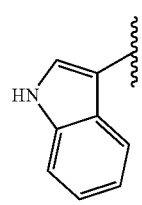 | 817A 817B | 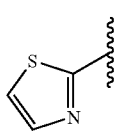 |
| 818A 818B | 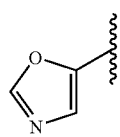 | 819A 819B | 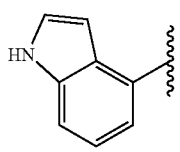 | 820A 820B | 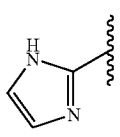 |
| 821A 821B | 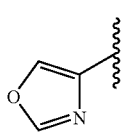 | 822A 822B | 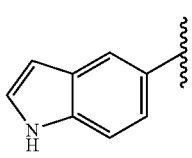 | 823A 823B | 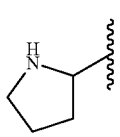 |
| 824A 824B | 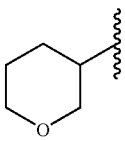 | 825A 825B | 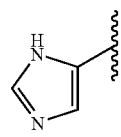 | 826A 826B | 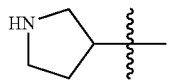 |
| 827A 827B | 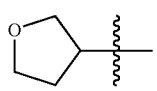 | 828A 828B | 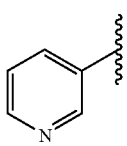 | 829A 829B | 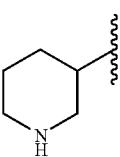 |
| 830A 830B | 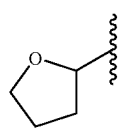 | 831A 831B | 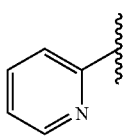 | 832A 832B | 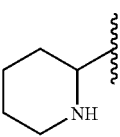 |
| 833A 833B | 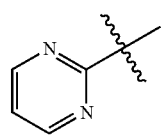 | 834A 834B | 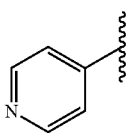 | 835A 835B | 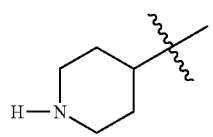 |

EXAMPLE TABLE 10-continued
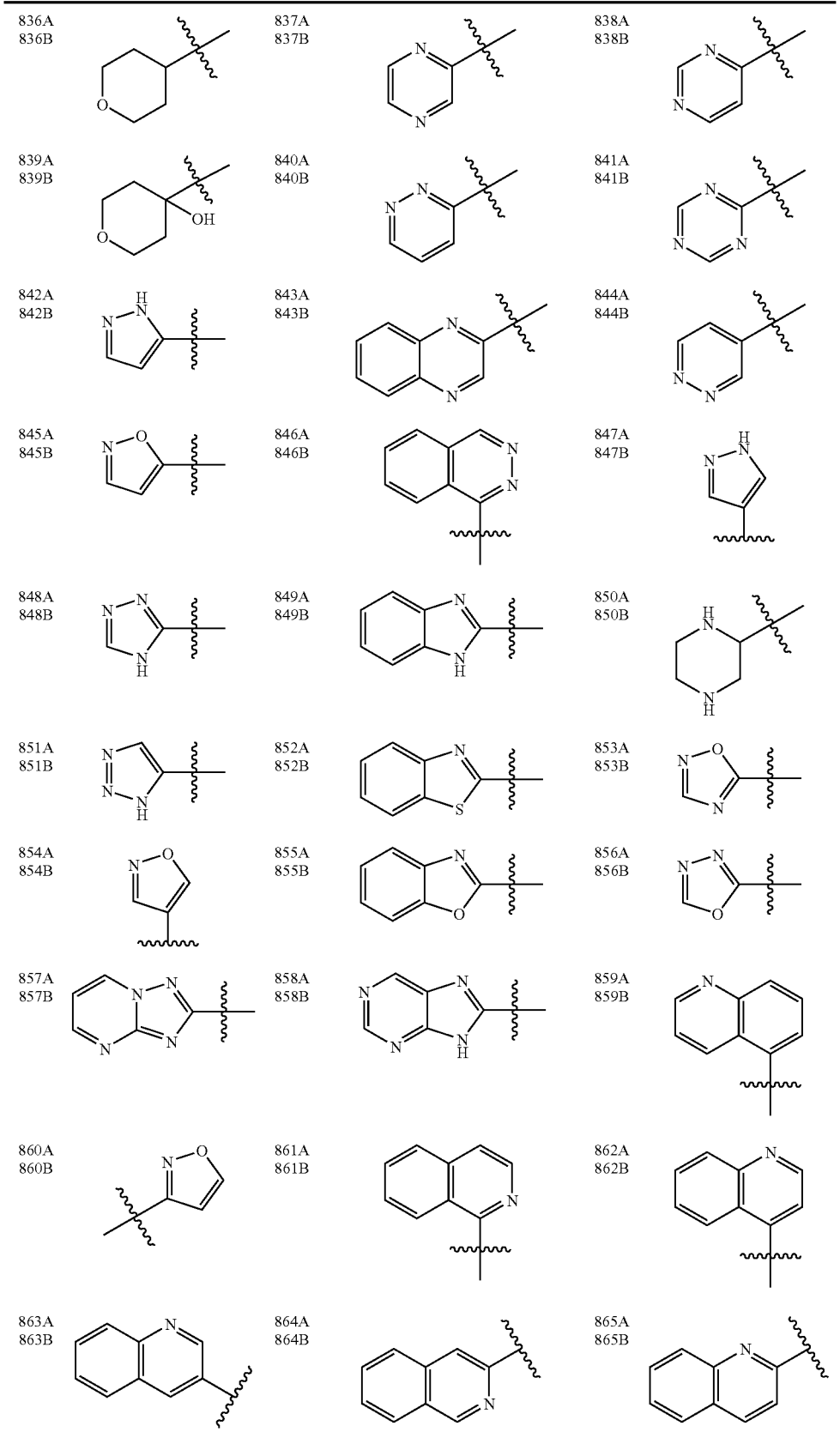

EXAMPLE TABLE 10-continued
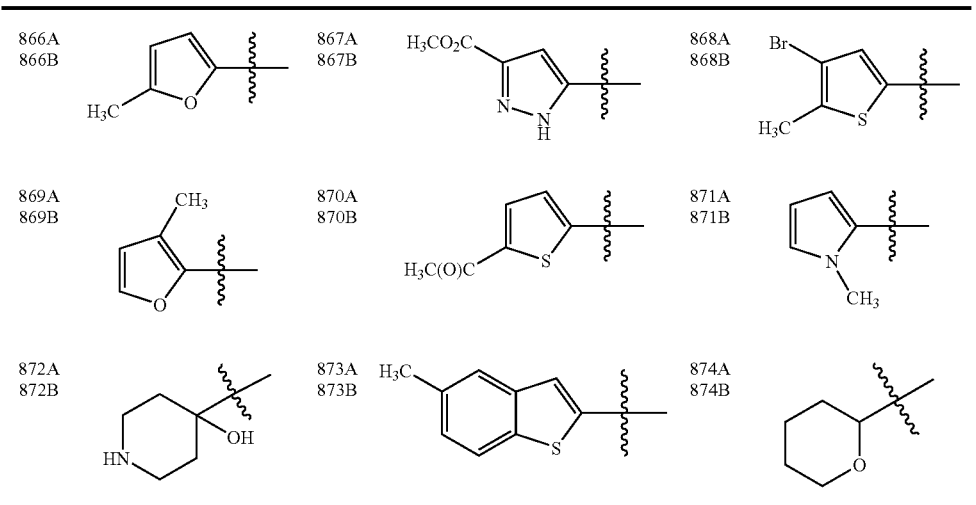
EXAMPLE TABLE 11
Substituted 1-{4-(Amino)phenyl}-3-[2,6-dimethoxy-(4-heteroaryl or 4-heterocylic)-phenyl]-2-propen-1-ones.
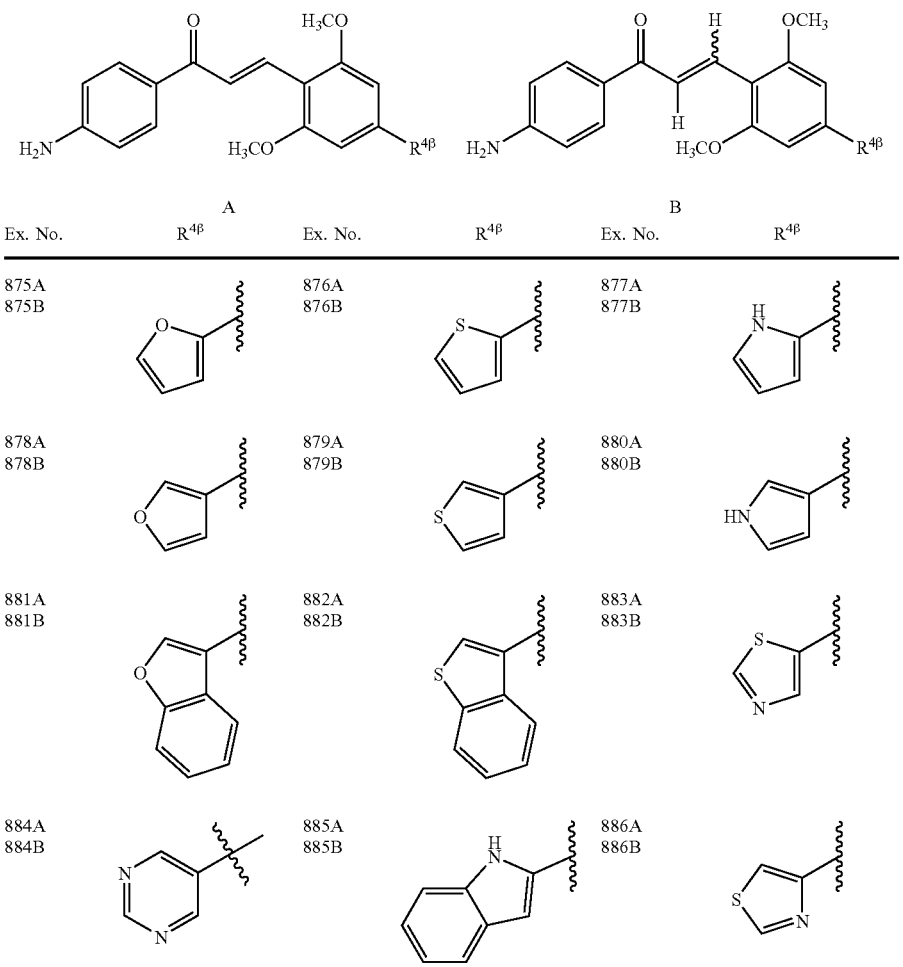

EXAMPLE TABLE 11-continued
Substituted 1-{4-(Amino)phenyl}-3-[2,6-dimethoxy-(4-heteroaryl or 4-heterocylic)-phenyl]-2-propen-1-ones.
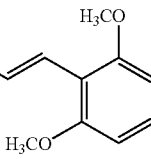
A
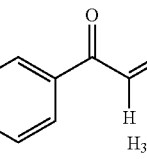
B
| Ex. No. | R$^{4\beta}$ | Ex. No. | R$^{4\beta}$ | Ex. No. | R$^{4\beta}$ |
|---|---|---|---|---|---|
| 887A 887B | 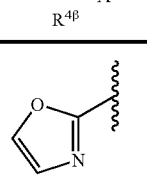 | 888A 888B | 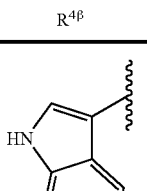 | 889A 889B | 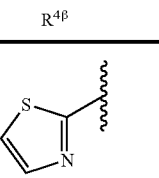 |
| 890A 890B | 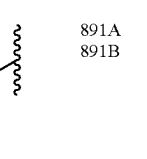 | 891A 891B | 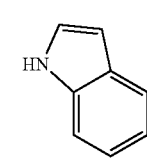 | 892A 892B | 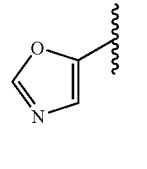 |
| 893A 893B | 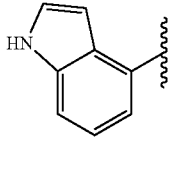 | 894A 894B | 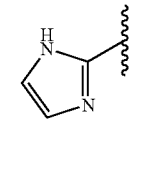 | 895A 895B | 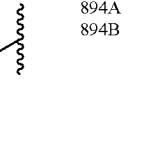 |
| 896A 896B | 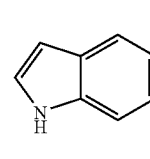 | 897A 897B | 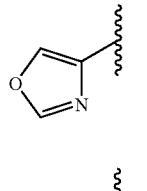 | 898A 898B | 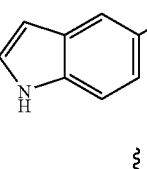 |
| 899A 899B | 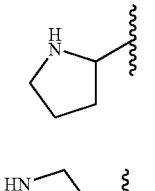 | 900A 900B | 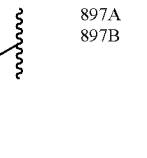 | 901A 901B | 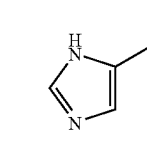 |
| 902A 902B | 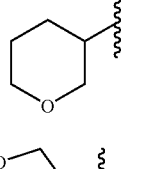 | 903A 903B | 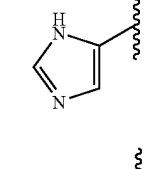 | 904A 904B | 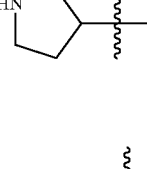 |
| 905A 905B | 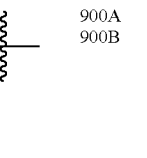 | 906A 906B | 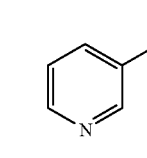 | 907A 907B | 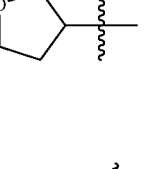 |
| 908A 908B | 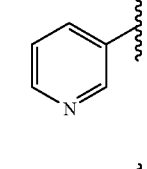 | 909A 909B | 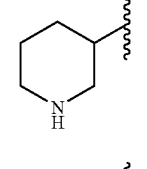 | 910A 910B | 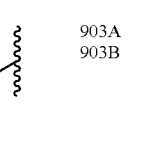 |

EXAMPLE TABLE 11-continued
Substituted 1-{4-(Amino)phenyl}-3-[2,6-dimethoxy-(4-heteroaryl or 4-heterocylic)-phenyl]-2-propen-1-ones.
A
B
| Ex. No. | $R^{4\beta}$ | Ex. No. | $R^{4\beta}$ | Ex. No. | $R^{4\beta}$ |
|---|---|---|---|---|---|
| 911A 911B | 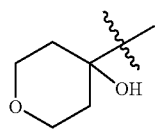 | 912A 912B | 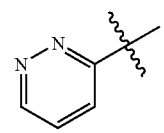 | 913A 913B | 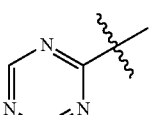 |
| 914A 914B | 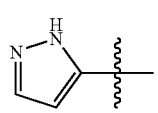 | 915A 915B | 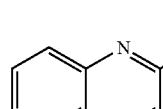 | 916A 916B | 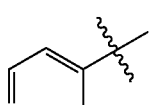 |
| 917A 917B | 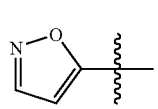 | 918A 918B | 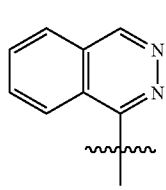 | 919A 919B | 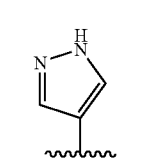 |
| 920A 920B | 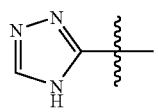 | 921A 921B | 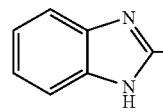 | 922A 922B | 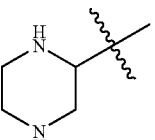 |
| 923A 923B | 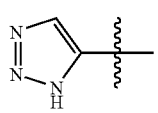 | 924A 924B | 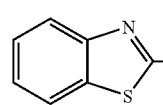 | 925A 925B | 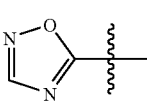 |
| 926A 926B | 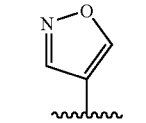 | 927A 927B | 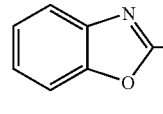 | 928A 928B | 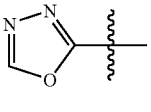 |
| 929A 929B | 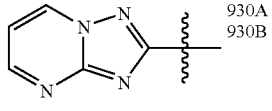 | 930A 930B | 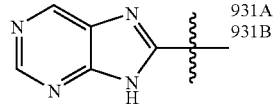 | 931A 931B | 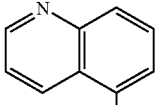 |
| 932A 932B | 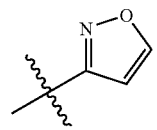 | 933A 933B | 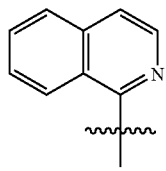 | 934A 934B | 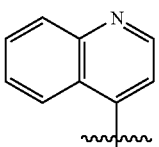 |

EXAMPLE TABLE 11-continued

Substituted 1-{4-(Amino)phenyl}-3-[2,6-dimethoxy-(4-heteroaryl or 4-heterocylic)-phenyl]-2-propen-1-ones.

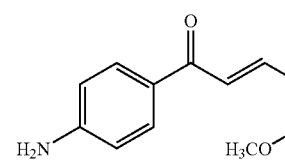
A

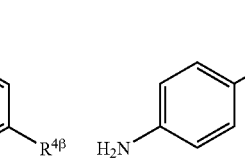
B

| Ex. No. | R$^{4\beta}$ | Ex. No. | R$^{4\beta}$ | Ex. No. | R$^{4\beta}$ |
|---|---|---|---|---|---|
| 935A 935B | 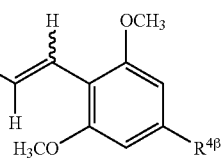 | 936A 936B | 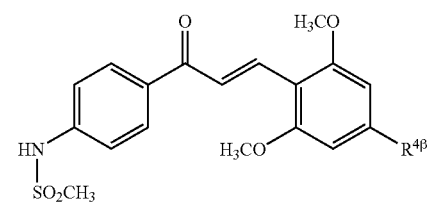 | 937A 937B | 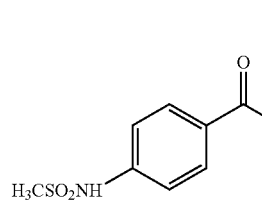 |

EXAMPLE TABLE 12

Substituted 1-{4-(Methanesulfonylamino)phenyl}-3-[2,6-dimethoxy-(4-heteroaryl or 4-heterocylic)phenyl]-2-propen-1-ones.

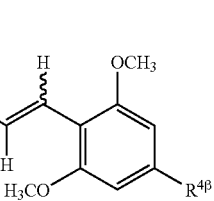
A

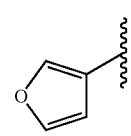
B

| Ex. No. | R$^{4\beta}$ | Ex. No. | R$^{4\beta}$ | Ex. No. | R$^{4\beta}$ |
|---|---|---|---|---|---|
| 938A 938B | 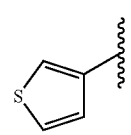 | 939A 939B | 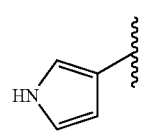 | 940A 940B | 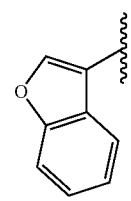 |
| 941A 941B | 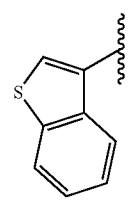 | 942A 942B | 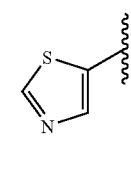 | 943A 943B | 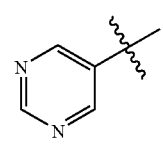 |
| 944A 944B | 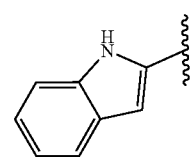 | 945A 945B | 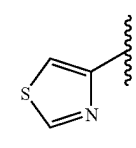 | 946A 946B | |
| 947A 947B | | 948A 948B | | 949A 949B | |

EXAMPLE TABLE 12-continued
Substituted 1-{4-(Methanesulfonylamino)phenyl}-3-[2,6-dimethoxy-(4-heteroaryl or 4-heterocylic)phenyl]-2-propen-1-ones.
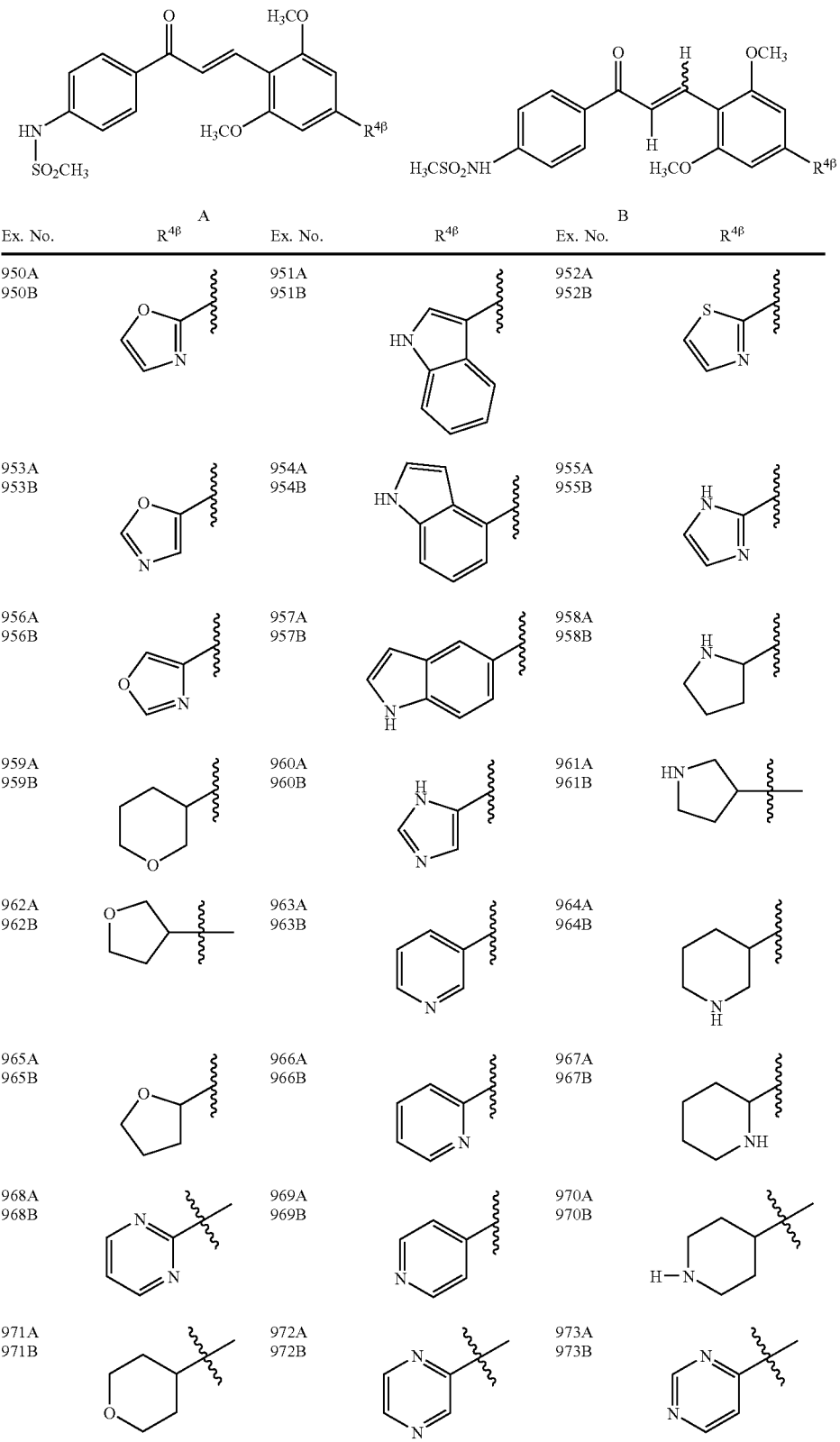

EXAMPLE TABLE 12-continued

Substituted 1-{4-(Methanesulfonylamino)phenyl}-3-[2,6-dimethoxy-(4-heteroaryl or 4-heterocylic)phenyl]-2-propen-1-ones.

| Ex. No. | R$^{4\beta}$ A | Ex. No. | R$^{4\beta}$ | Ex. No. B | R$^{4\beta}$ |
|---|---|---|---|---|---|
| 974A 974B | tetrahydropyran-4-ol-4-yl | 975A 975B | pyridazin-3-yl | 976A 976B | 1,3,5-triazin-2-yl |
| 977A 977B | 1H-pyrazol-5-yl | 978A 978B | quinoxalin-2-yl | 979A 979B | pyridazin-4-yl |
| 980A 980B | isoxazol-5-yl | 981A 981B | phthalazin-1-yl | 982A 982B | 1H-pyrazol-4-yl |
| 983A 983B | 1H-1,2,4-triazol-3-yl | 984A 984B | 1H-benzimidazol-2-yl | 985A 985B | piperazin-2-yl |
| 986A 986B | 1H-1,2,3-triazol-5-yl | 987A 987B | benzothiazol-2-yl | 988A 988B | 1,3,4-oxadiazol-2-yl |
| 989A 989B | isoxazol-4-yl | 990A 990B | benzoxazol-2-yl | 991A 991B | 1,3,4-oxadiazol-2-yl |
| 992A 992B | [1,2,4]triazolo[1,5-a]pyrimidin-2-yl | 993A 993B | 1H-imidazo[4,5-d]pyrimidin-2-yl | 994A 994B | quinolin-5-yl |
| 995A 995B | isoxazol-3-yl | 996A 996B | isoquinolin-1-yl | 997A 997B | quinolin-4-yl |

EXAMPLE TABLE 12-continued
Substituted 1-{4-(Methanesulfonylamino)phenyl}-3-[2,6-dimethoxy-(4-heteroaryl or 4-heterocylic)phenyl]-2-propen-1-ones.
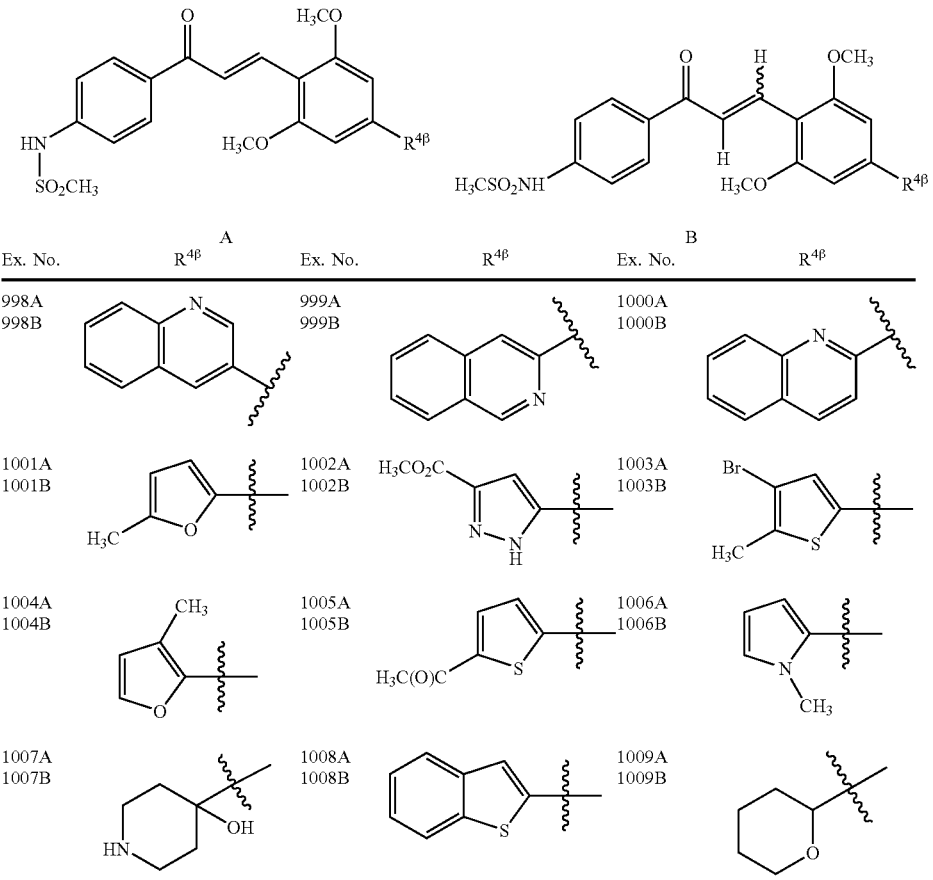
EXAMPLE TABLE 13
Substituted 1-(1H-Indol-5-yl)-3-{2,4-dimethoxy-5-(heteroaryl or heterocyclic)phenyl}-propen-2-ones.
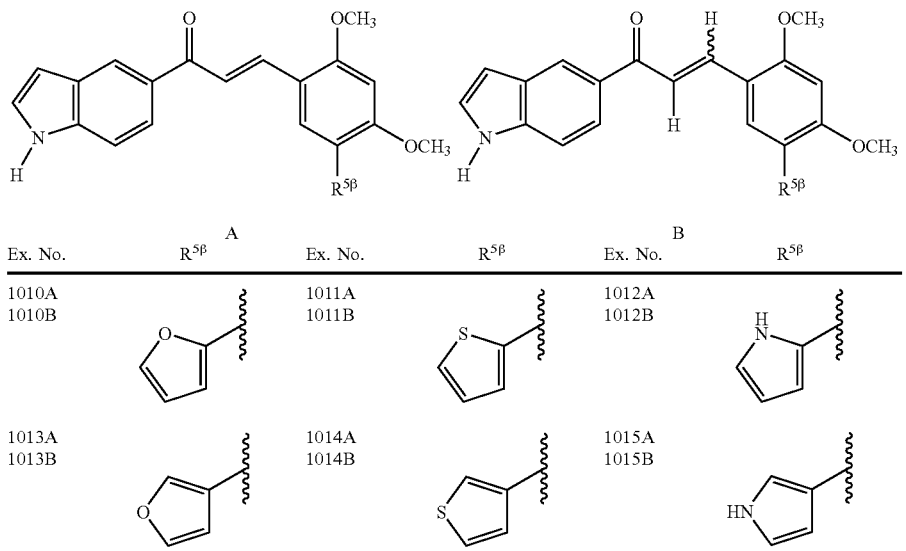

EXAMPLE TABLE 13-continued
Substituted 1-(1H-Indol-5-yl)-3-{2,4-dimethoxy-5-(heteroaryl or heterocyclic)phenyl}-propen-2-ones.
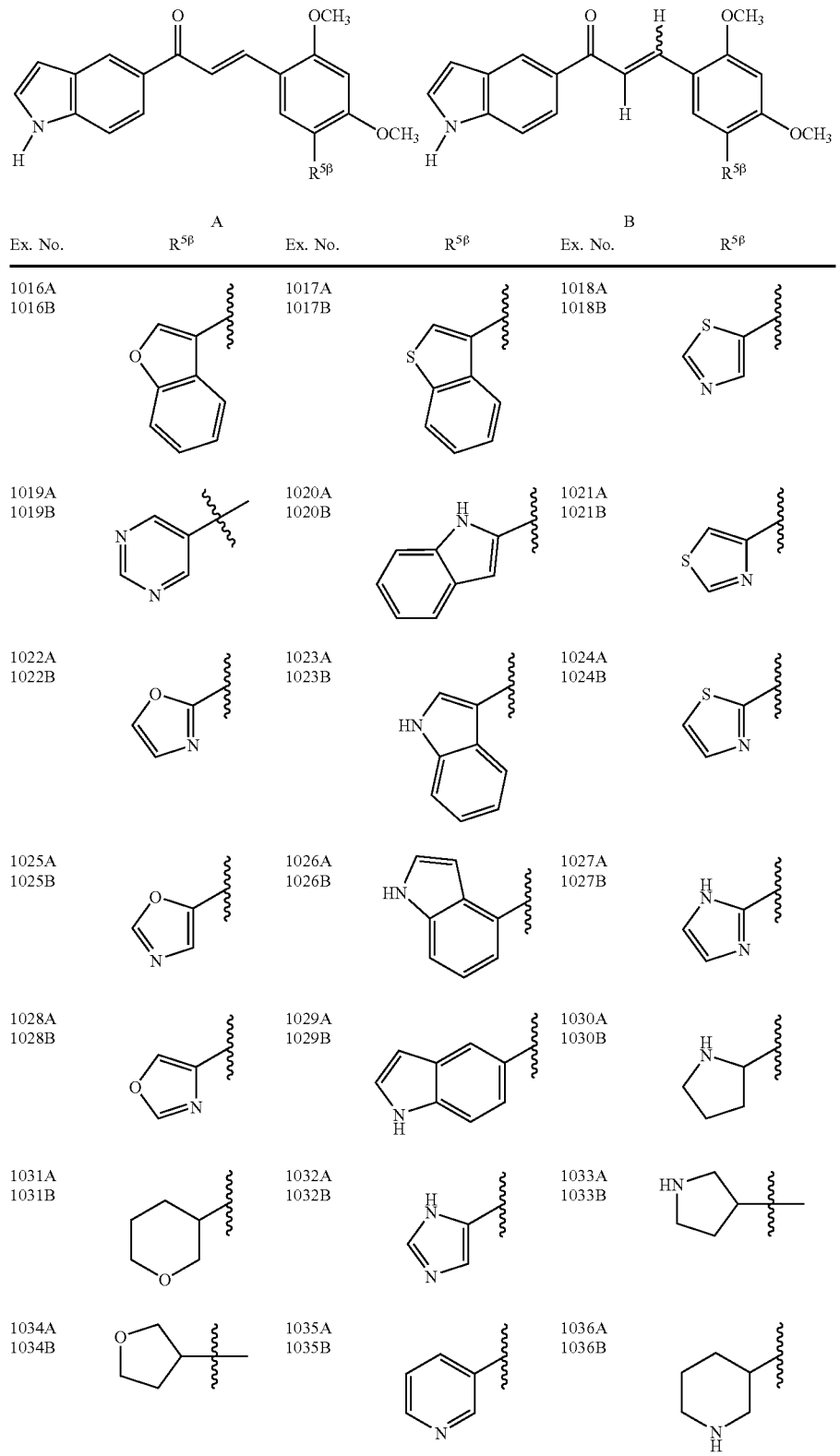

EXAMPLE TABLE 13-continued

Substituted 1-(1H-Indol-5-yl)-3-{2,4-dimethoxy-5-(heteroaryl or heterocyclic)phenyl}-propen-2-ones.

A / B

| Ex. No. | R$^{5\beta}$ | Ex. No. | R$^{5\beta}$ | Ex. No. | R$^{5\beta}$ |
|---|---|---|---|---|---|
| 1037A 1037B | tetrahydrofuran-2-yl | 1038A 1038B | pyridin-2-yl | 1039A 1039B | piperidin-2-yl |
| 1040A 1040B | pyrimidin-2-yl | 1041A 1041B | pyridin-4-yl | 1042A 1042B | piperidin-4-yl |
| 1043A 1043B | tetrahydropyran-4-yl | 1044A 1044B | pyrazin-2-yl | 1045A 1045B | pyrimidin-4-yl |
| 1046A 1046B | 4-hydroxy-tetrahydropyran-4-yl | 1047A 1047B | pyridazin-3-yl | 1048A 1048B | 1,3,5-triazin-2-yl |
| 1049A 1049B | 1H-pyrazol-3-yl | 1050A 1050B | quinoxalin-2-yl | 1051A 1051B | pyridazin-4-yl |
| 1052A 1052B | isoxazol-5-yl | 1053A 1053B | phthalazin-1-yl | 1054A 1054B | 1H-pyrazol-4-yl |
| 1055A 1055B | 1H-1,2,4-triazol-3-yl | 1056A 1056B | 1H-benzimidazol-2-yl | 1057A 1057B | piperazin-2-yl |
| 1058A 1058B | 1H-1,2,3-triazol-4-yl | 1059A 1059B | benzothiazol-2-yl | 1060A 1060B | 1,3,4-oxadiazol-2-yl |

EXAMPLE TABLE 13-continued
Substituted 1-(1H-Indol-5-yl)-3-{2,4-dimethoxy-5-(heteroaryl or heterocyclic)phenyl}-propen-2-ones.
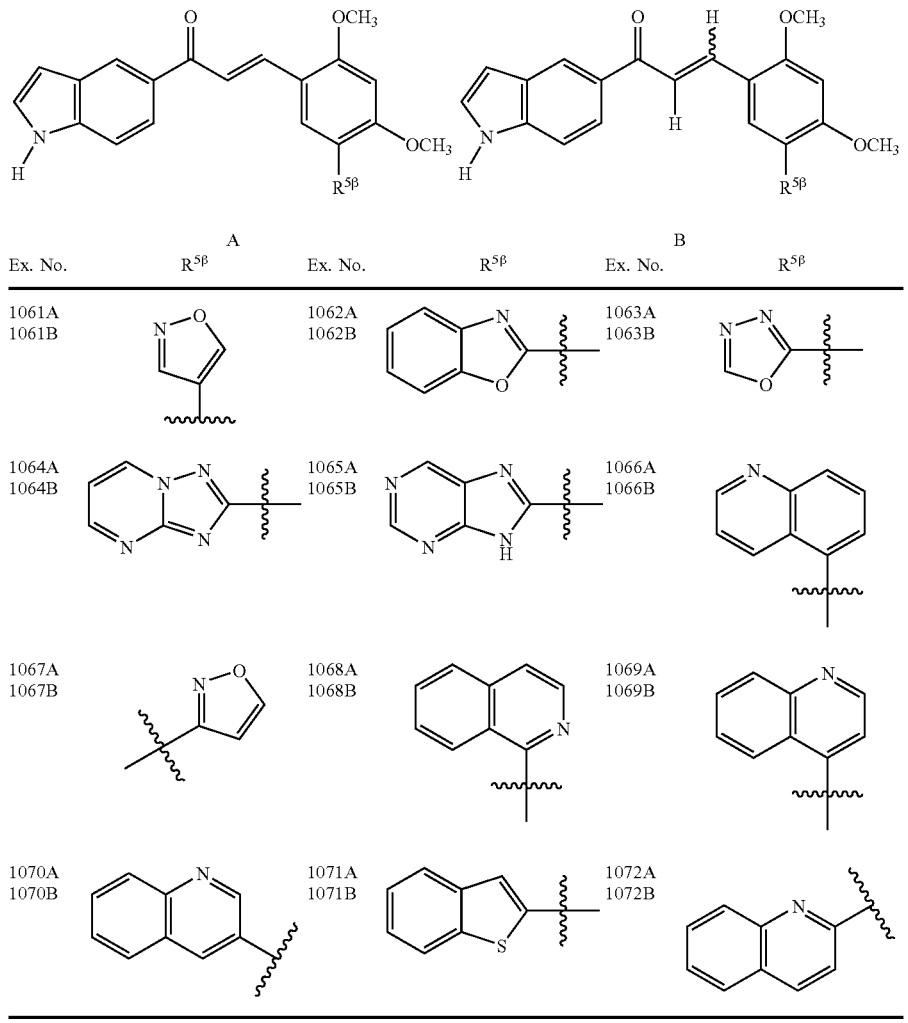
EXAMPLE TABLE 14
Substituted 1-(1H-Indol-5-yl)-3-{3,4-dimethoxy-5-(heteroaryl or heterocyclic)phenyl}-propen-2-ones.
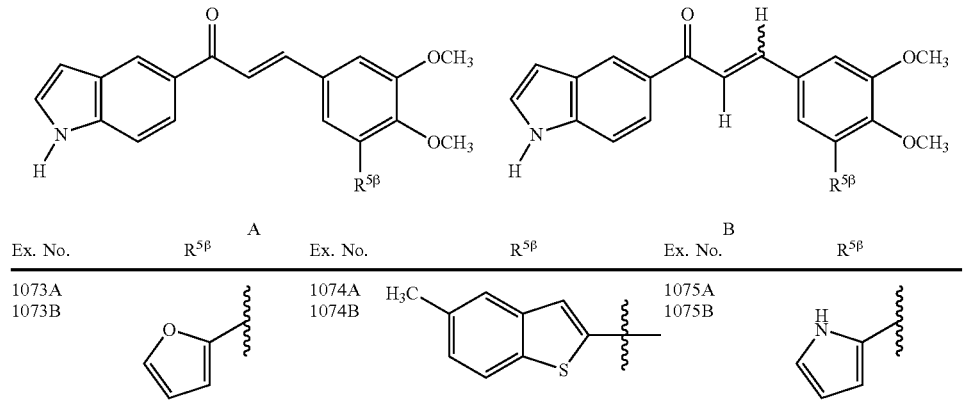

EXAMPLE TABLE 14-continued

Substituted 1-(1H-Indol-5-yl)-3-{3,4-dimethoxy-5-(heteroaryl or heterocyclic)phenyl}-propen-2-ones.

A / B

| Ex. No. | R⁵β | Ex. No. | R⁵β | Ex. No. | R⁵β |
|---|---|---|---|---|---|
| 1076A 1076B | furan-3-yl | 1077A 1077B | thiophen-3-yl | 1078A 1078B | 1H-pyrrol-3-yl |
| 1079A 1079B | benzofuran-3-yl | 1080A 1080B | benzothiophen-3-yl | 1081A 1081B | thiazol-5-yl |
| 1082A 1082B | pyrimidin-5-yl (with CH) | 1083A 1083B | 1H-indol-2-yl | 1084A 1084B | thiazol-4-yl |
| 1085A 1085B | oxazol-2-yl | 1086A 1086B | 1H-indol-3-yl | 1087A 1087B | thiazol-2-yl |
| 1088A 1088B | oxazol-5-yl | 1089A 1089B | 1H-indol-4-yl | 1090A 1090B | 1H-imidazol-2-yl |
| 1091A 1091B | oxazol-4-yl | 1092A 1092B | 1H-indol-5-yl | 1093A 1093B | pyrrolidin-2-yl |
| 1094A 1094B | tetrahydropyran-3-yl | 1095A 1095B | 1H-imidazol-4-yl | 1096A 1096B | pyrrolidin-3-yl (with CH) |

EXAMPLE TABLE 14-continued

Substituted 1-(1H-Indol-5-yl)-3-{3,4-dimethoxy-5-(heteroaryl or heterocyclic)phenyl}-propen-2-ones.

| Ex. No. | A R⁵ᵝ | Ex. No. | R⁵ᵝ | Ex. No. | B R⁵ᵝ |
|---|---|---|---|---|---|
| 1097A 1097B | tetrahydrofuran-3-yl | 1098A 1098B |  | 1099A 1099B | pyridin-3-yl | piperidin-3-yl |
| 1100A 1100B | tetrahydrofuran-2-yl | 1101A 1101B | pyridin-2-yl | 1102A 1102B | piperidin-2-yl |
| 1103A 1103B | pyrimidin-2-yl | 1104A 1104B | pyridin-4-yl | 1105A 1105B | piperidin-4-yl |
| 1106A 1106B | tetrahydropyran-4-yl | 1107A 1107B | pyrazin-2-yl | 1108A 1108B | pyrimidin-4-yl |
| 1109A 1109B | 4-hydroxytetrahydropyran-4-yl | 1110A 1110B | pyridazin-3-yl | 1111A 1111B | 1,3,5-triazin-2-yl |
| 1112A 1112B | 1H-pyrazol-5-yl | 1113A 1113B | quinoxalin-2-yl | 1114A 1114B | pyridazin-4-yl |
| 1115A 1115B | isoxazol-5-yl | 1116A 1116B | phthalazin-1-yl | 1117A 1117B | 1H-pyrazol-4-yl |
| 1118A 1118B | 1H-1,2,4-triazol-3-yl | 1119A 1119B | 1H-benzimidazol-2-yl | 1120A 1120B | piperazin-3-yl |

EXAMPLE TABLE 14-continued
Substituted 1-(1H-Indol-5-yl)-3-{3,4-dimethoxy-5-(heteroaryl or heterocyclic)phenyl}-propen-2-ones.
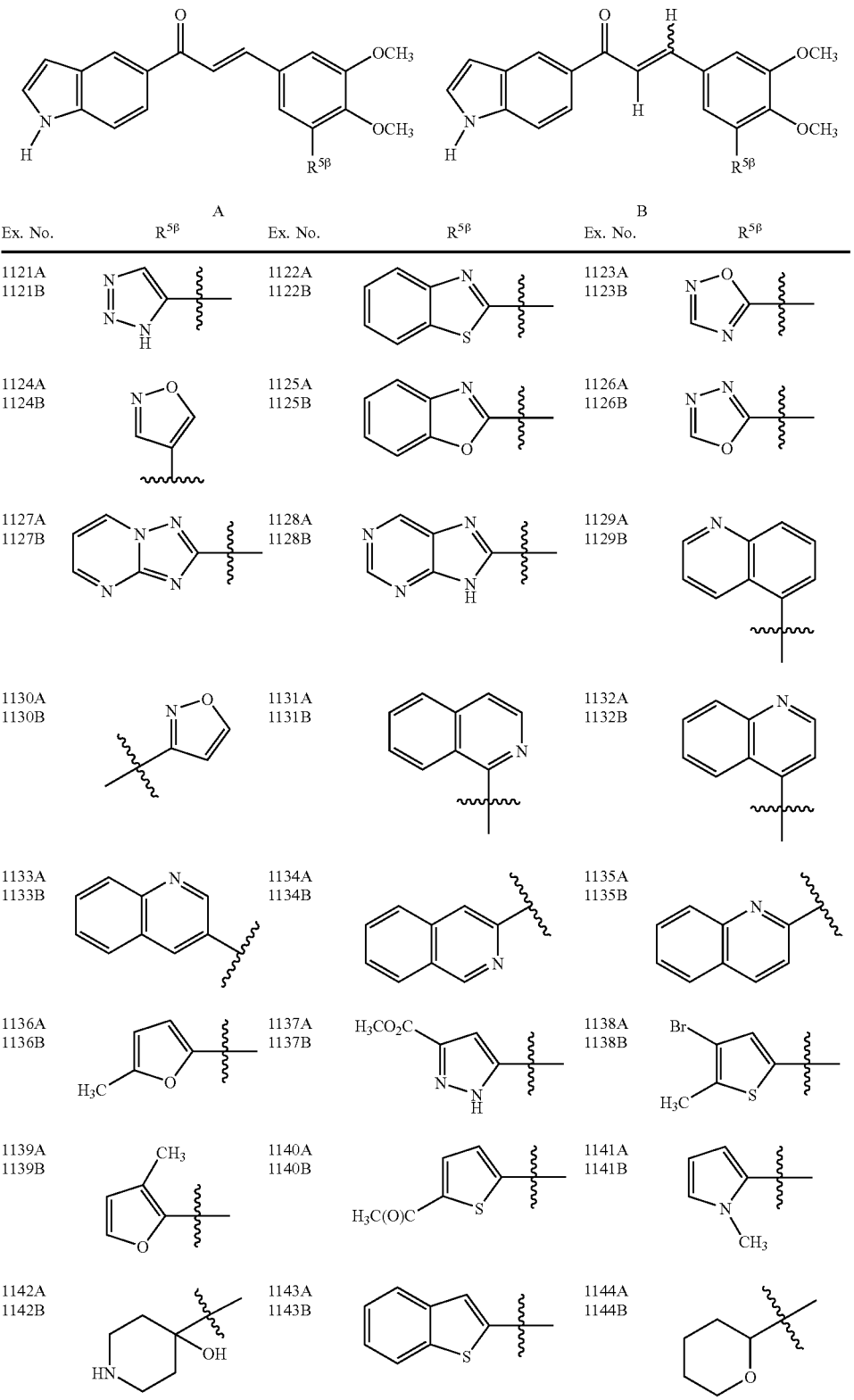

EXAMPLE TABLE 15

Substituted 1-(1H-1-Methyl-indol-5-yl)-3-{2,4-dimethoxy-5-(heteroaryl or heterocyclic)phenyl}-propen-2-ones.

| Ex. No. | A R$^{5\beta}$ | Ex. No. | R$^{5\beta}$ | Ex. No. | B R$^{5\beta}$ |
|---|---|---|---|---|---|
| 1145A 1156B | 2-furyl | 1146A 1146B | 2-thienyl | 1147A 1147B | 2-pyrrolyl |
| 1148A 1148B | 3-furyl | 1149A 1149B | 3-thienyl | 1150A 1150B | 3-pyrrolyl |
| 1151A 1151B | benzofuran-3-yl | 1152A 1152B | benzothiophen-3-yl | 1153A 1153B | thiazol-5-yl |
| 1154A 1154B | pyrimidin-5-yl | 1155A 1155B | indol-2-yl | 1156A 1156B | thiazol-4-yl |
| 1157A 1157B | oxazol-2-yl | 1158A 1158B | indol-3-yl | 1159A 1159B | thiazol-2-yl |
| 1160A 1160B | oxazol-5-yl | 1161A 1161B | indol-4-yl | 1162A 1162B | imidazol-2-yl |
| 1163A 1163B | oxazol-4-yl | 1164A 1164B | indol-5-yl | 1165A 1165B | pyrrolidin-2-yl |

EXAMPLE TABLE 15-continued

Substituted 1-(1H-1-Methyl-indol-5-yl)-3-{2,4-dimethoxy-5-(heteroaryl or heterocyclic)phenyl}-propen-2-ones.

A: 1-(1-methyl-1H-indol-5-yl)-3-(2,4-dimethoxy-5-R⁵ᵝ-phenyl)-prop-2-en-1-one (E-isomer)
B: 1-(1-methyl-1H-indol-5-yl)-3-(2,4-dimethoxy-5-R⁵ᵝ-phenyl)-prop-2-en-1-one (Z-isomer)

| Ex. No. | R⁵ᵝ | Ex. No. | R⁵ᵝ | Ex. No. | R⁵ᵝ |
|---|---|---|---|---|---|
| 1166A, 1166B | tetrahydropyran-3-yl | 1167A, 1167B | 1H-imidazol-5-yl | 1168A, 1168B | pyrrolidin-3-yl |
| 1169A, 1169B | tetrahydrofuran-3-yl | 1170A, 1170B | pyridin-3-yl | 1171A, 1171B | piperidin-3-yl |
| 1172A, 1172B | tetrahydrofuran-2-yl | 1173A, 1173B | pyridin-2-yl | 1174A, 1174B | piperidin-2-yl |
| 1175A, 1175B | pyrimidin-2-yl | 1176A, 1176B | pyridin-4-yl | 1177A, 1177B | piperidin-4-yl |
| 1178A, 1178B | tetrahydropyran-4-yl | 1179A, 1179B | pyrazin-2-yl | 1180A, 1180B | pyrimidin-4-yl |
| 1181A, 1181B | 4-hydroxy-tetrahydropyran-4-yl | 1182A, 1182B | pyridazin-3-yl | 1183A, 1183B | 1,3,5-triazin-2-yl |
| 1184A, 1184B | 1H-pyrazol-3-yl | 1185A, 1185B | quinoxalin-2-yl | 1186A, 1186B | pyridazin-4-yl |
| 1187A, 1187B | isoxazol-5-yl | 1188A, 1188B | phthalazin-1-yl | 1189A, 1189B | 1H-pyrazol-4-yl |

EXAMPLE TABLE 15-continued
Substituted 1-(1H-1-Methyl-indol-5-yl)-3-{2,4-dimethoxy-5-(heteroaryl or heterocyclic)phenyl}-propen-2-ones.
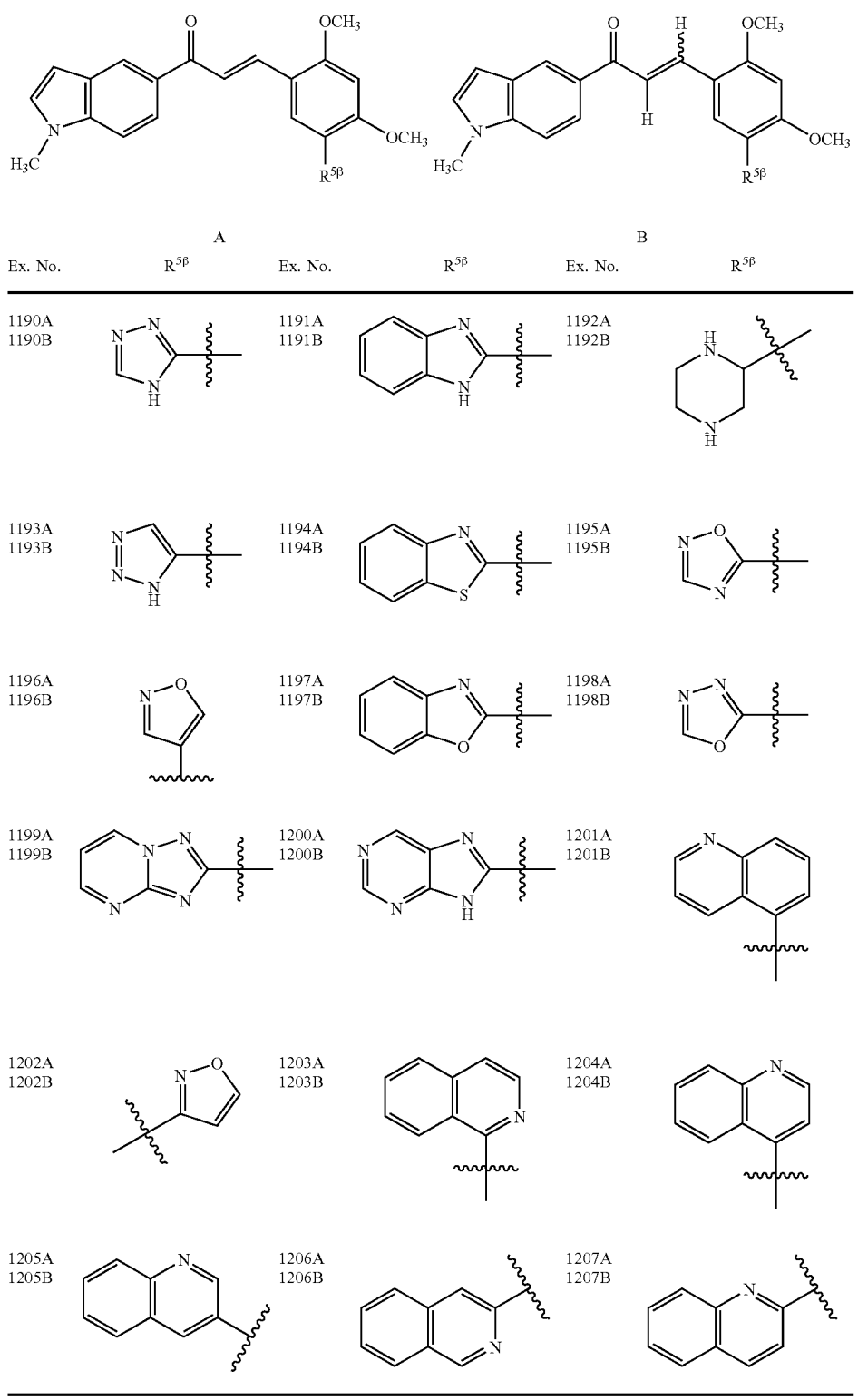

EXAMPLE TABLE 17
Substituted 1-(1H-1-Methyl-indol-5-yl)-3-{3,4-dimethoxy-5-(heteroaryl or heterocyclic)phenyl}-propen-2-ones.
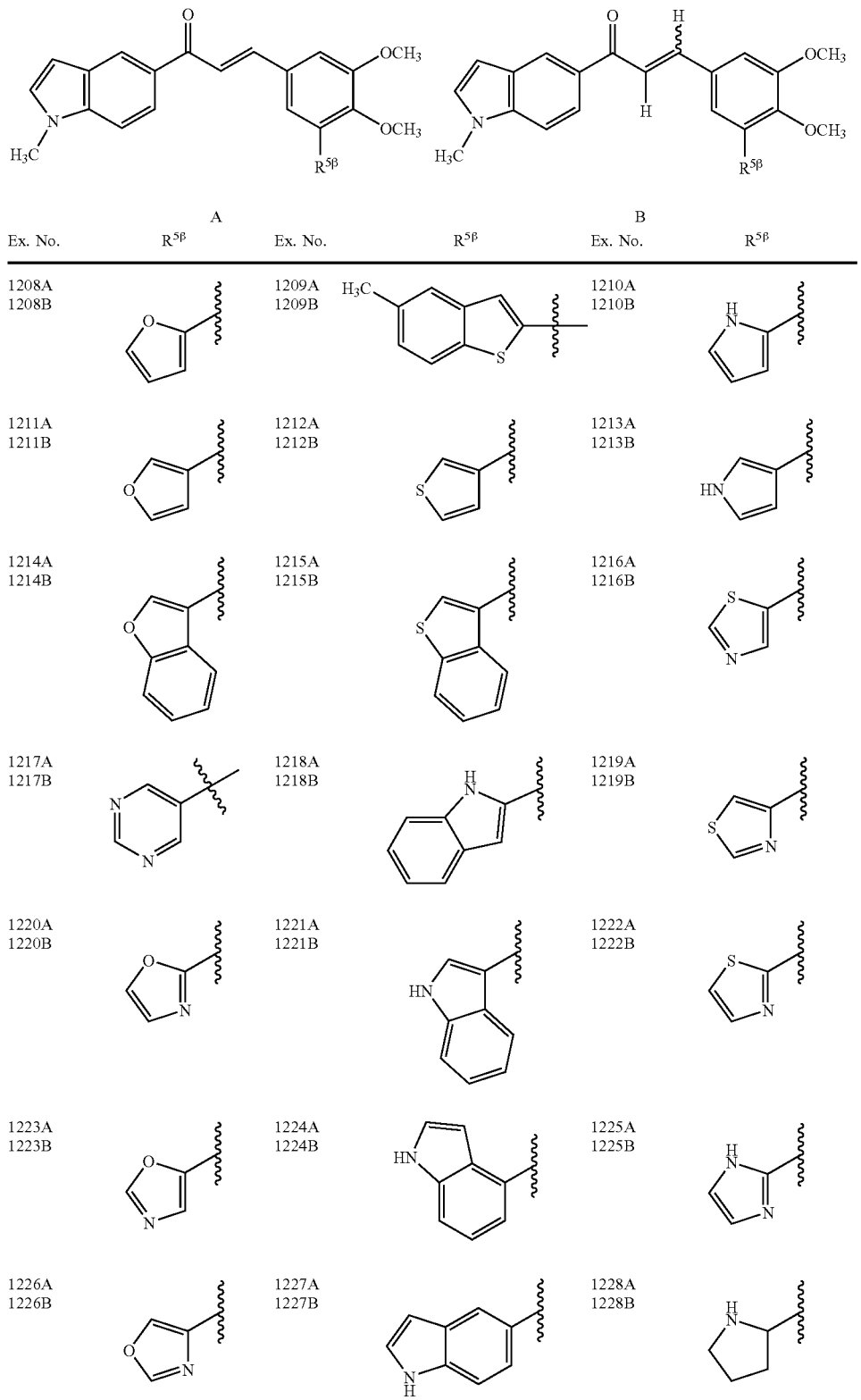

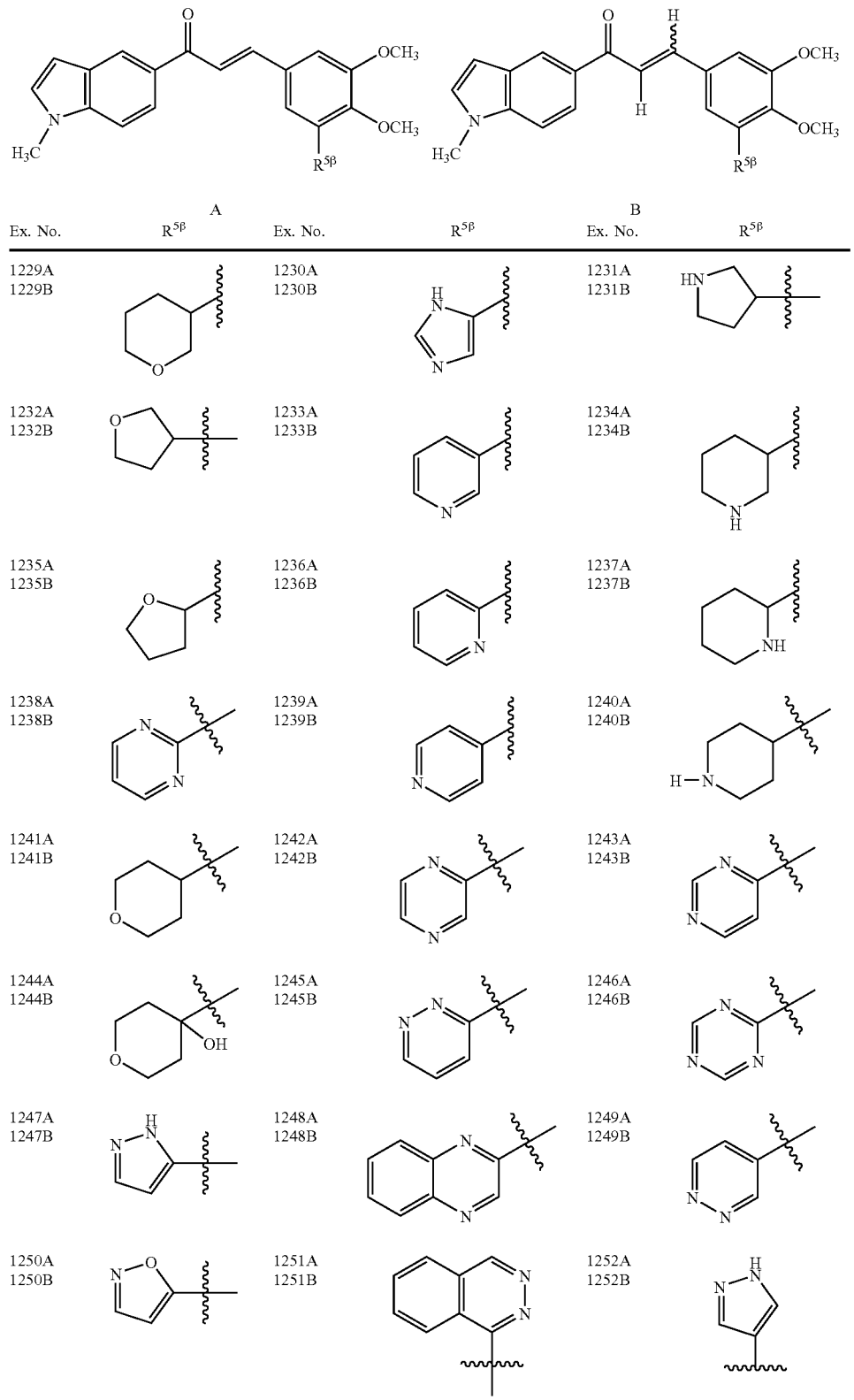

EXAMPLE TABLE 17-continued

Substituted 1-(1H-1-Methyl-indol-5-yl)-3-{3,4-dimethoxy-5-(heteroaryl or heterocyclic)phenyl}-propen-2-ones.

| Ex. No. | R$^{5\beta}$ (A) | Ex. No. | R$^{5\beta}$ | Ex. No. | R$^{5\beta}$ (B) |
|---|---|---|---|---|---|
| 1253A 1253B | triazole | 1254A 1254B | benzimidazole | 1255A 1255B | piperazine |
| 1256A 1256B | triazole | 1257A 1257B | benzothiazole | 1258A 1258B | oxadiazole |
| 1259A 1259B | isoxazole | 1260A 1260B | benzoxazole | 1261A 1261B | oxadiazole |
| 1262A 1262B | triazolopyrimidine | 1263A 1263B | imidazopyrimidine | 1264A 1264B | quinoline (5-yl) |
| 1265A 1265B | isoxazole | 1266A 1266B | isoquinoline | 1267A 1267B | quinoline (4-yl) |
| 1268A 1268B | quinoline (3-yl) | 1269A 1269B | isoquinoline | 1270A 1270B | quinoline (2-yl) |
| 1271A 1271B | 5-methylfuran | 1272A 1272B | methyl pyrazole-carboxylate | 1273A 1273B | 4-bromo-5-methylthiophene |
| 1274A 1274B | 3-methylfuran | 1275A 1275B | 5-acetylthiophene | 1276A 1276B | 1-methylpyrrole |

EXAMPLE TABLE 17-continued

Substituted 1-(1H-1-Methyl-indol-5-yl)-3-{3,4-dimethoxy-5-(heteroaryl or heterocyclic)phenyl}-propen-2-ones.

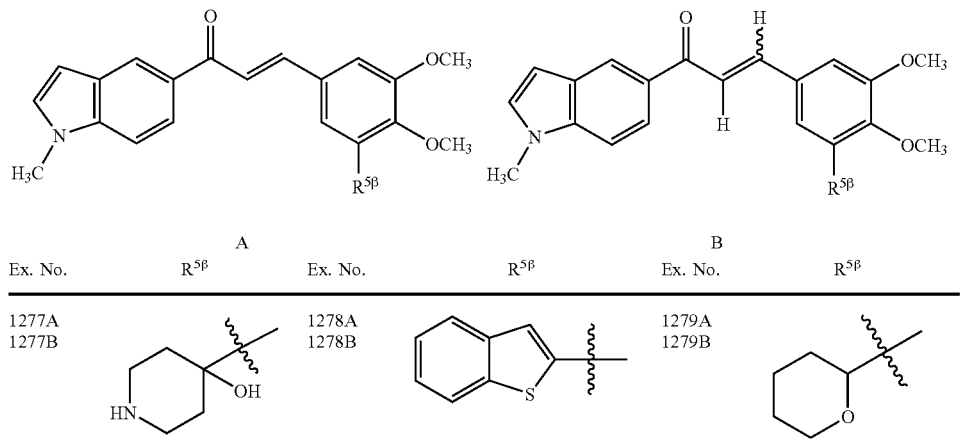

| Ex. No. | R⁵ᵝ | Ex. No. | R⁵ᵝ | Ex. No. | R⁵ᵝ |
|---|---|---|---|---|---|
| 1277A 1277B | 4-hydroxypiperidinyl | 1278A 1278B | benzothiophene | 1279A 1279B | tetrahydropyran |

EXAMPLE TABLE 17

Substituted 4-[3-{2-(Pyrrolidin-1-yl)-(4-heteroaryl or 4-heterocyclic)-phenyl}-acryloyl]-benzoic Acids.

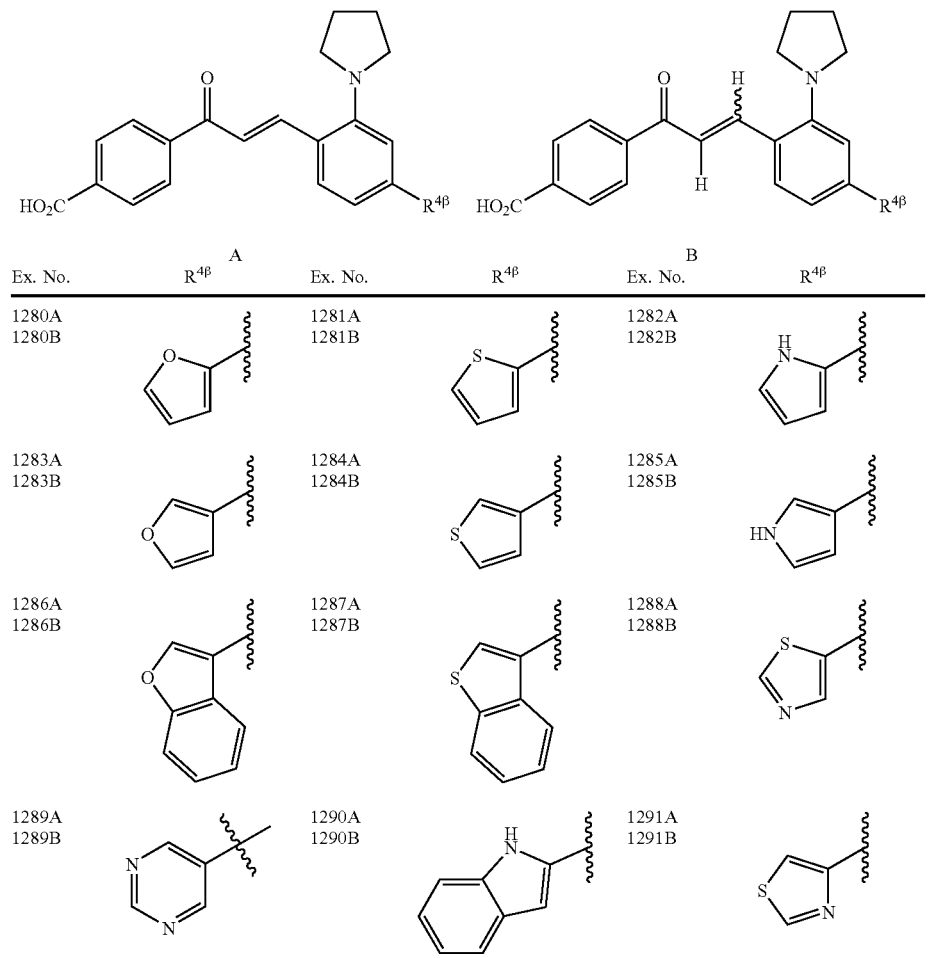

| Ex. No. | R⁴ᵝ | Ex. No. | R⁴ᵝ | Ex. No. | R⁴ᵝ |
|---|---|---|---|---|---|
| 1280A 1280B | 2-furyl | 1281A 1281B | 2-thienyl | 1282A 1282B | 2-pyrrolyl |
| 1283A 1283B | 3-furyl | 1284A 1284B | 3-thienyl | 1285A 1285B | 3-pyrrolyl |
| 1286A 1286B | 3-benzofuryl | 1287A 1287B | 3-benzothienyl | 1288A 1288B | 5-thiazolyl |
| 1289A 1289B | 5-pyrimidinyl | 1290A 1290B | 2-indolyl | 1291A 1291B | 4-thiazolyl |

EXAMPLE TABLE 17-continued
Substituted 4-[3-{2-(Pyrrolidin-1-yl)-(4-heteroaryl or 4-heterocyclic)-phenyl}-acryloyl]-benzoic Acids.
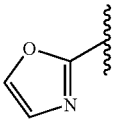
A
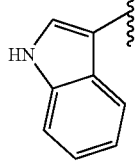
B
| Ex. No. | $R^{4\beta}$ | Ex. No. | $R^{4\beta}$ | Ex. No. | $R^{4\beta}$ |
|---|---|---|---|---|---|
| 1292A 1292B | 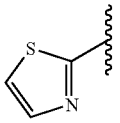 | 1293A 1293B | 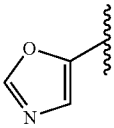 | 1294A 1294B | 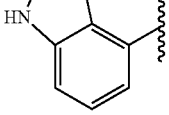 |
| 1295A 1295B | 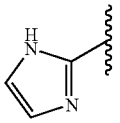 | 1296A 1296B | 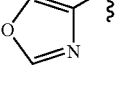 | 1297A 1297B | 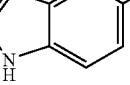 |
| 1298A 1298B | 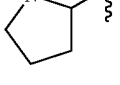 | 1299A 1299B | 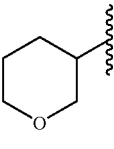 | 1300A 1300B | 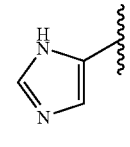 |
| 1301A 1301B | 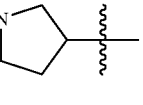 | 1302A 1302B | 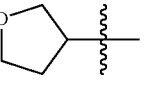 | 1303A 1303B | 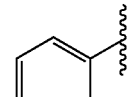 |
| 1304A 1304B | 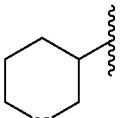 | 1305A 1305B | 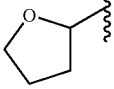 | 1306A 1306B | 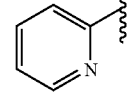 |
| 1307A 1307B | 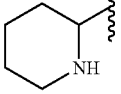 | 1308A 1308B | 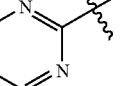 | 1309A 1309B | 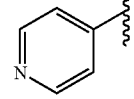 |
| 1310A 1310B | 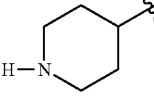 | 1311A 1311B | 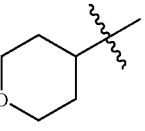 | 1312A 1312B | 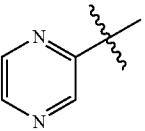 |
| 1313A 1313B | 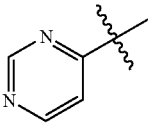 | 1314A 1314B | | 1315A 1315B | |

EXAMPLE TABLE 17-continued
Substituted 4-[3-{2-(Pyrrolidin-1-yl)-(4-heteroaryl or 4-heterocyclic)-phenyl}-acryloyl]-benzoic Acids.
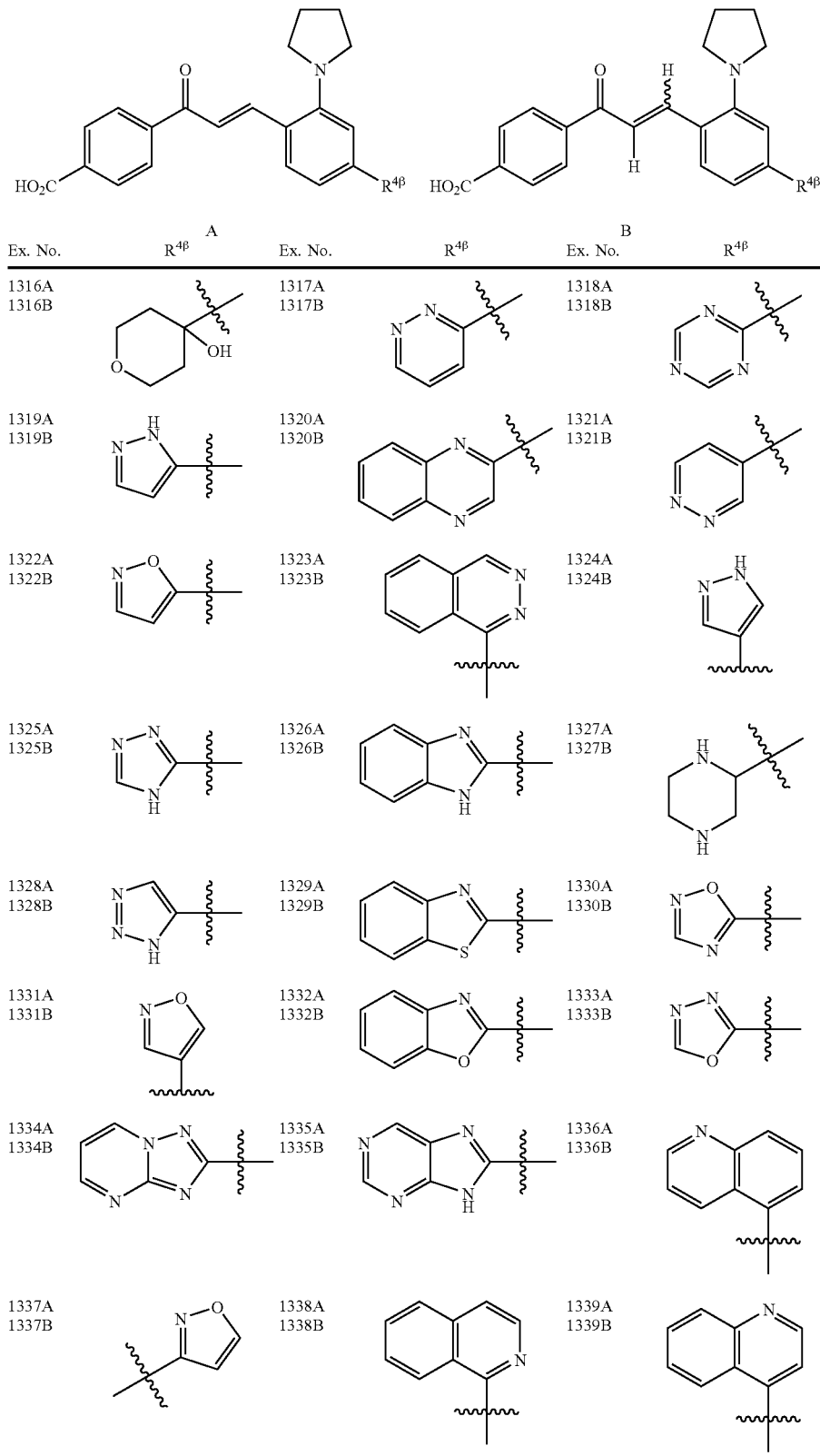

EXAMPLE TABLE 17-continued

Substituted 4-[3-{2-(Pyrrolidin-1-yl)-(4-heteroaryl or 4-heterocyclic)-phenyl}-acryloyl]-benzoic Acids.

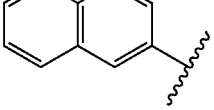

| Ex. No. | R⁴ᵝ | Ex. No. | R⁴ᵝ | Ex. No. | R⁴ᵝ |
|---|---|---|---|---|---|
| 1340A<br>1340B | quinolin-3-yl | 1341A<br>1341B | isoquinolin-3-yl | 1342A<br>1342B | quinolin-2-yl |
| 1343A<br>1343B | 5-methylfuran-2-yl | 1344A<br>1344B | 3-(methoxycarbonyl)-1H-pyrazol-5-yl | 1345A<br>1345B | 4-bromo-5-methylthiophen-2-yl |
| 1346A<br>1346B | 3-methylfuran-2-yl | 1347A<br>1347B | 5-acetylthiophen-2-yl | 1348A<br>1348B | 1-methyl-1H-pyrrol-2-yl |
| 1349A<br>1349B | 4-hydroxypiperidin-4-yl | 1350A<br>1350B | benzo[b]thiophen-2-yl | 1351A<br>1351B | tetrahydro-2H-pyran-2-yl |

EXAMPLE TABLE 18

Substituted 4-[3-{(5-Heteroaryl or 5-heterocyclic)-2,4-dimethoxyphenyl}-acryloyl]-benzoic Acids.

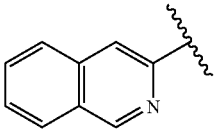

| Ex. No. | R⁵ᵝ | Ex. No. | R⁵ᵝ | Ex. No. | R⁵ᵝ |
|---|---|---|---|---|---|
| 1352A<br>1352B | furan-2-yl | 1353A<br>1353B | 5-methylbenzo[b]thiophen-2-yl | 1354A<br>1354B | 1H-pyrrol-2-yl |
| 1355A<br>1355B | furan-3-yl | 1356A<br>1356B | thiophen-3-yl | 1357A<br>1357B | 1H-pyrrol-3-yl |

EXAMPLE TABLE 18-continued

Substituted 4-[3-{(5-Heteroaryl or 5-heterocyclic)-2,4-dimethoxyphenyl}-acryloyl]-benzoic Acids.

| Ex. No. | R⁵ᵝ | Ex. No. | R⁵ᵝ | Ex. No. | R⁵ᵝ |
|---|---|---|---|---|---|
| 1358A / 1358B | benzofuran-3-yl | 1359A / 1359B | benzothiophen-3-yl | 1360A / 1360B | thiazol-5-yl |
| 1361A / 1361B | pyrimidin-5-yl | 1362A / 1362B | 1H-indol-2-yl | 1363A / 1363B | thiazol-4-yl |
| 1364A / 1364B | oxazol-2-yl | 1365A / 1365B | 1H-indol-3-yl | 1366A / 1366B | thiazol-2-yl |
| 1367A / 1367B | oxazol-5-yl | 1368A / 1368B | 1H-indol-4-yl | 1369A / 1369B | 1H-imidazol-2-yl |
| 1370A / 1370B | oxazol-4-yl | 1371A / 1371B | 1H-indol-5-yl | 1372A / 1372B | pyrrolidin-2-yl |
| 1373A / 1373B | tetrahydropyran-3-yl | 1374A / 1374B | 1H-imidazol-4-yl | 1375A / 1375B | pyrrolidin-3-yl |
| 1376A / 1376B | tetrahydrofuran-3-yl | 1377A / 1377B | pyridin-3-yl | 1378A / 1378B | piperidin-3-yl |

EXAMPLE TABLE 18-continued

Substituted 4-[3-{(5-Heteroaryl or 5-heterocyclic)-2,4-dimethoxyphenyl}-acryloyl]-benzoic Acids.

| Ex. No. | $R^{5\beta}$ | Ex. No. | $R^{5\beta}$ | Ex. No. | $R^{5\beta}$ |
|---|---|---|---|---|---|
| 1379A 1379B | tetrahydrofuran-2-yl | 1380A 1380B | pyridin-2-yl | 1381A 1381B | piperidin-2-yl |
| 1382A 1382B | pyrimidin-2-yl | 1383A 1383B | pyridin-4-yl | 1384A 1384B | piperidin-4-yl |
| 1385A 1385B | tetrahydropyran-4-yl | 1386A 1386B | pyrazin-2-yl | 1387A 1387B | pyrimidin-4-yl |
| 1388A 1388B | 4-hydroxy-tetrahydropyran-4-yl | 1389A 1389B | pyridazin-3-yl | 1390A 1390B | 1,3,5-triazin-2-yl |
| 1391A 1391B | 1H-pyrazol-5-yl | 1392A 1392B | quinoxalin-2-yl | 1393A 1393B | pyridazin-4-yl |
| 1394A 1394B | isoxazol-5-yl | 1395A 1395B | phthalazin-1-yl | 1396A 1396B | 1H-pyrazol-4-yl |
| 1397A 1397B | 1H-1,2,4-triazol-3-yl | 1398A 1398B | 1H-benzimidazol-2-yl | 1399A 1399B | piperazin-2-yl |
| 1400A 1400B | 1H-1,2,3-triazol-4-yl | 1401A 1401B | benzothiazol-2-yl | 1402A 1402B | 1,3,4-oxadiazol-2-yl |

EXAMPLE TABLE 18-continued

Substituted 4-[3-{(5-Heteroaryl or 5-heterocyclic)-2,4-dimethoxyphenyl}-acryloyl]-benzoic Acids.

| Ex. No. | R$^{5\beta}$ | Ex. No. | R$^{5\beta}$ | Ex. No. | R$^{5\beta}$ |
|---|---|---|---|---|---|
| 1403A 1403B | isoxazol-4-yl | 1404A 1404B | benzoxazol-2-yl | 1405A 1405B | 1,3,4-oxadiazol-2-yl |
| 1406A 1406B | [1,2,4]triazolo[1,5-a]pyrimidin-2-yl | 1407A 1407B | 9H-purin-8-yl | 1408A 1408B | quinolin-5-yl |
| 1409A 1409B | isoxazol-3-yl | 1410A 1410B | isoquinolin-1-yl | 1411A 1411B | quinolin-4-yl |
| 1412A 1412B | quinolin-3-yl | 1413A 1413B | isoquinolin-3-yl | 1414A 1414B | quinolin-2-yl |

EXAMPLE TABLE 19

Substituted 3-[3-{(5-Heteroaryl or 5-heterocyclic)-2,4-dimethoxyphenyl}-acryloyl]-benzoic Acids.

| Ex. No. | R$^{5\beta}$ | Ex. No. | R$^{5\beta}$ | Ex. No. | R$^{5\beta}$ |
|---|---|---|---|---|---|
| 1415A 1415B | furan-2-yl | 1416A 1416B | thiophen-2-yl | 1417A 1417B | 1H-pyrrol-2-yl |

EXAMPLE TABLE 19-continued
Substituted 3-[3-{(5-Heteroaryl or 5-heterocyclic)-2,4-dimethoxyphenyl}-acryloyl]-benzoic Acids.
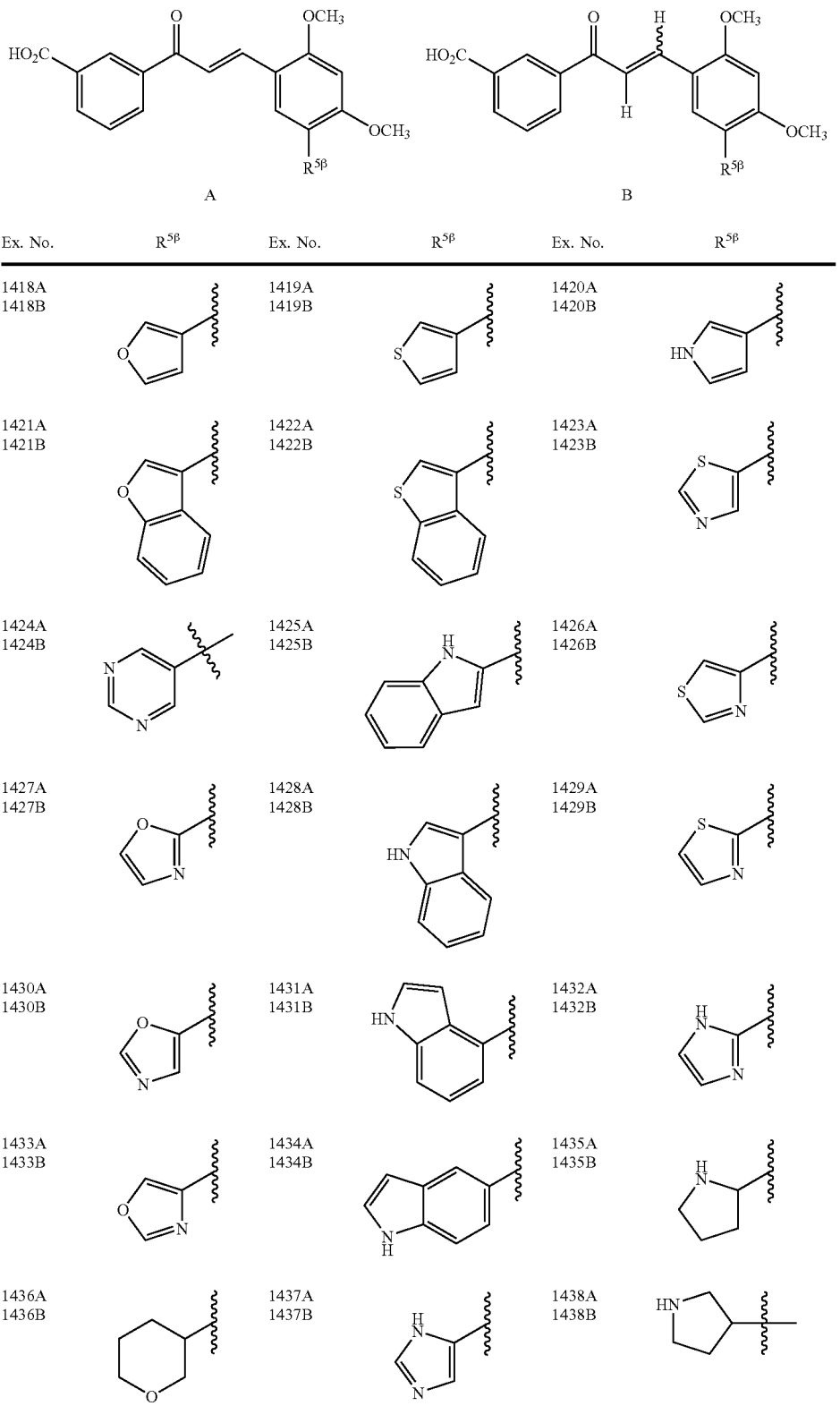

EXAMPLE TABLE 19-continued
Substituted 3-[3-{(5-Heteroaryl or 5-heterocyclic)-2,4-dimethoxyphenyl}-acryloyl]-benzoic Acids.
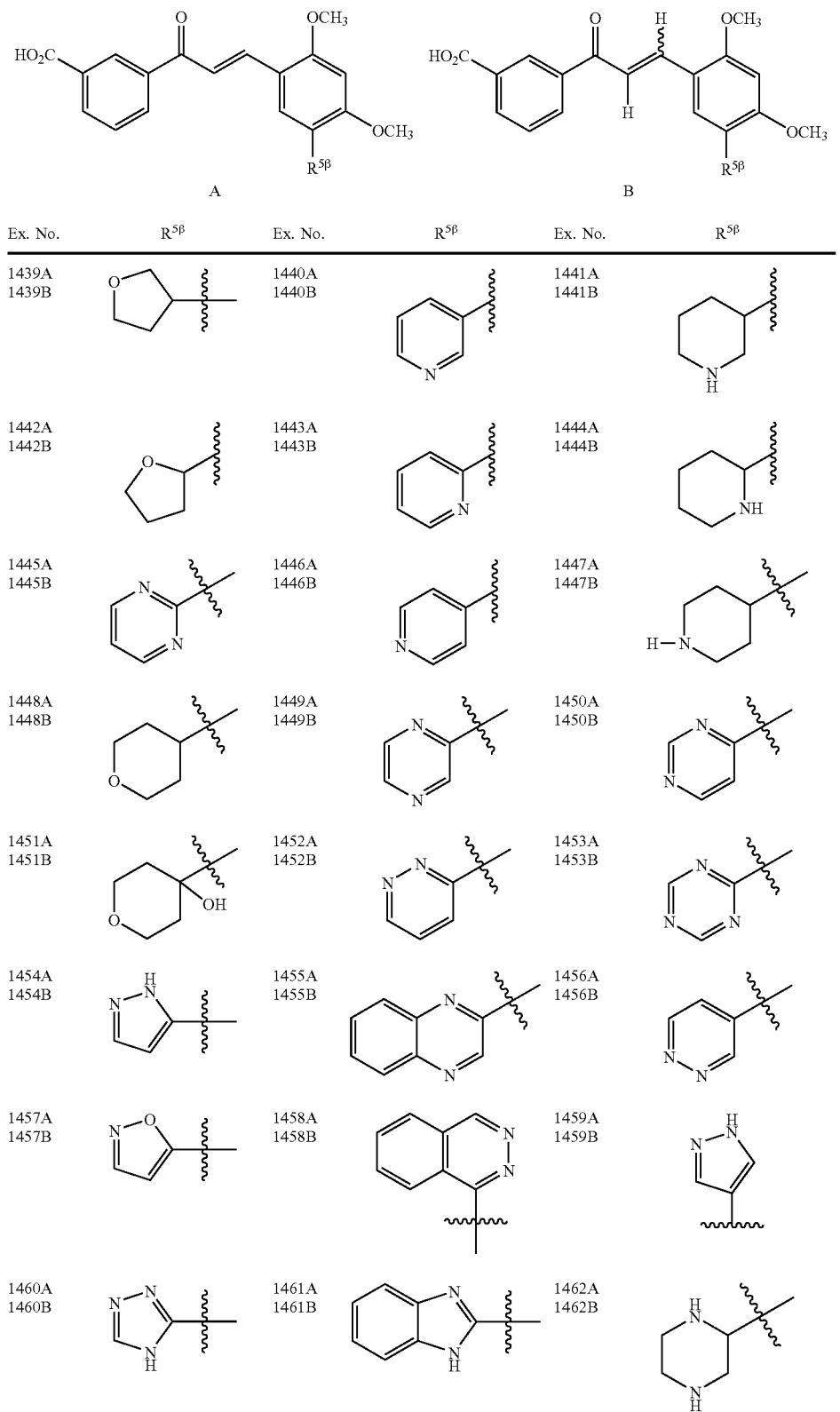

EXAMPLE TABLE 19-continued

Substituted 3-[3-{(5-Heteroaryl or 5-heterocyclic)-2,4-dimethoxyphenyl}-acryloyl]-benzoic Acids.

| Ex. No. | $R^{5\beta}$ | Ex. No. | $R^{5\beta}$ | Ex. No. | $R^{5\beta}$ |
|---|---|---|---|---|---|
| 1463A, 1463B | triazole | 1464A, 1464B | benzothiazole | 1465A, 1465B | 1,2,4-oxadiazole |
| 1466A, 1466B | isoxazole | 1467A, 1467B | benzoxazole | 1468A, 1468B | 1,3,4-oxadiazole |
| 1469A, 1469B | [1,2,4]triazolo[1,5-a]pyrimidine | 1470A, 1470B | imidazo[4,5-d]pyrimidine | 1471A, 1471B | quinoline-5-yl |
| 1473A, 1473B | isoxazole | 1474A, 1474B | isoquinoline | 1475A, 1475B | quinoline-4-yl |
| 1476A, 1476B | quinoline-3-yl | 1477A, 1477B | isoquinoline | 1478A, 1478B | quinoline-2-yl |
| 1479A, 1479B | 5-methylfuran | 1480A, 1480B | methyl pyrazole-carboxylate | 1481A, 1481B | 3-bromo-2-methylthiophene |
| 1482A, 1482B | 3-methylfuran | 1483A, 1383B | 5-acetylthiophene | 1484A, 1484B | N-methylpyrrole |
| 1485A, 1485B | 4-hydroxypiperidine | 1486A, 1486B | benzothiophene | 1487A, 1487B | tetrahydropyran |

EXAMPLE TABLE 20

Substituted 2-[3-{(5-Heteroaryl or 5-heterocyclic)-2,4-dimethoxyphenyl}-acryloyl]-benzoic Acids.

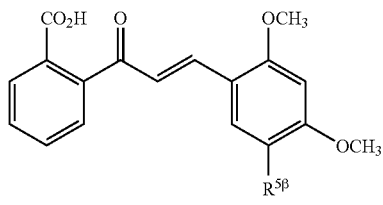
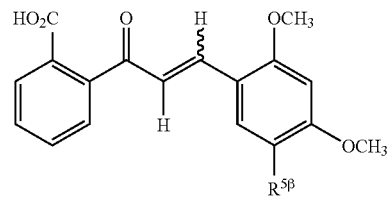

A B

| Ex. No. | R$^{5\beta}$ | Ex. No. | R$^{5\beta}$ | Ex. No. | R$^{5\beta}$ |
|---|---|---|---|---|---|
| 1488A 1488B | 2-furyl | 1489A 1489B | 2-thienyl | 1490A 1490B | 2-pyrrolyl |
| 1491A 1491B | 3-furyl | 1492A 1492B | 3-thienyl | 1493A 1493B | 3-pyrrolyl |
| 1494A 1494B | 3-benzofuranyl | 1495A 1495B | 3-benzothienyl | 1496A 1496B | 5-thiazolyl |
| 1497A 1497B | 5-pyrimidinyl | 1498A 1498B | 2-indolyl | 1499A 1499B | 4-thiazolyl |
| 1500A 1500B | 2-oxazolyl | 1501A 1501B | 3-indolyl | 1502A 1502B | 2-thiazolyl |
| 1503A 1503B | 5-oxazolyl | 1504A 1504B | 4-indolyl | 1505A 1505B | 2-imidazolyl |
| 1506A 1506B | 4-oxazolyl | 1507A 1507B | 5-indolyl | 1508A 1508B | 2-pyrrolidinyl |

EXAMPLE TABLE 20-continued

Substituted 2-[3-{(5-Heteroaryl or 5-heterocyclic)-2,4-dimethoxyphenyl}-acryloyl]-benzoic Acids.

EXAMPLE TABLE 20-continued
Substituted 2-[3-{(5-Heteroaryl or 5-heterocyclic)-2,4-dimethoxyphenyl}-acryloyl]-benzoic Acids.
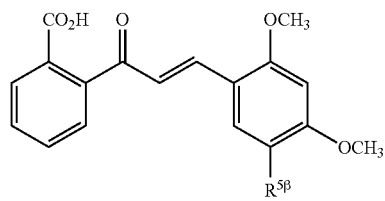
A
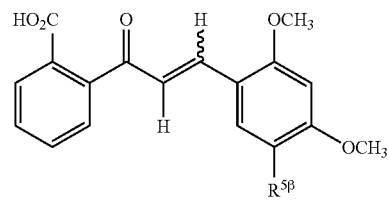
B

EXAMPLE TABLE 21

Substituted 2-[3-{(5-Heteroaryl or 5-heterocyclic)-2,4-dimethoxyphenyl}-acryloyl]-5-methanesulfonylamino-benzoic Acids.

| Ex. No. | A R⁵ᵝ | Ex. No. | R⁵ᵝ | Ex. No. | B R⁵ᵝ |
|---|---|---|---|---|---|
| 1551A 1551B | furan-2-yl | 1552A 1552B | thiophen-2-yl | 1553A 1553B | pyrrol-2-yl |
| 1554A 1554B | furan-3-yl | 1555A 1552B | thiophen-3-yl | 1556A 1556B | pyrrol-3-yl |
| 1557A 1557B | benzofuran-3-yl | 1558A 1558B | benzothiophen-3-yl | 1559A 1559B | thiazol-5-yl |
| 1560A 1560B | pyrimidin-5-yl | 1561A 1561B | indol-2-yl | 1562A 1562B | thiazol-4-yl |
| 1563A 1563B | oxazol-2-yl | 1564A 1564B | indol-3-yl | 1565A 1565B | thiazol-2-yl |
| 1566A 1566B | oxazol-5-yl | 1567A 1567B | indol-4-yl | 1568A 1568B | imidazol-2-yl |
| 1569A 1569B | oxazol-4-yl | 1570A 1570B | indol-5-yl | 1571A 1571B | pyrrolidin-2-yl |
| 1572A 1572B | tetrahydropyran-3-yl | 1573A 1573B | imidazol-5-yl | 1574A 1574B | pyrrolidin-3-yl |

EXAMPLE TABLE 21-continued

Substituted 2-[3-{(5-Heteroaryl or 5-heterocyclic)-2,4-dimethoxyphenyl}-acryloyl]-5-methanesulfonylamino-benzoic Acids.

A: 2-[3-(aryl)-acryloyl]-5-methanesulfonylaminobenzoic acid structure with $R^{5\beta}$ substituent
B: isomeric structure with $R^{5\beta}$ substituent

| Ex. No. | A $R^{5\beta}$ | Ex. No. | $R^{5\beta}$ | Ex. No. | B $R^{5\beta}$ |
|---|---|---|---|---|---|
| 1575A / 1575B | tetrahydrofuran-3-yl | 1576A / 1576B | pyridin-3-yl | 1577A / 1577B | piperidin-3-yl |
| 1578A / 1578B | tetrahydrofuran-2-yl | 1579A / 1579B | pyridin-2-yl | 1580A / 1580B | piperidin-2-yl |
| 1581A / 1581B | pyrimidin-2-yl | 1582A / 1582B | pyridin-4-yl | 1583A / 1583B | piperidin-4-yl |
| 1584A / 1584B | tetrahydropyran-4-yl | 1585A / 1585B | pyrazin-2-yl | 1586A / 1586B | pyrimidin-4-yl |
| 1587A / 1587B | 4-hydroxytetrahydropyran-4-yl | 1588A / 1588B | pyridazin-3-yl | 1589A / 1589B | 1,3,5-triazin-2-yl |
| 1590A / 1590B | 1H-pyrazol-3-yl | 1591A / 1591B | quinoxalin-2-yl | 1592A / 1592B | pyridazin-4-yl |
| 1593A / 1593B | isoxazol-5-yl | 1594A / 1594B | phthalazin-1-yl | 1595A / 1595B | 1H-pyrazol-4-yl |
| 1596A / 1596B | 1H-1,2,4-triazol-3-yl | 1597A / 1597B | benzimidazol-2-yl | 1598A / 1598B | piperazin-3-yl |

EXAMPLE TABLE 21-continued

Substituted 2-[3-{(5-Heteroaryl or 5-heterocyclic)-2,4-dimethoxyphenyl}-acryloyl]-5-methanesulfonylamino-benzoic Acids.

A: 5-(methanesulfonylamino)-2-[3-(2,4-dimethoxy-5-$R^{5\beta}$-phenyl)-acryloyl]-benzoic acid (carboxyl ortho to acryloyl, methanesulfonylamino para to carboxyl)

B: isomeric arrangement with HO$_2$C and CH$_3$SO$_2$NH positions as shown

| Ex. No. | $R^{5\beta}$ (A) | Ex. No. | $R^{5\beta}$ | Ex. No. | $R^{5\beta}$ |
|---|---|---|---|---|---|
| 1599A / 1599B | 1H-1,2,3-triazol-4-yl | 1600A / 1600B | benzothiazol-2-yl | 1601A / 1601B | 1,2,4-oxadiazol-5-yl |
| 1602A / 1602B | isoxazol-4-yl | 1603A / 1603B | benzoxazol-2-yl | 1604A / 1605B | 1,3,4-oxadiazol-2-yl |
| 1605A / 1605B | [1,2,4]triazolo[1,5-a]pyrimidin-2-yl | 1606A / 1606B | 1H-imidazo[4,5-d]pyrimidin-2-yl | 1607A / 1607B | quinolin-5-yl |
| 1608A / 1608B | isoxazol-3-yl | 1609A / 1609B | isoquinolin-1-yl | 1610A / 1610B | quinolin-4-yl |
| 1611A / 1611B | quinolin-3-yl | 1612A / 1612B | isoquinolin-3-yl | 1613A / 1613B | quinolin-2-yl |
| 1614A / 1614B | 5-methyl-furan-2-yl | 1615A / 1615B | 3-(methoxycarbonyl)-1H-pyrazol-5-yl | 1616A / 1616B | 4-bromo-5-methyl-thien-2-yl |
| 1617A / 1617B | 3-methyl-furan-2-yl | 1618A / 1618B | 5-acetyl-thien-2-yl | 1619A / 1619B | 1-methyl-pyrrol-2-yl |
| 1620A / 1620B | 4-hydroxy-piperidin-4-yl | 1621A / 1621B | benzothien-2-yl | 1622A / 1622B | tetrahydro-2H-pyran-2-yl |

EXAMPLE TABLE 22

Substituted 5-Amino-2-[3-{(5-heteroaryl or 5-heterocyclic)-2,4-dimethoxy-phenyl}-acryloyl]-benzoic Acids.

| Ex. No. | A R$^{5\beta}$ | Ex. No. | R$^{5\beta}$ | Ex. No. | B R$^{5\beta}$ |
|---|---|---|---|---|---|
| 1623A 1623B | 2-furyl | 1624A 1624B | 2-thienyl | 1625A 1625B | 2-pyrrolyl (NH) |
| 1626A 1626B | 3-furyl | 1627A 1627B | 3-thienyl | 1628A 1628B | 3-pyrrolyl (NH) |
| 1629A 1629B | benzofuran-3-yl | 1630A 1630B | benzothiophen-3-yl | 1631A 1631B | thiazol-5-yl |
| 1632A 1632B | pyrimidin-5-yl | 1633A 1633B | indol-2-yl | 1634A 1634B | thiazol-4-yl |
| 1635A 1635B | oxazol-2-yl | 1636A 1636B | indol-3-yl | 1637A 1637B | thiazol-2-yl |
| 1638A 1638B | oxazol-5-yl | 1639A 1639B | | 1640A 1640B | imidazol-2-yl |
| 1641A 1641B | oxazol-4-yl | 1642A 1642B | indol-5-yl | 1643A 1643B | pyrrolidin-2-yl |
| 1644A 1644B | tetrahydropyran-3-yl | 1645A 1645B | imidazol-5-yl | 1646A 1646B | pyrrolidin-3-yl |

EXAMPLE TABLE 22-continued
Substituted 5-Amino-2-[3-{(5-heteroaryl or 5-heterocyclic)-2,4-dimethoxy-phenyl}-acryloyl]-benzoic Acids.
| Ex. No. | A R5β | Ex. No. | R5β | Ex. No. | B R5β |
|---|---|---|---|---|---|
| 1647A 1647B | 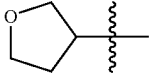 | 1648A 1648B | 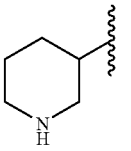 | 1649A 1649B | 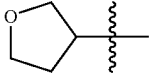 |
| 1650A 1650B | 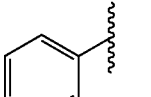 | 1651A 1651B | 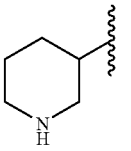 | 1652A 1652B | 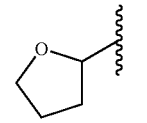 |
| 1653A 1653B | 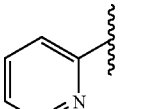 | 1654A 1654B | 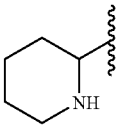 | 1655A 1655B | 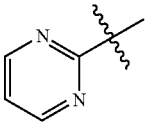 |
| 1656A 1656B | 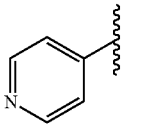 | 1657A 1657B | 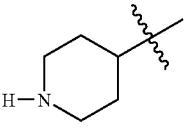 | 1658A 1658B | 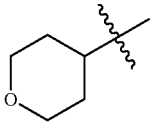 |
| 1659A 1659B | 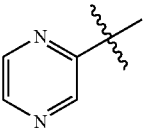 | 1660A 1660B | 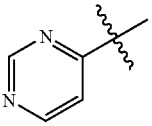 | 1661A 1661B | 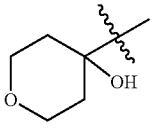 |
| 1662A 1662B | 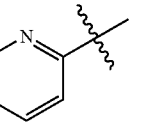 | 1663A 1663B | 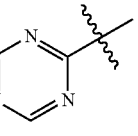 | 1664A 1664B | 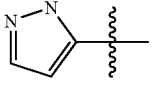 |
| 1665A 1665B | 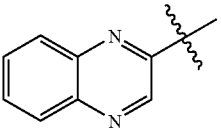 | 1666A 1666B | 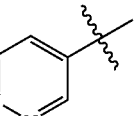 | 1667A 1667B | 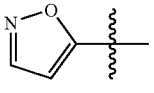 |
| 1688A 1688B | 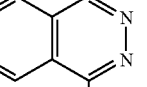 | 1669A 1669B | 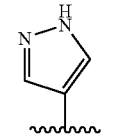 | 1670A 1670B | 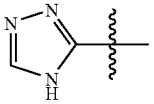 |

EXAMPLE TABLE 22-continued

Substituted 5-Amino-2-[3-{(5-heteroaryl or 5-heterocyclic)-2,4-dimethoxy-phenyl}-acryloyl]-benzoic Acids.

A

B

| Ex. No. | R⁵ᵝ | Ex. No. | R⁵ᵝ | Ex. No. | R⁵ᵝ |
|---|---|---|---|---|---|
| 1671A 1671B | 1H-triazolyl | 1672A 1672B | benzothiazolyl | 1673A 1673B | 1,3,4-oxadiazolyl |
| 1674A 1674B | isoxazolyl | 1675A 1675B | benzoxazolyl | 1676A 1676B | 1,3,4-oxadiazolyl |
| 1677A 1677B | [1,2,4]triazolo[1,5-a]pyrimidinyl | 1678A 1678B | imidazo-pyrimidinyl | 1679A 1679B | quinolin-5-yl |
| 1680A 1680B | isoxazol-3-yl | 1681A 1681B | isoquinolin-1-yl | 1682A 1682B | quinolin-4-yl |
| 1683A 1683B | quinolin-3-yl | 1684A 1684B | isoquinolin-3-yl | 1685A 1685B | quinolin-2-yl |

EXAMPLE TABLE 23

Substituted 4-[3-{(5-Heteroaryl or 5-heterocyclic)-3,4-dimethoxyphenyl}-acryloyl]-benzoic Acids.

A

B

| Ex. No. | R⁵ᵝ | Ex. No. | R⁵ᵝ | Ex. No. | R⁵ᵝ |
|---|---|---|---|---|---|
| 1686A 1686B | furan-2-yl | 1687A 1687B | thiophen-2-yl | 1688A 1688B | 1H-pyrrol-2-yl |

EXAMPLE TABLE 23-continued

Substituted 4-[3-{(5-Heteroaryl or 5-heterocyclic)-3,4-dimethoxyphenyl}-acryloyl]-benzoic Acids.

| Ex. No. | A R$^{5\beta}$ | Ex. No. | R$^{5\beta}$ | Ex. No. | B R$^{5\beta}$ |
|---|---|---|---|---|---|
| 1689A 1689B | | 1690A 1690B | furan-3-yl | 1691A 1691B | benzothiophen-2-yl |
| | | | | | pyrrol-3-yl |
| 1692A 1692B | benzofuran-3-yl | 1693A 1693B | benzothiophen-3-yl | 1694A 1694B | thiazol-5-yl |
| 1695A 1695B | pyrimidin-5-yl | 1696A 1696B | 1H-indol-2-yl | 1697A 1697B | thiazol-4-yl |
| 1698A 1698B | oxazol-2-yl | 1699A 1699B | 1H-indol-3-yl | 1700A 1700B | thiazol-2-yl |
| 1701A 1701B | oxazol-5-yl | 1702A 1702B | 1H-indol-4-yl | 1703A 1703B | imidazol-2-yl |
| 1704A 1704B | oxazol-4-yl | 1705A 1705B | 1H-indol-5-yl | 1706A 1706B | pyrrolidin-2-yl |
| 1707A 1707B | tetrahydropyran-3-yl | 1708A 1708B | imidazol-5-yl | 1709A 1709B | pyrrolidin-3-yl |

EXAMPLE TABLE 23-continued

Substituted 4-[3-{(5-Heteroaryl or 5-heterocyclic)-3,4-dimethoxyphenyl}-acryloyl]-benzoic Acids.

| Ex. No. | A R⁵ᵝ | Ex. No. | R⁵ᵝ | Ex. No. | B R⁵ᵝ |
|---|---|---|---|---|---|
| 1710A 1710B | tetrahydrofuran-3-yl | 1711A 1711B | pyridin-3-yl | 1712A 1712B | piperidin-3-yl |
| 1713A 1713B | tetrahydrofuran-2-yl | 1714A 1714B | pyridin-2-yl | 1715A 1715B | piperidin-2-yl |
| 1716A 1716B | pyrimidin-2-yl | 1717A 1717B | pyridin-4-yl | 1718A 1718B | piperidin-4-yl |
| 1719A 1719B | tetrahydropyran-4-yl | 1720A 1720B | pyrazin-2-yl | 1721A 1721B | pyrimidin-4-yl |
| 1722A 1722B | 4-hydroxy-tetrahydropyran-4-yl | 1723A 1723B | pyridazin-3-yl | 1724A 1724B | 1,3,5-triazin-2-yl |
| 1725A 1725B | pyrazol-3-yl | 1726A 1726B | quinoxalin-2-yl | 1727A 1727B | pyridazin-4-yl |
| 1728A 1728B | isoxazol-5-yl | 1729A 1729B | phthalazin-1-yl | 1730A 1730B | pyrazol-4-yl |
| 1731A 1731B | 1,2,4-triazol-3-yl | 1732A 1732B | benzimidazol-2-yl | 1733A 1733B | piperazin-2-yl |

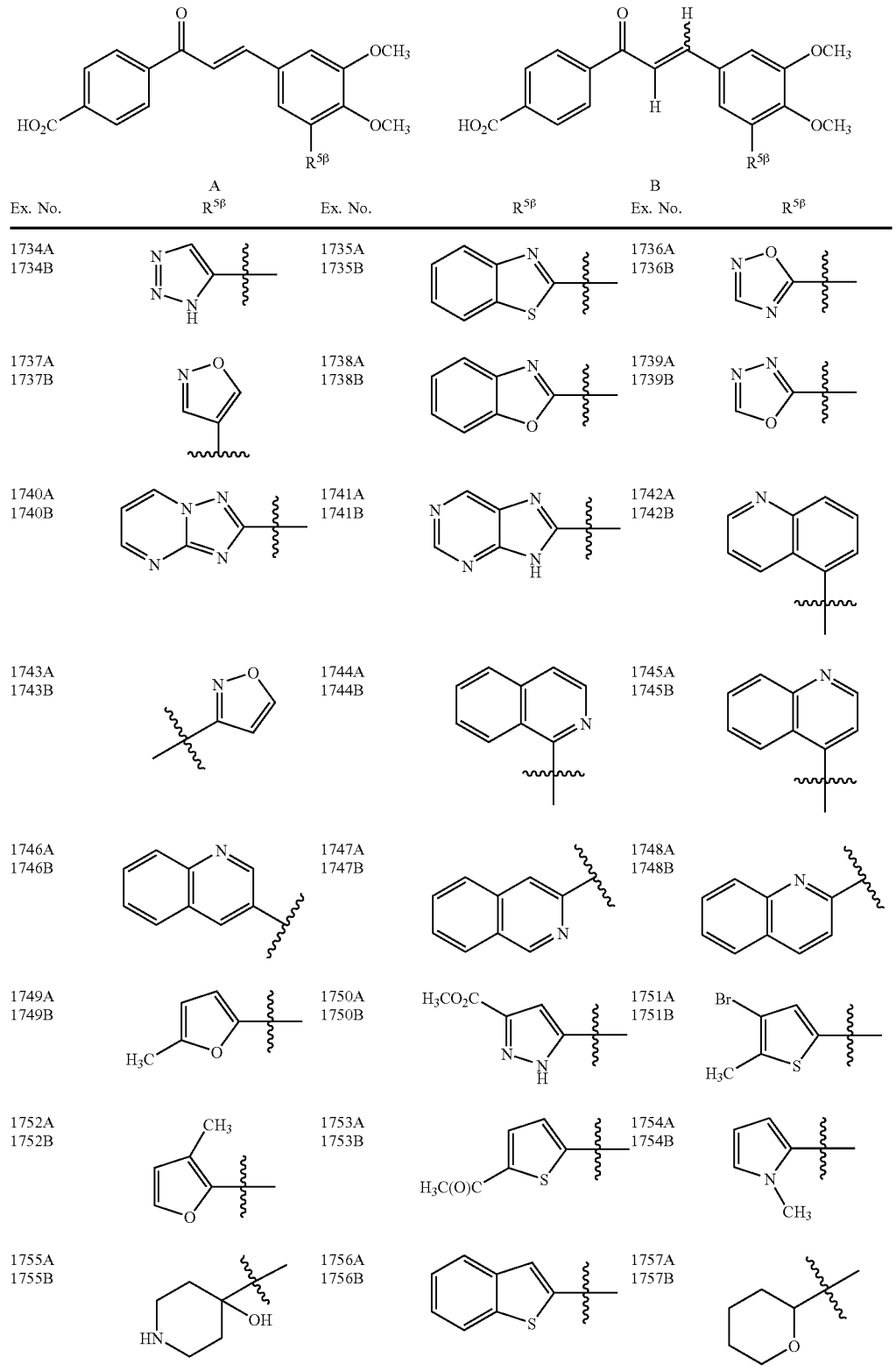

EXAMPLE TABLE 24
Substituted 3-[3-{(5-Heteroaryl or 5-heterocyclic)-3,4-dimethoxyphenyl}-acryloyl]-5-benzoic Acids.
| Ex. No. | A R⁵ᵝ | Ex. No. | R⁵ᵝ | Ex. No. | B R⁵ᵝ |
|---|---|---|---|---|---|
| 1758A 1758B | 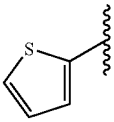 | 1759A 1759B | 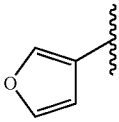 | 1760A 1760B | 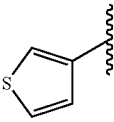 |
| 1761A 1761B | 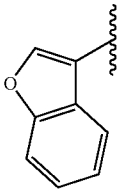 | 1762A 1762B | 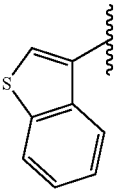 | 1763A 1763B | 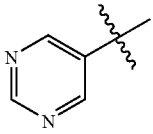 |
| 1764A 1764B | 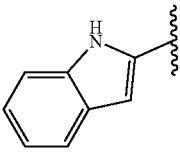 | 1765A 1765B | 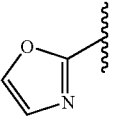 | 1766A 1766B | 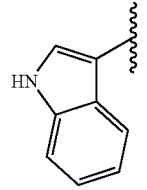 |
| 1767A 1767B | 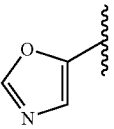 | 1768A 1768B | 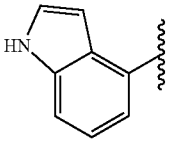 | 1769A 1769B | 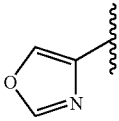 |
| 1770A 1770B | 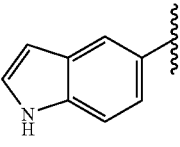 | 1771A 1771B | 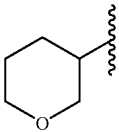 | 1772A 1772B | 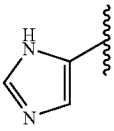 |
| 1773A 1733B | 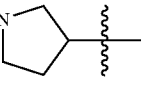 | 1774A 1774B | | 1775A 1775B | |
| 1776A 1776B | | 1777A 1777B | | 1778A 1778B | |
| 1779A 1779B | | 1780A 1780B | | 1781A 1781B | |

EXAMPLE TABLE 24-continued

Substituted 3-[3-{(5-Heteroaryl or 5-heterocyclic)-3,4-dimethoxyphenyl}-acryloyl]-5-benzoic Acids.

| Ex. No. | A $R^{5\beta}$ | Ex. No. | $R^{5\beta}$ | Ex. No. | B $R^{5\beta}$ |
|---|---|---|---|---|---|
| 1782A 1782B | tetrahydrofuran-3-yl | 1783A 1783B | pyridin-3-yl | 1784A 1784B | piperidin-3-yl |
| 1785A 1785B | tetrahydrofuran-2-yl | 1786A 1786B | pyridin-2-yl | 1787A 1787B | piperidin-2-yl |
| 1788A 1788B | pyrimidin-2-yl | 1789A 1789B | pyridin-4-yl | 1790A 1790B | piperidin-4-yl |
| 1791A 1791B | tetrahydropyran-4-yl | 1792A 1792B | pyrazin-2-yl | 1793A 1793B | pyrimidin-4-yl |
| 1794A 1794B | 4-hydroxytetrahydropyran-4-yl | 1795A 1795B | pyridazin-3-yl | 1796A 1796B | 1,3,5-triazin-2-yl |
| 1797A 1797B | 1H-pyrazol-3-yl | 1798A 1798B | quinoxalin-2-yl | 1799A 1799B | pyridazin-4-yl |
| 1800A 1800B | isoxazol-5-yl | 1801A 1801B | phthalazin-1-yl | 1802A 1802B | 1H-pyrazol-4-yl |
| 1803A 1803B | 1H-1,2,4-triazol-3-yl | 1804A 1804B | 1H-benzimidazol-2-yl | 1805A 1805B | piperazin-2-yl |

EXAMPLE TABLE 24-continued

Substituted 3-[3-{(5-Heteroaryl or 5-heterocyclic)-3,4-dimethoxyphenyl}-acryloyl]-5-benzoic Acids.

A / B structures shown with $R^{5\beta}$ substituent.

| Ex. No. | $R^{5\beta}$ (A) | Ex. No. | $R^{5\beta}$ | Ex. No. | $R^{5\beta}$ |
|---------|------------------|---------|--------------|---------|--------------|
| 1806A / 1806B | 1H-triazole | 1807A / 1807B | benzothiazole | 1808A / 1808B | 1,2,4-oxadiazole |
| 1809A / 1809B | isoxazole | 1810A / 1810B | benzoxazole | 1811A / 1811B | 1,3,4-oxadiazole |
| 1812A / 1812B | [1,2,4]triazolo[1,5-a]pyrimidine | 1813A / 1813B | purine-like (imidazopyrimidine) | 1814A / 1814B | quinoline (5-yl) |
| 1815A / 1815B | isoxazol-3-yl | 1816A / 1816B | isoquinolin-1-yl | 1817A / 1817B | quinolin-4-yl |
| 1818A / 1818B | quinolin-3-yl | 1819A / 1819B | isoquinolin-3-yl | 1820A / 1820B | quinolin-2-yl |

EXAMPLE TABLE 25

Substituted 2-[3-{(5-Heteroaryl or 5-heterocyclic)-3,4-dimethoxyphenyl}-acryloyl]-benzoic Acids.

A / B structures shown with $R^{5\beta}$ substituent.

| Ex. No. | $R^{5\beta}$ (A) | Ex. No. | $R^{5\beta}$ | Ex. No. | $R^{5\beta}$ |
|---------|------------------|---------|--------------|---------|--------------|
| 1821A / 1821B | furan-2-yl | 1822A / 1822B | thiophen-2-yl | 1823A / 1823B | 1H-pyrrol-2-yl |

EXAMPLE TABLE 25-continued

Substituted 2-[3-{(5-Heteroaryl or 5-heterocyclic)-3,4-dimethoxyphenyl}-acryloyl]-benzoic Acids.

| Ex. No. | A R$^{5\beta}$ | Ex. No. | R$^{5\beta}$ | Ex. No. | B R$^{5\beta}$ |
|---|---|---|---|---|---|
| 1842A 1842B | 3-furyl | 1825A 1825B | 3-thienyl | 1826A 1826B | 3-pyrrolyl |
| 1827A 1827B | 3-benzofuryl | 1828A 1828B | 3-benzothienyl | 1829A 1829B | 5-thiazolyl |
| 1830A 1830B | 5-pyrimidinyl (α-methyl) | 1831A 1811B | 2-indolyl | 1832A 1832B | 4-thiazolyl |
| 1833A 1833B | 2-oxazolyl | 1834A 1834B | 3-indolyl | 1835A 1835B | 2-thiazolyl |
| 1836A 1836B | 5-oxazolyl | 1837A 1837B | 4-indolyl | 1838A 1838B | 2-imidazolyl |
| 1839A 1839B | 4-oxazolyl | 1840A 1840B | 5-indolyl | 1841A 1841B | 2-pyrrolidinyl |
| 1842A 1842B | 3-tetrahydropyranyl | 1843A 1843B | 4-imidazolyl | 1844A 1844B | 3-pyrrolidinyl (α-methyl) |

EXAMPLE TABLE 25-continued

Substituted 2-[3-{(5-Heteroaryl or 5-heterocyclic)-3,4-dimethoxyphenyl}-acryloyl]-benzoic Acids.

| Ex. No. | A R⁵ᵝ | Ex. No. | R⁵ᵝ | Ex. No. | B R⁵ᵝ |
|---|---|---|---|---|---|
| 1845A 1845B | tetrahydrofuran-3-yl | 1846A 1846B | pyridin-3-yl | 1847A 1847B | piperidin-3-yl |
| 1848A 1848B | tetrahydrofuran-2-yl | 1849A 1849B | pyridin-2-yl | 1850A 1850B | piperidin-2-yl |
| 1851A 1851B | pyrimidin-2-yl | 1852A 1852B | pyridin-4-yl | 1853A 1853B | piperidin-4-yl |
| 1854A 1854B | tetrahydropyran-4-yl | 1855A 1855B | pyrazin-2-yl | 1856A 1856B | pyrimidin-4-yl |
| 1857A 1857B | 4-hydroxytetrahydropyran-4-yl | 1858A 1858B | pyridazin-3-yl | 1859A 1859B | 1,3,5-triazin-2-yl |
| 1860A 1860B | pyrazol-3-yl | 1861A 1861B | quinoxalin-2-yl | 1862A 1862B | pyridazin-4-yl |
| 1863A 1863B | isoxazol-5-yl | 1864A 1864B | phthalazin-1-yl | 1865A 1865B | pyrazol-4-yl |
| 1866A 1866B | 1,2,4-triazol-3-yl | 1867A 1867B | benzimidazol-2-yl | 1868A 1868B | piperazin-2-yl |

EXAMPLE TABLE 25-continued

Substituted 2-[3-{(5-Heteroaryl or 5-heterocyclic)-3,4-dimethoxyphenyl}-acryloyl]-benzoic Acids.

EXAMPLE TABLE 26
Substituted 4-[3-{(5-Heteroaryl or 5-heterocyclic)-4-fluorophenyl}-acryloyl]-benzoic Acids.
| Ex. No. | A R$^{5\beta}$ | Ex. No. | R$^{5\beta}$ | Ex. No. | B R$^{5\beta}$ |
|---|---|---|---|---|---|
| 1893A 1893B |  | 1894A 1894B |  | 1895A 1895B |  |
| 1896A 1896B | 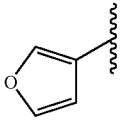 | 1897A 18972B | 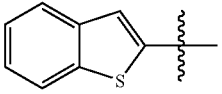 | 1898A 1898B | 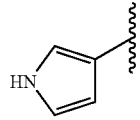 |
| 1899A 1899B | 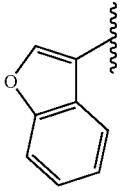 | 1900A 1900B | 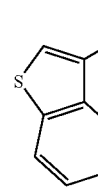 | 1901A 1901B | 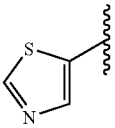 |
| 1902A 1902B | 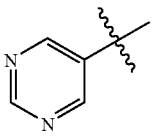 | 1903A 1903B | 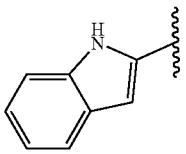 | 1904A 1904B | 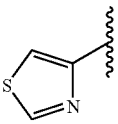 |
| 1905A 1905B | 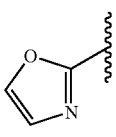 | 1906A 1906B | 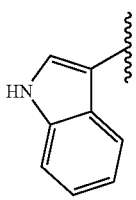 | 1907A 1907B | 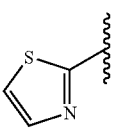 |
| 1908A 1908B | 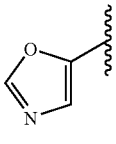 | 1909A 1909B | 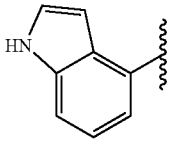 | 1910A 1910B | 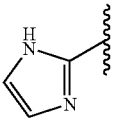 |
| 1911A 1911B | 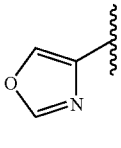 | 1912A 1912B | 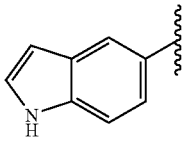 | 1913A 1913B | 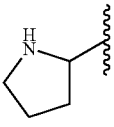 |
| 1914A 1914B | 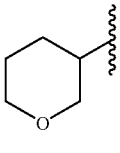 | 1915A 1915B | 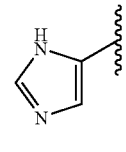 | 1916A 1916B | 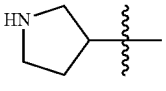 |

EXAMPLE TABLE 26-continued
Substituted 4-[3-{(5-Heteroaryl or 5-heterocyclic)-4-fluorophenyl}-acryloyl]-benzoic Acids.
| Ex. No. | A R⁵ᵝ | Ex. No. | B R⁵ᵝ | Ex. No. | R⁵ᵝ |
|---|---|---|---|---|---|
| 1917A 1917B | 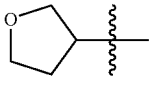 | 1918A 1918B | 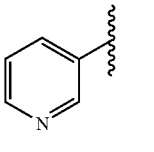 | 1919A 1919B | 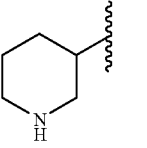 |
| 1920A 1920B | 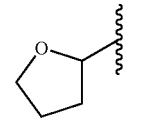 | 1921A 1921B | 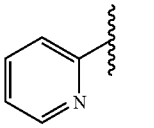 | 1922A 1922B | 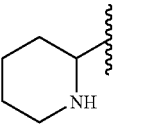 |
| 1923A 1923B | 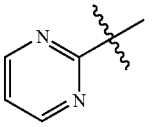 | 1924A 1924B | 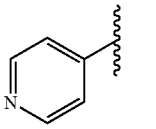 | 1925A 1925B | 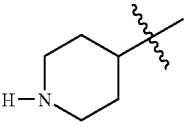 |
| 1926A 1926B | 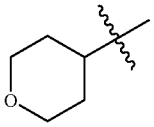 | 1927A 1927B | 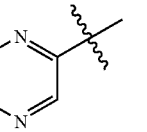 | 1928A 1928B | 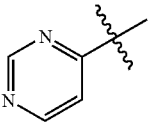 |
| 1929A 1929B | 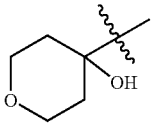 | 1930A 1930B | 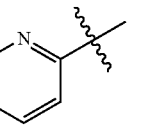 | 1931A 1931B | 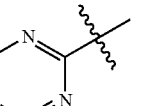 |
| 1932A 1932B | 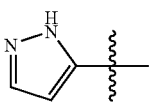 | 1933A 1933B | 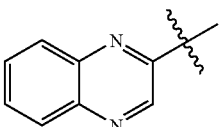 | 1934A 1934B | 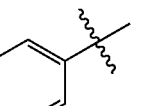 |
| 1935A 1935B | 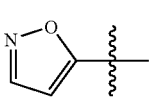 | 1936A 1936B | 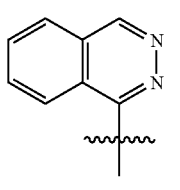 | 1937A 1937B | 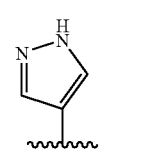 |
| 1938A 1938B | 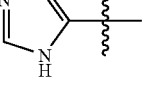 | 1939A 1939B | 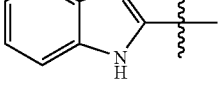 | 1940A 1940B | 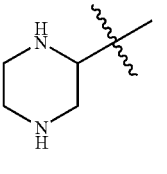 |

EXAMPLE TABLE 26-continued

Substituted 4-[3-{(5-Heteroaryl or 5-heterocyclic)-4-fluorophenyl}-acryloyl]-benzoic Acids.

| Ex. No. | A<br>R^5β | Ex. No. | R^5β | Ex. No. | R^5β |
|---|---|---|---|---|---|
| 1941A<br>1941B | 1H-triazole | 1942A<br>1942B | benzothiazole | 1943A<br>1943B | 1,3,4-oxadiazole |
| 1944A<br>1944B | isoxazole (4-yl) | 1945A<br>1945B | benzoxazole | 1946A<br>1946B | 1,3,4-oxadiazole |
| 1947A<br>1947B | [1,2,4]triazolo[1,5-a]pyrimidine | 1948A<br>1948B | purine | 1949A<br>1949B | quinoline (5-yl) |
| 1950A<br>1950B | isoxazole (3-yl) | 1951A<br>1951B | isoquinoline (1-yl) | 1952A<br>1952B | quinoline (4-yl) |
| 1953A<br>1953B | quinoline (3-yl) | 1954A<br>1954B | isoquinoline (3-yl) | 1955A<br>1955B | quinoline (2-yl) |

EXAMPLE TABLE 27

Substituted 4-[3-{(3-Heteroaryl or 3-heterocyclic)-4-(pyrrolidin-1-yl)-phenyl}acryloyl]-benzoic Acids.

| Ex. No. | A<br>R^5β | Ex. No. | R^5β | Ex. No. | R^5β |
|---|---|---|---|---|---|
| 1956A<br>1956B | furan | 1957A<br>1957B | thiophene | 1958A<br>1958B | pyrrole |

EXAMPLE TABLE 27-continued

Substituted 4-[3-{(3-Heteroaryl or 3-heterocyclic)-4-(pyrrolidin-1-yl)-phenyl}acryloyl]-benzoic Acids.

A / B structures with $R^{5\beta}$ substituents.

| Ex. No. | $R^{5\beta}$ | Ex. No. | $R^{5\beta}$ | Ex. No. | $R^{5\beta}$ |
|---|---|---|---|---|---|
| 1959A 1959B | 3-furyl | 1960A 1960B | 3-thienyl | 1961A 1961B | 3-pyrrolyl |
| 1962A 1962B | 3-benzofuryl | 1963A 1963B | 3-benzothienyl | 1964A 1964B | 5-thiazolyl |
| 1965A 1965B | 5-pyrimidinyl (methyl) | 1966A 1966B | 2-indolyl | 1967A 1967B | 4-thiazolyl |
| 1968A 1968B | 2-oxazolyl | 1969A 1969B | 3-indolyl | 1970A 1970B | 2-thiazolyl |
| 1971A 1971B | 5-oxazolyl | 1972A 1972B | 4-indolyl | 1973A 1973B | 2-imidazolyl |
| 1974A 1974B | 4-oxazolyl | 1975A 1975B | 5-indolyl | 1976A 1976B | 2-pyrrolidinyl |
| 1977A 1977B | 3-tetrahydropyranyl | 1978A 1978B | 4-imidazolyl | 1979A 1979B | 3-pyrrolidinyl |

EXAMPLE TABLE 27-continued

Substituted 4-[3-{(3-Heteroaryl or 3-heterocyclic)-4-(pyrrolidin-1-yl)-phenyl}acryloyl]-benzoic Acids.

| Ex. No. | A R⁵ᵝ | Ex. No. | R⁵ᵝ | Ex. No. | B R⁵ᵝ |
|---|---|---|---|---|---|
| 1980A 1980B | tetrahydrofuran-3-yl | 1981A 1981B | pyridin-3-yl | 1982A 1982B | piperidin-3-yl |
| 1983A 1983B | tetrahydrofuran-2-yl | 1984A 1984B | pyridin-2-yl | 1985A 1985B | piperidin-2-yl |
| 1986A 1986B | pyrimidin-2-yl | 1987A 1987B | pyridin-4-yl | 1988A 1988B | piperidin-4-yl |
| 1989A 1989B | tetrahydropyran-4-yl | 1990A 1990B | pyrazin-2-yl | 1991A 1991B | pyrimidin-4-yl |
| 1992A 1992B | 4-hydroxytetrahydropyran-4-yl | 1993A 1993B | pyridazin-3-yl | 1994A 1994B | 1,3,5-triazin-2-yl |
| 1995A 1995B | pyrazol-3-yl | 1996A 1996B | quinoxalin-2-yl | 1997A 1997B | pyridazin-4-yl |
| 1998A 1998B | isoxazol-5-yl | 1999A 1999B | phthalazin-1-yl | 2000A 2000B | pyrazol-4-yl |
| 2001A 2001B | 1,2,4-triazol-3-yl | 2002A 2002B | benzimidazol-2-yl | 2003A 2003B | piperazin-3-yl |

EXAMPLE TABLE 27-continued

Substituted 4-[3-{(3-Heteroaryl or 3-heterocyclic)-4-(pyrrolidin-1-yl)-phenyl}acryloyl]-benzoic Acids.

| Ex. No. | A R$^{5\beta}$ | Ex. No. | R$^{5\beta}$ | Ex. No. | B R$^{5\beta}$ |
|---|---|---|---|---|---|
| 2004A 2004B | 1,2,3-triazole | 2005A 2005B | benzothiazole | 2006 2006B | 1,3,4-oxadiazole |
| 2007A 2007B | isoxazole | 2008A 2008B | benzoxazole | 2009A 2009B | 1,3,4-oxadiazole |
| 2010A 2010B | [1,2,4]triazolo[1,5-a]pyrimidine | 2011A 2011B | imidazo[4,5-d]pyrimidine | 2012A 2012B | quinoline-5-yl |
| 2013A 2013B | isoxazol-3-yl | 2014A 2014B | isoquinolin-1-yl | 2015A 2015B | quinolin-4-yl |
| 2016A 2016B | quinolin-3-yl | 2017A 2017B | isoquinolin-3-yl | 2018A 2018B | quinolin-2-yl |
| 2019A 2019B | 5-methylfuran-2-yl | 2020A 2020B | 3-methoxycarbonyl-pyrazol-5-yl | 2021A 2021B | 3-bromo-5-methyl-thiophen-2-yl |
| 2022A 2022B | 3-methylfuran-2-yl | 2023A 2023B | 5-acetylthiophen-2-yl | 2024A 2024B | 1-methylpyrrol-2-yl |
| 2025A 2025B | 4-hydroxypiperidin-4-yl | 2026A 2026B | benzothiophen-2-yl | 2027A 2027B | tetrahydropyran-2-yl |

EXAMPLE TABLE 28

Substituted 4-[3-{(5-Heteroaryl or 5-heterocyclic)-2,4-dimethoxyphenyl}-acryloyl]benzonitriles.

| Ex. No. | A R⁵ᵝ | Ex. No. | B R⁵ᵝ | Ex. No. | R⁵ᵝ |
|---|---|---|---|---|---|
| 2028A 2028B | 2-furyl | 2029A 2029B | 2-thienyl | 2030A 2030B | 2-pyrrolyl |
| 2031A 2031B | 3-furyl | 2032A 2032B | 3-thienyl | 2033A 2033B | 3-pyrrolyl |
| 2034A 2034B | 3-benzofuryl | 2035A 2035B | 3-benzothienyl | 2036A 2036B | 5-thiazolyl |
| 2037A 2037B | 5-pyrimidinyl | 2038A 2038B | 2-indolyl | 2039A 2039B | 4-thiazolyl |
| 2040A 2040B | 2-oxazolyl | 2041A 2041B | 3-indolyl | 2042A 2042B | 2-thiazolyl |
| 2043A 2043B | 5-oxazolyl | 2044A 2044B | 4-indolyl | 2045A 2045B | 2-imidazolyl |
| 2046A 2046B | 4-oxazolyl | 2047A 2047B | 5-indolyl | 2048A 2048B | 2-pyrrolidinyl |
| 2049A 2049B | 3-tetrahydropyranyl | 2050A 2050B | 4-imidazolyl | 2051A 2051B | 3-pyrrolidinyl |

EXAMPLE TABLE 28-continued

Substituted 4-[3-{(5-Heteroaryl or 5-heterocyclic)-2,4-dimethoxyphenyl}-acryloyl]benzonitriles.

A: (E)-isomer structure with $R^{5\beta}$
B: (E/Z)-mixture structure with $R^{5\beta}$

| Ex. No. | $R^{5\beta}$ | Ex. No. | $R^{5\beta}$ | Ex. No. | $R^{5\beta}$ |
|---|---|---|---|---|---|
| 2052A, 2052B | tetrahydrofuran-3-yl | 2053A, 2053B | pyridin-3-yl | 2054A, 2054B | piperidin-3-yl |
| 2055A, 2055B | tetrahydrofuran-2-yl | 2056A, 2056B | pyridin-2-yl | 2057A, 2057B | piperidin-2-yl |
| 2058A, 2058B | pyrimidin-2-yl | 2059A, 2059B | pyridin-4-yl | 2060A, 2060B | piperidin-4-yl |
| 2061A, 2061B | tetrahydropyran-4-yl | 2062A, 2062B | pyrazin-2-yl | 2063A, 2063B | pyrimidin-4-yl |
| 2064A, 2064B | 4-hydroxy-tetrahydropyran-4-yl | 2065A, 2065B | pyridazin-3-yl | 2066A, 2066B | 1,3,5-triazin-2-yl |
| 2067A, 2067B | 1H-pyrazol-3-yl | 2068A, 2068B | quinoxalin-2-yl | 2069A, 2069B | pyridazin-4-yl |
| 2070A, 2070B | isoxazol-5-yl | 2071A, 2071B | phthalazin-1-yl | 2072A, 2072B | 1H-pyrazol-4-yl |
| 2073A, 2073B | 1H-1,2,4-triazol-3-yl | 2074A, 2074B | 1H-benzimidazol-2-yl | 2075A, 2075B | piperazin-3-yl |

EXAMPLE TABLE 28-continued

Substituted 4-[3-{(5-Heteroaryl or 5-heterocyclic)-2,4-dimethoxyphenyl}-acryloyl]benzonitriles.

| Ex. No. | A $R^{5\beta}$ | Ex. No. | $R^{5\beta}$ | Ex. No. | B $R^{5\beta}$ |
|---|---|---|---|---|---|
| 2076A 2076B | triazole | 2077A 2077B | benzothiazole | 2078A 2078B | oxadiazole |
| 2079A 2079B | isoxazole | 2080A 2080B | benzoxazole | 2081A 2081B | oxadiazole |
| 2082A 2082B | triazolopyrimidine | 2083A 2083B | imidazopyrimidine | 2084A 2084B | quinoline |
| 2085A 2085B | isoxazole | 2086A 2086B | isoquinoline | 2087A 2087B | quinoline |
| 2088A 20881B | quinoline | 2089A 2089B | isoquinoline | 2090A 2090B | quinoline |

EXAMPLE TABLE 29

Substituted 3-[2,4-Dimethoxy-(5-heteroaryl or 5-heterocyclic)phenyl]-1-[4-(2H-tetrazol-5-yl)phenyl]-2-propen-1-ones.

| Ex. No. | A $R^{5\beta}$ | Ex. No. | $R^{5\beta}$ | Ex. No. | B $R^{5\beta}$ |
|---|---|---|---|---|---|
| 2091A 2091B | furan | 2092A 2092B | thiophene | 2093A 2093B | pyrrole |

EXAMPLE TABLE 29-continued

Substituted 3-[2,4-Dimethoxy-(5-heteroaryl or 5-heterocyclic)phenyl]-1-[4-(2H-tetrazol-5-yl)phenyl]-2-propen-1-ones.

A / B (E/Z isomers of the same core structure with $R^{5\beta}$ substituent)

| Ex. No. | $R^{5\beta}$ | Ex. No. | $R^{5\beta}$ | Ex. No. | $R^{5\beta}$ |
|---|---|---|---|---|---|
| 2094A / 2094B | furan-3-yl | 2095A / 2095B | thiophen-3-yl | 2096A / 2096B | 1H-pyrrol-3-yl |
| 2097A / 2097B | benzofuran-3-yl | 2098A / 2098B | benzothiophen-3-yl | 2099A / 2099B | thiazol-5-yl |
| 2100A / 2100B | pyrimidin-5-yl (1-methyl) | 2101A / 2101B | 1H-indol-2-yl | 2102A / 2102B | thiazol-4-yl |
| 2103A / 2103B | oxazol-2-yl | 2104A / 2104B | 1H-indol-3-yl | 2105A / 2105B | thiazol-2-yl |
| 2106A / 2106B | oxazol-5-yl | 2107A / 2107B | 1H-indol-4-yl | 2108A / 2108B | 1H-imidazol-2-yl |
| 2109A / 2109B | oxazol-4-yl | 2110A / 2110B | 1H-indol-5-yl | 2111A / 2111B | pyrrolidin-2-yl |
| 2112A / 2112B | tetrahydropyran-3-yl | 2113A / 2113B | 1H-imidazol-4-yl | 2114A / 2114B | pyrrolidin-3-yl (1-methyl) |

EXAMPLE TABLE 29-continued

Substituted 3-[2,4-Dimethoxy-(5-heteroaryl or 5-heterocyclic)phenyl]-1-[4-(2H-tetrazol-5-yl)phenyl]-2-propen-1-ones.

A: (E)-isomer with tetrazolyl-phenyl-C(=O)-CH=CH-aryl(2,4-diOCH₃, 5-R⁵ᵝ)
B: (Z)-isomer with same substitution pattern

| Ex. No. (A) | R⁵ᵝ | Ex. No. | R⁵ᵝ | Ex. No. | R⁵ᵝ |
|---|---|---|---|---|---|
| 2115A / 2115B | tetrahydrofuran-3-yl | 2116A / 2116B | pyridin-3-yl | 2117A / 2117B | piperidin-3-yl |
| 2118A / 2118B | tetrahydrofuran-2-yl | 2119A / 2119B | pyridin-2-yl | 2120A / 2120B | piperidin-2-yl |
| 2121A / 2121B | pyrimidin-2-yl | 2122A / 2122B | pyridin-4-yl | 2123A / 2123B | piperidin-4-yl |
| 2124A / 2124B | tetrahydropyran-3-yl | 2125A / 2125B | pyrazin-2-yl | 2126A / 2126B | pyrimidin-4-yl |
| 2127A / 2127B | 4-hydroxytetrahydropyran-4-yl | 2128A / 2128B | pyridazin-3-yl | 2129A / 2129B | 1,3,5-triazin-2-yl |
| 2130A / 2130B | 1H-pyrazol-3-yl | 2131A / 2131B | quinoxalin-2-yl | 2132A / 2132B | pyridazin-4-yl |
| 2133A / 2133B | isoxazol-5-yl | 2134A / 2134B | phthalazin-1-yl | 2135A / 2135B | 1H-pyrazol-4-yl |
| 2136A / 2136B | 1H-1,2,4-triazol-3-yl | 2137A / 2137B | 1H-benzimidazol-2-yl | 2138A / 2138B | piperazin-2-yl |

EXAMPLE TABLE 29-continued

Substituted 3-[2,4-Dimethoxy-(5-heteroaryl or 5-heterocyclic)phenyl]-1-[4-(2H-tetrazol-5-yl)phenyl]-2-propen-1-ones.

| Ex. No. | A R5β | Ex. No. | R5β | Ex. No. | B R5β |
|---|---|---|---|---|---|
| 2139A 2139B | triazole | 2140A 2130B | benzothiazole | 2141A 2141B | oxadiazole |
| 2142A 2142B | isoxazole | 2143A 2143B | benzoxazole | 2144A 2145B | oxadiazole |
| 2145A 2145B | triazolopyrimidine | 2146A 2146B | imidazopyrimidine | 2147A 2147B | quinoline |
| 2148A 2148B | isoxazole | 2149A 2149B | isoquinoline | 2150A 2150B | quinoline |
| 2151A 2151B | quinoline | 2152A 2152B | isoquinoline | 2153A 2153B | quinoline |
| 2154A 2154B | methylfuran | 2155A 2155B | methylester pyrazole | 2156A 2156B | bromomethylthiophene |
| 2157A 2157B | methylfuran | 2158A 2158B | acetylthiophene | 2159A 2159B | N-methylpyrrole |
| 2160A 2160B | hydroxypiperidine | 2161A 2161B | benzothiophene | 2162A 2162B | tetrahydropyran |

EXAMPLE TABLE 30

Substituted 4-[3-{(4-Heteroaryl or 4-heterocyclic)phenyl}-acryloyl]-benzoic Acids.

A: HO₂C-C₆H₄-C(O)-CH=CH-C₆H₄-R^4β

B: HO₂C-C₆H₄-C(O)-C(H)=C(H)-C₆H₄-R^4β

| Ex. No. | R^4β | Ex. No. | R^4β | Ex. No. | R^4β |
|---|---|---|---|---|---|
| 2163A, 2163B | 2-furyl | 2164A, 2164B | 2-benzothienyl | 2165A, 2165B | 2-pyrrolyl |
| 2166A, 2166B | 3-furyl | 2167A, 2167B | 5-methyl-2-benzothienyl | 2168A, 2168B | 3-pyrrolyl |
| 2169A, 2169B | 3-benzofuranyl | 2170A, 2170B | 3-benzothienyl | 2171A, 2171B | 5-thiazolyl |
| 2172A, 2172B | 5-pyrimidinyl | 2173A, 2173B | 2-indolyl | 2174A, 2174B | 4-thiazolyl |
| 2175A, 2175B | 2-oxazolyl | 2176A, 2176B | 3-indolyl | 2177A, 2177B | 3-thienyl |
| 2178A, 2178B | 5-oxazolyl | 2179A, 2179B | 4-indolyl | 2180A, 2180B | 2-imidazolyl |
| 2181A, 2181B | 4-oxazolyl | 2182A, 2182B | 5-indolyl | 2183A, 2183B | 2-pyrrolidinyl |
| 2184A, 2184B | 3-tetrahydropyranyl | 2185A, 2185B | 4-imidazolyl | 2186A, 2186B | 3-pyrrolidinyl |

EXAMPLE TABLE 30-continued

Substituted 4-[3-{(4-Heteroaryl or 4-heterocyclic)phenyl}-acryloyl]-benzoic Acids.

| Ex. No. | A R$^{4\beta}$ | Ex. No. | B R$^{4\beta}$ | Ex. No. | R$^{4\beta}$ |
|---|---|---|---|---|---|
| 2187A 2187B | tetrahydrofuran-3-yl | 2188A 2188B | pyridin-3-yl | 2189A 2189B | piperidin-3-yl |
| 2190A 2190B | tetrahydrofuran-2-yl | 2191A 2191B | pyridin-2-yl | 2192A 2192B | piperidin-2-yl |
| 2193A 2193B | 2-methylpyrimidin-5-yl | 2194A 2194B | pyridin-4-yl | 2195A 2195B | piperidin-4-yl |
| 2196A 2196B | tetrahydropyran-4-yl | 2197A 2197B | pyrazin-2-yl | 2198A 2198B | pyrimidin-4-yl |
| 2199A 2199B | 4-hydroxy-tetrahydropyran-4-yl | 2200A 2200B | pyridazin-3-yl | 2201A 2201B | 1,3,5-triazin-2-yl |
| 2202A 2202B | 1H-pyrazol-3-yl | 2203A 2203B | quinoxalin-2-yl | 2204A 2204B | pyridazin-4-yl |
| 2205A 2205B | isoxazol-5-yl | 2206A 2206B | phthalazin-1-yl | 2207A 2207B | 1H-pyrazol-4-yl |
| 2208A 2208B | 1H-1,2,4-triazol-3-yl | 2209A 2209B | 1H-benzimidazol-2-yl | 2210A 2210B | piperazin-2-yl |
| 2211A 2211B | 1H-1,2,3-triazol-5-yl | 2212A 2212B | benzothiazol-2-yl | 2213A 2213B | 1,3,4-oxadiazol-5-yl |

EXAMPLE TABLE 30-continued
Substituted 4-[3-{(4-Heteroaryl or 4-heterocyclic)phenyl}-acryloyl]-benzoic Acids.
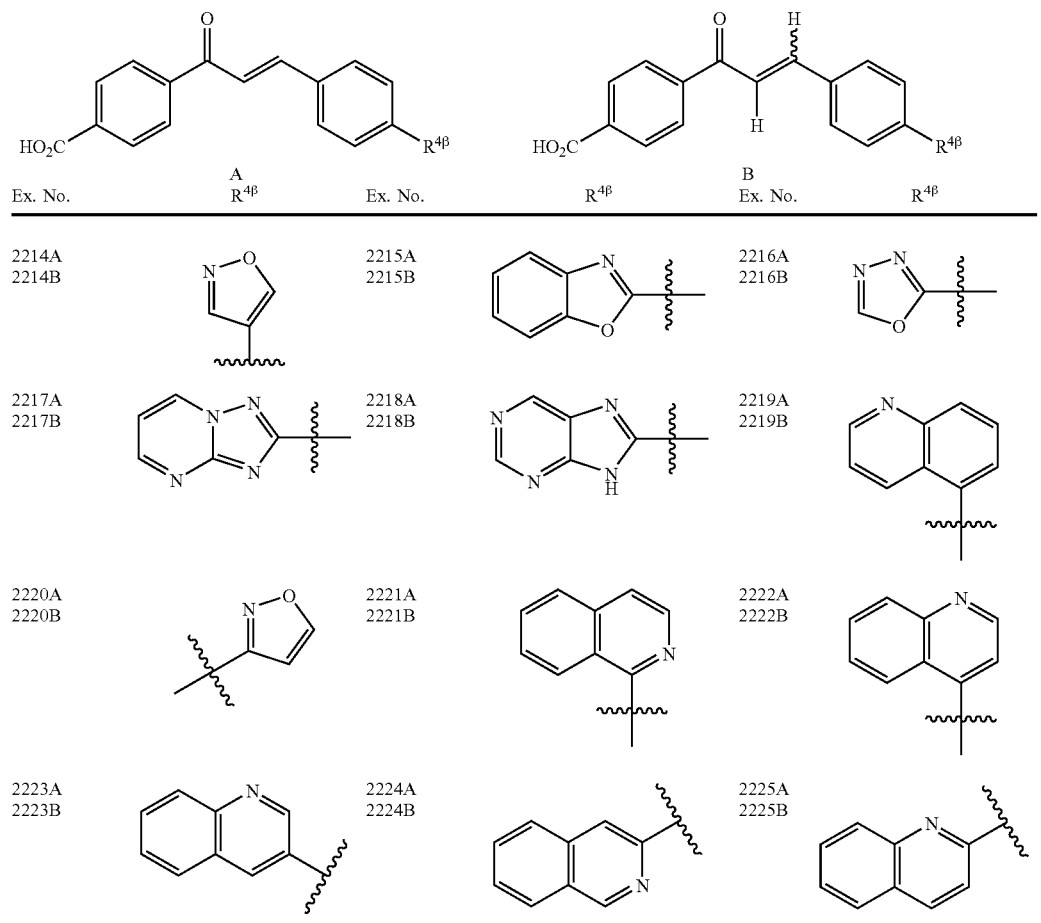
EXAMPLE TABLE 31
Substituted 4-[3-{(4-Heteroaryl or 4-heterocyclic)phenyl}-3-oxo-propenyl]-benzoic Acids.
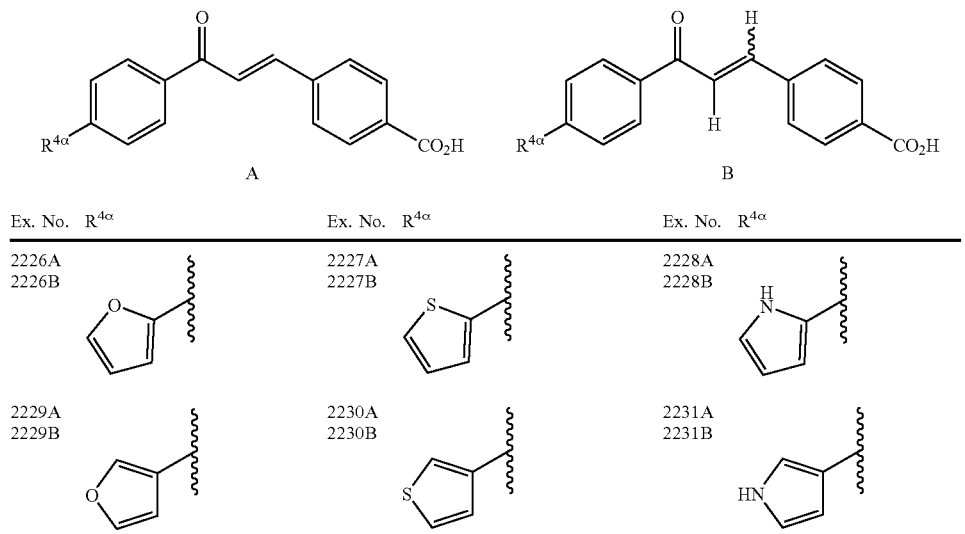

EXAMPLE TABLE 31-continued

Substituted 4-[3-{(4-Heteroaryl or 4-heterocyclic)phenyl}-3-oxo-propenyl]-benzoic Acids.

A

B

| Ex. No. | R⁴ᵅ | Ex. No. | R⁴ᵅ | Ex. No. | R⁴ᵅ |
|---|---|---|---|---|---|
| 2232A, 2232B | benzofuran-3-yl | 2233A, 2233B | benzothiophen-3-yl | 2234A, 2234B | thiazol-5-yl |
| 2235A, 2235B | pyrimidin-5-yl | 2236A, 2236B | 1H-indol-2-yl | 2237A, 2237B | thiazol-4-yl |
| 2238A, 2238B | oxazol-2-yl | 2239A, 2239B | 1H-indol-3-yl | 2240A, 2240B | thiazol-2-yl |
| 2241A, 2241B | oxazol-5-yl | 2242A, 2242B | 1H-indol-4-yl | 2243A, 2243B | 1H-imidazol-2-yl |
| 2244A, 2244B | oxazol-4-yl | 2245A, 2245B | 1H-indol-5-yl | 2246A, 2246B | pyrrolidin-2-yl |
| 2247A, 2247B | tetrahydropyran-3-yl | 2248A, 2248B | 1H-imidazol-5-yl | 2249A, 2249B | pyrrolidin-3-yl |
| 2250A, 2250B | tetrahydrofuran-3-yl | 2251A, 2251B | pyridin-3-yl | 2252A, 2252B | piperidin-3-yl |

EXAMPLE TABLE 31-continued
Substituted 4-[3-{(4-Heteroaryl or 4-heterocyclic)phenyl}-3-oxo-propenyl]-benzoic Acids.
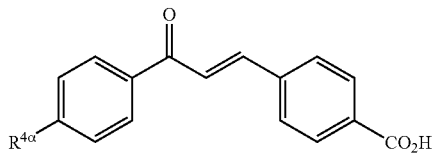
A
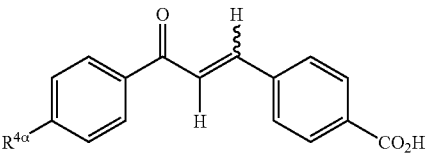
B
| Ex. No. | R^4α | Ex. No. | R^4α | Ex. No. | R^4α |
|---|---|---|---|---|---|
| 2253A 2253B | 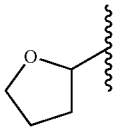 | 2254A 2254B | 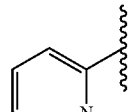 | 2255A 2255B | 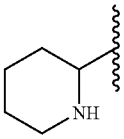 |
| 2256A 2256B | 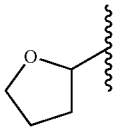 | 2257A 2257B | 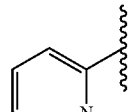 | 2258A 2258B | 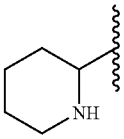 |
| 2259A 2259B | 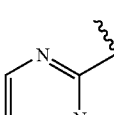 | 2260A 2260B | 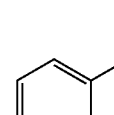 | 2261A 2261B | 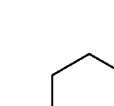 |
| 2262A 2262B | 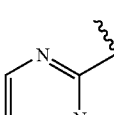 | 2263A 2263B | 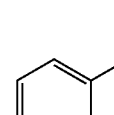 | 2264A 2264B | 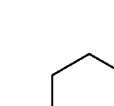 |
| 2265A 2265B | 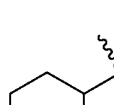 | 2266A 2266B | 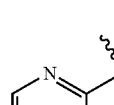 | 2267A 2267B | 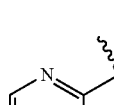 |
| 2268A 2268B | 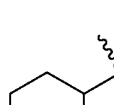 | 2269A 2269B | 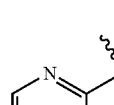 | 2270A 2270B | 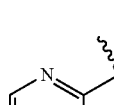 |
| 2271A 2271B | 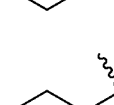 | 2272A 2272B | 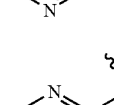 | 2273A 2273B | 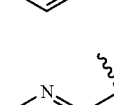 |
| 2274A 2274B | 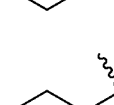 | 2275A 2275B | 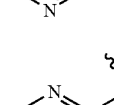 | 2276A 2276B | 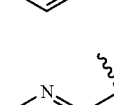 |

EXAMPLE TABLE 31-continued

Substituted 4-[3-{(4-Heteroaryl or 4-heterocyclic)phenyl}-3-oxo-propenyl]-benzoic Acids.

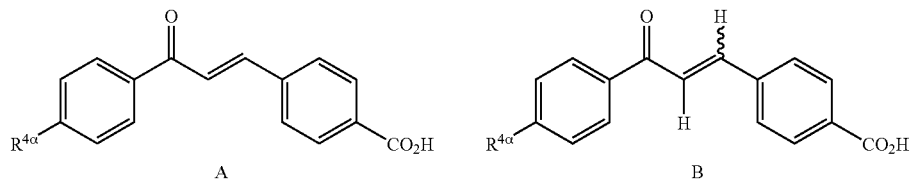

| Ex. No. | R$^{4\alpha}$ | Ex. No. | R$^{4\alpha}$ | Ex. No. | R$^{4\alpha}$ |
|---|---|---|---|---|---|
| 2277A 2277B | isoxazol-4-yl | 2278A 2278B | benzoxazol-2-yl | 2279A 2279B | 1,3,4-oxadiazol-2-yl |
| 2280A 2280B | [1,2,4]triazolo[1,5-a]pyrimidin-2-yl | 2281A 2281B | 1H-imidazo[4,5-d]pyrimidin-2-yl | 2282A 2282B | quinolin-5-yl |
| 2283A 2283B | isoxazol-3-yl | 2284A 2284B | isoquinolin-1-yl | 2285A 2285B | quinolin-4-yl |
| 2286A 2286B | quinolin-3-yl | 2287A 2287B | isoquinolin-3-yl | 2288A 2288B | quinolin-2-yl |
| 2289A 2289B | 5-methylfuran-2-yl | 2290A 2290B | 5-methoxycarbonyl-1H-pyrazol-3-yl | 2291A 2291B | 4-bromo-5-methylthiophen-2-yl |
| 2292A 2292B | 3-methylfuran-2-yl | 2293A 2293B | 5-acetylthiophen-2-yl | 2294A 2294B | 1-methylpyrrol-2-yl |
| 2295A 2295B | 4-hydroxypiperidin-4-yl | 2296A 2296B | benzothiophen-2-yl | 2297A 2297B | tetrahydropyran-2-yl |

EXAMPLE TABLE 32

Substituted 4-[3-{(4-Heteroaryl or 4-heterocyclic)-2,6-dimethoxyphenyl}-acryloyl]-benzoic Acids.

| Ex. No. | R$^{4\beta}$ | Ex. No. | R$^{4\beta}$ | Ex. No. | R$^{4\beta}$ |
|---|---|---|---|---|---|
| 2298A / 2298B | 2-furyl | 2299A / 2299B | 2-thienyl | 2300A / 2300B | 2-pyrrolyl |
| 2301A / 2301B | 3-furyl | 2302A / 2302B | 3-thienyl | 2303A / 2303B | 3-pyrrolyl |
| 2304A / 2304B | 3-benzofuryl | 2305A / 2305B | 3-benzothienyl | 2306A / 2306B | 5-thiazolyl |
| 2307A / 2307B | 5-pyrimidinyl (with methyl) | 2308A / 2308B | 2-indolyl | 2309A / 2309B | 4-thiazolyl |
| 2310A / 2310B | 2-oxazolyl | 2311A / 2311B | 3-indolyl | 2312A / 2312B | 2-thiazolyl |
| 2313A / 2313B | 5-oxazolyl | 2314A / 2314B | 4-indolyl | 2315A / 2315B | 2-imidazolyl |
| 2316A / 2316B | 4-oxazolyl | 2317A / 2317B | 5-indolyl | 2318A / 2318B | 2-pyrrolidinyl |

EXAMPLE TABLE 32-continued
Substituted 4-[3-{(4-Heteroaryl or 4-heterocyclic)-2,6-dimethoxyphenyl}-acryloyl]-benzoic Acids.
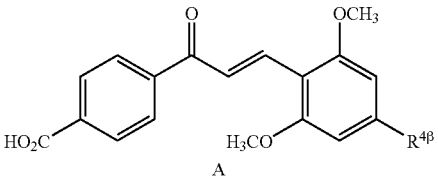

EXAMPLE TABLE 32-continued
Substituted 4-[3-{(4-Heteroaryl or 4-heterocyclic)-2,6-dimethoxyphenyl}-acryloyl]-benzoic Acids.
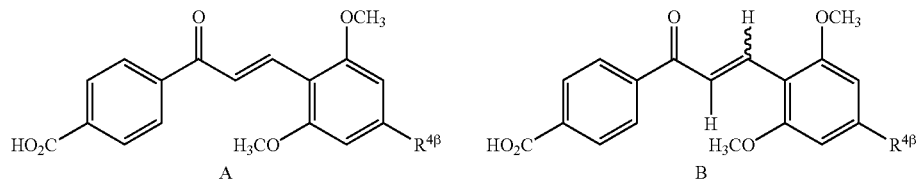
| Ex. No. | R$^{4\beta}$ | Ex. No. | R$^{4\beta}$ | Ex. No. | R$^{4\beta}$ |
|---|---|---|---|---|---|
| 2343A 2343B | 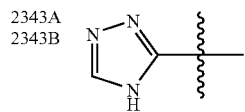 | 2344A 2344B | 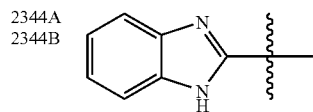 | 2345A 2345B | 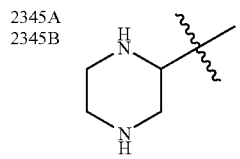 |
| 2346A 2346B | 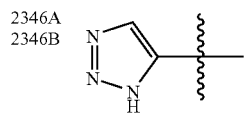 | 2347A 2347B | 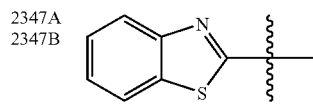 | 2348A 2348B | 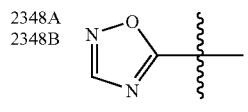 |
| 2349A 2349B | 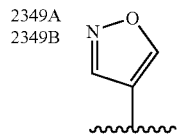 | 2350A 2350B | 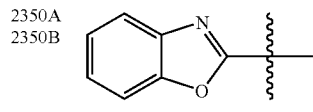 | 2351A 2351B | 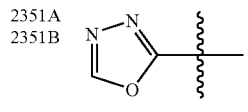 |
| 2352A 2352B | 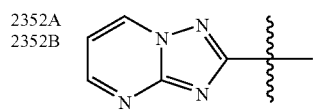 | 2353A 2353B | 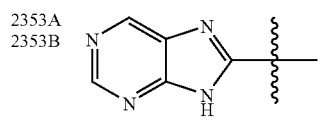 | 2354A 2354B | 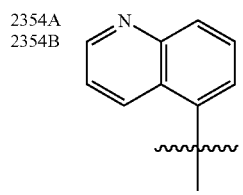 |
| 2355A 2355B | 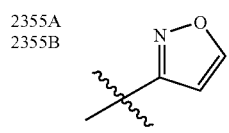 | 2356A 2356B | 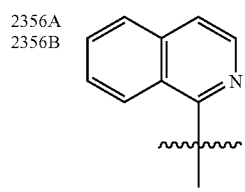 | 2357A 2357B | 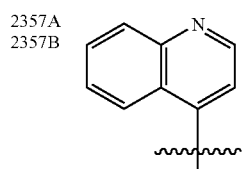 |
| 2358A 2358B | 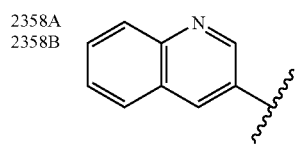 | 2359A 2359B | 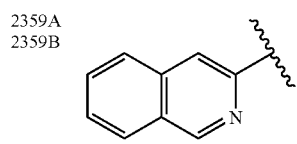 | 2360A 2360B | 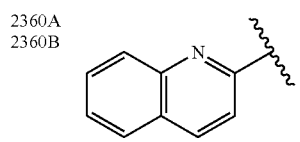 |

EXAMPLE TABLE 33

Substituted 4-[3-{(5-Heteroaryl or 5-heterocyclic)-2,4-dimethoxyphenyl}-acryloyl]-benzoic Acids.

[Structure A: HO₂C-phenyl-C(=O)-CH=CH-(2,4-dimethoxyphenyl with R⁵ᵝ substituent), trans configuration]

[Structure B: HO₂C-phenyl-C(=O)-CH=CH-(2,4-dimethoxyphenyl with R⁵ᵝ substituent), cis/mixed configuration]

| Ex. No. | $R^{5\beta}$ | Ex. No. | $R^{5\beta}$ | Ex. No. | $R^{5\beta}$ |
|---|---|---|---|---|---|
| 2361A, 2361B | 5-methyl-furan-2-yl | 2362A, 2362B | 3-(methoxycarbonyl)-1H-pyrazol-5-yl | 2363A, 2363B | 4-bromo-5-methyl-thiophen-2-yl |
| 2364A, 2364B | 3-methyl-furan-2-yl | 2365A, 2365B | 5-acetyl-thiophen-2-yl | 2366A, 2366B | 1-methyl-pyrrol-2-yl |
| 2367A, 2367B | 4-hydroxy-piperidin-4-yl | 2368A, 2368B | benzothiophen-2-yl | 2369A, 2369B | tetrahydropyran-2-yl |

Stereoisomerism and Polymorphism

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Pharmaceutically Acceptable Salt Formulations

In cases where compounds are sufficiently basic or acidic to form stable nontoxic acid or base salts, administration of the compound as a pharmaceutically acceptable salt may be appropriate. The term "pharmaceutically acceptable salts" or "complexes" refers to salts or complexes that retain the desired biological activity of the compounds of the present invention and exhibit minimal undesired toxicological effects.

Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts may also be formed, including, sulfate, nitrate, bicarbonate and carbonate salts. Alternatively, the pharmaceutically acceptable salts may be made with sufficiently basic compounds such as an amine with a suitable acid affording a physiologically acceptable anion. Alkali metal (for example, sodium, potassium or lithium) or alkaline earth metal (for example calcium) salts of carboxylic acids can also be made.

Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Particular FDA-approved salts can be conveniently divided between anions and cations (Approved Drug Products with Therapeutic Equivalence Evaluations (1994) U.S. Department of Health and Human Services, Public Health Service, FDA, Center for Drug Evaluation and Research, Rockville, Md.; L. D. Bighley, S. M. Berge and D. C. Monkhouse, Salt Forms of Drugs and Absorption, *Encyclopedia of Pharmaceutical Technology*, Vol. 13, J. Swarbridk and J. Boylan, eds., Marcel Dekker, NY (1996)). Among the approved anions include aceglumate, acephyllinate, acetamidobenzoate, acetate, acetylasparaginate, acetylaspartate, adipate, aminosalicylate, anhydromethylenecitrate, ascorbate, aspartate, benzoate, besylate, bicarbonate, bisulfate, bitartrate, borate, bromide, camphorate, camsylate, carbonate, chloride, chlorophenoxyacetate, citrate,closylate, cromesilate, cyclamate, dehydrocholate, dihydrochloride, dimalonate, edentate, edisylate, estolate, esylate, ethylbromide, ethylsulfate, fendizoate, fosfatex, fumarate, gluceptate, gluconate, glucuronate, glutamate, glycerophosphate, glysinate, glycollylarsinilate, glycyrrhizate, hippurate, hemisulfate, hexylresorcinate, hybenzate, hydrobromide, hydrochloride, hydroiodid, hydroxybenzenesulfonate, hydroxybenzoate, hydroxynaphthoate, hyclate, iodide, isethionate, lactate, lactobionate, lysine, malate, maleate, mesylate, methylbromide, methyliodide, methylnitrate, methylsulfate, monophosadenine, mucate, napadisylate, napsylate, nicotinate, nitrate, oleate, orotate, oxalate, oxoglurate, pamoate, pantothenate, pectinate, phenylethylbarbiturate, phosphate, pacrate, plicrilix, polistirex, polygalacturonate, propionate, pyridoxylphosphate, saccharinate, salicylate, stearate, succinate, stearylsulfate, subacetate, succinate, sulfate, sulfosalicylate, tannate, tartrate, teprosilate, terephthalate, teoclate, thiocyante, tidiacicate, timonacicate, tosylate, triethiodide, triethiodide, undecanoate, and xinafoate. The approved cations include ammonium, benethamine, benzathine, betaine, calcium, carnitine, clemizole, chlorcyclizine, choline, dibenylamine, diethanolamine, diethylamine, diethylammonium diolamine, eglumine, erbumine, ethylenediamine, heptaminol, hydrabamine, hydroxyethylpyrrolidone, imadazole, meglumine, olamine, piperazine, 4-phenylcyclohexylamine, procaine, pyridoxine, triethanolamine, and tromethamine. Metallic cations include, aluminum, bismuth, calcium lithium, magnesium, neodymium, potassium, rubidium, sodium, strontium and zinc.

A particular class of salts can be classified as organic amine salts. The organic amines used to form these salts can be primary amines, secondary amines or tertiary amines, and the substituents on the amine can be straight, branched or cyclic groups, including ringed structures formed by attachment of two or more of the amine substituents. Of particular interest are organic amines that are substituted by one or more hydroxyalkyl groups, including alditol or carbohydrate moieties. These hydroxy substituted organic amines can be cyclic or acyclic, both classes of which can be primary amines, secondary amines or tertiary amines. A common class of cyclic hydroxy substituted amines are the amino sugars.

Carbohydrate moieties that can comprise one or more substituents in the amine salt include those made from substituted and unsubstituted monosaccharides, disaccharides, oligosaccharides, and polysaccharides. The saccharide can be an aldose or ketose, and may comprise 3, 4, 5, 6, or 7 carbons. In one embodiment the carbohydrates are monosaccharides. In another embodiment the carbohydrates are pyranose and furanose sugars. Non limiting examples of pyranose and furanose moieties that can be part of the organic amine salt include threose, ribulose, ketose, gentiobiose, aldose, aldotetrose, aldopentose, aldohexose, ketohexose, ketotetrose, ketopentose, erythrose, threose, ribose, deoxyribose, arabinose, xylose, lyxose, allose, altrose, glucose, mannose, gulose, idose, glactose, talose, erythrulose, ribulose, xylulose, psicose, fructose, sorbose, tagatose, dextrose, maltose, lactose, sucrose, cellulose, aldose, amylose, palatinose, trehalose, turanose, cellobiose, amylopectin, glucosamine, mannosamine, fucose, phamnose, glucuronate, gluconate, glucono-lactone, muramic acid, abequose, rhamnose, gluconic acid, glucuronic acid, and galactosamine. The carbohydrate moiety can optionally be deoxygenated at any corresponding C-position, and/or substituted with one or more moieties such as hydrogen, halo, haloalkyl, carboxyl, acyl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, thioester, thioether, oxime, hydrazine, carbamate, phosphonic acid, phosphonate, or any other viable functional group that does not inhibit the pharmacological activity of this compound. Exemplary substituents include amine and halo, particularly fluorine. The substituent or carbohydrate can be either unprotected, or protected as necessary, as known to those skilled in the art, for example, as taught in Greene, et al., *Protective Groups in Organic Synthesis*, John Wiley and Sons, Second Edition, 1991, hereby incorporated by reference. In one embodiment the monosaccharide is a furanose such as (L or D)-ribose.

Of particular interest among the acyclic organic amines are a class represented by the formula

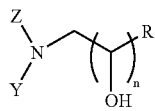

wherein Y and Z are independently hydrogen or lower alkyl or, may be taken together to form a ring, R is hydrogen, alkyl or hydroxyloweralkyl, and n is 1, 2, 3, 4, or 5. Among these hydroxyl amines are a particular class characterized when n is 4. A representative of this group is meglumine, represented when Y is hydrogen, Z is methyl and R is methoxy. Meglumine is also known in the art as N-methylglucamine, N-MG, and 1-deoxy-1-(methylamino)-D-glucitol.

The invention also includes pharmaceutically acceptable prodrugs of the compounds. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

Any of the compounds described herein can be administered as a prodrug to increase the activity, bioavailability, stability or otherwise alter the properties of the compound. A number of prodrug ligands are known. In general, alkylation, acylation or other lipophilic modification of the compound will increase the stability of the chalcone. Examples of substituent groups that can replace one or more hydrogens on the compound are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed compounds to achieve a desired effect.

The compounds can be used to treat inflammatory disorders that are mediated by VCAM-1 including, but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina and small artery disease.

The compounds disclosed herein can be used in the treatment of inflammatory skin diseases that are mediated by VCAM-1, and in particular, human endothelial disorders that are mediated by VCAM-1, which include, but are not limited to, psoriasis, dermatitis, including eczematous dermatitis, and Kaposi's sarcoma, as well as proliferative disorders of smooth muscle cells.

In yet another embodiment, the compounds disclosed herein can be selected to treat anti-inflammatory conditions that are mediated by mononuclear leucocytes.

In yet another embodiment, the compounds of the present invention can be selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. They are also indicated for the prevention or treatment of graft-versus-host disease, which sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In another aspect the invention provides pharmaceutical compositions for the treatment of diseases or disorders mediated by VCAM-1 wherein such compositions comprise a VCAM-1 inhibiting amount of a chalcone derivatives of the invention or a pharmaceutically acceptable salt thereof and/or a pharmaceutically acceptable carrier.

In another aspect the invention provides a method for treating a disease or disorder mediated by VCAM-1 comprising administering to a patient a VCAM-1 inhibiting effective amount of a compound of the invention or a pharmaceutically acceptable salt thereof.

In another aspect the invention provides a method for treating cardiovascular and inflammatory disorders in a patient in need thereof comprising administering to said patient an VCAM-1 inhibiting effective amount of a compound of the invention or a pharmaceutically acceptable salt thereof.

In another aspect the invention provides a method and composition for treating asthma or arthritis in a patient in need thereof comprising administering to said patient an effective amount of a compound of the invention or a pharmaceutically acceptable salt thereof.

The compounds of the present invention can be used to treat any disorder that is mediated by VCAM-1. VCAM-1 is upregulated in a wide variety of disease states, including but not limited to arthritis, asthma, dermatitis, psoriasis, cystic fibrosis, post transplantation late and chronic solid organ rejection, multiple sclerosis, systemic lupus erythematosis, inflammatory bowel diseases, autoimmune diabetes, diabetic retinopathy, diabetic nephropathy, diabetic vasculopathy, rhinitis, ischemia-reperfusion injury, post-angioplasty restenosis, chronic obstructive pulmonary disease (COPD), glomerulonephritis, Graves disease, gastrointestinal allergies, atherosclerosis, coronary artery disease, angina, small artery disease, and conjunctivitis.

Nonlimiting examples of arthritis include rheumatoid (such as soft-tissue rheumatism and non-articular rheumatism, fibromyalgia, fibrositis, muscular rheumatism, myofascil pain, humeral epicondylitis, frozen shoulder, Tietze's syndrome, fascitis, tendinitis, tenosynovitis, bursitis), juvenile chronic, spondyloarthropaties (ankylosing spondylitis), osteoarthritis, hyperuricemia and arthritis associated with acute gout, chronic gout and systemic lupus erythematosus.

Human endothelial disorders mediated by VCAM-1 include psoriasis, eczematous dermatitis, Kaposi's sarcoma, as well as proliferative disorders of smooth muscle cells.

In yet another embodiment, the compounds disclosed herein can be selected to treat anti-inflammatory conditions that are mediated by mononuclear leucocytes.

In one embodiment, the compounds of the present invention are selected for the prevention or treatment of tissue or organ transplant rejection. Treatment and prevention of organ or tissue transplant rejection includes, but are not limited to treatment of recipients of heart, lung, combined heart-lung, liver, kidney, pancreatic, skin, spleen, small bowel, or corneal transplants. The compounds can also be used in the prevention or treatment of graft-versus-host disease, such as sometimes occurs following bone marrow transplantation.

In an alternative embodiment, the compounds described herein are useful in both the primary and adjunctive medical treatment of cardiovascular disease. The compounds are used in primary treatment of, for example, coronary disease states including atherosclerosis, post-angioplasty restenosis, coronary artery diseases and angina. The compounds can be administered to treat small vessel disease that is not treatable by surgery or angioplasty, or other vessel disease in which surgery is not an option. The compounds can also be used to stabilize patients prior to revascularization therapy.

In addition to inhibiting the expression of VCAM-1, some of the compounds of the invention have the additional properties of inhibiting monocyte chemoattractant protein-1 (MCP-1) and/or smooth muscle proliferation. MCP-1 is a chemoattractant protein produced by endothelial cells, smooth muscle cells as well as macrophages. MCP-1 promotes integrin activation on endothelial cells thereby facilitating adhesion of leukocytes to VCAM-1, and MCP-1 is a chemoattractant for monocytes. MCP-1 has been shown to play a role in leukocyte recruitment in a number of chronic inflammatory diseases including atherosclerosis, rheumatoid arthritis, and asthma. Its expression is upregulated in these diseases and as such inhibition of MCP-1 expression represents a desirable property of anti-inflammatory therapeutics. Furthermore, smooth muscle cell hyperplasia and resulting tissue remodeling and decreased organ function is yet another characteristic of many chronic inflammatory diseases including atherosclerosis, chronic transplant rejection and asthma. Inhibition of the hyperproliferation of smooth muscle cells is another desirable property for therapeutic compounds.

Combination and Alternation Therapy

Any of the compounds disclosed herein can be administered in combination or alternation with a second biologically active agent to increase its effectiveness against the target disorder.

In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

The efficacy of a drug can be prolonged, augmented, or restored by administering the compound in combination or alternation with a second, and perhaps third, agent that induces a different biological pathway from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the condition.

Any method of alternation can be used that provides treatment to the patient. Nonlimiting examples of alternation patterns include 1–6 weeks of administration of an effective amount of one agent followed by 1–6 weeks of administration of an effective amount of a second agent. The alternation schedule can include periods of no treatment. Combination therapy generally includes the simultaneous administration of an effective ratio of dosages of two or more active agents.

Illustrative examples of specific agents that can be used in combination or alternation with the compounds of the present invention are described below in regard to asthma and arthritis. The agents set out below or others can alternatively be used to treat a host suffering from any of the other disorders listed above or that are mediated by VCAM-1 or MCP-1. Illustrative second biologically active agents for the treatment of cardiovascular disease are also provided below.

Asthma

In one embodiment, the compounds of the present invention are administered in combination or alternation with heparin, frusemide, ranitidine, an agent that effects respiratory function, such as DNAase, or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, leukotriene-$D_4$-receptor antagonists such as Accolate (zafirlukast), Ziflo (zileuton), leukotriene $C_1$ or $C_2$ antagonists and inhibitors of leukotriene synthesis such as zileuton for the treatment of asthma, or an inducible nitric oxide synthase inhibitor.

In another embodiment, the active compound is administered in combination or alternation with one or more other prophylactic agent(s). Examples of prophylactic agents that can be used in alternation or combination therapy include but are not limited to sodium cromoglycate, Intal (cromolyn sodium, Nasalcrom, Opticrom, Crolom, Ophthalmic Crolom), Tilade (nedocromil, nedocromil sodium) and ketotifen.

In another embodiment, the active compound is administered in combination or alternation with one or more other $\beta_2$-adrenergic agonist(s) ($\beta$ agonists). Examples of $\beta_2$-adrenergic agonists ($\beta$ agonists) that can be used in alternation or combination therapy include but are not limited to albuterol (salbutamol, Proventil, Ventolin), terbutaline, Maxair (pirbuterol), Serevent (salmeterol), epinephrine, metaproterenol (Alupent, Metaprel), Brethine (Bricanyl, Brethaire, terbutaline sulfate), Tornalate (bitolterol), isoprenaline, ipratropium bromide, bambuterol hydrochloride, bitolterol meslyate, broxaterol, carbuterol hydrochloride, clenbuterol hydrochloride, clorprenaline hydrochloride, efirmoterol fumarate, ephedra (source of alkaloids), ephedrine (ephedrine hydrochloride, ephedrine sulfate), etafedrine hydrochloride, ethylnoradrenaline hydrochloride, fenoterol hydrochloride, hexoprenaline hydrochloride, isoetharine hydrochloride, isoprenaline, mabuterol, methoxyphenamine hydrochloride, methylephedrine hydrochloride, orciprenaline sulphate, phenylephrine acid tartrate, phenylpropanolamine (phenylpropanolamine polistirex, phenylpropanolamine sulphate), pirbuterol acetate, procaterol hydrochloride, protokylol hydrochloride, psuedoephedrine (psuedoephedrine polixtirex, psuedoephedrine tannate, psuedoephedrine hydrochloride, psuedoephedrine sulphate), reproterol hydrochloride, rimiterol hydrobromide, ritodrine hydrochloride, salmeterol xinafoate, terbutaline sulphate, tretoquinol hydrate and tulobuterol hydrochloride.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other antihistimine(s) ($H_1$ receptor antagonists). Examples of antihistimines ($H_1$ receptor antagonists) that can be used in alternation or combination therapy include alkylamines, ethanolamines ethylenediamines, piperazines, piperidines or phenothiazines. Some non-limiting examples of antihistimes are Chlortrimeton (Teldrin, chlorpheniramine), Atrohist (brompheniramine, Bromarest, Bromfed, Dimetane), Actidil (triprolidine), Dexchlor (Poladex, Polaramine, dexchlorpheniramine), Benadryl (diphen-hydramine), Tavist (clemastine), Dimetabs (dimenhydrinate, Dramamine, Marmine), PBZ (tripelennamine), pyrilamine, Marezine (cyclizine), Zyrtec (cetirizine), hydroxyzine, Antivert (meclizine, Bonine), Allegra (fexofenadine), Hismanal (astemizole), Claritin (loratadine), Seldane (terfenadine), Periactin (cyproheptadine), Nolamine (phenindamine, Nolahist), Phenameth (promethazine, Phenergan), Tacaryl (methdilazine) and Temaril (trimeprazine).

Alternatively, the compound of the present invention is administered in combination or alternation with
(a) xanthines and methylxanthines, such as Theo-24 (theophylline, Slo-Phylline, Uniphyllin, Slobid, Theo-Dur), Choledyl (oxitriphylline), aminophylline;
(b) anticholinergic agents (antimuscarinic agents) such as belladonna alkaloids, Atrovent (ipratropium bromide), atropine, oxitropium bromide;
(c) phosphodiesterase inhibitors such as zardaverine;
(d) calcium antagonists such as nifedipine; or
(e) potassium activators such as cromakalim for the treatment of asthma.

Arthritic Disorders

In one embodiment, the compound of the present invention can also be administered in combination or alternation with apazone, amitriptyline, chymopapain, collegenase, cyclobenzaprine, diazepam, fluoxetine, pyridoxinee, ademetionine, diacerein, glucosamine, hylan (hyaluronate), misoprostol, paracetamol, superoxide dismutase mimics, TNFα receptor antagonists, TNFα antibodies, P38 Kinase inhibitors, tricyclic antidepressents, cJun kinase inhibitors or immunosuppressive agents, IV gamma globulin, troleandomycin, cyclosporin (Neoral), methotrexate, FK-506, gold compounds such as Myochrysine (gold sodium thiomalate), platelet activating factor (PAF) antagonists such as thromboxane inhibitors, and inducible nitric oxide sythase inhibitors.

In another embodiment, the active compound is administered in combination or alternation with one or more other corticosteriod(s). Examples of corticosteriods that can be used in alternation or combination therapy include but are not limited to glucocorticoids (GC), Aerobid (Aerobid-M, flunisolide), Azmacort (triamcinolone acetonide), Beclovet (Vanceril, beclomethasone dipropionate), Flovent (fluticasone), Pulmicort (budesonide), prednisolone, hydrocortisone, adrenaline, Alclometasone Dipropionate, Aldosterone, Amcinonide, Beclomethasone Dipropionate, Bendacort, Betamethasone (Betamethasone Acetate, Betamethasone Benzoate, Betamethasone Dipropionate, Betamethasone Sodium Phosphate, Betamethasone Valerate), Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate (Deoxycortone Pivalate), Deprodone, Desonide, Desoxymethasone, Dexamethasone (Dexamethasone Acetate, Dexamethasone Isonicotinate, Dexamethasone Phosphate, Dexamethasone Sodium Metasulphobenzoate, Dexamethasone Sodium Phosphate), Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone (Flumethasone Pivalate), Flunisolide, Fluocinolone Acetonide, Fluocinonide, Fluocortin Butyl, Fluocortolone (Fluocortolone Hexanoate, Fluocortolone Pivalate), Fluorometholone (Fluorometholone Acetate), Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone (Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate), Medrysone, Meprednisone, Methylprednisolone (Methylprednisolone Acetate, Methylprednisolone, Hemisuccinate, Methylprednisolone Sodium Succinate), Mometasone Furoate, Paramethasone Acetate, Prednicarbate, Prednisolamate Hydrochloride, Prednisolone (Prednisolone Acetate, Prednisolone Hemisuccinate, Prednisolone Hexanoate, Prednisolone Pivalate, Prednisolone Sodium Metasulphobenzoate, Prednisolone Sodium Phosphate, Prednisolone Sodium Succinate, Prednisolone Steaglate, Prednisolone Tebutate), Prednisone (Prednisone Acetate), Prednylidene, Procinonide, Rimexolone, Suprarenal Cortex, Tixocortol Pivalate, Triamcinolone (Triamcinolone Acetonide, Triamcinolone Diacetate and Triamcinolone Hexacetonide).

In another embodiment, the active compound is administered in combination or alternation with one or more other non-steroidal anti-inflammatory drug(s) (NSAIDS). Examples of NSAIDS that can be used in alternation or combination therapy are carboxylic acids, propionic acids, fenamates, acetic acids, pyrazolones, oxicans, alkanones, gold compounds and others that inhibit prostaglandin synthesis, preferably by selectively inhibiting cylcooxygenase-2 (COX-2). Some nonlimiting examples of COX-2 inhibitors are Celebrex (celecoxib), Bextra (valdecoxib), Dynastat (parecoxib sodium) and Vioxx (rofacoxib). Some non-limiting examples of NSAIDS are aspirin (acetylsalicylic acid), Dolobid (diflunisal), Disalcid (salsalate, salicylsalicylate), Trisilate (choline magnesium trisalicylate), sodium salicylate, Cuprimine (penicillamine), Tolectin (tolmetin), ibuprofen (Motrin, Advil, Nuprin Rufen), Naprosyn (naproxen, Anaprox, naproxen sodium), Nalfon (fenoprofen), Orudis (ketoprofen), Ansaid (flurbiprofen), Daypro (oxaprozin), meclofenamate (meclofanamic acid, Meclomen), mefenamic acid, Indocin (indomethacin), Clinoril (sulindac), tolmetin, Voltaren (diclofenac), Lodine (etodolac), ketorolac, Butazolidin (phenylbutazone), Tandearil (oxyphenbutazone), piroxicam (Feldene), Relafen (nabumetone), Myochrysine (gold sodium thiomalate), Ridaura (auranofin), Solganal (aurothioglucose), acetaminophen, colchicine, Zyloprim (allopurinol), Benemid (probenecid), Anturane (sufinpyrizone), Plaquenil (hydroxychloroquine), Aceclofenac, Acemetacin, Acetanilide, Actarit, Alclofenac, Alminoprofen, Aloxiprin, Aluminium Aspirin, Amfenac Sodium, Amidopyrine, Aminopropylone, Ammonium Salicylate, Ampiroxicam, Amyl Salicylate, Anirolac, Aspirin, Auranofin, Aurothioglucose, Aurotioprol, Azapropazone, Bendazac (Bendazac Lysine), Benorylate, Benoxaprofen, Benzpiperylone, Benzydamine, Hydrochloride, Bornyl Salicylate, Bromfenac Sodium, Bufexamac, Bumadizone Calcium, Butibufen Sodium, Capsaicin, Carbaspirin Calcium, Carprofen, Chlorthenoxazin, Choline Magnesium Trisalicylate, Choline Salicylate, Cinmetacin, Clofexamide, Clofezone, Clometacin, Clonixin, Cloracetadol, Cymene, Diacerein, Diclofenac (Diclofenac Diethylammonium Salt, Diclofenac Potassium, Diclofenac Sodium), Diethylamine Salicylate, Diethylsalicylamide, Difenpiramide, Diflunisal, Dipyrone, Droxicam, Epirizole, Etenzamide, Etersalate, Ethyl Salicylate, Etodolac, Etofenamate, Felbinac, Fenbufen, Fenclofenac, Fenoprofen Calcium, Fentiazac, Fepradinol, Feprazone, Floctafenine, Flufenamic, Flunoxaprofen, Flurbiprofen (Flurbiprofen Sodium), Fosfosal, Furprofen, Glafenine, Glucametacin, Glycol Salicylate, Gold Keratinate, Harpagophytum Procumbens, Ibufenac, Ibuprofen, Ibuproxam, Imidazole Salicylate, Indomethacin (Indomethacin Sodium), Indoprofen, Isamifazone, Isonixin, Isoxicam, Kebuzone, Ketoprofen, Ketorolac Trometamol, Lithium Salicylate, Lonazolac Calcium, Lomoxicam, Loxoprofen Sodium, Lysine Aspirin, Magnesium Salicylate, Meclofenamae Sodium, Mefenamic Acid, Meloxicam, Methyl Butetisalicylate, Methyl Gentisate, Methyl Salicylate, Metiazinic Acid, Metifenazone, Mofebutazone, Mofezolac, Morazone Hydrochloride, Morniflumate, Morpholine Salicylate, Nabumetone, Naproxen (Naproxen Sodium), Nifenazone, Niflumic Acid, Nimesulide, Oxametacin, Oxaprozin, Oxindanac, Oxyphenbutazone, Parsalmide, Phenybutazone, Phenyramidol Hydrochloride, Picenadol Hydrochloride, Picolamine Salicylate, Piketoprofen, Pirazolac, Piroxicam, Pirprofen, Pranoprofen, Pranosal, Proglumetacin Maleate, Proquazone, Protizinic Acid, Ramifenazone, Salacetamide, Salamidacetic Acid, Salicylamide, Salix, Salol, Salsalate, Sodium Aurothiomalate, Sodium Gentisate, Sodium Salicylate, Sodium Thiosalicylate, Sulindac, Superoxide Dismutase (Orgotein, Pegorgotein, Sudismase), Suprofen, Suxibuzone, Tenidap Sodium, Tenoxicam, Tetrydamine, Thurfyl Salicylate, Tiaprofenic, Tiaramide Hydrochloride, Tinoridine Hydrochloride, Tolfenamic Acid, Tometin Sodium, Triethanolamine Salicylate, Ufenamate, Zaltoprofen, Zidometacin and Zomepirac Sodium.

Cardiovascular Disease

Compounds useful for combining with the compounds of the present invention for the treatment of cardiovascular disease encompass a wide range of therapeutic compounds.

Ileal bile acid transporter (IBAT) inhibitors, for example, are useful in the present invention, and are disclosed in patent application no. PCT/US95/10863, herein incorporated by reference. More IBAT inhibitors are described in PCT/US97/04076, herein incorporated by reference. Still further IBAT inhibitors useful in the present invention are described in U.S. application Ser. No. 08/816,065, herein incorporated by reference. More IBAT inhibitor compounds useful in the present invention are described in WO 98/40375, and WO 00/38725, herein incorporated by reference. Additional IBAT inhibitor compounds useful in the present invention are described in U.S. application Ser. No. 08/816,065, herein incorporated by reference.

In another aspect, the second biologically active agent is a statin. Statins lower cholesterol by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy, S. M. *New Engl. J. Med.* 319, 24 (1988); Endo, A. *J. Lipid Res.* 33, 1569 (1992)). Depending on the agent and the dose used, statins may decrease plasma triglyceride levels and may increase HDLc. Currently the statins on the market are lovastatin (Merck), simvastatin (Merck), pravastatin (Sankyo and Squibb) and fluvastatin (Sandoz). A fifth statin, atorvastatin (Parke-Davis/Pfizer), is the most recent entrant into the statin market. Any of these statins or thers can be used in combination with the chalcones of the present invention.

MTP inhibitor compounds useful in the combinations and methods of the present invention comprise a wide variety of structures and functionalities. Some of the MTP inhibitor compounds of particular interest for use in the present invention are disclosed in WO 00/38725, the disclosure from which is incorporated by reference. Descriptions of these therapeutic compounds can be found in *Science,* 282, Oct. 23, 1998, pp. 751–754, herein incorporated by reference.

Cholesterol absorption antagonist compounds useful in the combinations and methods of the present invention comprise a wide variety of structures and functionalities. Some of the cholesterol absorption antagonist compounds of particular interest for use in the present invention are described in U.S. Pat. No. 5,767,115, herein incorporated by reference. Further cholesterol absorption antagonist compounds of particular interest for use in the present invention, and methods for making such cholesterol absorption antagonist compounds are described in U.S. Pat. No. 5,631,365, herein incorporated by reference.

A number of phytoisterols suitable for the combination therapies of the present invention are described by Ling and Jones in "Dietary Phytosterols: A Review of Metabolism, Benefits and Side Effects," *Life Sciences,* 57 (3), 195–206 (1995). Without limitation, some phytosterols of particular use in the combination of the present invention are Clofibrate, Fenofibrate, Ciprofibrate, Bezafibrate, Gemfibrozil. The structures of the foregoing compounds can be found in WO 00/38725.

Phytosterols are also referred to generally by Nes (*Physiology and Biochemistry of Sterols*, American Oil Chemists' Society, Champaign, Ill., 1991, Table 7-2). Especially preferred among the phytosterols for use in the combinations of the present invention are saturated phytosterols or stanols. Additional stanols are also described by Nes (Id.) and are useful in the combination of the present invention. In the combination of the present invention, the phytosterol preferably comprises a stanol. In one preferred embodiment the stanol is campestanol. In another preferred embodiment the stanol is cholestanol. In another preferred embodiment the stanol is clionastanol. In another preferred embodiment the stanol is coprostanol. In another preferred embodiment the stanol is 22,23-dihydrobrassicastanol. In another embodiment the stanol is epicholestanol. In another preferred embodiment the stanol is fucostanol. In another preferred embodiment the stanol is stigmastanol.

Another embodiment the present invention encompasses a therapeutic combination of a compound of the present invention and an HDLc elevating agent. In one aspect, the second HDLc elevating agent can be a CETP inhibitor. Individual CETP inhibitor compounds useful in the present invention are separately described in WO 00/38725, the disclosure of which is herein incorporated by reference. Other individual CETP inhibitor compounds useful in the present invention are separately described in WO 99/14174, EP818448, WO 99/15504, WO 99/14215, WO 98/04528, and WO 00/17166, the disclosures of which are herein incorporated by reference. Other individual CETP inhibitor compounds useful in the present invention are separately described in WO 00/18724, WO 00/18723, and WO 00/18721, the disclosures of which are herein incorporated by reference. Other individual CETP inhibitor compounds useful in the present invention are separately described in WO 98/35937 as well as U.S. Pat. Nos. 6,313,142, 6,310,075, 6,197,786, 6,147,090, 6,147,089, 6,140,343, and 6,140,343, the disclosures of which is herein incorporated by reference.

In another aspect, the second biologically active agent can be a fibric acid derivative. Fibric acid derivatives useful in the combinations and methods of the present invention comprise a wide variety of structures and functionalities which have been reported and published in the art.

In another embodiment the present invention encompasses a therapeutic combination of a compound of the present invention and an antihypertensive agent. Hypertension is defined as persistently high blood pressure. In another embodiment, the chalcone is administered in combination with an ACE inhibitor, a beta andrenergic blocker, alpha andrenergic blocker, angiotensin II receptor antagonist, vasodilator and diuretic.

Pharmaceutical Compositions

Any host organism, including a pateint, mammal, and specifically a human, suffering from any of the above-described conditions can be treated by the administration of a composition comprising an effective amount of the compound of the invention or a pharmaceutically acceptable salt thereof, optionally in a pharmaceutically acceptable carrier or diluent.

The composition can be administered in any desired manner, including oral, topical, parenteral, intravenous, intradermal, intra-articular, intra-synovial, intrathecal, intra-arterial, intracardiac, intramuscular, subcutaneous, intraorbital, intracapsular, intraspinal, intrastemal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems,* Sixth Edition, Williams & Wilkins (1995).

An effective dose for any of the herein described conditions can be readily determined by the use of conventional techniques and by observing results obtained under analogous circumstances. In determining the effective dose, a number of factors are considered, including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials that do not impair the desired action, or with materials that supplement the desired action. The compounds can also be administered in combination with non-steroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Any of the compounds described herein for combination or alternation therapy can be administered as any derivative that upon administration to the recipient, is capable of providing directly or indirectly, the parent compound, or that exhibits activity itself. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound. This can easily be assessed by preparing the derivative and testing its anti-inflammatory activity according to known methods.

Biological Activity of Active Compounds

The ability of a compound described herein to inhibit the expression of VCAM-1 or in the treatment of diseases in a host can be assessed using any known method, including that described in detail below.

In Vitro MCP-1 Activity Assay

Cultured human endothelial cells were seeded in 96-well plates. On the following day cells were stimulated with TNF-α (1 ng/ml) in the presence or absence of compounds dissolved in DMSO. To establish a dose curve and an $IC_{50}$, multiple concentrations in 2- to 5-fold increments were used. Cells were exposed to TNF-α and compounds for approximately 16 hours. The next day the cells were visually examined via light microscopy to score for visual signs of toxicity. Cell culture media, diluted 1:10, was analyzed by an MCP-1 immunoassay kit (R & D Systems). This assay is a sandwich immunoassay using immobilized anti-MCP-1 antibody in 96-well plate to capture secreted MCP-1 in cell culture media. Captured MCP-1 was subsequently detected with a horse radish peroxidase-conjugated anti-MCP-1 antibody for color development. Compound 3 expressed an $IC_{50}$ values of >10(the amount of compound (μM) required to achieve a 50% reduction compared to control (cells stimulated with TNF-α only)).

In Vitro VCAM-1 Assay

Cell Culture and compound dosing: Cultured primary human aortic (HAEC) or pulmonary (HPAEC) endothelial cells were obtained from Clonetics, Inc., and were used below passage 9. Cells were seeded in 96 well plates such that they would reach 90–95% confluency by the following day. On the following day the cells were stimulated with TNF-α (1 ng/ml) in the presence or absence of compounds dissolved in DMSO such that the final concentration of DMSO is 0.25% or less. To establish a dose curve for each compound, four concentrations in 2- to 5-fold increments were used. Cells were exposed to TNF-α and compounds for approximately 16 hours. The next day the cells were examined under microscope to score for visual signs of toxicity or cell stress.

Following 16 hr exposure to TNF-α and compound the media was discarded and the cells were washed once with Hanks Balanced Salt Solution (HBSS)/Phosphate buffered saline (PBS) (1:1). Primary antibodies against VCAM-1 (0.25 μg/ml in HBSS/PBS+5% FBS) were added and incubated for 30–60 minutes at 37° C. Cells were washed with HBSS/PBS three times, and secondary antibody Horse Radish Peroxidase (HRP)-conjugated goat anti-mouse IgG (1:500 in HBSS/PBS+5% FBS) were added and incubated for 30 minutes at 37° C. Cells were washed with HBSS/PBS four time and TMB substrate were added and incubated at room temperature in the dark until there was adequate development of blue color. The length of time of incubation was typically 5–15 minutes. 2N sulfuric acid was added to stop the color development and the data was collected by reading the absorbance on a BioRad ELISA plate reader at OD 450 nm. The results are expressed as $IC_{50}$ values (the concentration (micromolar) of compound required to inhibit 50% of the maximal response of the control sample stimulated by TNF-α only). Compounds exhibiting $IC_{50}$'s of less than 5 micromolar are tabulated in Biological Table 1.

TABLE 1

Biological

| Example Number | VCAM-1 IC50 (μM) |
|---|---|
| 1 | <1 |
| 2 | <5 |
| 3 | <1 |
| 4 | <10 |
| 5 | <1 |
| 6 | <1 |
| 7 | <1 |
| 8 | <1 |
| 9 | <5 |
| 10 | <5 |
| 11 | <5 |
| 12 | <5 |
| 13 | <5 |
| 14 | <1 |
| 15 | >10 |
| 16 | <5 |
| 17 | <5 |
| 18 | <5 |
| 19 | <1 |
| 20 | >10 |
| 21 | <5 |
| 22 | >10 |
| 23 | <1 |
| 24 | >10 |
| 25 | >10 |
| 26 | >10 |
| 27 | <5 |
| 28 | <5 |
| 29 | <1 |
| 30 | <1 |
| 31 | >10 |
| 32 | <5 |
| 33 | <5 |
| 34 | >10 |
| 35 | >10 |
| 36 | <5 |
| 37 | >10 |
| 38 | <10 |
| 39 | >10 |
| 40 | <1 |
| 41 | <5 |
| 42 | <5 |
| 43 | <5 |
| 44 | <1 |
| 45 | <5 |
| 46 | <10 |
| 47 | >10 |
| 48 | <10 |
| 49 | <10 |
| 50 | >10 |
| 51 | <5 |
| 52 | >10 |
| 53 | <5 |
| 54 | <10 |
| 55 | <5 |
| 56 | <1 |
| 57 | <5 |
| 58 | >10 |
| 59 | NE |
| 60 | <1 |
| 61 | <1 |
| 62 | <5 |
| 63 | <10 |

TABLE 1-continued

Biological

| Example Number | VCAM-1 IC50 (μM) |
|---|---|
| 64 | >10 |
| 65 | <1 |
| 66 | <1 |
| 67 | <10 |
| 68 | <5 |
| 69 | <5 |
| 70 | <5 |
| 71 | NE |
| 72 | 0 |
| 73 | 0 |
| 74 | >10 |
| 75 | >10 |
| 76 | >10 |
| 77 | <5 |
| 78 | <10 |
| 79 | <1 |
| 80 | <5 |
| 81 | <1 |
| 82 | NE |
| 83 | <1 |
| 84 | <5 |
| 85 | <1 |
| 86 | <5 |
| 87 | <1 |
| 88 | |
| 89 | NE |
| 90 | <1 |
| 91 | <5 |
| 92 | <1 |
| 93 | <1 |
| 94 | <1 |
| 95 | <1 |
| 96 | <5 |
| 97 | NE |
| 98 | <5 |
| 99 | >10 |
| 100 | >10 |
| 101 | >10 |
| 102 | >10 |
| 103 | >10 |
| 104 | NE |
| 105 | NE |
| 106 | <10 |
| 107 | NE |
| 108 | <10 |
| 109 | NE |
| 110 | >10 |
| 111 | >10 |
| 112 | NE |
| 113 | <5 |
| 114 | <5 |
| 115 | <5 |
| 116 | |
| 117 | <5 |
| 118 | <10 |
| 119 | |
| 120 | <1 |

Rheumatoid Arthritis Protocol

Male Lewis rats (150–175 g) from Charles River Laboratories were anesthetized on day 0 with 3–5% isoflurane anesthesia while the tail base was shaved and adjuvant mixture was injected. Fifty μL of adjuvant (10 mg/ml M. butyricum in mineral oil) was injected subcutaneously into two sites at the tail base. Paw swelling was monitored using a plethysmometer (UGO Basile), after shaving each leg to the level of the Achilles tendon to mark the level of immersion. A baseline paw measurement for both hindpaws was taken between d2-d5 and a second measurement was taken on day 7–8. Onset of paw swelling occurred rapidly between d9–11 and daily measurements were performed every weekday between d9 and day 15. Compounds of the invention and vehicles were dosed either prophylactically (d1–14), or therapeutically (d9–14) after swelling was confirmed. Solutions were injected subcutaneously or given orally by gavage 1–2 times per day. From day 0, rats were weighed every 2–3 days and overall health was monitored. Plasma drug levels, if desired, were measured in tail-vein derived blood samples taken on day 14. On day 15, blood samples were obtained by cardiac puncture, rats were euthanized with $CO_2$, selected organs removed and both hindpaws were amputated and placed in 10% buffered formalin for histopathological analysis. See Biological Table 2.

BIOLOGICAL TABLE 2

| Compound Example Number | % Inhibition 60 mg/Kg/day, sq, bid, d1–14 |
|---|---|
| 3 | 96 |
| 6 | 77 |
| 29 | 82 |
| 60 | 62* |

*75 mg/kg/day, sq, bid, dl–14

Asthma Protocol

Balb/C mice (6–8 weeks old) are sensitized to ovalbumin (ova) (8 ug ova absorbed in 3.3 mg Alum inject) on days 0 and 5. On day 12, the mice were aerosol challenged with 0.5% ovalbumin dissolved in sterile saline for 1 hr in the AM, and then again in the PM (at least 4 hr apart). On day 14, the mice were anesthetized with ketamine/xylazine/acepromazine cocktail, exsanguinated, and then euthanized. Following blood collection, bronchoaveolar lavage was performed on each animal. Total cell counts were conducted on the lavage fluid, which was subsequently diluted with cell media 1:1. Slides of the lavage fluid were made by spinning the samples with a cytospin centrifuge. Slides were airdried and stained with x. Cell differentials of the lavage fluid were completed at the conclusion of the study. All compounds except Example 2 were well tolerated with no body weight loss throughout the course of the study. Statistical analysis involved ANOVA and Tukey-Kramer post hoc tests. Compounds were administered except where noted by subcutaneous injection once daily from day 0–13. The formulations used contained various mixtures of the following excipients (pharmasolve, cremophor RH 40, tween 80, PEG 300). See Biological Table 3

BIOLOGICAL TABLE 3

| Compound Example Number | % Inhibition sc, daily dosing at 100 mg/kg from day 0–13 |
|---|---|
| 3 | 79 |
| 6 | 81 |
| 86 | 48 |
| 36 | 71 |
| 60 | 36 |
| 29 | 24 |

Effect of Serum IgE Levels in Ovalbumin Sensitized Balb/c Mice

Peripheral blood samples were collected from ovalbumin (Calbiochem) or vehicle (2% Cremophor/Bicarbonate) treated Balb/c mice (Charles River) with or without administration of test compound (100 mg/kg/d, from day 0 to day 14). Serum was obtained by centrifugation and transferred into Microtainer serum tubes and frozen at −80° C. Mouse IgE ELISA Quantitation Kit (Bethyl Laboratories, Inc. Montgomery, Tex. or PharMingen, San Diego, Calif.) was applied to measure the IgE levels of serum samples. Immuno-reactions were performed as Kit protocol with IgE standard and serum samples in duplicates. The results were read in a microplate reader (Bio-Rad Model 550) at 450 nm and the amounts of IgE were calculated according to the standard curve. The limit of detection in our experiments was 7 ng/ml. Compound 3 administered at 100 mg/kg/d from day 0 to day 14, reduced serum IgE levels by 38% in ovalbumin sensitized Balb/c mice compared with vehicle treated mice.

Effect of Levels of IL-13, IL-5, IL4, IFN-Gamma and IL-2 mRNA in Mouse Lungs of Balb/c Mice with Ovalbumin Sensitization and Challenge Lung tissues were collected from ovalbumin (Calbiochem) or vehicle (2% Cremophor/Bicarbonate) sensitized Balb/c mice (Charles River) with or without treatment of test compound (100 mg/kg/d, from day 0 to day 14). Total RNA samples were isolated by the Trizol method (Life Technologies, Grand Island, N.Y.) and quantitatively measured by UV spectrophotometer, as well as qualitatively examined by ethidum bromide stained gel electrophoresis. First strand cDNA templates were generated with oligo (dT) by Reverse Transcription Kit (Invitrogen, Carlsbad, Calif.). The initial amounts of mRNA of each samples were quantitatively determined by running a SYBR Green (Qiagen, Valencia, Calif.) based real-time PCR (programmed as: initial denaturation at 95° C. for 15 minutes, denaturation at 95° C. for 15 seconds, annealing and elongation at 51±1° C. for 1 minute for total 40 cycles) with a specific pair of primers (IDT Corporation, Coralville, Iowa) and control primers for GAPDH in iCycler IQ Optical System (Hercules, Calif.). The data were statistically analyzed by ANOVA and t-tests with multiple comparisons of means (n=5 and P<0.05 were considered significant). Compound 3 administered at 100 mg/kg/d, significantly inhibited ovalbumin induced levels of IL-13, IL-5 and IL-4 mRNA in the lung of Balb/c mice by 82%, 98% and 68% respectively; without significantly affecting IFN-gamma and IL-2 compared with vehicle treated mice.

to 0.05 µM were used. Rapamycin (at 1 and 0.1 µM) was used as a positive control for the assay. After a 20 hour incubation with or without test compounds, 3H-thymidine (0.5 µCi/well) was added to the cells for 4 hours of labeling. Washed cells were then lysed in NaOH and the amount of 3H-thymidine incorporation was determined. Cytotoxicity of the drug was measured by use of the CytolTox 96 assay kit (Promega, Madison, Wis.). Compound 3 had an $IC_{50}$ of 0.5 µM.

Effect of Test Compounds on LPS-Stimulated IL-1β

Human peripheral blood mononuclear cells were treated with or without Compound 3 for 1 hour, then stimulated with LPS (1–2 µg/ml) for 3 hours. Condition media was collected and IL-1β measured using an ELISA kit. Compound 3 demonstrated a dose dependent inhibition of LPS-stimulated IL-1β secretion. See Biological Table 4

BIOLOGICAL TABLE 4

| Amount of Compound 3 (µM) | Percent IL-1β Secreted |
|---|---|
| 1.25 | >40 |
| 2.5 | >10 |
| 5 | >5 |
| 10 | >1 |

Reduction of Plasma TNF-α Levels and Lung VCAM-1 mRNA Levels in LPS-Challenged Mice.

Balb/C mice (6–8 weeks) were injected with LPS (1 mg/kg; 5 mls/kg) and sacrificed 2 hr later. Blood was collected for plasma TNF-α levels and lungs for measurement of VCAM-1 mRNA levels by quantitative RT-PCR. Compound 3 administered subcutaneously at a dose of 100 mg/kg/d, 2 hr prior to LPS injection, inhibited TNF-α production by 80% and VCAM-1 expression by 60% compared with vehicle controls.

Disease Modifying Anti-Rheumatic Drug (DMARD) Activity in Rat Adjuvant Arthritis Compound 3 at twice daily subcutaneous doses of 60, 40 and 20 mg/kg/d was found to inhibit bone erosion in the ankle joint by histopathological analysis when administered List of Primers used in above experiments:

| Primer Name | Forward Sequence | Reverse Sequence | Annealing Temperature |
|---|---|---|---|
| GAPDH | CTA CCC CCA ATG TGT CC | CTG CTT CAC CAC CTT CTT | 52.2 |
| IL-13 | AAF AFF AGA GCA AAT GAA AG | CTG TGT AAC CTT CCC AAC A | 51.3 |
| IL-4 | TGA ATG AGT CCA AGT CCA | AGC ATG GTG GCT CAG TA | 51.2 |
| IL5 | AGC TCT GTT GAC AAG CAA T | CCC TGA AAG ATT TCT CCA ATG | 52.4 |
| IL-2 | GTC GAC TTT CTG AGG AGA TG | ATG TGT TGT AAG GAG GAG GT | 53.2 |
| IFN-γ | TTC TGT CTC CTC AAC TAT TTC T | CAA TCA CAG TCT TGG CTA AT | 51.3 |

Smooth Muscle Cell Proliferation Protocol

Human Aortic Smooth Mucle Cells (HAoSMC) were obtained from Clonetics, Inc. and were used below passage 10. Cells were seeded in 24-well plates. When cells were 80% confluent, they were made quiescent by adding media containing 0.2% serum (as compared to 5% serum in normal culture media) for 48 hours. The cells were, then, stimulated by 5% serum in the presence or absence of compounds dissolved in DMSO. To establish a dose curve and $IC_{50}$ for each compound, multiple concentrations in the range of 20 prophylactically in the rat adjuvant arthritis model. The evaluation was carried out with hematoxylin and eosin stained ankle cross sections by a certified veterinary pathologist. When dosed prophylactically at doses of 100, 50 and 25 mg/kg/d, b.i.d., s.c., Compound 3 was also found to inhibit splenomegaly. Splenomegaly tracks with bone erosion in the adjuvant arthritis model and is thought to be a predictor of DMARDs activity.

Modifications and variations of the present invention relating to compounds and methods of treating diseases will be obvious to those skilled in the art from the foregoing detailed description of the invention. Such modifications and variations are intended to come within the scope of the appended claims.

What is claimed is:

1. A compound of Formula I

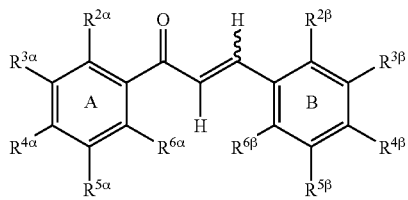

or its pharmaceutically acceptable salt or ester, wherein:
the wavy line indicates that the compound can be in the form of the E- or Z- isomer;

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked optionally substituted saturated or unsaturated thienyl or benzothienyl;

wherein when one of $R^{2\beta}$, $R^{3\beta}$, $R^{4\beta}$, $R^{5\beta}$ or $R^{6\beta}$ is a carbon-carbon linked optionally substituted saturated or unsaturated thienyl or benzothienyl, only one of $R^{2\beta}$, $R^{3\beta}$, $R^{4\beta}$, $R^{5\beta}$ or $R^{6\beta}$ can be —OCH$_3$; and wherein when one of $R^{2\beta}$, $R^{3\beta}$, $R^{4\beta}$, $R^{5\beta}$ or $R^{6\beta}$ is a carbon-carbon linked optionally substituted saturated or unsaturated thienyl or benzothienyl, only one of $R^{2\beta}$, $R^{3\beta}$, $R^{4\beta}$, $R^{5\beta}$ or $R^{6\beta}$ can be —OCH$_3$;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one sulfur, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC($R^1$)$_2$C(O)OH; or at least one of $R^{2\alpha}$, $R^{3\alpha}$, $R^{4\alpha}$, $R^{5\alpha}$, $R^{6\alpha}$ or one of $R^{2\beta}$, $R^{3\beta}$, $R^{4\beta}$, $R^{5\beta}$, $R^{6\beta}$ must be selected from the group consisting of cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)NH$R^2$, —C(O)NHC(O)N($R^2$)$_2$, —C(O)NHC(O)N$R^7R^8$, —C(O)NHSO$_2$NH$R^2$, —C(O)NHSO$_2$N($R^2$), —C(O)NHSO$_2$N$R^7R^8$, —C(O)NHC(O)$R^2$, —C(O)NHSO$_2R^2$, —C(CH$_3$)$_2$C(O)OH, (CH$_2$)$_y$C(O)OH, wherein is 1, 2, 3, 4, 5, or 6, thiol, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NH$R_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, —NH$R^2$, N($R^2$)$_2$, N$R^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —NHSO$_2$NH$R^2$, —NHSO$_2R^2$, —NHSO$_2$N$R^7R^8$, —N(C(O)NH$R^2$)$_2$, —N$R^2$SO$_2R^2$, —NHC(O)NH$R^2$, —NHC(O)N$R^7R^8$, and —NHC(O)N($R^2$)$_2$;

wherein all $R^1$, $R^2$, $R^7$, and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$.

2. The compound of claim 1 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)$R^2$, $R^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC($R^1$)$_2$C(O)OH, —OC($R^1$)$_2$C(O)O$R^2$, —OC($R^1$)$_2$C(O)NH$_2$, —OC($R^1$)$_2$C(O)NH$R^2$, —OC($R^1$)$_2$C(O)N($R^2$)$_2$, —OC($R^1$)$_2$C(O)N$R^7R^8$, amino, alkylamino, acylamino, dialkylamino, cycloalkylamino, arylamino, aralkylamino, heteroarylamino, heteroaralkylamino, heterocyclicamino, heterocyclicalkylamino, —NH$R^2$, N($R^2$)$_2$, —N$R^7R^8$, —NHC($R^1$)$_2$C(O)OH, —NHC($R^1$)$_2$C(O)O$R^2$, —NHC(O)$R^2$, —N($R^2$)C(O)$R^2$, —NHC(O)O$R^2$, —NHC(O)S$R^2$, —NHSO$_2$NH$R^2$, —NHSO$_2R^2$, —NHSO$_2$N$R^7R^8$, —N(C(O)NH$R^2$)$_2$, —N$R^2$SO$_2R^2$, —NHC(O)NH$R^2$, —NHC(O)N$R^7R^8$, —NHC(O)N($R^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC($R^1$)$_2$C(O)OH, —SC($R^1$)$_2$C(O)O$R^2$, —SCH$_2$C(O)OH, —SCF$_2$C(O)OH, —SO$_2$NH$_2$, —SO$_2$NH$R_2$, —SO$_2$N($R^2$)$_2$, SO$_2$N$R^7R^8$, —SO$_2$NHC(O)$R^2$, —S$R_2$, —SO$_2$NHC(O)NH$R^2$, —SO$_2$NHC(O)N($R^2$)$_2$, —SO$_2$NHC(O)N$R^7R^8$, sulfonic acid, sulfonate, sulfate, sulfinic acid, sulfenic acid, cyano, tetrazol-5-yl, carboxy, —C(O)O$R^2$, —C(O)NH$_2$, —C(O)NH$R^2$, —C(O)N($R^2$)$_2$, —C(O)N$R^7R^8$, —C(O)NHC(O)$R^2$, —C(O)NHC(O)NH$R^2$, —C(O)NHC(O)N($R^2$)$_2$, —C(O)NHC(O)N$R^7R^8$, —C(O)NHSO$_2R^2$, —C(O)NHSO$_2$NH$R^2$, —C(O)NHSO$_2$N($R^2$), —C(O)NHSO$_2$N$R^7R^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P($R^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —N$R^7R^8$, alkoxy, oxo, cyano, carboxy, carboxyalkyl, alkoxycarbonyl, —C(O)N$R^7R^8$, and —C(O)N($R^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein one of $R^{2\beta}$, $R^{3\beta}$, $R^{4\beta}$, $R^{5\beta}$ or $R^{6\beta}$, or one of $R^{2\alpha}$, $R^{3\alpha}$, $R^{4\alpha}$, $R^{5\alpha}$ or $R^{6\alpha}$ must be a carbon-carbon linked saturated or unsaturated thienyl or benzothienyl;

wherein when one of $R^{2\beta}$, $R^{3\beta}$, $R^{4\beta}$, $R^{5\beta}$ or $R^{6\beta}$ is a carbon-carbon linked saturated or unsaturated thienyl or benzothienyl, only one of $R^{2\beta}$, $R^{3\beta}$, $R^{4\beta}$, $R^{5\beta}$ or $R^{6\beta}$ can be —OCH$_3$; and wherein when one of $R^{2\beta}$, $R^{3\beta}$, $R^{4\beta}$, $R^{5\beta}$ or $R^{6\beta}$ is a carbon-carbon linked saturated or unsaturated thienyl or benzothienyl, only one of $R^{2\beta}$, $R^{3\beta}$, $R^{4\beta}$, $R^{5\beta}$ or $R^{6\beta}$ can be —OCH$_3$;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one sulfur, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R$^1$)$_2$C(O)OH; and at least one of $R^{2\alpha}$, $R^{3\alpha}$, $R^{4\alpha}$, or one of $R^{2\beta}$, $R^{3\beta}$, $R^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

3. The compound of claim 1 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein when one of $R^{2\beta}$, $R^{3\beta}$, $R^{4\beta}$, $R^{5\beta}$ or $R^{6\beta}$ is a carbon-carbon linked saturated or unsaturated thienyl or benzothienyl, only one of $R^{2\beta}$, $R^{3\beta}$, $R^{4\beta}$, $R^{5\beta}$ or $R^{6\beta}$ can be —OCH$_3$;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one sulfur, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R$^1$)$_2$C(O)OH; and with the proviso that at least one of $R^{2\alpha}$, $R^{3\alpha}$, $R^{4\alpha}$, or one of $R^{2\beta}$, $R^{3\beta}$, $R^{4\beta}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

4. The compound of claim 3 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —NR$^7$R$^8$, and halo; or $R^{2\alpha}$ and $R^{3\alpha}$ taken together or $R^{3\alpha}$ and $R^{4\alpha}$ taken together or $R^{4\alpha}$ and $R^{5\alpha}$ taken together or $R^{2\beta}$ and $R^{3\beta}$ taken together or $R^{3\beta}$ and $R^{4\beta}$ taken together or $R^{4\beta}$ and $R^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ cannot be —OC(R$^1$)$_2$C(O)OH; and with the proviso that at least one of $R^{2\alpha}$, $R^{3\alpha}$, or $R^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

5. The compound of claim 4 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkylthio lower alkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$^2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$)$_2$, —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

6. The compound of claim 5 or its pharmaceutically acceptable salt or ester, wherein: $R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$)$_2$, —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, beteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein one of $R^{4\beta}$, $R^{5\beta}$ or $R^{6\beta}$ must be a carbon-carbon linked heterocyclic or heteroaryl, and only one of $R^{2\alpha}$, $R^{3\alpha}$, $R^{4\alpha}$, $R^{5\alpha}$ or $R^{6\alpha}$ can be —OCH$_3$;

with the proviso that at least one of $R^{2\alpha}$, $R^{3\alpha}$, or $R^{4\alpha}$ must be selected from the group consisting of cyano, tetrazol-5-yl, carboxy, —C(O)OR$^2$, —C(CH$_3$)$_2$C(O)OH, —(CH$_2$)$_y$C(O)OH, wherein y is 1, 2, 3, 4, 5, or 6;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

7. The compound of claim 6 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O) R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC (R$^1$)$_2$C(O)OH, —OC(R$^1$)$_2$C(O)OR$^2$, —OC(R$^1$)$_2$C(O) NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC (R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC (R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O) NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O) NHSO$_2$N(R$^2$), —C(O)NHSO$_2$NR$^7$R$^8$, —C(CH$_3$)$_2$C (O)OH, and —(CH$_2$)$_y$C(O)OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein one of R$^{4\beta}$, R$^{5\beta}$ or R$^{6\beta}$ must be a carbon-carbon linked saturated or unsaturated thienyl or benzothienyl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\alpha}$, R$^{3\alpha}$, R$^{4\alpha}$ must be selected from the group consisting of cyano, tetrazol-5-yl, carboxy, —C(O)OR$^2$, —C(CH$_3$)$_2$C(O)OH, —(CH$_2$)$_y$C(O)OH, wherein y is 1, 2, 3, 4, 5, or 6;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

8. The compound of claim 7 or its pharmaceutically acceptable salt or ester, wherein: R$^{5\beta}$ and R$^{6\beta}$ are independently selected from the group consisting of hydrogen, halogen, alkyl, lower alkyl, alkenyl, alkynyl, cycloalkyl, cycloalkylalkyl, haloalkyl, heteroaryl, heteroaryl lower alkyl, heterocyclic, heterocyclic lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, heteroarylamino lower alkyl, heterocyclicamino lower alkyl, hydroxyl, hydroxyalkyl, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)N(R$^2$)$_2$, —OC(R$^1$)$_2$C (O)NR$^7$R$^8$, amino, alkylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —N(R$^2$)C(O)R$^2$, —NHSO$_2$NR$^7$R$^8$, —N(C(O)NHR$^2$)$_2$, —NHC(O)NR$^7$R$^8$, —NHC(O)N(R$^2$)$_2$, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC (O)NR$^7$R$^8$, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC (O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O) NHSO$_2$NR$^7$R$^8$, —C(CH$_3$)$_2$C(O)OH, and —(CH$_2$)$_y$C(O) OH, wherein y is 1, 2, 3, 4, 5, or 6, all of which can be optionally substituted by one or more selected from the group consisting of halo, alkyl, lower alkyl, alkenyl, cycloalkyl, acyl, hydroxy, hydroxyalkyl, heterocyclic, amino, R$^1$ is independently selected from the group consisting of hydrogen, lower alkyl, cycloalkyl, aryl, arylalkyl, heteroarylalkyl, and heterocyclicalkyl, wherein all may be optionally substituted by one or more selected from the group consisting of halo, alkyl, lower alkyl, substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, oxo, cyano, —C(O)NR$^7$R$^8$, and —C(O)N(R$^2$)$_2$; aryl, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, —C(O)NR$^7$R$^8$, and —C(O)N(R$^2$)$_2$;

R⁷ and R⁸ are independently selected from the group consisting of alkyl, alkenyl and aryl and linked together forming a 4- to 12-membered monocyclic, bicyclic, tricyclic or benzofused ring;

wherein one of R⁴ᵝ, R⁵ᵝ or R⁶ᵝ must be a carbon-carbon linked saturated or unsaturated thienyl or benzothienyl, and only one of R²ᵝ, R³ᵝ, R⁴ᵝ, R⁵ᵝ or R⁶ᵝ can be —OCH₃;

with the proviso that at least one of R²ᵅ, R³ᵅ, R⁴ᵅ must be selected from the group consisting of cyano, tetrazol-5-yl, carboxy, —C(O)OR², —C(CH₃)₂C(O)OH, —(CH₂)ᵧC(O)OH, wherein y is 1, 2, 3, 4, 5, or 6;

wherein all R¹, R², R⁷ and R⁸ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR⁷R⁸, alkoxy, oxo, cyano, —C(O)NR⁷R⁸, and —C(O)N(R²)₂.

9. The compound of claim 8 or its pharmaceutically acceptable salt or ester, wherein:

R²ᵅ, R³ᵅ, R⁴ᵅ, R⁵ᵅ, R⁶ᵅ, R²ᵝ, R³ᵝ, R⁴ᵝ, R⁵ᵝ and R⁶ᵝ are independently selected from the group consisting of hydrogen, halogen, alkyl, lower alkyl, cycloalkyl, cycloalkylalkyl, haloalkyl, heteroaryl, heteroaryl lower alkyl, heterocyclic, heterocyclic lower alkyl, heterocyclicamino lower alkyl, hydroxyl, alkoxy, lower alkoxy, —(O(CH₂)₂)₁₋₃—O-lower alkyl, polyoxyalkylene, cycloalkyloxy, cycloalkylalkoxy, heteroarylalkoxy, heteroaryl lower alkoxy, heterocyclicoxy, heterocyclicalkoxy, heterocyclic lower alkoxy, dialkylamino, N(R²)₂, —NR⁷R⁸, tetrazol-5-yl, carboxy, —C(O)OR², —C(O)N(R²)₂, —C(O)NR⁷R⁸, —C(CH₃)₂C(O)OH, and —(CH₂)ᵧC(O)OH, wherein y is 1, 2, 3, 4, 5, or 6, all of which can be optionally substituted by one or more selected from the group consisting of halo, alkyl, lower alkyl, cycloalkyl, hydroxy, hydroxyalkyl, heterocyclic, amino, aminoalkyl, —NR⁷R⁸, —C(O)NR⁷R⁸, and —C(O)N(R²)₂;

R² is independently selected from the group consisting of alkyl, lower alkyl, cycloalkyl, arylalkyl, heteroarylalkyl, and heterocyclicalkyl, wherein all may be substituted by one or more selected from the group consisting of halo, lower alkyl, hydroxyalkyl, heterocyclic, amino, aminoalkyl, —NR⁷R⁸, alkoxy, —C(O)NR⁷R⁸, and —C(O)N(R²)₂;

R⁷ and R⁸ are independently selected from the group consisting of alkyl, alkenyl and aryl and linked together forming a 4- to 8-membered monocyclic or benzofused ring;

wherein one of R⁴ᵝ, R⁵ᵝ or R⁶ᵝ must be a carbon-carbon linked saturated or unsaturated thienyl or benzothienyl, and only one of R²ᵝ, R³ᵝ, R⁴ᵝ, R⁵ᵝ or R⁶ᵝ can be —OCH₃;

with the proviso that at least one of R²ᵅ, R³ᵅ, R⁴ᵅ must be selected from the group consisting of cyano, tetrazol-5-yl, carboxy, —C(O)OR², —C(CH₃)₂C(O)OH, —(CH₂)ᵧC(O)OH, wherein y is 1, 2, 3, 4, 5, or 6;

wherein all R¹, R², R⁷ and R⁸ substituents can be optionally substituted with one or more selected from the group consisting of halo, alkyl, lower alkyl, hydroxyalkyl, heterocyclic, amino, aminoalkyl, —NR⁷R⁸, —C(O)NR⁷R⁸, and —C(O)N(R²)₂.

10. The compound of claim 9 or its pharmaceutically acceptable salt or ester, wherein:

R²ᵅ, R³ᵅ, R⁴ᵅ, R⁵ᵅ, R⁶ᵅ, R²ᵝ, R³ᵝ, R⁴ᵝ, R⁵ᵝ and R⁶ᵝ are independently selected from the group consisting of hydrogen, halogen, lower alkyl, heteroaryl, heteroaryl lower alkyl, heterocyclic, heterocyclic lower alkyl, alkoxy, lower alkoxy, —(O(CH₂)₂)₁₋₃—O-lower alkyl, polyoxyalkylene, heteroaryl lower alkoxy, heterocyclicalkoxy, heterocyclic lower alkoxy, carboxy, —C(O)OR², —C(O)N(R²)₂, and —C(O)NR⁷R⁸, all of which can be optionally substituted by one or more selected from the group consisting of halo, alkyl, lower alkyl, cycloalkyl, hydroxy, hydroxyalkyl, heterocyclic, —NR⁷R⁸, —C(O)NR⁷R⁸, and —C(O)N(²)₂;

R² is independently selected from the group consisting of alkyl, and lower alkyl, wherein all may be substituted by one or more selected from the group consisting of halo, lower alkyl, —NR⁷R⁸, alkoxy, —C(O)NR⁷R⁸, and —C(O)N(R²)₂;

R⁷ and R⁸ are independently alkyl, and linked together forming a 5- to 7-membered monocyclic or benzofused ring;

wherein one of R⁴ᵝ, R⁵ᵝ or R⁶ᵝ must be a carbon-carbon linked saturated or unsaturated thienyl or benzothienyl, and only one of R²ᵝ, R³ᵝ, R⁴ᵝ, R⁵ᵝ or R⁶ᵝ can be —OCH₃;

with the proviso that at least one of R²ᵅ, R³ᵅ, or R⁴ᵅ must be selected from carboxy or —C(O)OR²;

wherein all R², R⁷ and R⁸ substituents can be optionally substituted with one or more selected from the group consisting of halo, lower alkyl, —NR⁷R⁸, —C(O)NR⁷R⁸, and —C(O)N(R²)₂.

11. The compound of claim 10 or its pharmaceutically acceptable salt or ester, wherein:

R²ᵅ, R³ᵅ, R⁴ᵅ, R⁵ᵅ, R⁶ᵅ, R²ᵝ, R³ᵝ, R⁴ᵝ, R⁵ᵝ and R⁶ᵝ are independently selected from the group consisting of hydrogen, halogen, heteroaryl, heterocyclic, lower alkoxy, —(O(CH₂)₂)₁₋₃—O-lower alkyl, heteroaryl lower alkoxy, heterocyclic lower alkoxy, and carboxy, all of which can be optionally substituted; by one or more selected from the group consisting of hydroxy, hydroxyalkyl, —NR⁷R⁸, —C(O)NR⁷R⁸, and —C(O)N(R²)₂;

R² is lower alkyl;

R⁷ and R⁸ are independently alkyl, and linked together forming a 6-membered monocyclic or benzofused ring;

wherein one of R⁴ᵝ, R⁵ᵝ or R⁶ᵝ must be a carbon-carbon linked saturated or unsaturated thienyl or benzothienyl, and only one of R²ᵝ, R³ᵝ, R⁴ᵝ, R⁵ᵝ or R⁶ᵝ can be —OCH₃;

with the proviso that at least one of R²ᵅ, R³ᵅ, or R⁴ᵅ must be carboxy.

12. The compound of claim 11 or its pharmaceutically acceptable salt or ester, wherein:

R²ᵅ, R³ᵅ, R⁴ᵅ, R⁵ᵅ, and R⁶ᵅ are independently selected from the group consisting of hydrogen and carboxy;

R²ᵝ, R³ᵝ, R⁴ᵝ, R⁵ᵝ and R⁶ᵝ are independently selected from the group consisting of hydrogen, halogen, heteroaryl, heterocyclic, lower alkoxy, —(O(CH₂)₂)₁₋₃—O-lower alkyl, heteroaryl lower alkoxy, and heterocyclic lower alkoxy, all of which can be optionally substituted by one or more selected from the group consisting of hydroxy, hydroxyalkyl, —NR⁷R⁸, —C(O)NR⁷R⁸, and —C(O)N(R²)₂;

R² is lower alkyl;

R⁷ and R⁸ are independently alkyl, and linked together forming a 6-membered monocyclic or benzofused ring;

wherein one of R⁴ᵝ, R⁵ᵝ or R⁶ᵝ must be a carbon-carbon linked saturated or unsaturated thienyl or benzothienyl;

with the proviso that at least one of R²ᵅ, R³ᵅ, or R⁴ᵅ must be carboxy.

13. The compound of claim 12 or its pharmaceutically acceptable salt or ester, wherein:
$R^{2\alpha}$, $R^{3\alpha}$, $R^{4\alpha}$, $R^{5\alpha}$, and $R^{6\alpha}$ are independently selected from the group consisting of hydrogen and carboxy;
$R^{2\beta}$, $R^{3\beta}$, $R^{4\beta}$, $R^{5\beta}$ and $R^{6\beta}$ are independently selected from the group consisting of hydrogen, halogen, heteroaryl, lower alkoxy, —(O(CH$_2$)$_2$)$_{1-3}$—O-lower alkyl, heteroaryl lower alkoxy, and heterocyclic lower alkoxy, all of which can be optionally substituted by one or more selected from the group consisting of hydroxy, hydroxyalkyl, —NR$^7$R$^8$, —C(O)NR$^7$R$^8$, and —C(O)N(R$^2$)$_2$;
$R^2$ is lower alkyl;
$R^7$ and $R^8$ are independently alkyl, and linked together forming a 6-membered monocyclic or benzofused ring;
wherein one of $R^{4\beta}$, $R^{5\beta}$ or $R^{6\beta}$ must be a carbon-carbon linked saturated thienyl or benzothienyl;
with the proviso that at least one of $R^{2\alpha}$, $R^{3\alpha}$, or $R^{4\alpha}$ must be carboxy.

14. The compound of claim 13 or its pharmaceutically acceptable salt or ester, wherein:
$R^{2\alpha}$, $R^{3\alpha}$, $R^{4\alpha}$, $R^{5\alpha}$, and $R^{6\alpha}$ are independently selected from the group consisting of hydrogen and carboxy;
$R^{2\beta}$, $R^{3\beta}$, $R^{4\beta}$, $R^{5\beta}$ and $R^{6\beta}$ are independently selected from the group consisting of hydrogen, fluorine, chlorine, methoxy, ethoxy, propoxy, 3-(1-morpholino) propoxy, 2-(1-morpholino) ethoxy, CH$_3$O(CH$_2$)$_2$O(CH$_2$)$_2$—,

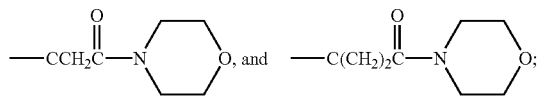

wherein one of $R^{4\beta}$, $R^{5\beta}$ or $R^{6\beta}$ must be selected from the group consisting of thiophen-2-yl, thiophen-3-yl, benzo[b]thiophen-2-yl, benzo[b]thiophen-3-yl,
with the proviso that at least one of $R^{2\alpha}$, $R^{3\alpha}$, or $R^{4\alpha}$ must be carboxy.

15. The compound of claim 14 or its pharmaceutically acceptable salt or ester, wherein:
$R^{2\alpha}$, $R^{3\alpha}$, $R^{4\alpha}$, $R^{5\alpha}$, and $R^{6\alpha}$ are independently selected from the group consisting of hydrogen and carboxy;
$R^{2\beta}$, $R^{3\beta}$, $R^{4\beta}$, $R^{5\beta}$ and $R^{6\beta}$ are independently selected from the group consisting of hydrogen, methoxy, 3-(1-morpholino) propoxy, 2-(1-morpholino) ethoxy, and CH$_3$O(CH$_2$)$_2$O(CH$_2$)$_2$;
wherein one of $R^{4\beta}$, $R^{5\beta}$ or $R^{6\beta}$ must be selected from the group consisting of thiophen-2-yl, benzo[b]thiophen-2-yl;
with the proviso that at least one of $R^{2\alpha}$, $R^{3\alpha}$, or $R^{4\alpha}$ must be carboxy.

16. The compound of claim 15 selected from the group consisting of:
4-[3E-(5-Benzo[b]thien-2-yl-2,4-dimethoxyphenyl)-acryloyl]-benzoic acid;
4-[3E-(2,4-Dimethoxy-5-thiophen-2-yl-phenyl)-acryloyl]-benzoic acid;
2-[3E-(5-Benzo[b]thiophen-2-yl-2,4-dimethoxy-phenyl)-acryloyl]-benzoic acid;
4-[3E-(3,4-Dimethoxy-5-thiophen-2-yl-phenyl)-acryloyl]-benzoic acid;
2-[3E-(5-Benzo[b]thiophen-2-yl-2,4-dimethoxy-phenyl)-acryloyl]-benzoic acid, sodium salt;
4-[3E-(4-Thiophen-2-yl-phenyl)-acryloyl]-benzoic acid;
4-[3-{4-(thien-2-yl)-phenyl}-3-oxo-E-propenyl]-benzoic acid, sodium salt;
4-[3-{4-(thien-2-yl)-phenyl}-3-oxo-E-propenyl]-benzoic acid;
4-[3-(2-Methoxy-4-thiophen-2-yl-phenyl)-3-oxo-E-propenyl]-benzoic acid;
4-[3E-(4-Pyrrolidin-1-yl-3-thiophen-2-yl-phenyl)-acryloyl]-benzoic acid;
4-[3E-{4-Fluoro-3-(thiophen-2-yl)-phenyl}-acryloyl]-benzoic acid;
4-(3E-{4-Methoxy-2-[2-(2-methoxyethoxy)ethoxy]-5-thiophen-2-yl-phenyl}-acryloyl)-benzoic Acid;
4-[3E-(2-Fluoro-4-thiophen-2-yl-phenyl)-acryloyl]-benzoic acid;
4-[3E-(2-Cyclopropylmethoxy-4-methoxy-5-thiophen-2-yl-phenyl)-acryloyl]-benzoic acid;
4-[3E-(4-Methoxy-2-thiophen-2-yl-phenyl)-acryloyl]-benzoic acid;
2-[3E-(2,4-Dimethoxy-5-thiophen-2-yl-phenyl)-acryloyl]-benzoic acid;
2-[3E-(2,6-Dimethoxy-4-thiophen-2-yl-phenyl)-acryloyl]-benzoic acid;
4-[3E-(2,4-Dimethoxy-6-thiophen-2-yl-phenyl)-acryloyl]-benzoic acid;
4-{3E-[2,4-Dimethoxy-5-(5-methyl-thiophen-2-yl)-phenyl]-acryloyl}-benzoic acid;
4-[3E-(4-Methoxy-3-thiophen-2-yl-phenyl)-acryloyl]-benzoic acid;
4-[3E-(3-Thiophen-2-yl-phenyl)-acryloyl]-benzoic acid;
3-[3E-(2,4-Dimethoxy-5-thiophen-2-yl-phenyl)-acryloyl]-benzoic acid;
4-[3E-(3-Benzo[b]thiophen-2-yl-2,4-dimethoxy-phenyl)-acryloyl]-benzoic acid;
4-[3E-(2-Methoxy-5-thiophen-2-yl-phenyl)-acryloyl]-benzoic acid;
4-{3E-[4-(1-Carboxy-1-methyl-ethoxy)-2-methoxy-5-thiophen-2-yl-phenyl]-acryloyl}-benzoic acid;
2-[3E-(4-Methoxy-3-thiophen-2-yl-phenyl)-acryloyl]-benzoic acid;
4-(3E-{2-Methoxy-4-[2-(2-methoxy-ethoxy)-ethoxy]-5-thiophen-2-yl-phenyl}-acryloyl)-benzoic acid;
4-{3E-[4-(3-Hydroxy-2-hydroxymethyl-propoxy)-2-methoxy-5-thiophen-2-yl-phenyl]-acryloyl}-benzoic acid;
5-{5-[3-(4-Carboxy-phenyl)-3-oxo-E-propenyl]-2,4-dimethoxy-phenyl}-thiophene-2-carboxylic acid methyl ester;
5-{5-[3-(4-Carboxy-phenyl)-3-oxo-E-propenyl]-2,4-dimethoxy-phenyl}-thiophene-2-carboxylic acid;
4-[3E-(4-Ethoxy-2-methoxy-5-thiophen-2-yl-phenyl)-acryloyl]-benzoic acid;
4-[3E-(4-Hydroxy-2-methoxy-5-thiophen-2-yl-phenyl)-acryloyl]-benzoic acid;
4-[3E-(5-Benzo[b]thiophen-2-yl-2,4-dimethoxy-phenyl)-acryloyl]-benzoic acid, sodium salt;
4-[3E-(2-Hydroxy-4-methoxy-5-thiophen-2-yl-phenyl)-acryloyl]-benzoic acid;
4-{3E-[2-(1-Carboxy-1-methyl-ethoxy)-4-methoxy-5-thiophen-2-yl-phenyl]-acryloyl}-benzoic acid;
4-{3E-[4-Methoxy-2-(2-morpholin-4-yl-ethoxy)-5-thiophen-2-yl-phenyl]-acryloyl}-benzoic acid, hydrochloride;
4-{3E-[2-(3,5-Dimethyl-isoxazol-4-ylmethoxy)-4-methoxy-5-thiophen-2-yl-phenyl]-acryloyl}-benzoic acid;
4-[3E-(2-Pyrrolidin-1-yl-5-thiophen-2-yl-phenyl)-acryloyl]-benzoic acid;

4-{3E-[2-(3-Hydroxy-2-hydroxymethyl-propoxy)-4-methoxy-5-thiophen-2-yl-phenyl]-acryloyl}-benzoic acid;

4-{3E-[2-(3-Morpholin-4-yl-propoxy)-5-thiophen-2-yl-phenyl]-acryloyl}-benzoic acid, hydrochloride;

4-{3E-[4-Methoxy-2-(3-morpholin-4-yl-propoxy)-5-thiophen-2-yl-phenyl]-acryloyl}-benzoic acid, hydrochloride;

4-[3E-(2-Dimethylcarbamoylmethoxy-4-methoxy-5-thiophen-2-yl-phenyl)-acryloyl]-benzoic acid;

4-[3E-(4-Methoxy-2-{2-[2-(2-methoxy-ethoxy)-ethoxy]-ethoxy}-5-thiophen-2-yl-phenyl)-acryloyl]-benzoic acid;

4-[3E-(2-Carbamoylmethoxy-4-methoxy-5-thiophen-2-yl-phenyl)-acryloyl]-benzoic acid;

4-{3E-[4-Methoxy-2-(2-morpholin-4-yl-2-oxo-ethoxy)-5-thiophen-2-yl-phenyl]-acryloyl}-benzoic acid;

4-(3E-{4-Methoxy-2-[2-(1-methyl-pyrrolidin-2-yl)-ethoxy]-5-thiophen-2-yl-phenyl}-acryloyl)-benzoic acid, hydrochloride;

2-{4-[3E-(2,4-Dimethoxy-5-thiophen-2-yl-phenyl)-acryloyl]-phenyl}-2-methyl-propionic acid; and 4-[3E-(5-Benzo[b]thiophen-2-yl-2,4-dimethoxy-phenyl)-acryloyl]-benzoic acid ethyl ester, or its pharmaceutically acceptable salt or ester.

17. The compound of claim 16 selected from the group consisting of:

4-[3E-(5-Benzo[b]thien-2-yl-2,4-dimethoxyphenyl)-acryloyl]-benzoic acid;

4-[3E-(2,4-Dimethoxy-5-thiophen-2-yl-phenyl)-acryloyl]-benzoic acid;

4-(3E-{4-Methoxy-2-[2-(2-methoxyethoxy)ethoxy]-5-thiophen-2-yl-phenyl}-acryloyl)-benzoic Acid; and 4-{3E-[4-Methoxy-2-(2-morpholin-4-yl-ethoxy)-5-thiophen-2-yl-phenyl]-acryloyl}-benzoic acid, hydrochloride,or its pharmaceutically acceptable salt or ester.

18. The compound of claim 17 wherein the compound is 4-[3E-(5-Benzo[b]thien-2-yl-2,4-dimethoxyphenyl)-acryloyl]-benzoic acid or its pharmaceutically acceptable salt or ester.

19. The compound of claim 17 wherein the compound is 4-[3E-(2,4-Dimethoxy-5-thiophen-2-yl-phenyl)-acryloyl]-benzoic acid, or its pharmaceutically acceptable salt or ester.

20. The compound of claim 17 wherein the compound is 4-(3E-{4-Methoxy-2-[2-(2-methoxyethoxy)ethoxy]-5-thiophen-2-yl-phenyl}-acryloyl)-benzoic Acid; and,or its pharmaceutically acceptable salt or ester.

21. The compound of claim 17 wherein the compound is 4-{3E-[4-Methoxy-2-(2-morpholin-4-yl-ethoxy)-5-thiophen-2-yl-phenyl]-acryloyl}-benzoic acid, hydrochloride,or its pharmaceutically acceptable salt or ester.

22. The compound of claim 5 or its pharmaceutically acceptable salt or ester, wherein:

$R^{2\alpha}$, $R^{3\alpha}$, $R^{4\alpha}$, $R^{5\alpha}$, and $R^{6\alpha}$ are independently selected from the group consisting of hydrogen and carboxy;

$R^{2\beta}$, $R^{3\beta}$, $R^{4\beta}$, $R^{5\beta}$ and $R^{6\beta}$ are independently selected from the group consisting of hydrogen, halogen, heteroaryl, heterocyclic, lower alkoxy, $-(O(CH_2)_2)_{1-3}$—O-lower alkyl, heteroaryl lower alkoxy, and heterocyclic lower alkoxy, all of which can be optionally substituted by one or more selected from the group consisting of hydroxy, hydroxyalkyl, $-NR^7R^8$, $-C(O)NR^7R^8$, and $-C(O)N(R^2)_2$;

$R^2$ is lower alkyl;

$R^7$ and $R^8$ are independently alkyl, and linked together forming a 6-membered monocyclic or benzofused ring;

wherein one of $R^{4\beta}$, $R^{5\beta}$ or $R^{6\beta}$ must be a carbon-carbon linked saturated or unsaturated thienyl or benzothienyl; with the proviso that at least one of $R^{2\alpha}$, $R^{3\alpha}$, or $R^{4\alpha}$ must be carboxy.

23. The compound of claim 22 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, $-C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, $-(O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, $-OC(R^1)_2C(O)OH$, $-OC(R^1)_2C(O)OR^2$, $-OC(R^1)_2C(O)NH_2$, $-OC(R^1)_2C(O)NHR^2$, $-OC(R^1)_2C(O)N(R^2)_2$, $-OC(R^1)_2C(O)NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, $-NHR^2$, $N(R^2)_2$, $-NR^7R^8$, $-NHC(R^1)_2C(O)OH$, $-NHC(R^1)_2C(O)OR^2$, $-NHC(O)R^2$, $-N(R^2)C(O)R^2$, $-NHC(O)OR^2$, $-NHC(O)SR^2$, $-NHSO_2NHR^2$, $-NHSO_2R^2$, $-NHSO_2NR^7R^8$, $-N(C(O)NHR^2)_2$, $-NR^2SO_2R^2$, $-NHC(O)NHR^2$, $-NHC(O)NR^7R^8$, $-NHC(O)N(R^2)_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, $-SC(R^1)_2C(O)OH$, $-SC(R^1)_2C(O)OR^2$, $-SCH_2C(O)OH$, $-SCF_2C(O)OH$, $-SO_2NH_2$, $-SO_2NHR_2$, $-SO_2N(R^2)_2$, $SO_2NR^7R^8$, $-SO_2NHC(O)R^2$, $-SR_2$, $-SO_2NHC(O)NHR^2$, $-SO_2NHC(O)N(R^2)_2$, $-SO_2NHC(O)NR^7R^8$, sulfonic acid, sulfonate, sulfate, sulfinic acid, sulfenic acid, cyano, tetrazol-5-yl, carboxy, $-C(O)OR^2$, $-C(O)NH_2$, $-C(O)NHR^2$, $-C(O)N(R^2)_2$, $-C(O)NR^7R^8$, $-C(O)NHC(O)R^2$, $-C(O)NHC(O)NHR^2$, $-C(O)NHC(O)N(R^2)_2$, $-C(O)NHC(O)NR^7R^8$, $-C(O)NHSO_2R^2$, $-C(O)NHSO_2NHR^2$, $-C(O)NHSO_2N(R^2)$, $-C(O)NHSO_2NR^7R^8$, $-C(CH_3)_2C(O)OH$, $-(CH_2)_yC(O)OH$, wherein y is 1, 2, 3, 4, 5, or 6, $-PO_2H_2$, $-PO_3H_2$, $-P(R^2)O_2H$, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, $-NR^7R^8$, alkoxy, oxo, cyano, carboxy, carboxyalkyl, alkoxycarbonyl, $-C(O)NR^7R^8$, and $-C(O)N(R^2)_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein when one of R$^{4\beta}$, R$^{5\beta}$, R$^{6\beta}$ must be a carbon-carbon linked saturated or unsaturated thienyl or benzothienyl, and only one of R$^{2\beta}$, R$^{3\beta}$, R$^{4\beta}$, R$^{5\beta}$ or R$^{6\beta}$ can be —OCH$_3$;

with the proviso at least one of R$^{2\alpha}$, R$^{3\alpha}$, R$^{4\alpha}$ must be selected from the group consisting of —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

24. The compound of claim 5 or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein when one of R$^{4\beta}$, R$^{5\beta}$, R$^{6\beta}$ must be a carbon-carbon linked saturated or unsaturated thienyl or benzothienyl, and only one of R$^{2\beta}$, R$^{3\beta}$, R$^{4\beta}$, R$^{5\beta}$ or R$^{6\beta}$ can be —OCH$_3$;

with the proviso at least one of R$^{2\alpha}$, R$^{3\alpha}$, R$^{4\alpha}$ must be selected from the group consisting of thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

25. The compound of claim 5 or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicyclic, tricyclic or benzofused ring;

wherein when one of R$^{4\beta}$, R$^{5\beta}$, R$^{6\beta}$ must be a carbon-carbon linked saturated or unsaturated thienyl or benzothienyl, and only one of R$^{2\beta}$, R$^{3\beta}$, R$^{4\beta}$, R$^{5\beta}$ or R$^{6\beta}$ can be —OCH$_3$;

with the proviso that at least one of R$^{2\alpha}$, R$^{3\alpha}$, or R$^{4\alpha}$ must be selected from the group consisting of amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$;

wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

26. The compound of claim 5 or its pharmaceutically acceptable salt or ester, wherein:

R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC ($R^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^7$ and $R^8$ are independently selected from the group consisting of alkyl, alkenyl and aryl and linked together forming a 4- to 12-membered monocyclic, bicyclic, tricyclic or benzofused ring;

wherein when one of $R^{4\beta}$, $R^{5\beta}$, $R^{6\beta}$ must be a carbon-carbon linked saturated or unsaturated thienyl or benzothienyl, and only one of $R^{2\beta}$, $R^{3\beta}$, $R^{4\beta}$, $R^{5\beta}$ or $R^{6\beta}$ can be —OCH$_3$;

with the proviso that at least one of $R^{2\alpha}$, $R^{3\alpha}$, or $R^{4\alpha}$ must be selected from the group consisting of —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

27. The compound of claim 3 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl loweralkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-S(O)$_2$-lower alkyl, arylsulfinyl lower alkyl, arylsulfonyl lower alkyl, —C(O)R$^2$, R$^2$C(O)alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —(O(CH$_2$)$_2$)$_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, alkylamino, acylamino, dialkylamino, cycloalkylamino, arylamino, aralkylamino, heteroarylamino, heteroaralkylamino, heterocyclicamino, heterocyclicalkylamino, —NHR$^2$, N(R$^2$)$_2$, —NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, —NHC(O)N(R$^2$)$_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, sulfonic acid, sulfonate, sulfate, sulfinic acid, sulfenic acid, cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)R$^2$, —C(O)NHC(O)NHR$^2$, —C(O)NHC(O)N(R$^2$)$_2$, —C(O)NHC(O)NR$^7$R$^8$, —C(O)NHSO$_2$R$^2$, —C(O)NHSO$_2$NHR$^2$, —C(O)NHSO$_2$N(R$^2$), —C(O)NHSO$_2$NR$^7$R$^8$, —C(CH$_3$)$_2$C(O)OH, —(CH$_2$)$_y$C(O)OH, wherein y is 1, 2, 3, 4, 5, or 6, —PO$_2$H$_2$, —PO$_3$H$_2$, —P(R$^2$)O$_2$H, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^7$ and $R^8$ are independently selected from the group consisting of alkyl, alkenyl and aryl and linked together forming a 4- to 12-membered monocyclic, bicyclic, tricyclic or benzofused ring;

wherein when one of $R^{4\beta}$, $R^{5\beta}$, $R^{6\beta}$ must be a carbon-carbon linked saturated or unsaturated thienyl or benzothienyl, and only one of $R^{2\beta}$, $R^{3\beta}$, $R^{4\beta}$, $R^{5\beta}$ or $R^{6\beta}$ can be —$OCH_3$;

with the proviso that $R^{2\alpha}$ and $R^{3\alpha}$ taken together or $R^{3\alpha}$ and $R^{4\alpha}$ taken together or $R^{4\alpha}$ and $R^{5\alpha}$ taken together, or $R^{2\beta}$ and $R^{3\beta}$ taken together or $R^{3\beta}$ and $R^{4\beta}$ taken together or $R^{4\beta}$ and $R^{5\beta}$ taken together form a heterocyclic or heteroaryl optionally substituted by one or more alkoxycarbonylalkyl, carboxyalkyl, hydroxyalkyl or aminoalkyl and optionally substituted with one or more selected from the group consisting of hydroxy, alkyl, carboxy, hydroxyalkyl, carboxyalkyl, amino, cyano, alkoxy, alkoxycarbonyl, acyl, oxo, —$NR^7R^8$, and halo; and with the proviso that at least one of $R^{2\alpha}$, $R^{3\alpha}$, or $R^{4\alpha}$ must be selected from the group consisting of cyano, tetrazol-5-yl, carboxy, —$C(O)OR^2$, —$C(O)NH_2$, —$C(O)NHR^2$, —$C(O)N(R^2)_2$, —$C(O)NR^7R^8$, —$C(O)NHC(O)NHR^2$, —$C(O)NHC(O)N(R^2)_2$, —$C(O)NHC(O)NR^7R^8$, —$C(O)NHSO_2NHR^2$, —$C(O)NHSO_2N(R^2)$, —$C(O)NHSO_2NR^7R^8$, —$C(O)NHC(O)R^2$, —$C(O)NHSO_2R^2$, —$C(CH_3)_2C(O)OH$, —$(CH_2)_yC(O)OH$, wherein y is 1, 2, 3, 4, 5, or 6, thiol, —$SC(R^1)_2C(O)OH$, —$SC(R^1)_2C(O)OR^2$, —$SCH_2C(O)OH$, —$SCF_2C(O)OH$, —$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, —$OC(R^1)_2C(O)OH$, —$OC(R^1)_2C(O)OR^2$, —$OC(R^1)_2C(O)NH_2$, —$OC(R^1)_2C(O)NHR^2$, —$OC(R^1)_2C(O)N(R^2)_2$, —$OC(R^1)_2C(O)NR^7R^8$, amino, —$NHR^2$, $N(R^2)_2$, $NR^7R^8$, —$NHC(R^1)_2C(O)OH$, —$NHC(R^1)_2C(O)OR^2$, —$NHC(O)R^2$, —$N(R^2)C(O)R^2$, —$NHC(O)OR^2$, —$NHC(O)SR^2$, —$NHSO_2NHR^2$, —$NHSO_2R^2$, —$NHSO_2NR^7R^8$, —$N(C(O)NHR^2)_2$, —$NR^2SO_2R^2$, —$NHC(O)NHR^2$, —$NHC(O)NR^7R^8$, and —$NHC(O)N(R^2)_2$;

wherein all $R^1$, $R^2$, $R^7$ and $R^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$.

28. The compound of claim 3 or its pharmaceutically acceptable salt or ester, wherein:

$R^{2\alpha}$, $R^{3\alpha}$, $R^{4\alpha}$, $R^{5\alpha}$, $R^{6\alpha}$, $R^{2\beta}$, $R^{3\beta}$, $R^{4\beta}$, $R^{5\beta}$ and $R^{6\beta}$ are independently selected from the group consisting of hydrogen, halogen, nitro, alkyl, lower alkyl, alkenyl, alkynyl, carbocycle, cycloalkyl, cycloalkylalkyl, haloalkyl, aryl, arylalkyl, heteroaryl, heteroaryl lower alkyl, heterocyclic, heterocyclic lower alkyl, alkylthioalkyl, cycloalkylthioalkyl, arylthio lower alkyl, aralkyl lower thioalkyl, heteroarylthio lower alkyl, heteroaralkyl lower thioalkyl, heterocyclicthio lower alkyl, heterocyclicalkyl lower thioalkyl, lower alkyl S(O)-lower alkyl, lower alkyl-$S(O)_2$-lower alkyl, arylsulfinyl lower alkyl, arylsulfonyl lower alkyl, —$C(O)R^2$, $R^2C(O)$alkyl, aminoalkyl, cycloalkylaminoalkyl, arylamino lower alkyl, heteroarylamino lower alkyl, heterocyclicamino lower alkyl, hydroxyl, hydroxyalkyl, alditol, carbohydrate, polyol alkyl, alkoxy, lower alkoxy, —$(O(CH_2)_2)_{1-3}$—O-lower alkyl, polyoxyalkylene, cycloalkyloxy, cycloalkylalkoxy, haloalkoxy, aryloxy, arylalkoxy, heteroaryloxy, heteroarylalkoxy, heteroaryl lower alkoxy, heterocyclicoxy, heterocyclicalkoxy, heterocyclic lower alkoxy, —$OC(R^1)_2C(O)OH$, —$OC(R^1)_2C(O)OR^2$, —$OC(R^1)_2C(O)NH_2$, —$OC(R^1)_2C(O)NHR^2$, —$OC(R^1)_2C(O)N(R^2)_2$, —$OC(R^1)_2C(O)NR^7R^8$, amino, alkylamino, acylamino, dialkylamino, cycloalkylamino, arylamino, aralkylamino, heteroarylamino, heteroaralkylamino, heterocyclicamino, heterocyclicalkylamino, —$NHR^2$, $N(R^2)_2$, —$NR^7R^8$, —$NHC(R^1)_2C(O)OH$, —$NHC(R^1)_2C(O)OR^2$, —$NHC(O)R^2$, —$N(R^2)C(O)R^2$, —$NHC(O)OR^2$, —$NHC(O)SR^2$, —$NHSO_2NHR^2$, —$NHSO_2R^2$, —$NHSO_2NR^7R^8$, —$N(C(O)NHR^2)_2$, —$NR^2SO_2R^2$, —$NHC(O)NHR^2$, —$NHC(O)NR^7R^8$, —$NHC(O)N(R^2)_2$, thiol, alkylthio, cycloalkylthio, cycloalkylalkylthio, haloalkylthio, arylthio, aralkylthio, heteroarylthio, heteroaralkylthio, heterocyclicthio, heterocyclicalkylthio, alkylsulfonyl, arylsulfonyl, haloalkylsulfonyl, —$SC(R^1)_2C(O)OH$, —$SC(R^1)_2C(O)OR^2$, —$SCH_2C(O)OH$, —$SCF_2C(O)OH$, —$SO_2NH_2$, —$SO_2NHR_2$, —$SO_2N(R^2)_2$, $SO_2NR^7R^8$, —$SO_2NHC(O)R^2$, —$SR_2$, —$SO_2NHC(O)NHR^2$, —$SO_2NHC(O)N(R^2)_2$, —$SO_2NHC(O)NR^7R^8$, sulfonic acid, sulfonate, sulfate, sulfinic acid, sulfenic acid, cyano, tetrazol-5-yl, carboxy, —$C(O)OR^2$, —$C(O)NH_2$, —$C(O)NHR^2$, —$C(O)N(R^2)_2$, —$C(O)NR^7R^8$, —$C(O)NHC(O)R^2$, —$C(O)NHC(O)NHR^2$, —$C(O)NHC(O)N(R^2)_2$, —$C(O)NHC(O)NR^7R^8$, —$C(O)NHSO_2R^2$, —$C(O)NHSO_2NHR^2$, —$C(O)NHSO_2N(R^2)$, —$C(O)NHSO_2NR^7R^8$, —$C(CH_3)_2C(O)OH$, —$(CH_2)_yC(O)OH$, wherein y is 1, 2, 3, 4, 5, or 6, —$PO_2H_2$, —$PO_3H_2$, —$P(R^2)O_2H$, and phosphate, all of which can be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^1$ is independently selected from the group consisting of hydrogen, lower alkyl, carbocycle, cycloalkyl, aryl, heteroaryl, heterocyclic, arylalkyl, heteroarylalkyl, and heterocyclicalkyl, wherein all may be optionally substituted by one or more selected from the group consisting of halo, alkyl, lower alkyl, alkenyl, cycloalkyl, acyl, hydroxy, hydroxyalkyl, heterocyclic, amino, aminoalkyl, —$NR^7R^8$, alkoxy, oxo, cyano, carboxy, carboxyalkyl, alkoxycarbonyl, —$C(O)NR^7R^8$, and —$C(O)N(R^2)_2$;

$R^2$ is independently selected from the group consisting of alkyl, lower alkyl, alkenyl, alkynyl, carbocycle, cycloalkyl, aryl, heteroaryl, heterocyclic, arylalkyl, heteroarylalkyl, and heterocyclicalkyl, wherein all may be substituted by one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$;

R$^7$ and R$^8$ are independently selected from the group consisting of alkyl, alkenyl and aryl and linked together forming a 4- to 12-membered monocyclic, bicylic, tricyclic or benzofused ring;

wherein when one of R$^{4\beta}$, R$^{5\beta}$, R$^{6\beta}$ must be a carbon-carbon linked saturated or unsaturated thienyl or benzothienyl, and only one of R$^{2\beta}$, R$^{3\beta}$, R$^{4\beta}$, R$^{5\beta}$ or R$^{6\beta}$ can be —OCH$_3$;

with the proviso that R$^{2\alpha}$ and R$^{3\alpha}$ taken together or R$^{3\alpha}$ and R$^{4\alpha}$ taken together or R$^{4\alpha}$ and R$^{5\alpha}$ taken together or R$^{2\beta}$ and R$^{3\beta}$ taken together or R$^{3\beta}$ and R$^{4\beta}$ taken together or R$^{4\beta}$ and R$^{5\beta}$ taken together form a 5- or 6-membered ring containing one nitrogen, which may optionally be substituted with one or more selected from the group consisting of halo, alkyl, lower alkyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$; provided that R$^{2\alpha}$, R$^{3\alpha}$, R$^{4\alpha}$, R$^{5\alpha}$, R$^{6\alpha}$, R$^{2\beta}$, R$^{3\beta}$, R$^{4\beta}$, R$^{5\beta}$ and R$^{6\beta}$ cannot be —OC(R$^1$)$_2$C(O)OH; and with the proviso that at least one of R$^{2\alpha}$, R$^{3\alpha}$, or R$^{4\alpha}$ must be selected from the group consisting of cyano, tetrazol-5-yl, carboxy, —C(O)OR$^2$, —C(O)NH$_2$, —C(O)NHR$^2$, —C(O)N(R$^2$)$_2$, —C(O)NR$^7$R$^8$, —C(O)NHC(O)NHR$^2$, —C(O)NHC(O)N(R$^2$)$_2$, —C(O)NHC(O)NR$^7$R$^8$, —C(O)NHSO$_2$NHR$^2$, —C(O)NHSO$_2$N(R$^2$), —C(O)NHSO$_2$NR$^7$R$^8$, —C(O)NHC(O)R$^2$, —C(O)NHSO$_2$R$^2$, —C(CH$_3$)$_2$C(O)OH, —(CH$_2$)$_y$C(O)OH, wherein y is 1, 2, 3, 4, 5, or 6, thiol, —SC(R$^1$)$_2$C(O)OH, —SC(R$^1$)$_2$C(O)OR$^2$, —SCH$_2$C(O)OH, —SCF$_2$C(O)OH, —SO$_2$NH$_2$, —SO$_2$NHR$_2$, —SO$_2$N(R$^2$)$_2$, SO$_2$NR$^7$R$^8$, —SO$_2$NHC(O)R$^2$, —SR$_2$, —SO$_2$NHC(O)NHR$^2$, —SO$_2$NHC(O)N(R$^2$)$_2$, —SO$_2$NHC(O)NR$^7$R$^8$, —OC(R$^1$)$_2$C(O)OH, —OC(R$^1$)$_2$C(O)OR$^2$, —OC(R$^1$)$_2$C(O)NH$_2$, —OC(R$^1$)$_2$C(O)NHR$^2$, —OC(R$^1$)$_2$C(O)N(R$^2$)$_2$, —OC(R$^1$)$_2$C(O)NR$^7$R$^8$, amino, —NHR$^2$, N(R$^2$)$_2$, NR$^7$R$^8$, —NHC(R$^1$)$_2$C(O)OH, —NHC(R$^1$)$_2$C(O)OR$^2$, —NHC(O)R$^2$, —N(R$^2$)C(O)R$^2$, —NHC(O)OR$^2$, —NHC(O)SR$^2$, —NHSO$_2$NHR$^2$, —NHSO$_2$R$^2$, —NHSO$_2$NR$^7$R$^8$, —N(C(O)NHR$^2$)$_2$, —NR$^2$SO$_2$R$^2$, —NHC(O)NHR$^2$, —NHC(O)NR$^7$R$^8$, and —NHC(O)N(R$^2$)$_2$, wherein all R$^1$, R$^2$, R$^7$ and R$^8$ substituents can be optionally substituted with one or more selected from the group consisting of halo, alkyl, lower alkyl, alkenyl, cycloalkyl, acyl, hydroxy, hydroxyalkyl, heterocyclic, amino, aminoalkyl, —NR$^7$R$^8$, alkoxy, oxo, cyano, carboxy, carboxyalkyl, alkoxycarbonyl, —C(O)NR$^7$R$^8$, and —C(O)N(R$^2$)$_2$.

29. A pharmaceutical composition comprising a therapeutically effective amount of a compound of claim 1, 2, 3, 4, 5, 6, 7, 8, 9, 10, 11, 12, 13, 14, 15, 16, 17, 18, 19, 20, 21, 22, 23, 24, 25, 26, 27, or 28, together with one or more pharmaceutically acceptable carrier.

30. A method for the treatment of an inflammatory disorder, comprising administering an effective amount of a compound of claim 1, 2, 3, 4, 5, 6, 7, 8, 9, 10, 11, 12, 13, 14, 15, 16, 17, 18, 19, 20, 21, 22, 23, 24, 25, 26, 27, or 28.

31. The method of claim 30, wherein the disorder is arthritis.

32. The method of claim 30, wherein the disorder is rheumatoid arthritis.

33. The method of claim 30, wherein the disorder is asthma.

34. The method of claim 30, wherein the treatment is disease modifying for the treatment of rheumatoid arthritis.

35. The method of claim 30, wherein the disorder is allergic rhinitis.

36. The method of claim 30, wherein the disorder is chronic obstructive pulmonary disease.

37. The method of claim 30, wherein the disorder is atherosclerosis.

38. The method of claim 30, wherein the disorder is restinosis.

39. A method for inhibiting the expression of VCAM-1, comprising administering an effective amount of a compound of claim 1, 2, 3, 4, 5, 6, 7, 8, 9, 10, 11, 12, 13, 14, 15, 16, 17, 18, 19, 20, 21, 22, 23, 24, 25, 26, 27, or 28.

* * * * *